US012479861B2

(12) United States Patent
Wolohan et al.

(10) Patent No.: US 12,479,861 B2
(45) Date of Patent: Nov. 25, 2025

(54) ORGANIC ELECTROLUMINESCENT MATERIALS AND DEVICES

(71) Applicant: Universal Display Corporation, Ewing, NJ (US)

(72) Inventors: Peter Wolohan, Princeton Junction, NJ (US); Tyler Fleetham, Newtown, PA (US); Jerald Feldman, Cherry Hill, NJ (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 0 days.

(21) Appl. No.: 18/410,105

(22) Filed: Jan. 11, 2024

(65) Prior Publication Data

US 2024/0246999 A1 Jul. 25, 2024

Related U.S. Application Data

(63) Continuation of application No. 17/063,884, filed on Oct. 6, 2020, now Pat. No. 11,919,914.
(Continued)

(51) Int. Cl.

| | |
|---|---|
| ***H01L 51/50*** | (2006.01) |
| ***C07D 517/22*** | (2006.01) |
| ***H10K 85/30*** | (2023.01) |
| ***H10K 85/40*** | (2023.01) |
| ***H10K 85/60*** | (2023.01) |
| *H10K 50/15* | (2023.01) |
| *H10K 50/16* | (2023.01) |
| *H10K 50/17* | (2023.01) |
| *H10K 50/18* | (2023.01) |

(52) U.S. Cl.
CPC ......... *C07D 517/22* (2013.01); *H10K 85/346* (2023.02); *H10K 85/40* (2023.02); *H10K 85/6572* (2023.02); *H10K 85/6574* (2023.02); *H10K 85/6576* (2023.02); *H10K 50/15* (2023.02); *H10K 50/16* (2023.02); *H10K 50/171* (2023.02); *H10K 50/18* (2023.02)

(58) Field of Classification Search
None
See application file for complete search history.

(56) References Cited

U.S. PATENT DOCUMENTS 4,769,292 A 9/1988 Tang et al.
5,061,569 A 10/1991 VanSlyke et al.
(Continued)

FOREIGN PATENT DOCUMENTS

CN 106467553 3/2017
CN 106467554 3/2017
(Continued)

OTHER PUBLICATIONS

Nakatsuka, Soichiro et al., "Divergent Synthesis of Heteroatom-Centered 4,8, 12-Triazatriangulenes", Angew. Chem. Int. Ed. 2017, 56, 5087-5090.
(Continued)

*Primary Examiner* — Gregory D Clark
(74) *Attorney, Agent, or Firm* — DUANE MORRIS LLP

(57) ABSTRACT

Provided are boron-containing compounds. Also provided are formulations comprising these boron-containing compounds. Further provided are OLEDs and related consumer products that utilize these boron-containing compounds.

20 Claims, 2 Drawing Sheets

Related U.S. Application Data

(60) Provisional application No. 62/982,883, filed on Feb. 28, 2020, provisional application No. 62/971,295, filed on Feb. 7, 2020, provisional application No. 62/926,035, filed on Oct. 25, 2019.

(56) References Cited

U.S. PATENT DOCUMENTS

| | | | | |
|---|---|---|---|---|
| 5,247,190 | A | 9/1993 | Friend et al. | |
| 5,703,436 | A | 12/1997 | Forrest et al. | |
| 5,707,745 | A | 1/1998 | Forrest et al. | |
| 5,834,893 | A | 11/1998 | Bulovic et al. | |
| 5,844,363 | A | 12/1998 | Gu et al. | |
| 6,013,982 | A | 1/2000 | Thompson et al. | |
| 6,087,196 | A | 7/2000 | Sturm et al. | |
| 6,091,195 | A | 7/2000 | Forrest et al. | |
| 6,097,147 | A | 8/2000 | Baldo et al. | |
| 6,294,398 | B1 | 9/2001 | Kim et al. | |
| 6,303,238 | B1 | 10/2001 | Thompson et al. | |
| 6,337,102 | B1 | 1/2002 | Forrest et al. | |
| 6,468,819 | B1 | 10/2002 | Kim et al. | |
| 6,528,187 | B1 | 3/2003 | Okada | |
| 6,687,266 | B1 | 2/2004 | Ma et al. | |
| 6,835,469 | B2 | 12/2004 | Kwong et al. | |
| 6,921,915 | B2 | 7/2005 | Takiguchi et al. | |
| 7,087,321 | B2 | 8/2006 | Kwong et al. | |
| 7,090,928 | B2 | 8/2006 | Thompson et al. | |
| 7,154,114 | B2 | 12/2006 | Brooks et al. | |
| 7,250,226 | B2 | 7/2007 | Tokito et al. | |
| 7,279,704 | B2 | 10/2007 | Walters et al. | |
| 7,332,232 | B2 | 2/2008 | Ma et al. | |
| 7,338,722 | B2 | 3/2008 | Thompson et al. | |
| 7,393,599 | B2 | 7/2008 | Thompson et al. | |
| 7,396,598 | B2 | 7/2008 | Takeuchi et al. | |
| 7,431,968 | B1 | 10/2008 | Shtein et al. | |
| 7,445,855 | B2 | 11/2008 | Mackenzie et al. | |
| 7,534,505 | B2 | 5/2009 | Lin et al. | |
| 2002/0034656 | A1 * | 3/2002 | Thompson | C09K 11/06 252/301.16 |
| 2002/0134984 | A1 | 9/2002 | Igarashi | |
| 2002/0158242 | A1 | 10/2002 | Son et al. | |
| 2003/0138657 | A1 | 7/2003 | Li et al. | |
| 2003/0152802 | A1 | 8/2003 | Tsuboyama et al. | |
| 2003/0162053 | A1 | 8/2003 | Marks et al. | |
| 2003/0175553 | A1 | 9/2003 | Thompson et al. | |
| 2003/0230980 | A1 | 12/2003 | Forrest et al. | |
| 2004/0036077 | A1 | 2/2004 | Ise | |
| 2004/0137267 | A1 | 7/2004 | Igarashi et al. | |
| 2004/0137268 | A1 | 7/2004 | Igarashi et al. | |
| 2004/0174116 | A1 | 9/2004 | Lu et al. | |
| 2005/0025993 | A1 | 2/2005 | Thompson et al. | |
| 2005/0037232 | A1 | 2/2005 | Tyan | |
| 2005/0112407 | A1 | 5/2005 | Ogasawara et al. | |
| 2005/0238919 | A1 | 10/2005 | Ogasawara | |
| 2005/0244673 | A1 | 11/2005 | Satoh et al. | |
| 2005/0260441 | A1 | 11/2005 | Thompson et al. | |
| 2005/0260449 | A1 | 11/2005 | Walters et al. | |
| 2006/0008670 | A1 | 1/2006 | Lin et al. | |
| 2006/0202194 | A1 | 9/2006 | Jeong et al. | |
| 2006/0240279 | A1 | 10/2006 | Adamovich et al. | |
| 2006/0251923 | A1 | 11/2006 | Lin et al. | |
| 2006/0263635 | A1 | 11/2006 | Ise | |
| 2006/0280965 | A1 | 12/2006 | Kwong et al. | |
| 2007/0190359 | A1 | 8/2007 | Knowles et al. | |
| 2007/0278938 | A1 | 12/2007 | Yabunouchi et al. | |
| 2008/0015355 | A1 | 1/2008 | Schafer et al. | |
| 2008/0018221 | A1 | 1/2008 | Egen et al. | |
| 2008/0106190 | A1 | 5/2008 | Yabunouchi et al. | |
| 2008/0124572 | A1 | 5/2008 | Mizuki et al. | |
| 2008/0220265 | A1 | 9/2008 | Xia et al. | |
| 2008/0297033 | A1 | 12/2008 | Knowles et al. | |
| 2009/0008605 | A1 | 1/2009 | Kawamura et al. | |
| 2009/0009065 | A1 | 1/2009 | Nishimura et al. | |
| 2009/0017330 | A1 | 1/2009 | Iwakuma et al. | |
| 2009/0030202 | A1 | 1/2009 | Iwakuma et al. | |
| 2009/0039776 | A1 | 2/2009 | Yamada et al. | |
| 2009/0045730 | A1 | 2/2009 | Nishimura et al. | |
| 2009/0045731 | A1 | 2/2009 | Nishimura et al. | |
| 2009/0101870 | A1 | 4/2009 | Prakash et al. | |
| 2009/0108737 | A1 | 4/2009 | Kwong et al. | |
| 2009/0115316 | A1 | 5/2009 | Zheng et al. | |
| 2009/0165846 | A1 | 7/2009 | Johannes et al. | |
| 2009/0167162 | A1 | 7/2009 | Lin et al. | |
| 2009/0179554 | A1 | 7/2009 | Kuma et al. | |
| 2011/0101312 | A1 | 5/2011 | Lecloux | |
| 2014/0070204 | A1 | 3/2014 | Nagao | |
| 2018/0094000 | A1 | 4/2018 | Hatakeyama | |
| 2019/0013478 | A1 | 1/2019 | Iijima et al. | |
| 2019/0115538 | A1 | 4/2019 | Lim | |
| 2019/0214577 | A1 | 7/2019 | Pan et al. | |
| 2020/0058885 | A1 | 2/2020 | Hong et al. | |
| 2020/0091431 | A1 | 3/2020 | Hatakeyama | |
| 2020/0270262 | A1 | 8/2020 | Fleetham | |
| 2021/0008872 | A1 | 1/2021 | Kimura | |
| 2021/0013423 | A1 | 1/2021 | Lee | |
| 2021/0193936 | A1 | 6/2021 | Li | |
| 2021/0367168 | A1 | 11/2021 | Heechoon | |
| 2022/0006022 | A1 | 1/2022 | Suh | |
| 2023/0189635 | A1 | 6/2023 | Heechoon | |
| 2023/0247902 | A1 | 8/2023 | No | |

FOREIGN PATENT DOCUMENTS

| | | | |
|---|---|---|---|
| CN | 108368045 | 8/2018 | |
| EP | 0650955 | 5/1995 | |
| EP | 1725079 | 11/2006 | |
| EP | 2034538 | 3/2009 | |
| EP | 3345911 | 11/2018 | |
| JP | 200511610 | 1/2005 | |
| JP | 2007123392 | 5/2007 | |
| JP | 2007254297 | 10/2007 | |
| JP | 2008074939 | 4/2008 | |
| JP | 2009231516 | 10/2009 | |
| KR | 20140145452 | 12/2014 | |
| KR | 2018120619 | * 11/2018 | H01L 51/50 |
| WO | 01/39234 | 5/2001 | |
| WO | 02/02714 | 1/2002 | |
| WO | 02015654 | 2/2002 | |
| WO | 03040257 | 5/2003 | |
| WO | 03060956 | 7/2003 | |
| WO | 2004093207 | 10/2004 | |
| WO | 2004107822 | 12/2004 | |
| WO | 2005014551 | 2/2005 | |
| WO | 2005019373 | 3/2005 | |
| WO | 2005030900 | 4/2005 | |
| WO | 2005089025 | 9/2005 | |
| WO | 2005123873 | 12/2005 | |
| WO | 2006009024 | 1/2006 | |
| WO | 2006056418 | 6/2006 | |
| WO | 2006072002 | 7/2006 | |
| WO | 2006082742 | 8/2006 | |
| WO | 2006098120 | 9/2006 | |
| WO | 2006100298 | 9/2006 | |
| WO | 2006103874 | 10/2006 | |
| WO | 2006114966 | 11/2006 | |
| WO | 2006132173 | 12/2006 | |
| WO | 2007002683 | 1/2007 | |
| WO | 2007004380 | 1/2007 | |
| WO | 2007063754 | 6/2007 | |
| WO | 2007063796 | 6/2007 | |
| WO | 2008056746 | 5/2008 | |
| WO | 2008101842 | 8/2008 | |
| WO | 2008132085 | 11/2008 | |
| WO | 2009000673 | 12/2008 | |
| WO | 2009003898 | 1/2009 | |
| WO | 2009008311 | 1/2009 | |
| WO | 2009018009 | 2/2009 | |
| WO | 2009021126 | 2/2009 | |
| WO | 2009050290 | 4/2009 | |
| WO | 2009062578 | 5/2009 | |
| WO | 2009063833 | 5/2009 | |
| WO | 2009066778 | 5/2009 | |
| WO | 2009066779 | 5/2009 | |
| WO | 2009086028 | 7/2009 | |

(56) References Cited

FOREIGN PATENT DOCUMENTS

| | | |
|---|---|---|
| WO | 2009100991 | 8/2009 |
| WO | 2015102118 | 7/2015 |
| WO | 2017018326 | 2/2017 |
| WO | 2018186670 | 10/2018 |
| WO | 2018203666 | 11/2018 |
| WO | 20190009052 | 1/2019 |
| WO | 2020/045681 | 3/2020 |

OTHER PUBLICATIONS

Liu, X., et al., "Isotope Effect in the Magento-Optoelectronic Response of Organic Light-Emitting Diodes Based on Donor-Acceptor Exciplexes," Adv. Mater., 2020, 32, 2004421, pp. 1-8.
Third Party Observation for European Application No. EP20220158225, submitted on Aug. 29, 2023.
S. Yumiao, et al., "The Applications of Carbazole and Carbazole-Related Compounds in Blue Emitting Organic Light-Emitting Diodes," Progress in Chemistry, 2015, vol. 27, Issue (10); 1384-1399; DOI: 10.7536/PC150304.
Adachi, Chihaya et al., "Organic Electroluminescent Device Having a Hole Conductor as an Emitting Layer," Appl. Phys. Lett., 55(15): 1489-1491 (1989).
Adachi, Chihaya et al., "Nearly 100% Internal Phosphorescence Efficiency in an Organic Light Emitting Device," J. Appl. Phys., 90(10): 5048-5051 (2001).
Adachi, Chihaya et al., "High-Efficiency Red Electrophosphorescence Devices," Appl. Phys. Lett., 78(11)1622-1624 (2001).
Aonuma, Masaki et al., "Material Design of Hole Transport Materials Capable of Thick-Film Formation in Organic Light Emitting Diodes," Appl. Phys. Lett., 90, Apr. 30, 2007, 183503-1-183503-3.
Baldo et al., Highly Efficient Phosphorescent Emission from Organic Electroluminescent Devices, Nature, vol. 395, 151-154, (1998).
Baldo et al., Very high-efficiency green organic light-emitting devices based on electrophosphorescence, Appl. Phys. Lett., vol. 75, No. 1, 4-6 (1999).
Gao, Zhiqiang et al., "Bright-Blue Electroluminescence From a Silyl-Substituted ter-(phenylene-vinylene) derivative," Appl. Phys. Lett., 74(6): 865-867 (1999).
Guo, Tzung-Fang et al., "Highly Efficient Electrophosphorescent Polymer Light-Emitting Devices," Organic Electronics, 1: 15-20 (2000).
Hamada, Yuji et al., "High Luminance in Organic Electroluminescent Devices with Bis(10-hydroxybenzo[h]quinolinato) beryllium as an Emitter," Chem. Lett., 905-906 (1993).
Holmes, R.J. et al., "Blue Organic Electrophosphorescence Using Exothermic Host-Guest Energy Transfer," Appl. Phys. Lett., 82(15):2422-2424 (2003).
Hu, Nan-Xing et al., "Novel High Tg Hole-Transport Molecules Based on Indolo[3,2-b]carbazoles for Organic Light-Emitting Devices," Synthetic Metals, 111-112:421-424 (2000).
Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).
Huang, Wei-Sheng et al., "Highly Phosphorescent Bis-Cyclometalated Iridium Complexes Containing Benzoimidazole-Based Ligands," Chem. Mater., 16(12):2480-2488 (2004).
Hung, L.S. et al., "Anode Modification in Organic Light-Emitting Diodes by Low-Frequency Plasma Polymerization of CHF3," Appl. Phys. Lett., 78(5):673-675 (2001).
Ikai, Masamichi et al., "Highly Efficient Phosphorescence From Organic Light-Emitting Devices with an Exciton-Block Layer," Appl. Phys. Lett., 79(2):156-158 (2001).
Ikeda, Hisao et al., "P-185 Low-Drive-Voltage OLEDs with a Buffer Layer Having Molybdenum Oxide," SID Symposium Digest, 37:923-926 (2006).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).
Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Kido, Junji et al., 1,2,4-Triazole Derivative as an Electron Transport Layer in Organic Electroluminescent Devices, Jpn. J. Appl. Phys., 32:L917-L920 (1993).
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).
Kwong, Raymond C. et al., "High Operational Stability of Electrophosphorescent Devices," Appl. Phys. Lett., 81(1) 162-164 (2002).
Lamansky, Sergey et al., "Synthesis and Characterization of Phosphorescent Cyclometalated Iridium Complexes," Inorg. Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).
Lo, Shih-Chun et al., "Blue Phosphorescence from Iridium(III) Complexes at Room Temperature," Chem. Mater., 18 (21)5119-5129 (2006).
Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).
Mi, Bao-Xiu et al., "Thermally Stable Hole-Transporting Material for Organic Light-Emitting Diode an Isoindole Derivative," Chem. Mater., 15(16):3148-3151 (2003).
Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).
Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and SHIROTA, Yasuhiko, "5,5'-Bis(dimesitylboryl)-2,2'-bithiophene and 5,5"-Bis (dimesitylboryl)-2,2'5',2"-terthiophene as a Novel Family of Electron-Transporting Amorphous Molecular Materials," J. Am. Chem. Soc., 120 (37):9714-9715 (1998).
Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based on Silole Derivatives and Their Exciplexes," Organic Electronics, 4:113-121 (2003).
Paulose, Betty Marie Jennifer S. et al., "First Examples of Alkenyl Pyridines as Organic Ligands for Phosphorescent Iridium Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8):1832-1833 (2000).
Salbeck, J. et al., "Low Molecular Organic Glasses for Blue Electroluminescence," Synthetic Metals, 91: 209-215 (1997).
Shirota, Yasuhiko et al., "Starburst Molecules Based on pi-Electron Systems as Materials for Organic Electroluminescent Devices," Journal of Luminescence, 72-74:985-991 (1997).
Sotoyama, Wataru et al., "Efficient Organic Light-Emitting Diodes with Phosphorescent Platinum Complexes Containing NCN-Coordinating Tridentate Ligand," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).

(56) References Cited

OTHER PUBLICATIONS

T. Östergård et al., "Langmuir-Blodgett Light-Emitting Diodes of Poly(3-Hexylthiophene) Electro-Optical Characteristics Related to Structure," Synthetic Metals, 88:171-177 (1997).
Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).
Tang, C.W. and VanSlyke, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II PHosphorescent Emitters," Adv. Mater., 17(8)1059-1064 (2005).
Van Slyke, S. A. et al., "Organic Electroluminescent Devices with Improved Stability," Appl. Phys. Lett., 69(15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).

* cited by examiner

ORGANIC ELECTROLUMINESCENT MATERIALS AND DEVICES

CROSS-REFERENCE TO RELATED APPLICATIONS

This application is a continuation of U.S. patent application Ser. No. 17/063,884, filed Oct. 6, 2020, which claims priority under 35 U.S.C. § 119(e) to U.S. Provisional Application No. 62/926,035, filed on Oct. 25, 2019, U.S. Provisional Application No. 62/971,295, filed on Feb. 7, 2020, U.S. Provisional Application No. 62/982,883, filed on Feb. 28, 2020, the entire contents of all are incorporated herein by reference.

FIELD

The present disclosure generally relates to boron-containing compounds and formulations and their various uses including as host materials and emitters in devices such as organic light emitting diodes and related electronic devices.

BACKGROUND

Opto-electronic devices that make use of organic materials are becoming increasingly desirable for various reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting diodes/devices (OLEDs), organic phototransistors, organic photovoltaic cells, and organic photodetectors. For OLEDs, the organic materials may have performance advantages over conventional materials.

OLEDs make use of thin organic films that emit light when voltage is applied across the device. OLEDs are becoming an increasingly interesting technology for use in applications such as flat panel displays, illumination, and backlighting.

One application for phosphorescent emissive molecules is a full color display. Industry standards for such a display call for pixels adapted to emit particular colors, referred to as "saturated" colors. In particular, these standards call for saturated red, green, and blue pixels. Alternatively, the OLED can be designed to emit white light. In conventional liquid crystal displays emission from a white backlight is filtered using absorption filters to produce red, green and blue emission. The same technique can also be used with OLEDs. The white OLED can be either a single emissive layer (EML) device or a stack structure. Color may be measured using CIE coordinates, which are well known to the art.

SUMMARY

In one aspect, the present disclosure provides a compound comprising a structure of Formula I:

Formula I

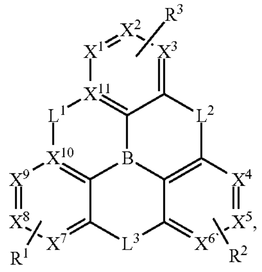

wherein $X^1$-$X^{11}$ are each independently C or N; no more than two N atoms are bonded to one another in the same ring; $L^1$, $L^2$, and $L^3$ are each independently selected from the group consisting of O, S, Se, and SiRR'; $L^1$ can be present and $X^{10}$ and $X^{11}$ are both C when $L^1$ is present; $L^2$ and $L^3$ are always present; $R^1$, $R^2$, and $R^3$ each independently represent zero, mono, or up to a maximum allowed substitution to its associated ring; each of $R^1$, $R^2$, and $R^3$ is independently a hydrogen or a substituent comprising a structure selected from the group consisting of Formulae II, III, IV, V, VI, VII, VIII, deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof, with at least one of $R^1$, $R^2$, and $R^3$ comprising a structure selected from the group consisting of Formulae II, III, IV, V, VI, VII, VIII, and their aza variants as defined in the disclosure.

In another aspect, the present disclosure provides a formulation of a compound comprising a structure of Formula I as described herein.

In yet another aspect, the present disclosure provides an OLED having an organic layer comprising a compound comprising a structure of Formula I as described herein.

In yet another aspect, the present disclosure provides a consumer product comprising an OLED with an organic layer comprising a compound comprising a structure of Formula I as described herein.

In yet another aspect, the present disclosure provides an OLED comprising an emissive layer comprising a first compound and a second compound with the first compound being a boron compound possessing a trigonal planar geometry as described herein, and the second compound being a Pt(II) complex possessing a square planar geometry.

DETAILED DESCRIPTION

A. Terminology

Figure 1:
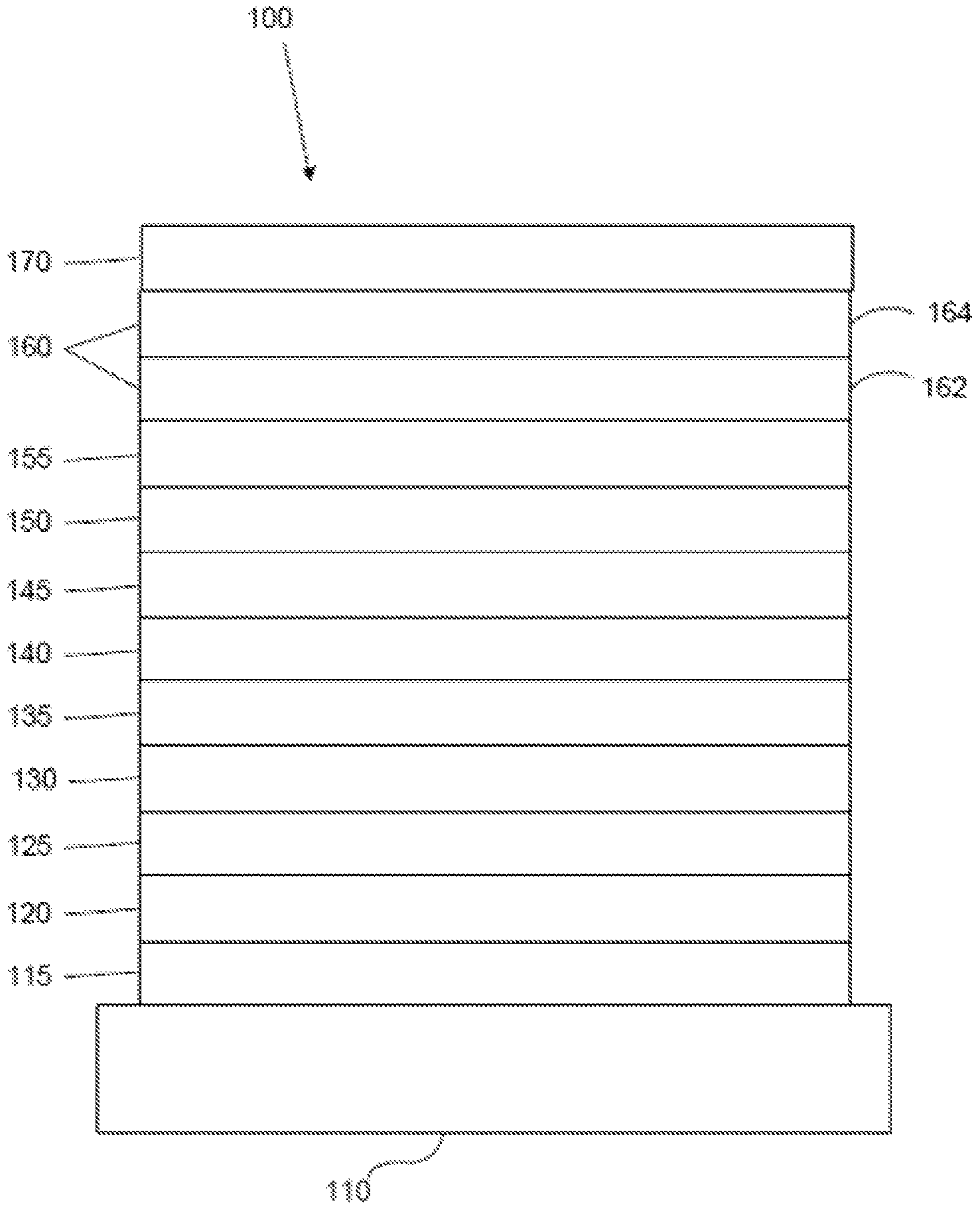
FIG. 1 shows an organic light emitting device.

Unless otherwise specified, the below terms used herein are defined as follows:

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processable" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

The terms "halo," "halogen," and "halide" are used interchangeably and refer to fluorine, chlorine, bromine, and iodine.

The term "acyl" refers to a substituted carbonyl radical ($C(O)—R_s$).

The term "ester" refers to a substituted oxycarbonyl ($—O—C(O)—R_s$ or $—C(O)—O—R_s$) radical.

The term "ether" refers to an $—OR_s$ radical.

The terms "sulfanyl" or "thio-ether" are used interchangeably and refer to a $—SR_s$ radical.

The term "sulfinyl" refers to a $—S(O)—R_s$ radical.

The term "sulfonyl" refers to a $—SO_2—R_s$ radical.

The term "phosphino" refers to a $—P(R_s)_3$ radical, wherein each $R_s$ can be same or different.

The term "silyl" refers to a $—Si(R_s)_3$ radical, wherein each $R_s$ can be same or different.

The term "boryl" refers to a $—B(R_s)_2$ radical or its Lewis adduct $—B(R_s)_3$ radical, wherein $R_s$ can be the same or different.

In each of the above, $R_s$ can be hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, and combination thereof. Preferred $R_s$ is selected from the group consisting of alkyl, cycloalkyl, aryl, heteroaryl, and combination thereof.

The term "alkyl" refers to and includes both straight and branched chain alkyl radicals. Preferred alkyl groups are those containing from one to fifteen carbon atoms and includes methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, and the like. Additionally, the alkyl group can be substituted.

The term "cycloalkyl" refers to and includes monocyclic, polycyclic, and spiro alkyl radicals. Preferred cycloalkyl groups are those containing 3 to 12 ring carbon atoms and includes cyclopropyl, cyclopentyl, cyclohexyl, bicyclo[3.1.1]heptyl, spiro[4.5]decyl, spiro[5.5]undecyl, adamantyl, and the like. Additionally, the cycloalkyl group can be substituted.

The terms "heteroalkyl" or "heterocycloalkyl" refer to an alkyl or a cycloalkyl radical, respectively, having at least one carbon atom replaced by a heteroatom. Optionally the at least one heteroatom is selected from O, S, N, P, B, Si and Se, preferably, O, S or N. Additionally, the heteroalkyl or heterocycloalkyl group can be substituted.

The term "alkenyl" refers to and includes both straight and branched chain alkene radicals. Alkenyl groups are essentially alkyl groups that include at least one carbon-carbon double bond in the alkyl chain. Cycloalkenyl groups are essentially cycloalkyl groups that include at least one carbon-carbon double bond in the cycloalkyl ring. The term "heteroalkenyl" as used herein refers to an alkenyl radical having at least one carbon atom replaced by a heteroatom. Optionally the at least one heteroatom is selected from O, S, N, P, B, Si, and Se, preferably, O, S, or N. Preferred alkenyl, cycloalkenyl, or heteroalkenyl groups are those containing two to fifteen carbon atoms. Additionally, the alkenyl, cycloalkenyl, or heteroalkenyl group can be substituted.

The term "alkynyl" refers to and includes both straight and branched chain alkyne radicals. Alkynyl groups are essentially alkyl groups that include at least one carbon-carbon triple bond in the alkyl chain. Preferred alkynyl groups are those containing two to fifteen carbon atoms. Additionally, the alkynyl group can be substituted.

The terms "aralkyl" or "arylalkyl" are used interchangeably and refer to an alkyl group that is substituted with an aryl group. Additionally, the aralkyl group can be substituted.

The term "heterocyclic group" refers to and includes aromatic and non-aromatic cyclic radicals containing at least one heteroatom. Optionally the at least one heteroatom is selected from O, S, N, P, B, Si, and Se, preferably, O, S, or N. Hetero-aromatic cyclic radicals may be used interchangeably with heteroaryl. Preferred hetero-non-aromatic cyclic groups are those containing 3 to 7 ring atoms which includes at least one hetero atom, and includes cyclic amines such as morpholino, piperidino, pyrrolidino, and the like, and cyclic ethers/thio-ethers, such as tetrahydrofuran, tetrahydropyran, tetrahydrothiophene, and the like. Additionally, the heterocyclic group can be substituted.

The term "aryl" refers to and includes both single-ring aromatic hydrocarbyl groups and polycyclic aromatic ring systems. The polycyclic rings may have two or more rings in which two carbons are common to two adjoining rings (the rings are "fused") wherein at least one of the rings is an aromatic hydrocarbyl group, e.g., the other rings can be cycloalkyls, cycloalkenyls, aryl, heterocycles, and/or heteroaryls. Preferred aryl groups are those containing six to thirty carbon atoms, preferably six to twenty carbon atoms, more preferably six to twelve carbon atoms. Especially preferred is an aryl group having six carbons, ten carbons or twelve carbons. Suitable aryl groups include phenyl, biphenyl, triphenyl, triphenylene, tetraphenylene, naphthalene, anthracene, phenalene, phenanthrene, fluorene, pyrene, chrysene, perylene, and azulene, preferably phenyl, biphenyl, triphenyl, triphenylene, fluorene, and naphthalene. Additionally, the aryl group can be substituted.

The term "heteroaryl" refers to and includes both single-ring aromatic groups and polycyclic aromatic ring systems that include at least one heteroatom. The heteroatoms include, but are not limited to O, S, N, P, B, Si, and Se. In many instances, O, S, or N are the preferred heteroatoms. Hetero-single ring aromatic systems are preferably single rings with 5 or 6 ring atoms, and the ring can have from one to six heteroatoms. The hetero-polycyclic ring systems can have two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. The hetero-polycyclic aromatic ring systems can have from one to six heteroatoms per ring of the polycyclic aromatic ring system. Preferred heteroaryl groups are those containing three to thirty carbon atoms, preferably three to twenty carbon atoms, more preferably three to twelve carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof. Additionally, the heteroaryl group can be substituted.

Of the aryl and heteroaryl groups listed above, the groups of triphenylene, naphthalene, anthracene, dibenzothiophene, dibenzofuran, dibenzoselenophene, carbazole, indolocarbazole, imidazole, pyridine, pyrazine, pyrimidine, triazine, and benzimidazole, and the respective aza-analogs of each thereof are of particular interest.

The terms alkyl, cycloalkyl, heteroalkyl, heterocycloalkyl, alkenyl, cycloalkenyl, heteroalkenyl, alkynyl, aralkyl, heterocyclic group, aryl, and heteroaryl, as used herein, are independently unsubstituted, or independently substituted, with one or more general substituents.

In many instances, the general substituents are selected from the group consisting of deuterium, halogen, alkyl, cycloalkyl, heteroalkyl, heterocycloalkyl, arylalkyl, alkoxy, aryloxy, amino, silyl, boryl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof.

In some instances, the preferred general substituents are selected from the group consisting of deuterium, fluorine, alkyl, cycloalkyl, heteroalkyl, alkoxy, aryloxy, amino, silyl, boryl, alkenyl, cycloalkenyl, heteroalkenyl, aryl, heteroaryl, nitrile, isonitrile, sulfanyl, and combinations thereof.

In some instances, the preferred general substituents are selected from the group consisting of deuterium, fluorine, alkyl, cycloalkyl, alkoxy, aryloxy, amino, silyl, boryl, aryl, heteroaryl, sulfanyl, and combinations thereof.

In yet other instances, the more preferred general substituents are selected from the group consisting of deuterium, fluorine, alkyl, cycloalkyl, aryl, heteroaryl, and combinations thereof.

The terms "substituted" and "substitution" refer to a substituent other than H that is bonded to the relevant position, e.g., a carbon or nitrogen. For example, when $R^1$ represents mono-substitution, then one $R^1$ must be other than H (i.e., a substitution). Similarly, when $R^1$ represents di-substitution, then two of $R^1$ must be other than H. Similarly, when $R^1$ represents zero or no substitution, $R^1$, for example, can be a hydrogen for available valencies of ring atoms, as in carbon atoms for benzene and the nitrogen atom in pyrrole, or simply represents nothing for ring atoms with fully filled valencies, e.g., the nitrogen atom in pyridine. The maximum number of substitutions possible in a ring structure will depend on the total number of available valencies in the ring atoms.

As used herein, "combinations thereof" indicates that one or more members of the applicable list are combined to form a known or chemically stable arrangement that one of ordinary skill in the art can envision from the applicable list. For example, an alkyl and deuterium can be combined to form a partial or fully deuterated alkyl group; a halogen and alkyl can be combined to form a halogenated alkyl substituent; and a halogen, alkyl, and aryl can be combined to form a halogenated arylalkyl. In one instance, the term substitution includes a combination of two to four of the listed groups. In another instance, the term substitution includes a combination of two to three groups. In yet another instance, the term substitution includes a combination of two groups. Preferred combinations of substituent groups are those that contain up to fifty atoms that are not hydrogen or deuterium, or those which include up to forty atoms that are not hydrogen or deuterium, or those that include up to thirty atoms that are not hydrogen or deuterium. In many instances, a preferred combination of substituent groups will include up to twenty atoms that are not hydrogen or deuterium.

The "aza" designation in the fragments described herein, i.e. aza-dibenzofuran, aza-dibenzothiophene, etc. means that one or more of the C—H groups in the respective aromatic ring can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

As used herein, "deuterium" refers to an isotope of hydrogen. Deuterated compounds can be readily prepared using methods known in the art. For example, U.S. Pat. No. 8,557,400, Patent Pub. No. WO 2006/095951, and U.S. Pat. Application Pub. No. US 2011/0037057, which are hereby incorporated by reference in their entireties, describe the making of deuterium-substituted organometallic complexes. Further reference is made to Ming Yan, et al., *Tetrahedron* 2015, 71, 1425-30 and Atzrodt et al., *Angew. Chem. Int. Ed.* (*Reviews*) 2007, 46, 7744-65, which are incorporated by reference in their entireties, describe the deuteration of the methylene hydrogens in benzyl amines and efficient pathways to replace aromatic ring hydrogens with deuterium, respectively.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

In some instance, a pair of adjacent substituents can be optionally joined or fused into a ring. The preferred ring is a five, six, or seven-membered carbocyclic or heterocyclic ring, includes both instances where the portion of the ring formed by the pair of substituents is saturated and where the portion of the ring formed by the pair of substituents is unsaturated. As used herein, "adjacent" means that the two substituents involved can be on the same ring next to each other, or on two neighboring rings having the two closest available substitutable positions, such as 2,2' positions in a biphenyl, or 1,8 position in a naphthalene, as long as they can form a stable fused ring system.

B. The Compounds of the Present Disclosure

In one aspect, the present disclosure provides a compound comprising a structure of Formula I

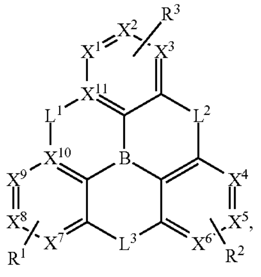

wherein:

$X^1$-$X^9$ are each independently C or N;

no more than two N atoms are bonded to one another in the same ring;

$L^2$, and $L^3$ are each independently selected from the group consisting of O, S, Se, and SiRR';

$L^1$ is not always present but when present, $L^1$ is selected from the group consisting of O, S, Se, and SiRR' and $X^{10}$ and $X^{11}$ are both C;

$L^2$ and $L^3$ are always present;

$R^1$, $R^2$, and $R^3$ each independently represent zero, mono, or up to a maximum allowed substitution to its associated ring;

each of $R^1$, $R^2$, and $R^3$ is independently a hydrogen or a substituent comprising a structure selected from the group consisting of Formulae II, III, IV, V, VI, VII, and VIII, deuterium, halogen, alkyl, cycloalkyl, heteroalkyl, heterocycloalkyl, arylalkyl, alkoxy, aryloxy, amino, silyl, boryl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof, with at least one of $R^1$, $R^2$, and $R^3$ comprising a structure selected from the group consisting of Formulae II, III, IV, V, VI, VII, and VIII, and their aza variants; wherein, Formulae II, III, IV, V, VI, VII, and VIII are defined as follows:

Formula II

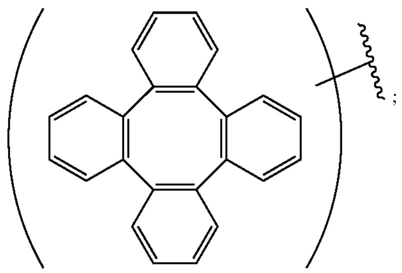

Formula III

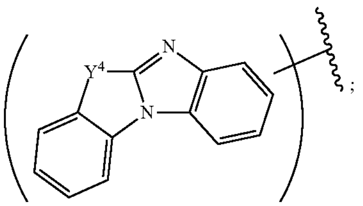

Formula IV

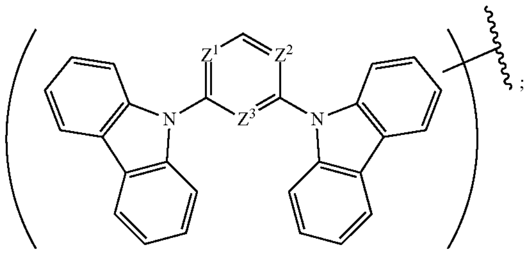

-continued

Formula V

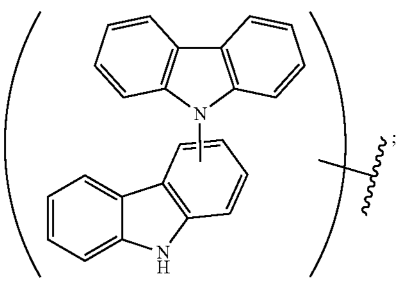

Formula VI

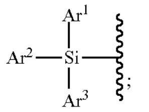

Formula VII

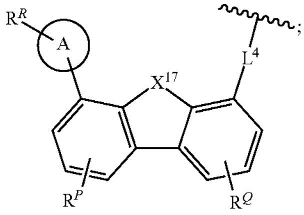

; and

Formula VIII

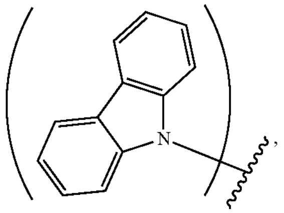

with the proviso that when $X^1$-$X^{11}$ are all C, at least one of $R^1$, $R^2$, and $R^3$ comprises a group selected from the group consisting of Formulas II, III, IV, V, VI, and VII;

when one of $R^1$, $R^2$, and $R^3$ comprises Formula VII, the compound has exactly one B atom;

when $X^1$-$X^{11}$ are all C and Formulas II, III, IV, V, VI, and VIII are absent, $R^2$ comprises Formula VII;

$Z^1$, $Z^2$, and $Z^3$ are each independently C or N;

at least one of $Z^1$, $Z^2$, and $Z^3$ is N;

$Ar^1$, $Ar^2$, and $Ar^3$ are each a substituted or unsubstituted aryl or heteroaryl ring:

$Y^4$ is selected from the group consisting of O, Se, BR, N, NR, CRR', SiRR', and GeRR';

$L^4$ is a direct bond or an aromatic group comprising one or more fused or unfused aromatic rings which can be further substituted;

$R^R$, $R^P$ and $R^Q$ each independently represents zero, mono, or up to a maximum allowed substitution to its associated ring;

each of $R^R$, $R^P$ and $R^Q$ is independently a hydrogen or a general substituent as described herein;

$X^{17}$ is selected from the group consisting of O, S, Se, $NR^4$, $CR^4R^5$, and $SiR^4R^5$;

each of R, $R^1$, $R^P$, $R^Q$, $R^4$ and $R^5$ is independently a hydrogen or a substituent selected from the group consisting of deuterium, halogen, alkyl, cycloalkyl, heteroalkyl, heterocycloalkyl, boryl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof;

$R^R$ is a hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof; ring A is a monocyclic or multicyclic ring system comprising one or more fused 5-membered or 6-membered carbocyclic or heterocyclic rings, when one of $R^1$, $R^2$, and $R^3$ comprises Formula VII, the compound consists of exactly one B atom;

any two of $R^1$, $R^2$, $R^3$, $R^4$, $R^5$, R, R', $R^P$, $R^Q$, and $R^R$ can be joined or fused to forma ring, with the proviso that none of $Ar^1$, $Ar^2$, and $Ar^3$ is joined to form a ring; and that the compound is not the following structure:

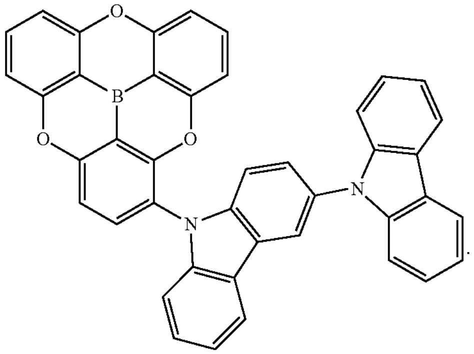 [SMILES: c1cc2c3c(c1)Oc1ccc(-n4c5ccccc5c5cc(-n6c7ccccc7c7ccccc76)ccc54)c4c1B3c1c(cccc1O4)O2]

In the above embodiment, each of Formulae II, III, IV, and V may be further substituted with general substituents as described herein. In the above embodiment, each of Formulae II, III, IV, and V may be attached to the structure of Formula I through any suitable atom of each formula, which is further illustrated by a pair of broad parentheses "( )".

In some embodiments, each of R, R', $R^1$, $R^2$, $R^3$ $R^4$, $R^5$, $R^P$ and $R^Q$ may be independently a hydrogen or a substituent selected from the group consisting of deuterium, fluorine, alkyl, cycloalkyl, heteroalkyl, alkoxy, aryloxy, amino, silyl, boryl, alkenyl, cycloalkenyl, heteroalkenyl, aryl, heteroaryl, nitrile, isonitrile, sulfanyl, and combinations thereof.

In some embodiments, $R^R$ is a hydrogen or a substituent selected from the group consisting of deuterium, fluorine, alkyl, cycloalkyl, heteroalkyl, alkoxy, aryloxy, amino, silyl, alkenyl, cycloalkenyl, heteroalkenyl, aryl, heteroaryl, nitrile, isonitrile, sulfanyl, and combinations thereof.

In some embodiments, $L^1$ may not be present. In some embodiments, $L^1$ may be present. In some embodiments, $L^1$ may be present, and $L^1$, $L^2$, and $L^3$ may each be independently selected from the group consisting of O, S, BR, and NR. In some embodiments, $L^1$ may be present, and $L^1$, $L^2$, and $L^3$ may each be O. In some embodiments, $L^2$ and $L^3$ may each be O. In some embodiments, $L^1$ may be present, and $L^1$, $L^2$, and $L^3$ may each be NR. In some embodiments, $L^2$ and $L^3$ may each be NR. In some embodiments, $L^1$ may be present, and $L^1$, $L^2$, and $L^3$ may each be S. In some embodiments, $L^2$ and $L^3$ may each be S. In some embodiments, $L^1$ may be present, and one of $L^1$, $L^2$, and $L^3$ may be S and the remainder may be O. In some embodiments, $L^1$ may be present, and two of $L^1$, $L^2$, and $L^3$ may be S and the remainder may be O. In some embodiments, $L^1$ may be present, and one of $L^1$, $L^2$, and $L^3$ may be NR and the remainder may be O. In some embodiments, $L^1$ may be present, and two of $L^1$, $L^2$, and $L^3$ may be NR and the remainder may be O. In some embodiments, $L^1$ may be present, and one of $L^1$, $L^2$, and $L^3$ may be NR and the remainder may be S. In some embodiments, $L^1$ may be present, and two of $L^1$, $L^2$, and $L^3$ may be NR and the remainder may be S. In some embodiments, one of $L^2$ and $L^3$ may be O and the other may be S. In some embodiments, one of $L^2$ and $L^3$ may be O and the other may be NR. In some embodiments, one of $L^2$ and $L^3$ may be S and the other may be NR.

In some embodiments, $L^4$ is a direct bond. In some embodiments, $L^4$ is phenyl or biphenyl.

In some embodiments, A is a benzene ring. In some embodiments, A is a 5-membered heterocyclic ring.

In some embodiments, R may be a 6-membered aromatic ring.

In some embodiments, exactly one of $R^1$, $R^2$, and $R^3$ may comprise a chemical structure selected from the group consisting of Formulae II, III, IV, V, VI, VII, VIII, and their aza variants.

In some embodiments, exactly one of $R^1$, $R^2$, and $R^3$ may comprise a chemical structure of Formula VI and one other chemical structure selected from the group consisting of Formulas II, III, IV, V, VII, VIII, and their aza variants.

In some embodiments, $R^R$ is an aryl or heteroaryl group. In some embodiments, $R^P$ and $R^Q$ is each hydrogen or deuterium.

In some embodiments, at least one of $R^P$ or $R^Q$ is aryl or heteroaryl. In some embodiments, $X^{17}$ is selected from the group consisting of O, S, Se, and $NR^4$.

In some embodiments, the compound may comprise a structure of Formula IX

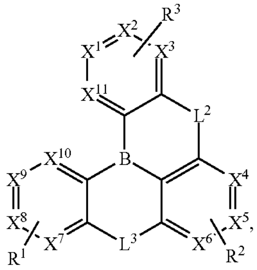

wherein all the variables are defined the same as before for Formula I. In some embodiments, at least one of $X^1$—$X^{11}$ may be N. In some embodiments, $X^{10}$ and $X^{11}$ may not be joined together by a one atom linker. In some embodiments, at least one of $R^1$, $R^2$, and $R^3$ may comprise a structure of Formula VIII. In some embodiments, substituents $R^1$ and $R^3$ may be joined to form a macrocyclic ring.

In some embodiments, the compound may comprise two structures of Formula I.

In some embodiments, the compound may comprise a structure selected from the group consisting of the structures shown in LIST 1 below:

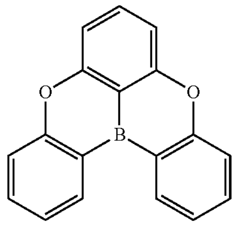
,
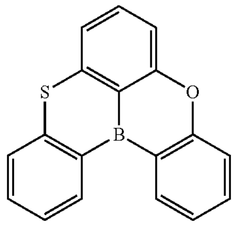
,
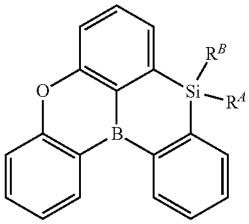
,
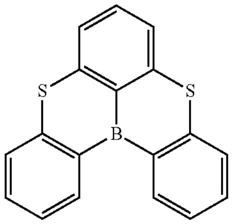
,
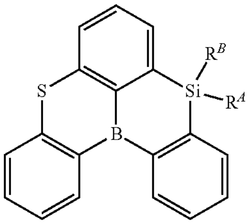
,
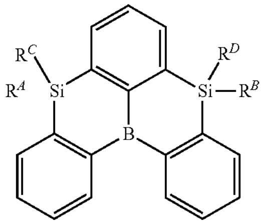
,
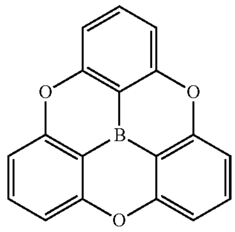
,
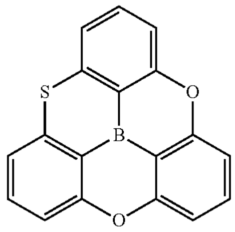
,
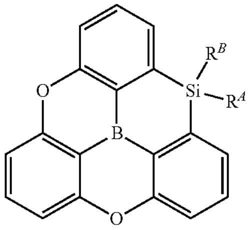
,
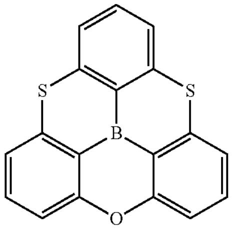
,
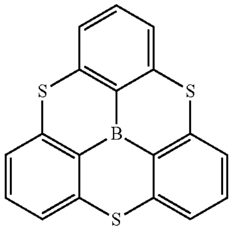
,
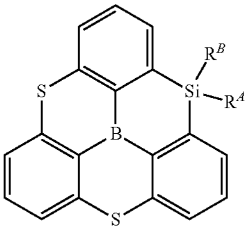
,
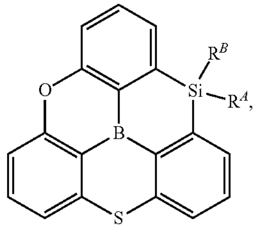
,
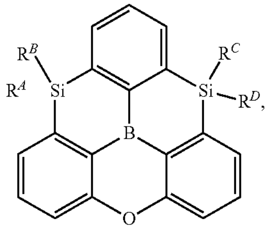
, -continued

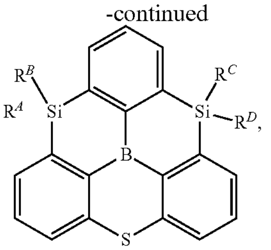

and

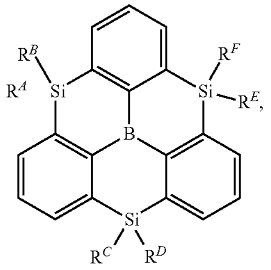

wherein each of $R^A$, $R^B$, $R^C$, and $R^F$ is independently a hydrogen or a substituent selected from the group consisting of deuterium, fluorine, alkyl, cycloalkyl, heteroalkyl, alkoxy, aryloxy, amino, silyl, boryl, alkenyl, cycloalkenyl, heteroalkenyl, aryl, heteroaryl, nitrile, isonitrile, sulfanyl, and combinations thereof.

In some embodiments, the compound may comprise a structure selected from the group consisting of:

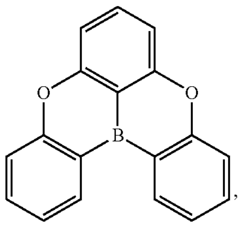

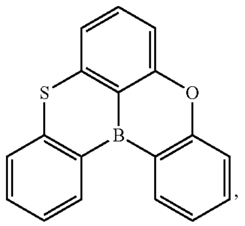

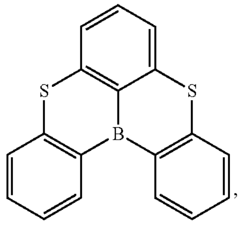

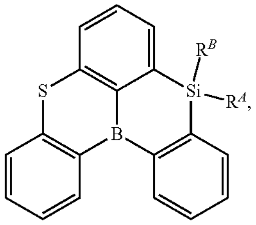

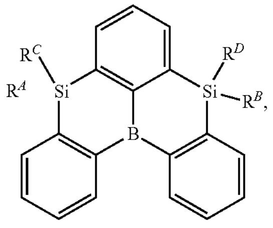

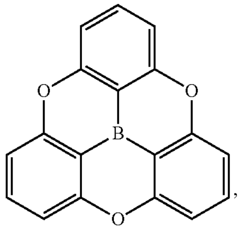

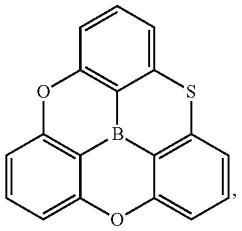

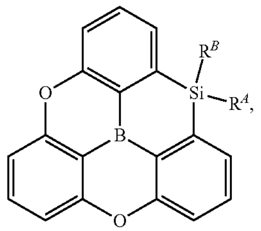

-continued

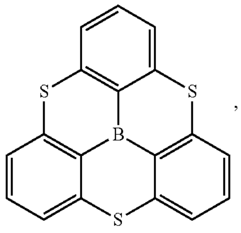

, and

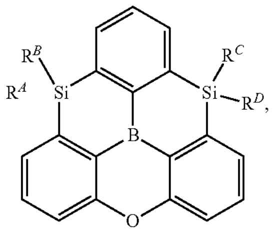

wherein all the variables are the same as previously defined.

In some embodiments, the compound may be selected from the group consisting of the structures shown in LIST 2 below:

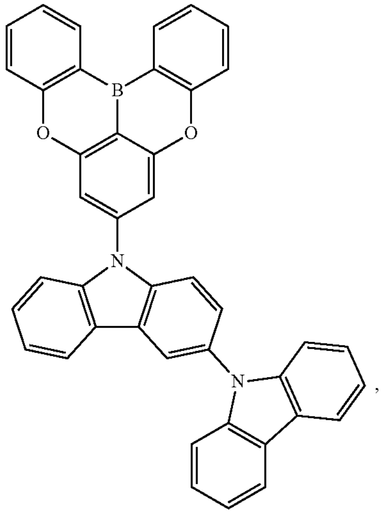

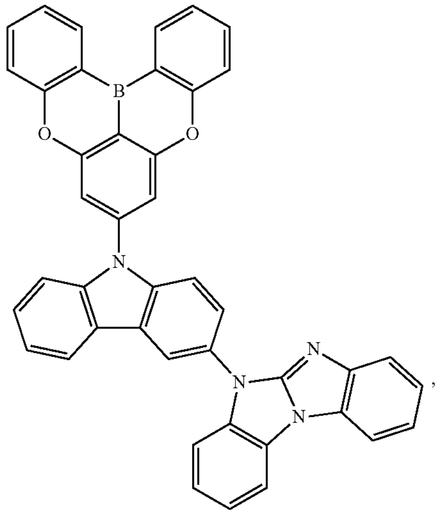

-continued
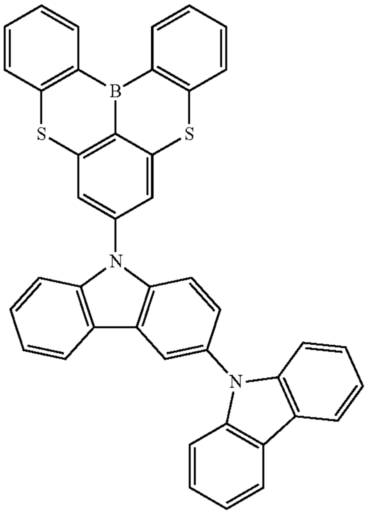
,
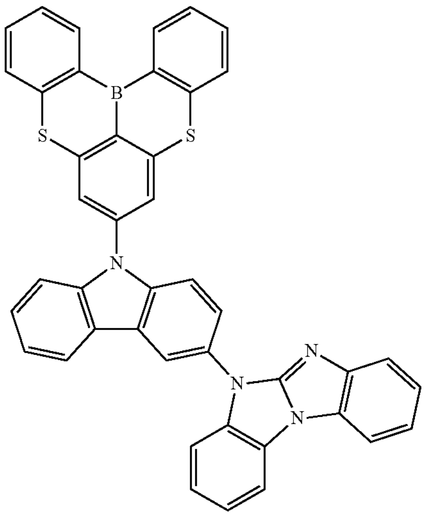
,
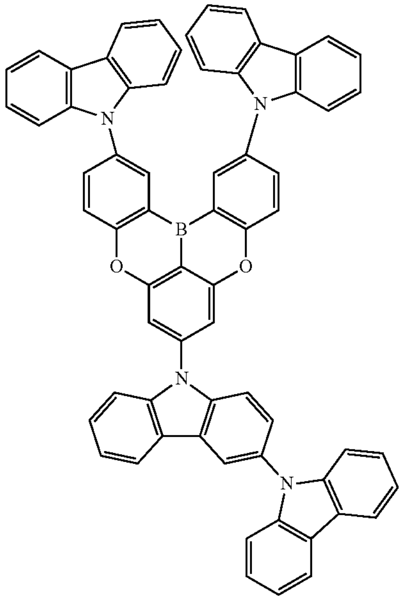
,
-continued
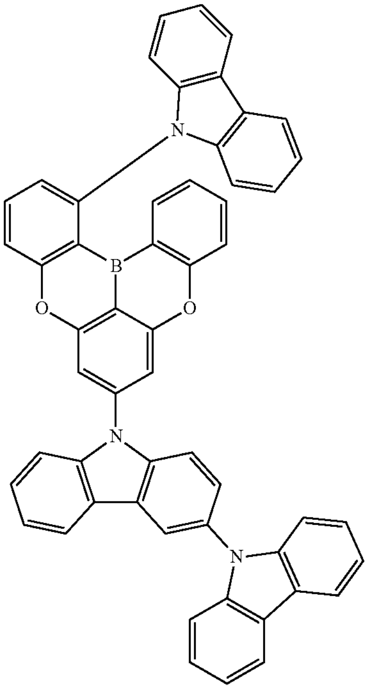
,
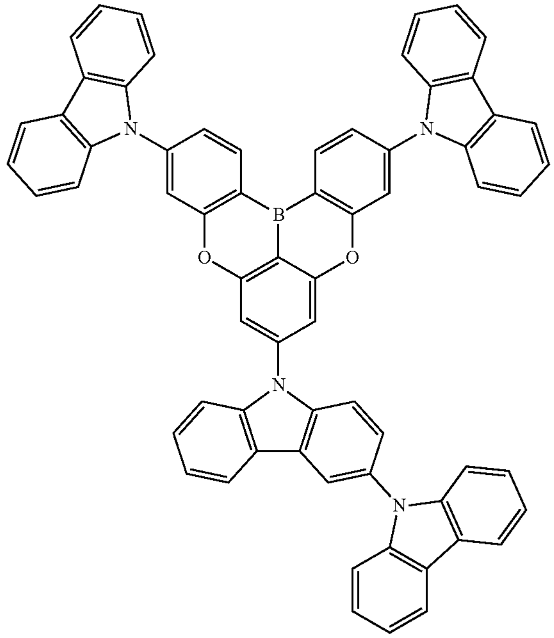
,
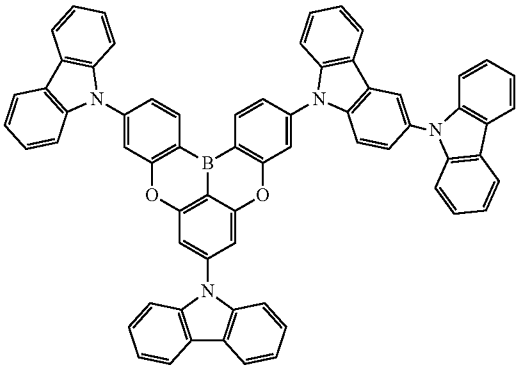
, -continued
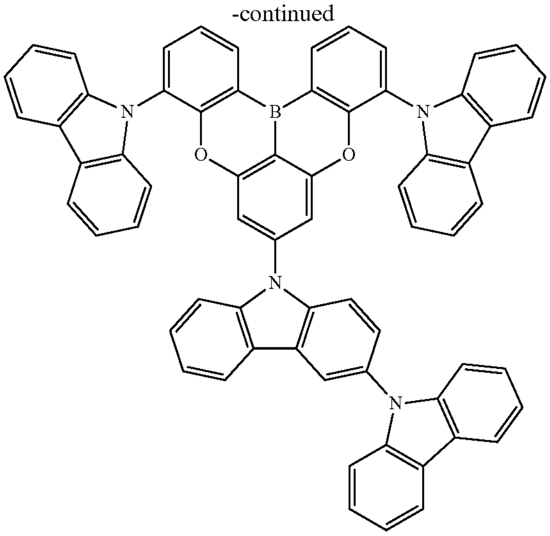
,
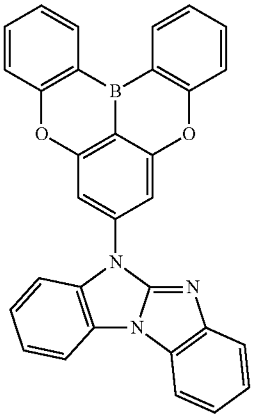
,
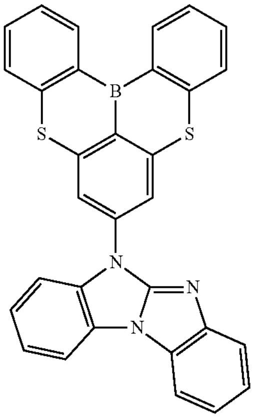
,
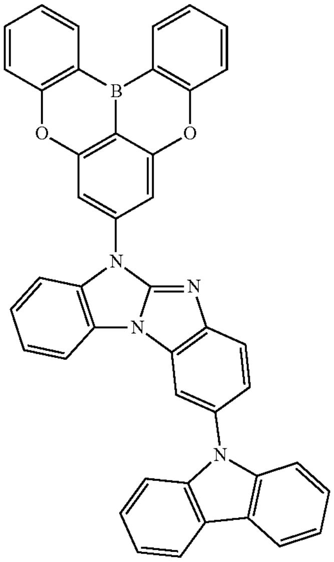
,
-continued
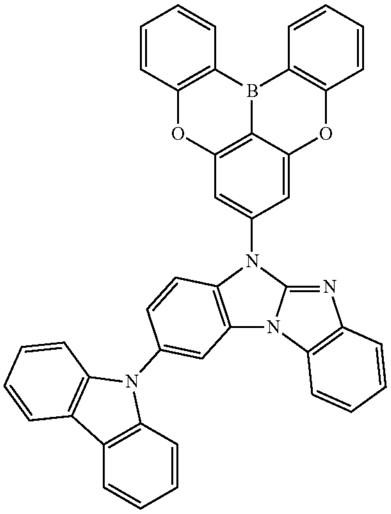
,
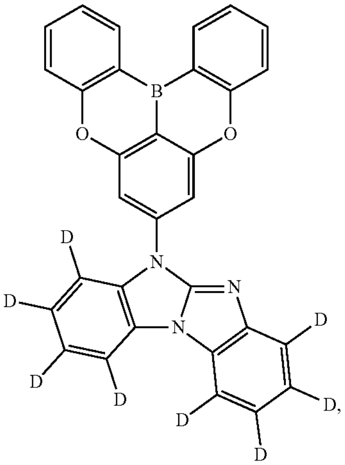
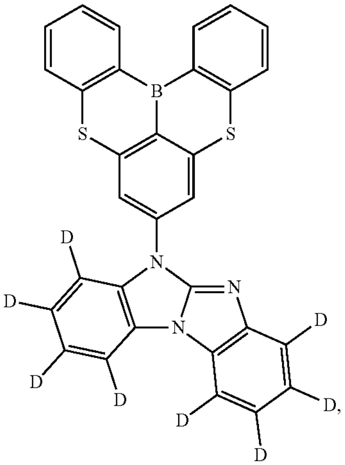

-continued
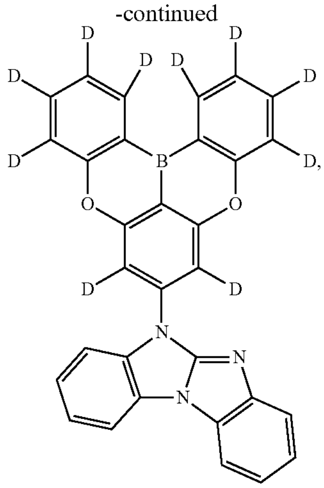
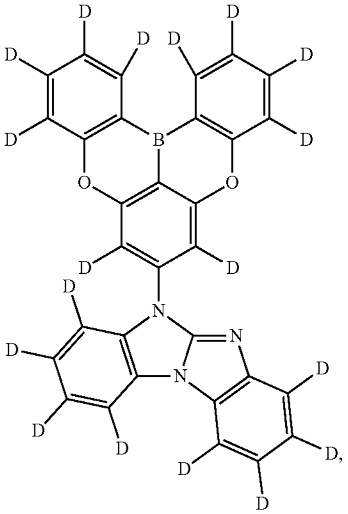
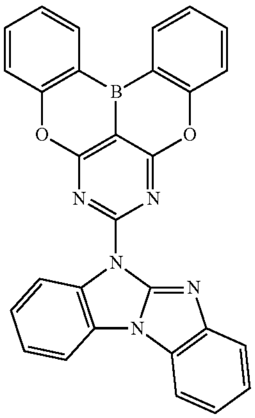
,
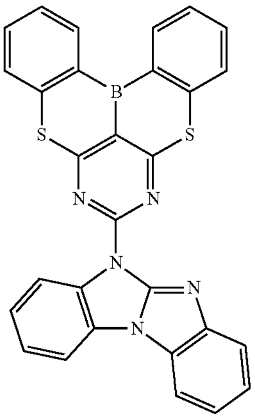
,
-continued
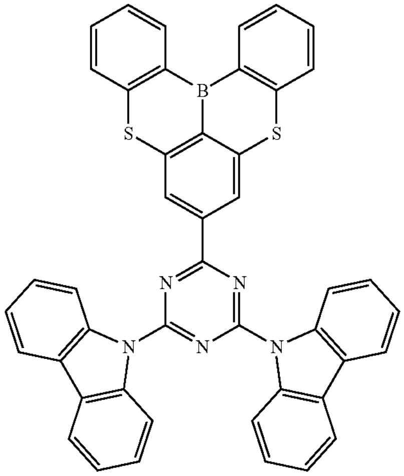
,
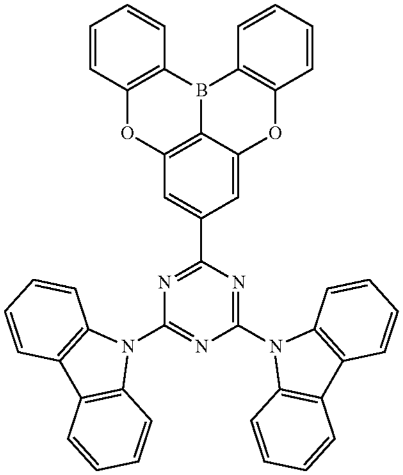
,
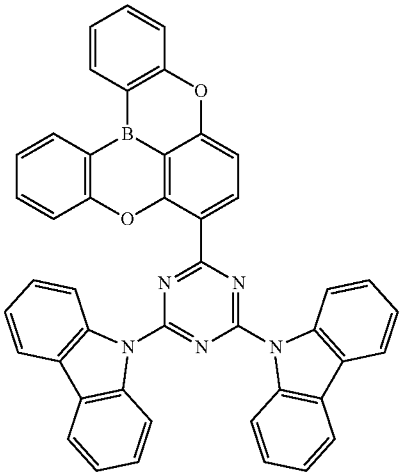
, -continued
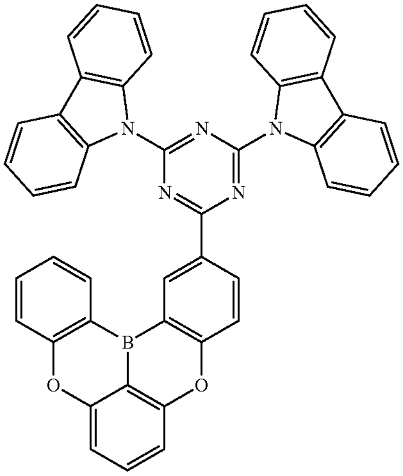
,
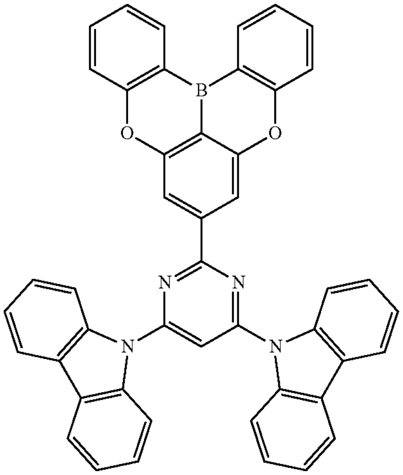
,
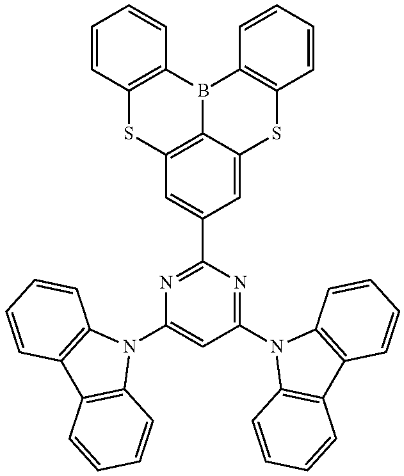
-continued
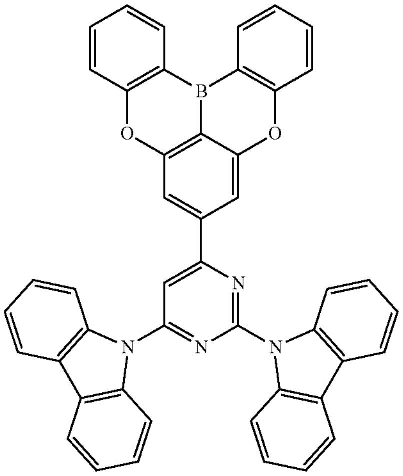
,
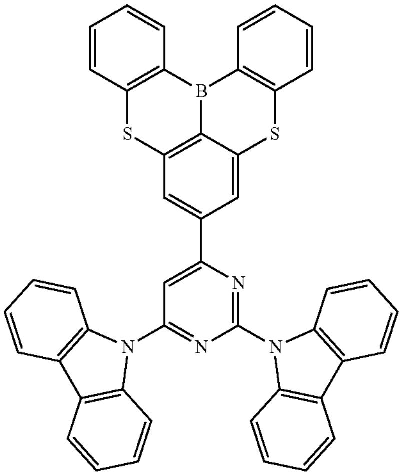
,
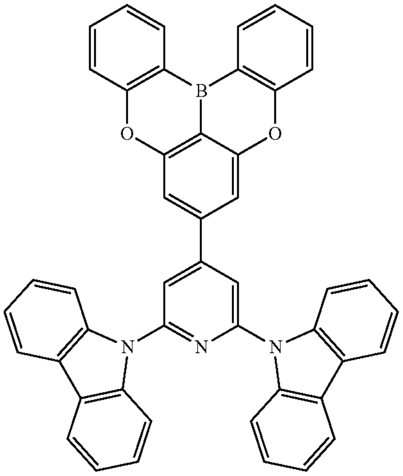
, -continued
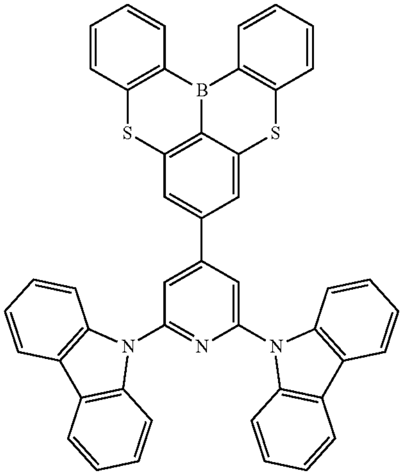
,
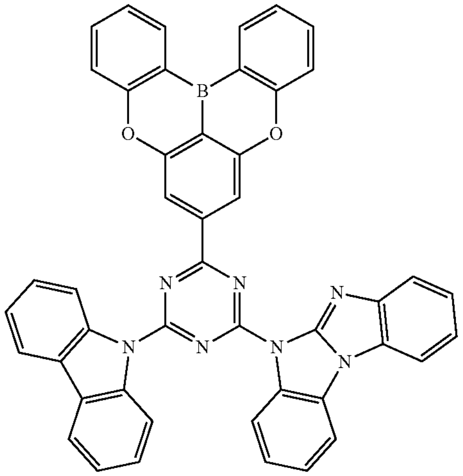
,
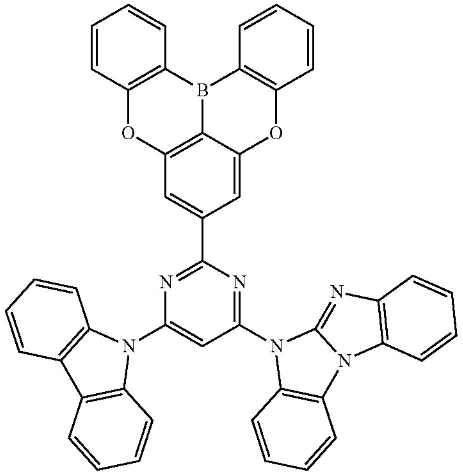
,
-continued
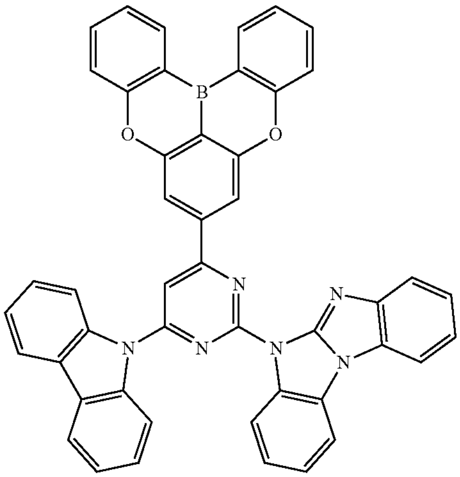
,
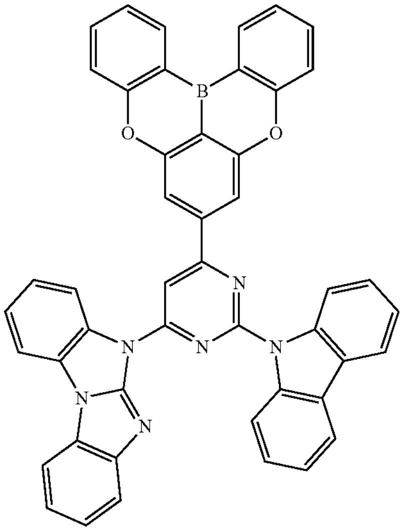
,
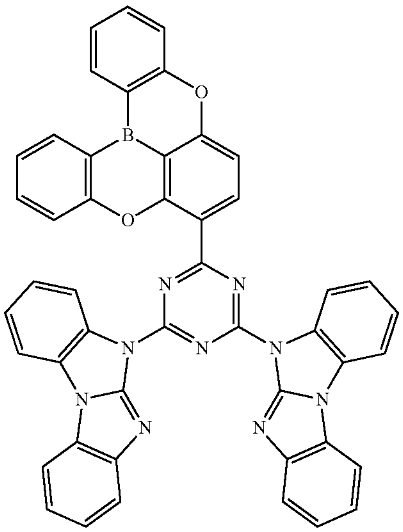
, -continued
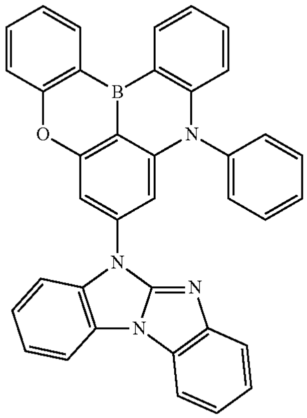
,
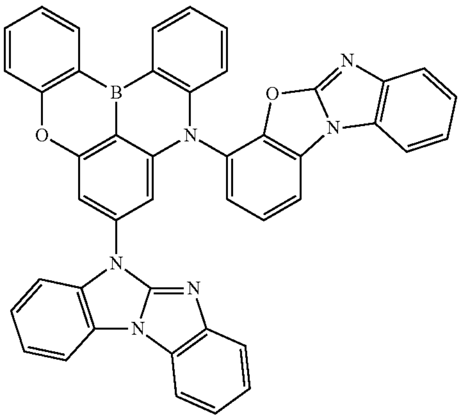
,
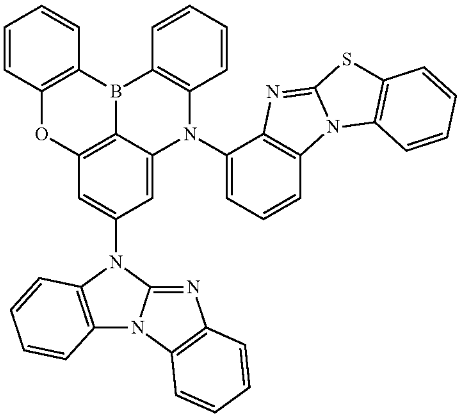
,
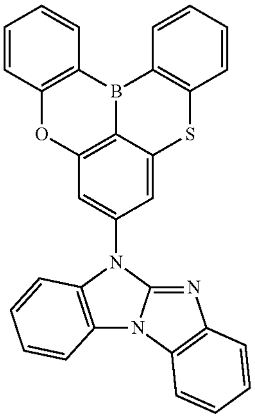
,
-continued
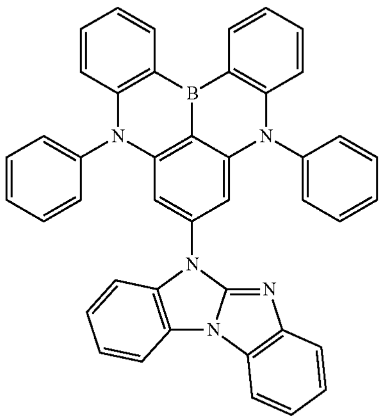
,
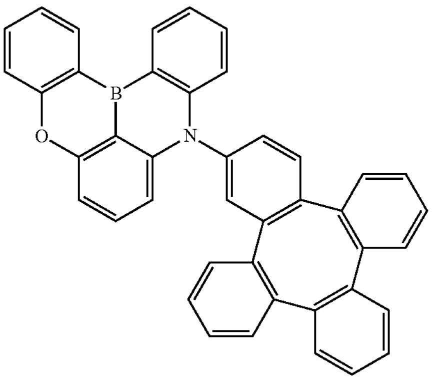
,
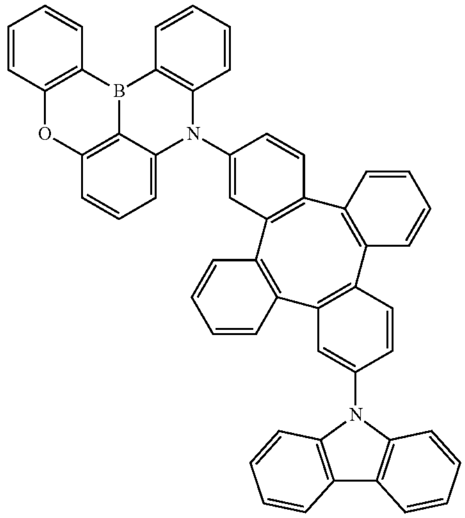
,
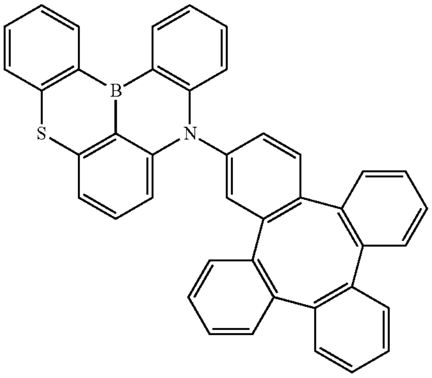
, -continued
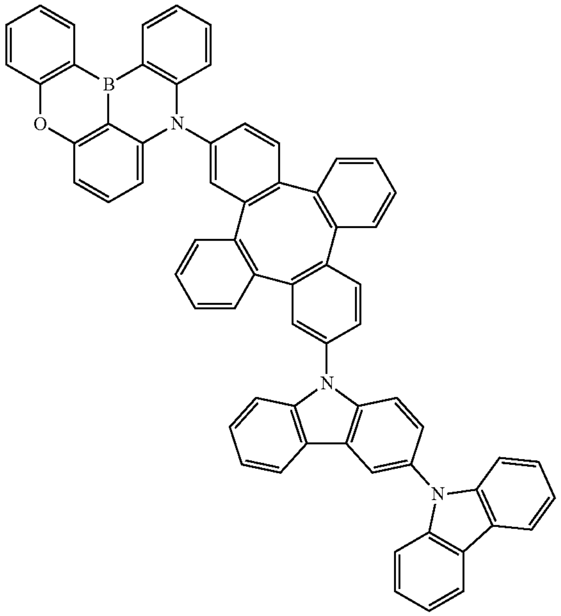
,
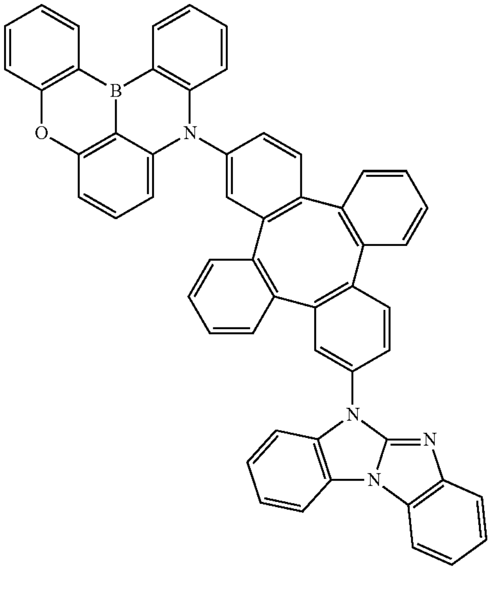
,
-continued
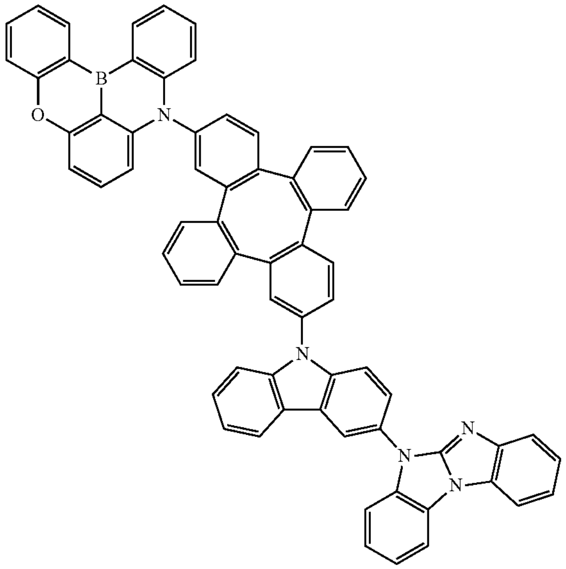
,
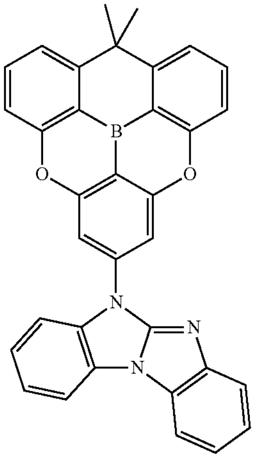
,
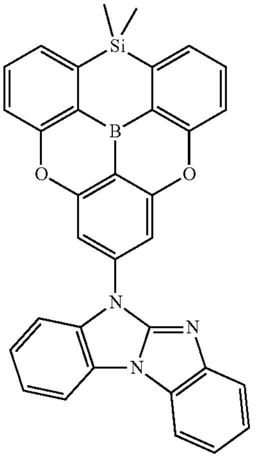
,
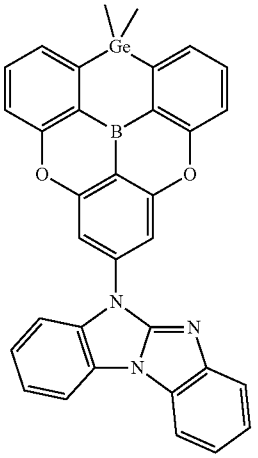
,
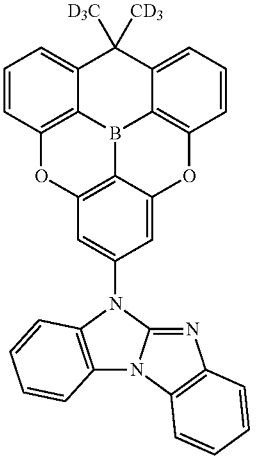
, -continued
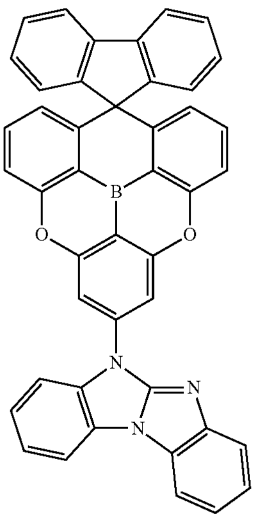
,
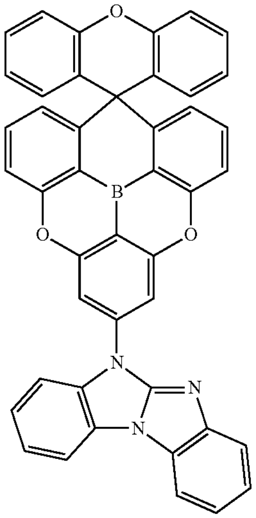
,
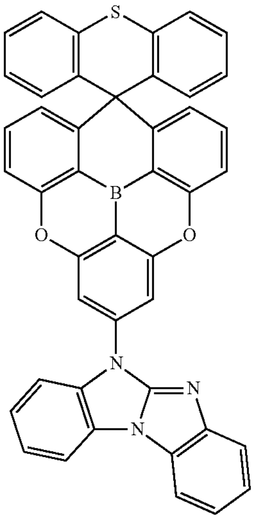
,
-continued
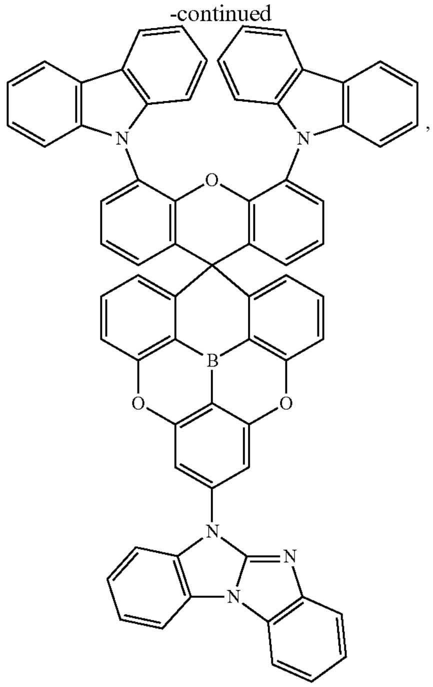
,
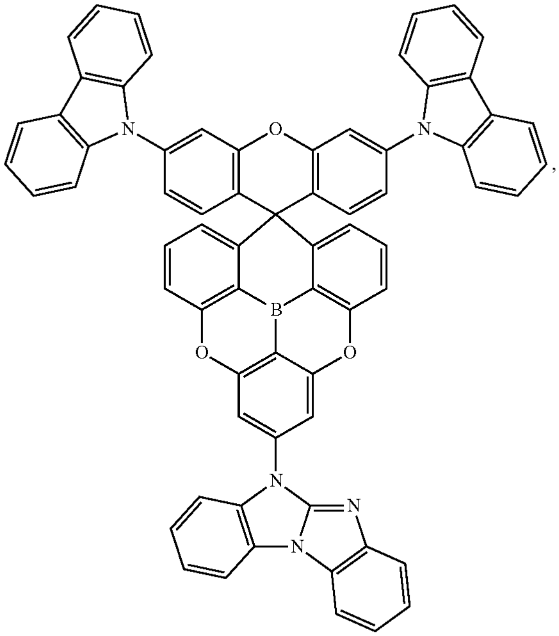
,
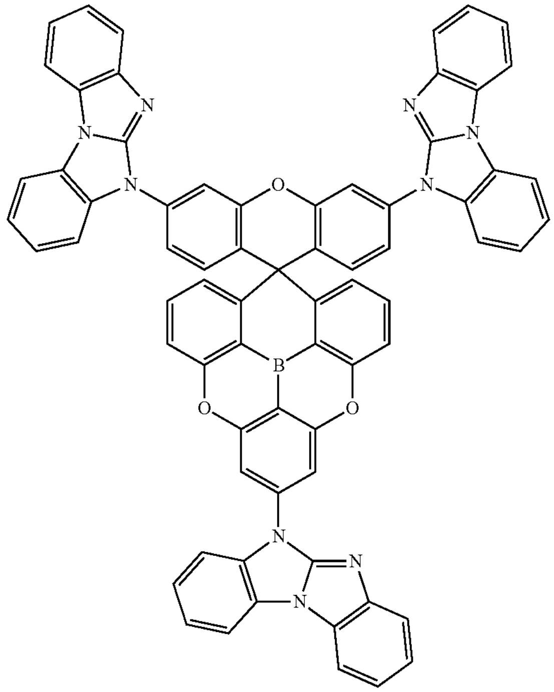
, -continued
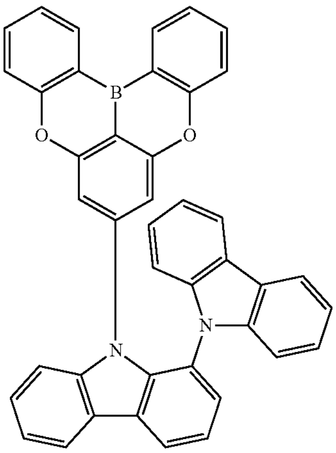
,
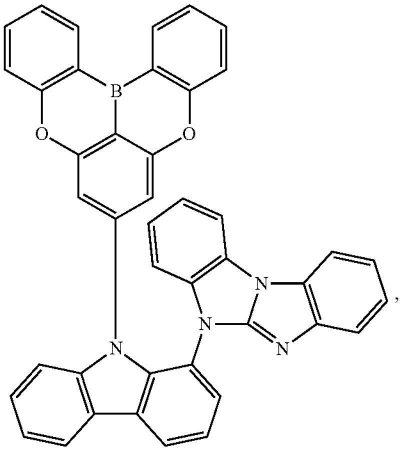
,
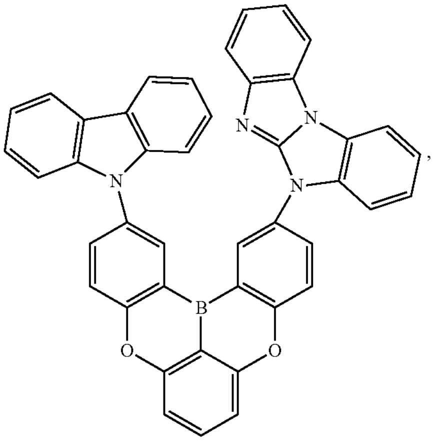
,
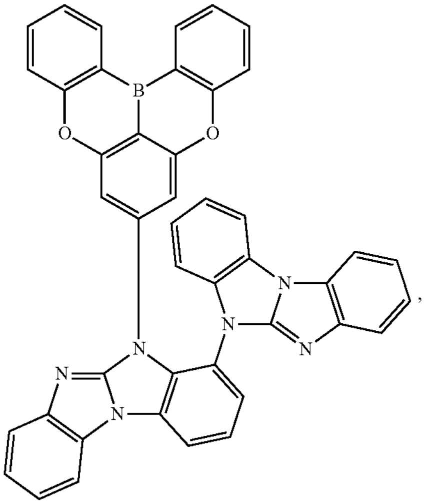
,
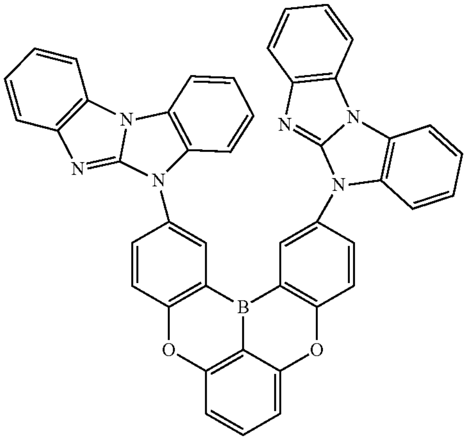
,
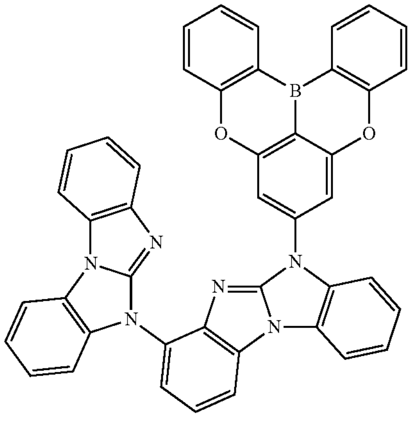
,
-continued -continued
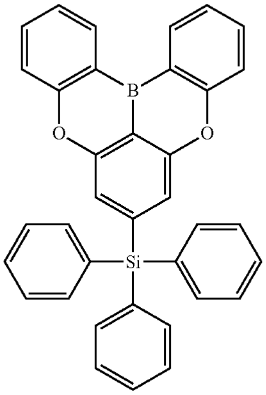
,
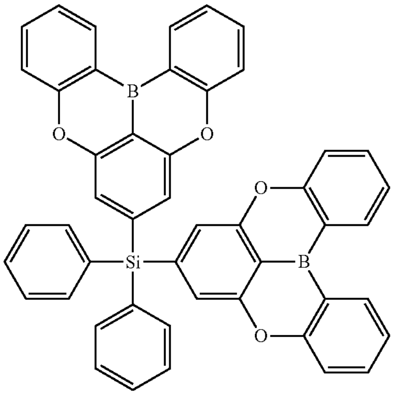
,
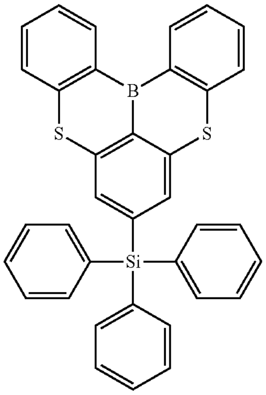
,
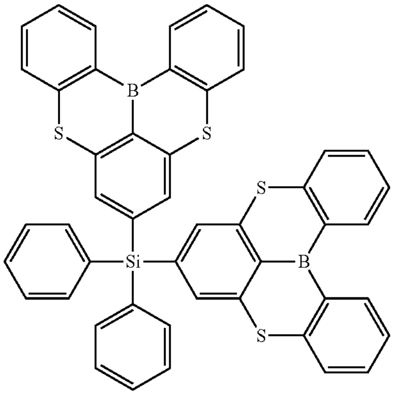
,
-continued
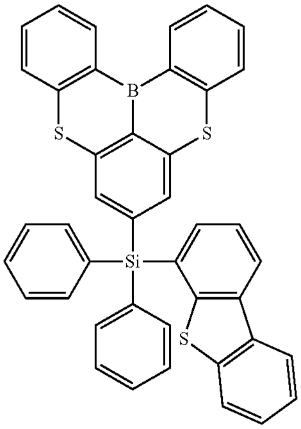
,
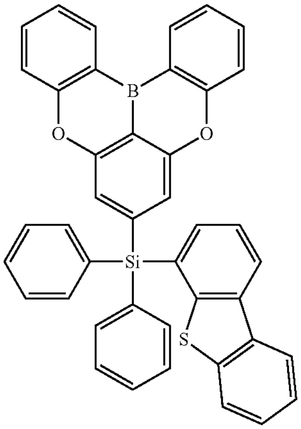
,
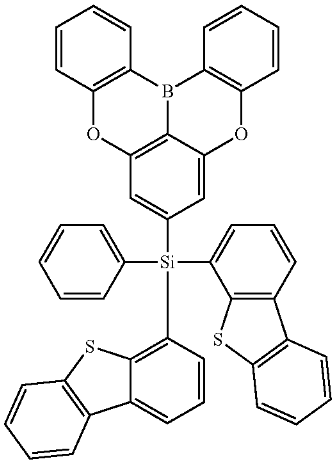
, -continued
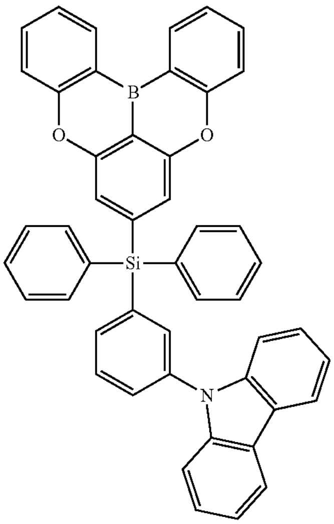
,
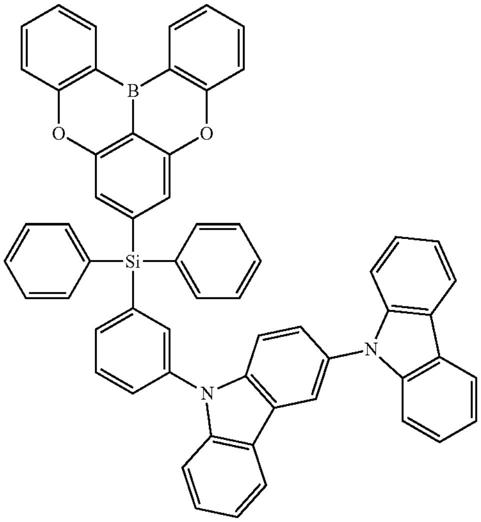
,
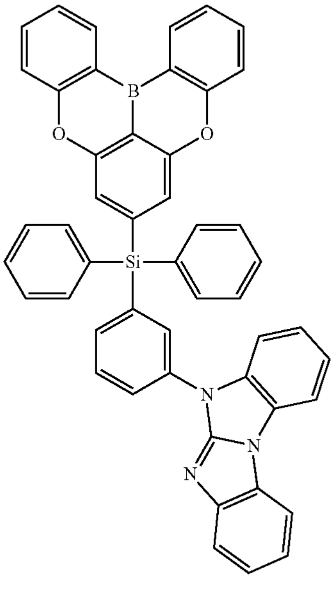
,
-continued
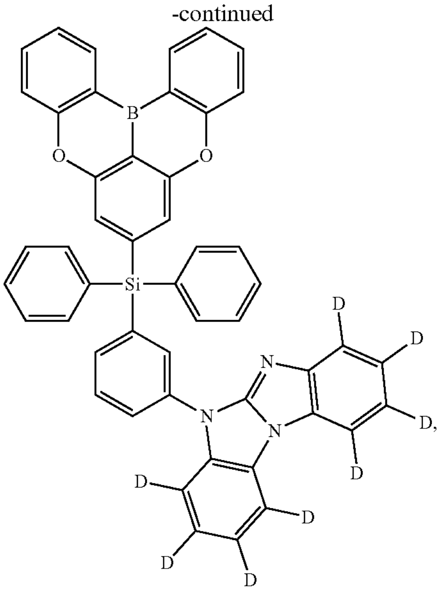
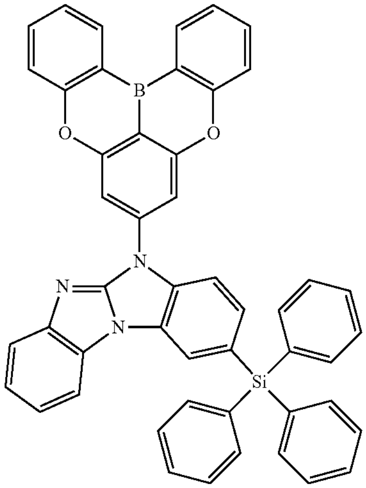
,
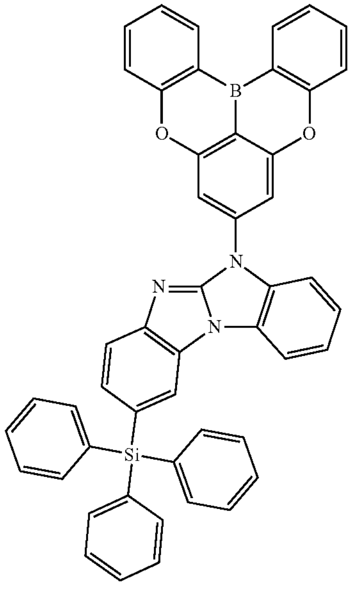
,

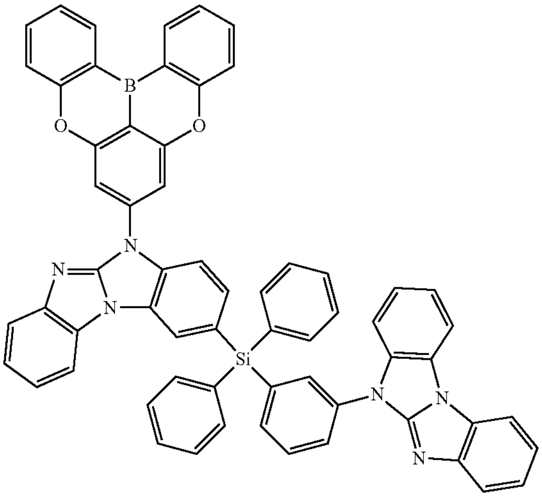
,
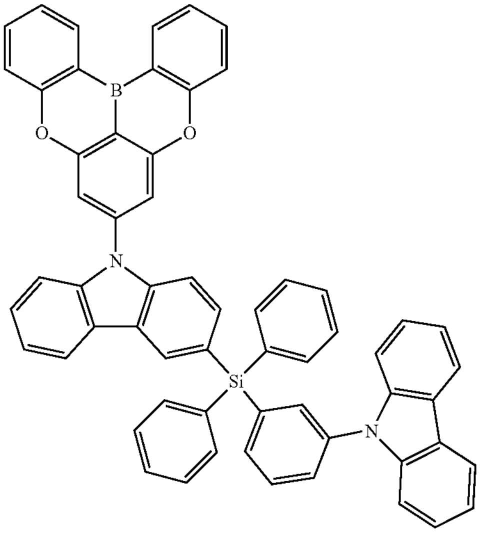
,
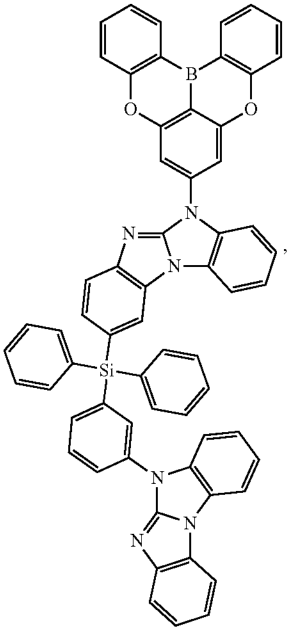
,
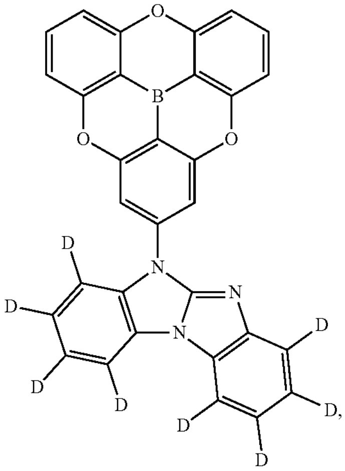
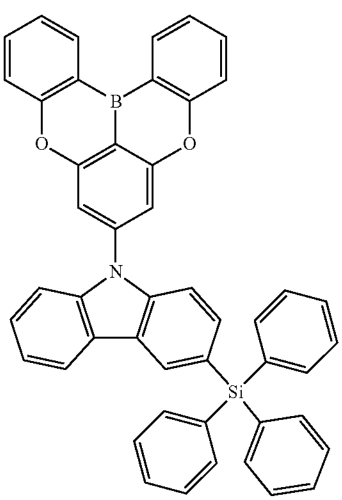
,
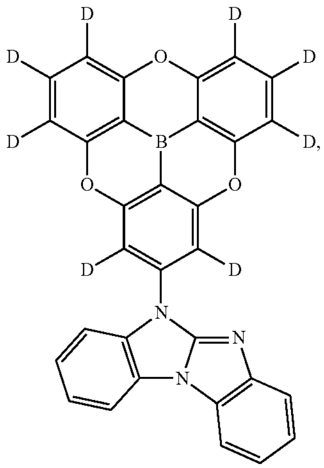

-continued
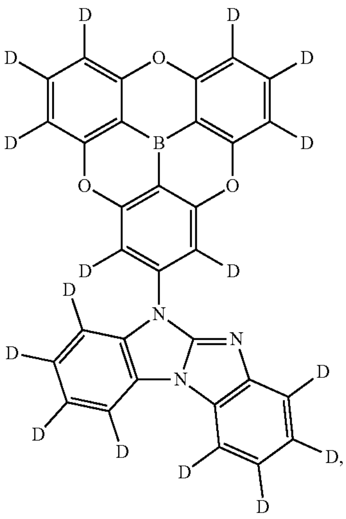
,
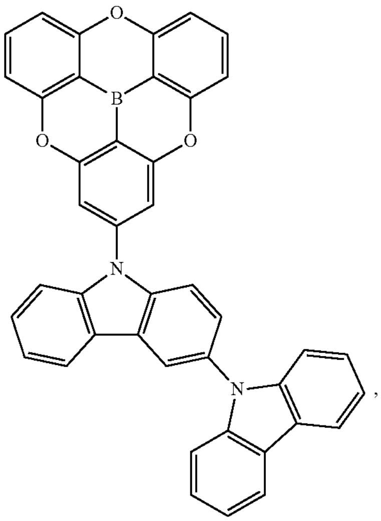
,
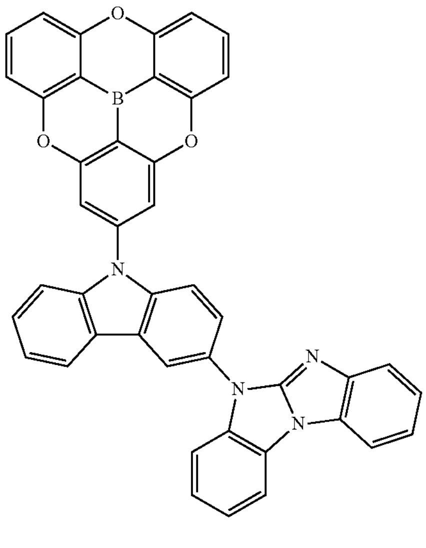
,
-continued
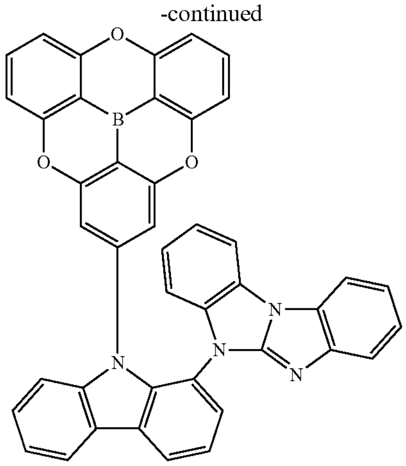
,
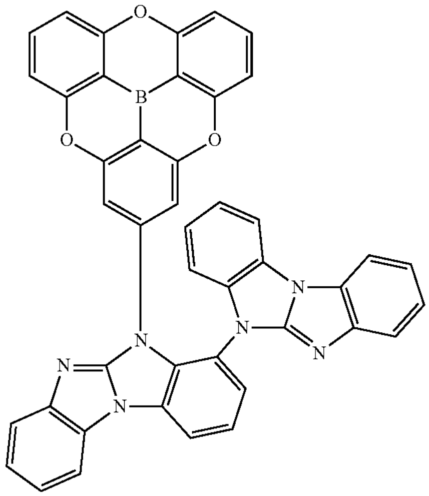
,
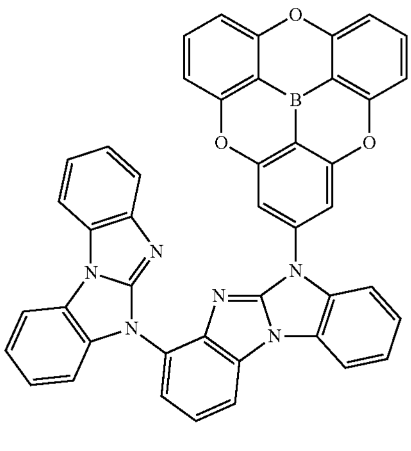
, -continued
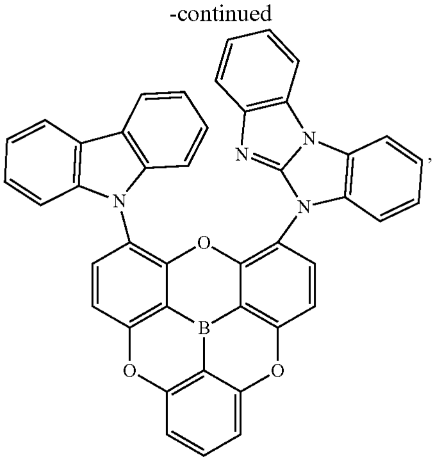
,
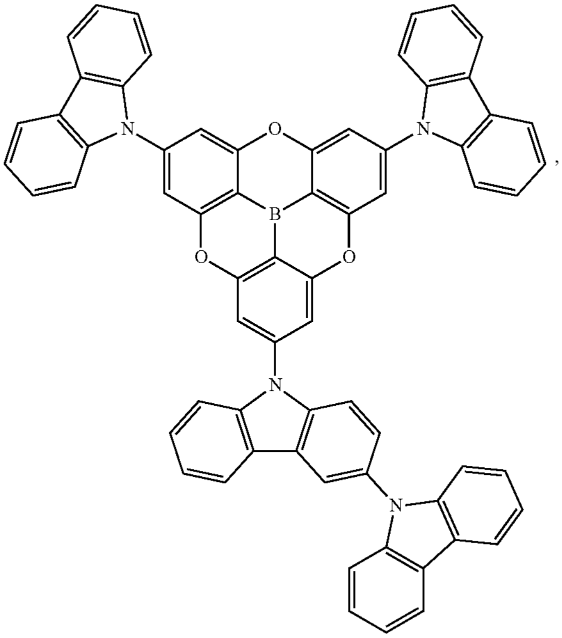
,
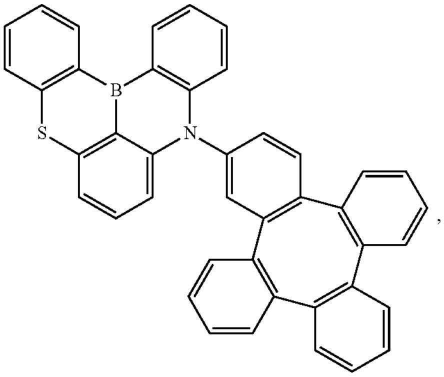
,
-continued
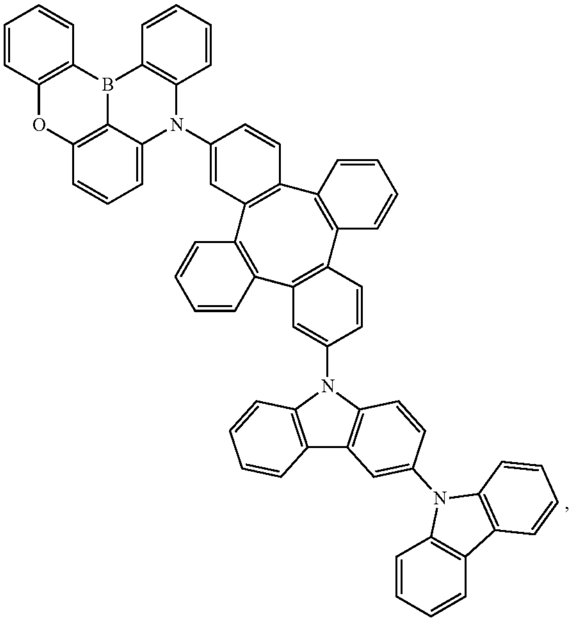
,
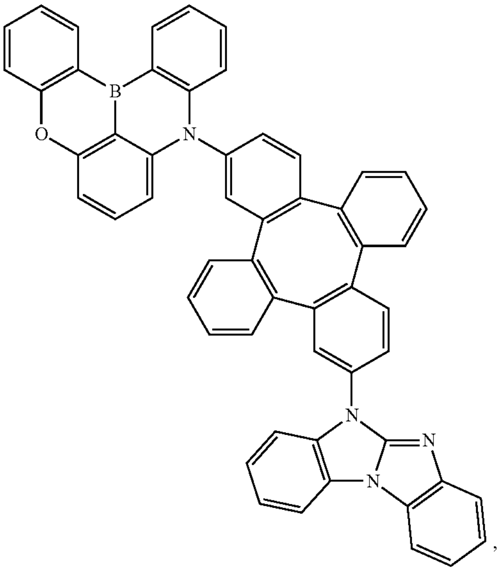
, -continued
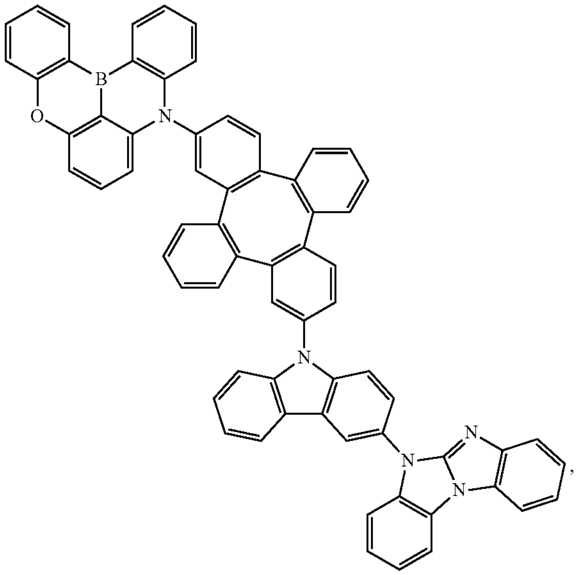
,
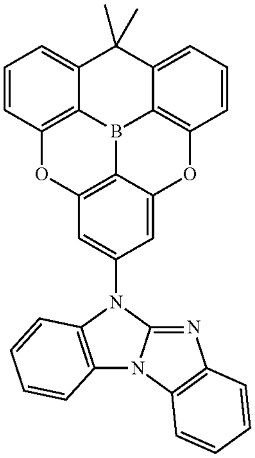
,
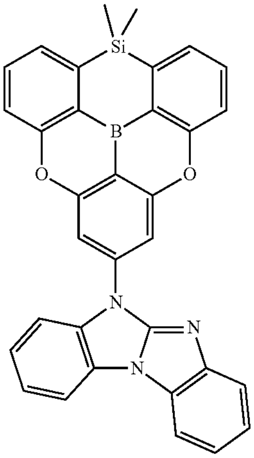
,
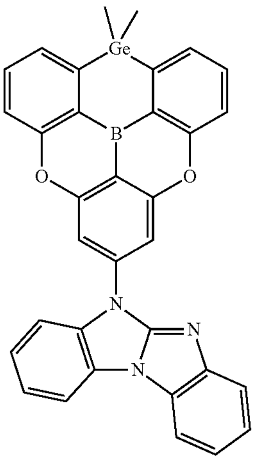
,
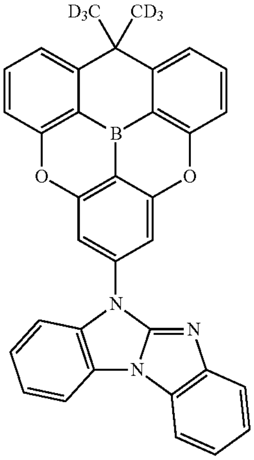
,
-continued
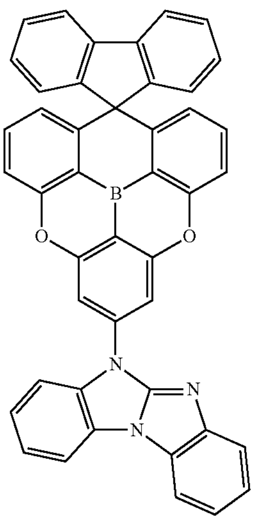
,
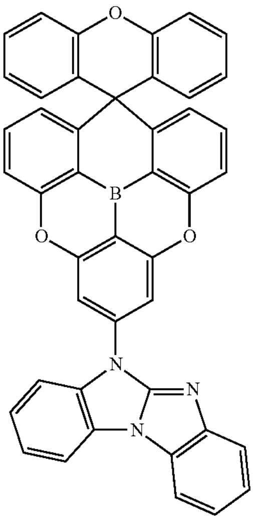
,
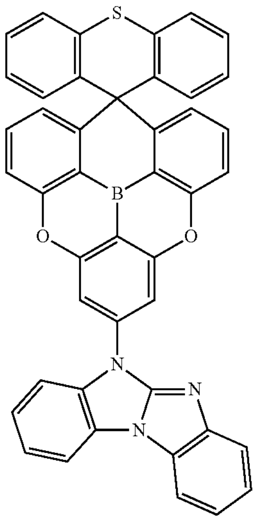
,
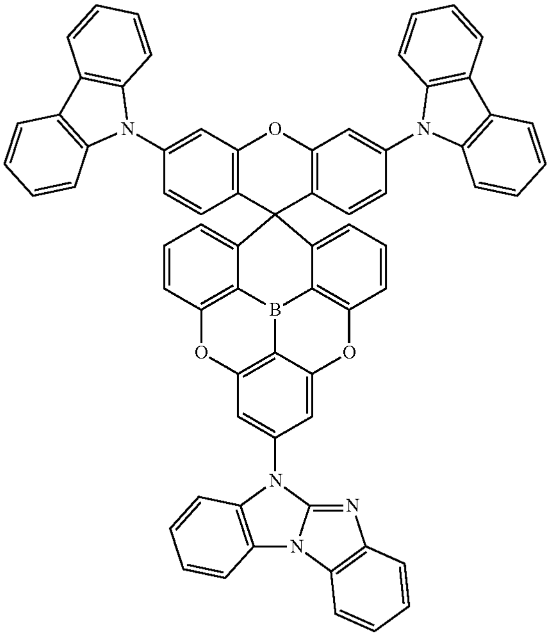
, -continued
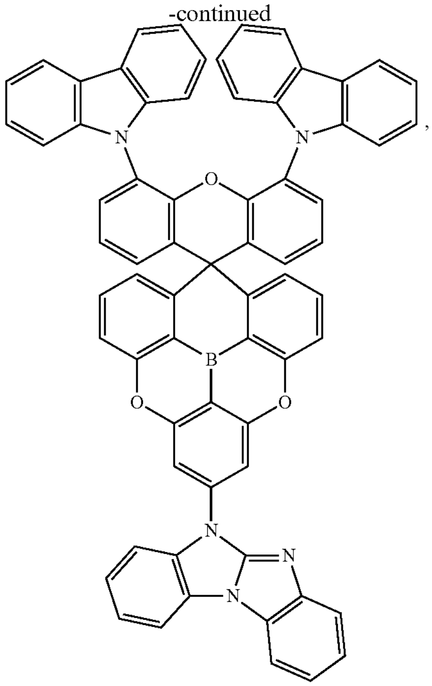
,
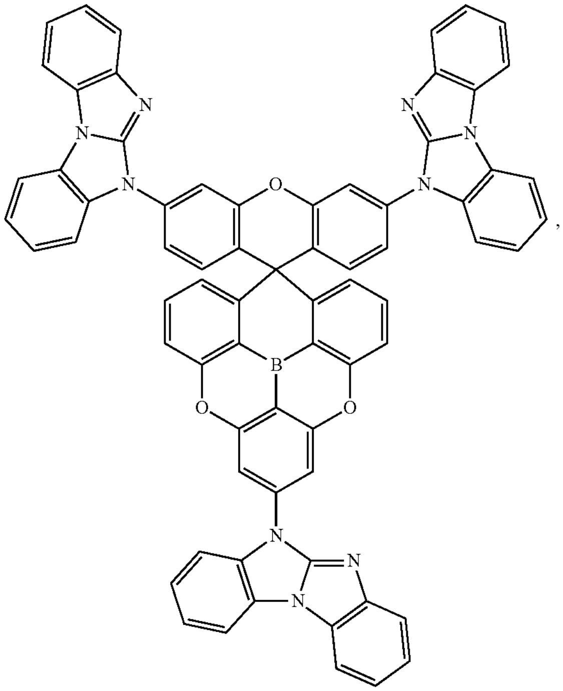 [SMILES: c1cc2c3c(c1)C1(c4ccc(-n5c6ccccc6n6c7ccccc7nc56)cc4Oc4cc(-n5c6ccccc6n6c7ccccc7nc56)ccc41)c1cccc4c1B3c1c(cc(-n3c5ccccc5n5c6ccccc6nc35)cc1O4)O2]
,
-continued
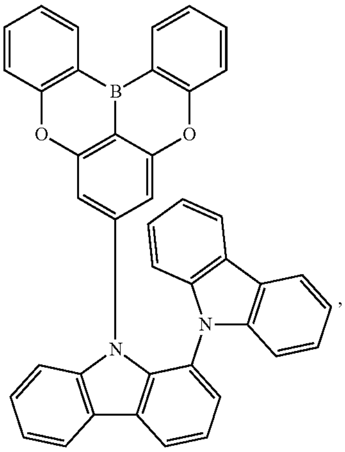
,
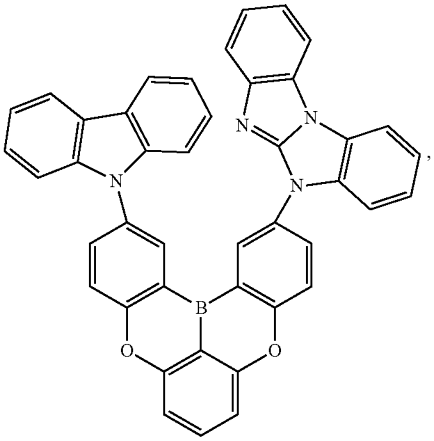
,
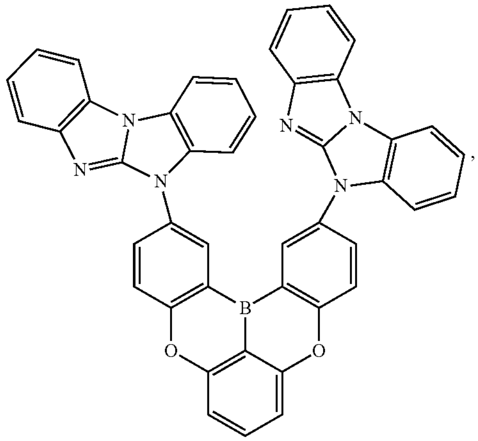
, -continued
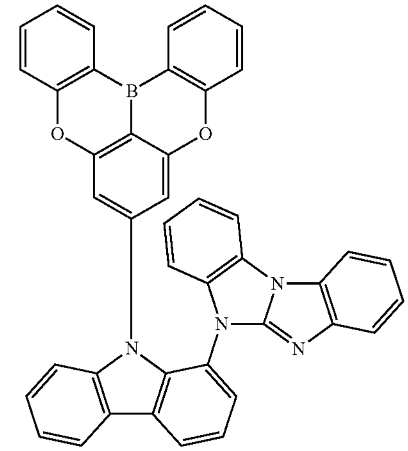
,
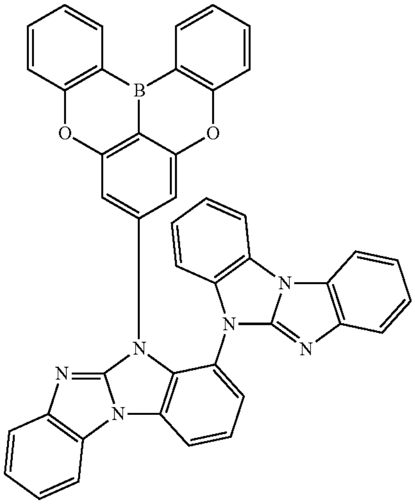
,
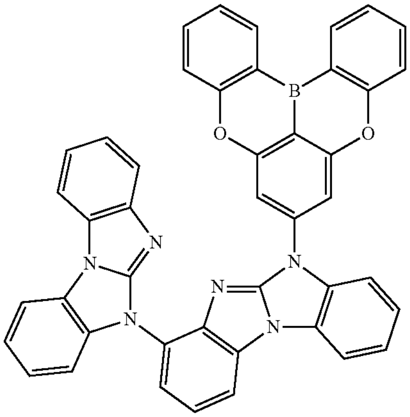
,
-continued
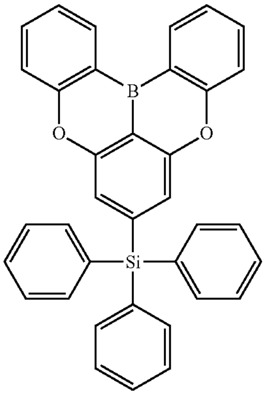
,
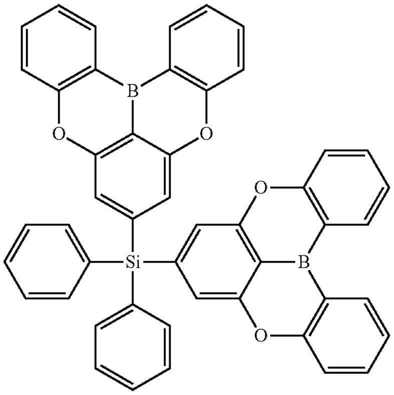
,
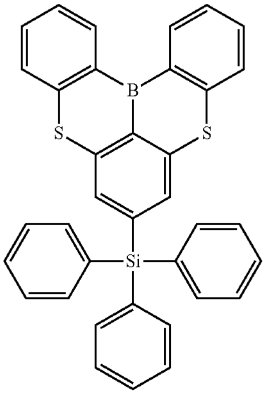
,
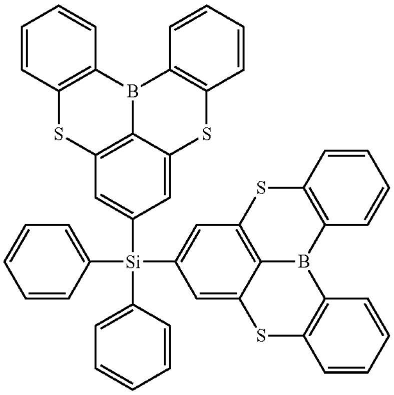
, -continued
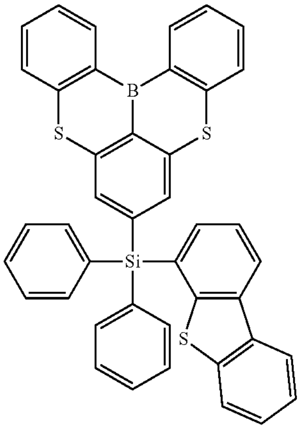
,
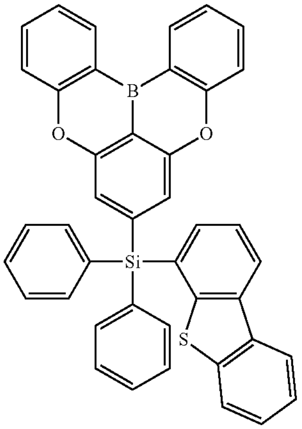
,
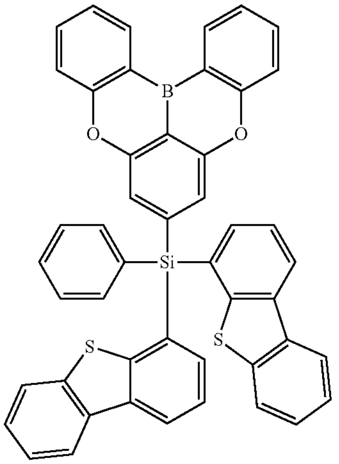
,
-continued
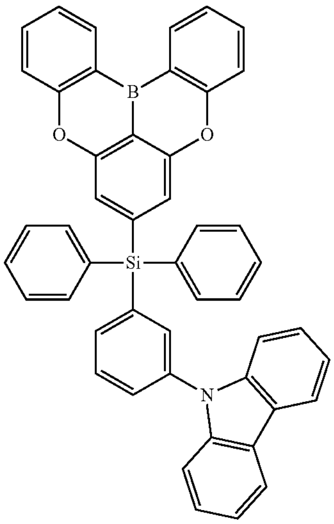
,
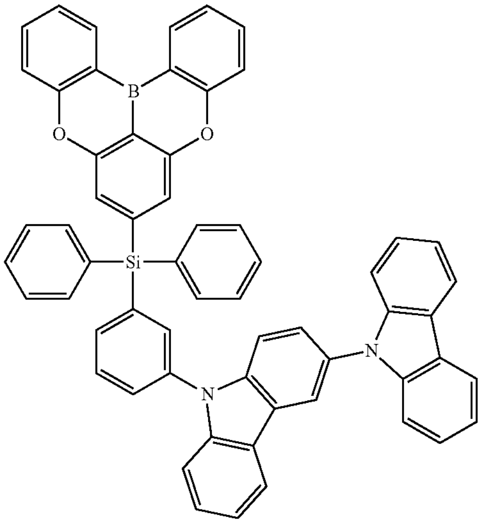
,
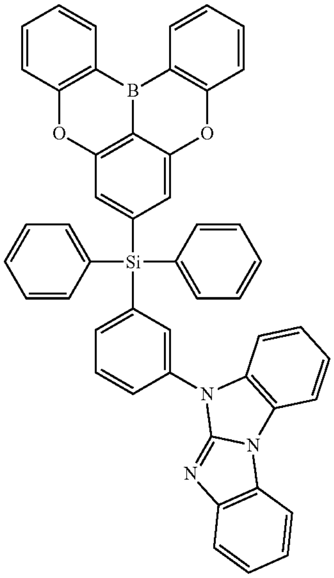
, -continued
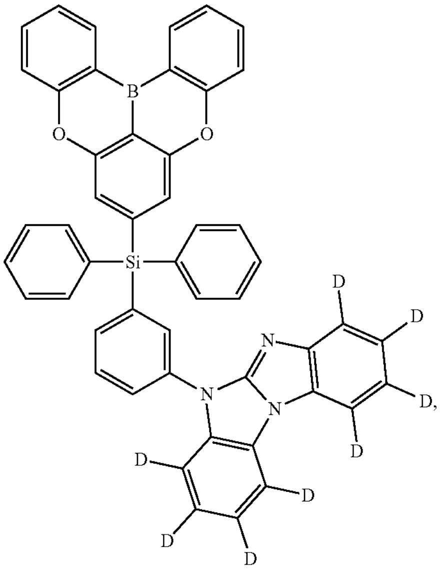
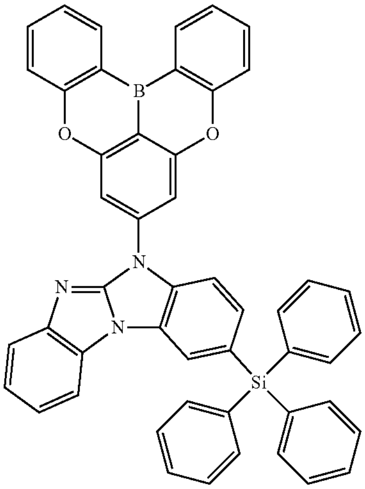
,
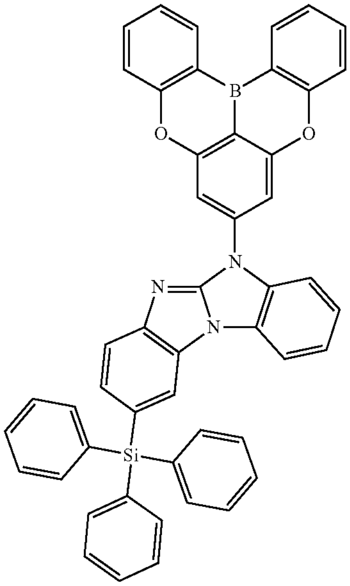
,
-continued
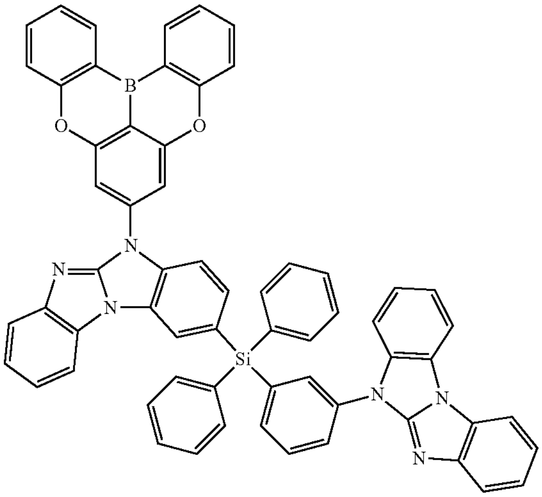
,
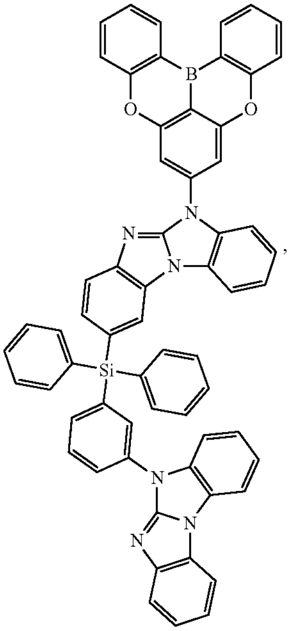
,
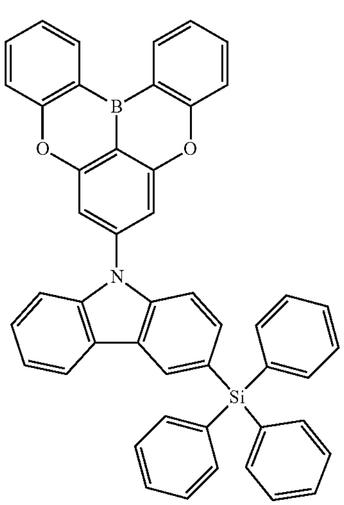
, -continued
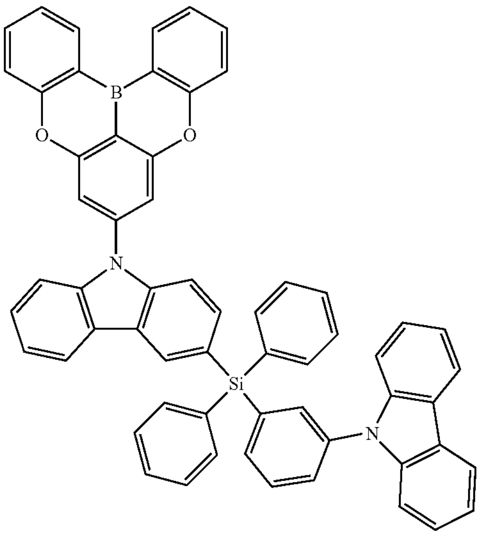
,
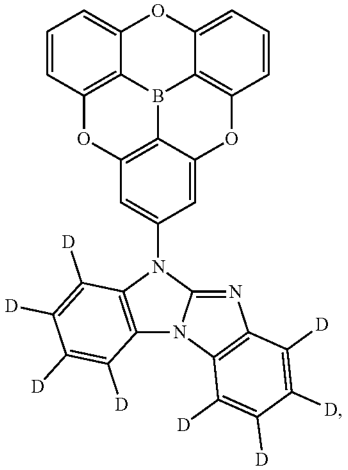
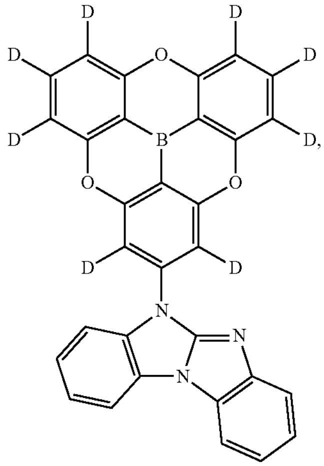
-continued
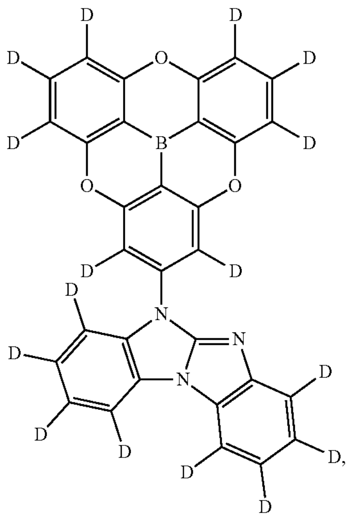
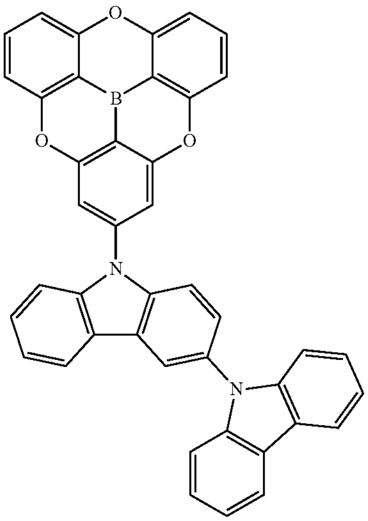
,
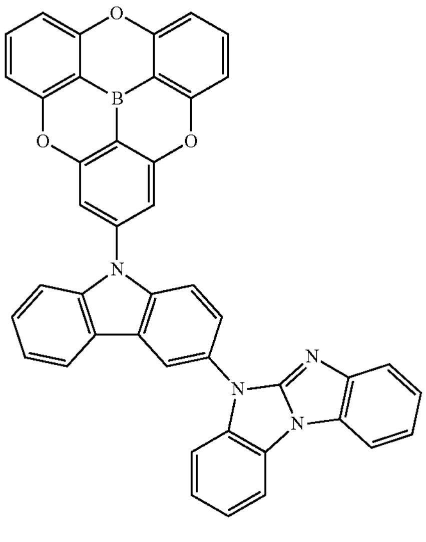
,

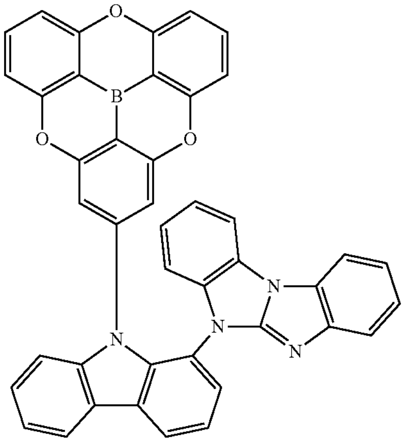
,
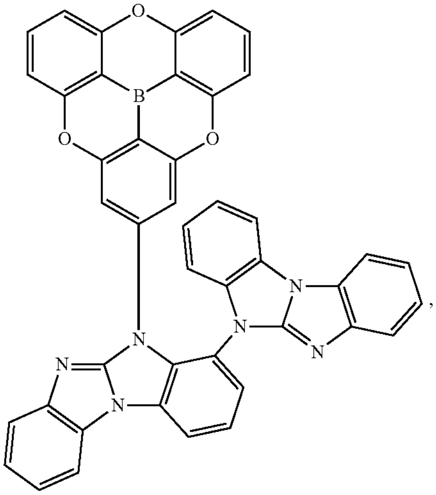
,
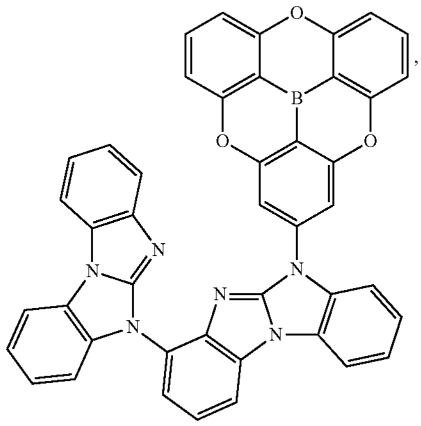
,
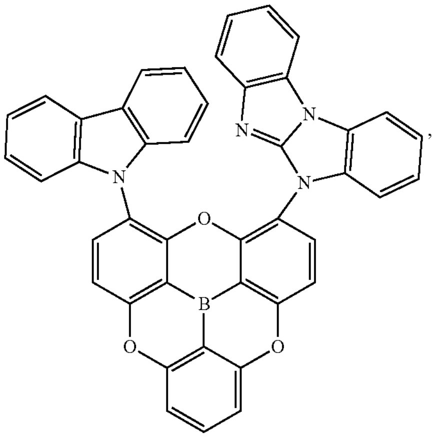
,
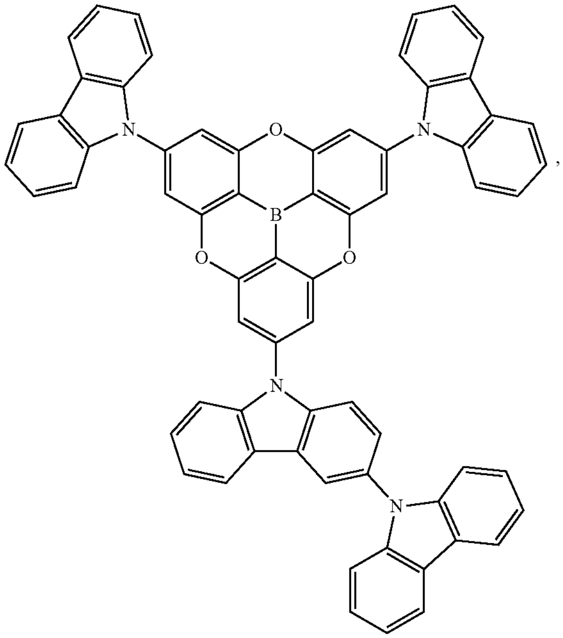
,
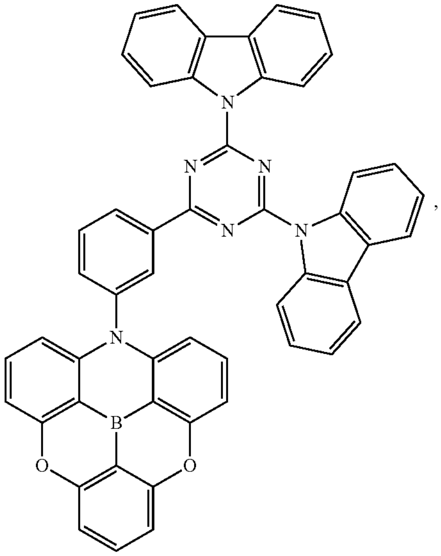
, -continued
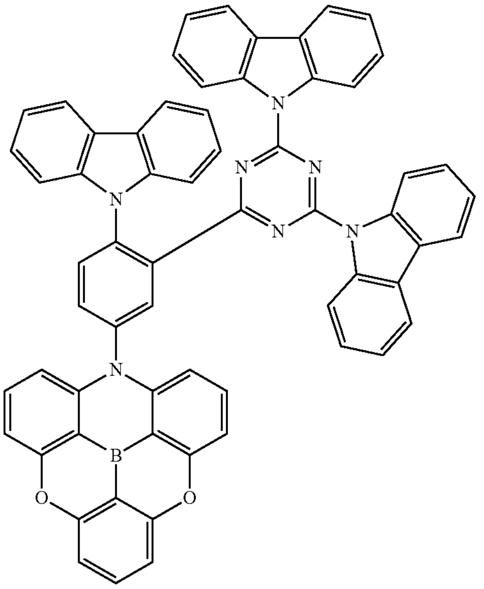
,
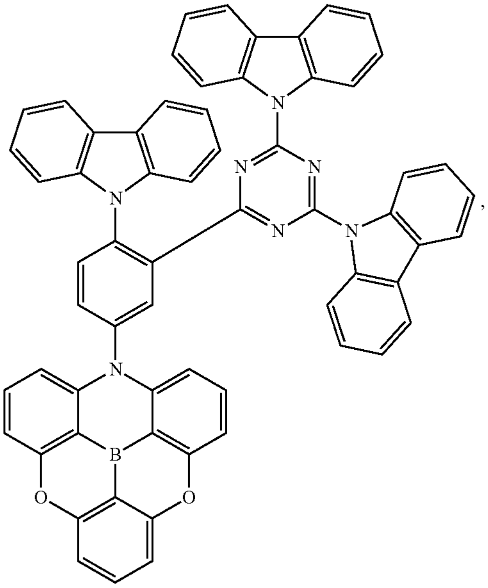
,
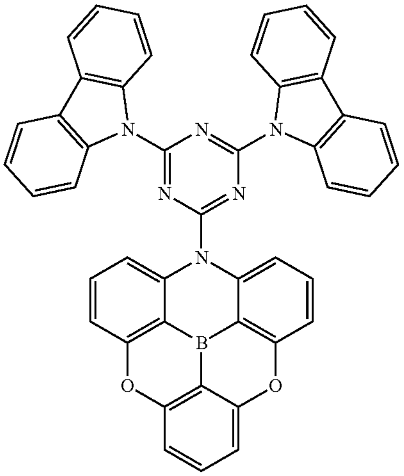
,
-continued
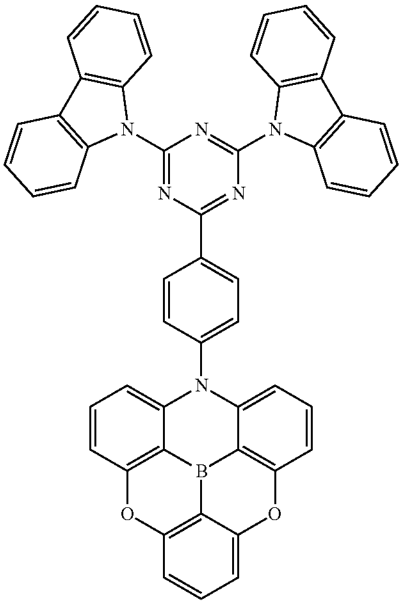
,
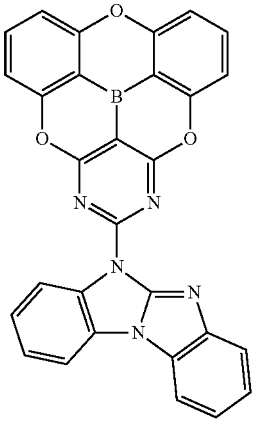
,
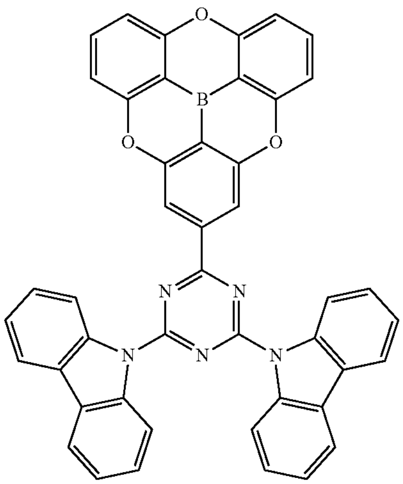
, -continued
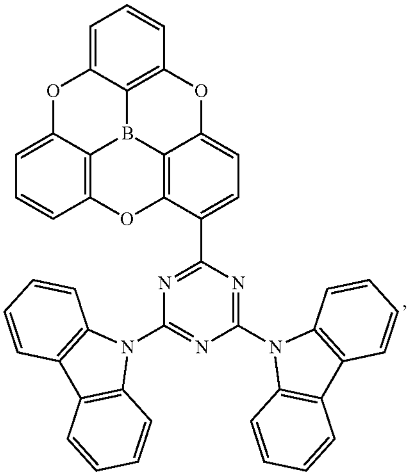
,
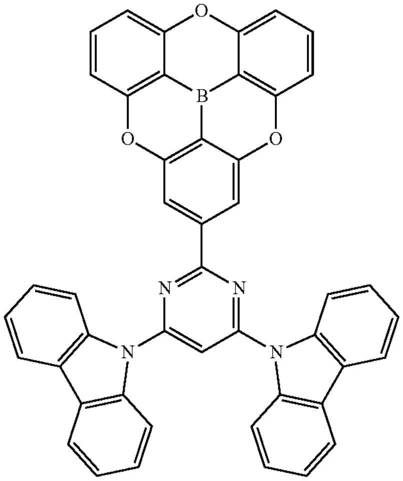
,
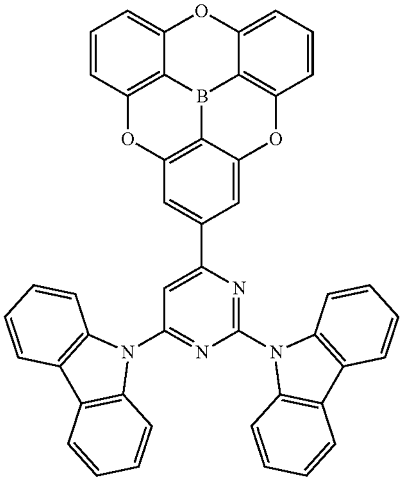
,
-continued
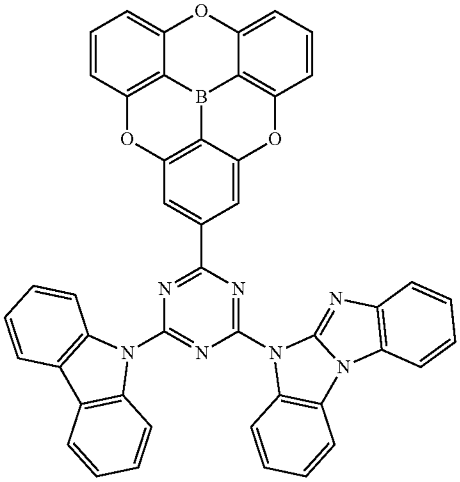
,
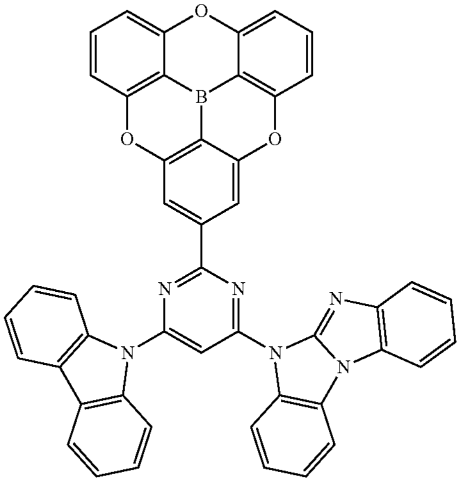
,
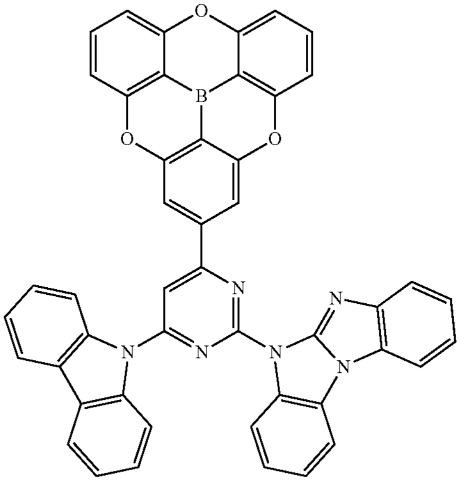
, -continued
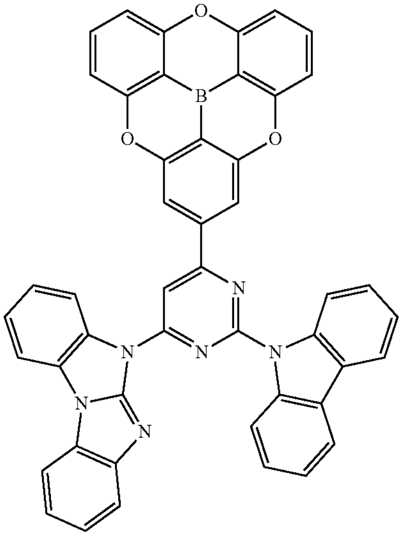
,
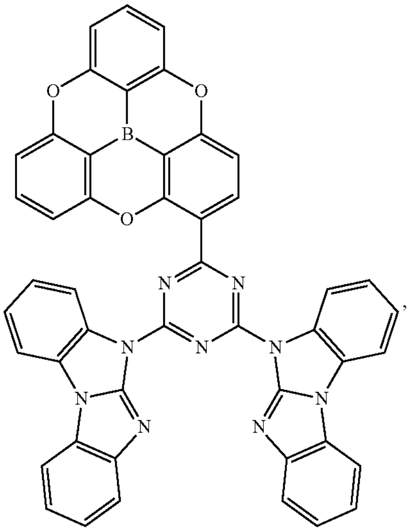
,
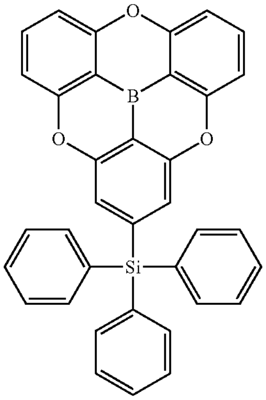
,
-continued
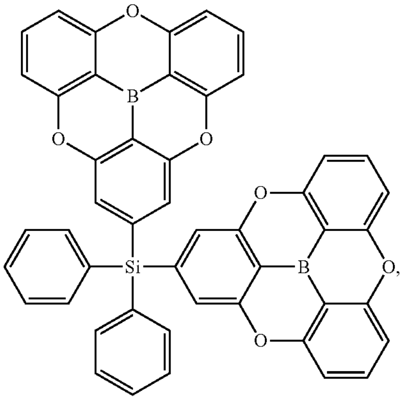
,
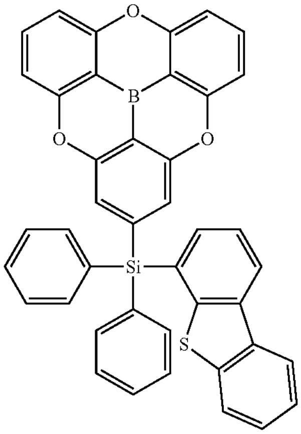
,
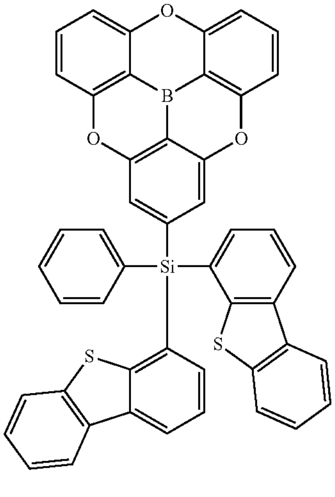
, -continued
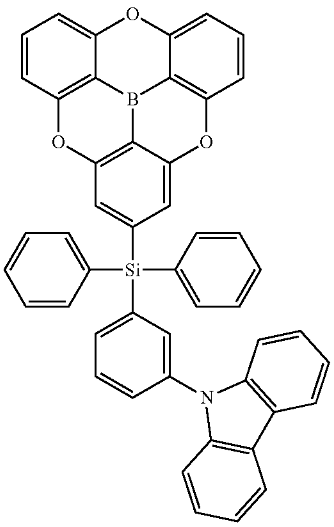
,
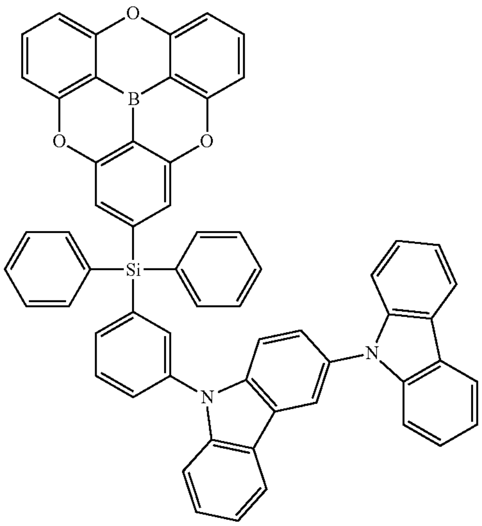
,
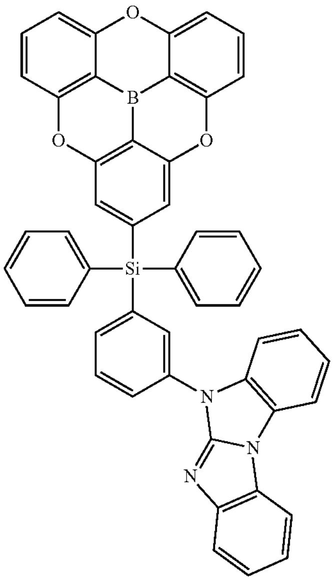
,
-continued
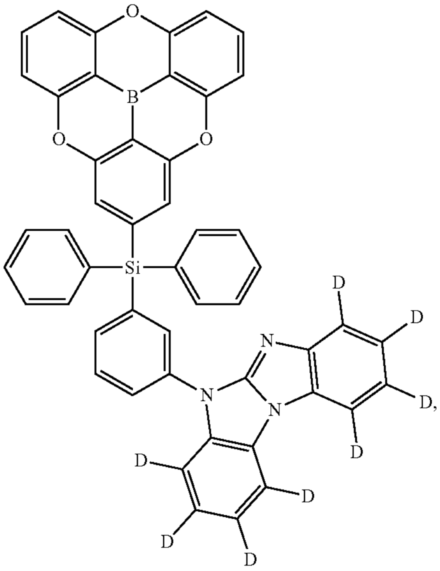
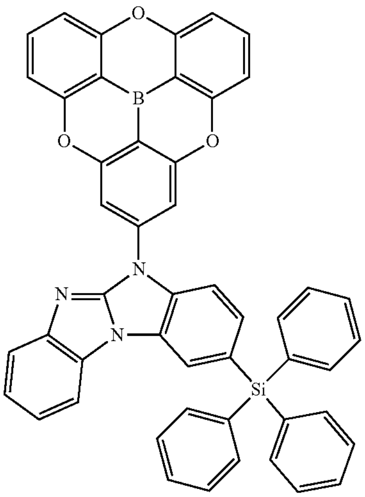
,
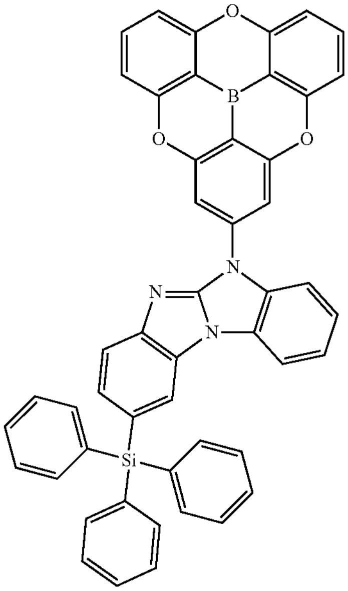
.

-continued
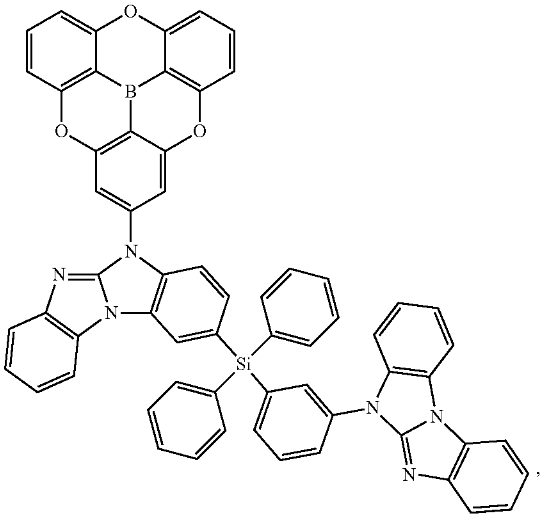
,
-continued
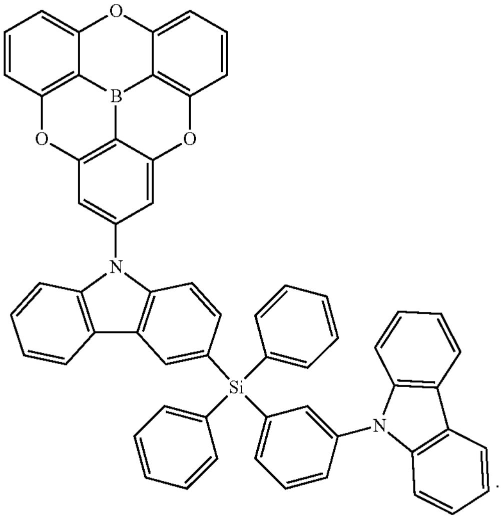
.
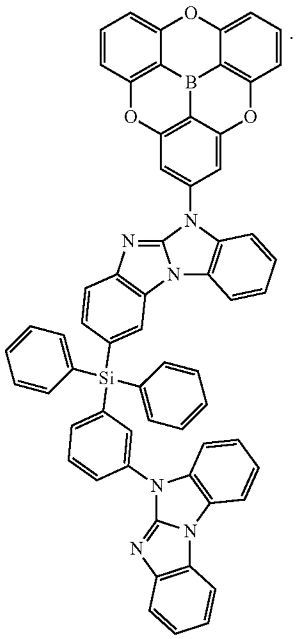
.
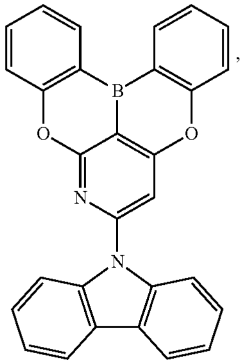
,
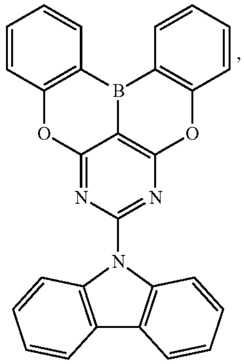
,
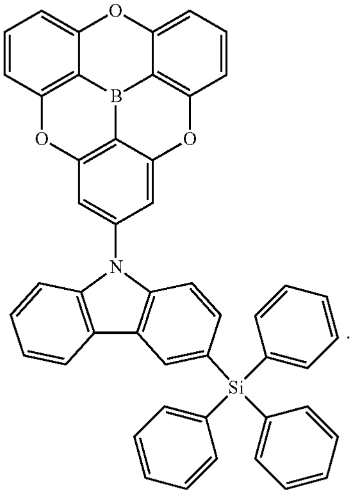
.
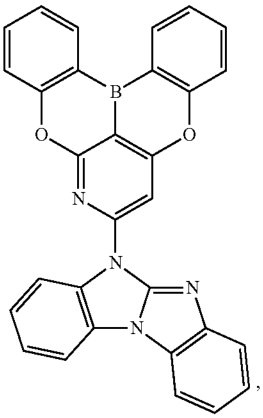
, -continued
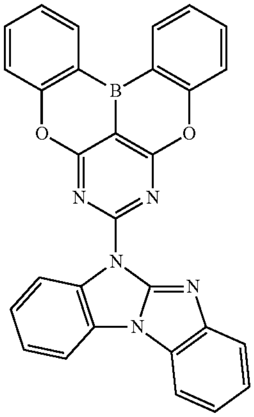
,
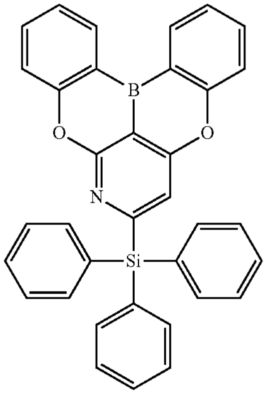
,
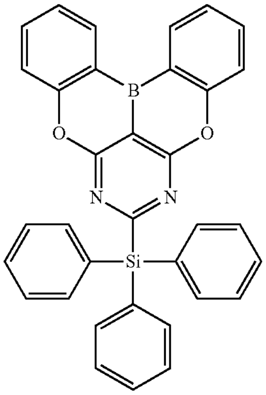
,
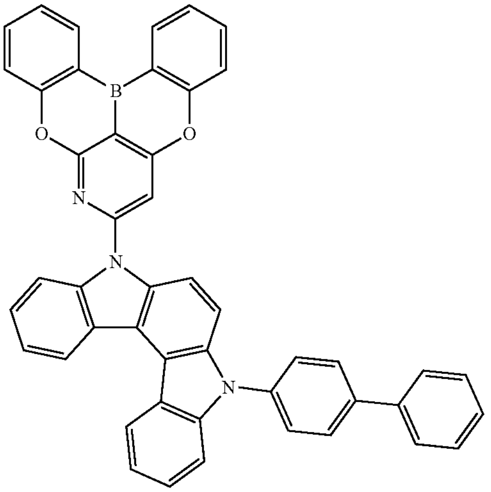
,
-continued
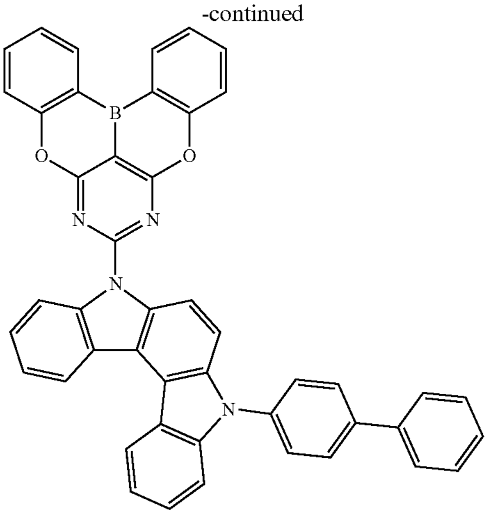
,
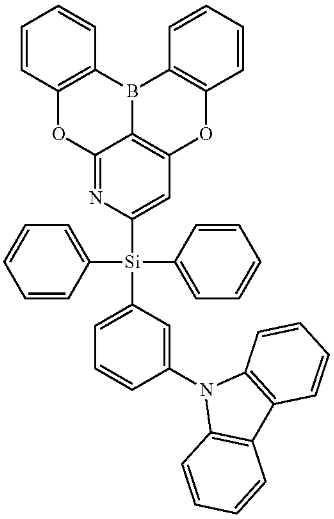
,
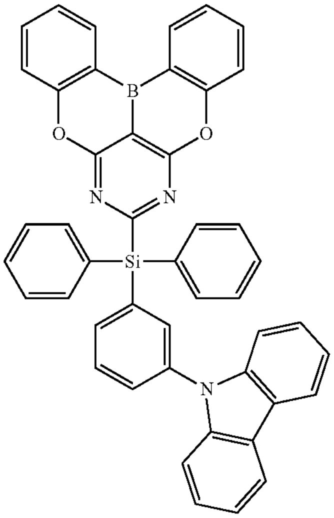
, -continued
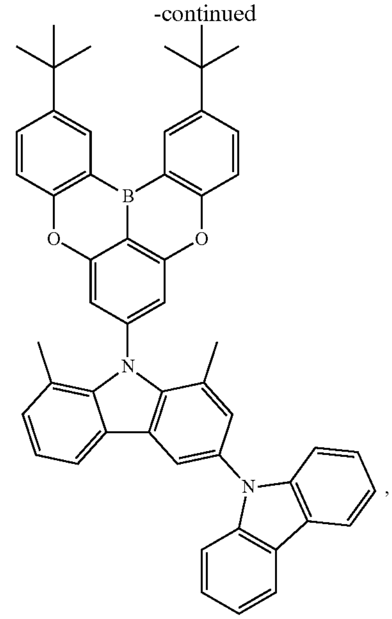
,
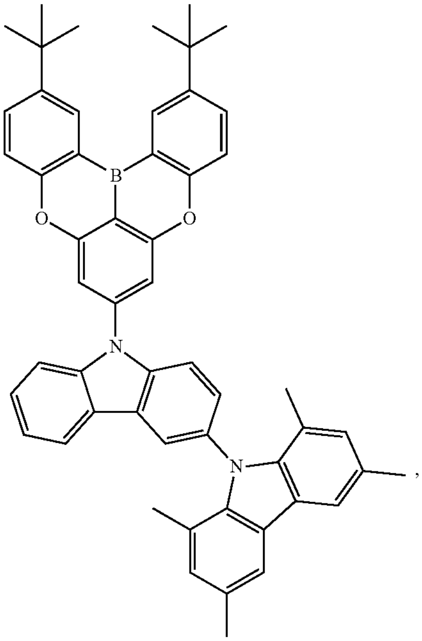
,
-continued
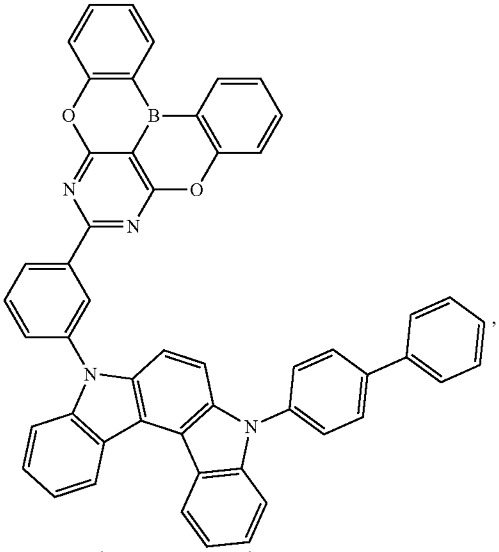
,
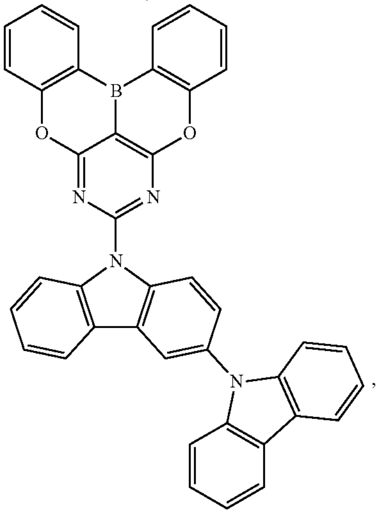
,
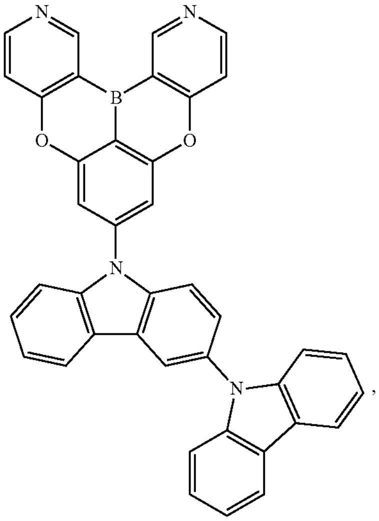
, -continued
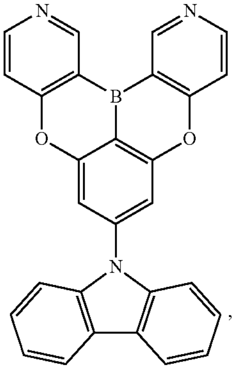
,
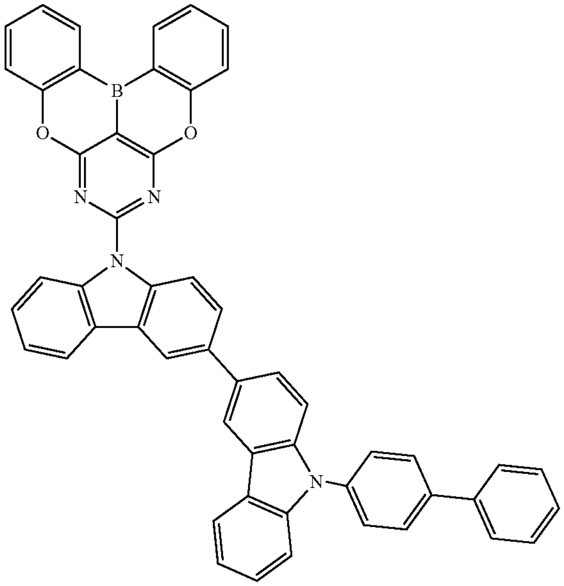
,
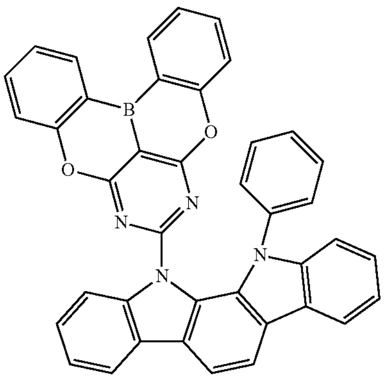
,
-continued
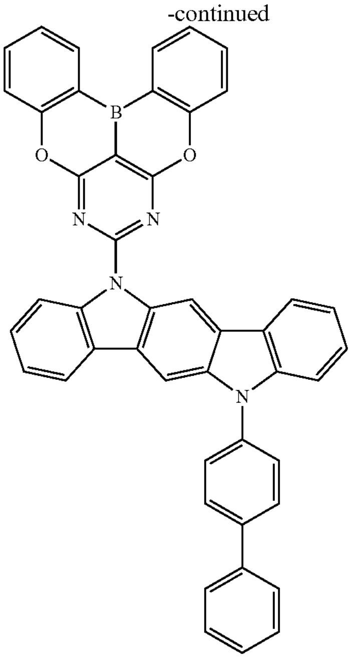
, and
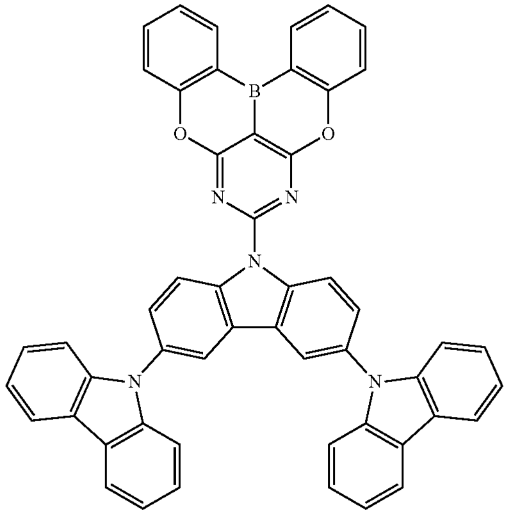
.
C. The OLEDs and the Devices of the Present Disclosure
In another aspect, the present disclosure also provides an OLED device comprising an organic layer that contains a compound as disclosed in the above compounds section of the present disclosure.

In some embodiments, the organic layer may comprise a compound comprising a structure of Formula I:

Formula I

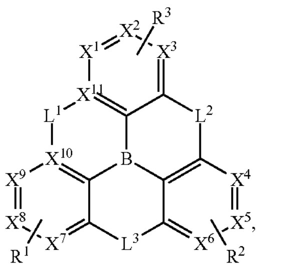

wherein $X^1$-$X^{11}$ are each independently C or N; no more than two N atoms are bonded to one another in the same ring; $L^2$, and $L^3$ are each independently selected from the group consisting of O, S, Se, BR, NR, CRR', SiRR', and GeRR'; $L^1$ is not always present but when present, $L^1$ is selected from the group consisting of O, S, Se, and SiRR' and $X^{10}$ and $X^{11}$ are both C; $L^2$ and $L^3$ are always present; $R^1$, $R^2$, and $R^3$ each independently represent zero, mono, or up to a maximum allowed substitution to its associated ring; each of R and R' is independently a hydrogen or a general substituent as described herein; each of $R^1$, $R^2$, and $R^3$ is independently a hydrogen or a substituent selected from the group consisting of Formulae II, III, IV, V, VI, VII, and VIII, deuterium, halogen, alkyl, cycloalkyl, heteroalkyl, heterocycloalkyl, arylalkyl, alkoxy, aryloxy, amino, silyl, boryl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof, with at least one of $R^1$, $R^2$, and $R^3$ being selected from the group consisting of Formulae II, III, IV, V, VI, VII, and VIII, and their aza variants as defined in the disclosure.

In some embodiments, the organic layer may be an emissive layer and the compound as described herein may be an emissive dopant or a non-emissive dopant.

In some embodiments, the compound as described herein may be a host.

In some embodiments, the organic layer may further comprise a phosphorescent emissive dopant; wherein the emissive dopant is a transition metal complex having at least one ligand or part of the ligand if the ligand is more than bidentate selected from the group consisting of LIST 3 shown below:

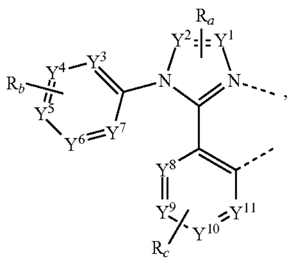

-continued

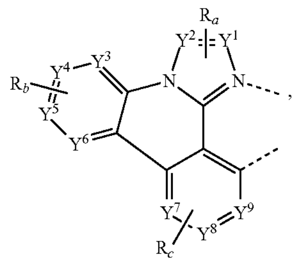

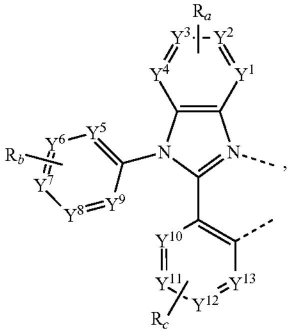

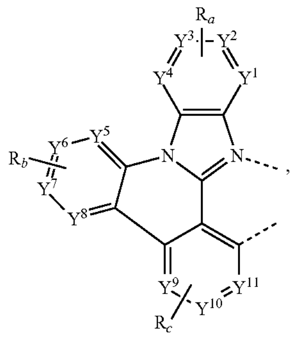

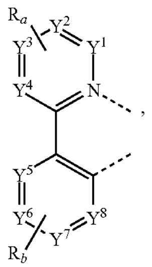

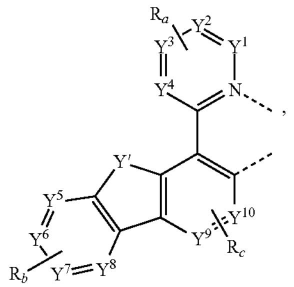

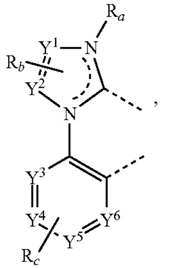

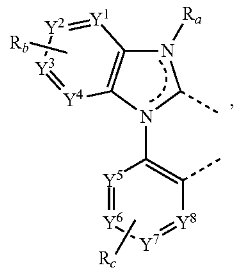

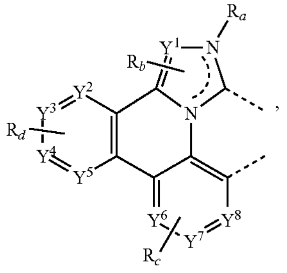

-continued

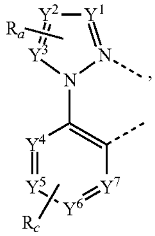,

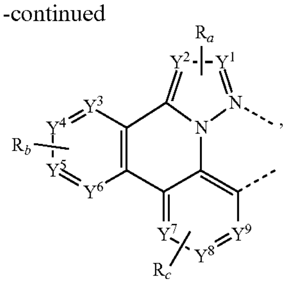,

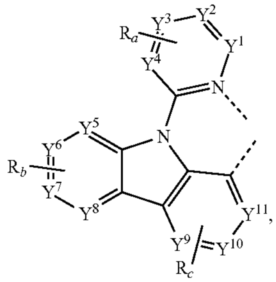,

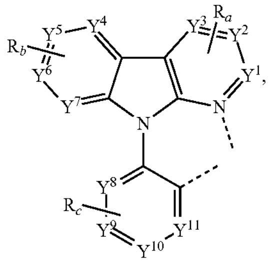 and

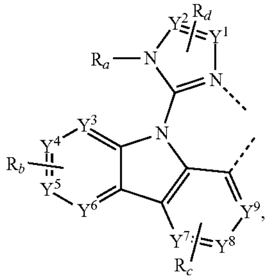, wherein each $Y^1$ to $Y^{13}$ are independently selected from the group consisting of carbon and nitrogen; wherein Y' is selected from the group consisting of $BR_e$, $NR_e$, $PR_e$, O, S, Se, C=O, S=O, $SO_2$, $CR_eR_f$, $SiR_eR_f$, and $GeR_eR_f$; wherein $R_e$ and $R_f$ can be fused or joined to form a ring; wherein each $R_a$, $R_b$, $R_c$, and $R_d$ may independently represent zero, mono, or up to a maximum allowed substitution to its associated ring; wherein each of $R_a$, $R_b$, $R_c$, $R_d$, $R_e$ and $R_f$ is independently hydrogen or a general substituent as described above; and wherein two adjacent substituents of $R_a$, $R_b$, $R_c$, and $R_d$ can be fused or joined to form a ring or form a multidentate ligand.

In some embodiments, the organic layer may be a transporting layer and the compound as described herein may be a transporting material in the organic layer.

In yet another aspect, the present disclosure also provides a consumer product comprising an organic light-emitting device (OLED) having an anode; a cathode; and an organic layer disposed between the anode and the cathode, wherein the organic layer may comprise a compound as disclosed in the above compounds section of the present disclosure.

In some embodiments, the consumer product comprises an organic light-emitting device (OLED) having an anode; a cathode; and an organic layer disposed between the anode and the cathode, wherein the organic layer may comprise a compound comprising a structure of Formula I as described herein.

In some embodiments, the consumer product may be one of a flat panel display, a computer monitor, a medical monitor, a television, a billboard, a light for interior or exterior illumination and/or signaling, a heads-up display, a fully or partially transparent display, a flexible display, a laser printer, a telephone, a cell phone, tablet, a phablet, a personal digital assistant (PDA), a wearable device, a laptop computer, a digital camera, a camcorder, a viewfinder, a micro-display that is less than 2 inches diagonal, a 3-D display, a virtual reality or augmented reality display, a vehicle, a video wall comprising multiple displays tiled together, a theater or stadium screen, a light therapy device, and a sign.

In yet another aspect, the present disclosure provides an OLED comprising an anode; a cathode; and an emissive layer disposed between the anode and the cathode, wherein the emissive layer comprises a first compound and a second compound; wherein the first compound is a boron compound possessing a trigonal planar geometry; and wherein the second compound is a Pt(II) complex possessing a square planar geometry.

In some embodiments, the first compound may comprise a structure of Formula I

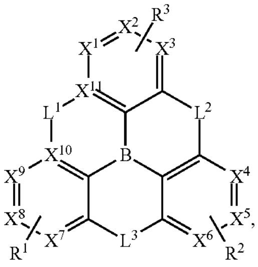, wherein:

$X^1$-$X^{11}$ are each independently C or N;

no more than two N atoms are bonded to one another in the same ring;

$L^2$, and $L^3$ are each independently selected from the group consisting of O, S, Se, BR, NR, CRR', SiRR', and GeRR';

$L^1$ is not always present but when present, $L^1$ is selected from the group consisting of O, S, Se, and SiRR' and $X^{10}$ and $X^{11}$ are both C when $L^1$ is present;

$L^2$ and $L^3$ are always present;

$R^1$, $R^2$, and $R^3$ each independently represent zero, mono, or up to a maximum allowed substitution to its associated ring;

each of R and R' is independently a hydrogen or a general substituent as described herein;

each of $R^1$, $R^2$, and $R^3$ is independently a hydrogen or a substituent selected from the group consisting of Formulae II, III, IV, V, VI, VII, and VIII, deuterium, halogen, alkyl, cycloalkyl, heteroalkyl, heterocycloalkyl, arylalkyl, alkoxy, aryloxy, amino, silyl, boryl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof, with at least one of $R^1$, $R^2$, and $R^3$ being selected from the group consisting of Formulae II, III, IV, V, VI, VII, and VIII, and their aza variants as described herein; and the second compound is a Pt complex capable of emitting light at room temperature upon photo or electrical excitation.

In some embodiments, the Pt complex may comprise a tetradentate ligand. In some embodiments, the Pt complex may comprise at least one Pt—C bond, and at least one Pt—N bond.

In some embodiments, the Pt complex may be a phosphorescent emitter.

In some embodiments, the Pt complex may have at least one ligand or part of the ligand if the ligand is more than bidentate selected from the group consisting of LIST 3 described above.

In some embodiments, the Pt complex may be selected from the group consisting of the structures shown in LIST 4 below:

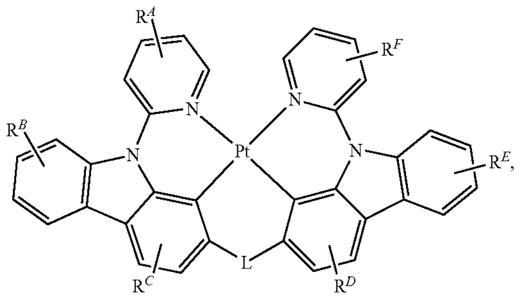

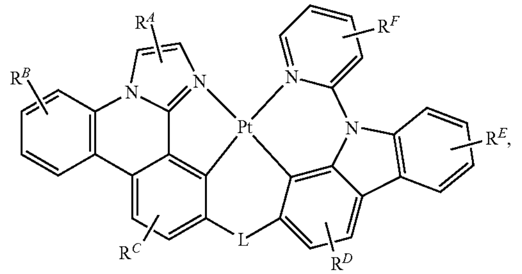

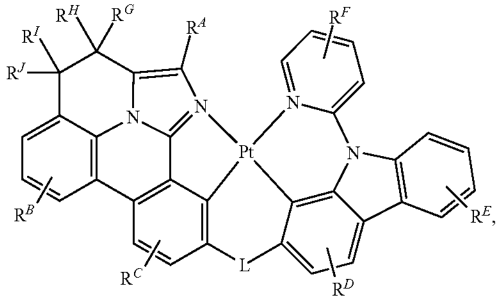

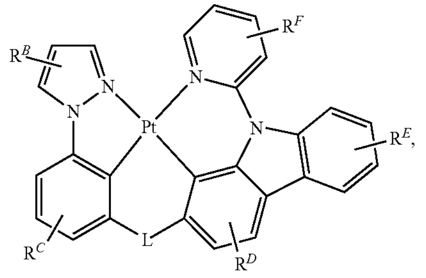

-continued

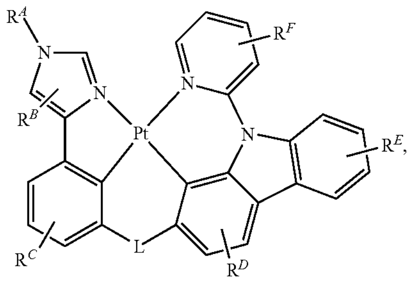

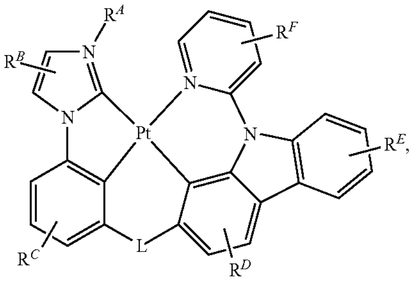

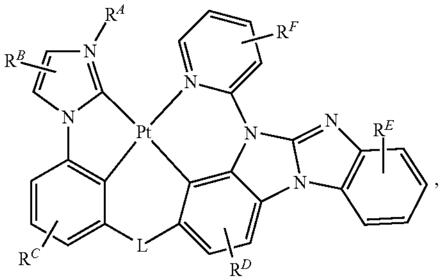

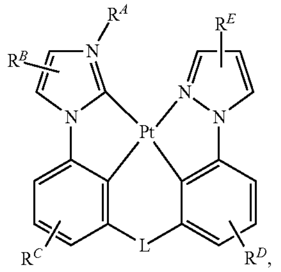

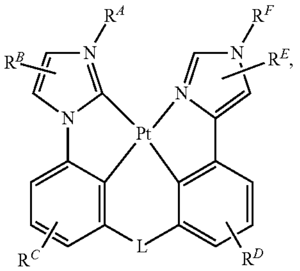

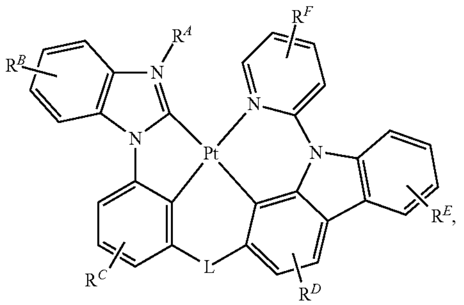

-continued
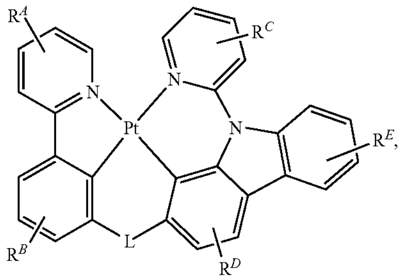
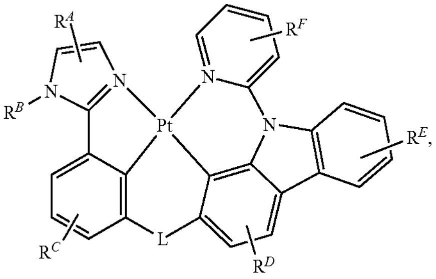
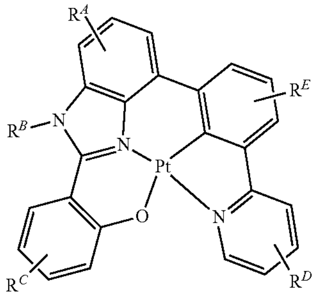
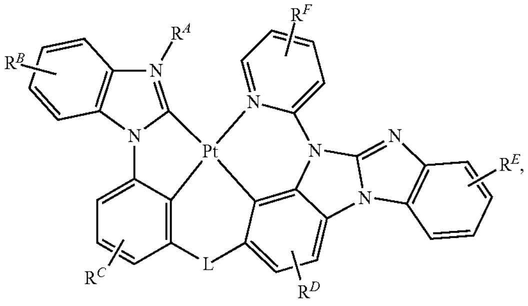
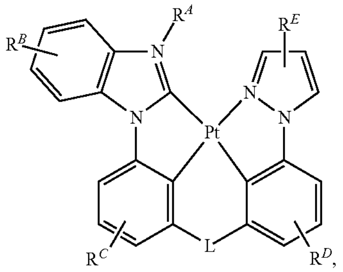
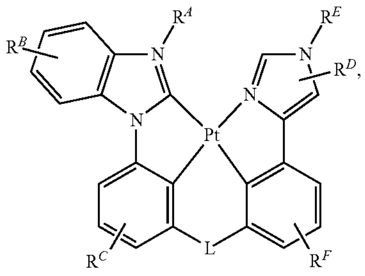
-continued
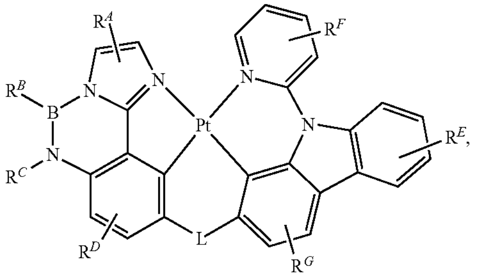
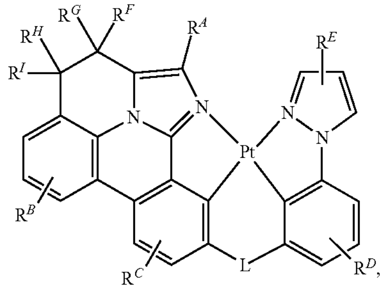
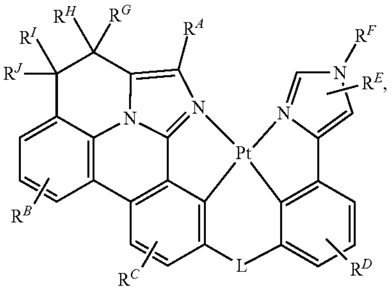
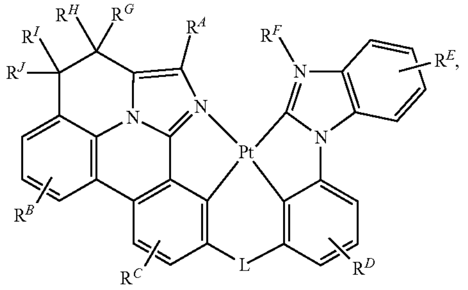
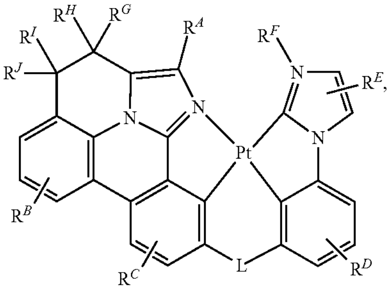
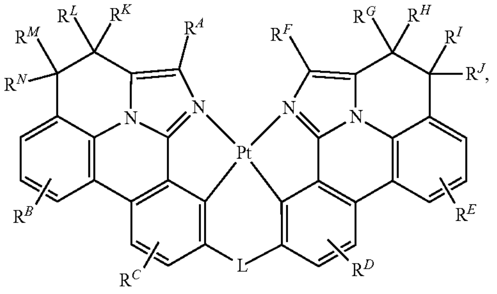

-continued

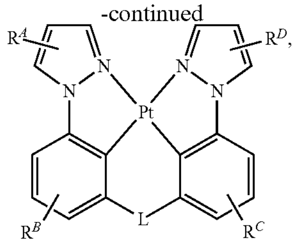

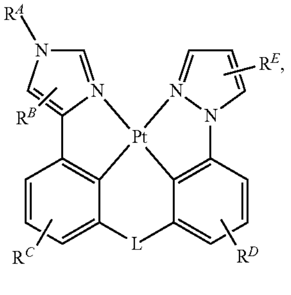

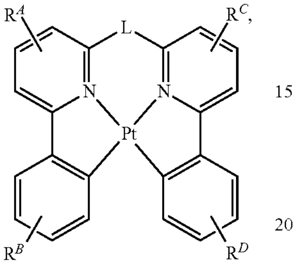

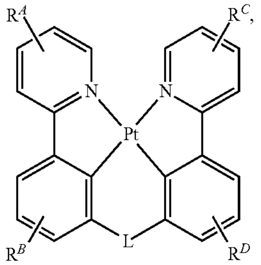

and

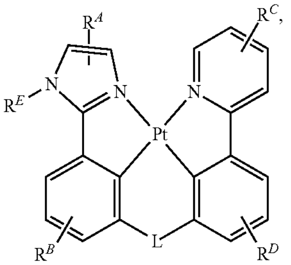

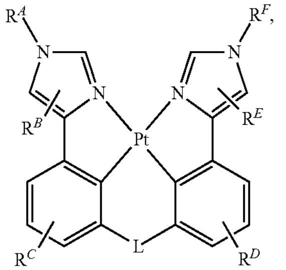

wherein each of $R^A$, $R^B$, $R^C$, $R^D$, $R^E$, $R^F$, $R^G$, $R^H$, $R^I$, $R^J$, $R^K$, $R^L$, $R^M$, $R^N$ in LIST 4 above is independently a hydrogen or a substituent selected from the group consisting of deuterium, fluorine, alkyl, cycloalkyl, heteroalkyl, alkoxy, aryloxy, amino, silyl, boryl, alkenyl, cycloalkenyl, heteroalkenyl, aryl, heteroaryl, nitrile, isonitrile, sulfanyl, and combinations thereof;

L for each occurrence is independently O, S, Se, BR, NR, CRR', SiRR', and GeRR'; and R and R' are the same as previously defined.

In some embodiments, each R, R', $R^1$, $R^2$, $R^3$, $R^D$, $R^E$, $R^P$, $R^Q$, $R^4$ and $R^5$ in LIST 4 above may be independently a hydrogen or a substituent selected from the group consisting of deuterium, fluorine, alkyl, cycloalkyl, heteroalkyl, alkoxy, aryloxy, amino, silyl, boryl, alkenyl, cycloalkenyl, heteroalkenyl, aryl, heteroaryl, nitrile, isonitrile, sulfanyl, and combinations thereof.

In some embodiments, $R^R$ is a hydrogen or a substituent selected from the group consisting of deuterium, fluorine, alkyl, cycloalkyl, heteroalkyl, alkoxy, aryloxy, amino, silyl, alkenyl, cycloalkenyl, heteroalkenyl, aryl, heteroaryl, nitrile, isonitrile, sulfanyl, and combinations thereof.

In some embodiments, $L^1$ may not be present. In some embodiments, $L^1$ may be present. In some embodiments, $L^1$ may be present, and $L^1$, $L^2$, and $L^3$ may each be independently selected from the group consisting of O, S, BR, and NR. In some embodiments, $L^1$ may be present, and $L^1$, $L^2$, and $L^3$ may each be O. In some embodiments, $L^2$ and $L^3$ may each be O. In some embodiments, $L^1$ may be present, and $L^1$, $L^2$, and $L^3$ may each be NR. In some embodiments, $L^2$ and $L^3$ may each be NR. In some embodiments, $L^1$ may be present, and $L^1$, $L^2$, and $L^3$ may each be S. In some embodiments, $L^2$ and $L^3$ may each be S. In some embodiments, $L^1$ may be present, and one of $L^1$, $L^2$, and $L^3$ may be S and the remainder may be O. In some embodiments, $L^1$ may be present, and two of $L^1$, $L^2$, and $L^3$ may be S and the remainder may be O. In some embodiments, $L^1$ may be present, and one of $L^1$, $L^2$, and $L^3$ may be NR and the remainder may be O. In some embodiments, $L^1$ may be present, and two of $L^1$, $L^2$, and $L^3$ may be NR and the remainder may be O. In some embodiments, $L^1$ may be present, and one of $L^1$, $L^2$, and $L^3$ may be NR and the remainder may be S. In some embodiments, $L^1$ may be present, and two of $L^1$, $L^2$, and $L^3$ may be NR and the remainder may be S. In some embodiments, one of $L^2$ and $L^3$ may be O and the other may be S. In some embodiments, one of $L^2$ and $L^3$ may be O and the other may be NR. In some embodiments, one of $L^2$ and $L^3$ may be S and the other may be NR.

In some embodiments, $L^4$ is a direct bond. In some embodiments, $L^4$ is phenyl or biphenyl.

In some embodiments, A is a benzene ring. In some embodiments, A is a 5-membered heterocyclic ring.

In some embodiments, R may be a 6-membered aromatic ring.

In some embodiments, at least one of $R^1$, $R^2$, and $R^3$ may comprise a chemical group selected from the group consisting of carbazole, dibenzofuran, dibenzothiophene, tetraphenylene, triazine, pyrimidine, pyridine, tetraphenylene, 5H-benzo[d]benzo[4,5]imidazo[3,2-a]imidazole, benzo[d]benzo[4,5]imidazo[2,1-b]oxazole, benzo[d]benzo[4,5]imidazo[2,1-b]thiazole, 6H-indolo[2,3-b]indole, 6H-benzofuro[2,3-b]indole, 6H-benzo[4,5]thieno[2,3-b]indole, and aza variants thereof.

In some embodiments, $R^R$ is an aryl or heteroaryl group. In some embodiments, $R^P$ and $R^Q$ is each hydrogen or deuterium. In some embodiments, at least one of $R^P$ or $R^Q$ is aryl or heteroaryl. In some embodiments, $X^{11}$ is selected from the group consisting of O, S, Se, and $NR^4$.

In some embodiments, the first compound may comprise a structure from the group consisting of the structures shown in

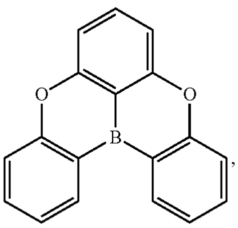,

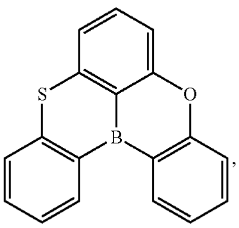,

-continued
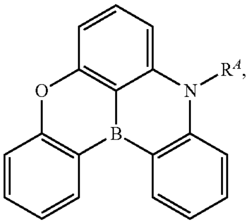
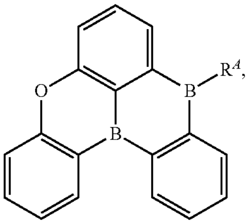
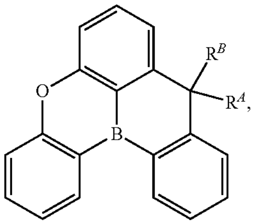
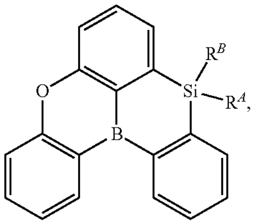
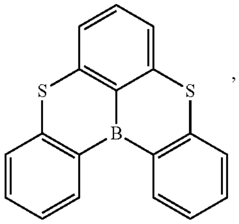
,
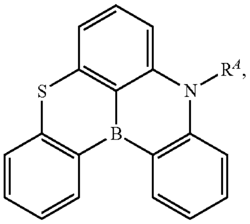
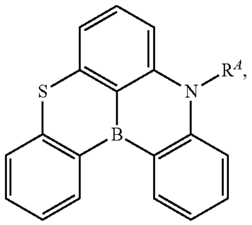
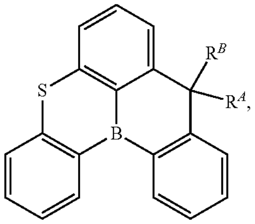
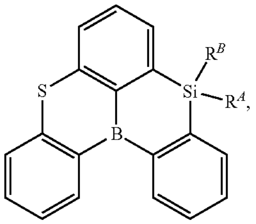
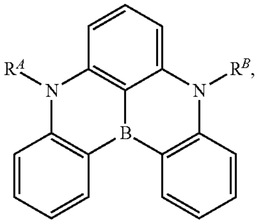
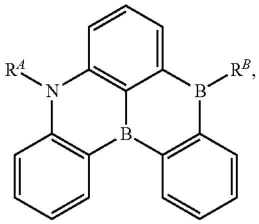
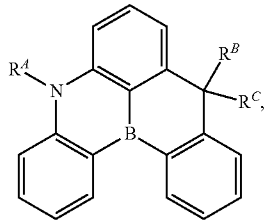
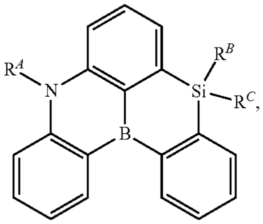
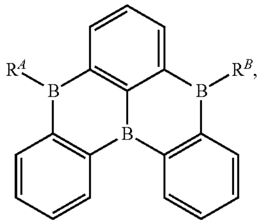
-continued
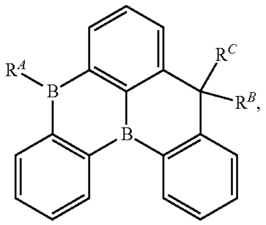
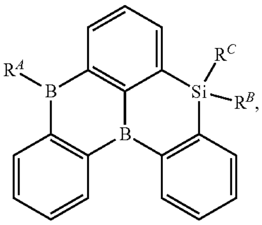
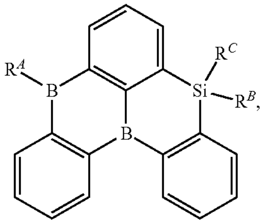
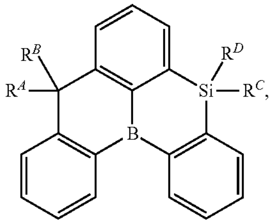
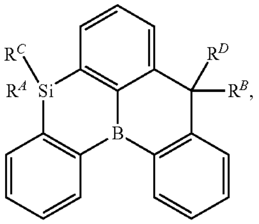
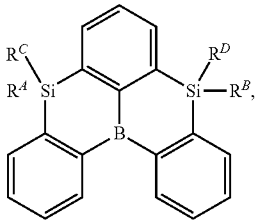
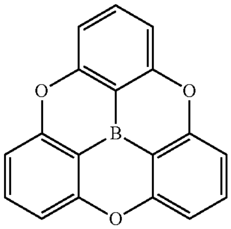
,
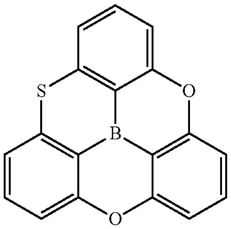
,
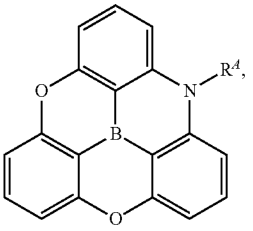
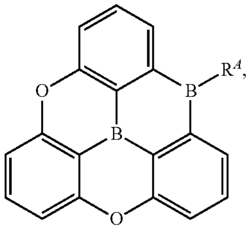
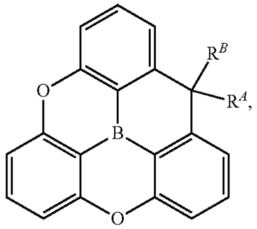
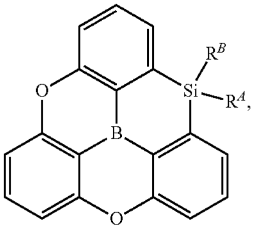
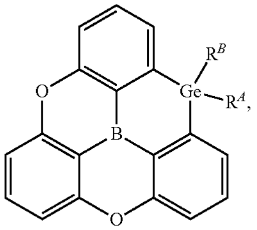
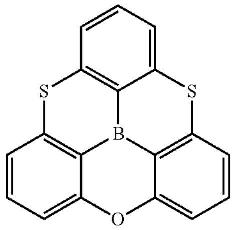
, -continued
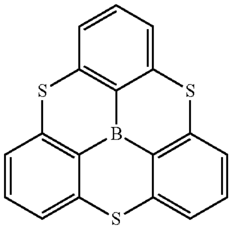
,
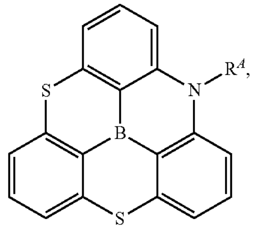
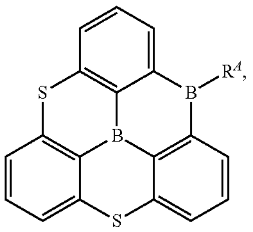
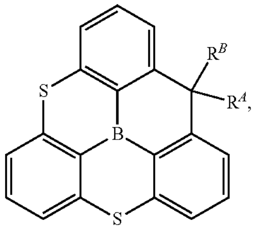
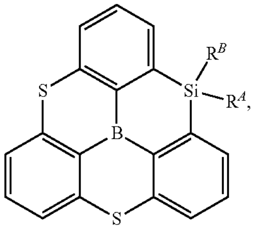
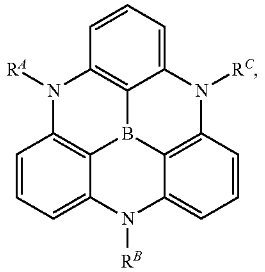
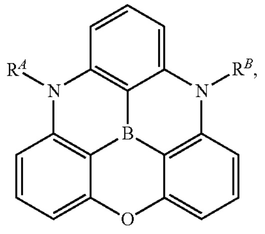
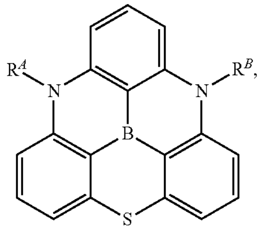
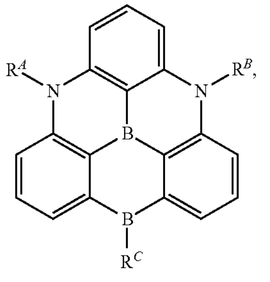
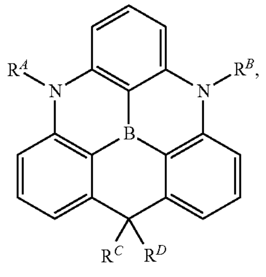
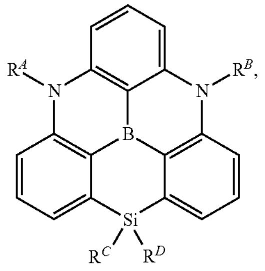
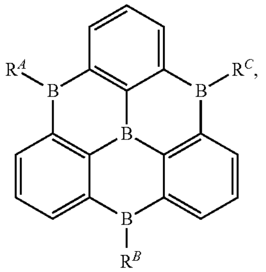
-continued
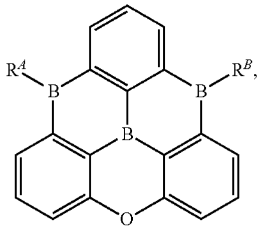
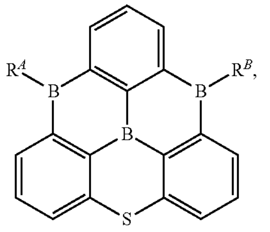
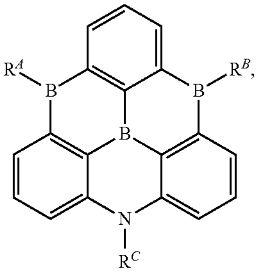
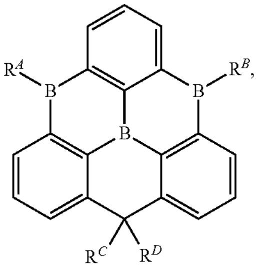
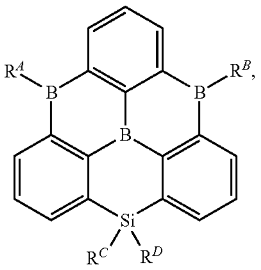
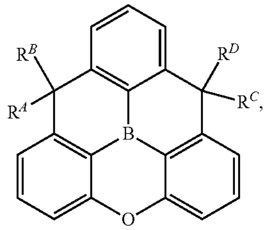
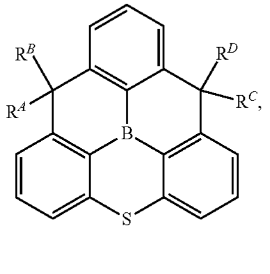
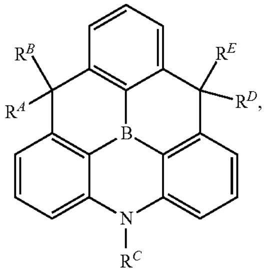
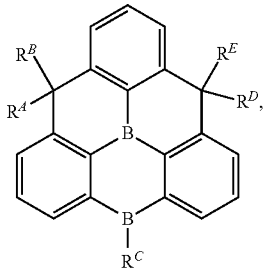
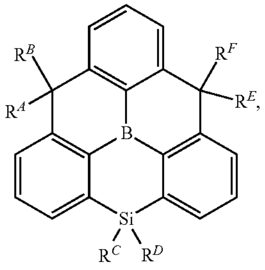
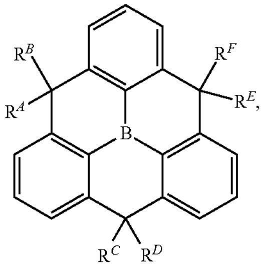
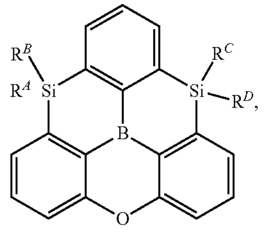

-continued
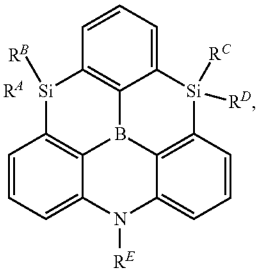
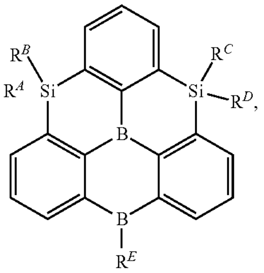
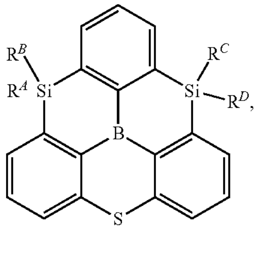
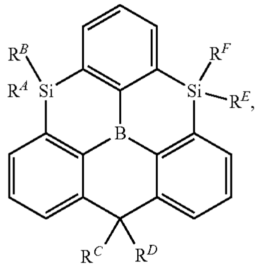
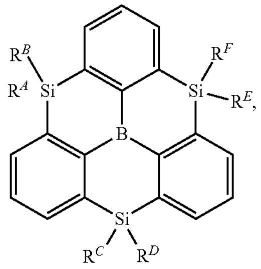
and
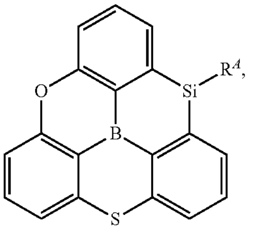
wherein all the variables are the same as previously defined.
In some embodiments, the first compound may be selected from the group consisting of the structures shown in LIST 6 below:
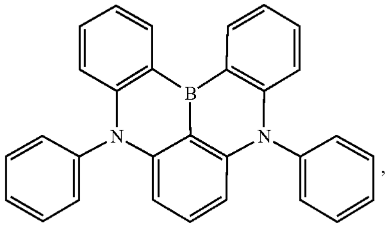
-continued
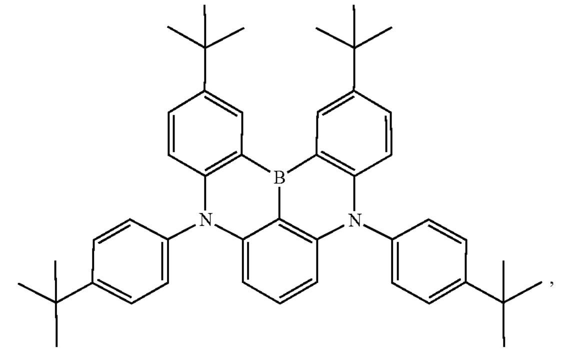
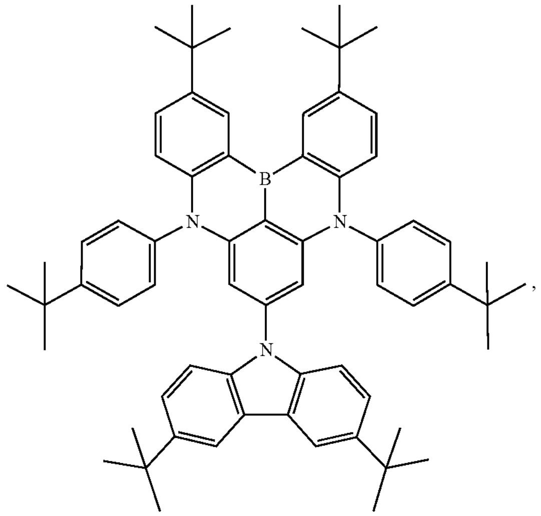
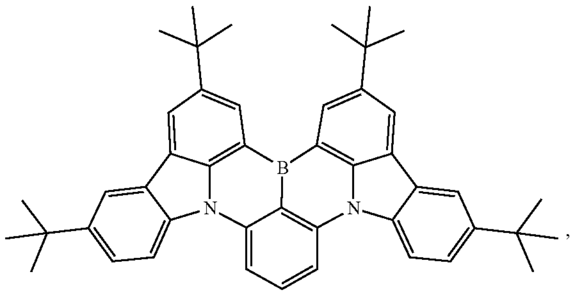
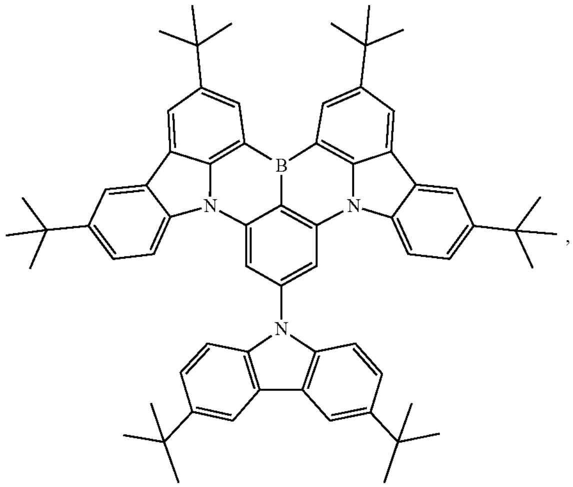

-continued
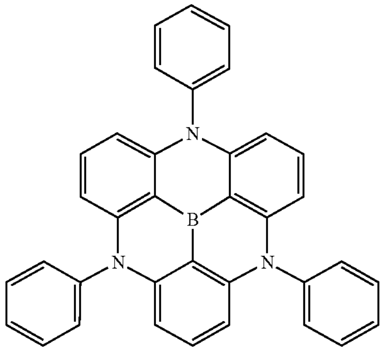
,
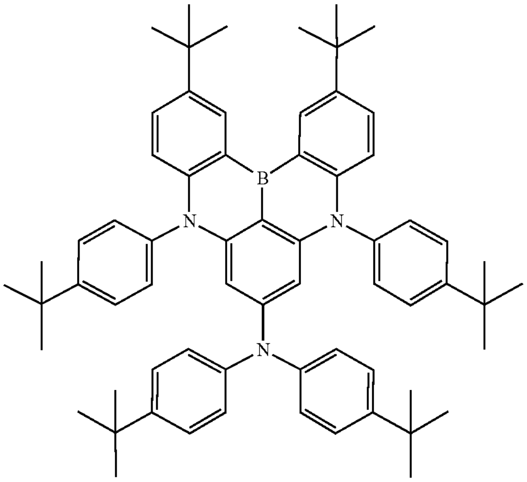
,
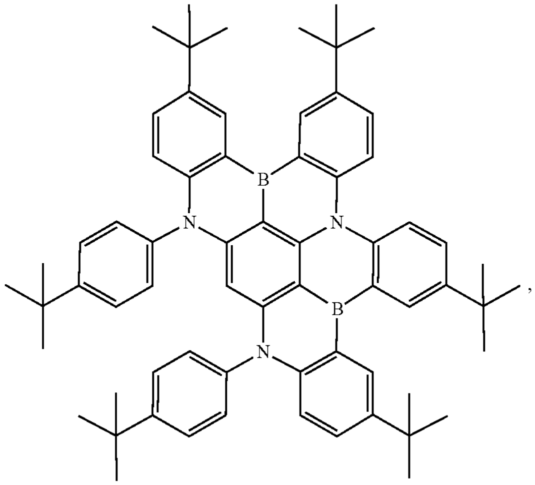
,
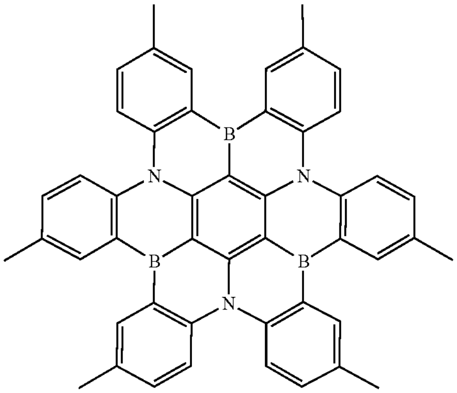
,
-continued
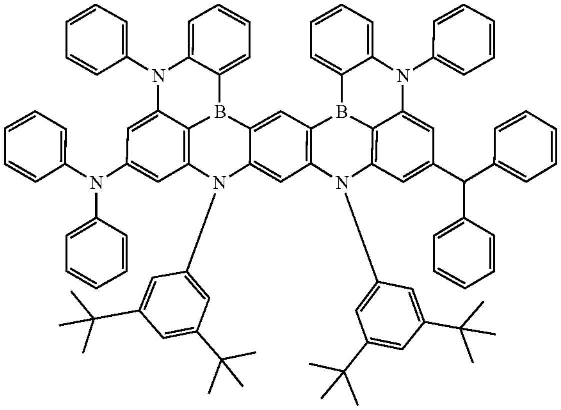
,
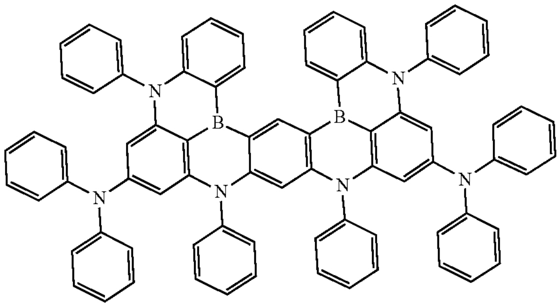
,
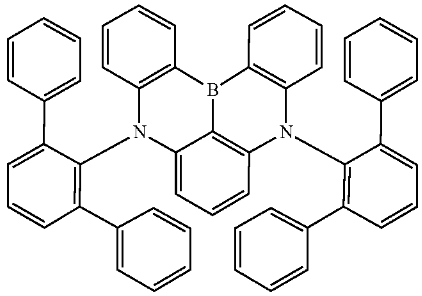
,
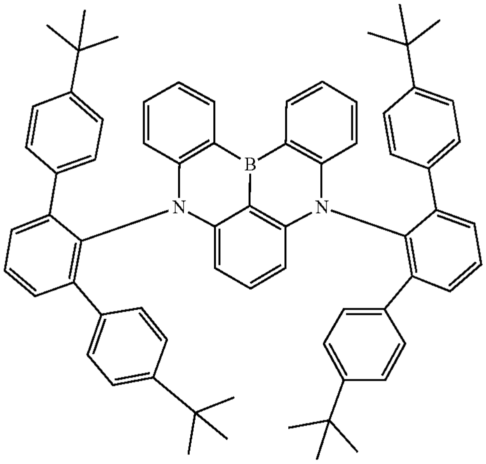
, -continued
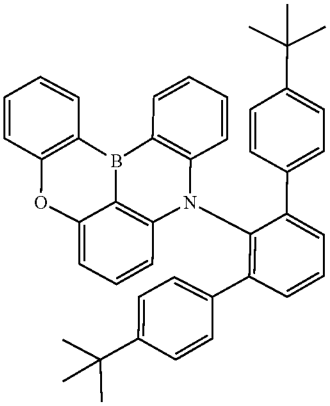
,
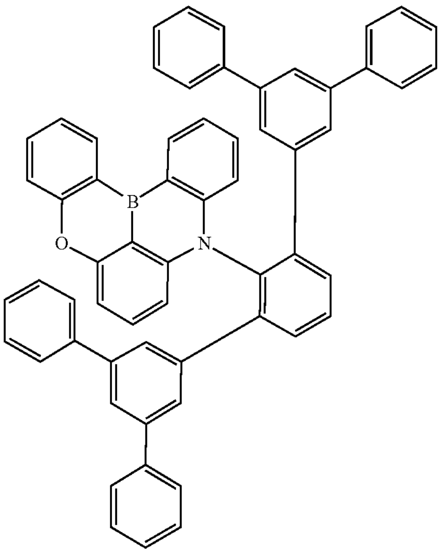
,
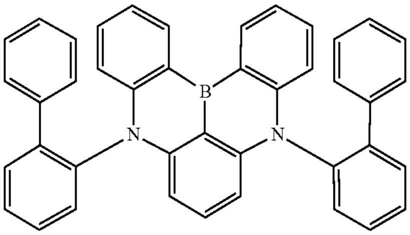
,
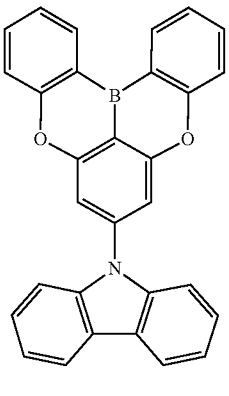
,
-continued
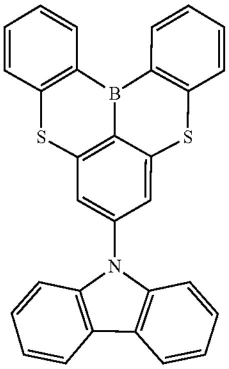
,
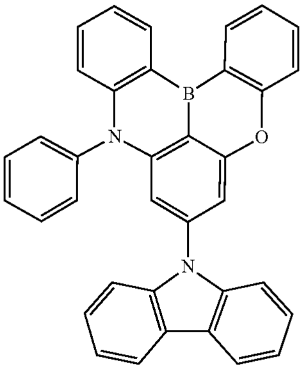
,
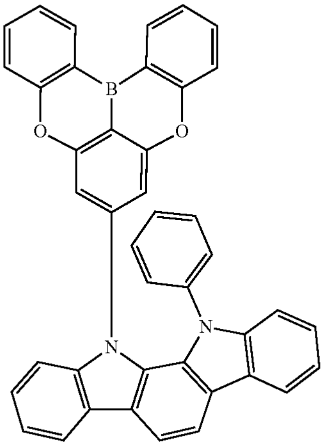
,
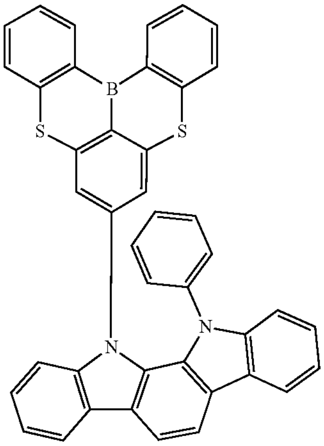
, -continued
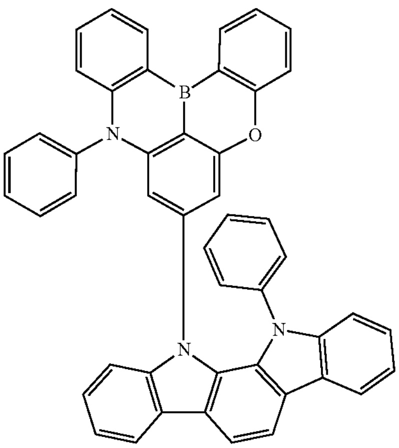
,
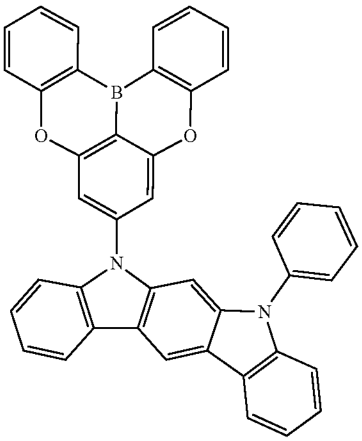
,
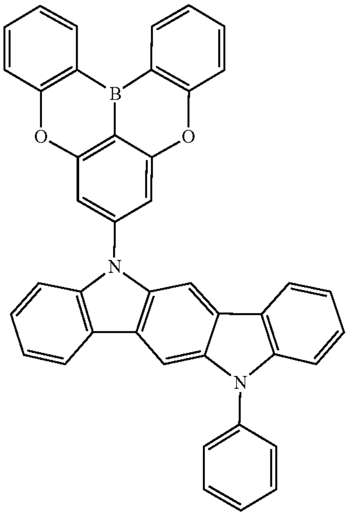
,
-continued
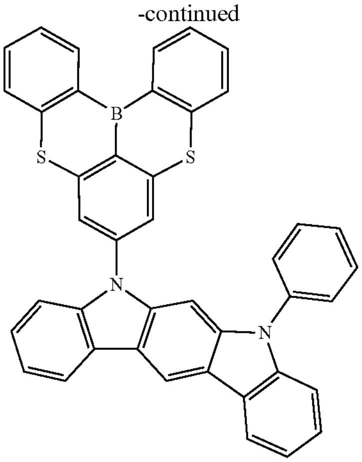
,
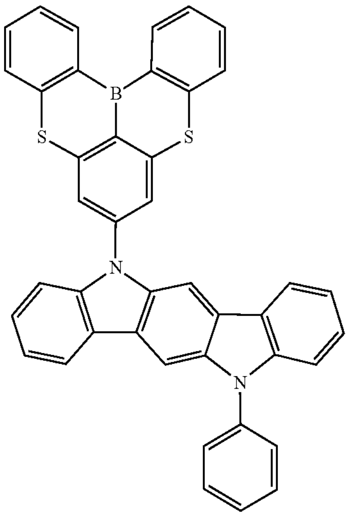
,
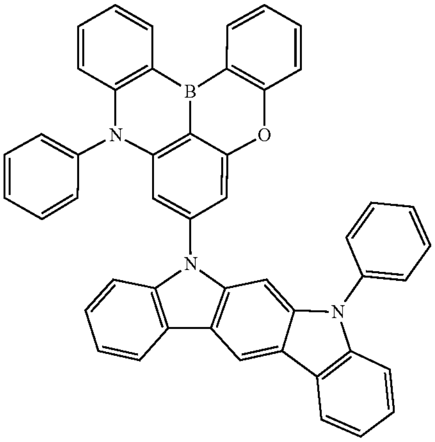
,

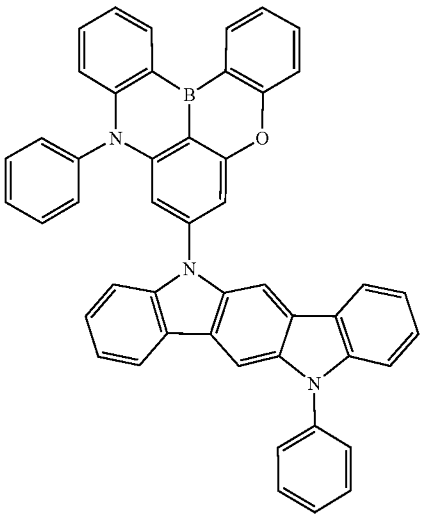
,
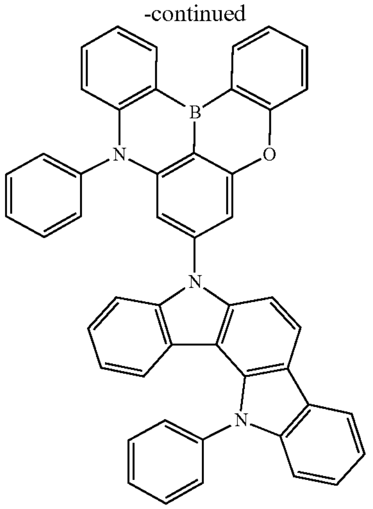
,
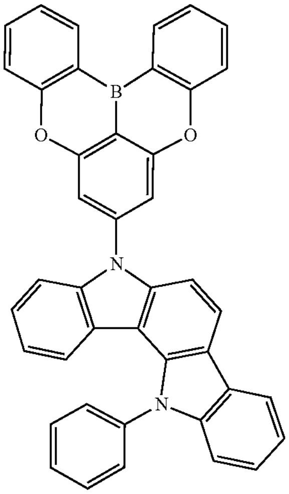
,
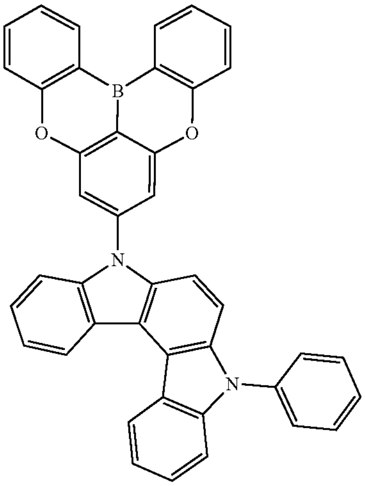
,
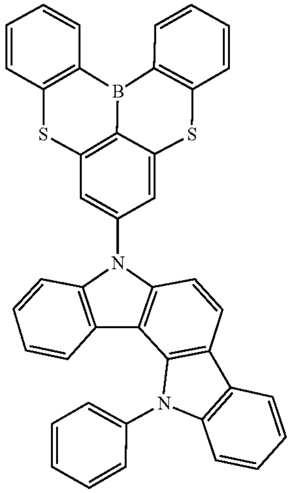
,
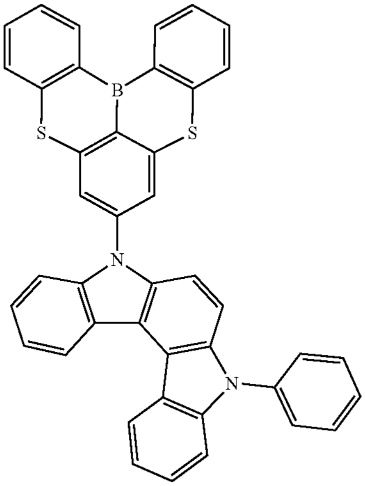
, -continued
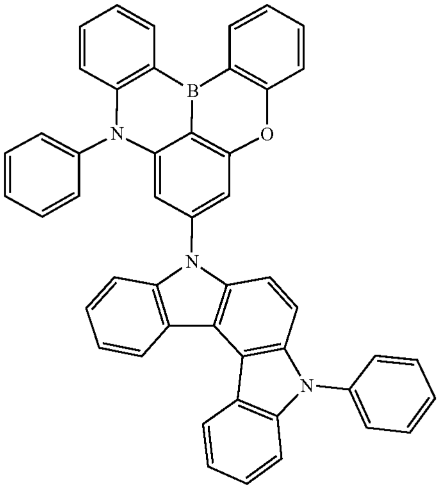
,
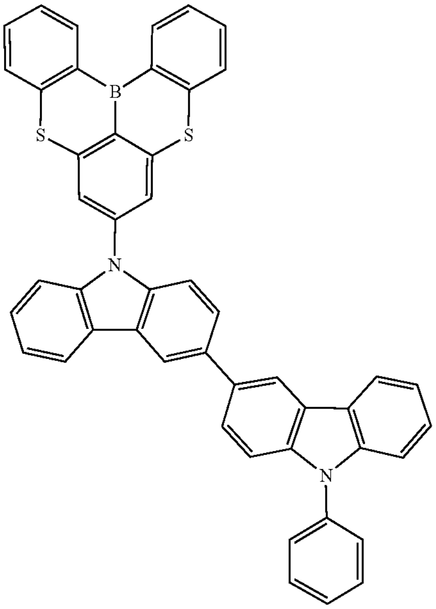
,
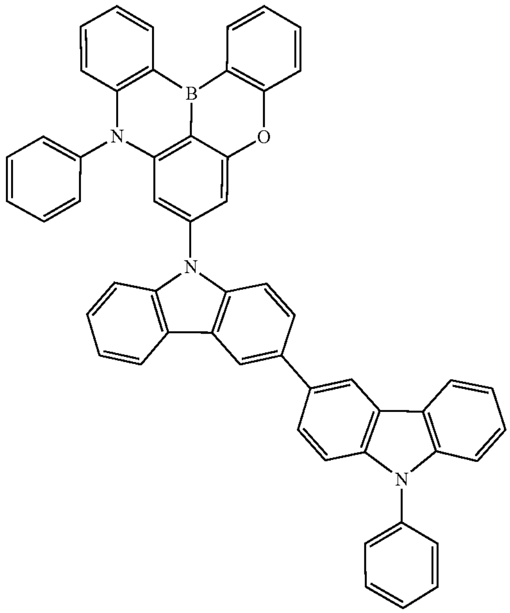
,
-continued
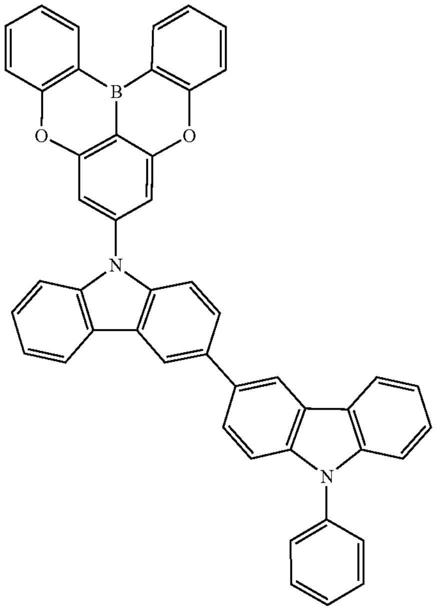
,
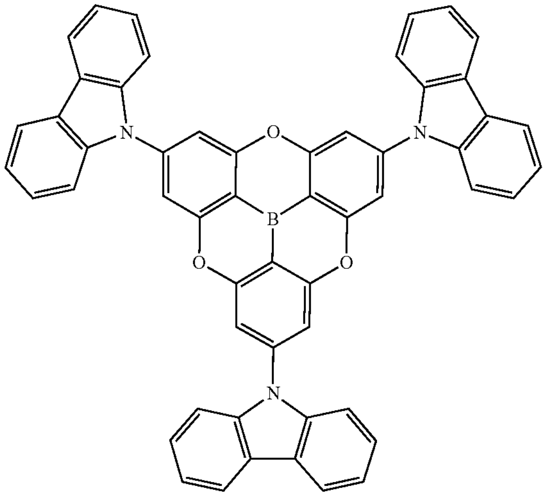
,
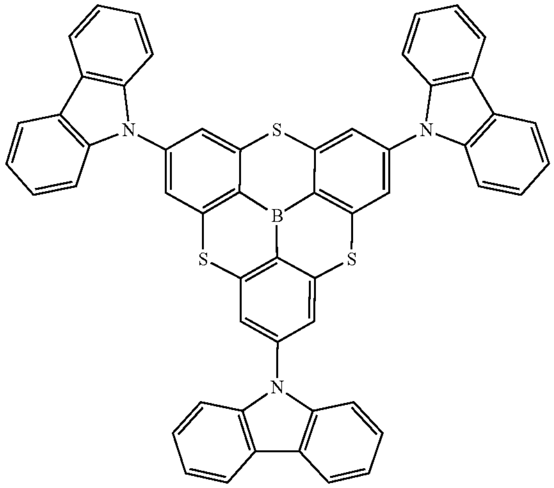
, -continued
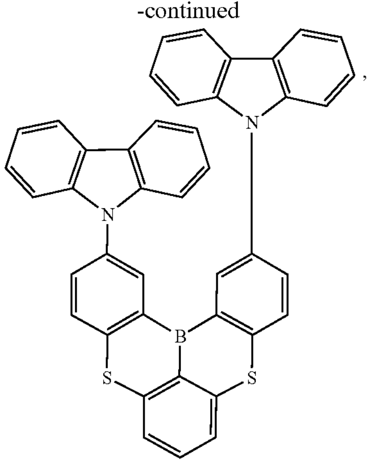
,
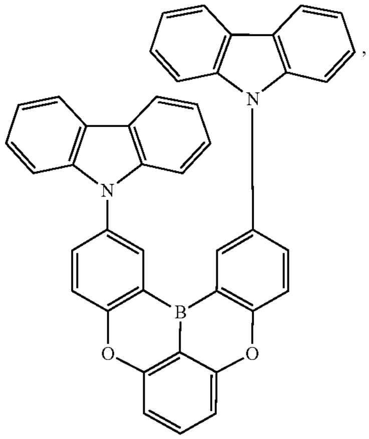
,
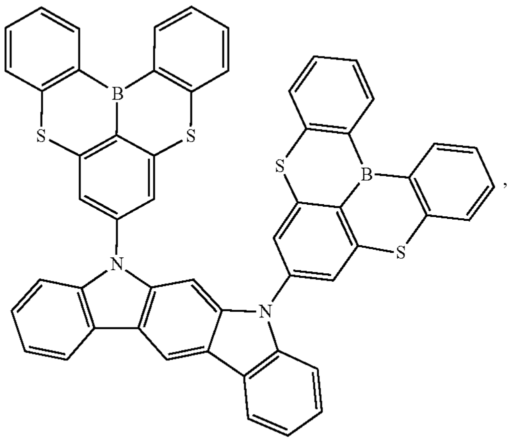
,
-continued
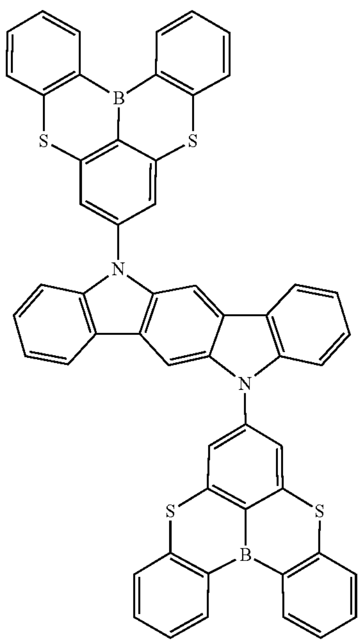
,
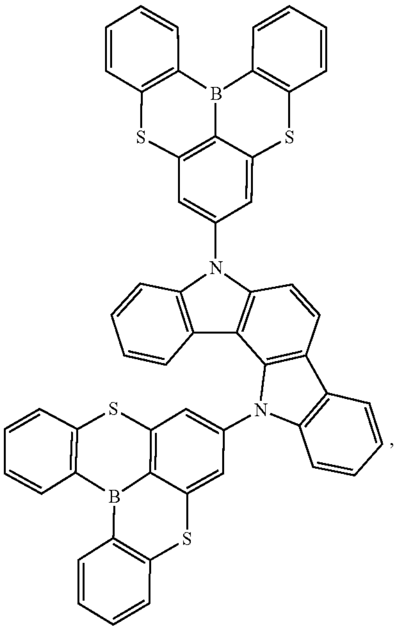
, -continued
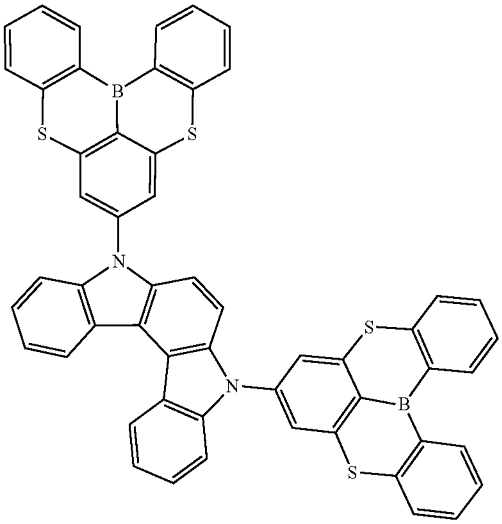
,
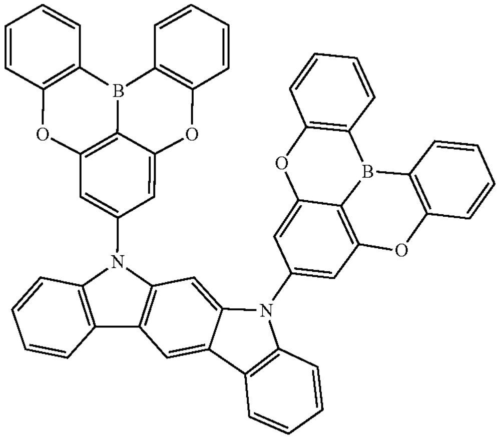
,
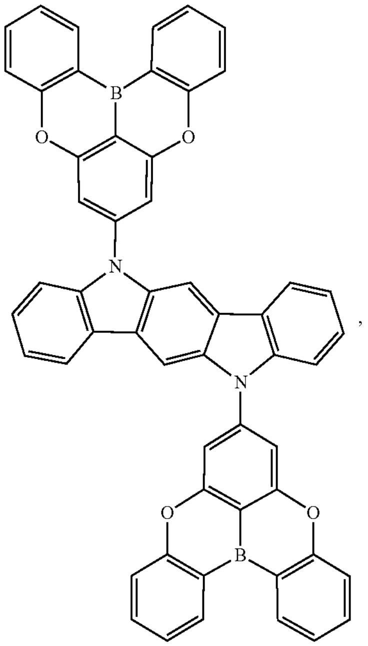
,
-continued
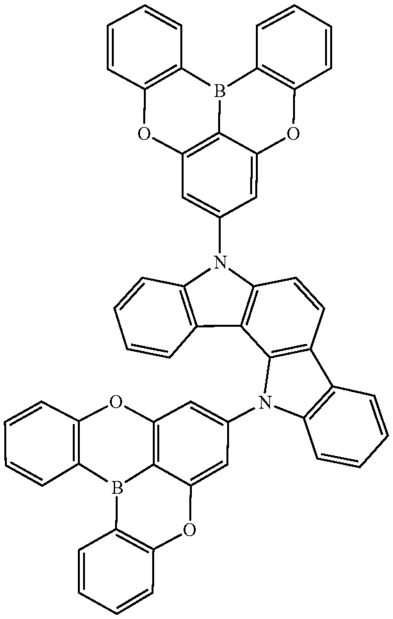
,
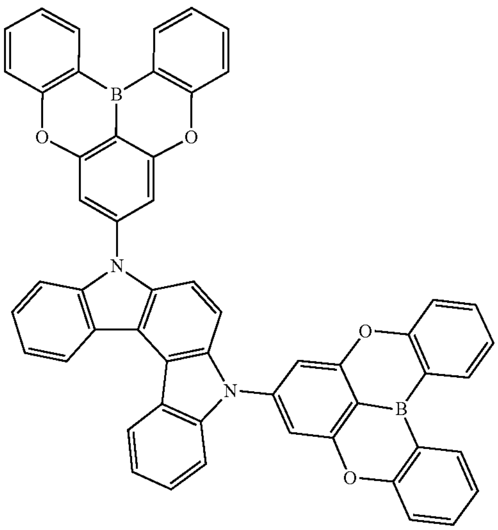
,
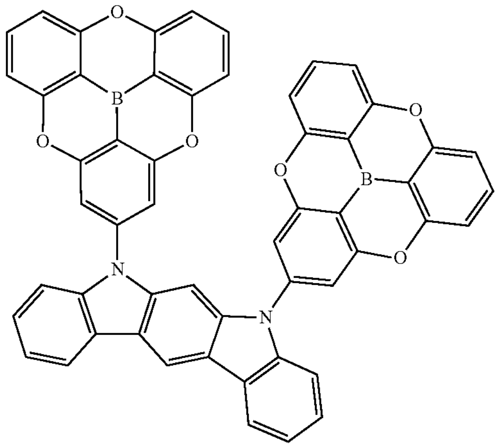
, -continued
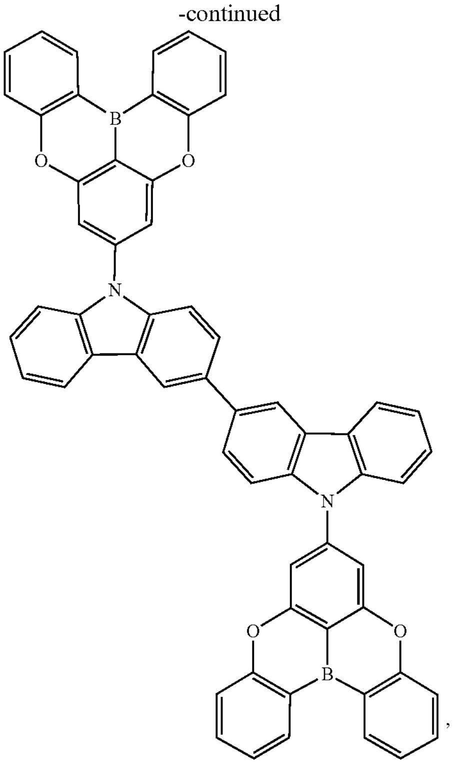
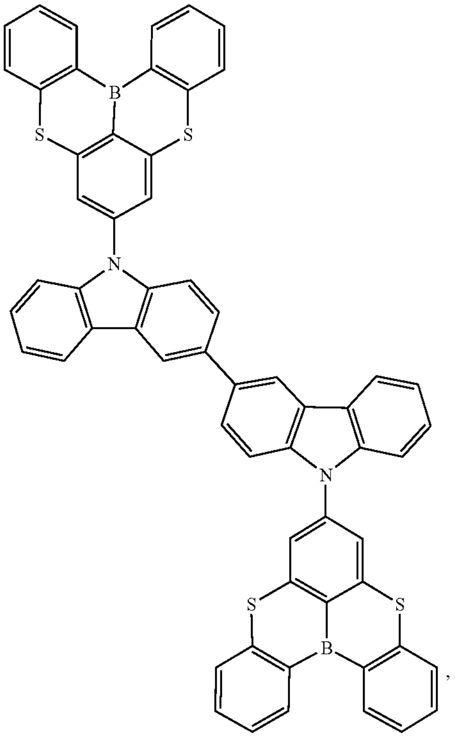
-continued
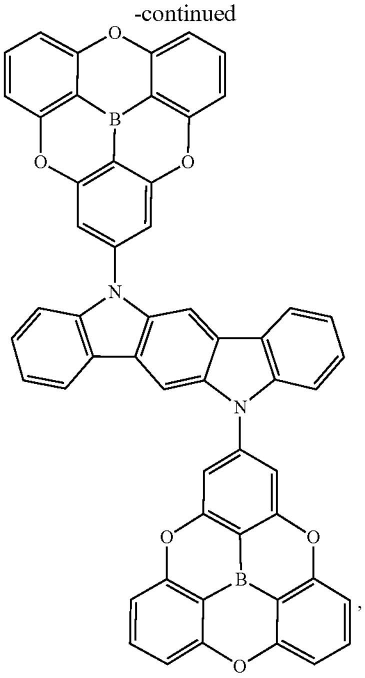
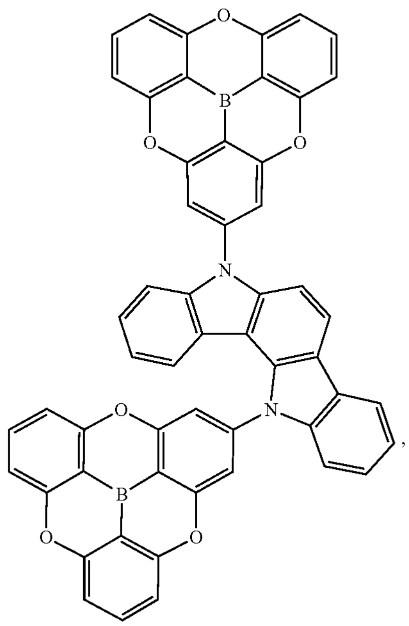

-continued
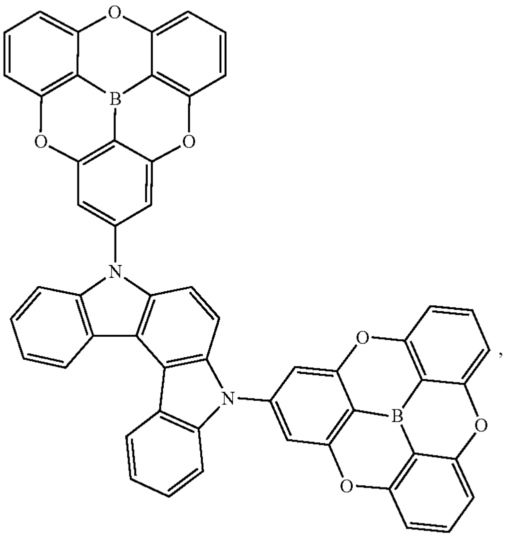
,
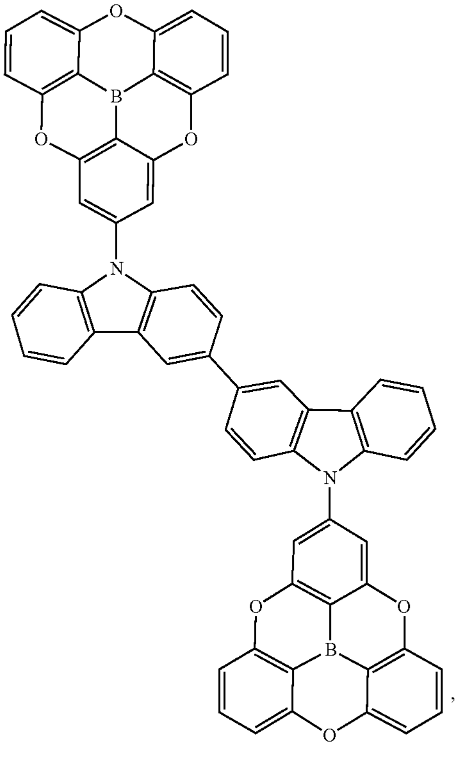
,
-continued
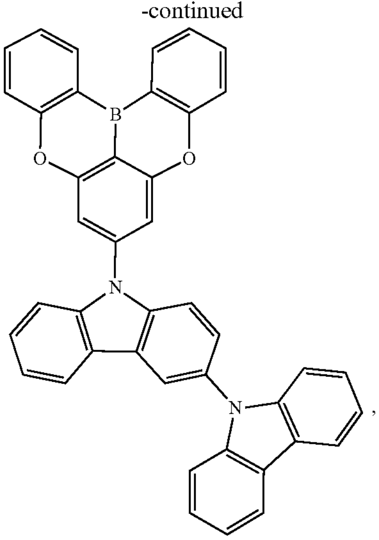
,
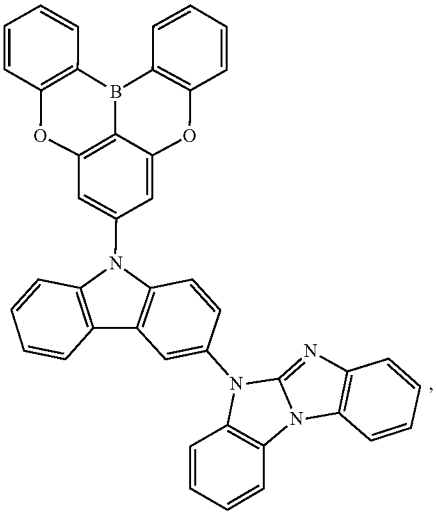
,
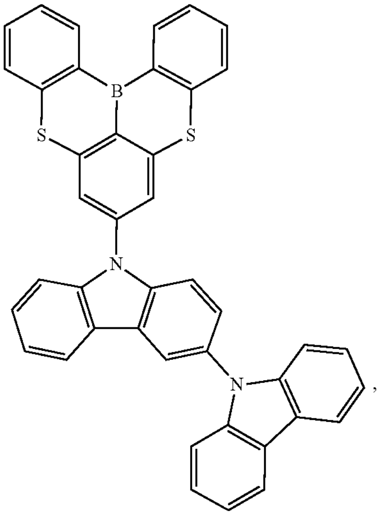
, -continued
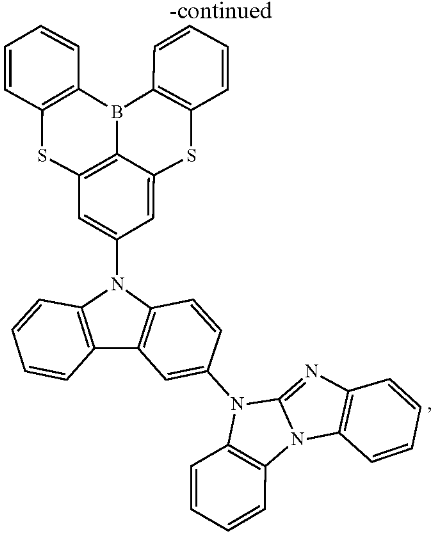
,
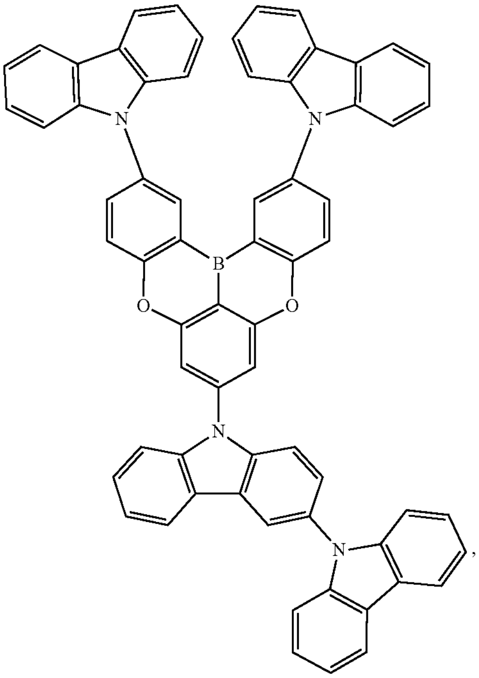
,
-continued
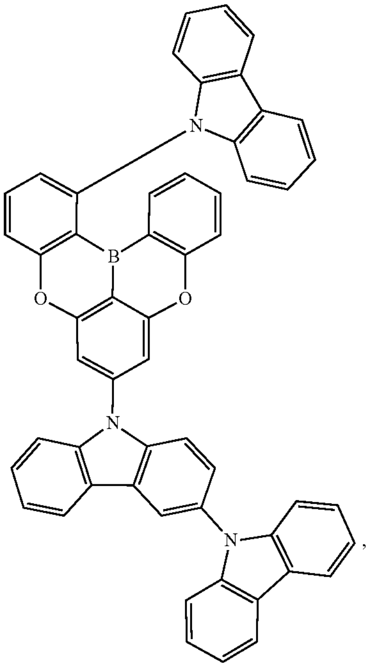
,
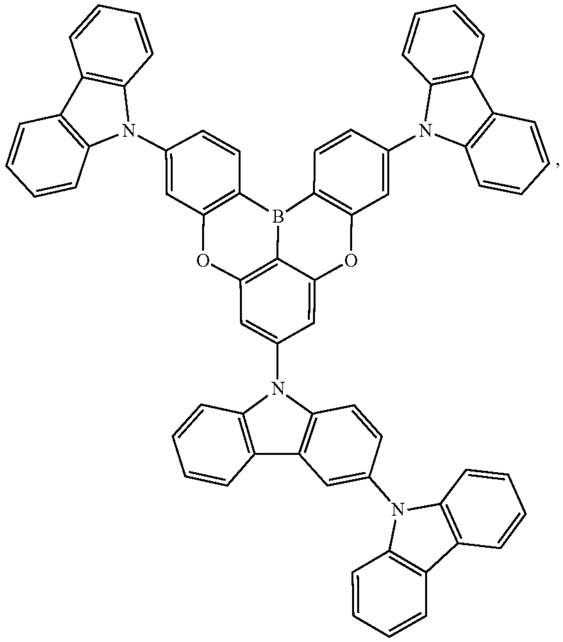
,
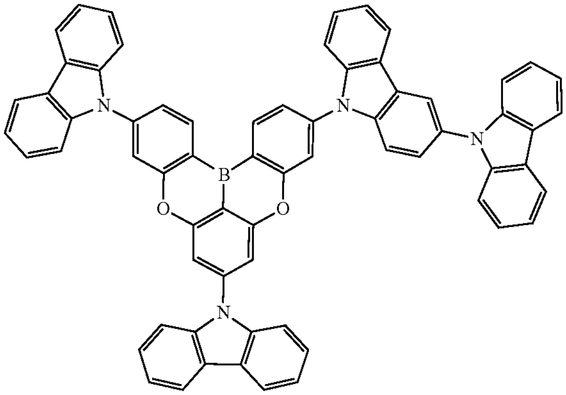
, -continued
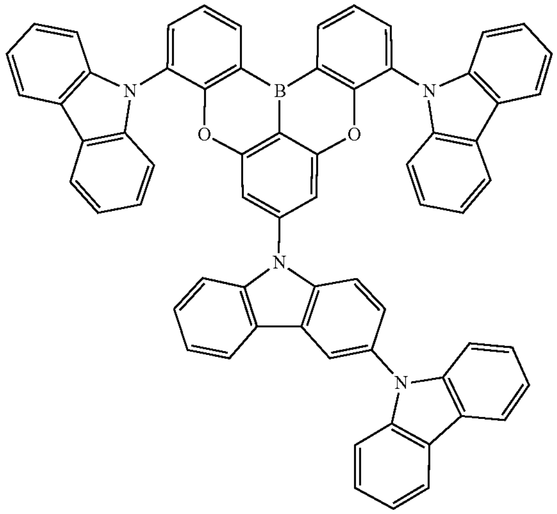
,
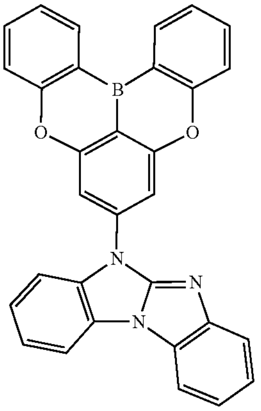
,
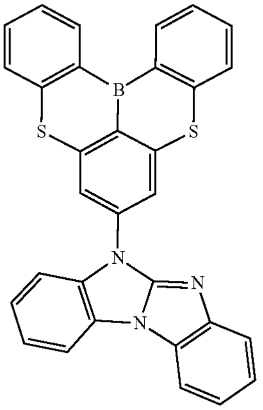
,
-continued
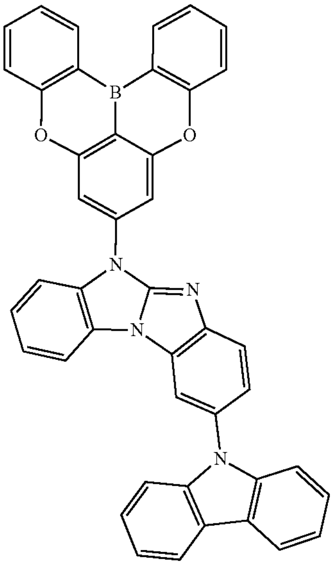
,
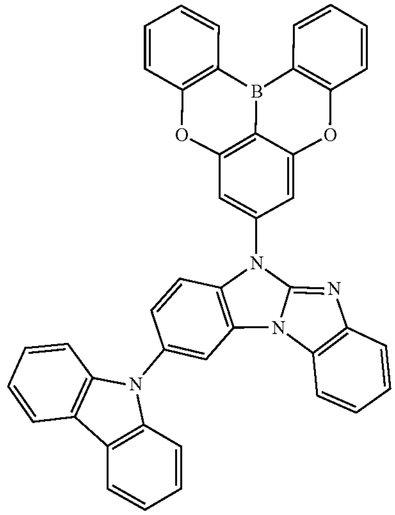
,
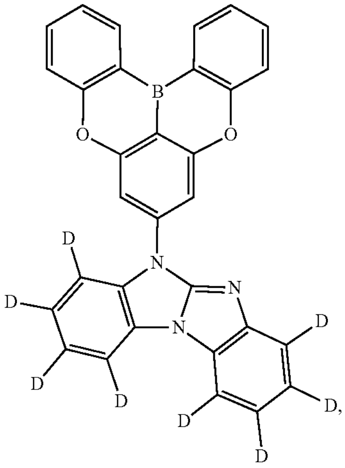
, -continued
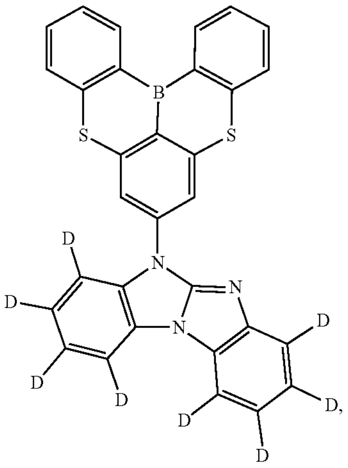
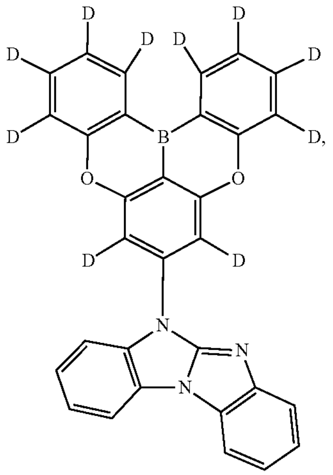
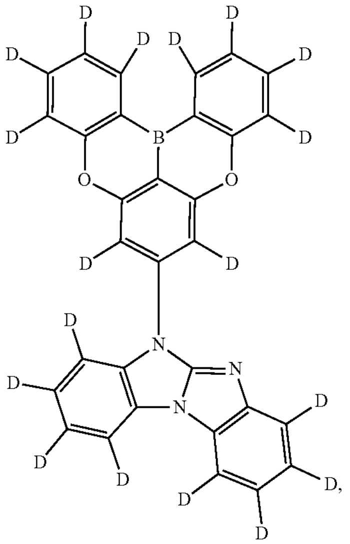
-continued
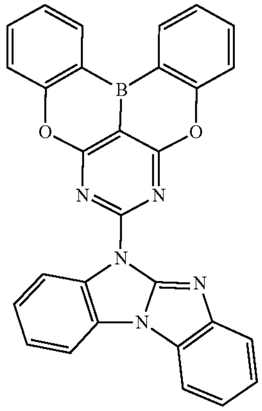
,
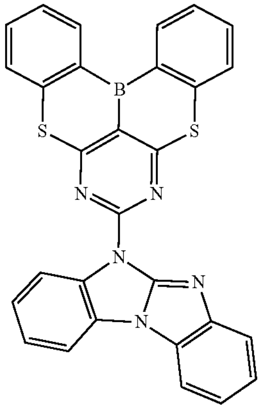
,
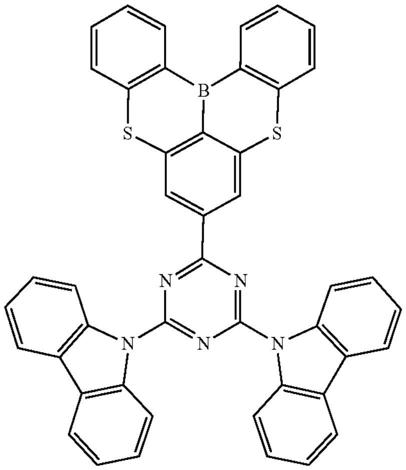
, -continued
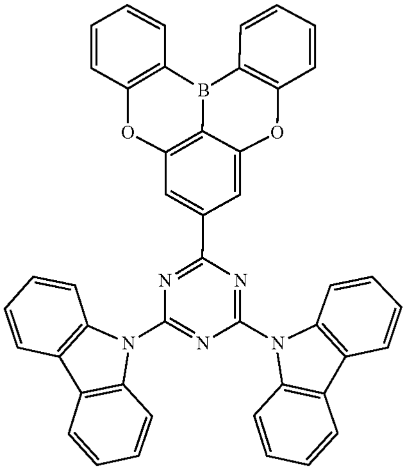
,
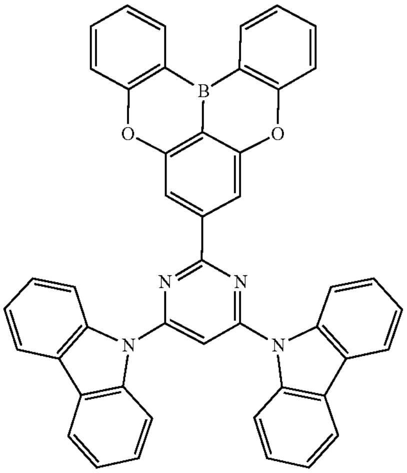
,
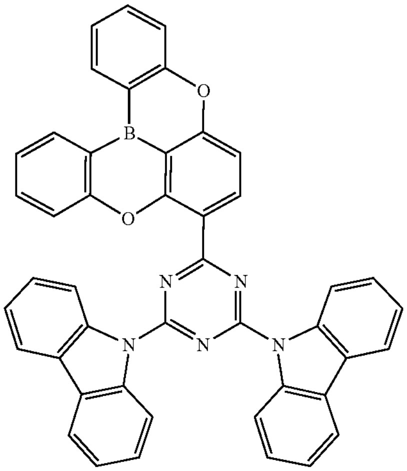
,
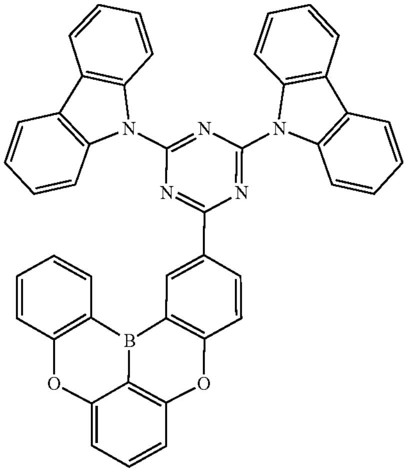
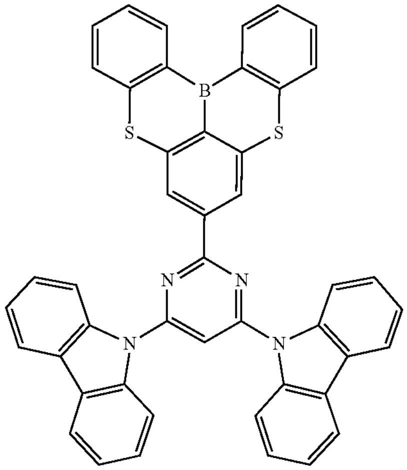
,
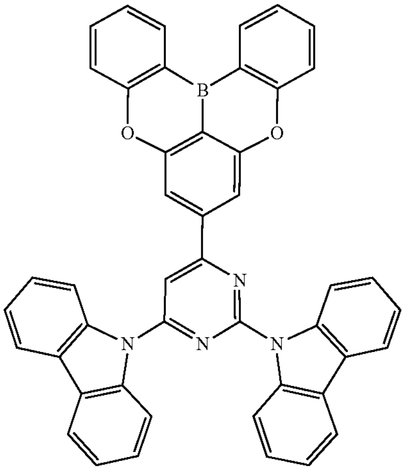
, -continued
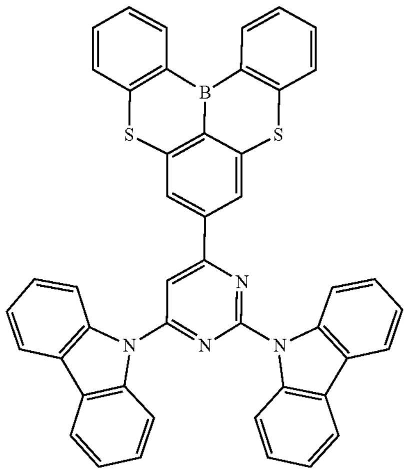
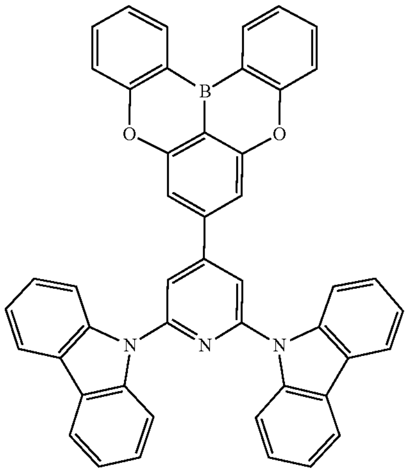
,
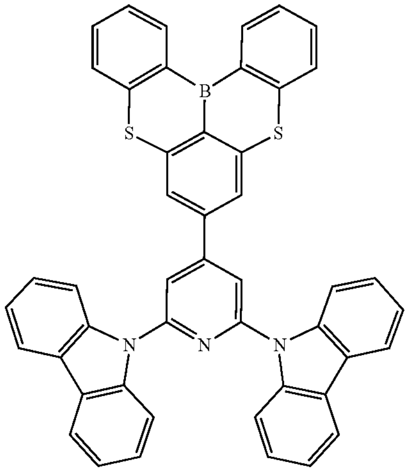
-continued
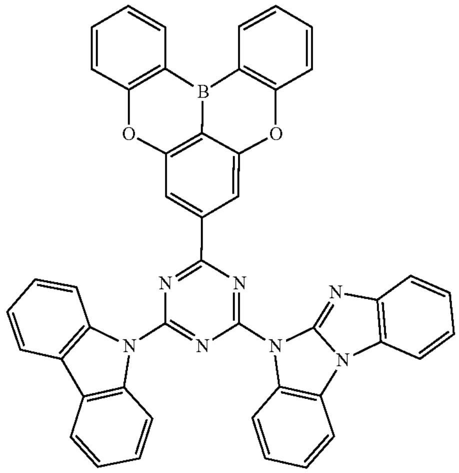
,
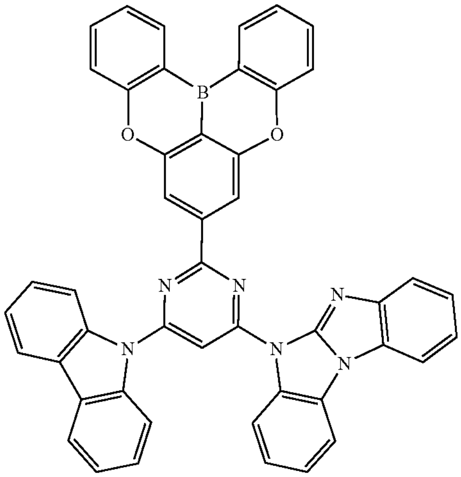
,
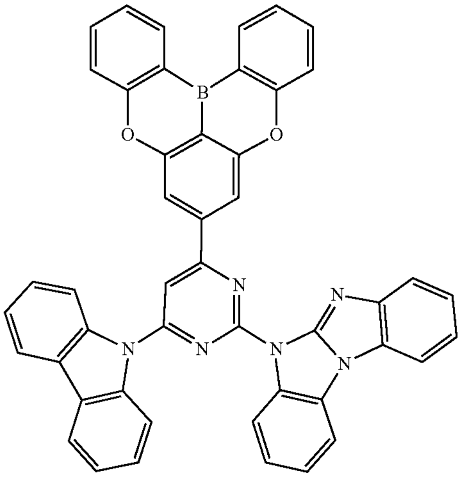
, -continued
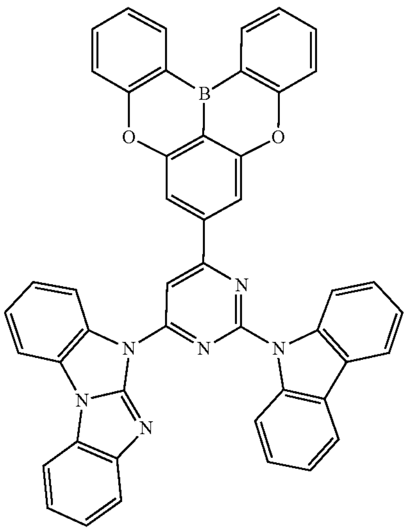
,
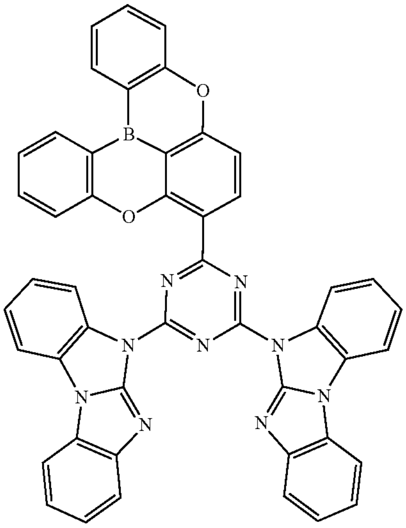
,
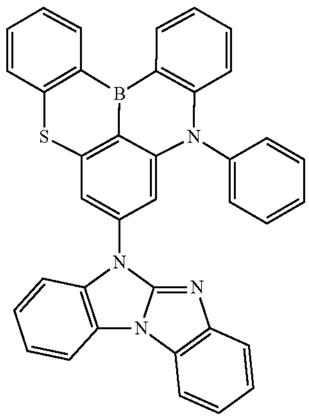
,
-continued
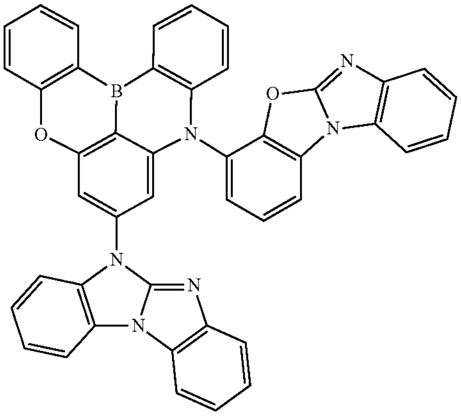
,
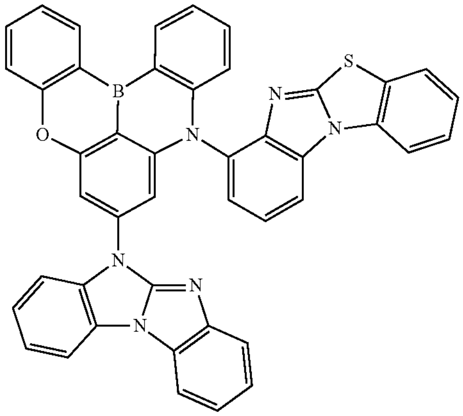
,
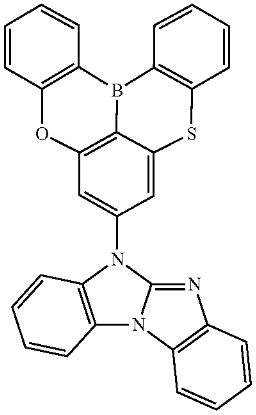
,
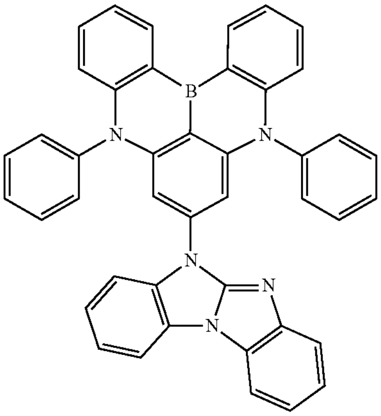
, -continued
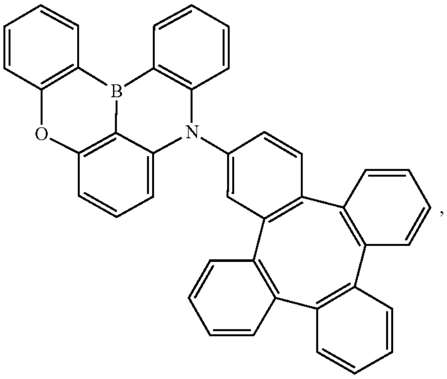
,
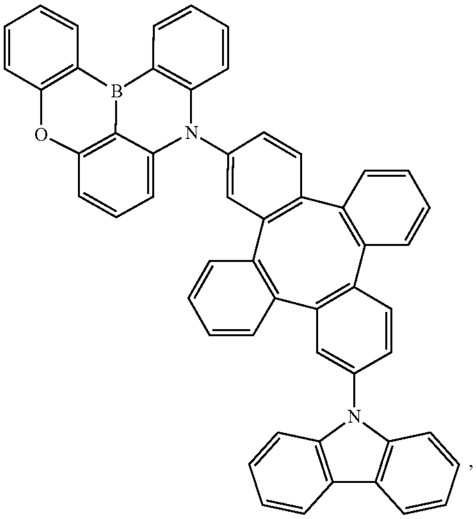
,
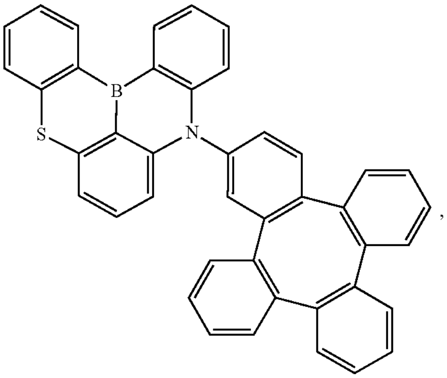
,
-continued
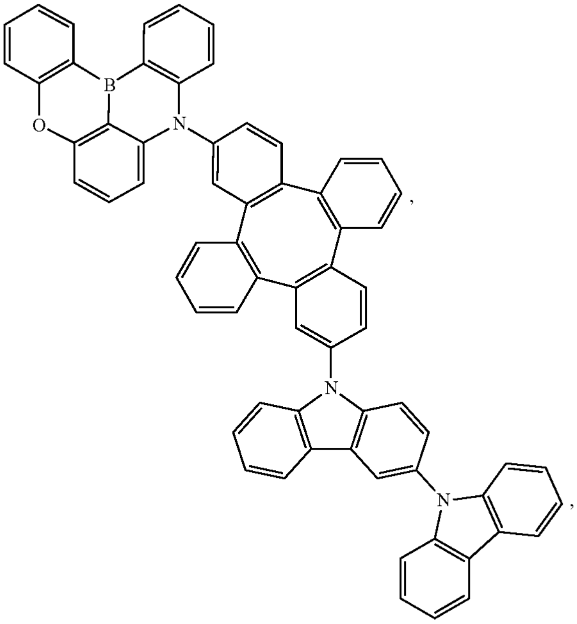
,
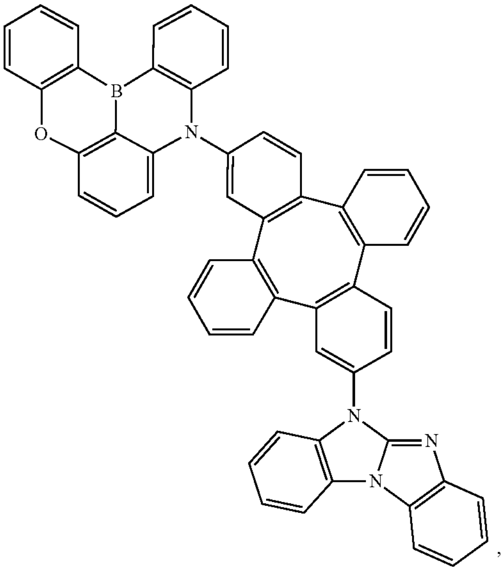
, -continued
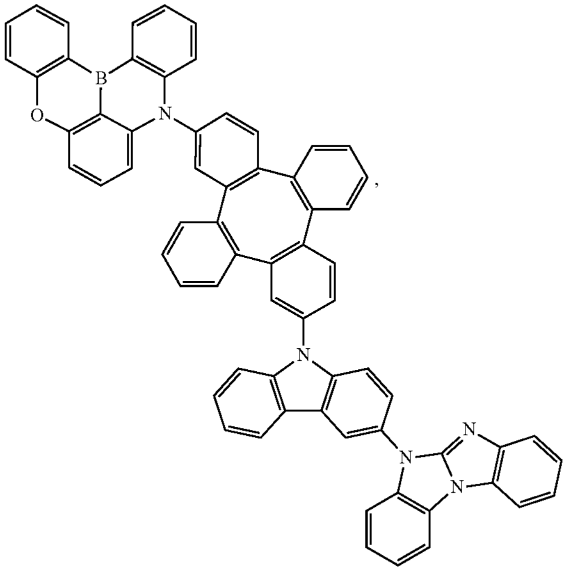
,
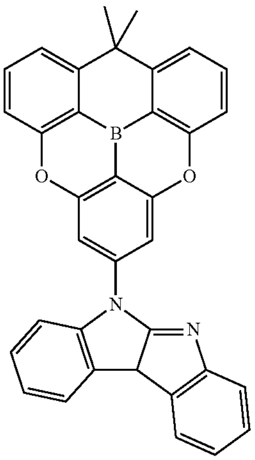
,
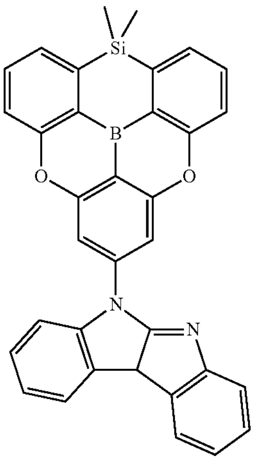
,
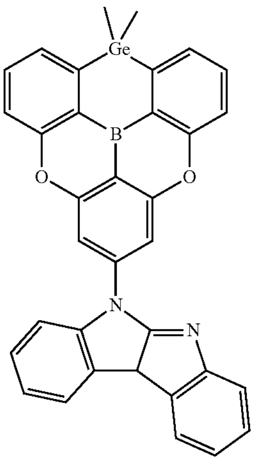
,
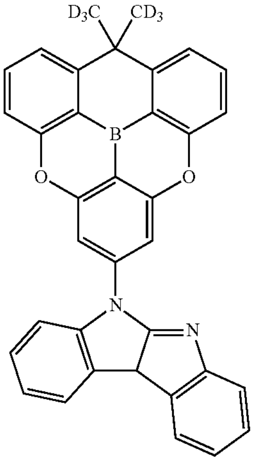
,
-continued
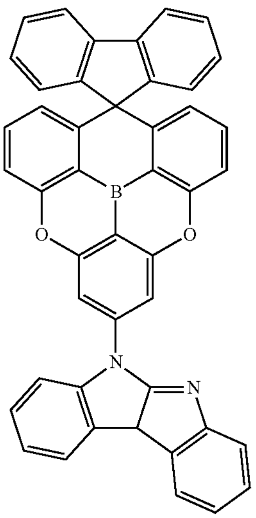
,
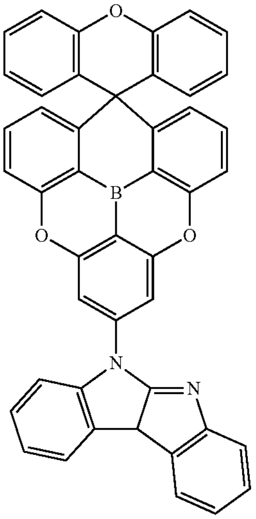
,
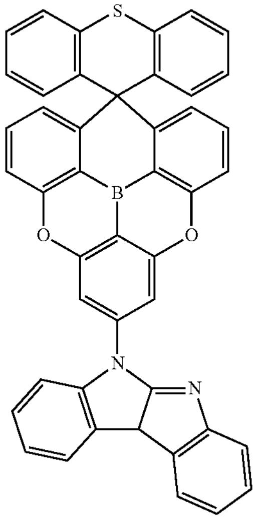
,
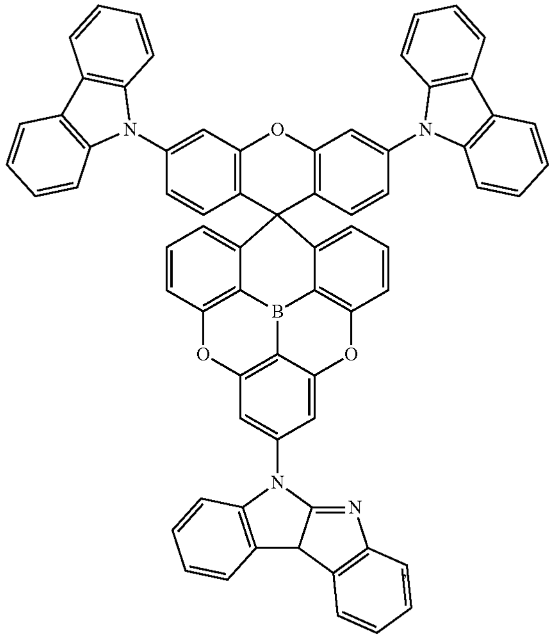
, -continued
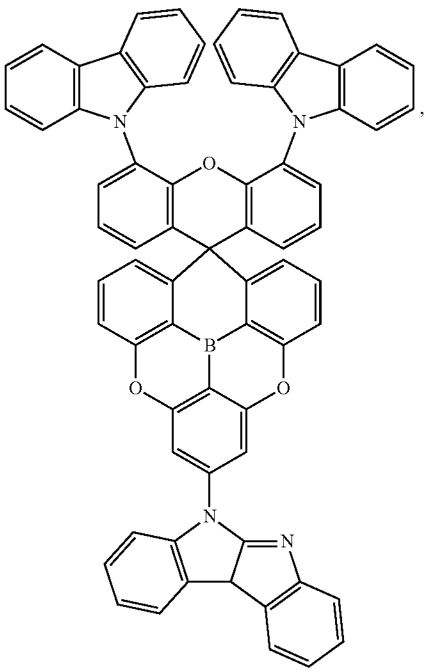
,
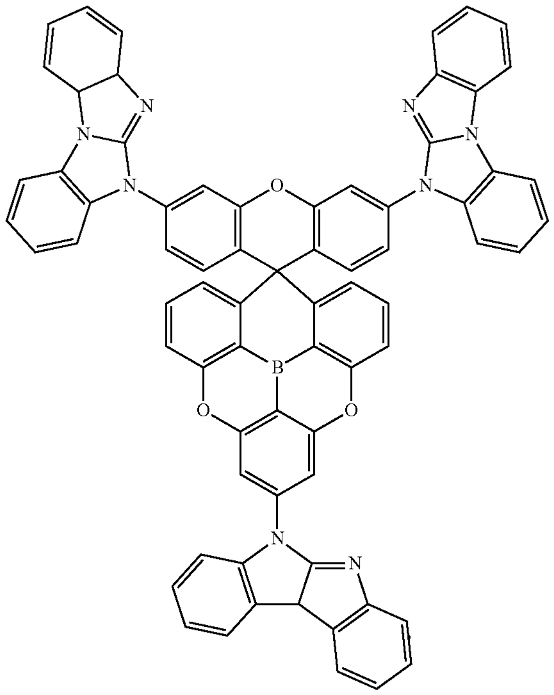
,
-continued
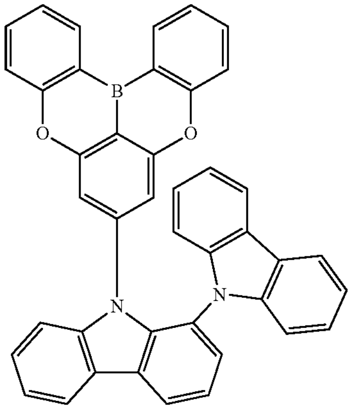
,
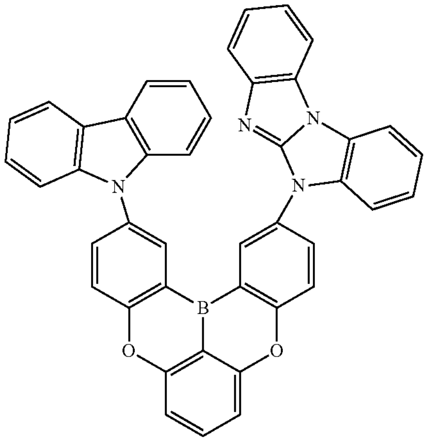
,
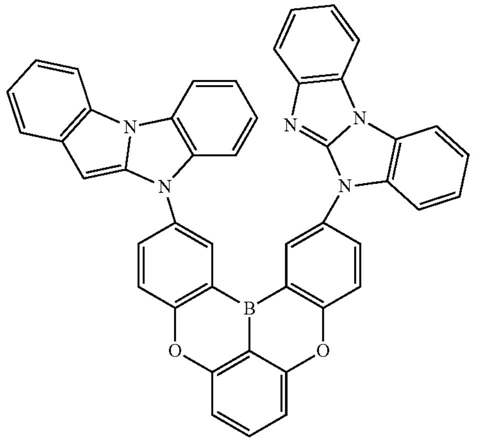
,
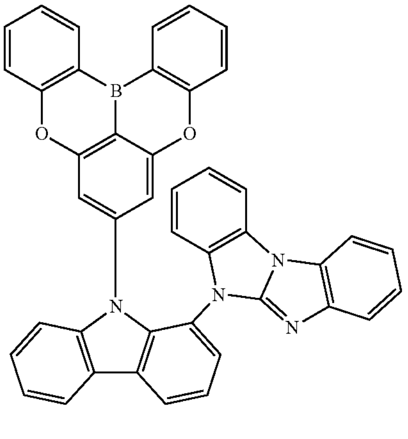
, -continued
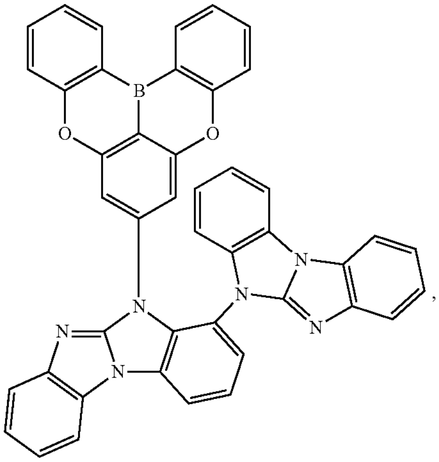
,
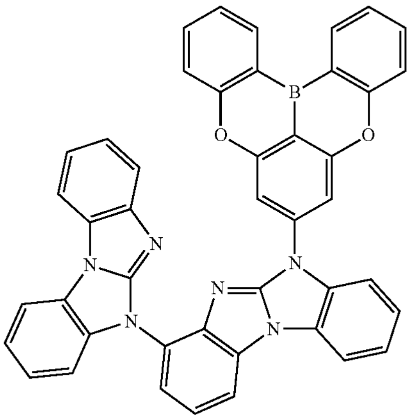
,
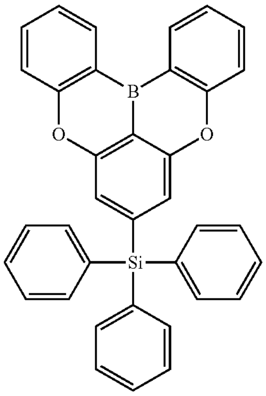
,
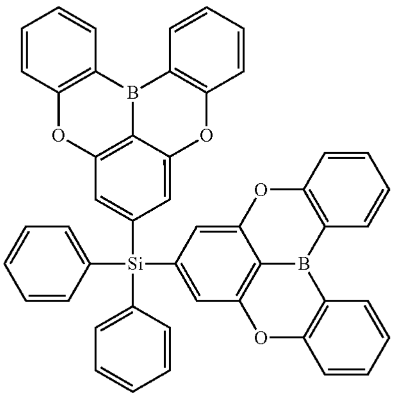
,
-continued
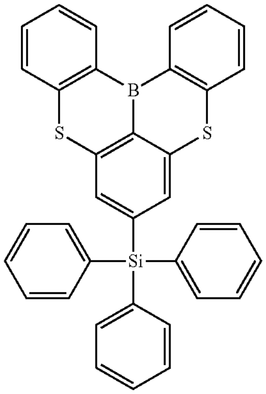
,
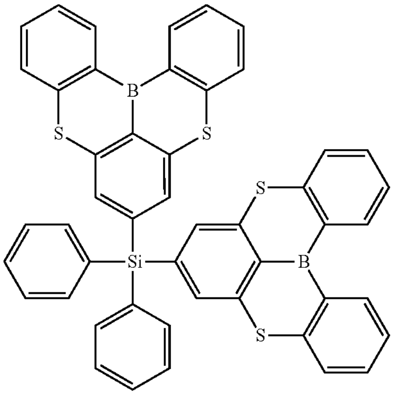
,
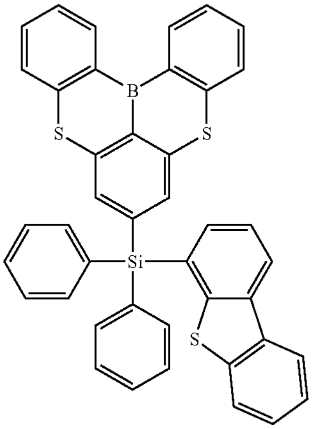
,
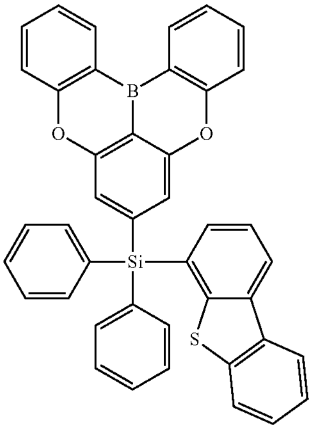
, -continued
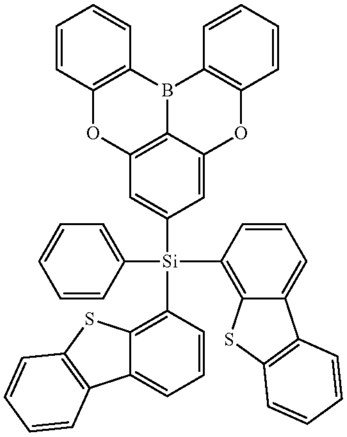
,
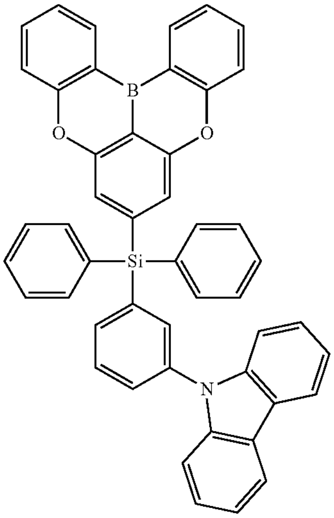
,
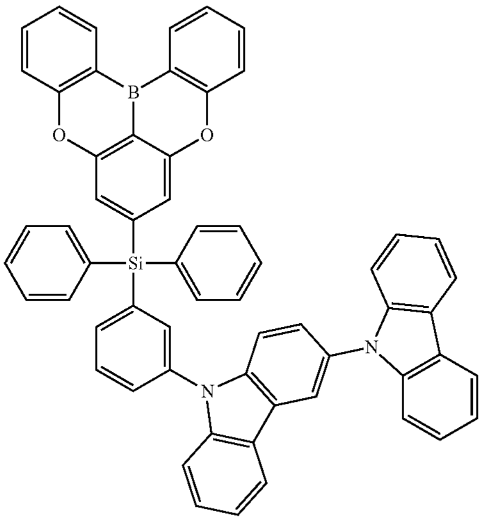
,
-continued
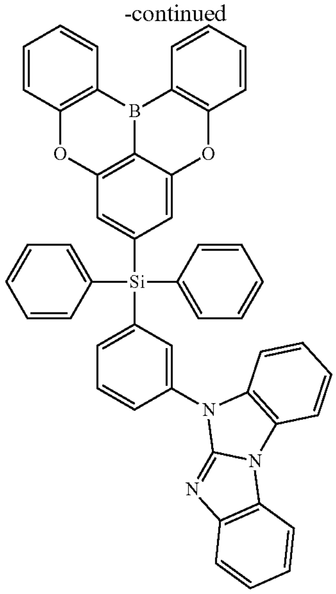
,
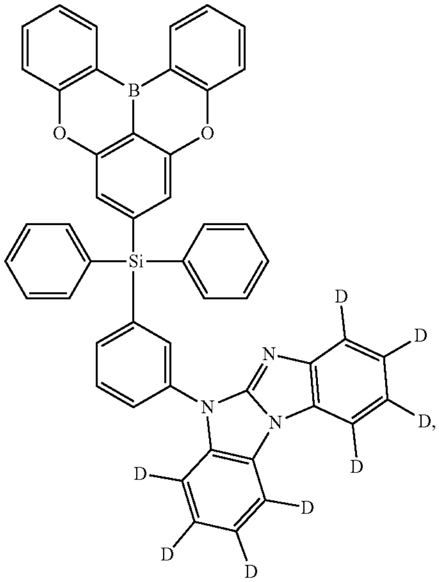
,
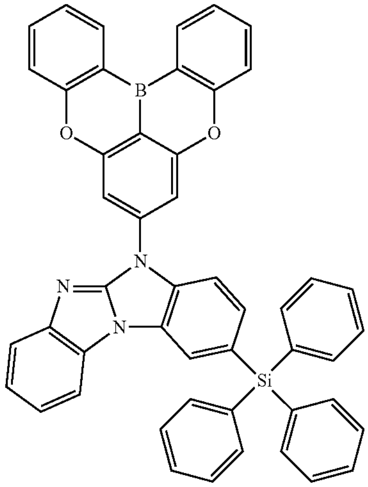
, -continued
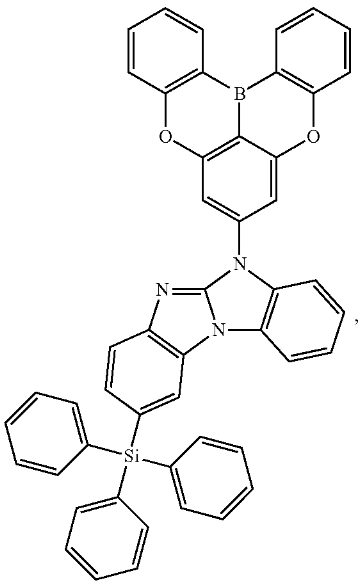
,
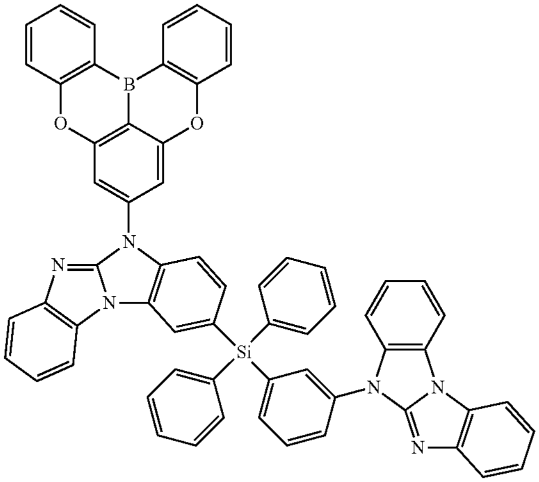
,
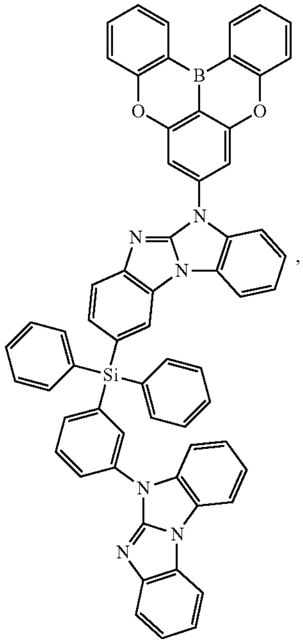
,
-continued
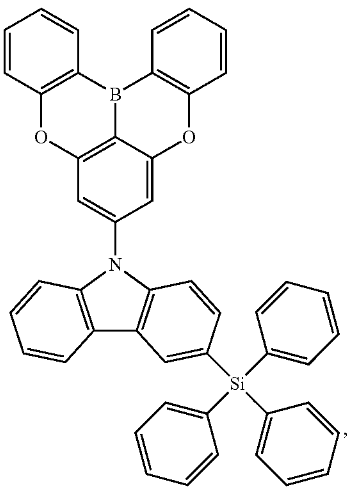
,
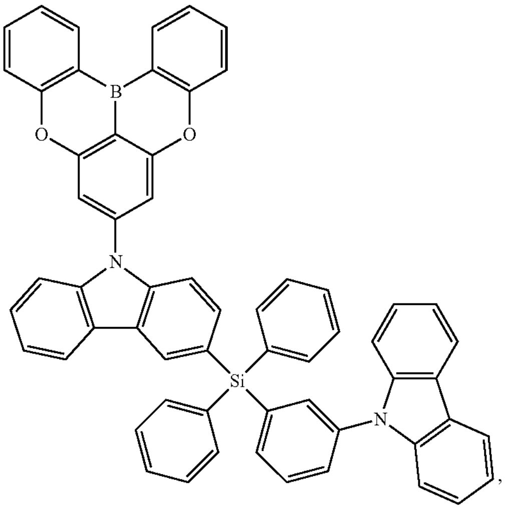
,
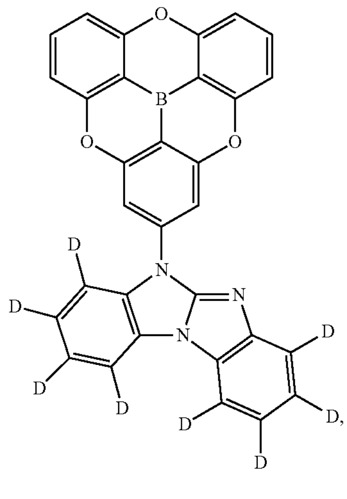
, -continued
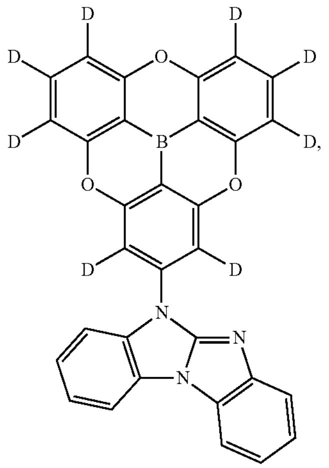
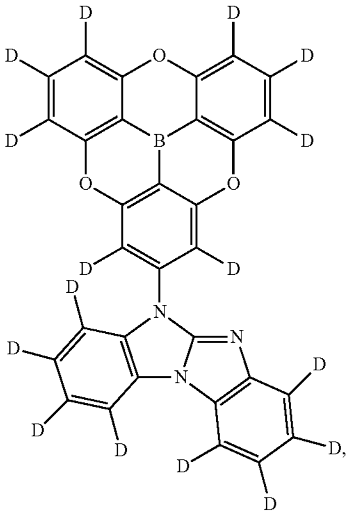
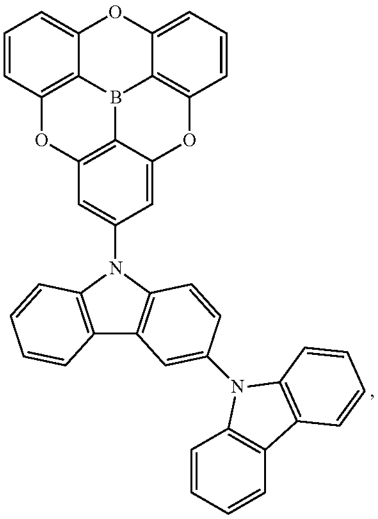
-continued
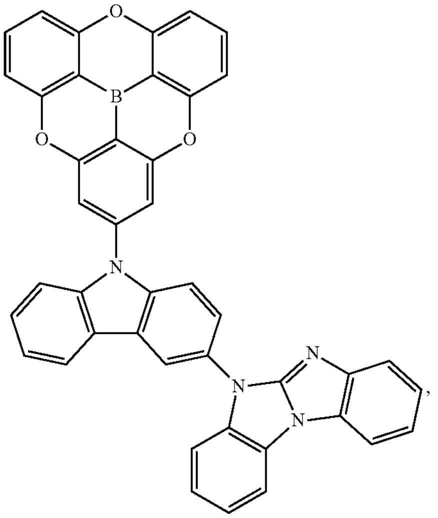
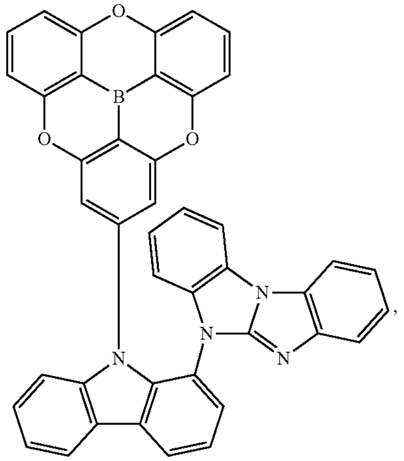
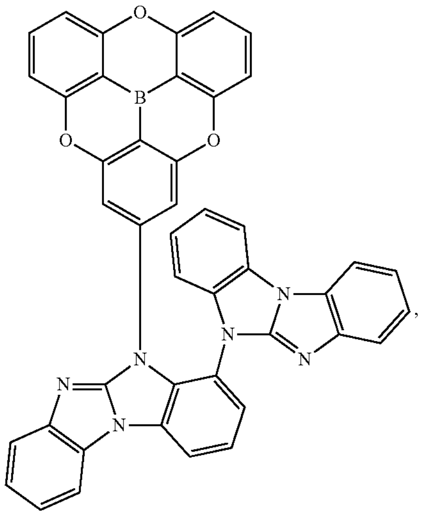

-continued
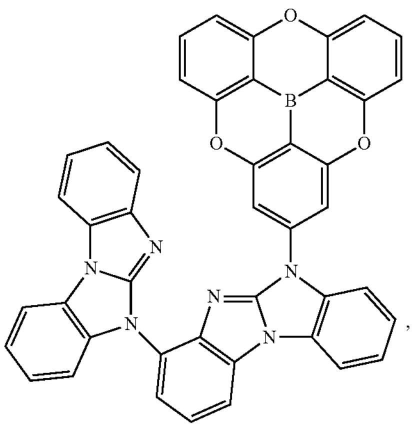
,
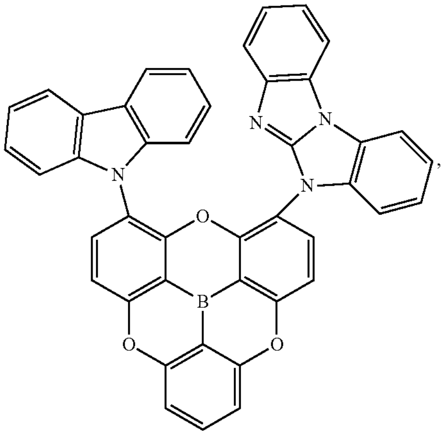
,
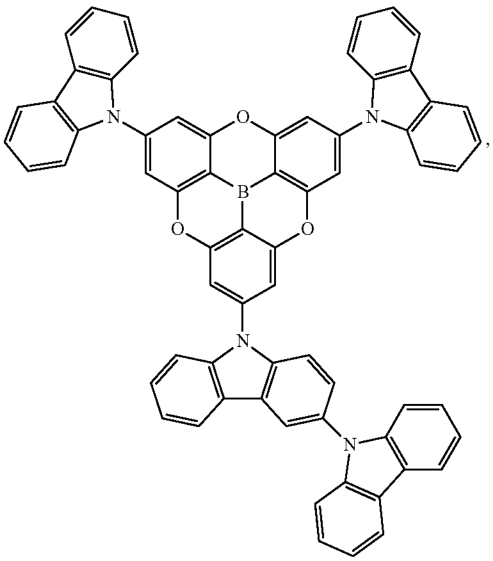
,
-continued
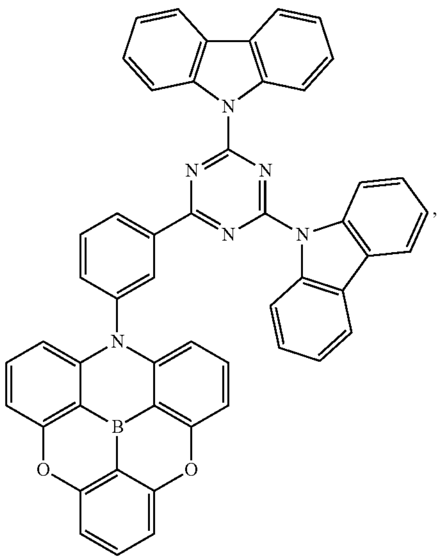
,
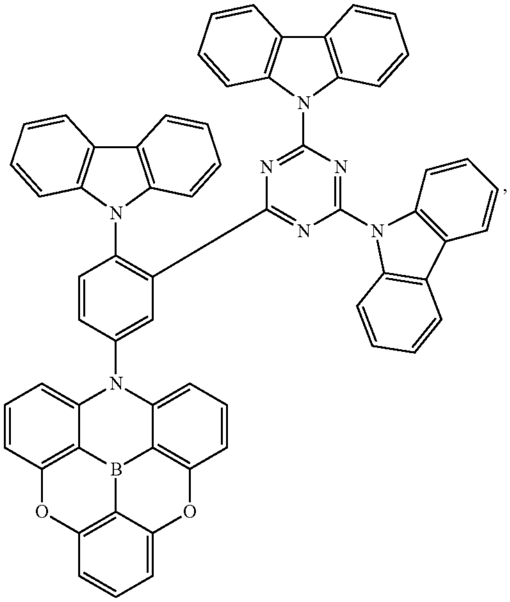
, -continued
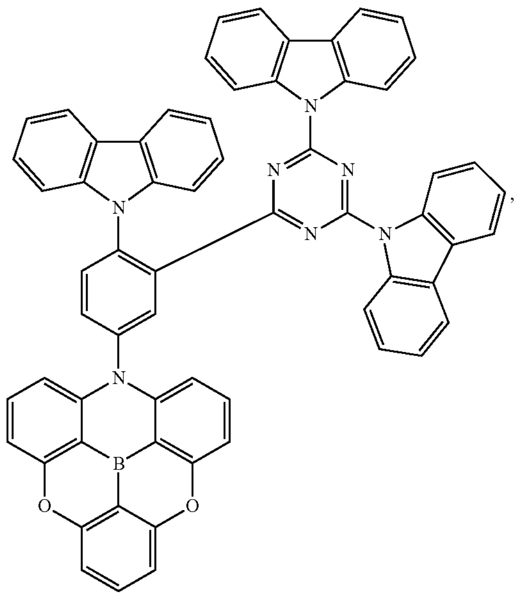
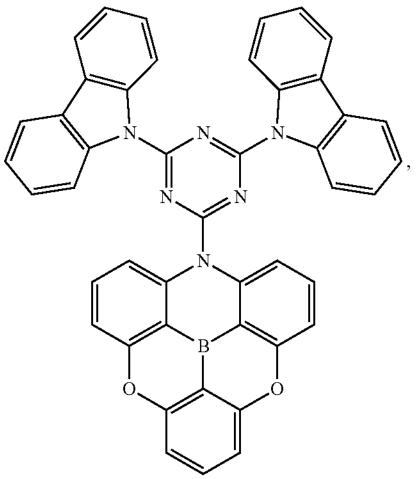
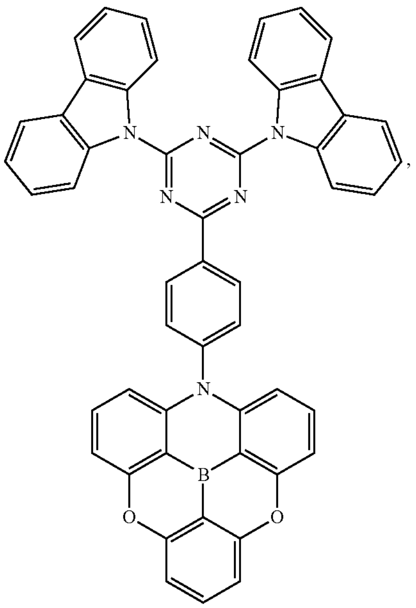
-continued
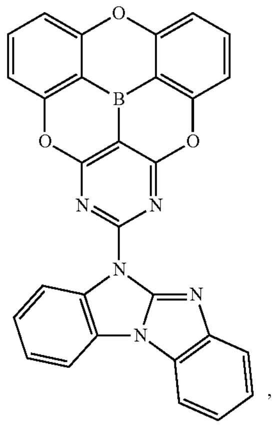
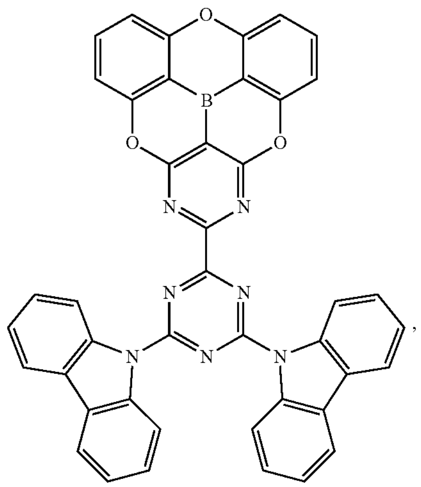
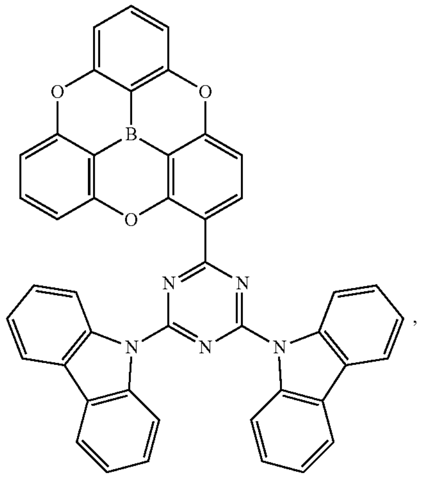

-continued
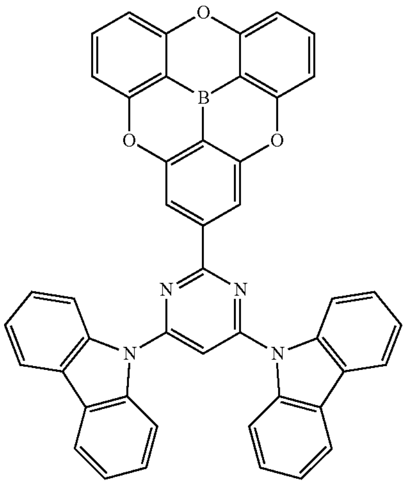
,
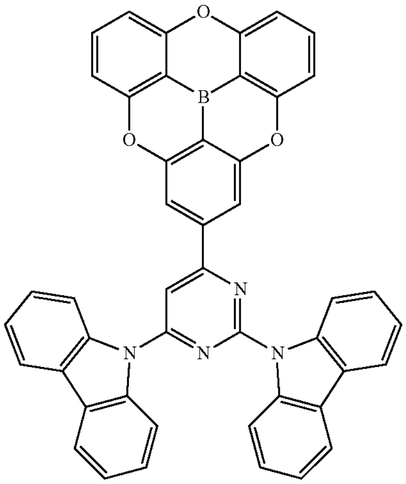
,
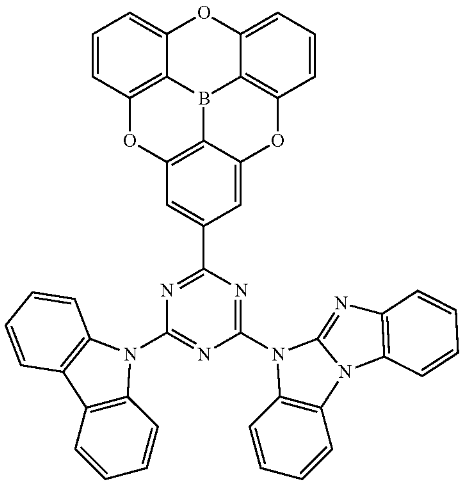
,
-continued
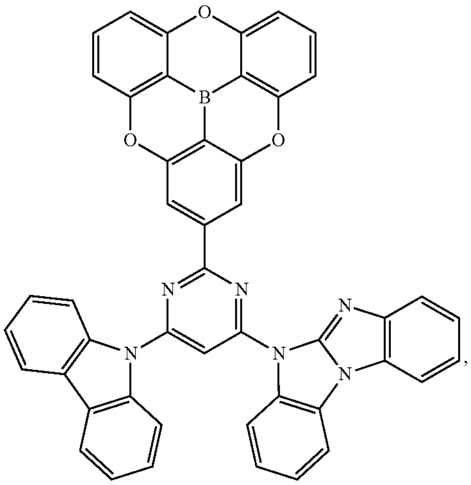
,
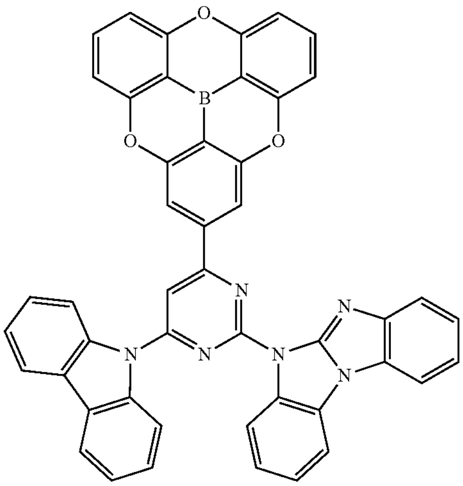
,
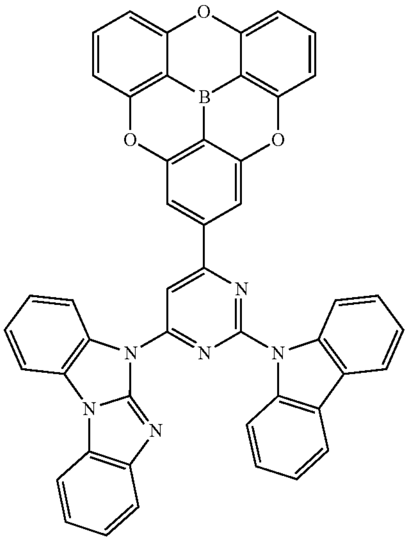
, -continued
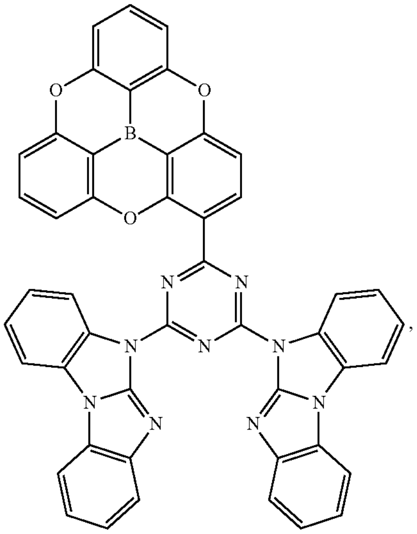
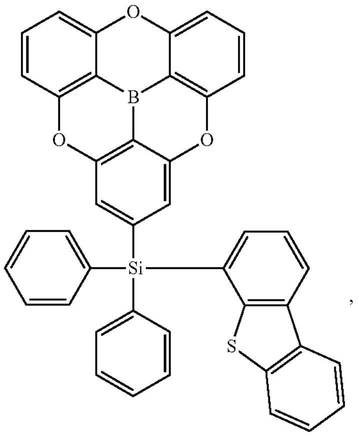
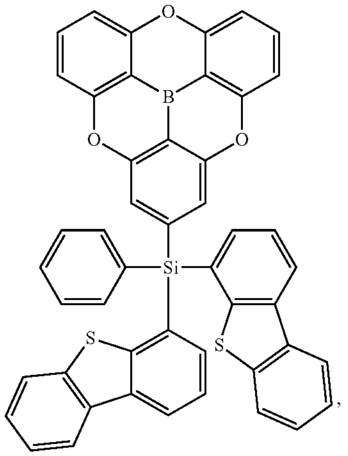
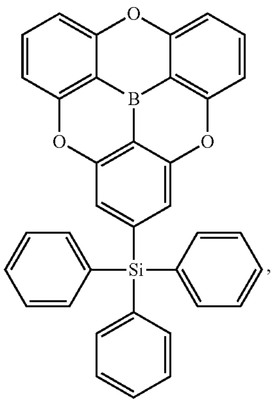
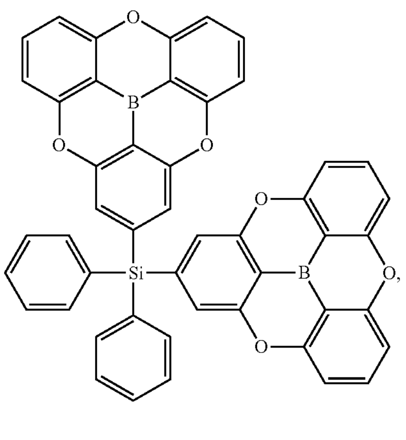
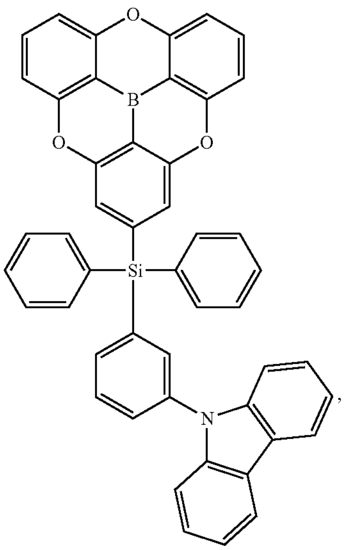

-continued
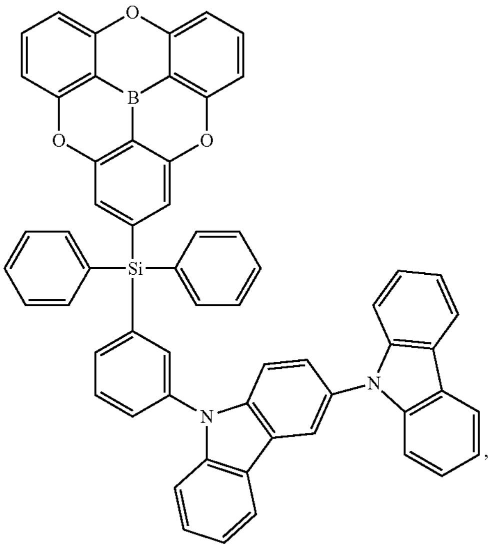
,
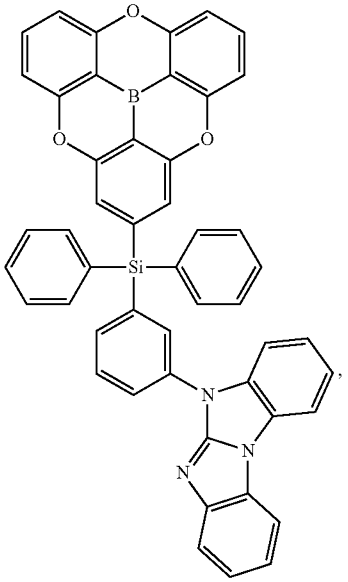
,
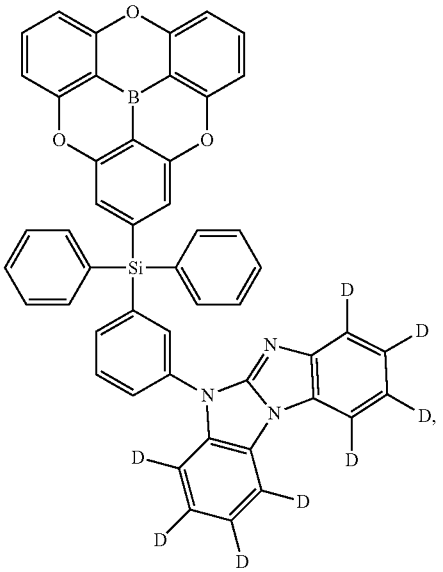
-continued
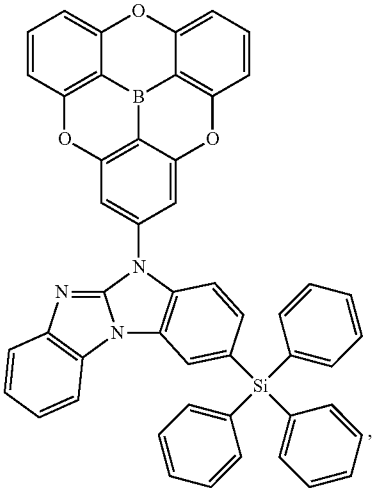
,
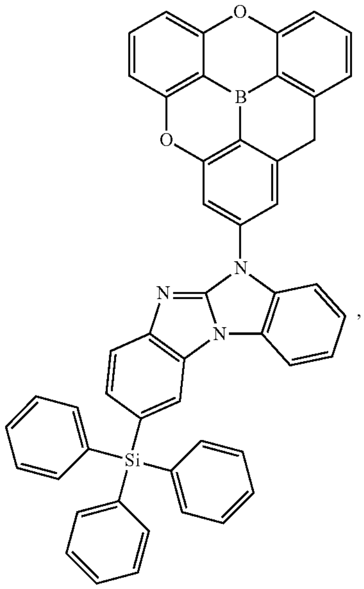
,
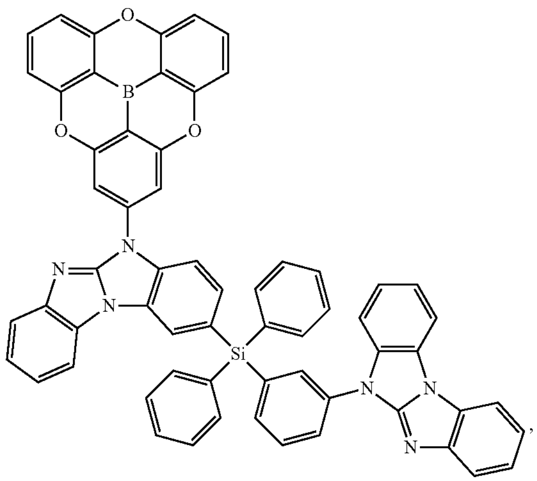
, -continued
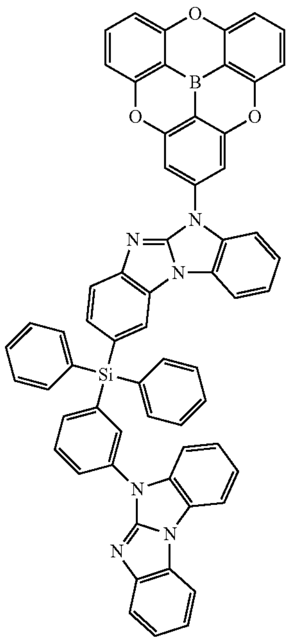
,
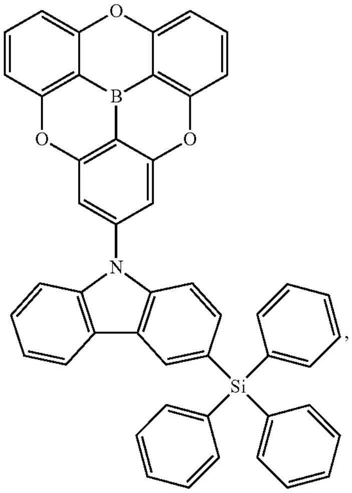
,
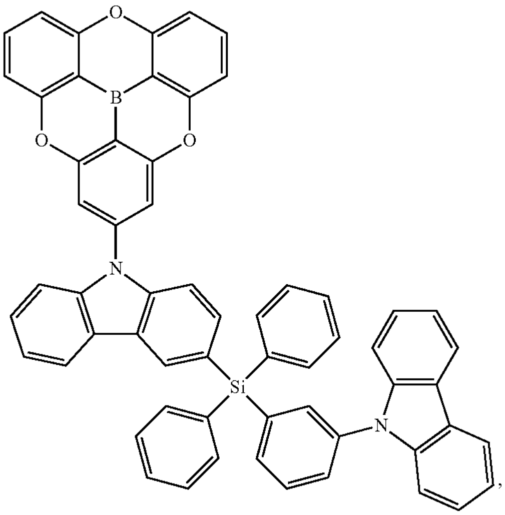
,
-continued
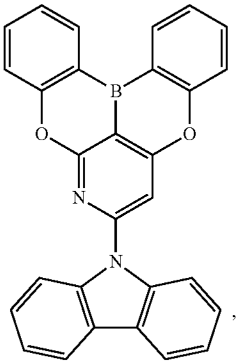
,
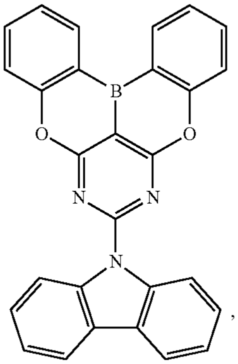
,
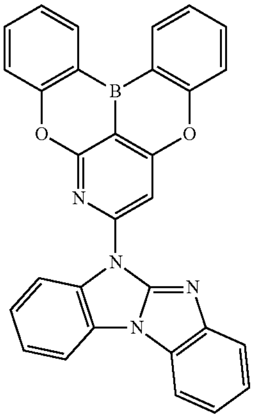
,
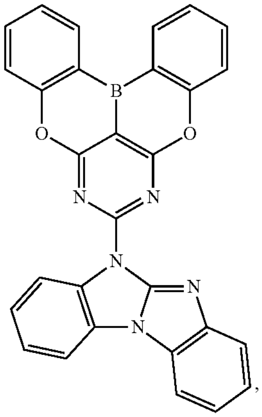
,
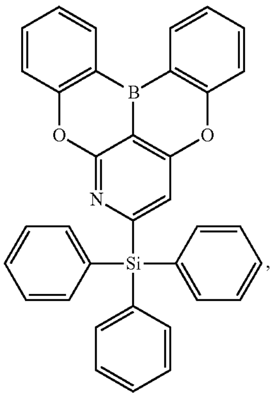
,
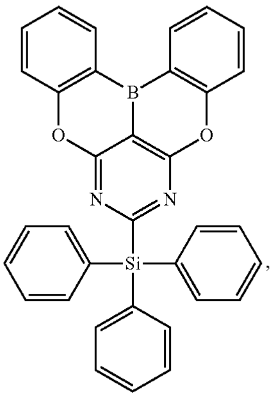
, -continued
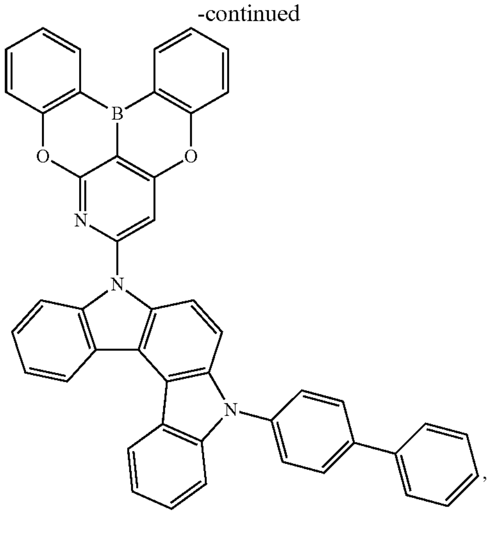
,
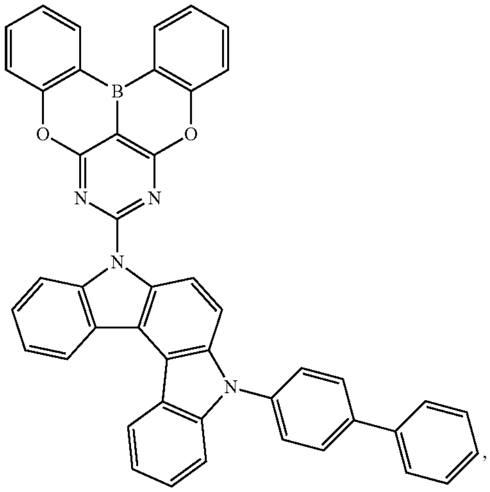
,
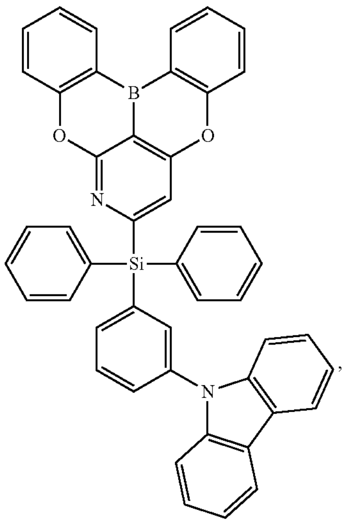
,
-continued
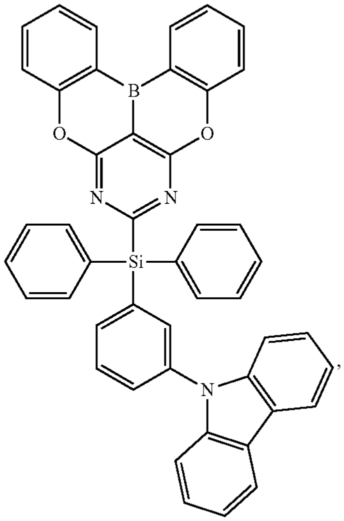
,
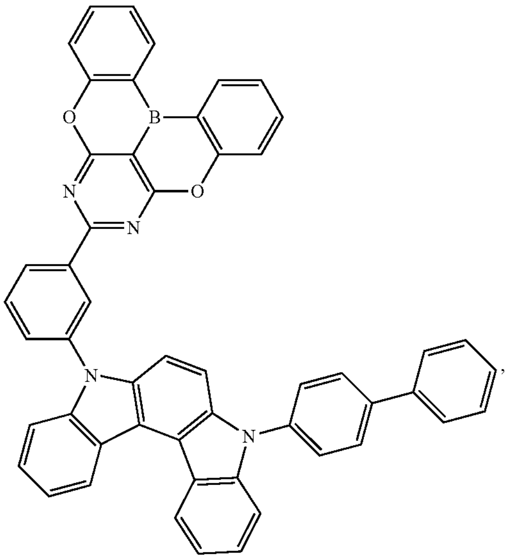
,
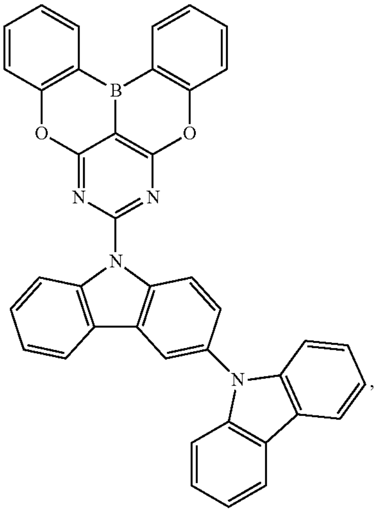
, -continued
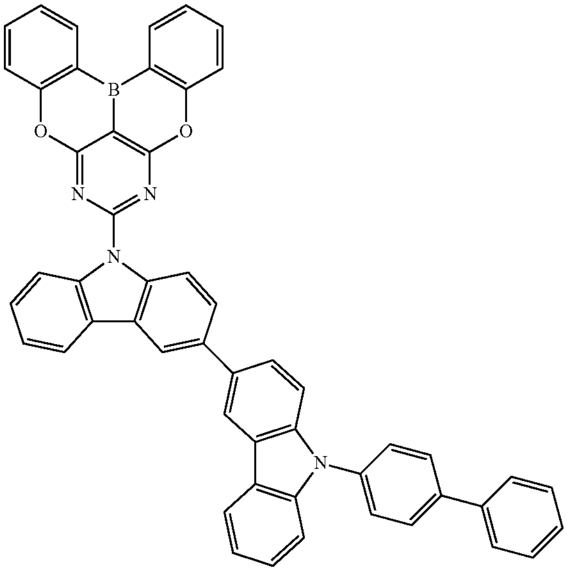
,
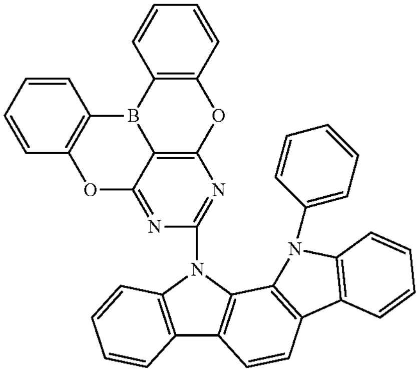
,
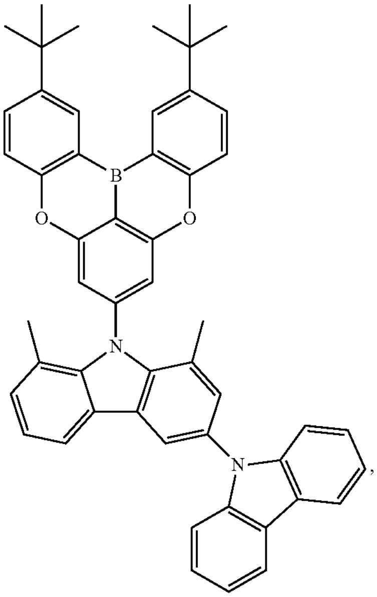
,
-continued
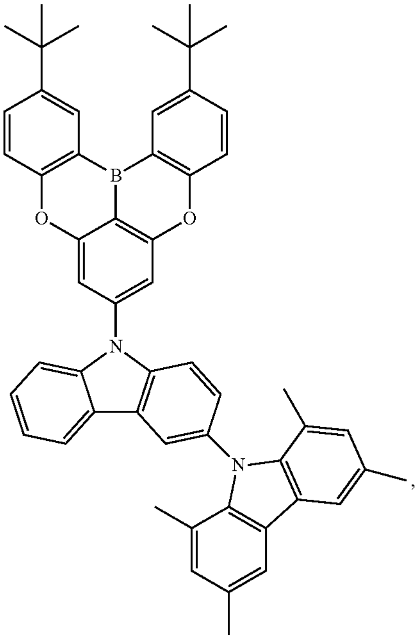
,
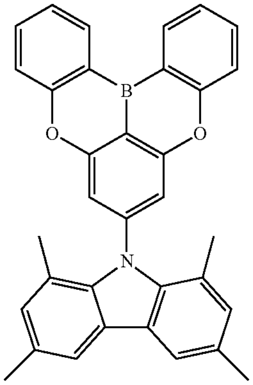
,
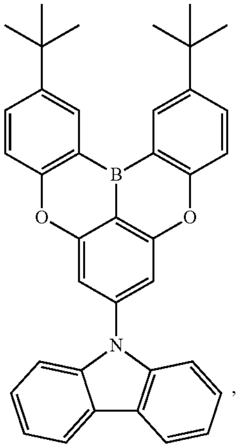
, -continued
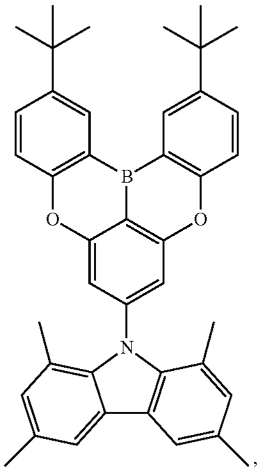
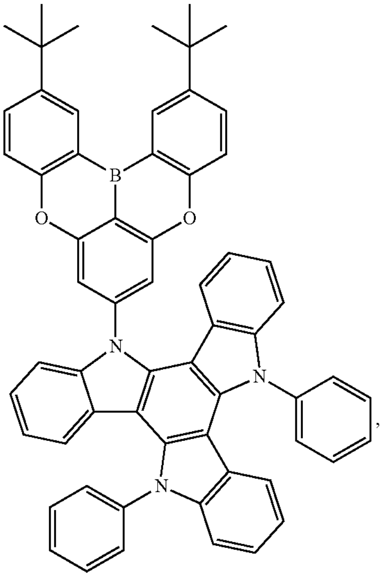
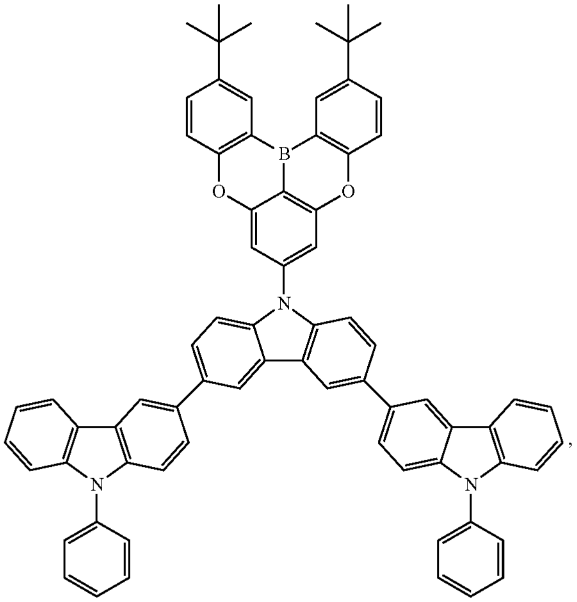
-continued
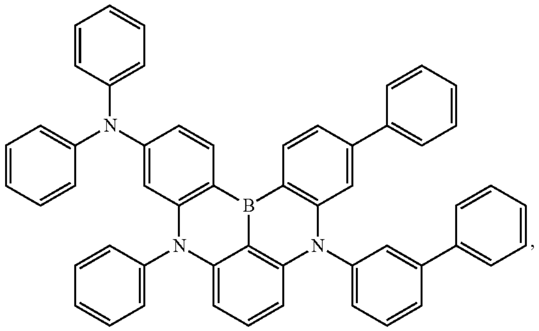
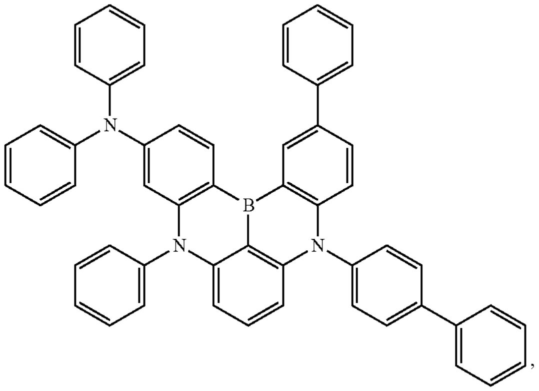
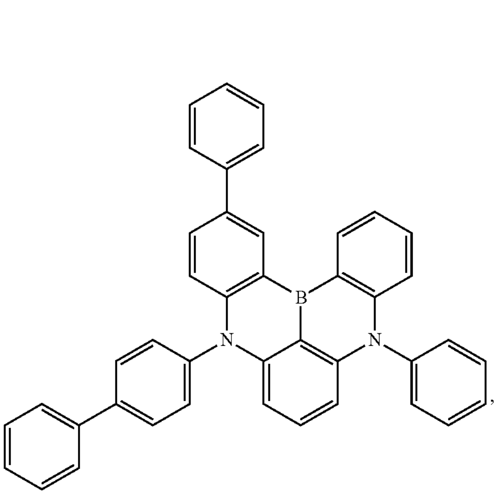

-continued
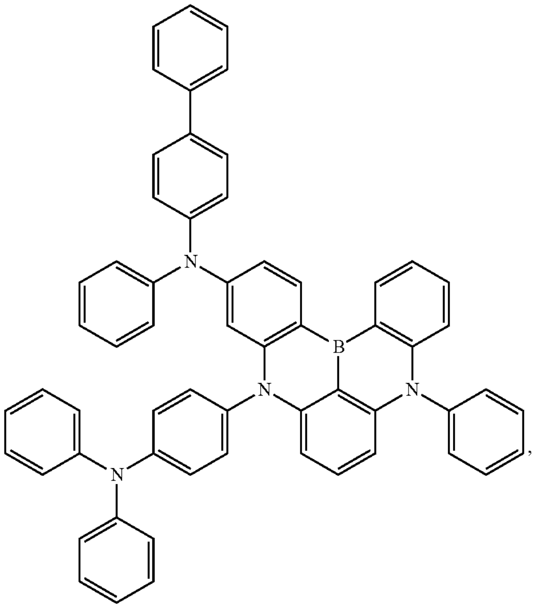
,
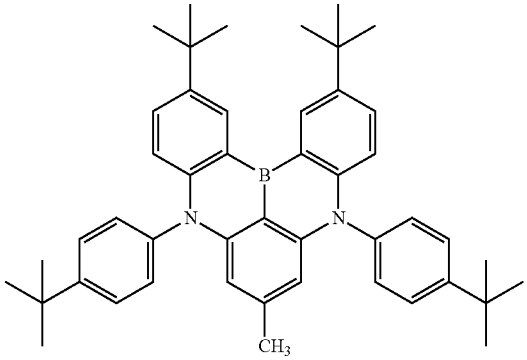
,
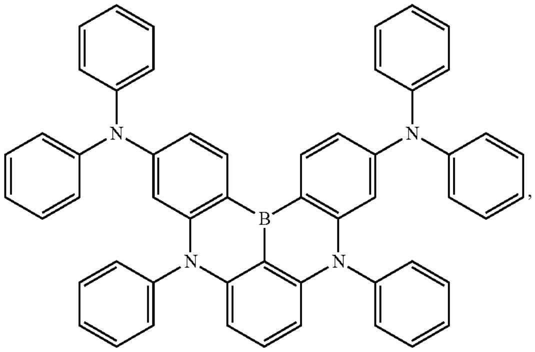
,
-continued
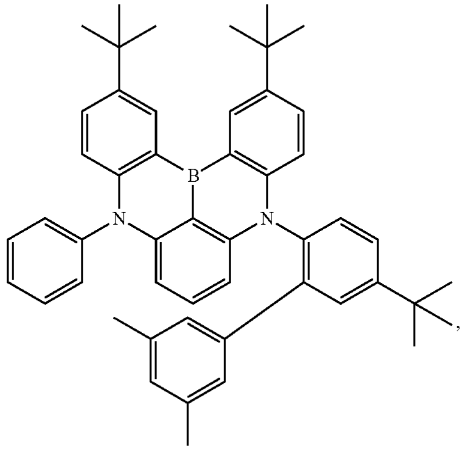
,
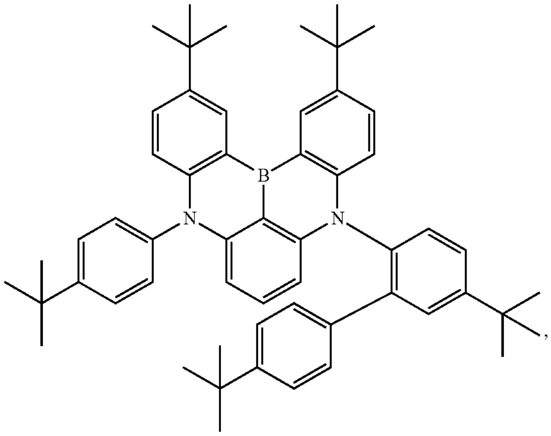
,
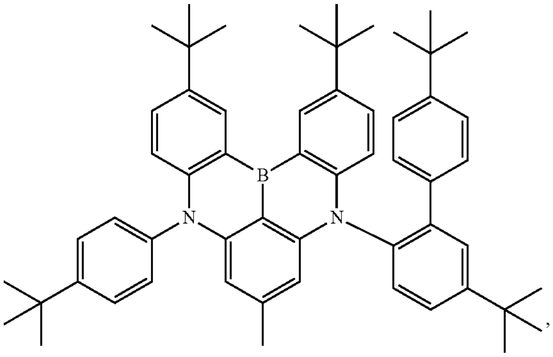
,
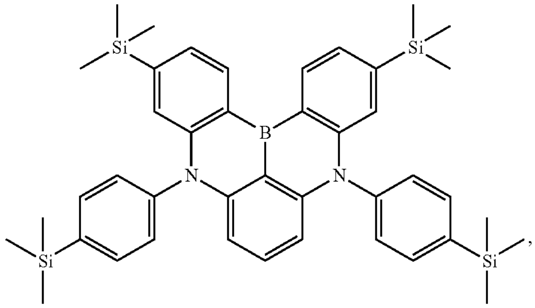
, -continued
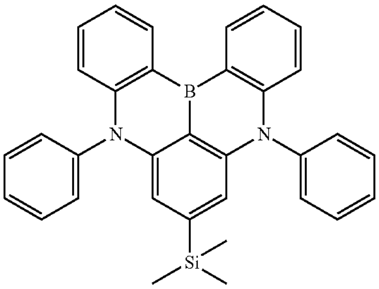
,
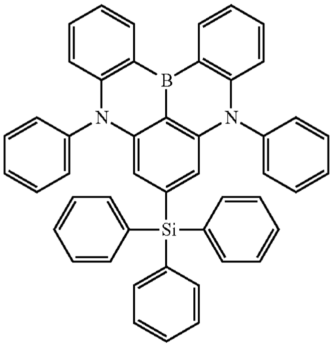
,
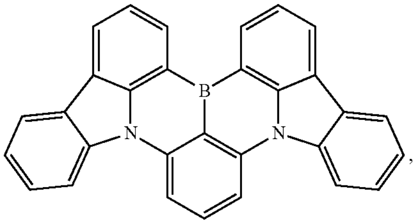
,
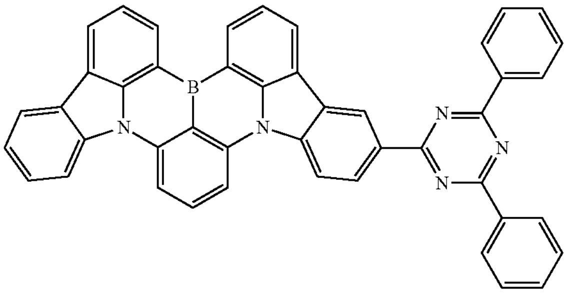
,
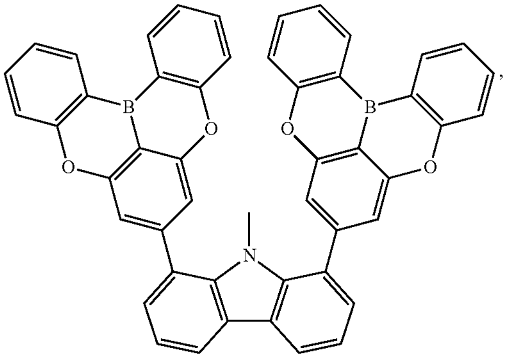
,
-continued
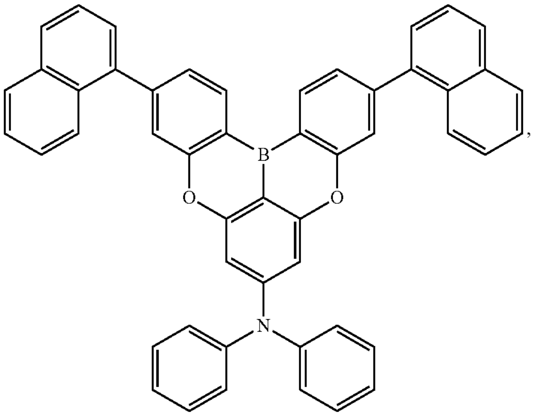
,
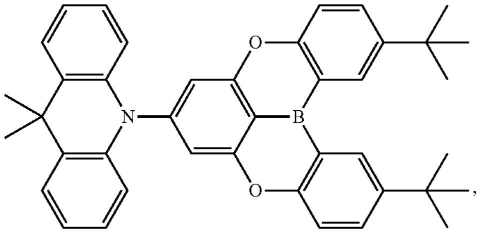
,
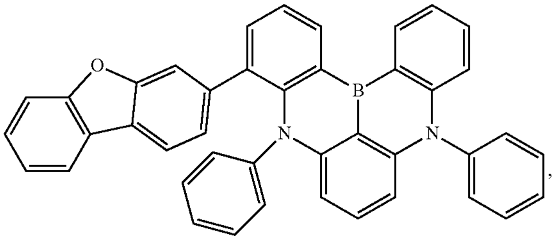
,
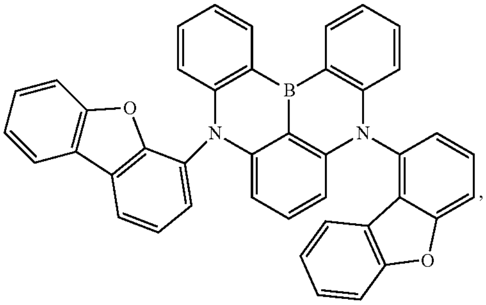
,
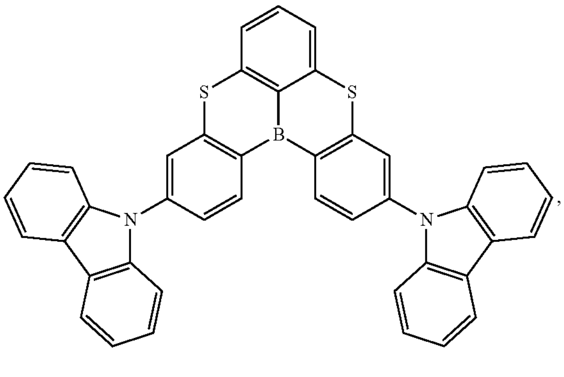
, -continued
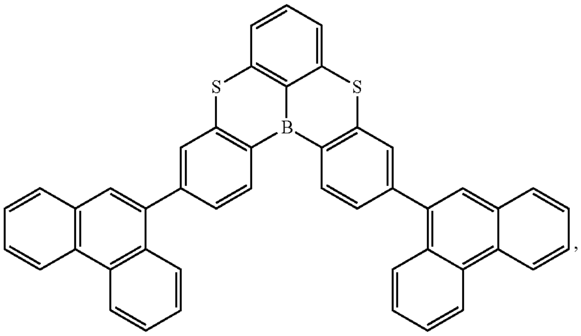
,
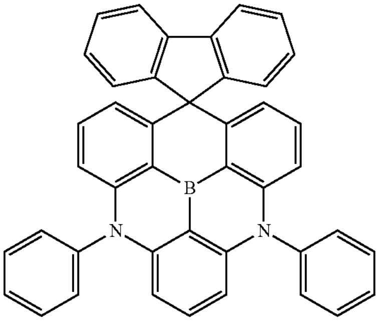
,
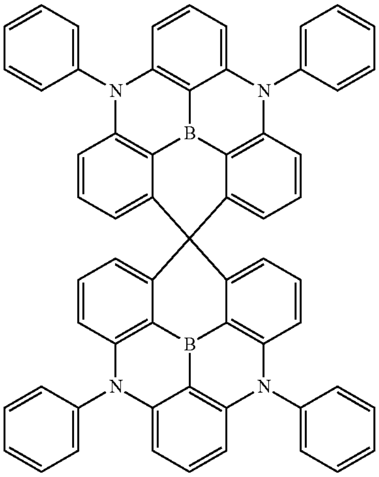
,
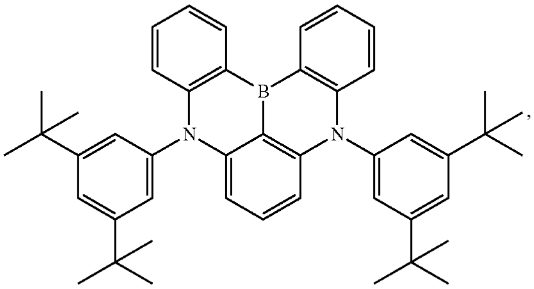
,
-continued
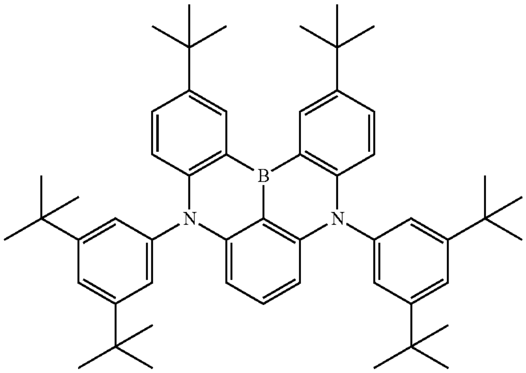
,
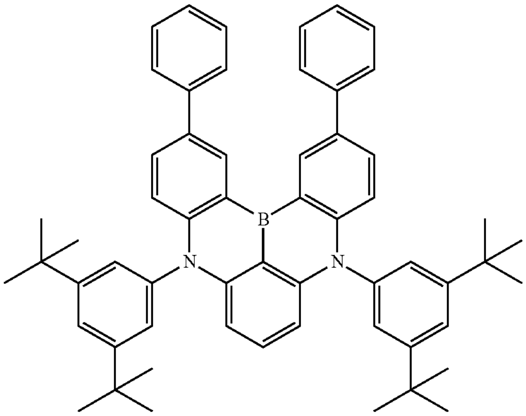
,
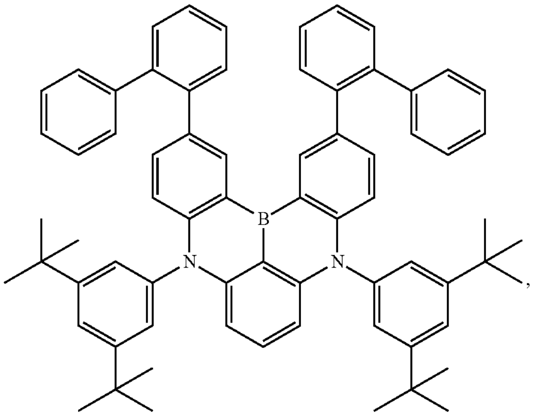
,
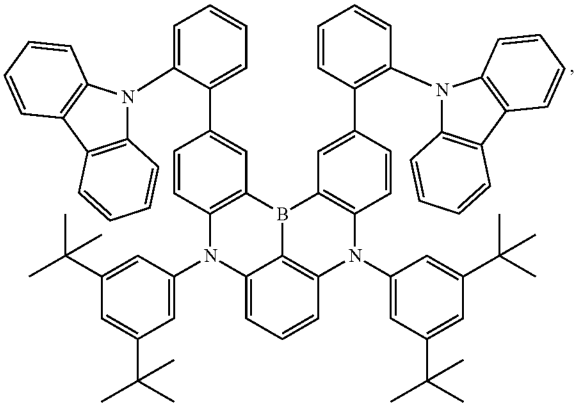
, -continued
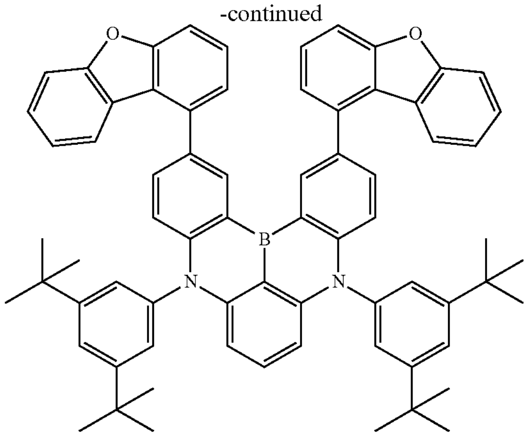
,
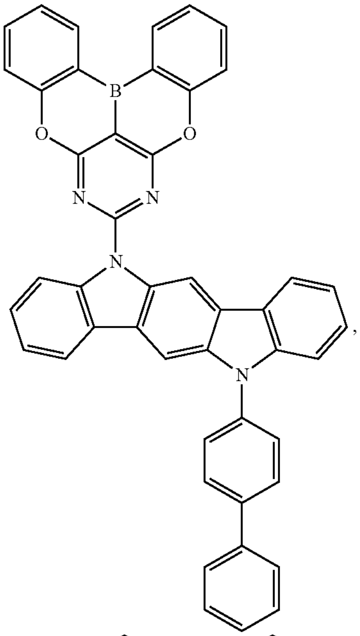
, and
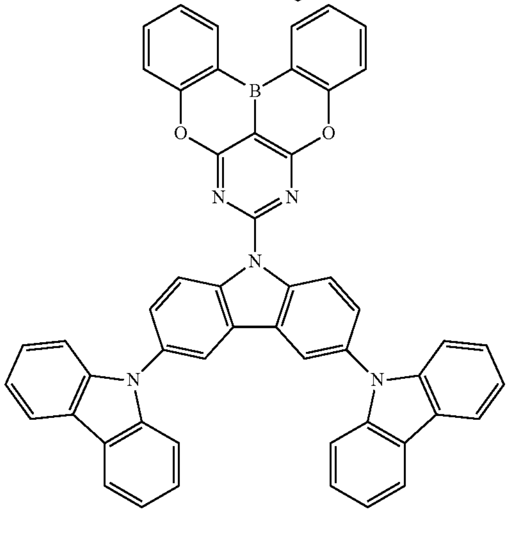
.
In some embodiments, the compound is selected from the group consisting of the structures shown in LIST 7 below:
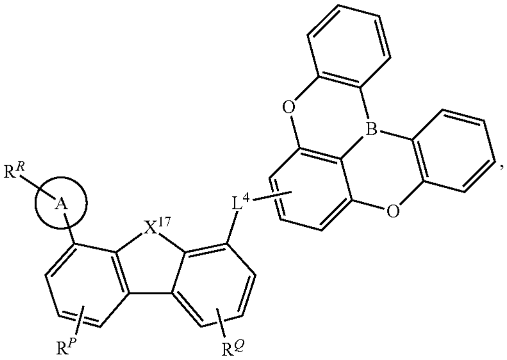
,
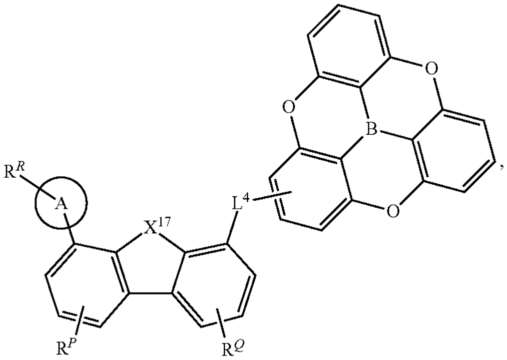
,
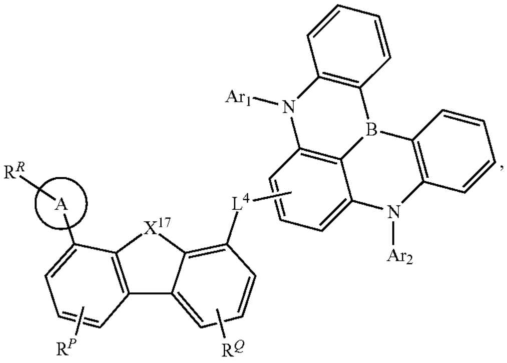
,
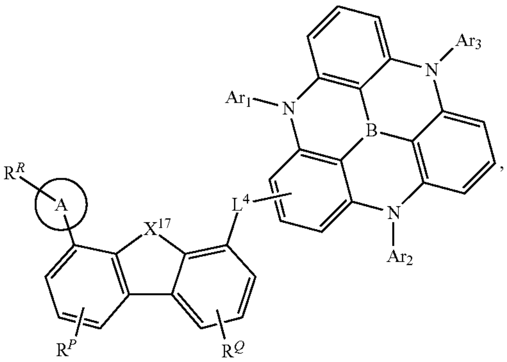
, -continued
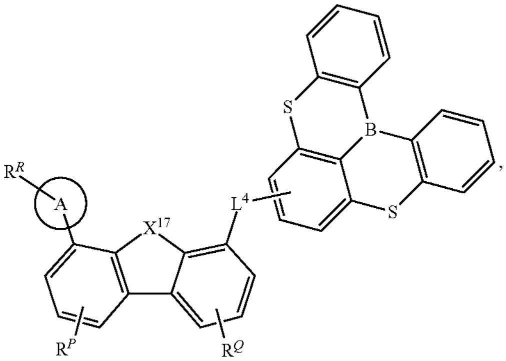
,
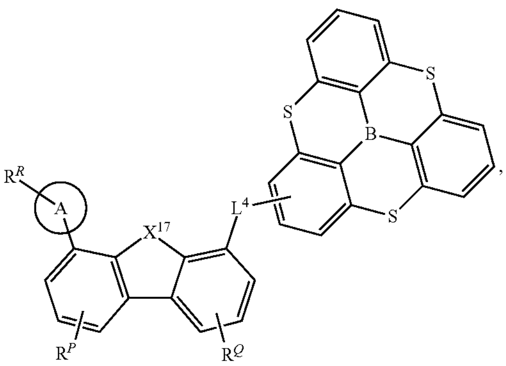
,
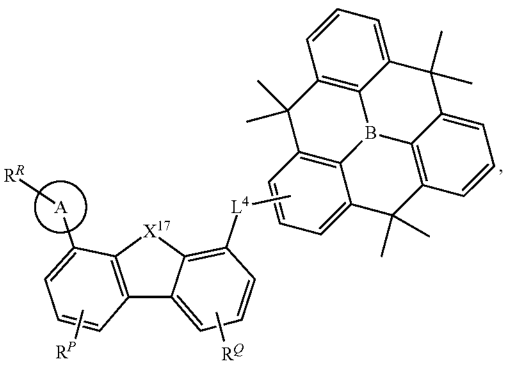
,
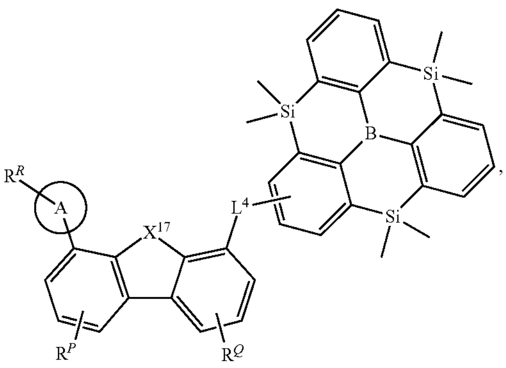
,
-continued
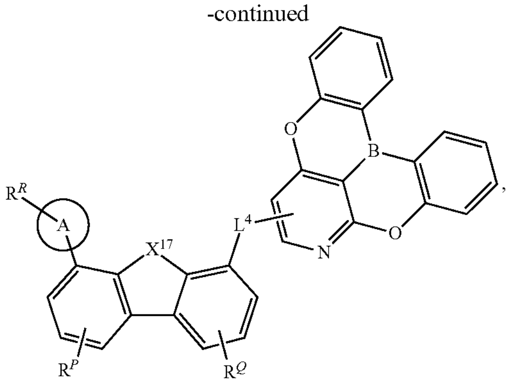
,
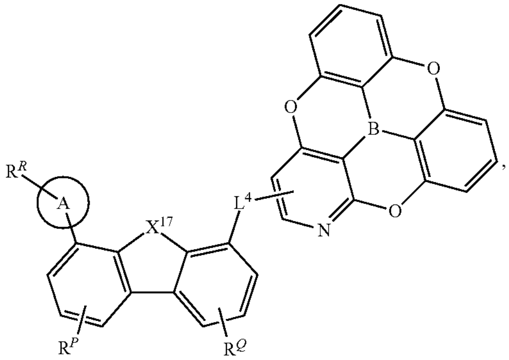
,
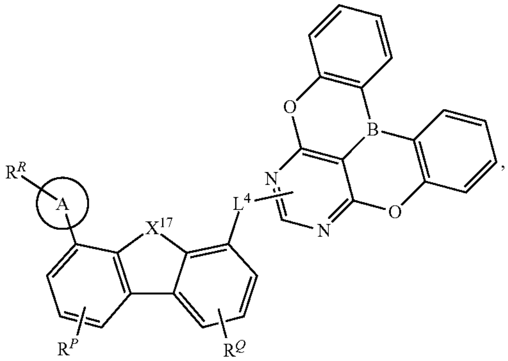
, and
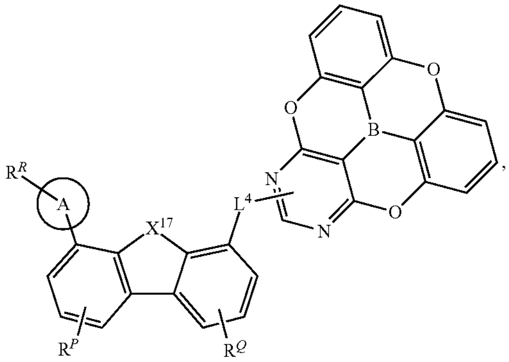
,
wherein all the variables are the same as previously defined.

In some embodiments, the compound is selected from the group consisting of the structures shown in LIST 8 below:
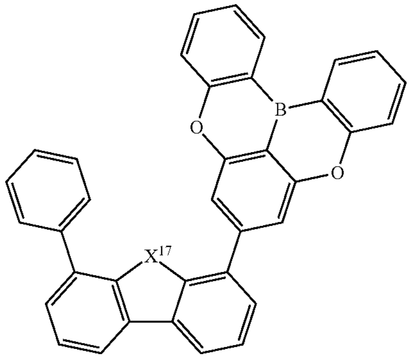
,
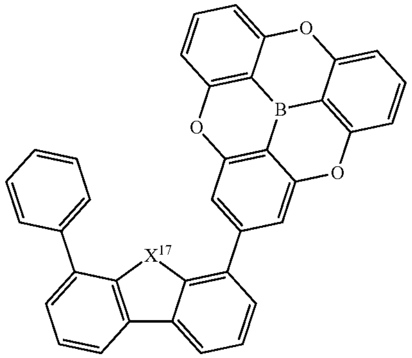
,
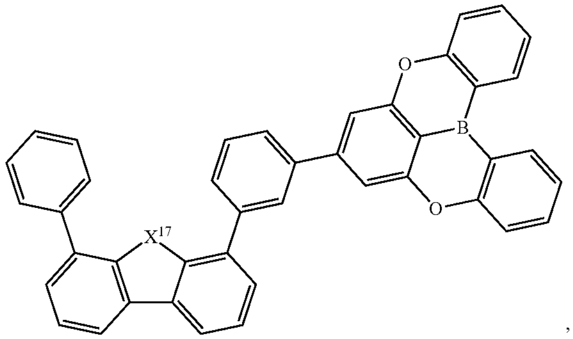
,
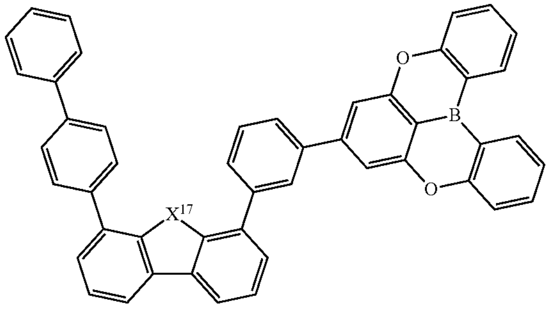
,
-continued
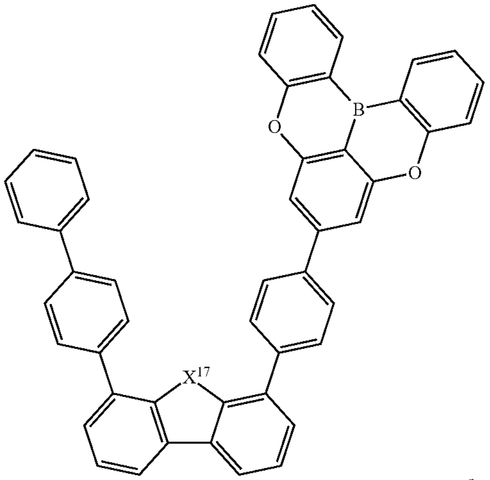
,
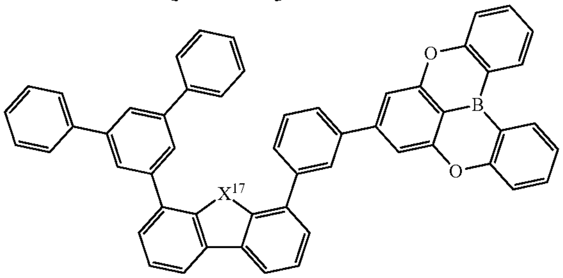
,
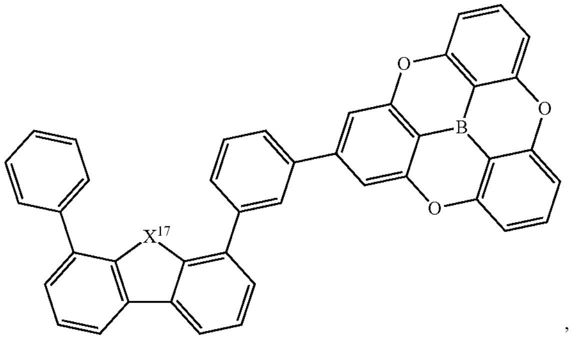
,
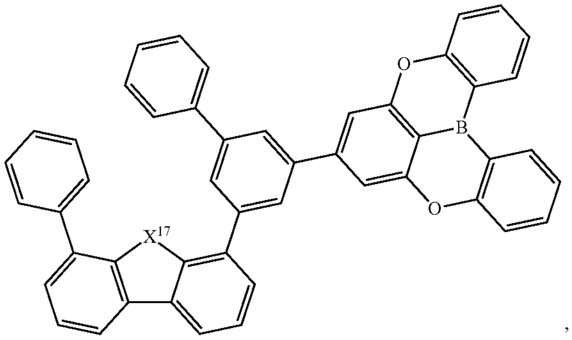
, -continued
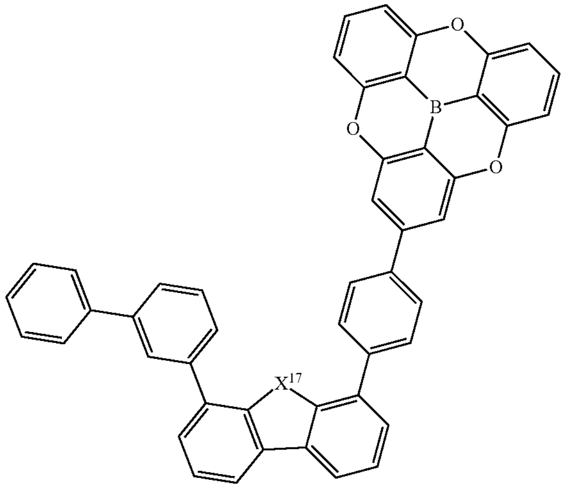
,
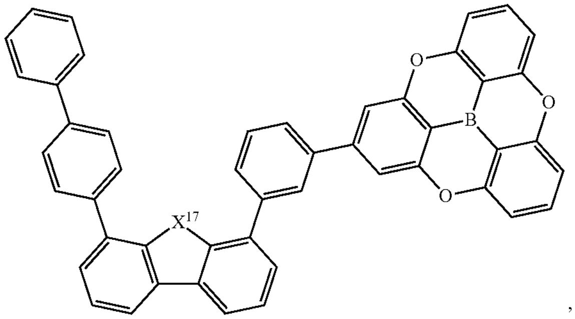
,
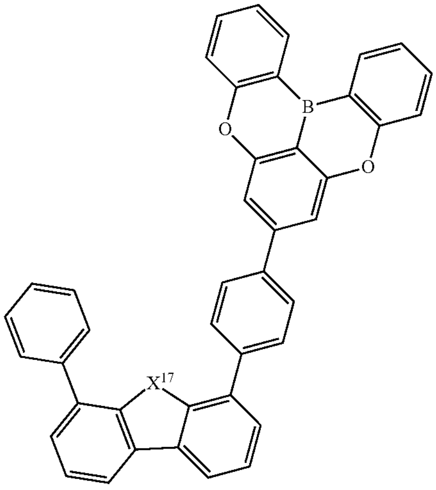
,
-continued
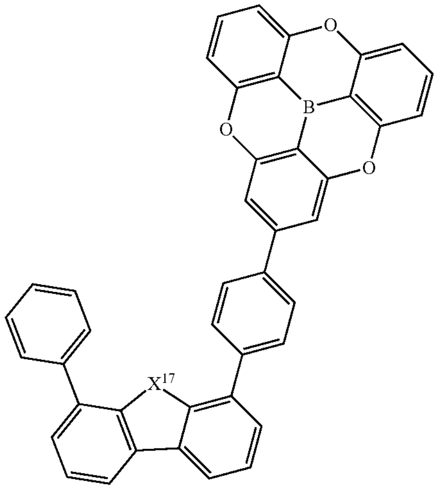
,
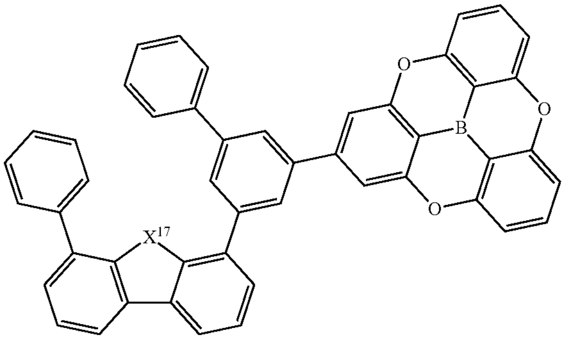
,
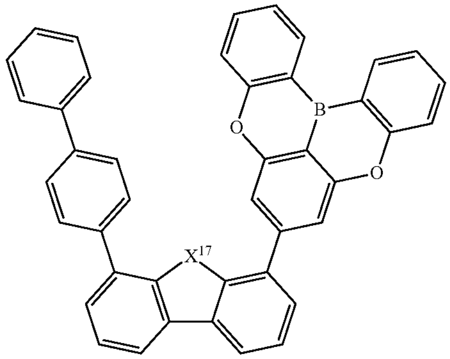
,
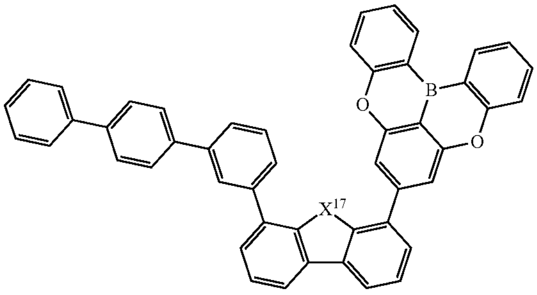
, -continued
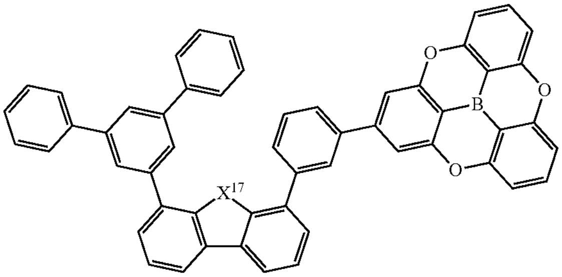
,
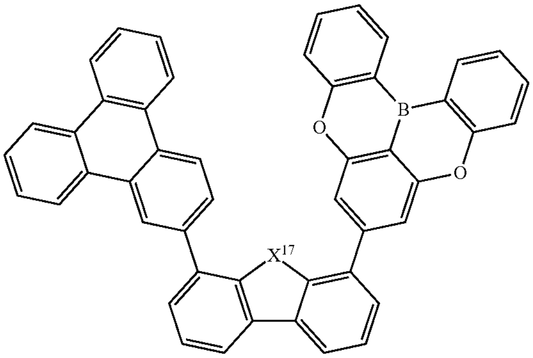
,
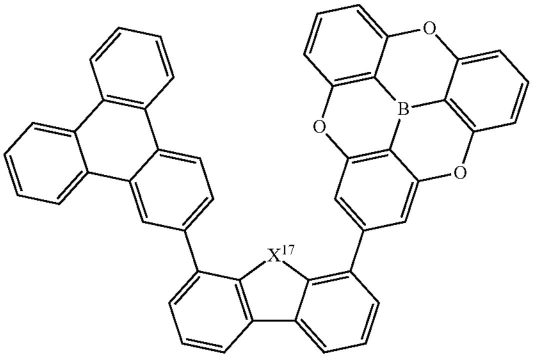
,
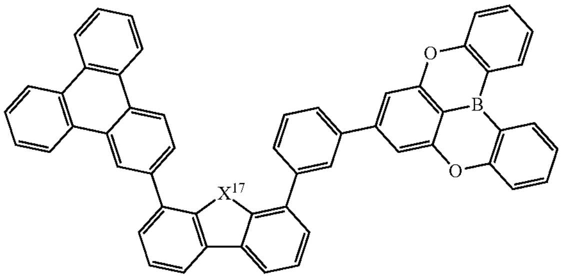
,
-continued
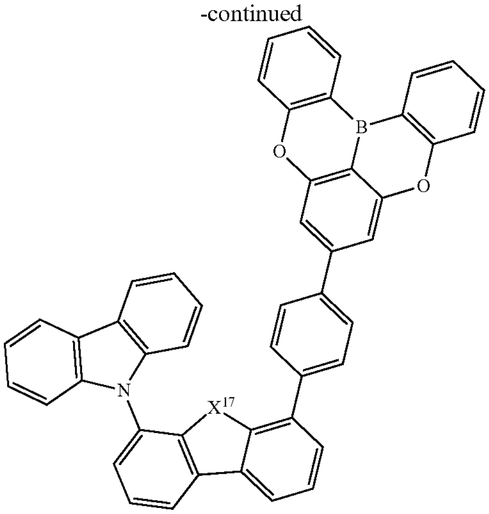
,
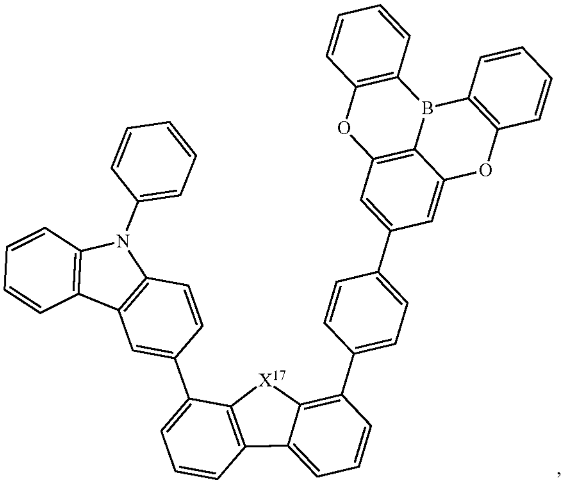
,
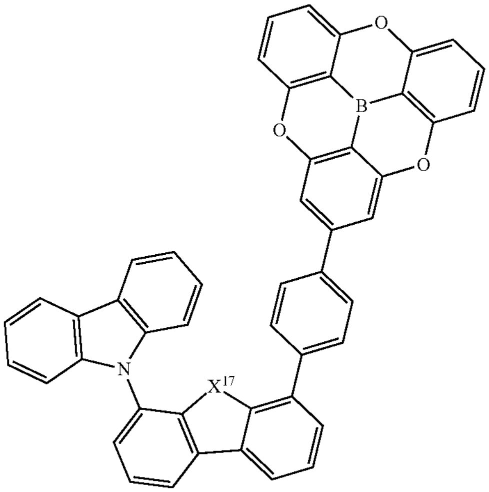
, -continued
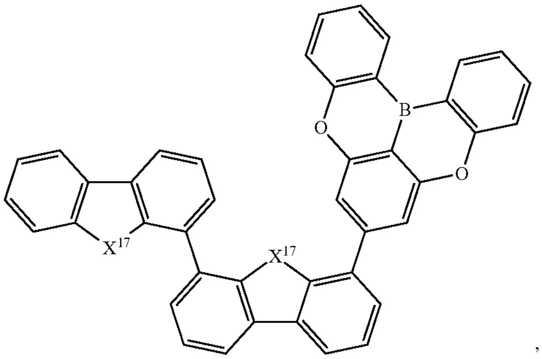
,
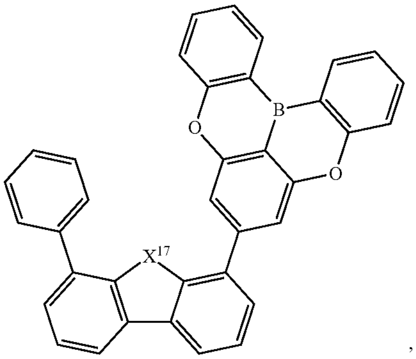
,
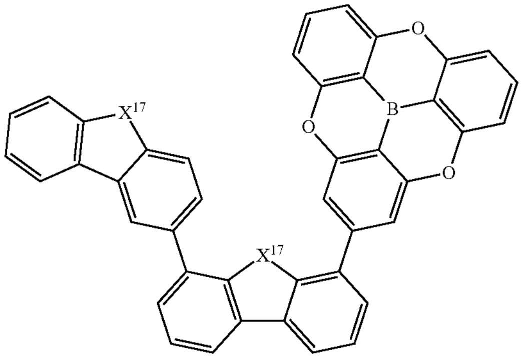
,
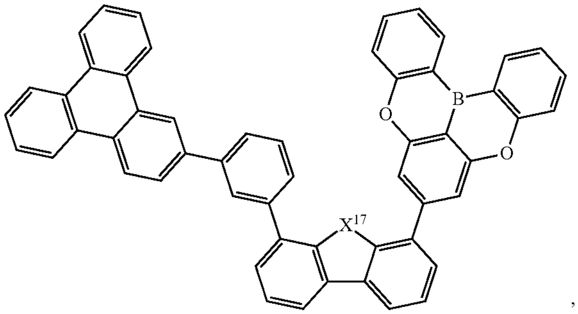
,
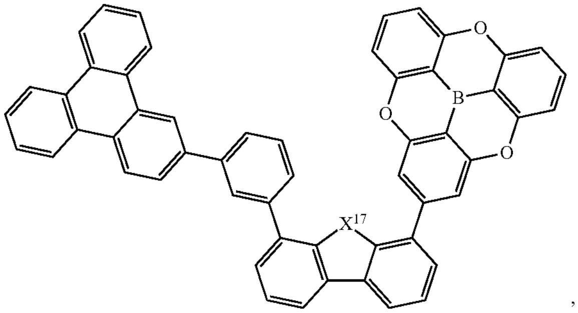
,
-continued
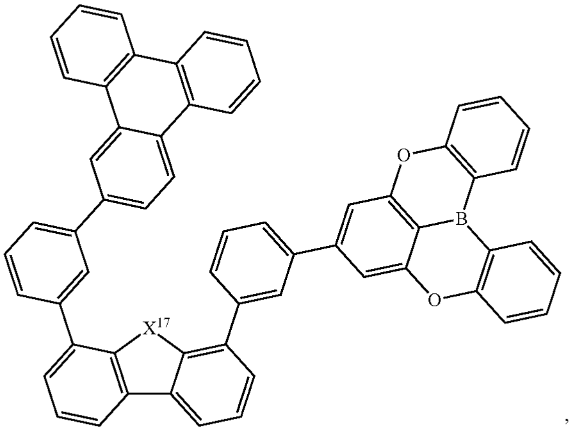
,
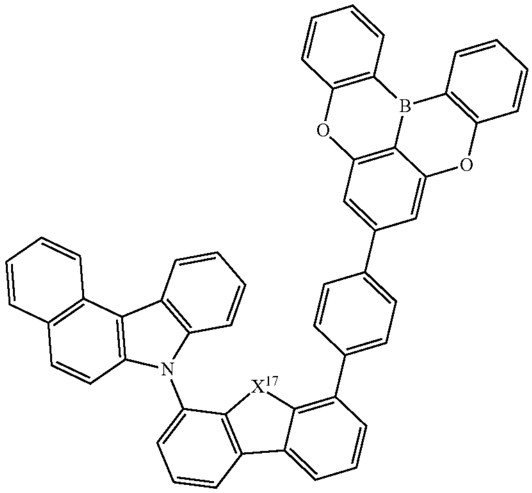
,
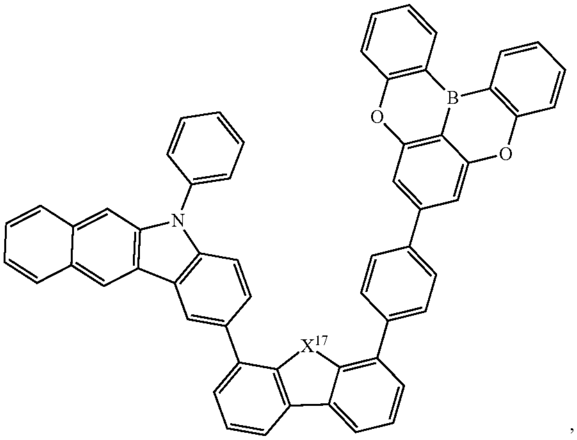
, -continued
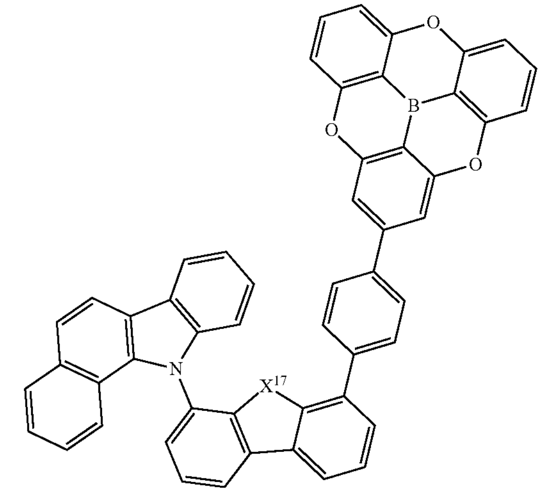
,
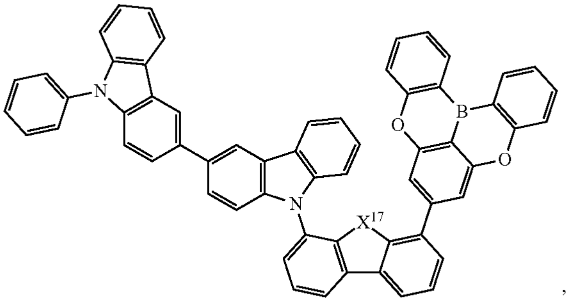
,
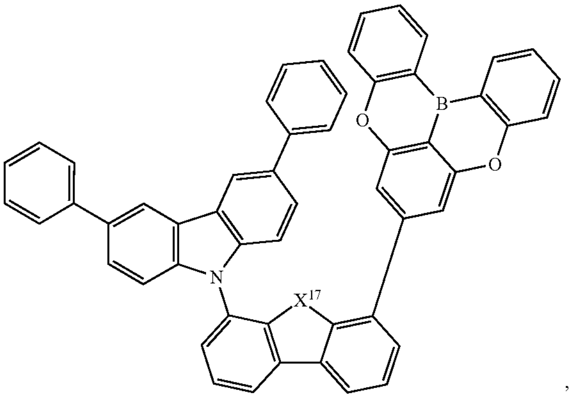
,
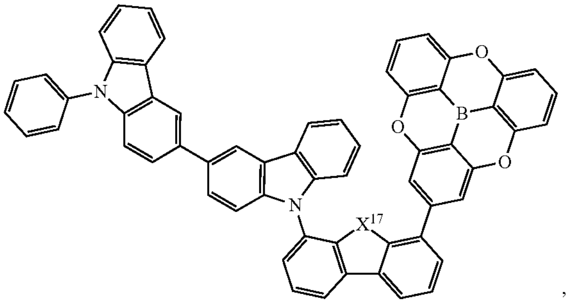
,
-continued
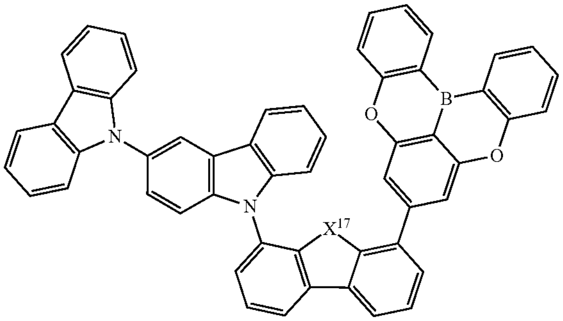
,
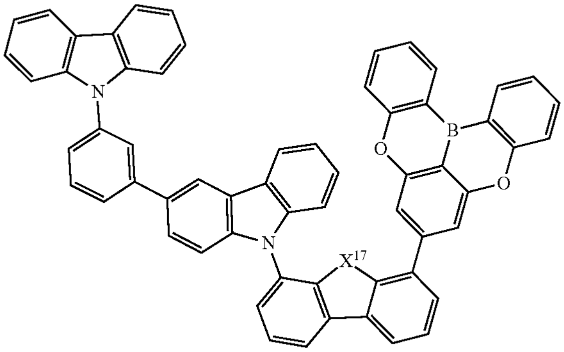
,
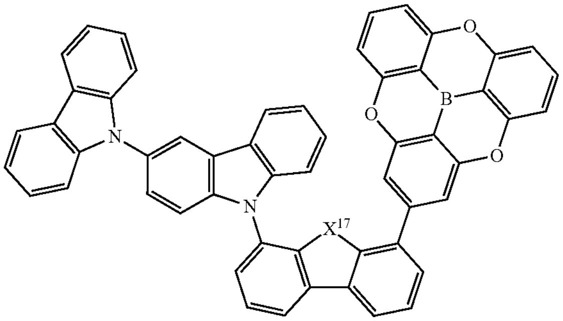
,
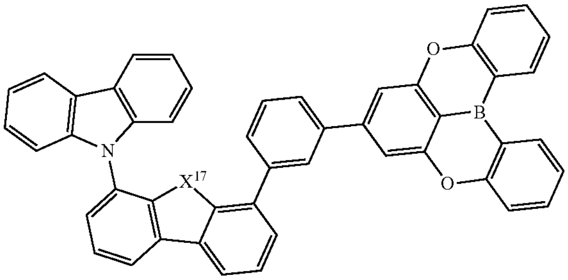
,
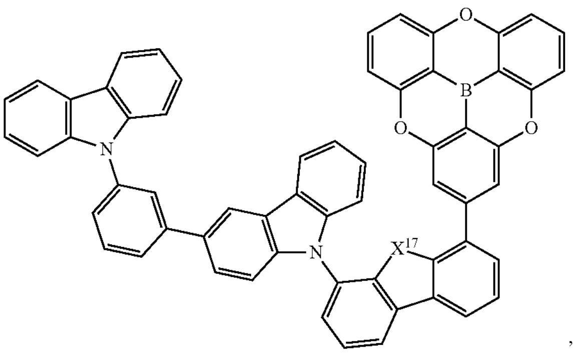
, -continued
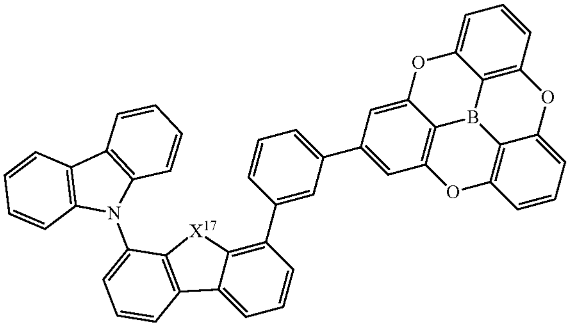
,
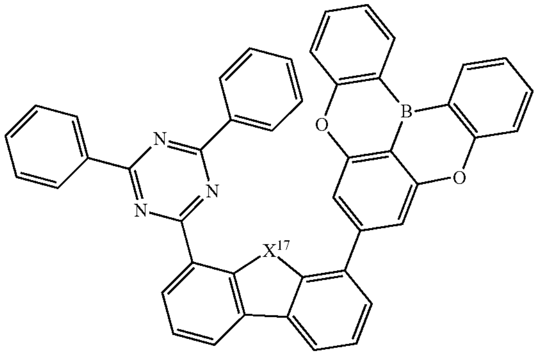
,
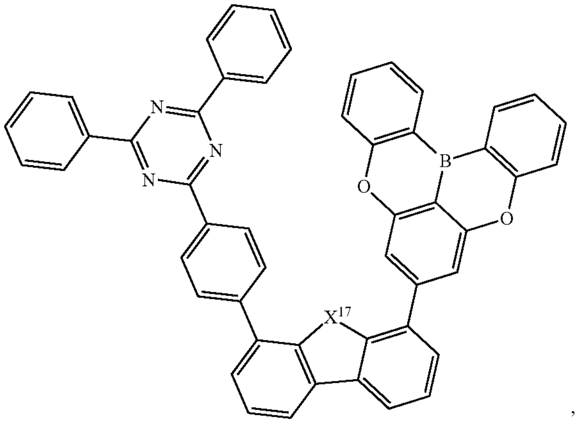
,
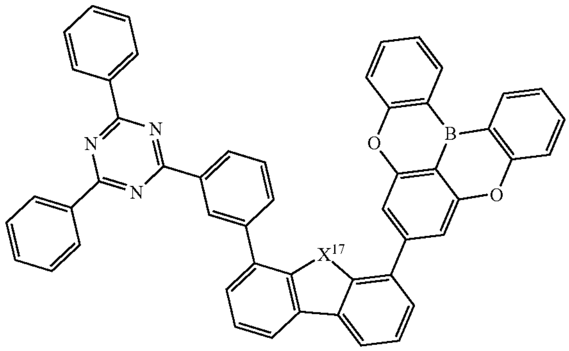
,
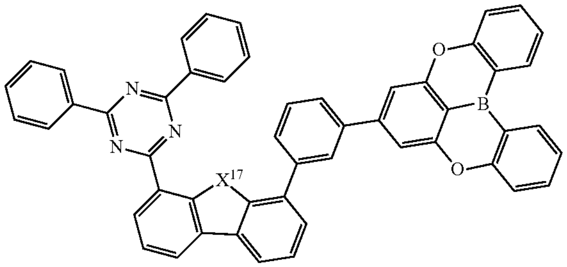
,
-continued
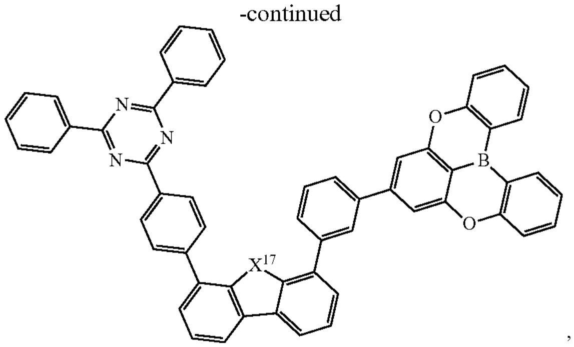
,
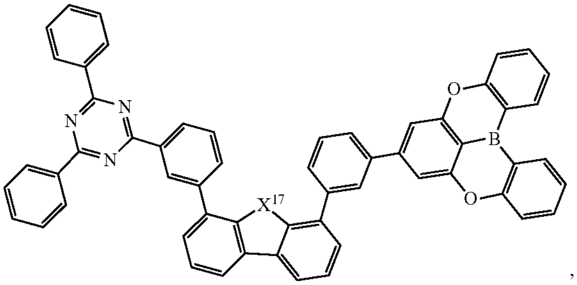
,
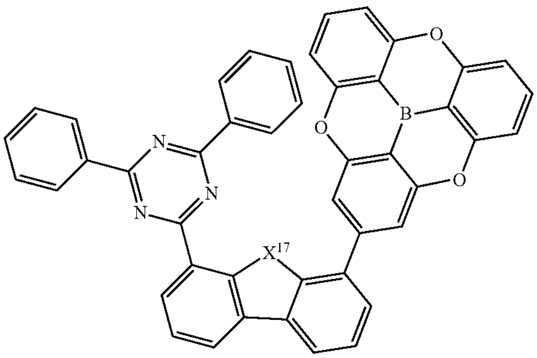
,
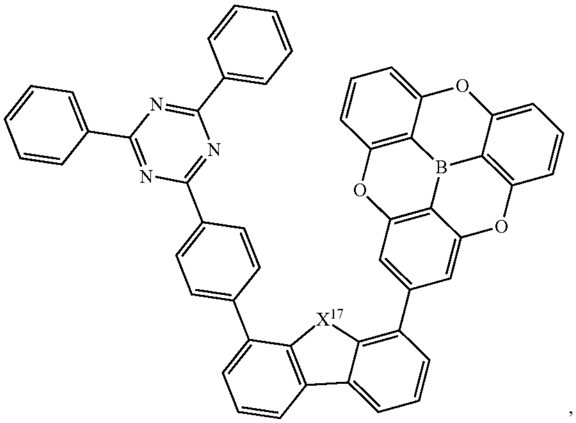
,
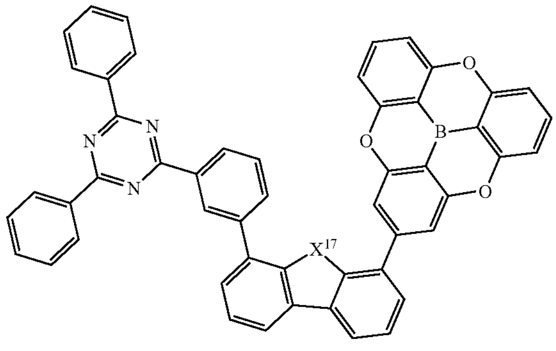
, -continued
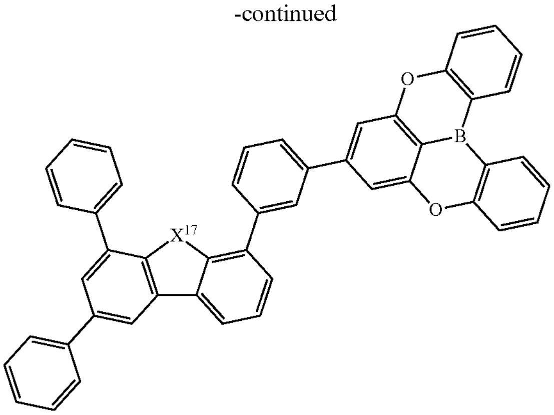
,
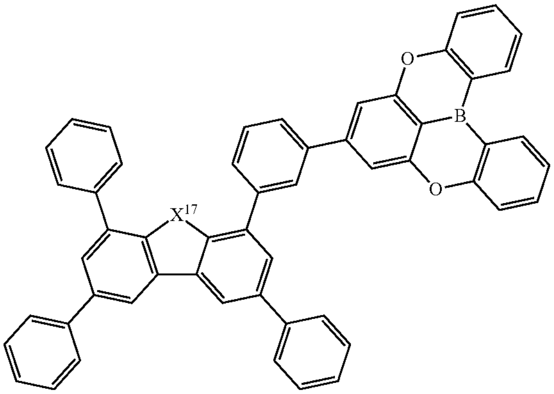
,
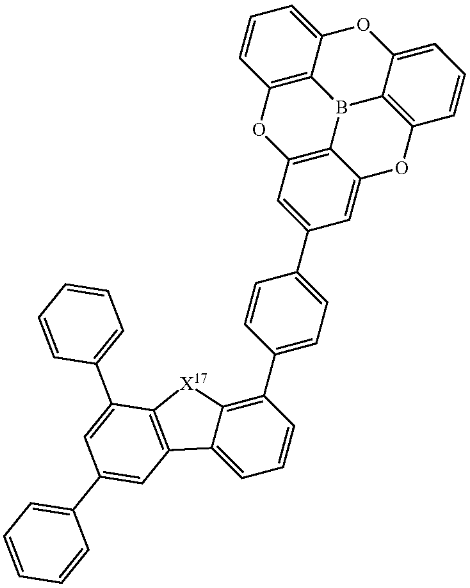
,
-continued
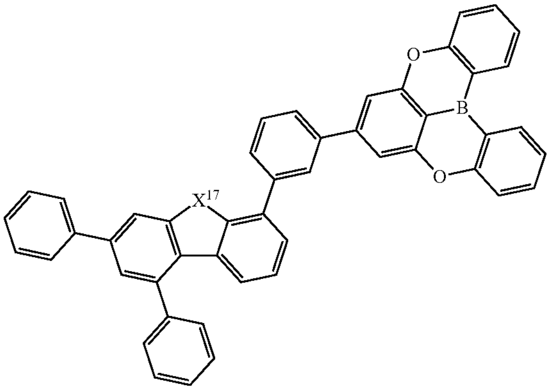
,
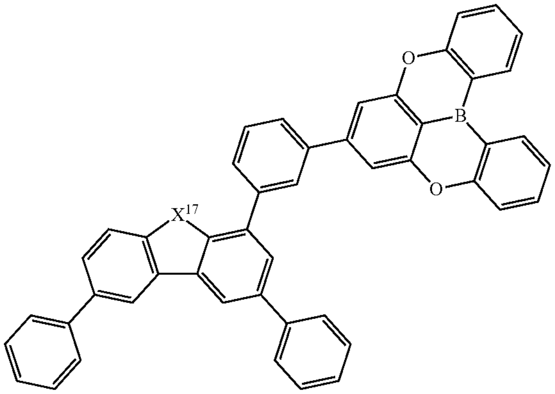
,
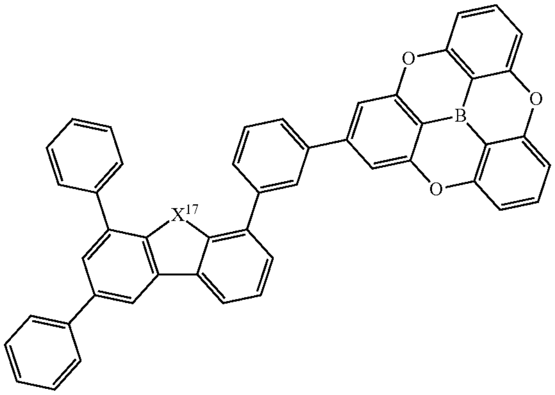
, -continued
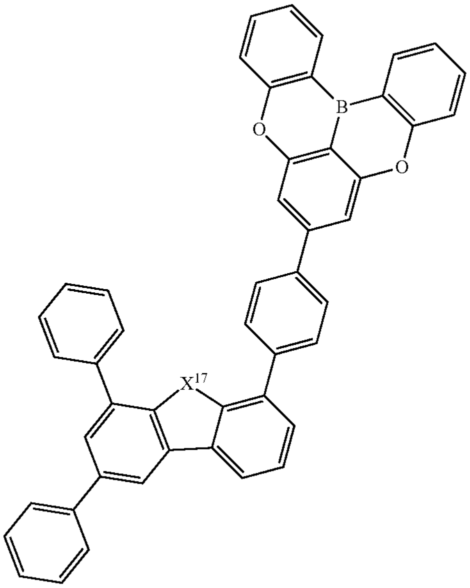
,
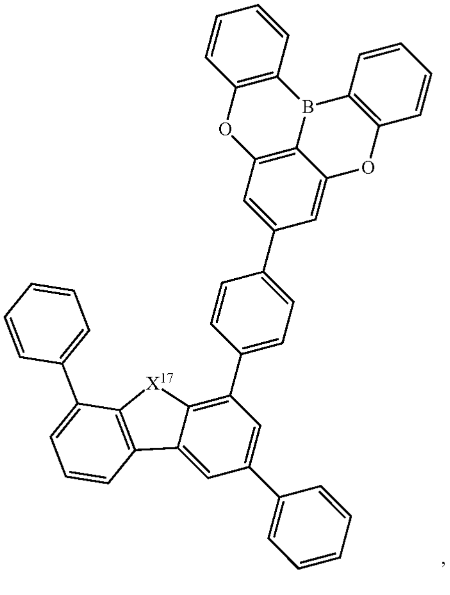
,
-continued
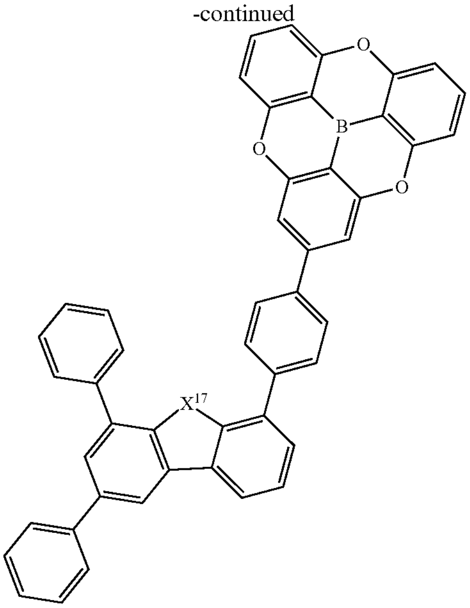
,
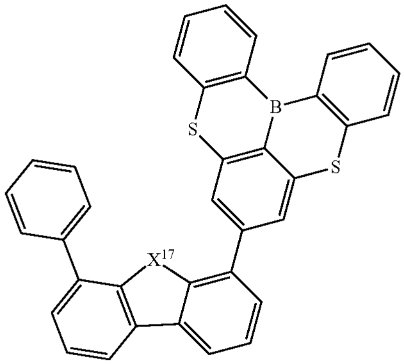
,
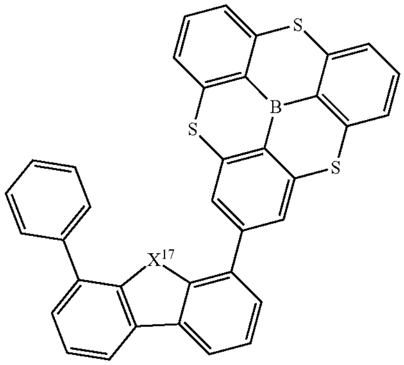
,
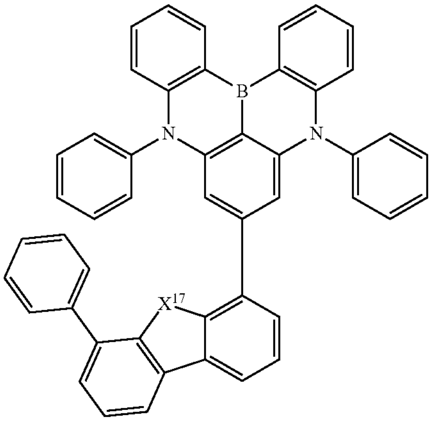
, -continued
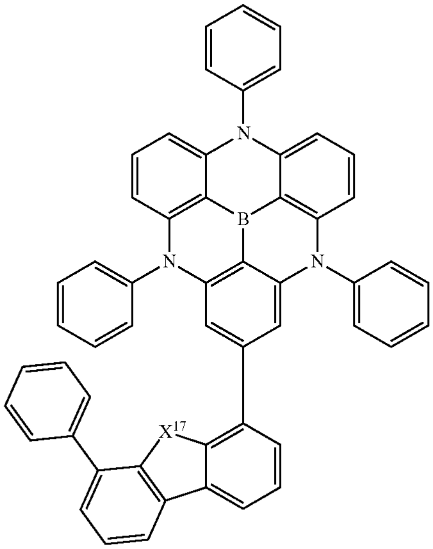
,
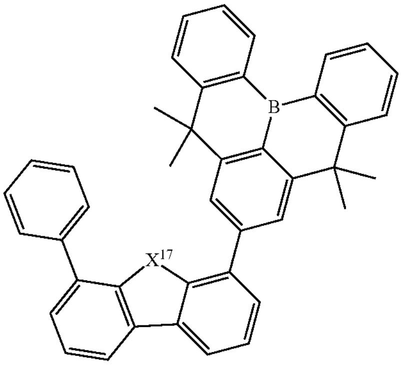
,
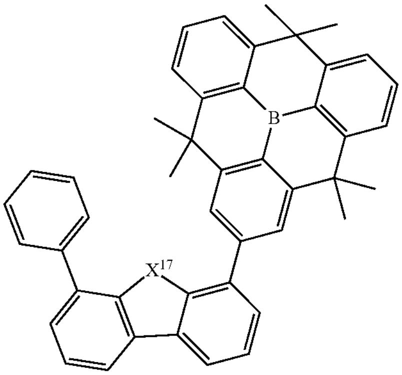
,
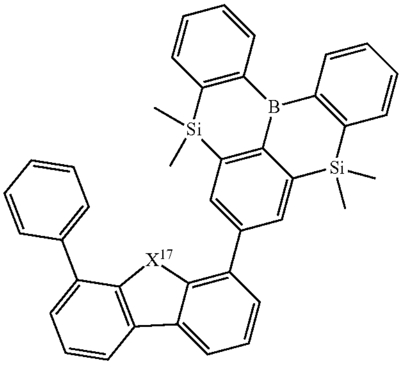
,
-continued
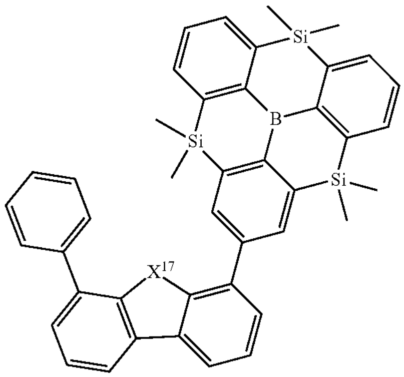
,
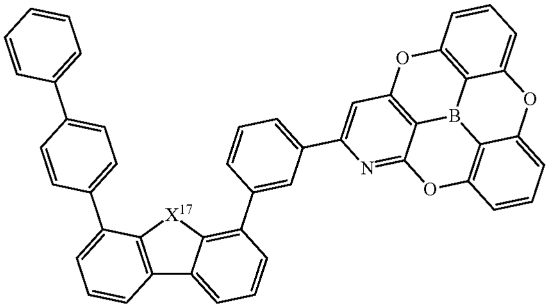
,
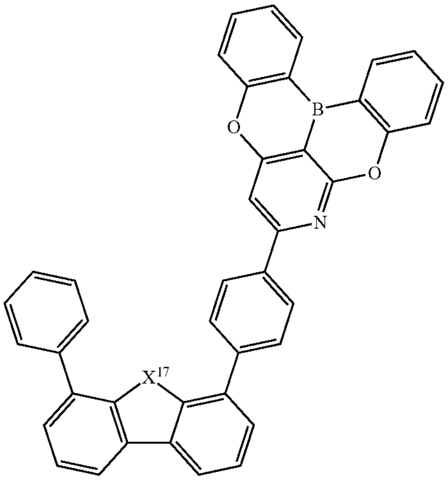
,
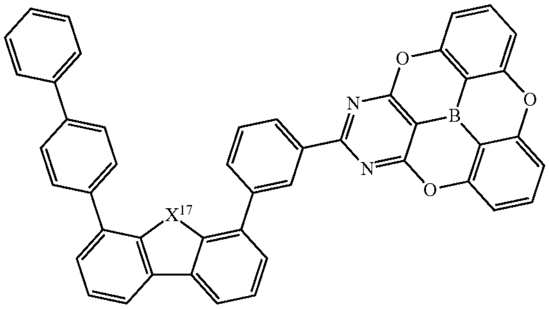
, -continued
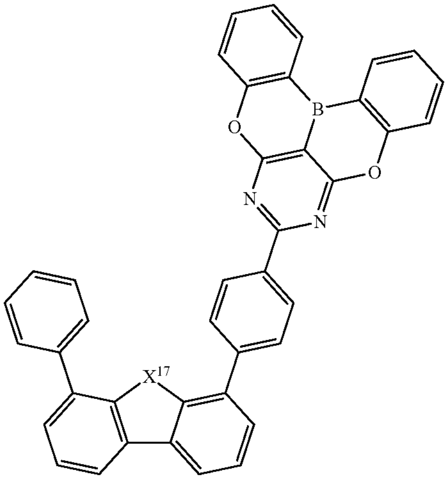
,
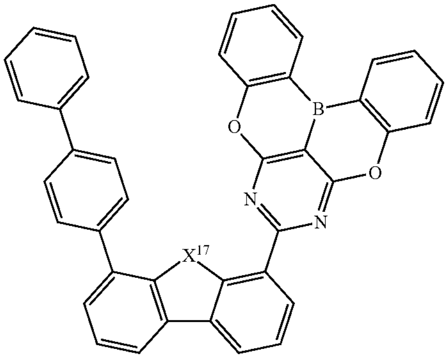
,
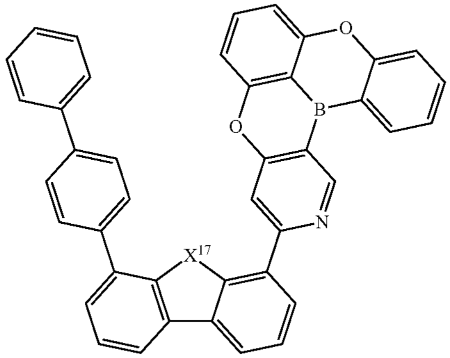
,
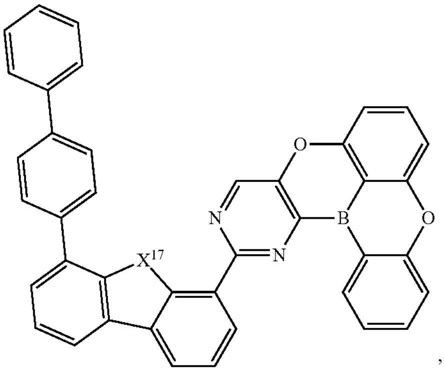
,
-continued
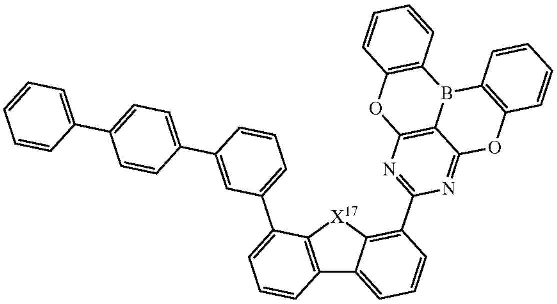
,
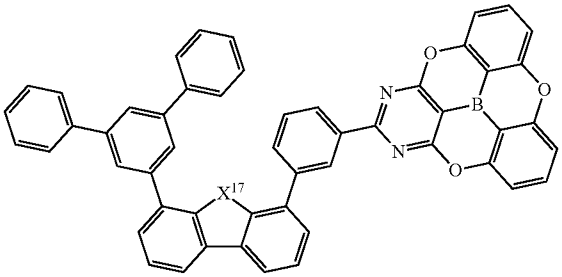
,
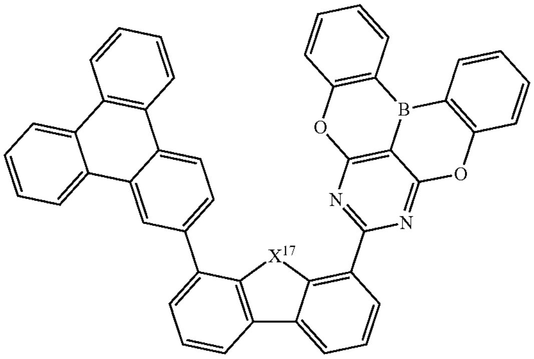
,
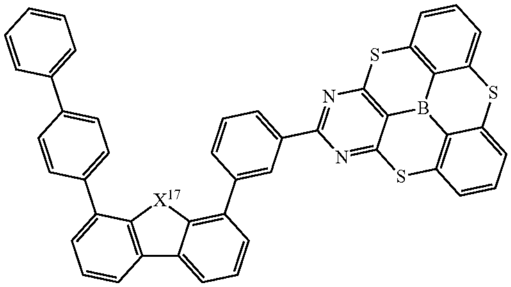
, and -continued

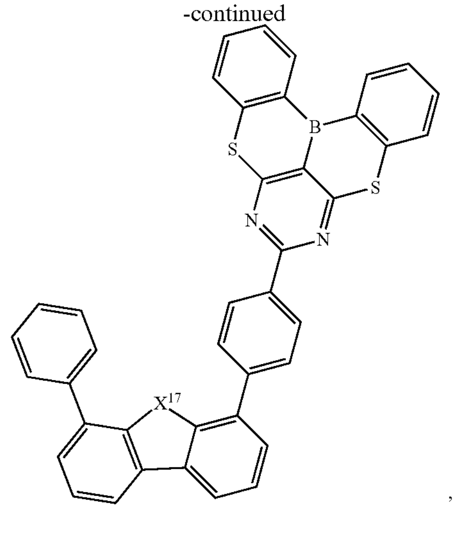

where $X^{17}$ is selected from the group consisting of O, S, Se, and $NR^4$.

In some embodiments, the first compound may be a host, and the second compound is an emitter.

In some embodiments, a consumer product comprising an organic light-emitting device (OLED) comprising an anode; a cathode; and an emissive layer disposed between the anode and the cathode, wherein the emissive layer comprises a first compound and a second compound; wherein the first compound is a boron compound possessing a trigonal planar geometry as described herein; and wherein the second compound is a Pt(II) complex possessing a square planar geometry.

In some embodiment, the consumer product may be one of a flat panel display, a computer monitor, a medical monitor, a television, a billboard, a light for interior or exterior illumination and/or signaling, a heads-up display, a fully or partially transparent display, a flexible display, a laser printer, a telephone, a cell phone, tablet, a phablet, a personal digital assistant (PDA), a wearable device, a laptop computer, a digital camera, a camcorder, a viewfinder, a micro-display that is less than 2 inches diagonal, a 3-D display, a virtual reality or augmented reality display, a vehicle, a video wall comprising multiple displays tiled together, a theater or stadium screen, a light therapy device, and a sign.

In yet another aspect, the OLED of the present disclosure may also comprise an emissive region containing a compound as disclosed in the above compounds section of the present disclosure.

In some embodiments, the emissive region may comprise a compound comprising a structure of Formula I

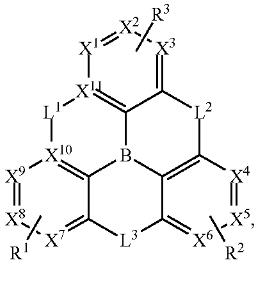

wherein $X^1$-$X^{11}$ are each independently C or N; no more than two N atoms are bonded to one another in the same ring; $L^2$, and $L^3$ are each independently selected from the group consisting of O, S, Se, BR, NR, CRR', SiRR', and GeRR'; $L^1$ is not always present but when present, $L^1$ is selected from the group consisting of O, S, Se, and SiRR' and $X^{10}$ and $X^{11}$ are both C when $L^1$ is present; $L^2$ and $L^3$ are always present; $R^1$, $R^2$, and $R^3$ each independently represent zero, mono, or up to a maximum allowed substitution to its associated ring; each of R and R' is independently a hydrogen or a general substituent as described herein; each of $R^1$, $R^2$, and $R^3$ is independently a hydrogen or a substituent selected from the group consisting of Formulae II, III, IV, V, VI, VII, and VIII, deuterium, halogen, alkyl, cycloalkyl, heteroalkyl, heterocycloalkyl, arylalkyl, alkoxy, aryloxy, amino, silyl, boryl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof, with at least one of $R^1$, $R^2$, and $R^3$ being selected from the group consisting of Formulae II, III, IV, V, VI, VII, and VIII, and their aza variants as defined in the disclosure.

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

Several OLED materials and configurations are described in U.S. Pat. Nos. 5,844,363, 6,303,238, and 5,707,745, which are incorporated herein by reference in their entirety.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), are incorporated by reference in their entireties. Phosphorescence is described in more detail in U.S. Pat. No. 7,279,704 at cols. 5-6, which are incorporated by reference.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
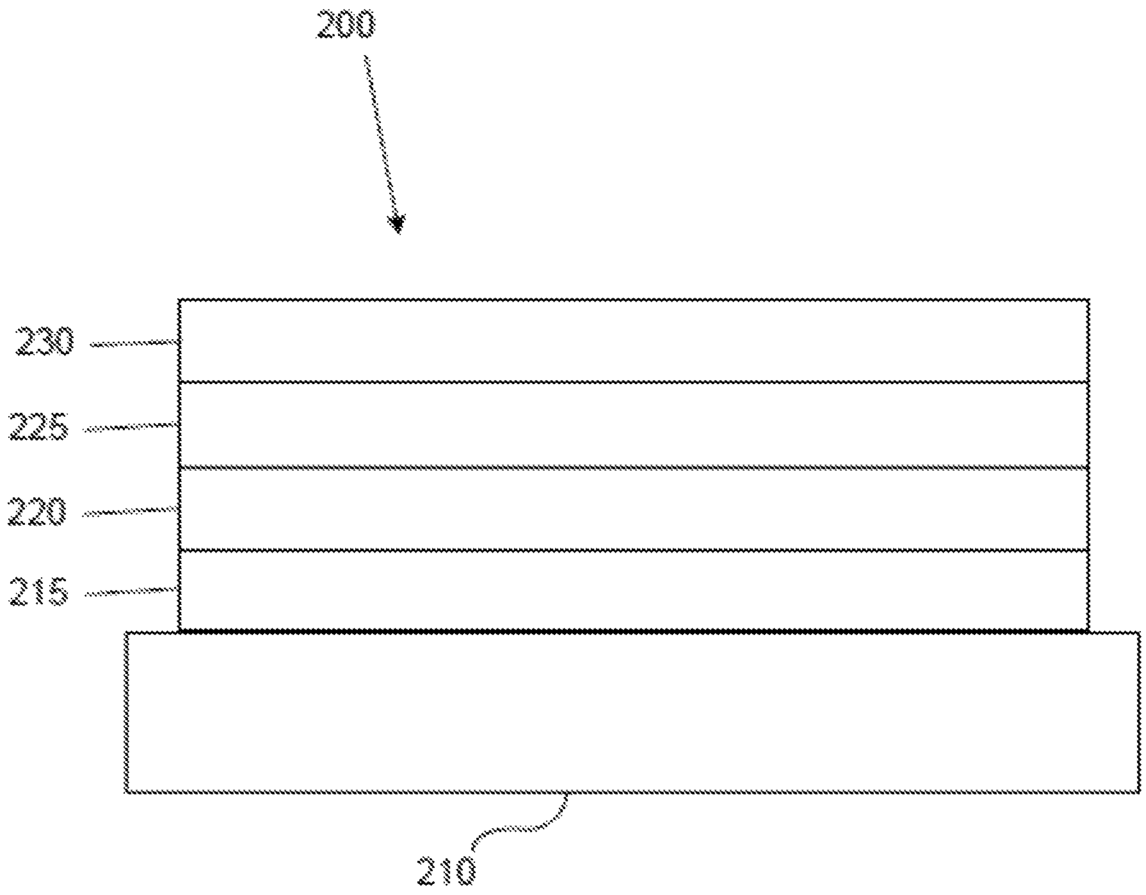
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the present disclosure may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and organic vapor jet printing (OVJP). Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons are a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the present disclosure may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the present disclosure can be incorporated into a wide variety of electronic component modules (or units) that can be incorporated into a variety of electronic products or intermediate components. Examples of such electronic products or intermediate components include display screens, lighting devices such as discrete light source devices or lighting panels, etc. that can be utilized by the end-user product manufacturers. Such electronic component modules can optionally include the driving electronics and/or power source(s). Devices fabricated in accordance with embodiments of the present disclosure can be incorporated into a wide variety of consumer products that have one or more of the electronic component modules (or units) incorporated therein. A consumer product comprising an OLED that includes the compound of the present disclosure in the organic layer in the OLED is disclosed. Such consumer products would include any kind of products that include one or more light source(s) and/or one or more of some type of visual displays. Some examples of such consumer products include flat panel displays, curved displays, computer monitors, medical monitors, televisions, billboards, lights for interior or exterior illumination and/or signaling, heads-up displays, fully or partially transparent displays, flexible displays, rollable displays, foldable displays, stretchable displays, laser printers, telephones, mobile phones, tablets, phablets, personal digital assistants (PDAs), wearable devices, laptop computers, digital cameras, camcorders, viewfinders, micro-displays (displays that are less than 2 inches diagonal), 3-D displays, virtual reality or augmented reality displays, vehicles, video walls comprising multiple displays tiled together, theater or stadium screen, a light therapy device, and a sign. Various control mechanisms may be used to control devices fabricated in accordance with the present disclosure, including passive matrix and active matrix. Many of the devices are intended for use in a temperature range comfortable to humans, such as 18° C. to 30° C., and more preferably at room temperature (20-25° C.), but could be used outside this temperature range, for example, from −40° C. to +80° C.

More details on OLEDs, and the definitions described above, can be found in U.S. Pat. No. 7,279,704, which is incorporated herein by reference in its entirety.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

In some embodiments, the OLED has one or more characteristics selected from the group consisting of being flexible, being rollable, being foldable, being stretchable, and being curved. In some embodiments, the OLED is transparent or semi-transparent. In some embodiments, the OLED further comprises a layer comprising carbon nanotubes.

In some embodiments, the OLED further comprises a layer comprising a delayed fluorescent emitter. In some embodiments, the OLED comprises a RGB pixel arrangement or white plus color filter pixel arrangement. In some embodiments, the OLED is a mobile device, a hand held device, or a wearable device. In some embodiments, the OLED is a display panel having less than 10 inch diagonal or 50 square inch area. In some embodiments, the OLED is a display panel having at least 10 inch diagonal or 50 square inch area. In some embodiments, the OLED is a lighting panel.

In some embodiments, the compound can be an emissive dopant. In some embodiments, the compound can produce emissions via phosphorescence, fluorescence, thermally activated delayed fluorescence, i.e., TADF (also referred to as E-type delayed fluorescence; see, e.g., U.S. application Ser. No. 15/700,352, which is hereby incorporated by reference in its entirety), triplet-triplet annihilation, or combinations of these processes. In some embodiments, the emissive dopant can be a racemic mixture, or can be enriched in one enantiomer. In some embodiments, the compound can be homoleptic (each ligand is the same). In some embodiments, the compound can be heteroleptic (at least one ligand is different from others). When there are more than one ligand coordinated to a metal, the ligands can all be the same in some embodiments. In some other embodiments, at least one ligand is different from the other ligands. In some embodiments, every ligand can be different from each other. This is also true in embodiments where a ligand being coordinated to a metal can be linked with other ligands being coordinated to that metal to form a tridentate, tetradentate, pentadentate, or hexadentate ligands. Thus, where the coordinating ligands are being linked together, all of the ligands can be the same in some embodiments, and at least one of the ligands being linked can be different from the other ligand(s) in some other embodiments.

In some embodiments, the compound can be used as a phosphorescent sensitizer in an OLED where one or multiple layers in the OLED contains an acceptor in the form of one or more fluorescent and/or delayed fluorescence emitters. In some embodiments, the compound can be used as one component of an exciplex to be used as a sensitizer. As a phosphorescent sensitizer, the compound must be capable of energy transfer to the acceptor and the acceptor will emit the energy or further transfer energy to a final emitter. The acceptor concentrations can range from 0.001% to 100%. The acceptor could be in either the same layer as the phosphorescent sensitizer or in one or more different layers. In some embodiments, the acceptor is a TADF emitter. In some embodiments, the acceptor is a fluorescent emitter. In some embodiments, the emission can arise from any or all of the sensitizer, acceptor, and final emitter.

In some embodiments, the compound is an acceptor, and the OLED further comprises a sensitizer selected from the group consisting of a delayed fluorescence emitter, a phosphorescent emitter, and combination thereof.

In some embodiments, the compound is a fluorescent emitter, a delayed fluorescence emitter, or a component of an exciplex that is a fluorescent emitter or a delayed fluorescence emitter.

In some embodiments, the compound is a sensitizer, and the OLED further comprises an acceptor selected from the group consisting of a fluorescent emitter, a delayed fluorescence emitter, and combination thereof.

According to another aspect, a formulation comprising the compound described herein is also disclosed.

The OLED disclosed herein can be incorporated into one or more of a consumer product, an electronic component module, and a lighting panel. The organic layer can be an emissive layer and the compound can be an emissive dopant in some embodiments, while the compound can be a non-emissive dopant in other embodiments.

In yet another aspect of the present disclosure, a formulation that comprises the novel compound disclosed herein is described. The formulation can include one or more components selected from the group consisting of a solvent, a host, a hole injection material, hole transport material, electron blocking material, hole blocking material, and an electron transport material, disclosed herein.

The present disclosure encompasses any chemical structure comprising the novel compound of the present disclosure, or a monovalent or polyvalent variant thereof. In other words, the inventive compound, or a monovalent or polyvalent variant thereof, can be a part of a larger chemical structure. Such chemical structure can be selected from the group consisting of a monomer, a polymer, a macromolecule, and a supramolecule (also known as supermolecule). As used herein, a "monovalent variant of a compound" refers to a moiety that is identical to the compound except that one hydrogen has been removed and replaced with a bond to the rest of the chemical structure. As used herein, a "polyvalent variant of a compound" refers to a moiety that is identical to the compound except that more than one hydrogen has been removed and replaced with a bond or bonds to the rest of the chemical structure. In the instance of a supramolecule, the inventive compound can also be incorporated into the supramolecule complex without covalent bonds.

D. Combination of the Compounds of the Present Disclosure with Other Materials The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

a) Conductivity Dopants:

A charge transport layer can be doped with conductivity dopants to substantially alter its density of charge carriers, which will in turn alter its conductivity. The conductivity is increased by generating charge carriers in the matrix material, and depending on the type of dopant, a change in the Fermi level of the semiconductor may also be achieved. Hole-transporting layer can be doped by p-type conductivity dopants and n-type conductivity dopants are used in the electron-transporting layer.

Non-limiting examples of the conductivity dopants that may be used in an OLED in combination with materials disclosed herein are exemplified below together with references that disclose those materials: EP01617493, EP01968131, EP2020694, EP2684932, US20050139810, US20070160905, US20090167167, US2010288362, WO06081780, WO2009003455, WO2009008277, WO2009011327, WO2014009310, US2007252140, US2015060804, US20150123047, and US2012146012.

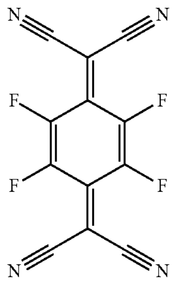

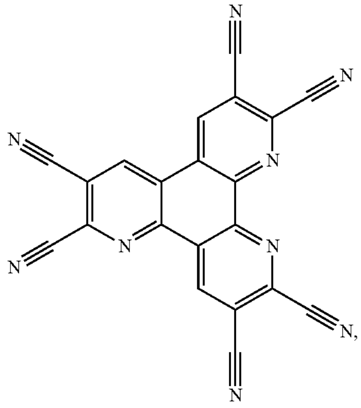
,

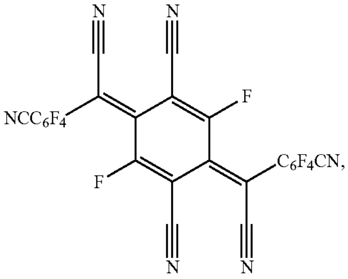
,

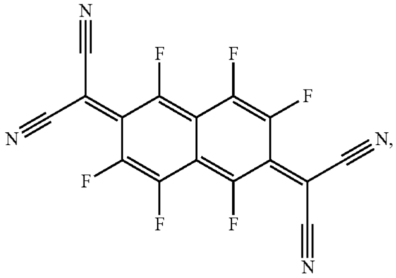
,

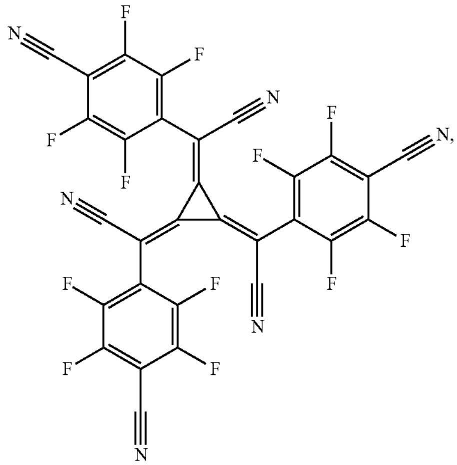
,

-continued

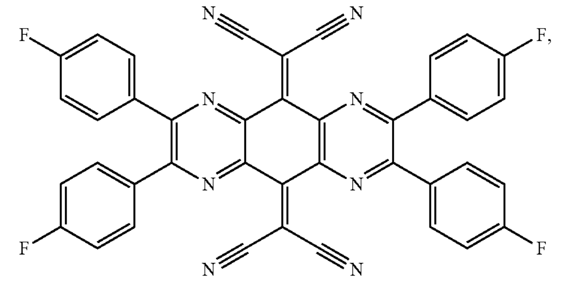

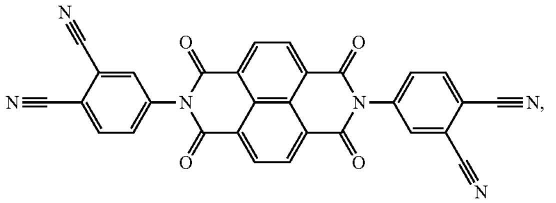

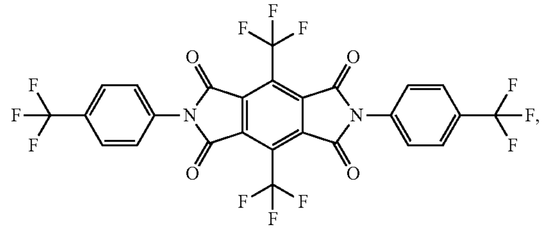

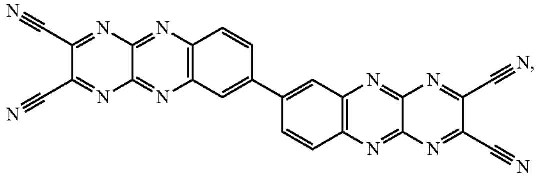

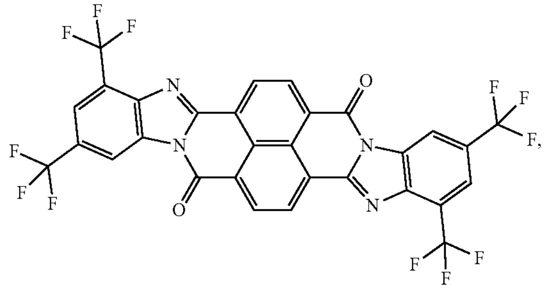

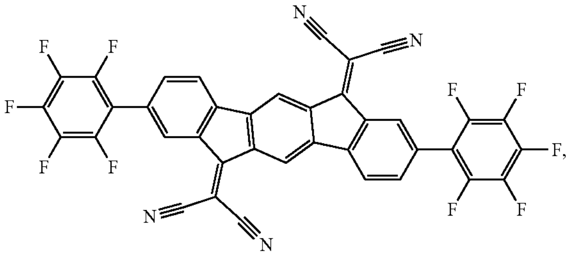

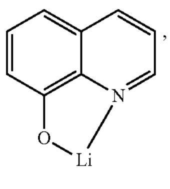

,

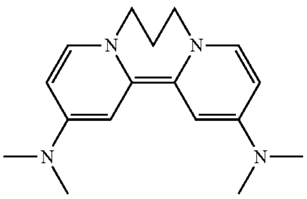

and

-continued

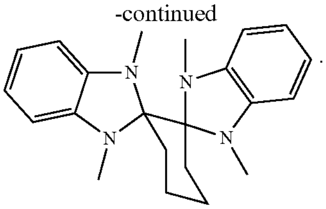

b) HIL/HTL:

A hole injecting/transporting material to be used in the present disclosure is not particularly limited, and any compound may be used as long as the compound is typically used as a hole injecting/transporting material. Examples of the material include, but are not limited to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

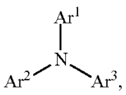

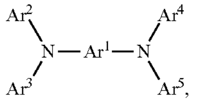

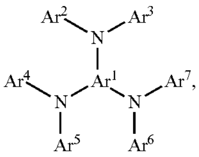

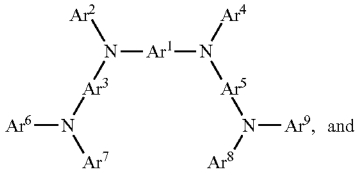

and

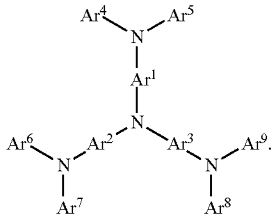

Each of $Ar^1$ to $Ar^9$ is selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each Ar may be unsubstituted or may be substituted by a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof.

In one aspect, $Ar^1$ to $Ar^9$ is independently selected from the group consisting of:

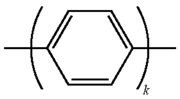
,
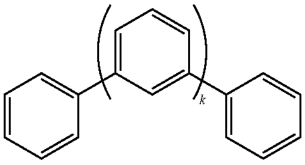
,

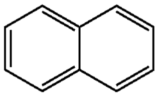
,
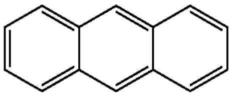
,

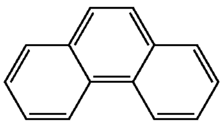
,
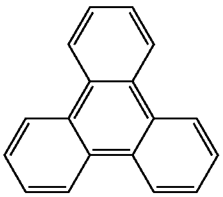
,

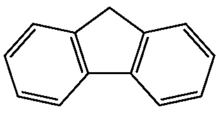
, and
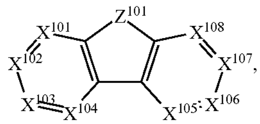

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but are not limited to the following general formula:

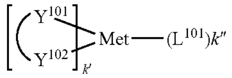

wherein Met is a metal, which can have an atomic weight greater than 40; ($Y^{101}$-$Y^{102}$) is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, ($Y^{101}$-$Y^{102}$) is a 2-phenylpyridine derivative. In another aspect, ($Y^{101}$-$Y^{102}$) is a carbene ligand. In another aspect, Met is selected from Ir, Pt, Os, and Zn. In a further aspect, the metal complex has a smallest oxidation potential in solution vs. $Fc^+$/Fc couple less than about 0.6 V.

Non-limiting examples of the HIL and HTL materials that may be used in an OLED in combination with materials disclosed herein are exemplified below together with references that disclose those materials: CN102702075, DE102012005215, EP01624500, EP01698613, EP01806334, EP01930964, EP01972613, EP01997799, EP02011790, EP02055700, EP02055701, EP1725079, EP2085382, EP2660300, EP650955, JP07-073529, JP2005112765, JP2007091719, JP2008021687, JP2014-009196, KR20110088898, KR20130077473, TW201139402, U.S. Ser. No. 06/517,957, US20020158242, US20030162053, US20050123751, US20060182993, US20060240279, US20070145888, US20070181874, US20070278938, US20080014464, US20080091025, US20080106190, US20080124572, US20080145707, US20080220265, US20080233434, US20080303417, US2008107919, US20090115320, US20090167161, US2009066235, US2011007385, US20110163302, US2011240968, US2011278551, US2012205642, US2013241401, US20140117329, US2014183517, U.S. Pat. Nos. 5,061,569, 5,639,914, WO05075451, WO07125714, WO08023550, WO08023759, WO2009145016, WO2010061824, WO2011075644, WO2012177006, WO2013018530, WO2013039073, WO2013087142, WO2013118812, WO2013120577, WO2013157367, WO2013175747, WO2014002873, WO2014015935, WO2014015937, WO2014030872, WO2014030921, WO2014034791, WO2014104514, WO2014157018.

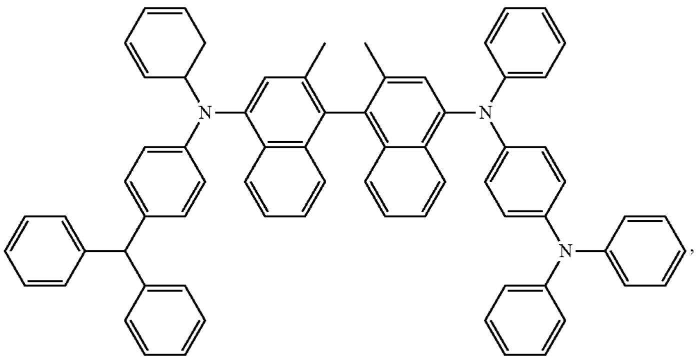,
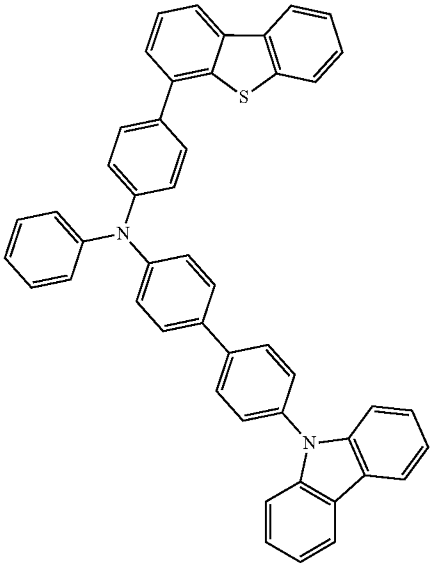,
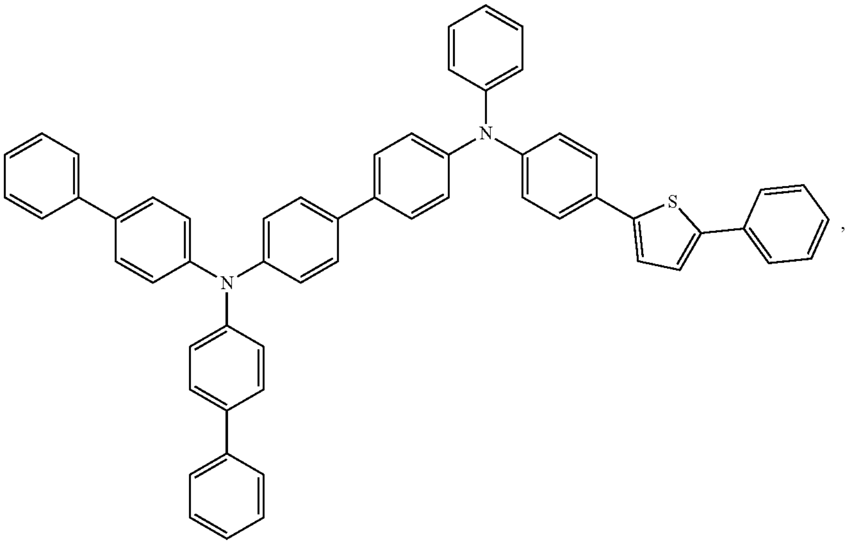,
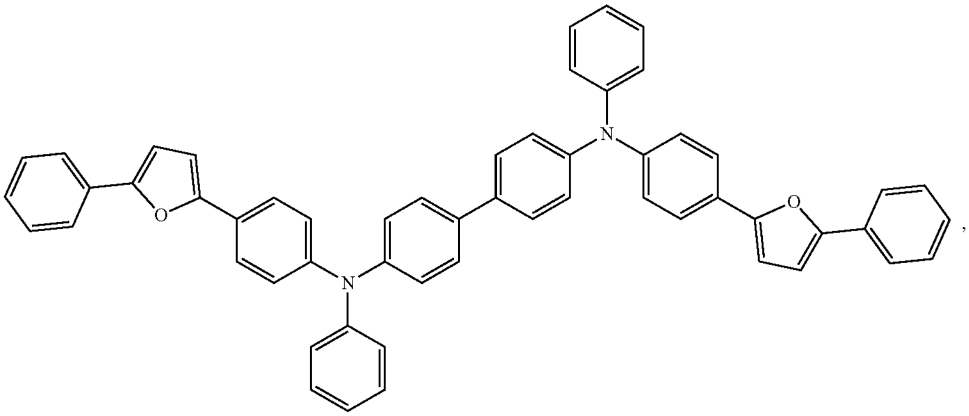,

-continued
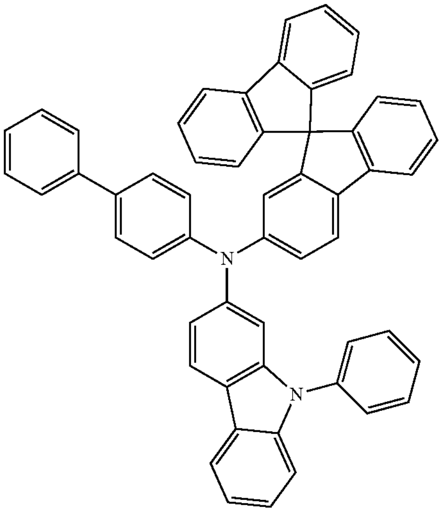
,
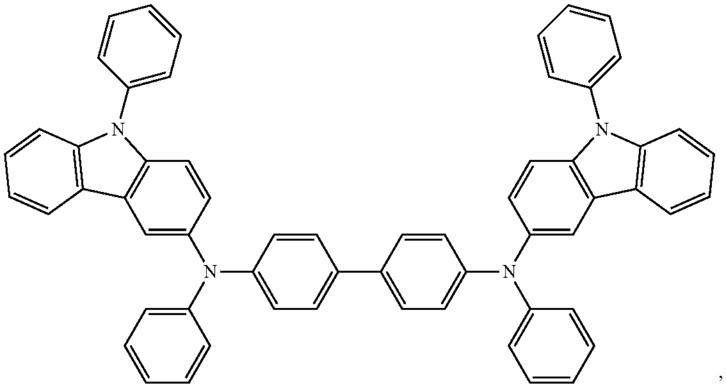
,
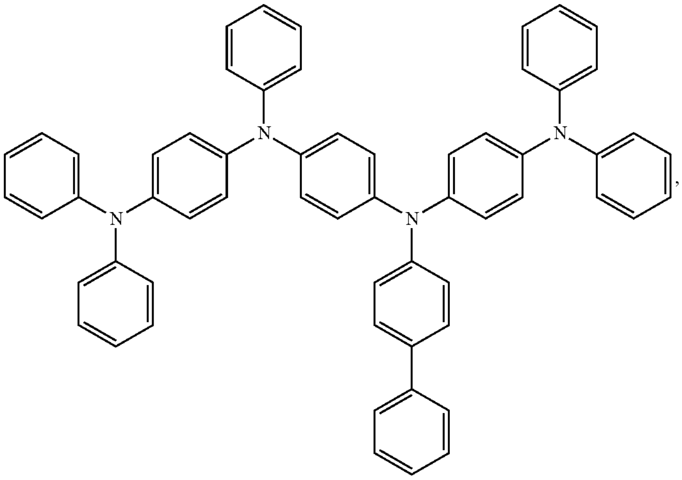
,
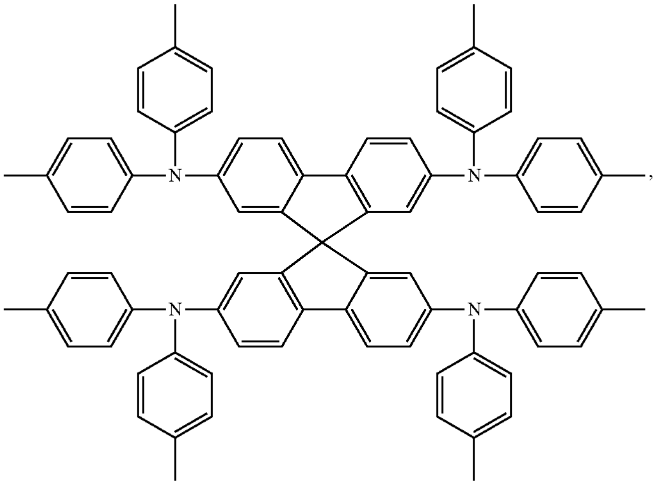
,

-continued
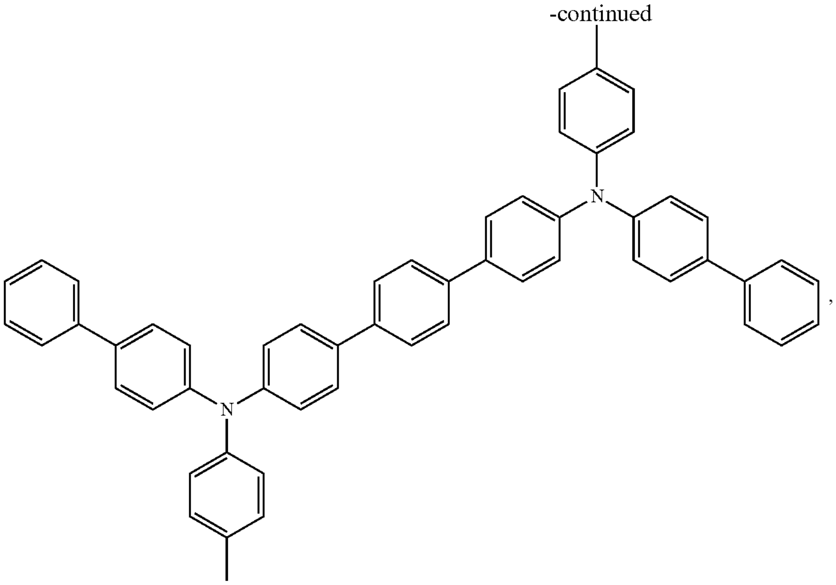
,
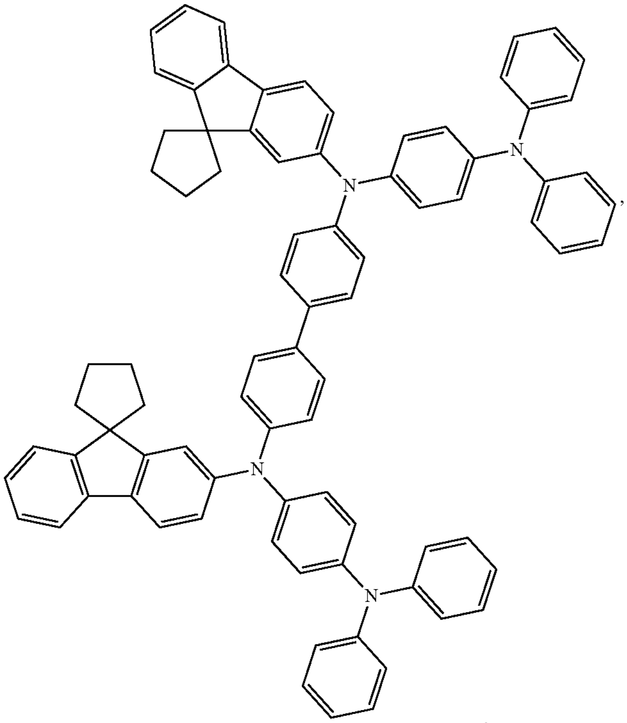
,
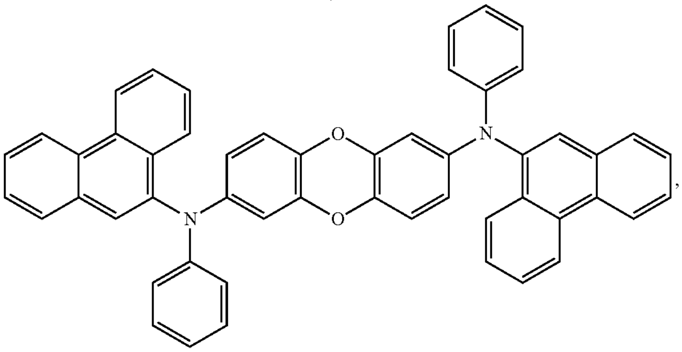
,

-continued
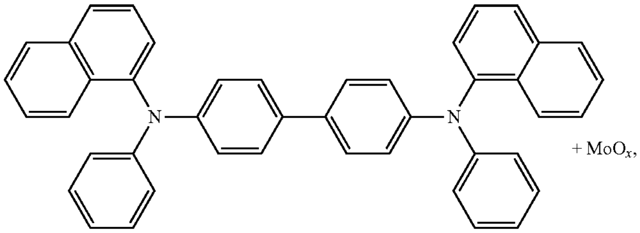
+ $MoO_x$,
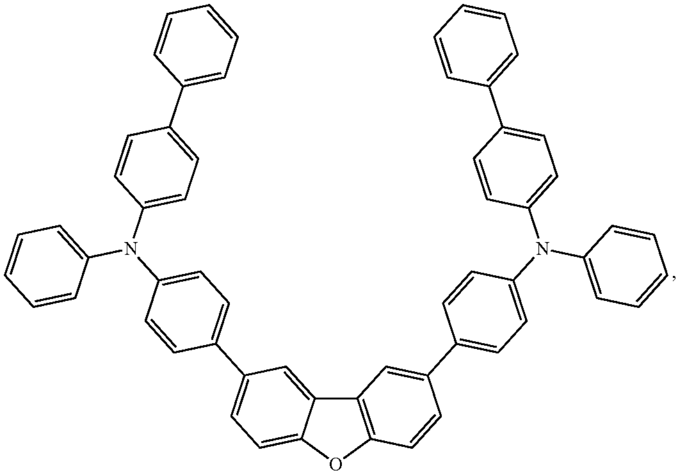
,
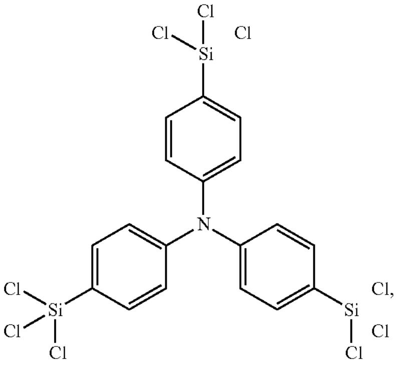
,
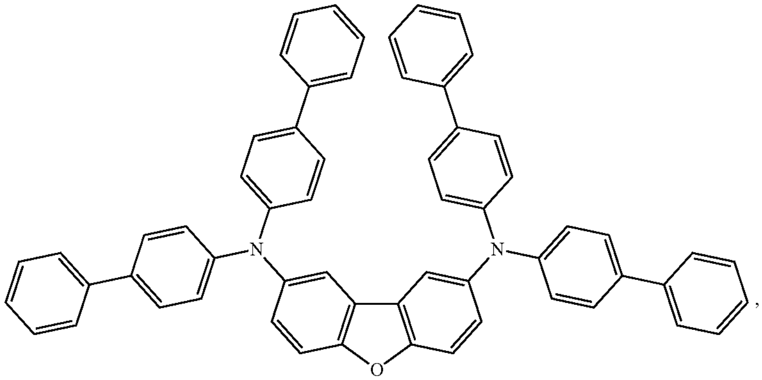
,
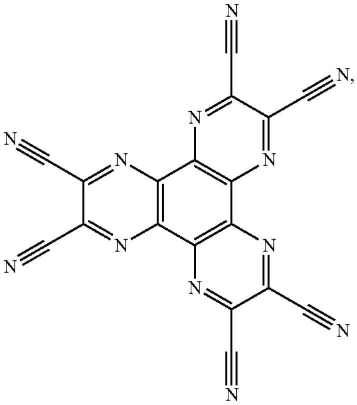
, -continued
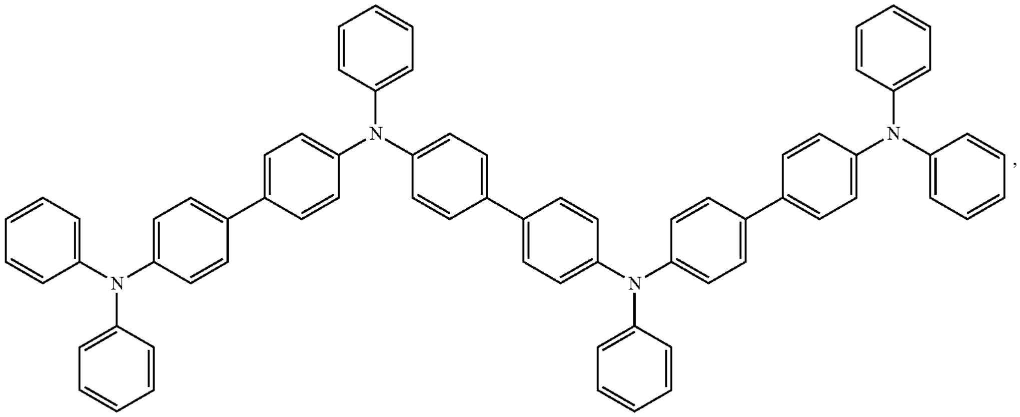
,
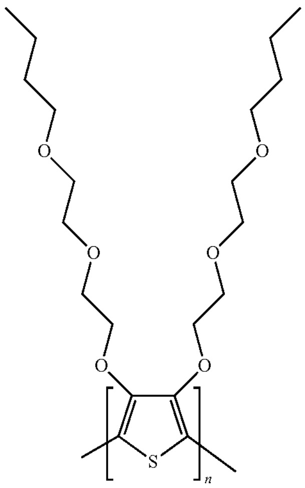
,
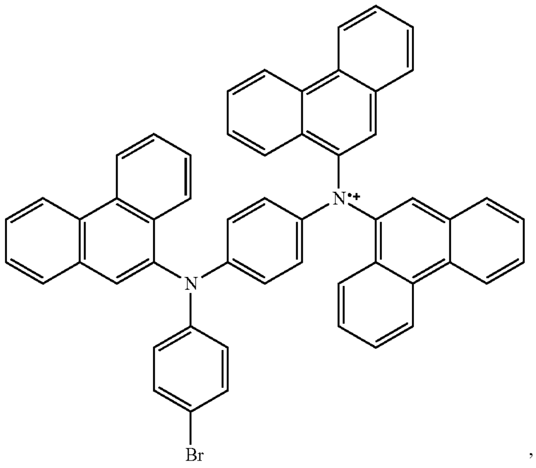
,
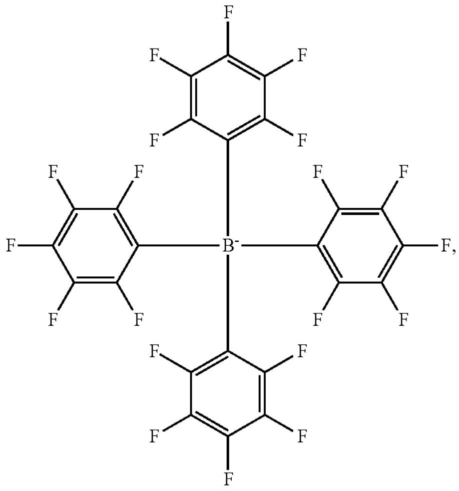
,
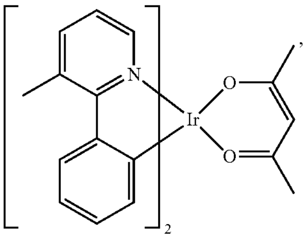
, -continued
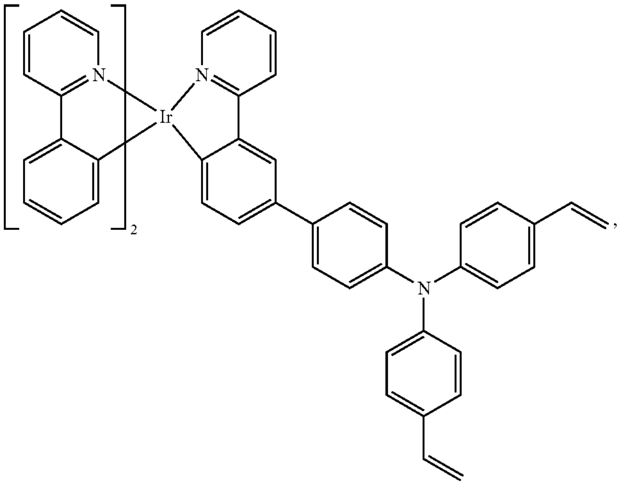
,
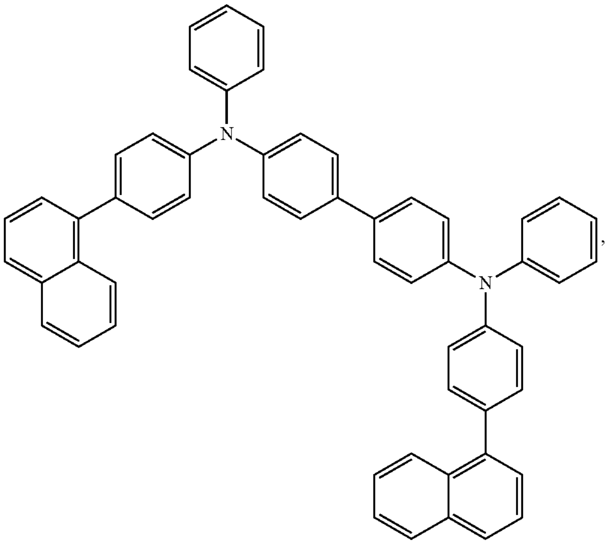
,
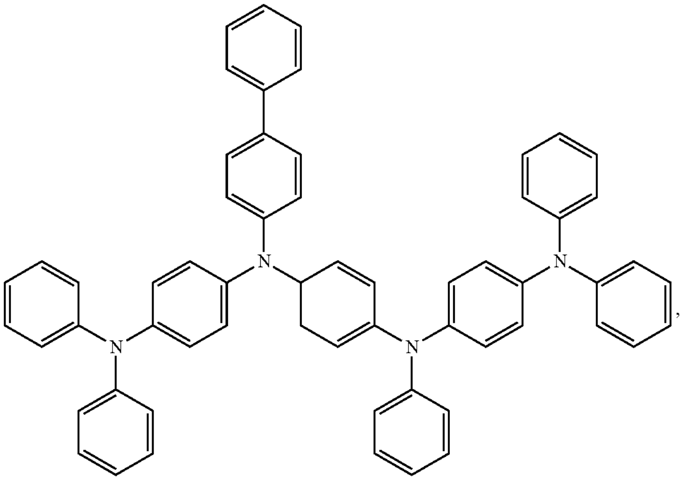
, -continued
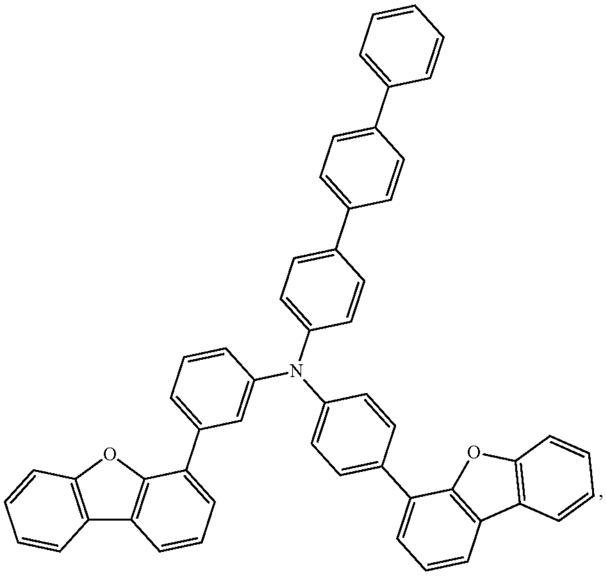
,
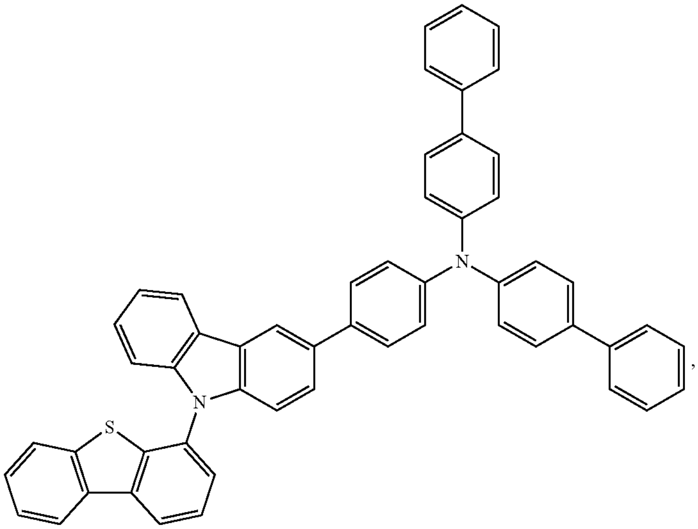
,
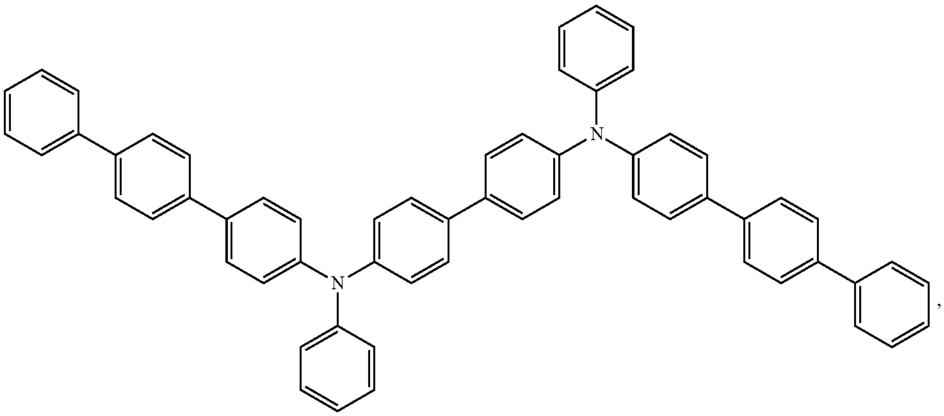
, -continued
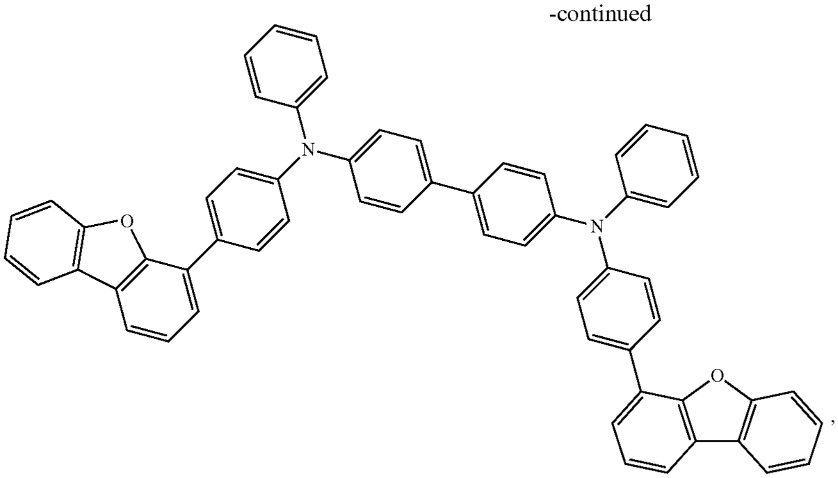
,
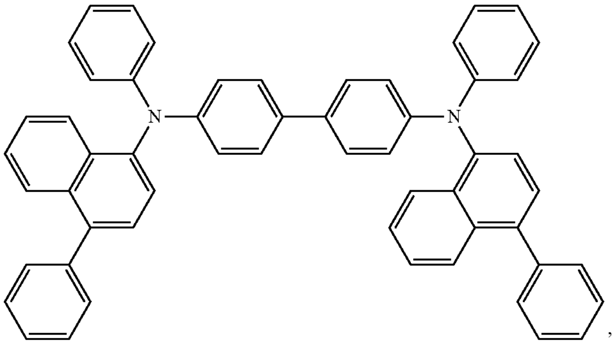
,
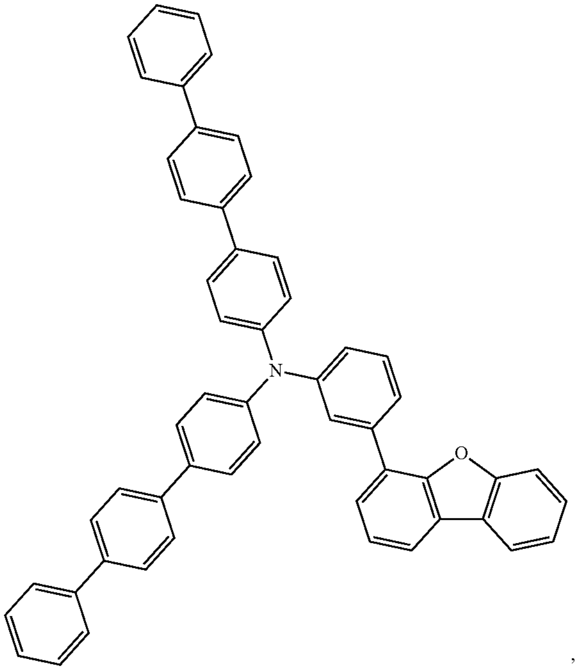
,
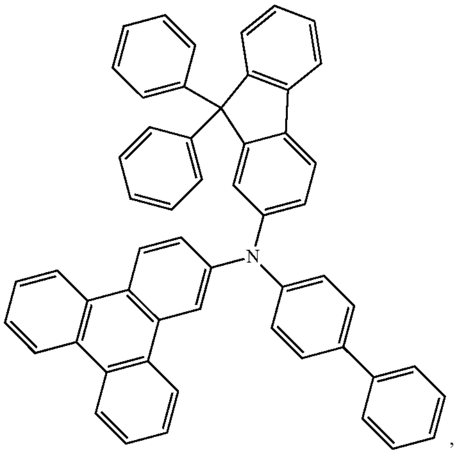
,
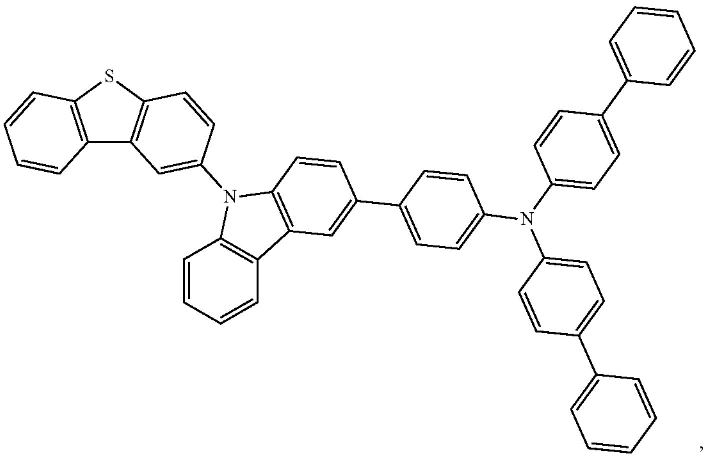
, -continued
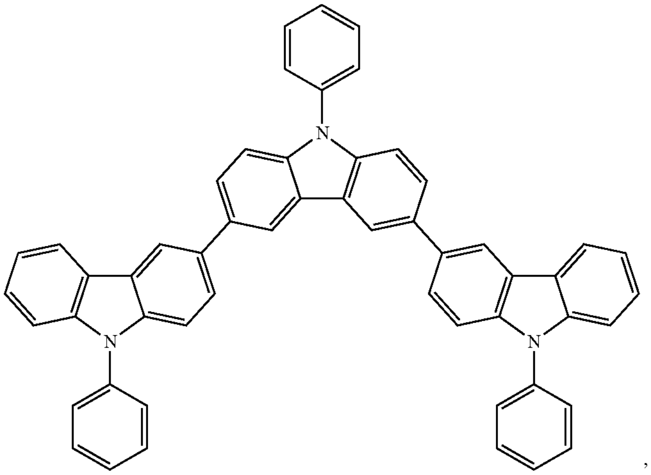
,
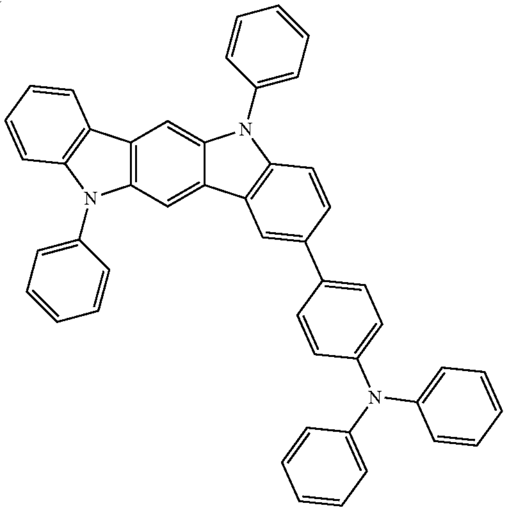
,
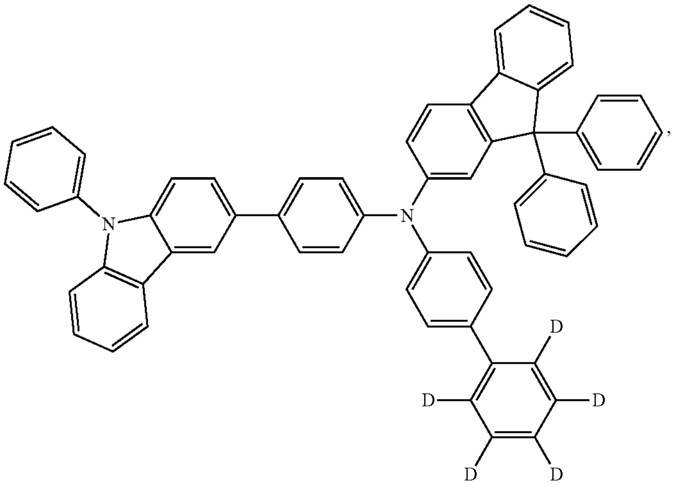
,
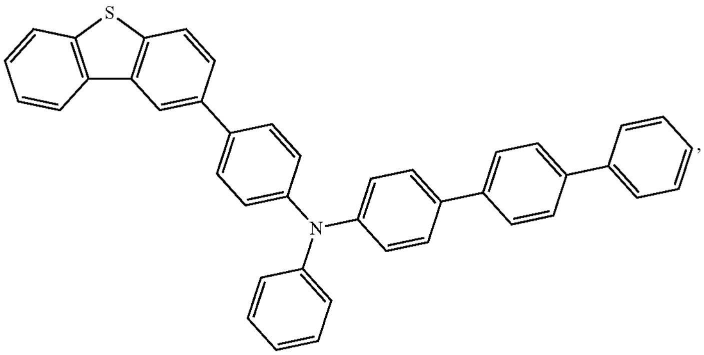
, -continued
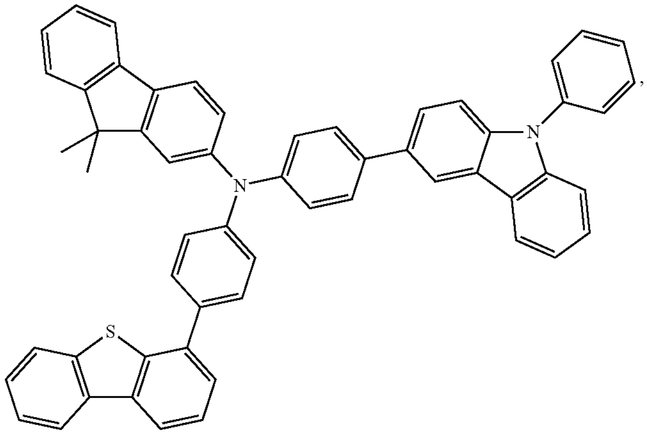
,
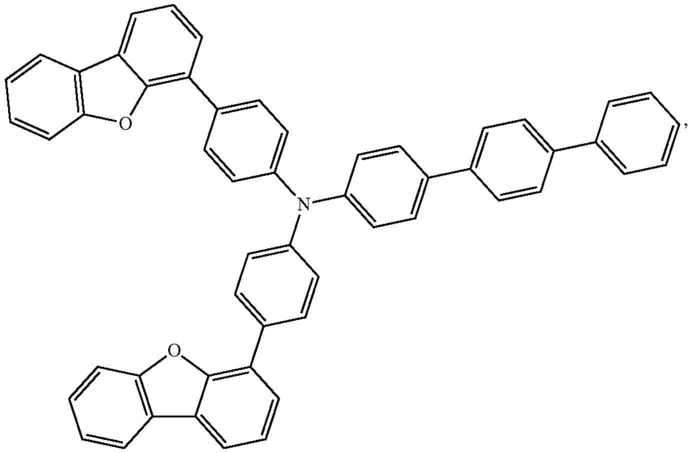
,
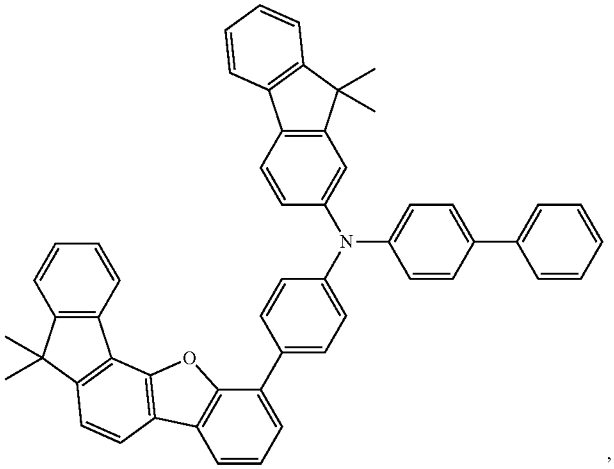
,
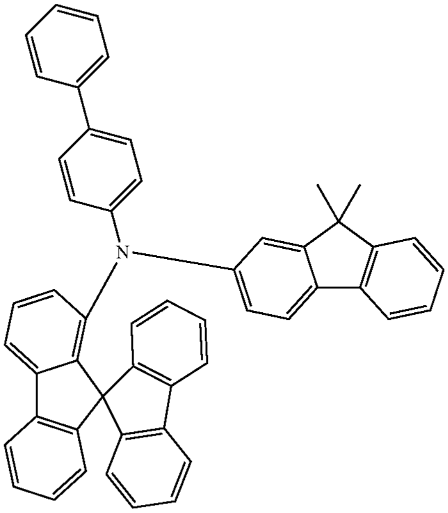
, -continued
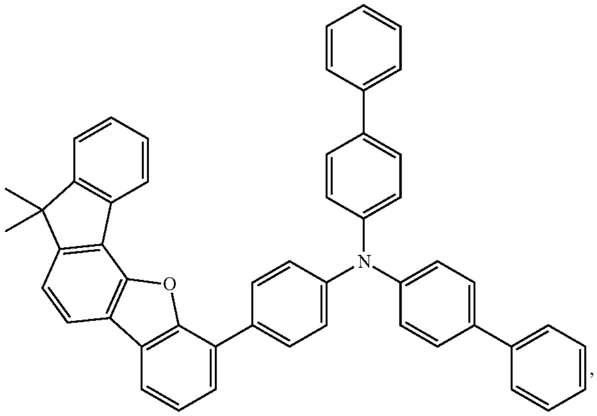
,
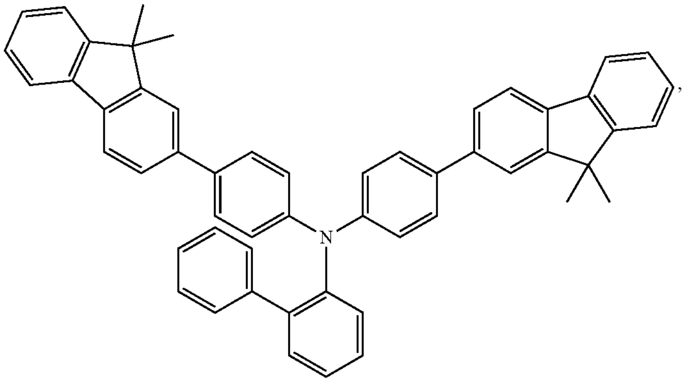
,
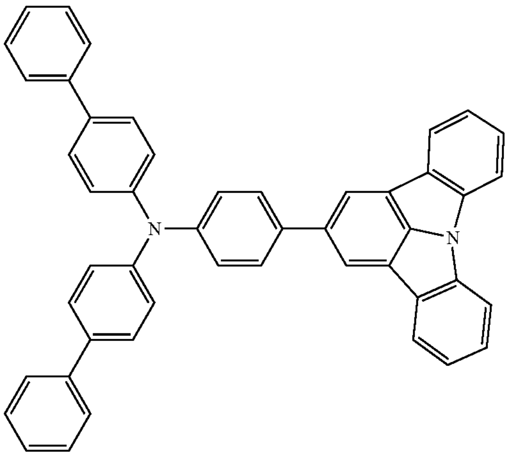
,
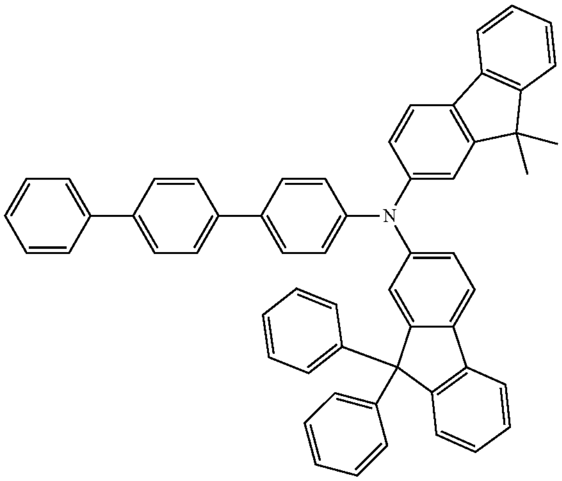
, -continued
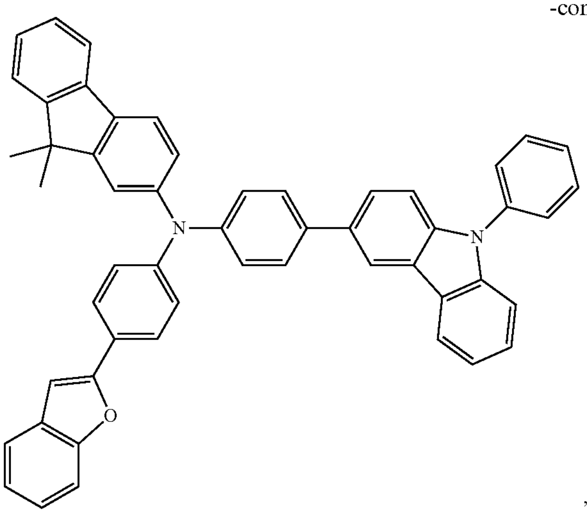
,
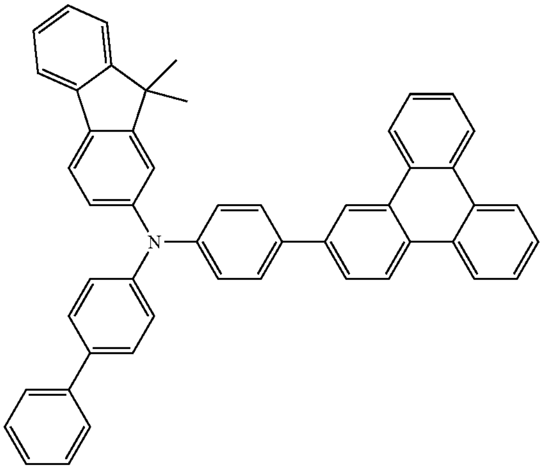
,
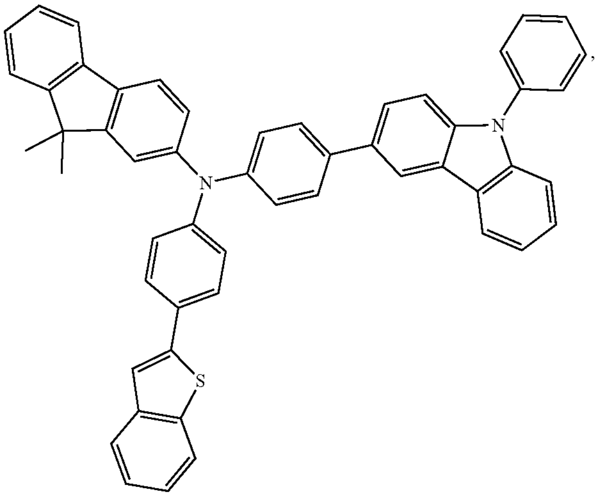
,
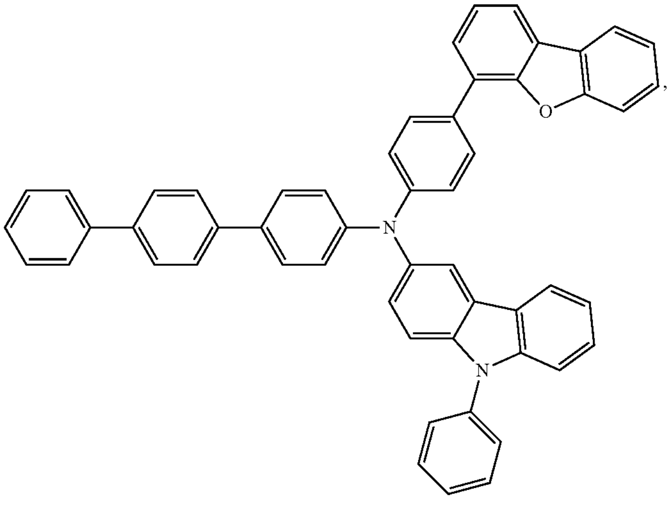
, -continued
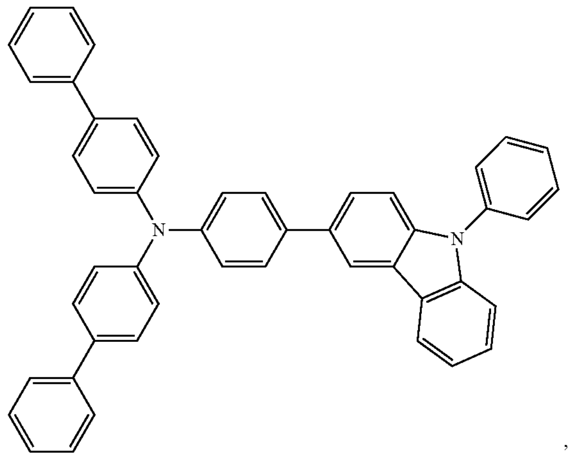
,
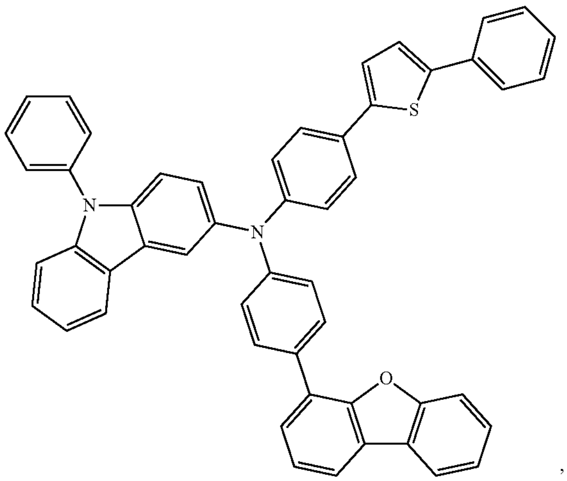
,
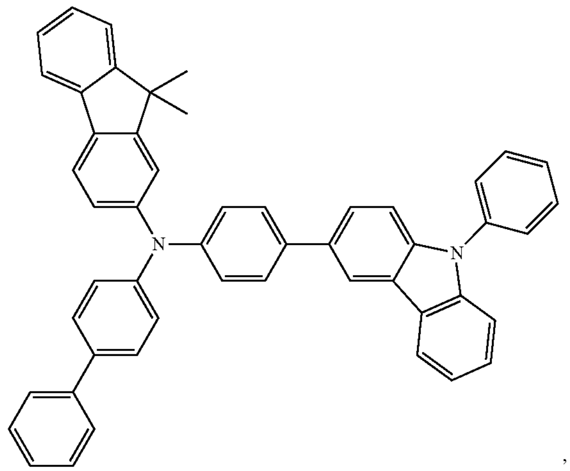
,
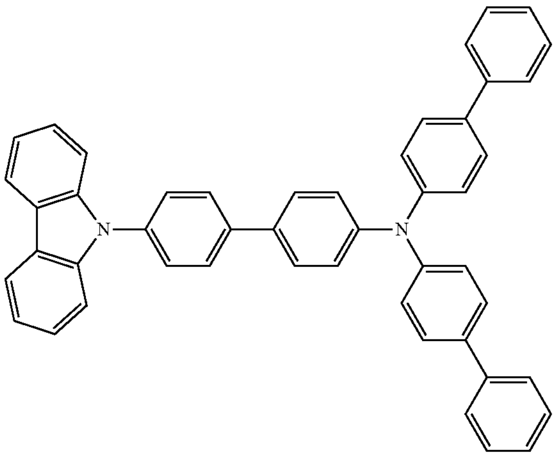
,
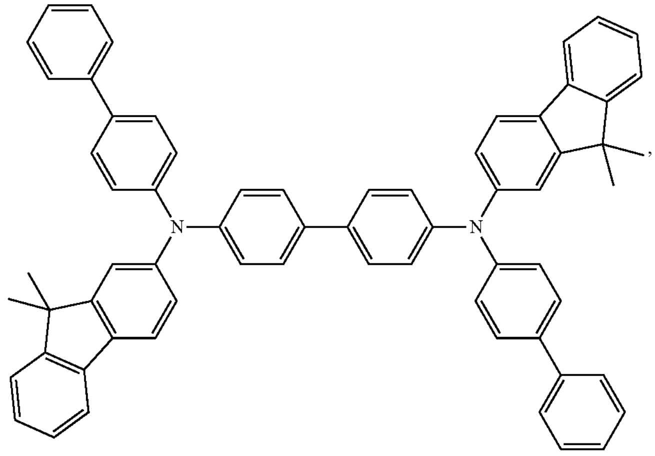
, -continued
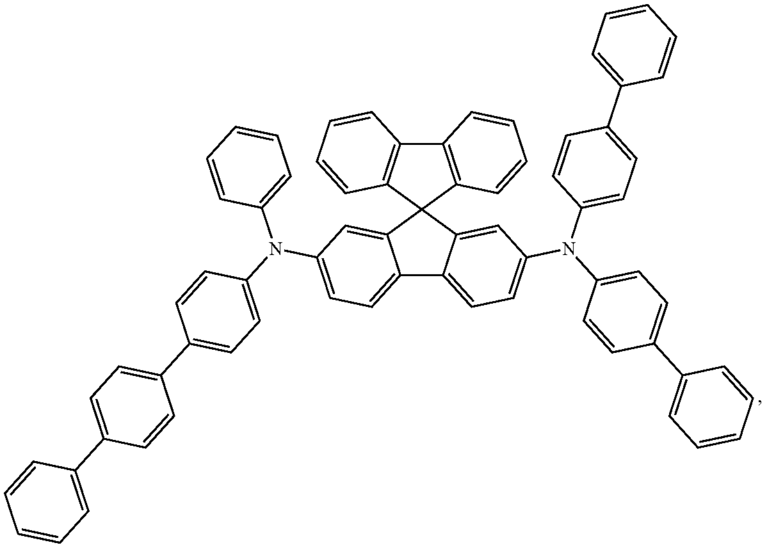
,
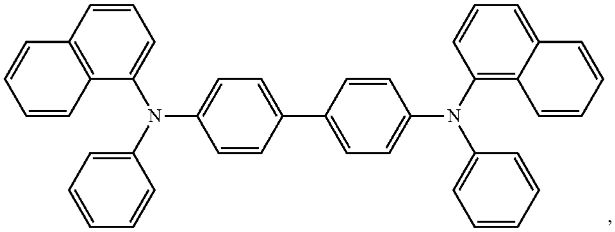
,
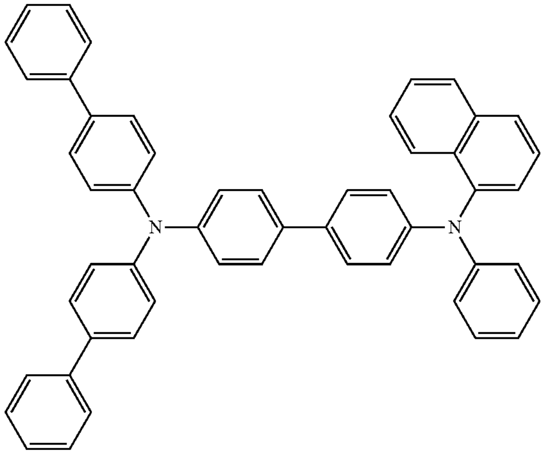
,
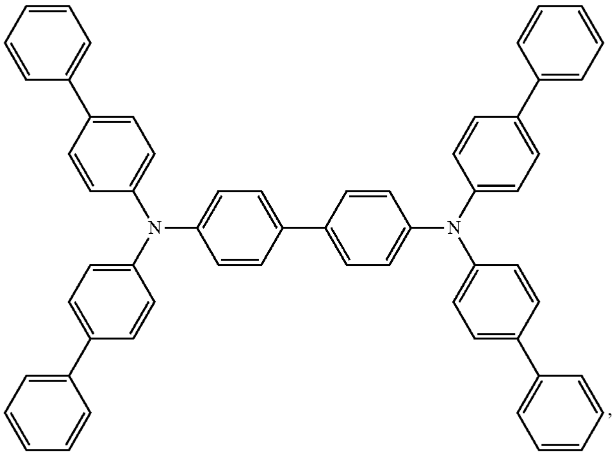
, -continued
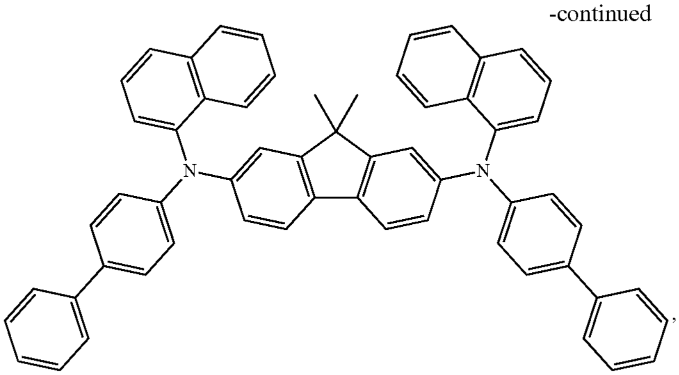
,
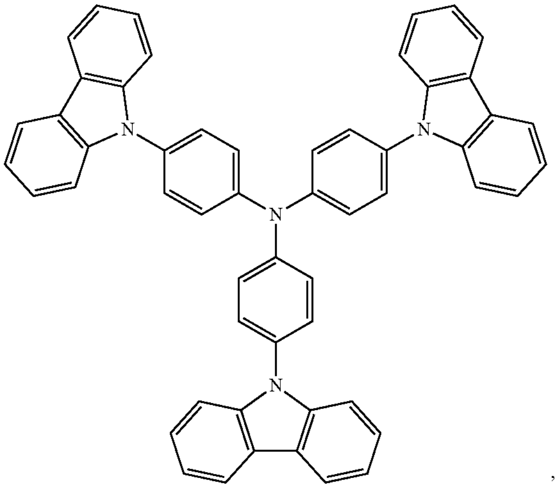
,
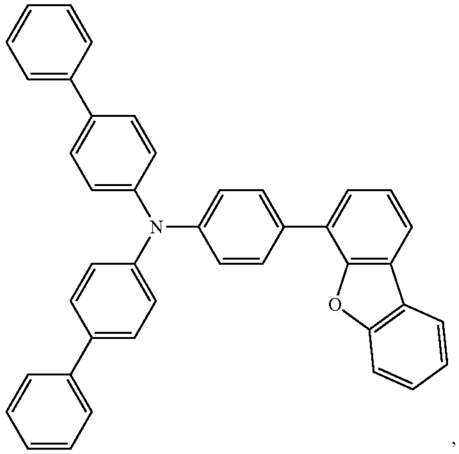
,
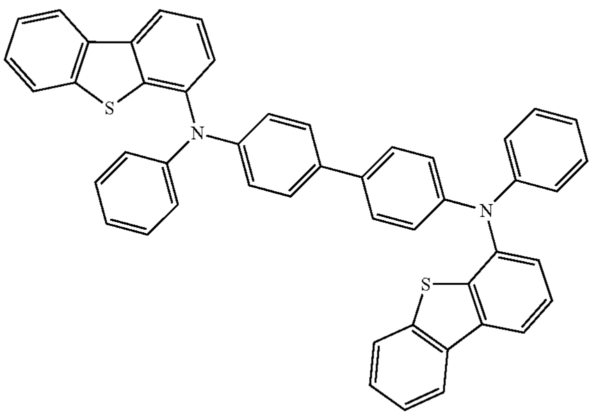
,
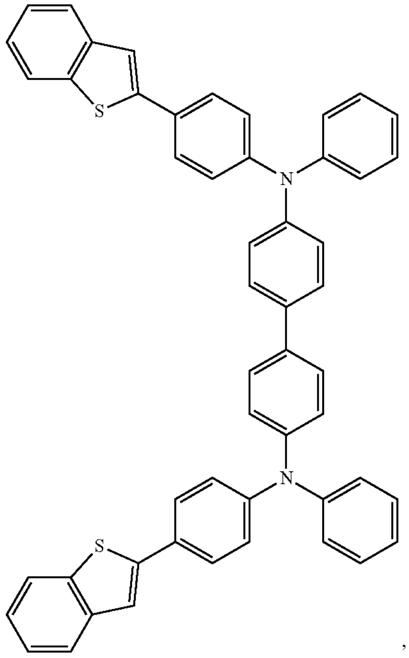
, and -continued

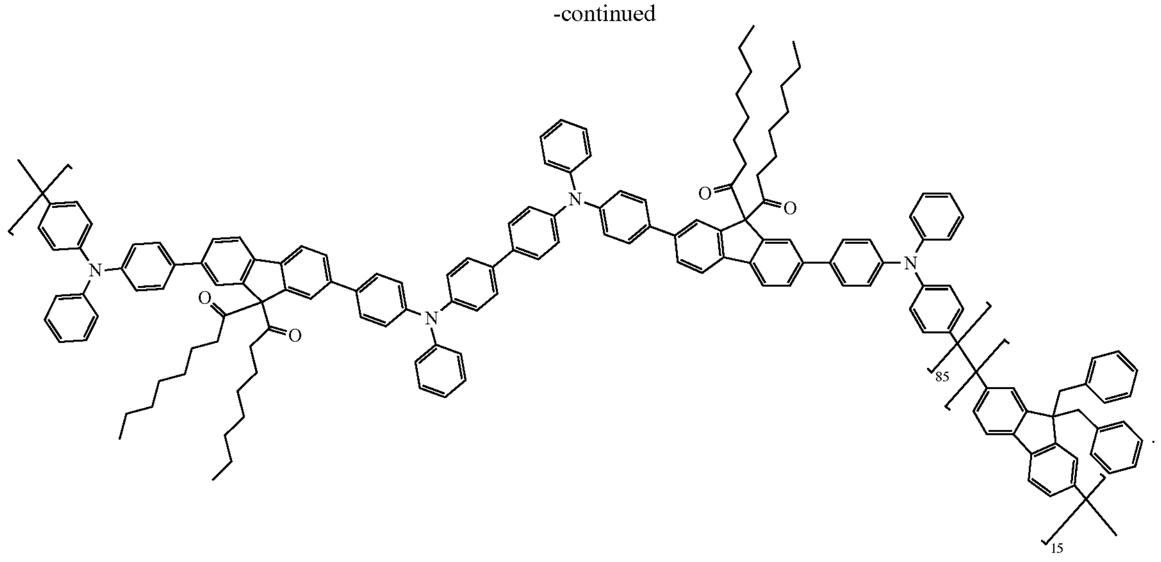

c) EBL:

An electron blocking layer (EBL) may be used to reduce the number of electrons and/or excitons that leave the emissive layer. The presence of such a blocking layer in a device may result in substantially higher efficiencies, and/or longer lifetime, as compared to a similar device lacking a blocking layer. Also, a blocking layer may be used to confine emission to a desired region of an OLED. In some embodiments, the EBL material has a higher LUMO (closer to the vacuum level) and/or higher triplet energy than the emitter closest to the EBL interface. In some embodiments, the EBL material has a higher LUMO (closer to the vacuum level) and/or higher triplet energy than one or more of the hosts closest to the EBL interface. In one aspect, the compound used in EBL contains the same molecule or the same functional groups used as one of the hosts described below.

d) Hosts:

The light emitting layer of the organic EL device of the present disclosure preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. Any host material may be used with any dopant so long as the triplet criteria is satisfied.

Examples of metal complexes used as host are preferred to have the following general formula:

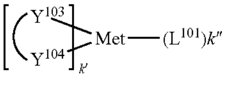

wherein Met is a metal; ($Y^{103}$-$Y^{104}$) is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

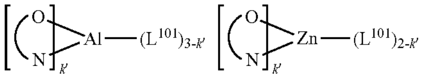

wherein (O—N) is a bidentate ligand, having metal coordinated to atoms O and N.

In another aspect, Met is selected from Ir and Pt. In a further aspect, ($Y^{103}$-$Y^{104}$) is a carbene ligand.

In one aspect, the host compound contains at least one of the following groups selected from the group consisting of aromatic hydrocarbon cyclic compounds such as benzene, biphenyl, triphenyl, triphenylene, tetraphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each option within each group may be unsubstituted or may be substituted by a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof.

In one aspect, the host compound contains at least one of the following groups in the molecule:

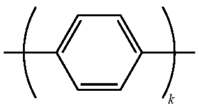,
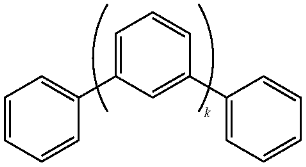,
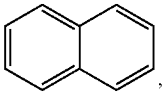,
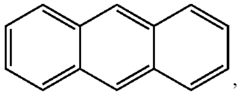,
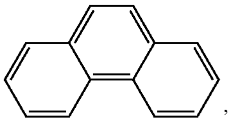,
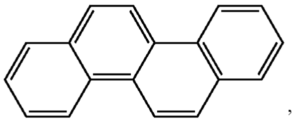,
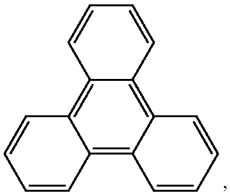,
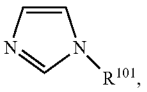,
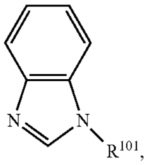,
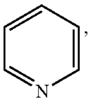,
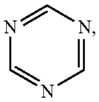,
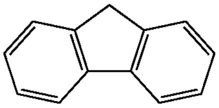,
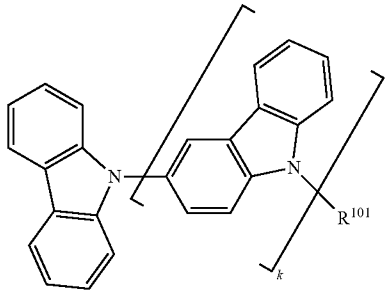,
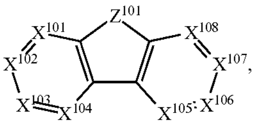,
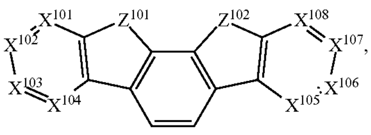,
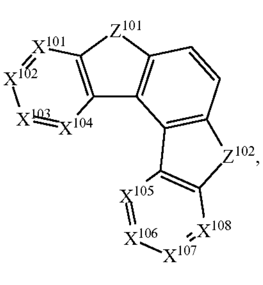, -continued

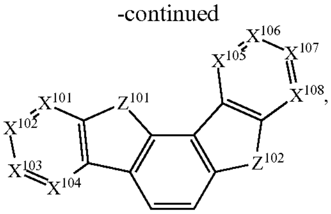,

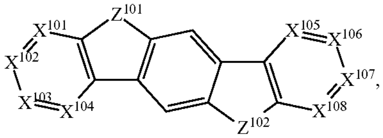, and

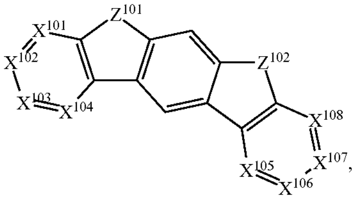, wherein $R^{101}$ is selected from the group consisting of hydrogen, deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof, and when it is aryl or heteroaryl, it has the similar definition as Ar's mentioned above. k is an integer from 0 to 20 or 1 to 20. $X^{101}$ to $X^{108}$ are independently selected from C (including CH) or N. $Z^{101}$ and $Z^{102}$ are independently selected from $NR^{104}$, O, or S.

Non-limiting examples of the host materials that may be used in an OLED in combination with materials disclosed herein are exemplified below together with references that disclose those materials: EP2034538, EP2034538A, EP2757608, JP2007254297, KR20100079458, KR20120088644, KR20120129733, KR20130115564, TW201329200, US20030175553, US20050238919, US20060280965, US20090017330, US20090030202, US20090167162, US20090302743, US20090309488, US20100012931, US20100084966, US20100187984, US2010187984, US2012075273, US2012126221, US2013009543, US2013105787, US2013175519, US2014001446, US20140183503, US20140225088, US2014034914, U.S. Pat. No. 7,154,114, WO2001039234, WO2004093207, WO2005014551, WO2005089025, WO2006072002, WO2006114966, WO2007063754, WO2008056746, WO2009003898, WO2009021126, WO2009063833, WO2009066778, WO2009066779, WO2009086028, WO2010056066, WO2010107244, WO2011081423, WO2011081431, WO2011086863, WO2012128298, WO2012133644, WO2012133649, WO2013024872, WO2013035275, WO2013081315, WO2013191404, WO2014142472, US20170263869, US20160163995, U.S. Pat. No. 9,466,803,

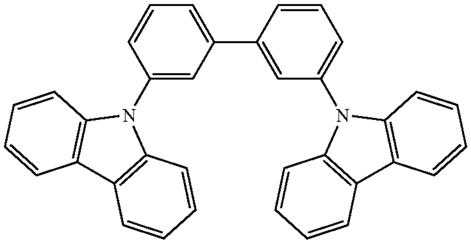,
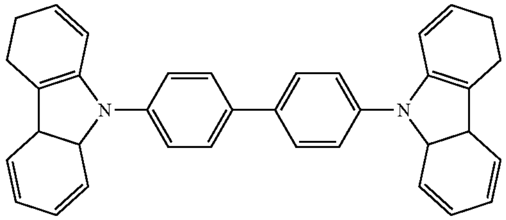,
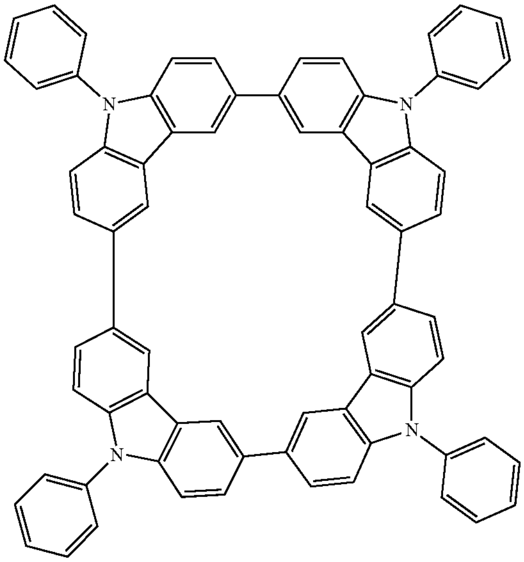,
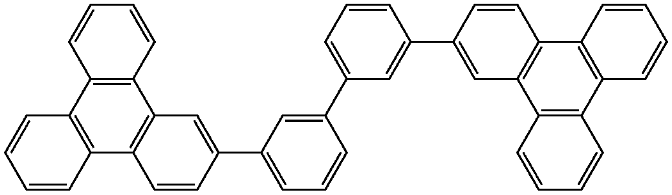,
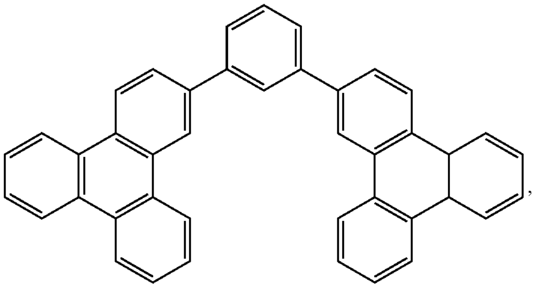,
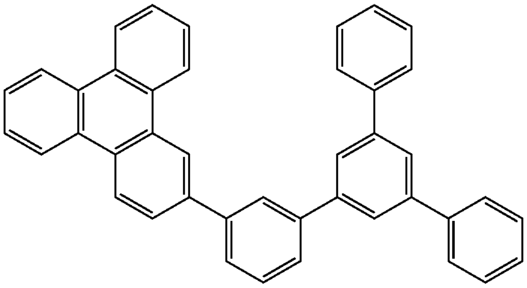,
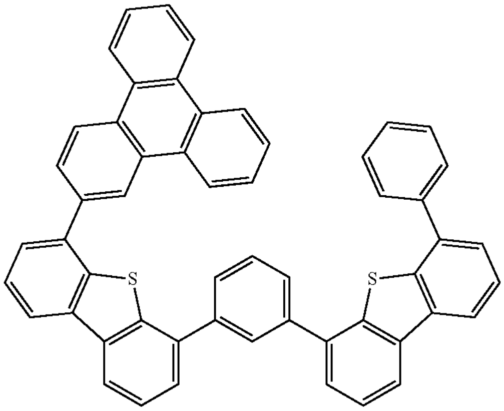,
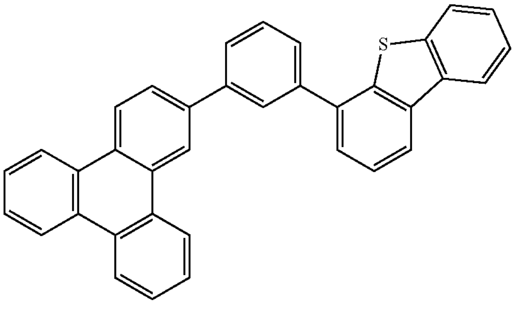, -continued
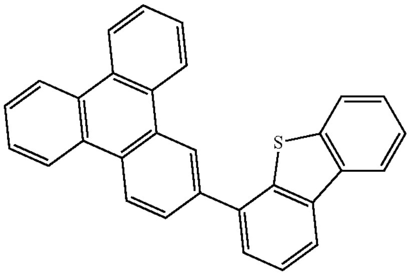,
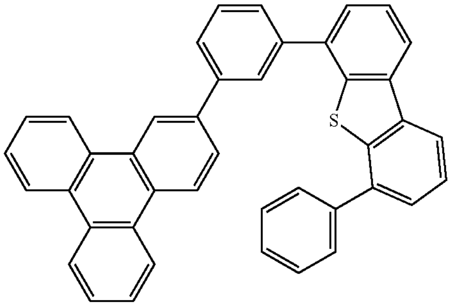,
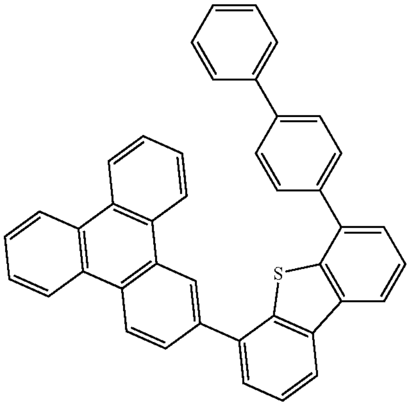,
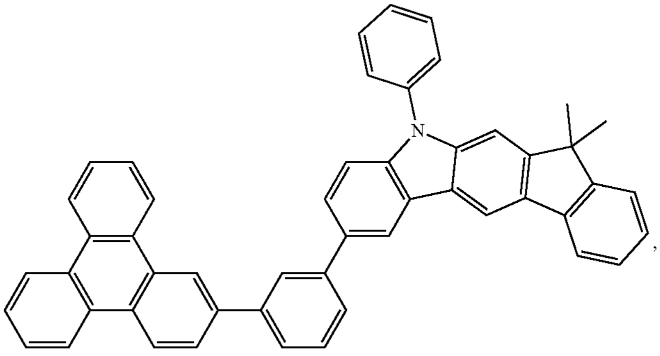,
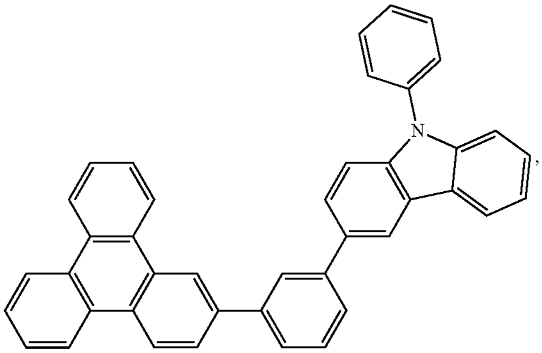,
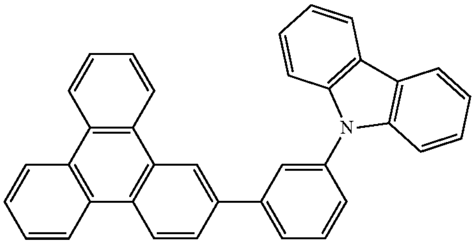,
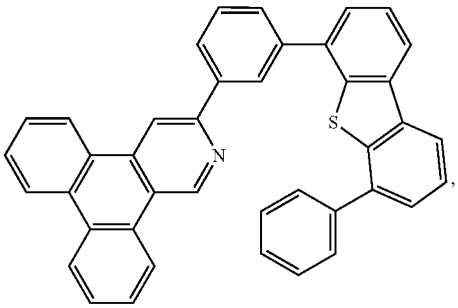,
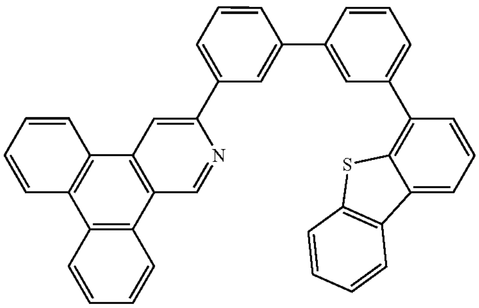,
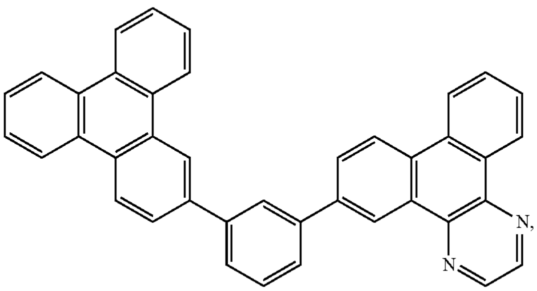,
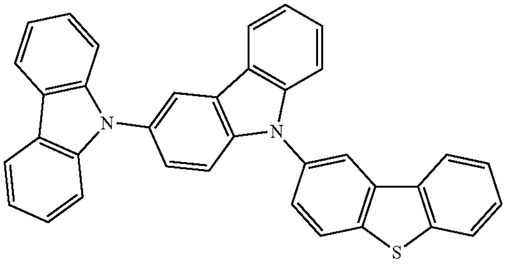, -continued
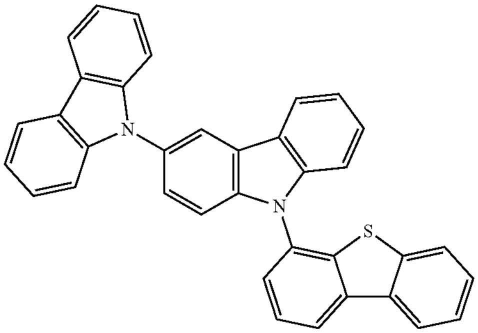
,
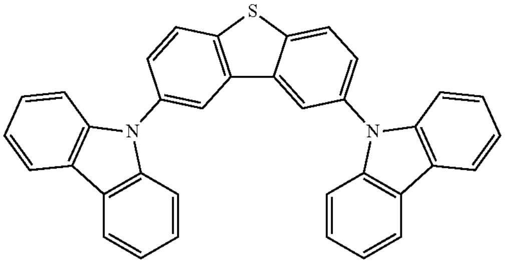
,
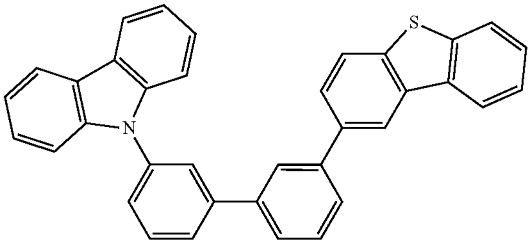
,
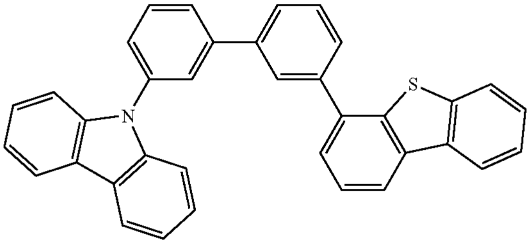
,
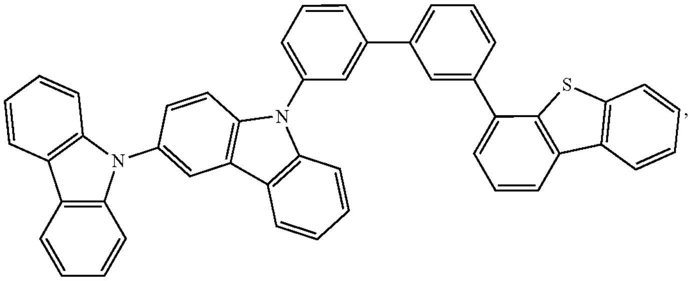
,
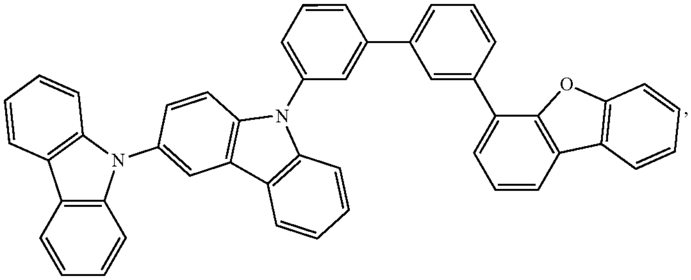
,
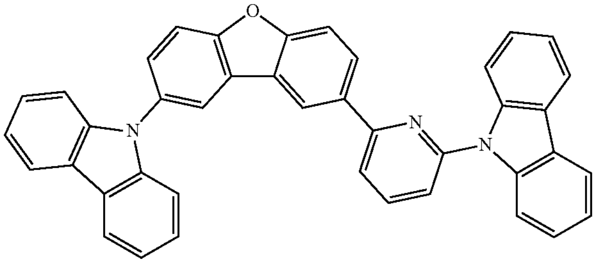
,
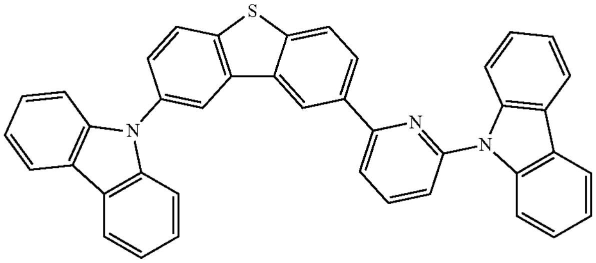
, -continued
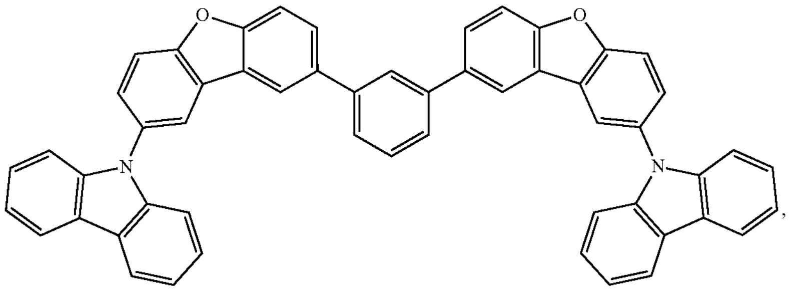,
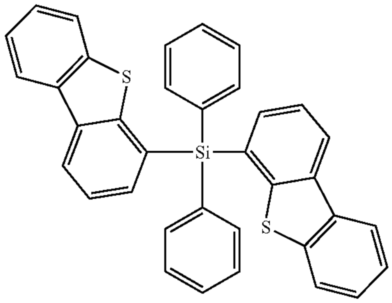,
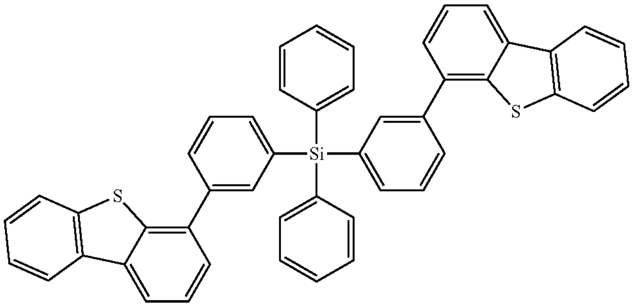,
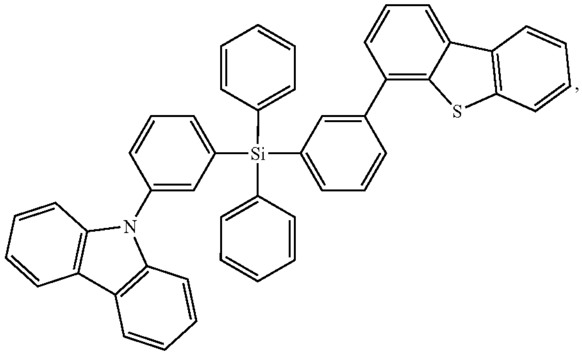,
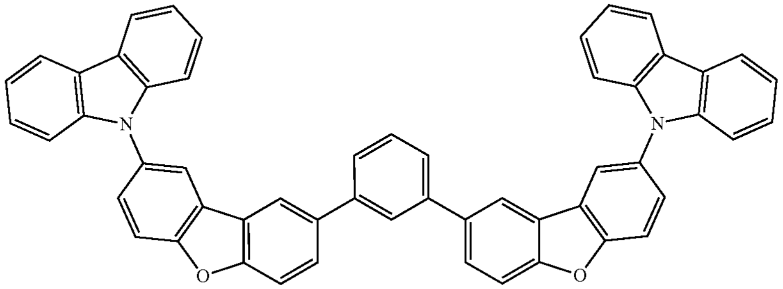,
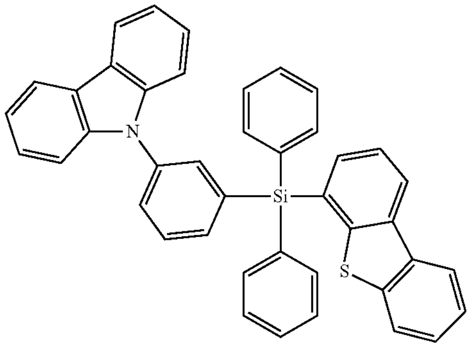,
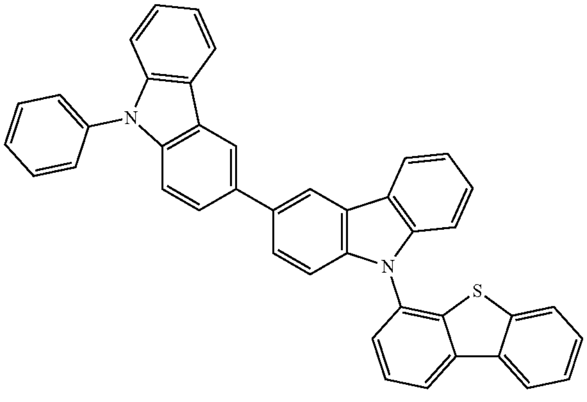, -continued
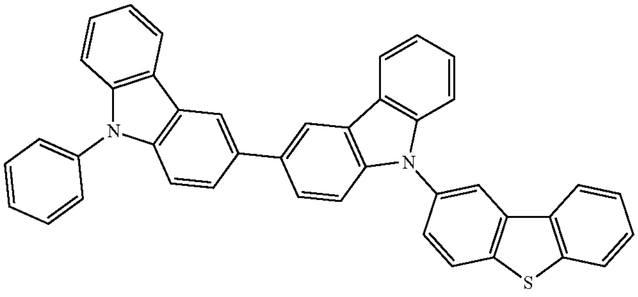,
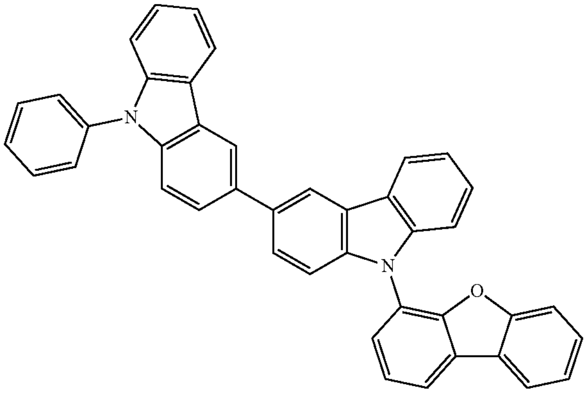,
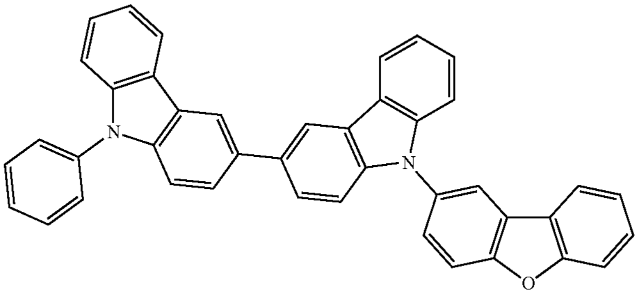,
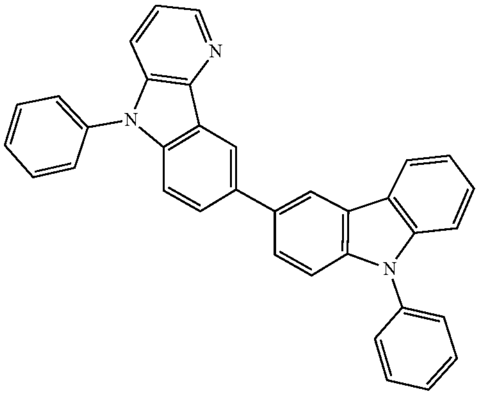,
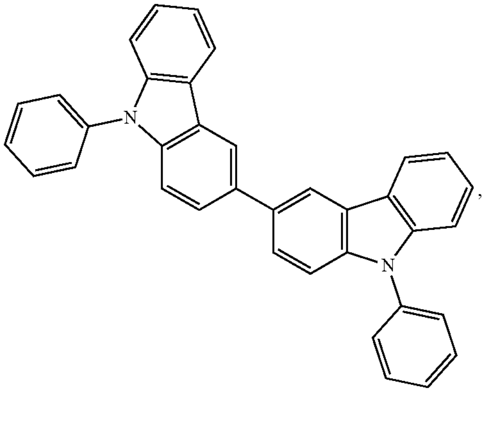,
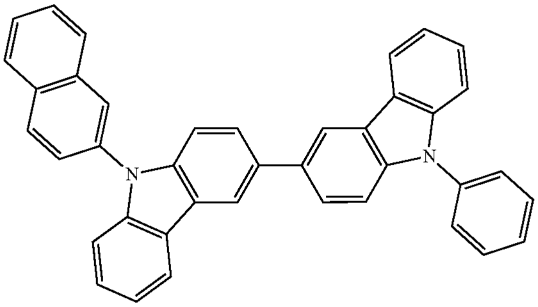, -continued
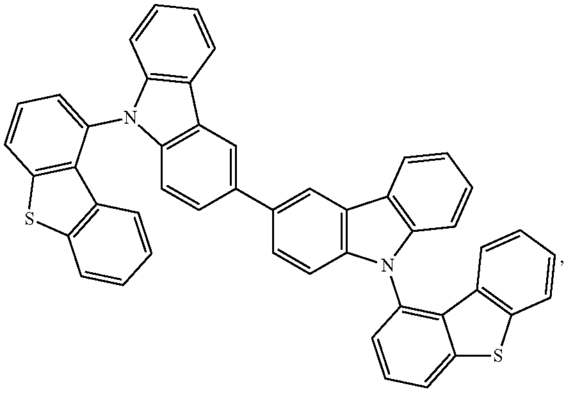,
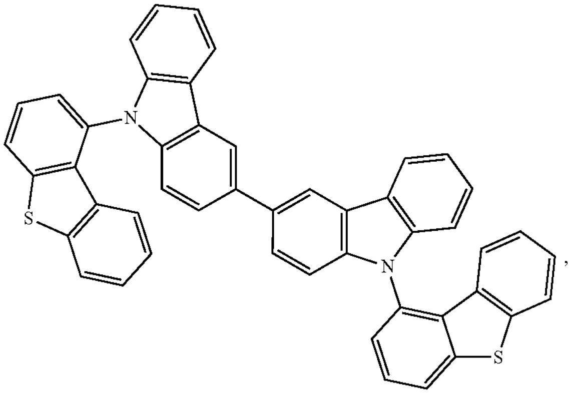,
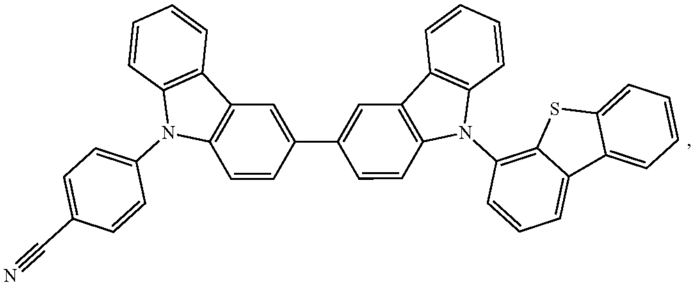,
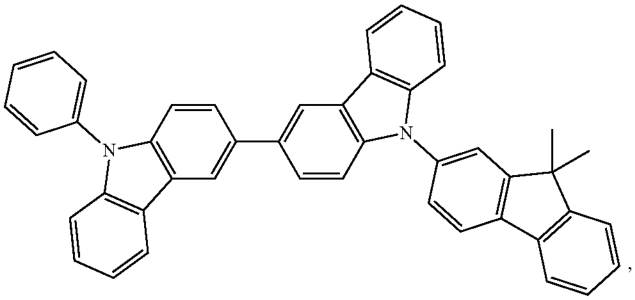,
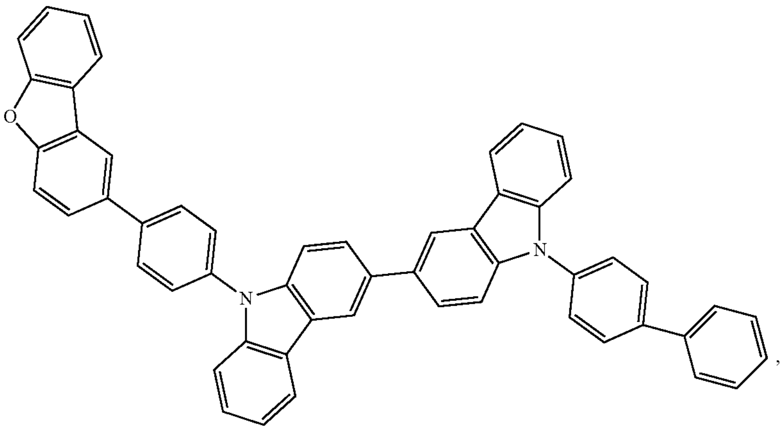, -continued
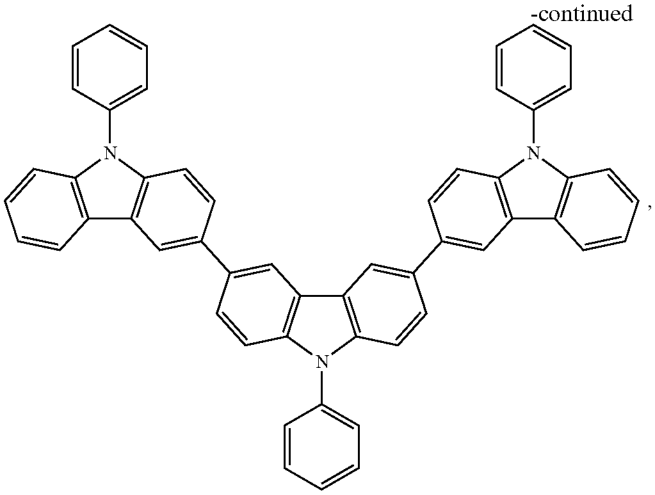
,
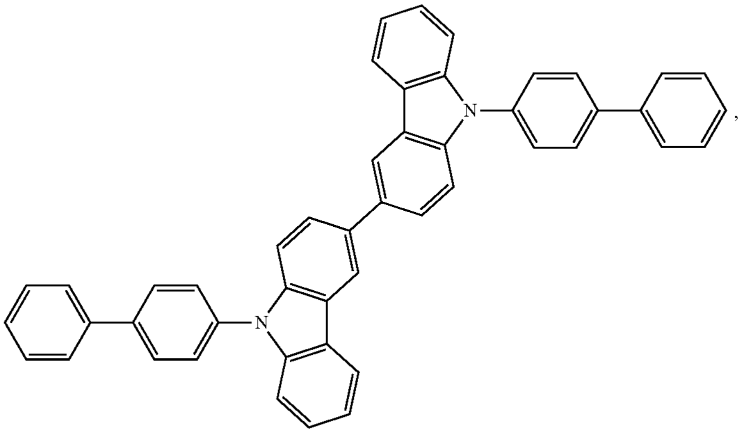
,
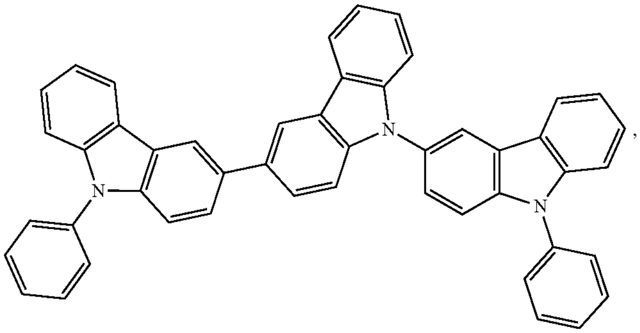
,
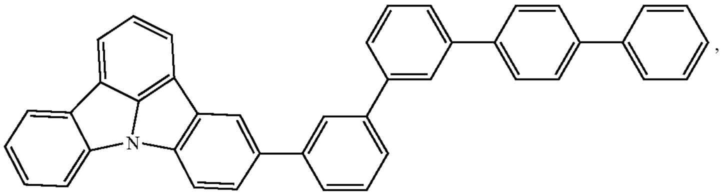
, -continued
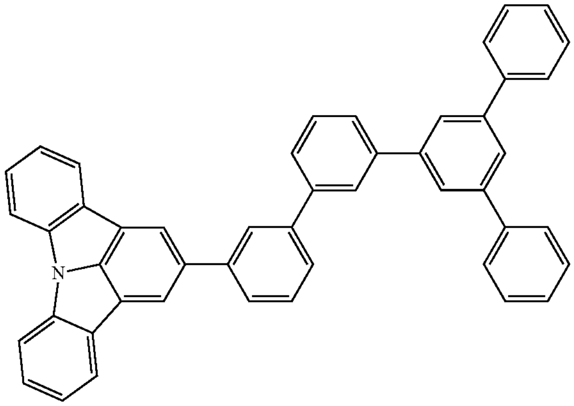
,
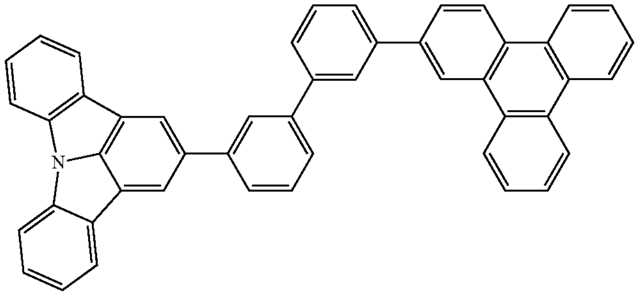
,
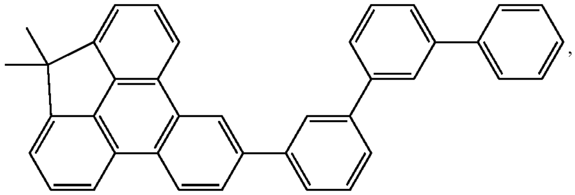
,
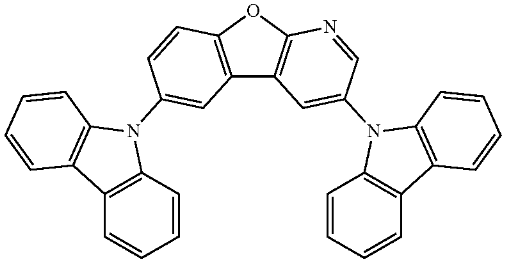
,
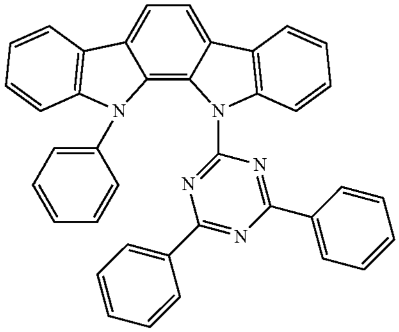
,
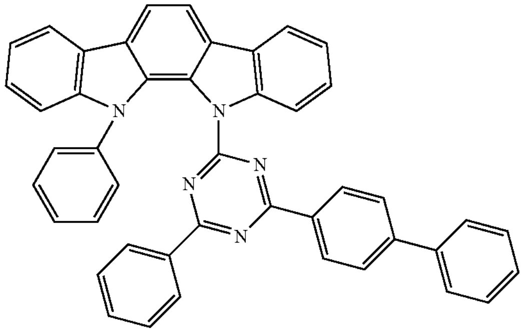
,
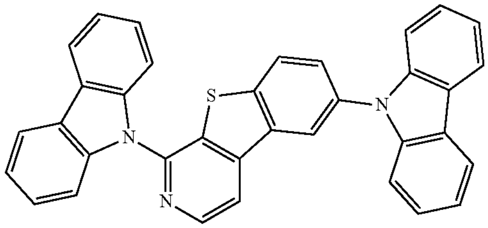
,
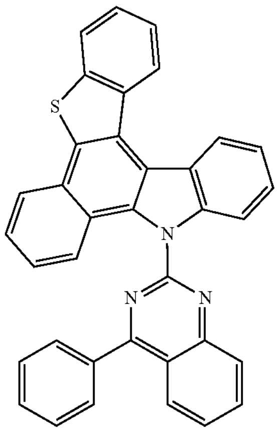
,
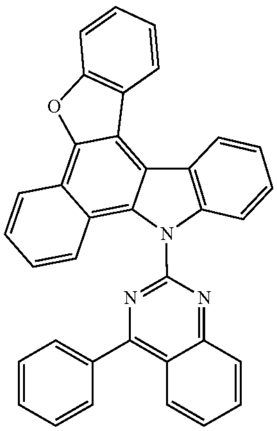
, -continued
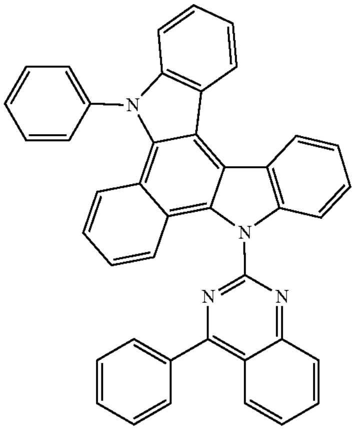
,
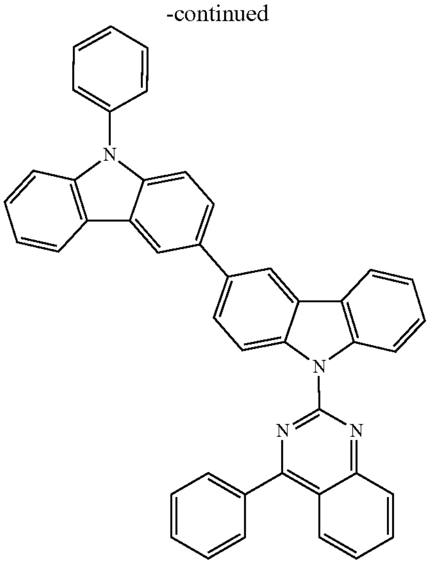
,
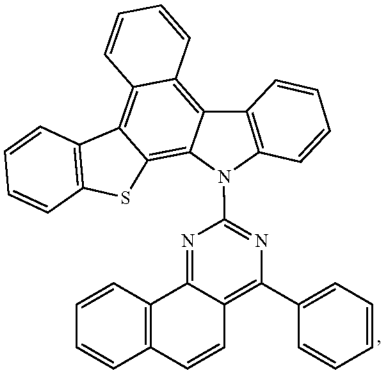
,
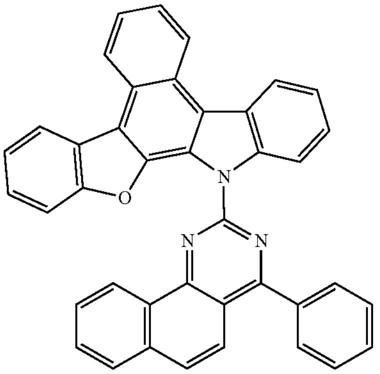
,
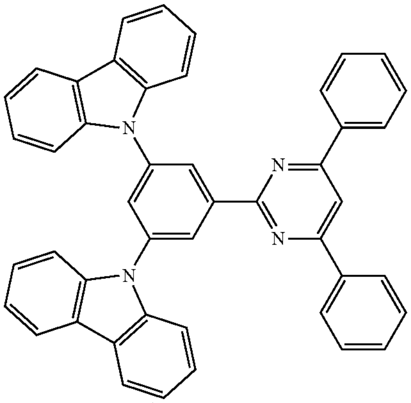
,
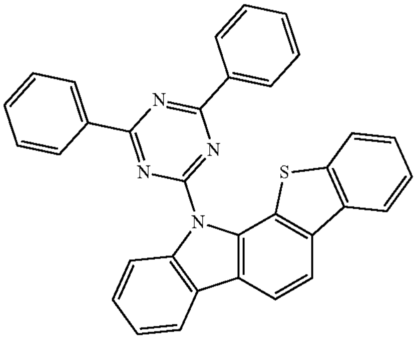
,
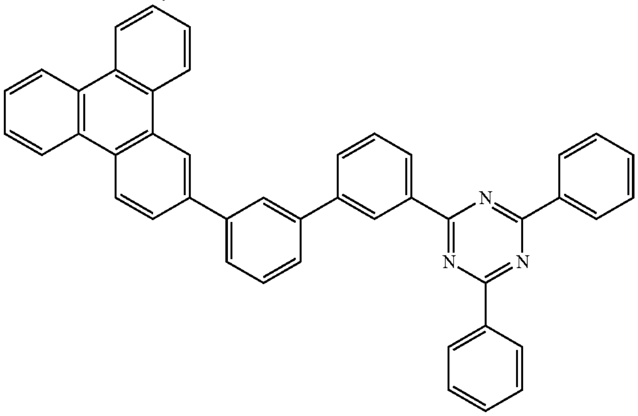
, -continued
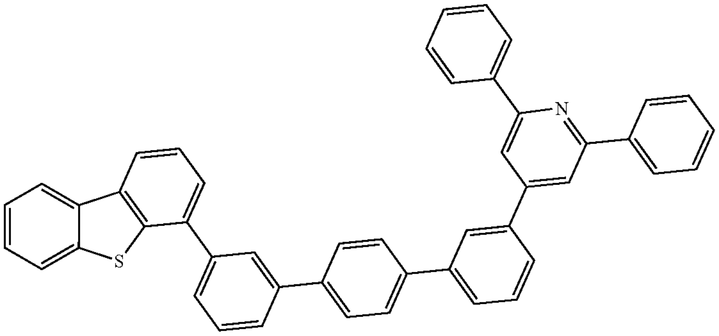
,
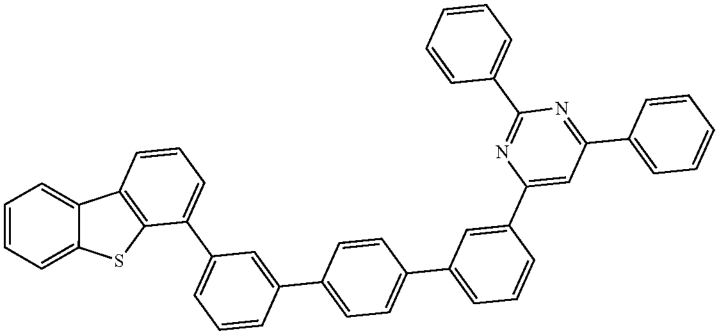
,
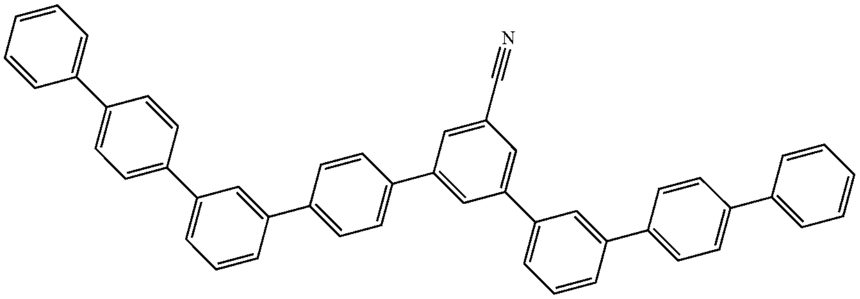
,
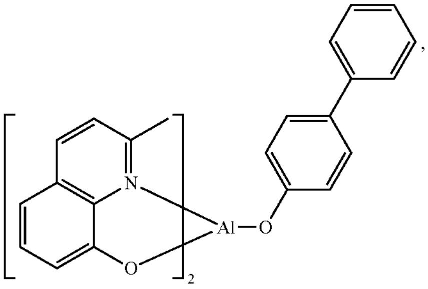
,
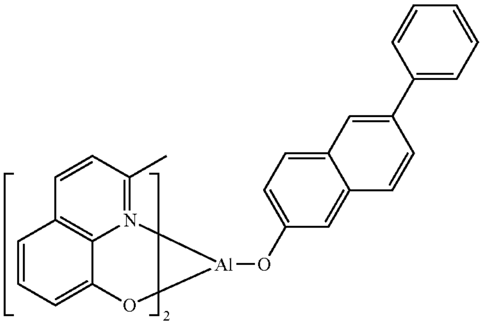
,
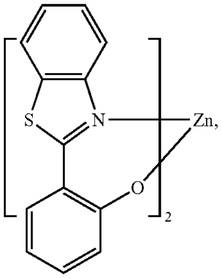
,
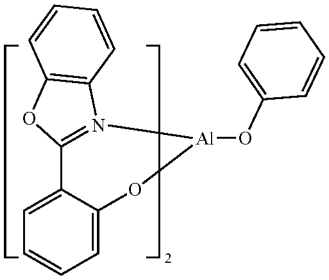
,
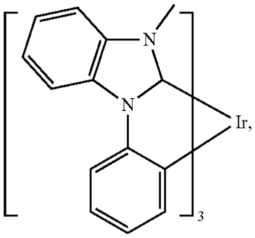
, -continued

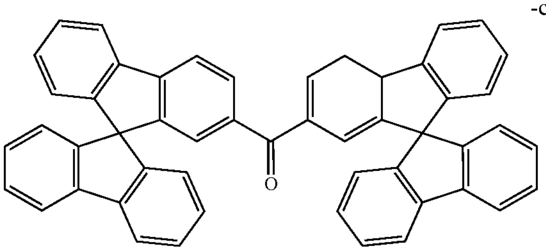

,

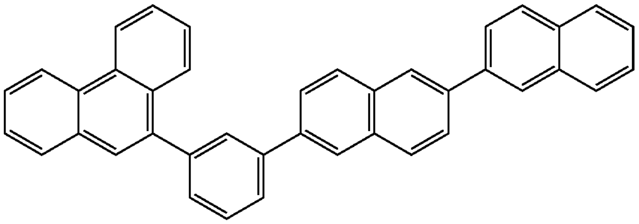

,

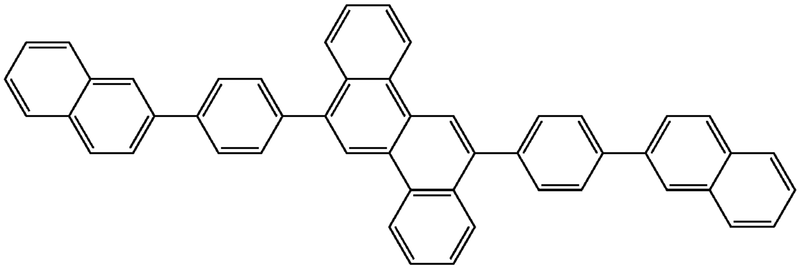

, and

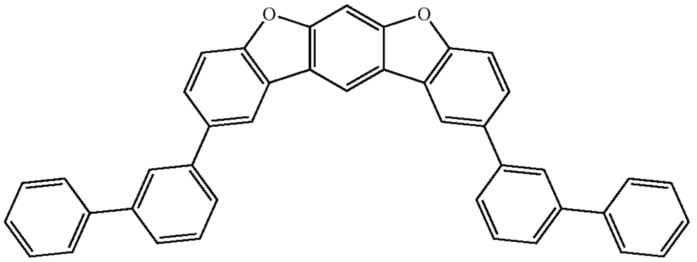

.

e) Additional Emitters:

One or more additional emitter dopants may be used in conjunction with the compound of the present disclosure. Examples of the additional emitter dopants are not particularly limited, and any compounds may be used as long as the compounds are typically used as emitter materials. Examples of suitable emitter materials include, but are not limited to, compounds which can produce emissions via phosphorescence, fluorescence, thermally activated delayed fluorescence, i.e., TADF (also referred to as E-type delayed fluorescence), triplet-triplet annihilation, or combinations of these processes.

Non-limiting examples of the emitter materials that may be used in an OLED in combination with materials disclosed herein are exemplified below together with references that disclose those materials: CN103694277, CN1696137, EB01238981, EP01239526, EP01961743, EP1239526, EP1244155, EP1642951, EP1647554, EP1841834, EP1841834B, EP2062907, EP2730583, JP2012074444, JP2013110263, JP4478555, KR1020090133652, KR20120032054, KR20130043460, TW201332980, U.S. Ser. No. 06/699,599, U.S. Ser. No. 06/916,554, US20010019782, US20020034656, US20030068526, US20030072964, US20030138657, US20050123788, US20050244673, US2005123791, US2005260449, US20060008670, US20060065890, US20060127696, US20060134459, US20060134462, US20060202194, US20060251923, US20070034863, US20070087321, US20070103060, US20070111026, US20070190359, US20070231600, US2007034863, US2007104979, US2007104980, US2007138437, US2007224450, US2007278936, US20080020237, US20080233410, US20080261076, US20080297033, US200805851, US2008161567, US2008210930, US20090039776, US20090108737, US20090115322, US20090179555, US2009085476, US2009104472, US20100090591, US20100148663, US20100244004, US20100295032, US2010102716, US2010105902, US2010244004, US2010270916, US20110057559, US20110108822, US20110204333, US2011215710, US2011227049, US2011285275, US2012292601, US20130146848, US2013033172, US2013165653, US2013181190, US2013334521, US20140246656, US2014103305, U.S. Pat. Nos. 6,303,238, 6,413,656, 6,653,654, 6,670,645, 6,687,266, 6,835,469, 6,921,915, 7,279,704, 7,332,232, 7,378,162, 7,534,505, 7,675,228, 7,728,137, 7,740,957, 7,759,489, 7,951,947, 8,067,099, 8,592,586, 8,871,361, WO06081973, WO06121811, WO07018067, WO07108362, WO07115970, WO07115981, WO08035571, WO2002015645, WO2003040257, WO2005019373, WO2006056418, WO2008054584, WO2008078800, WO2008096609, WO2008101842, WO2009000673, WO2009050281, WO2009100991, WO2010028151, WO2010054731, WO2010086089, WO2010118029, WO2011044988, WO2011051404, WO2011107491, WO2012020327, WO2012163471, WO2013094620, WO2013107487, WO2013174471, WO2014007565, WO2014008982, WO2014023377, WO2014024131, WO2014031977, WO2014038456, WO2014112450.
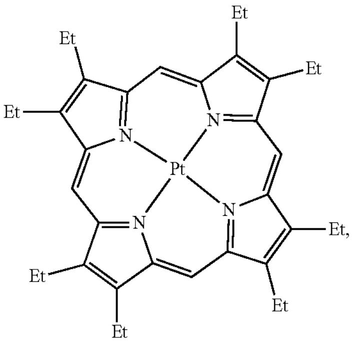
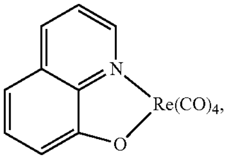
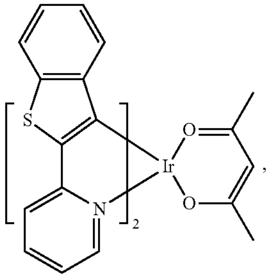
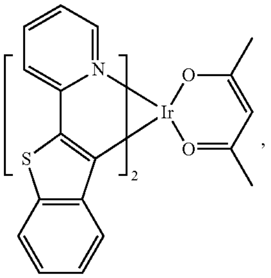
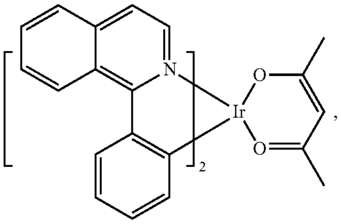
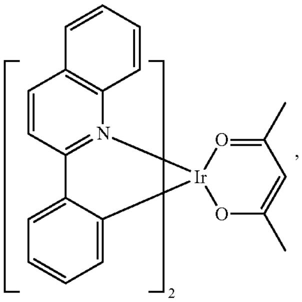
-continued
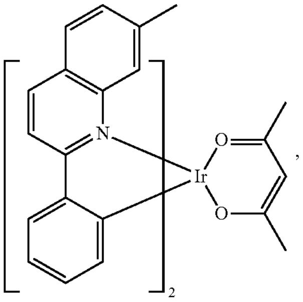
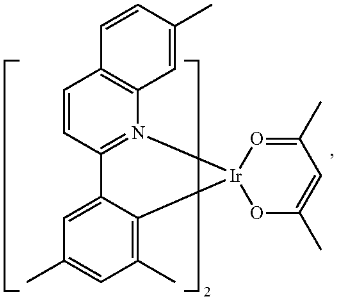
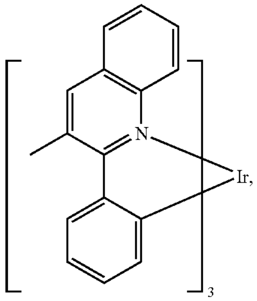
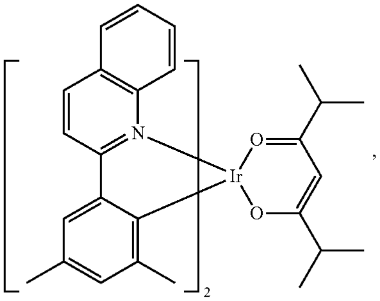
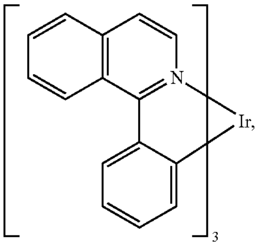

-continued
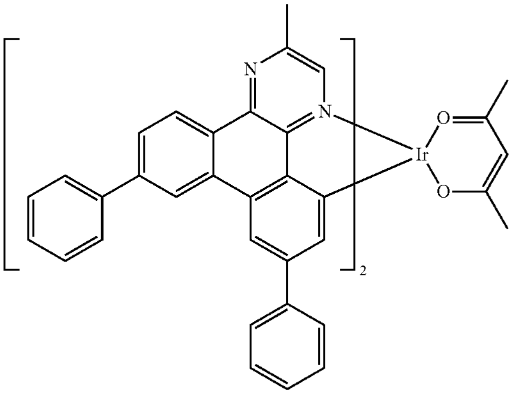
,
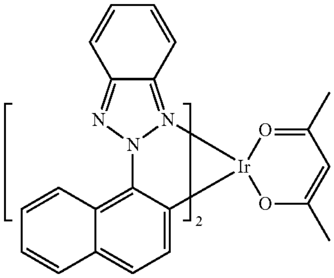
,
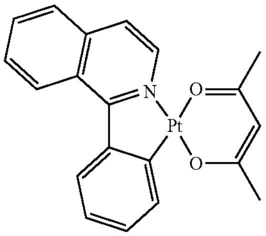
,
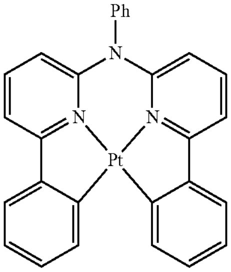
,
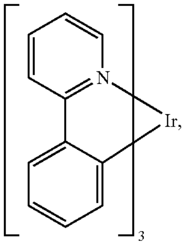
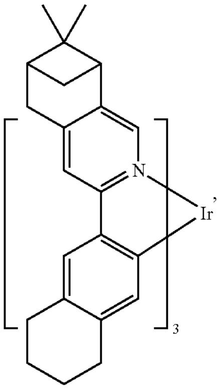
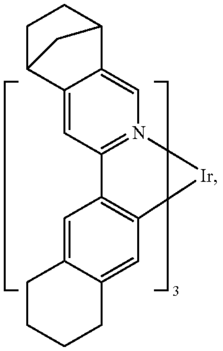
-continued
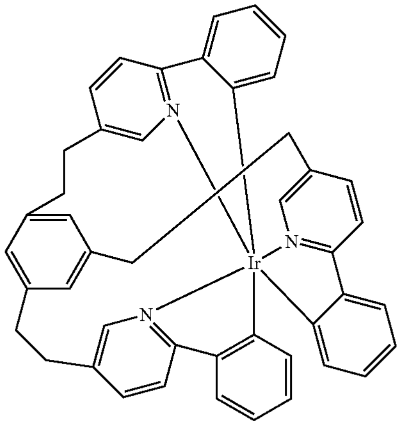
,
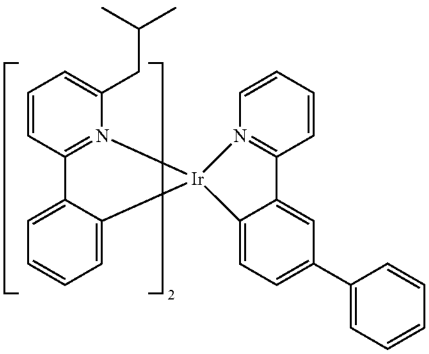
,
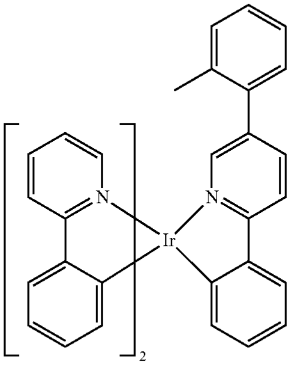
,
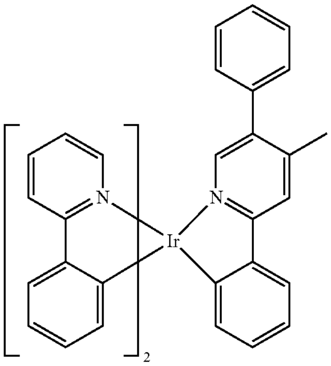
, -continued
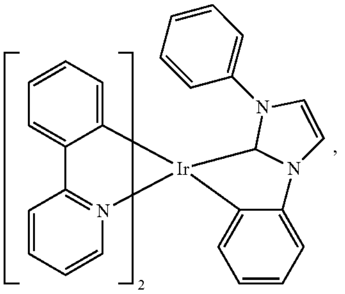
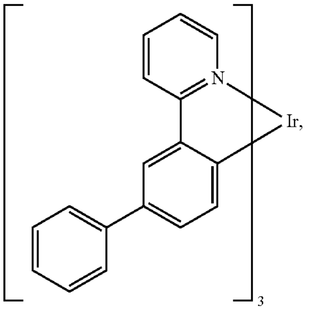
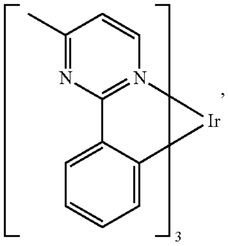
,
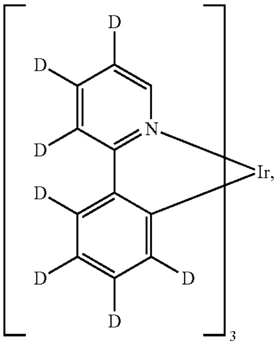
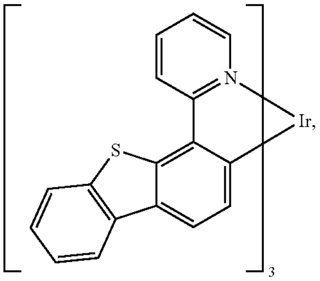
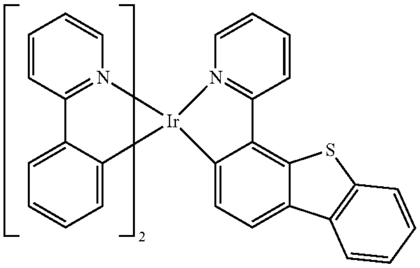
,
-continued
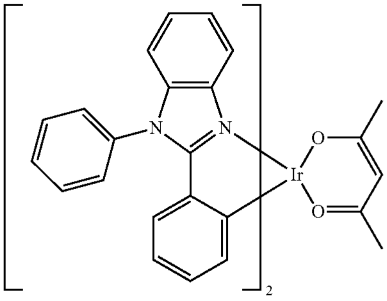
,
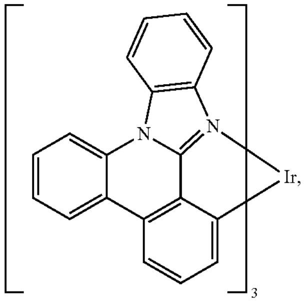
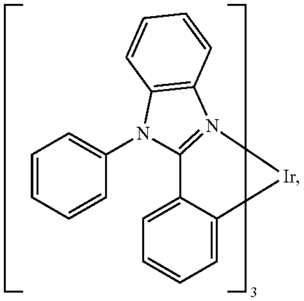
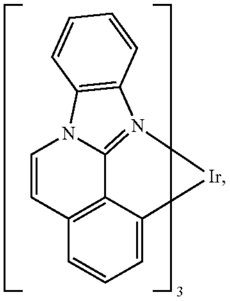
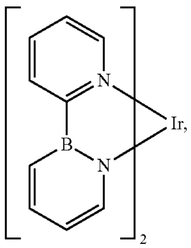
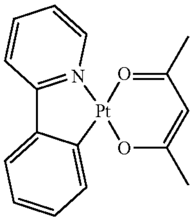
,
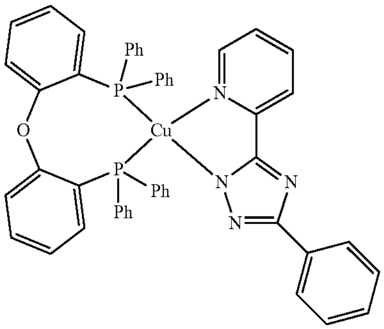
, -continued
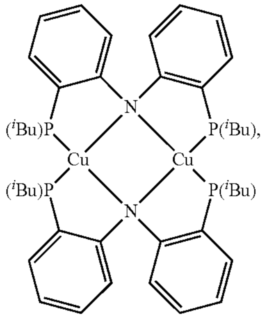
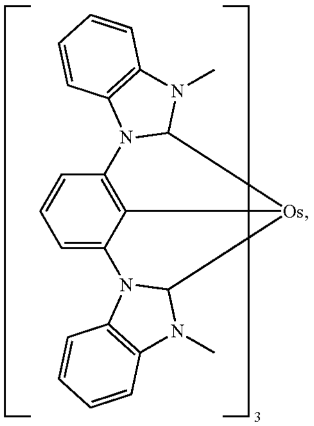
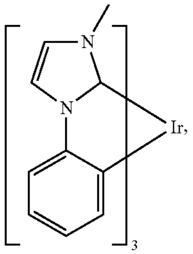
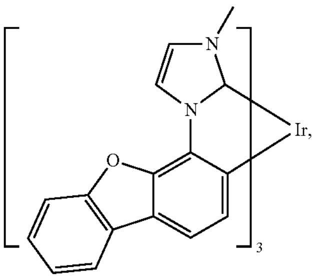
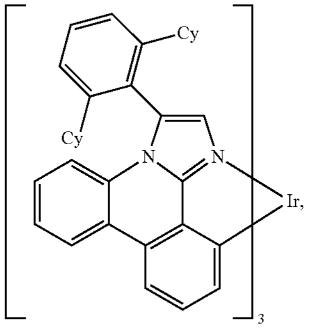
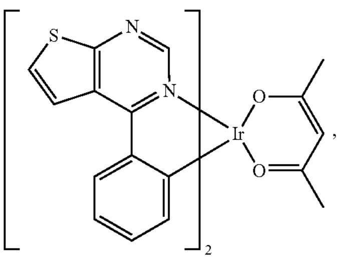
-continued
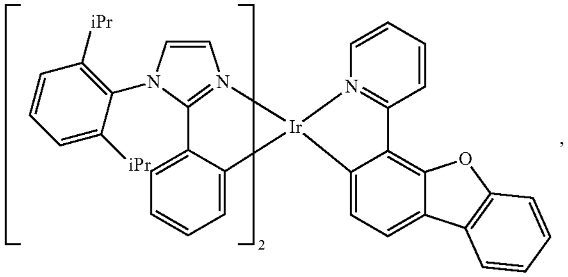
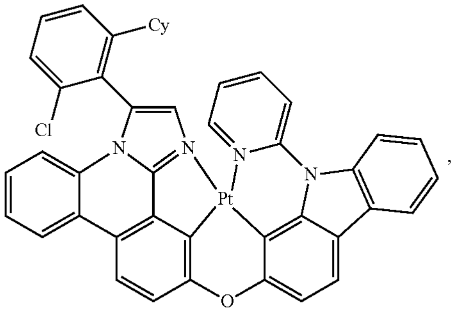
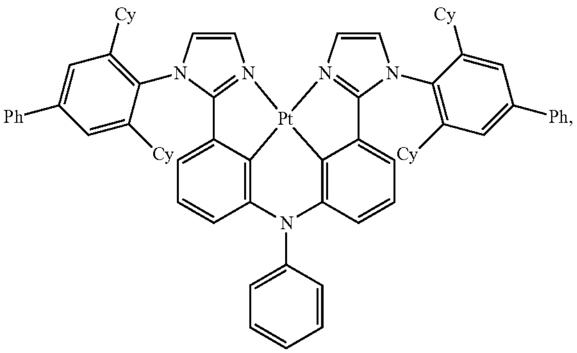
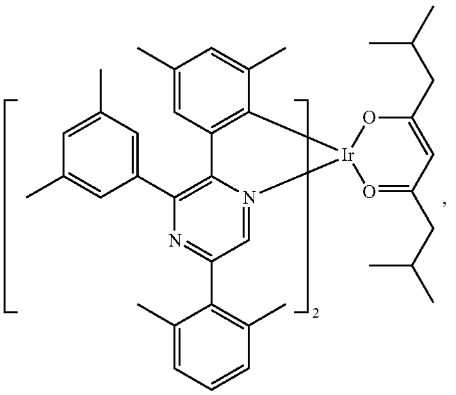
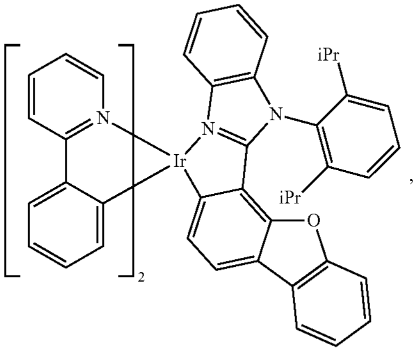

-continued
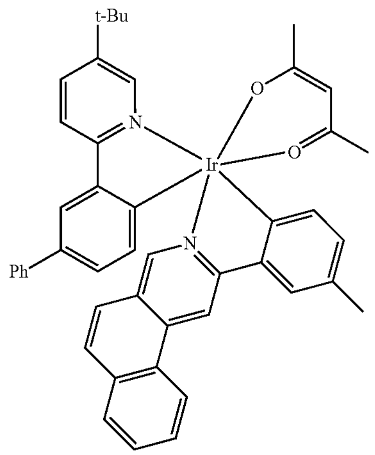
,
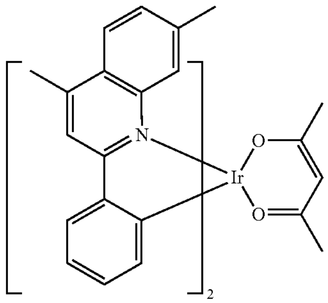
,
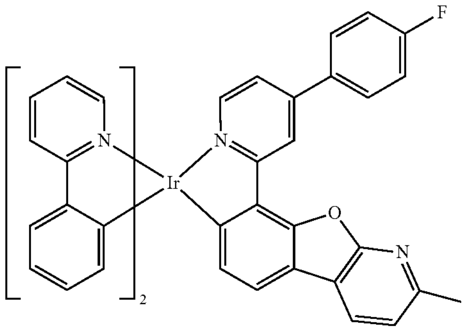
,
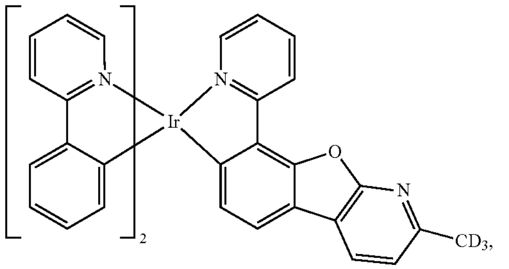
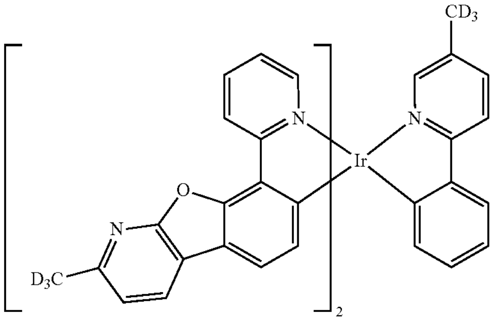
,
-continued
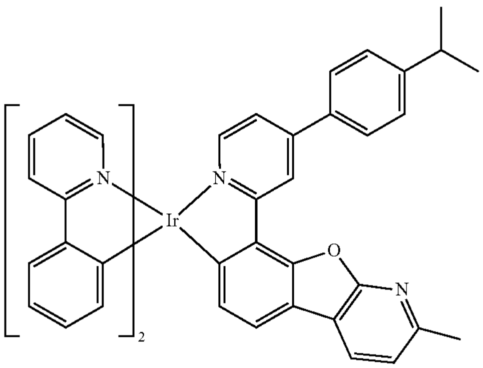
,
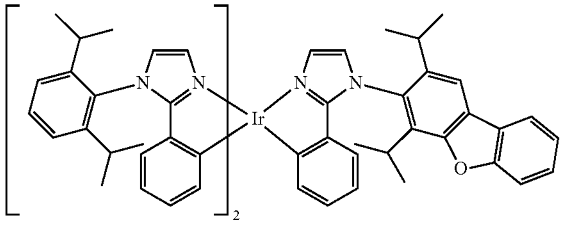
,
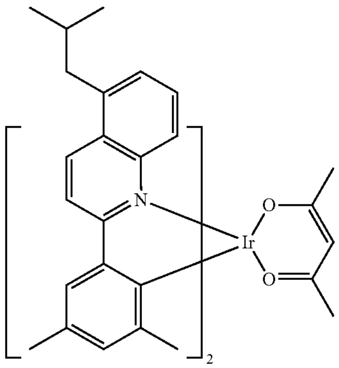
,
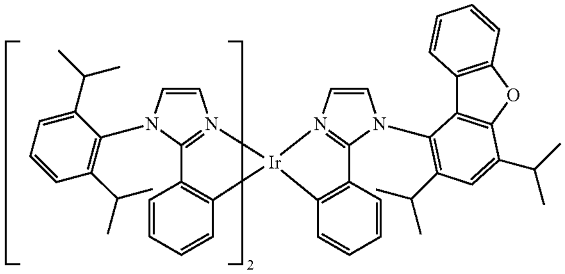
,
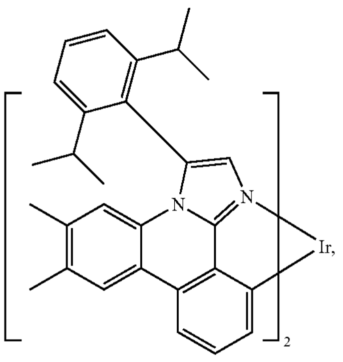

-continued
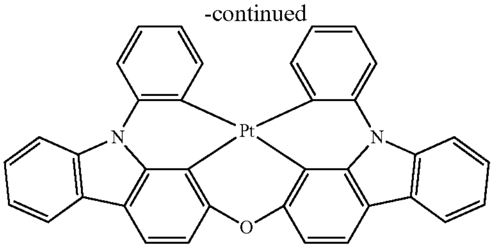
,
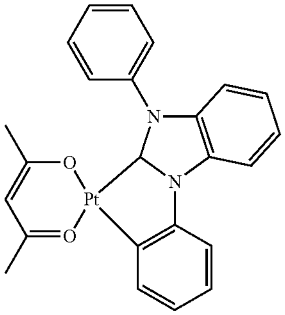
,
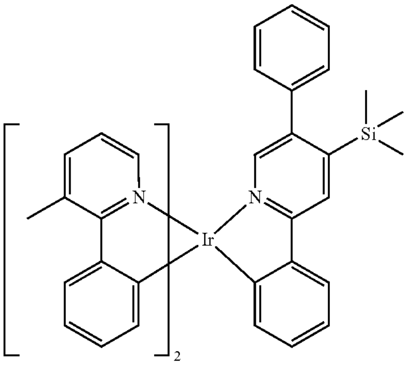
,
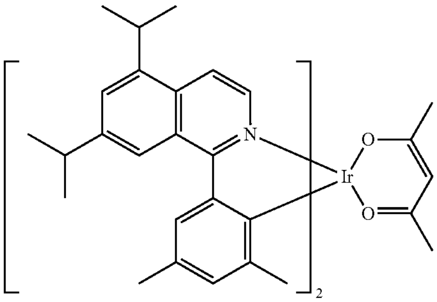
,
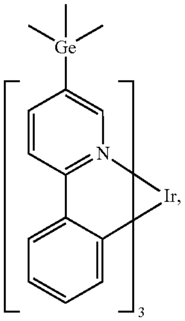
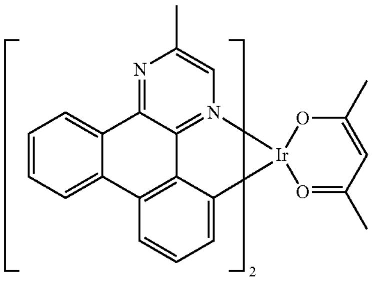
,
-continued
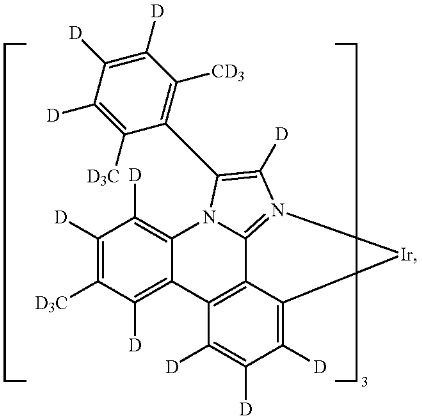
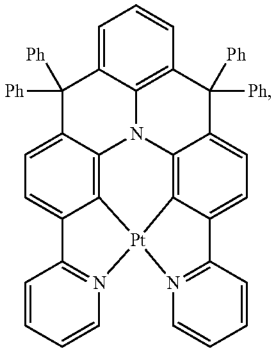
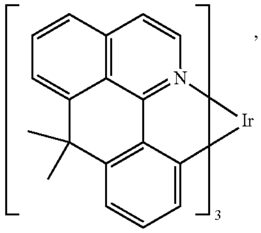
,
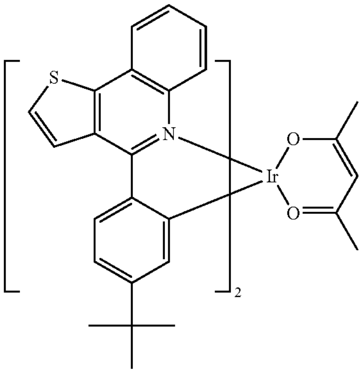
,
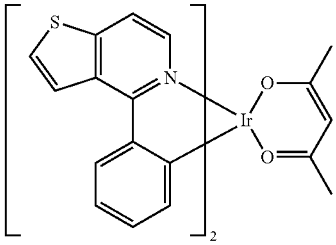
, -continued
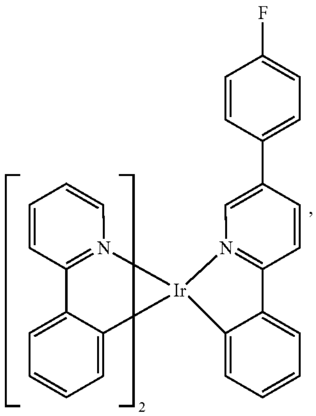
,
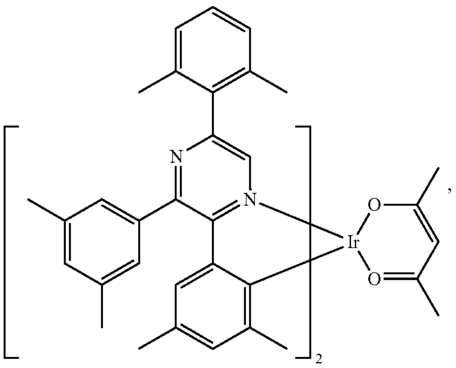
,
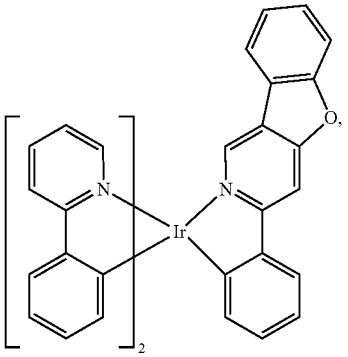
,
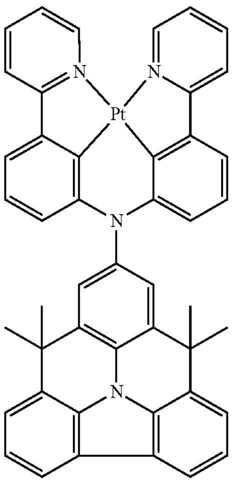
,
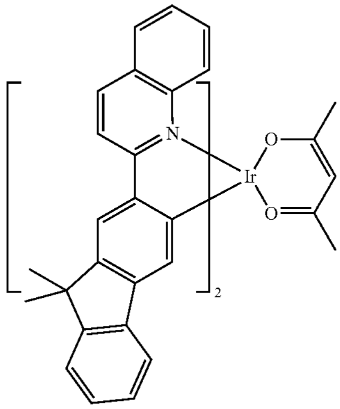
,
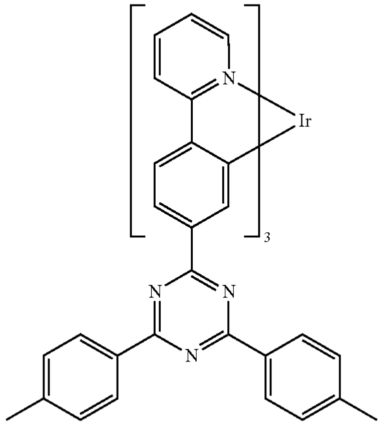
,
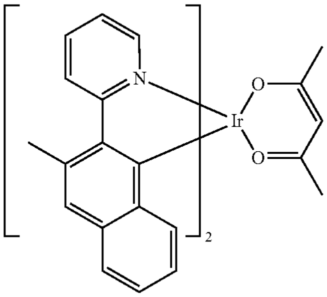
,
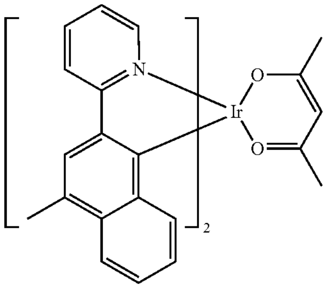
,
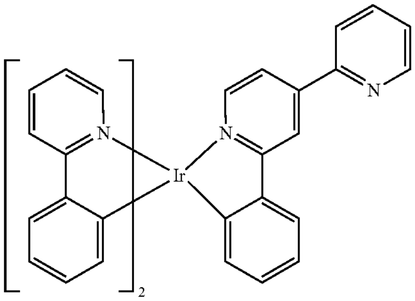
, -continued
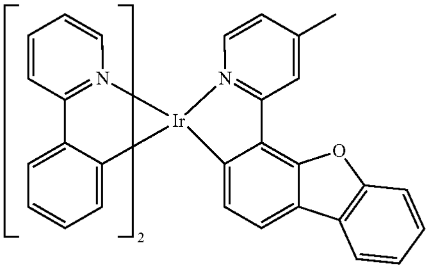
,
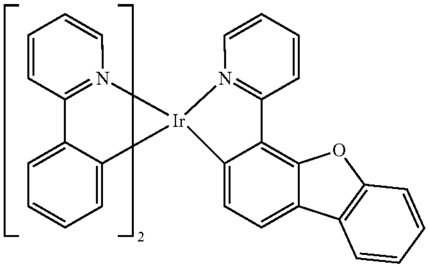
,
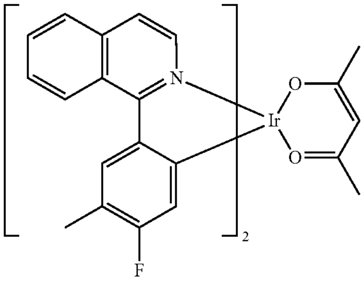
,
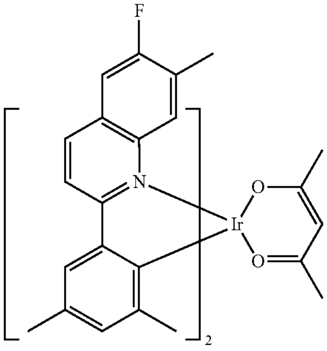
,
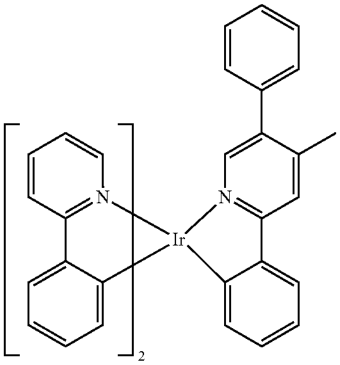
,
-continued
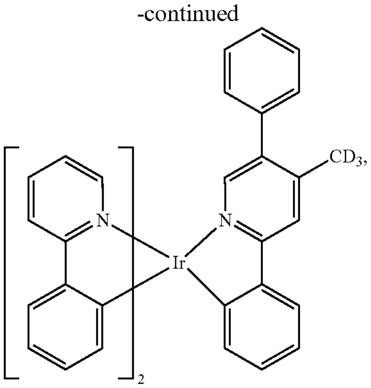
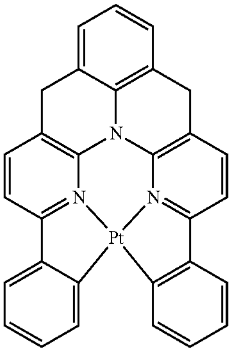
,
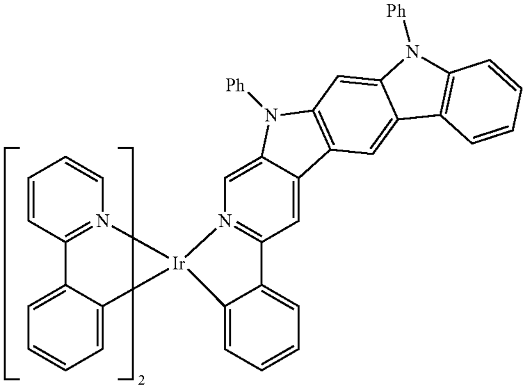
,
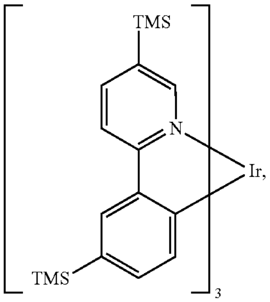
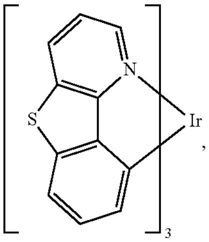
, -continued
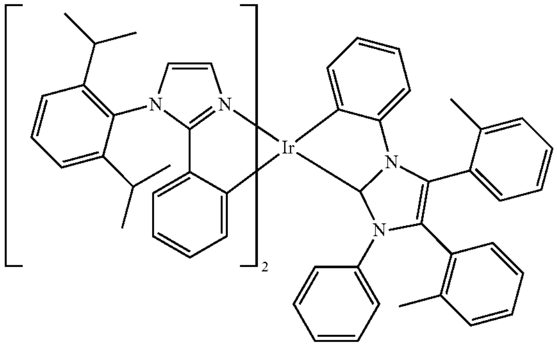
,
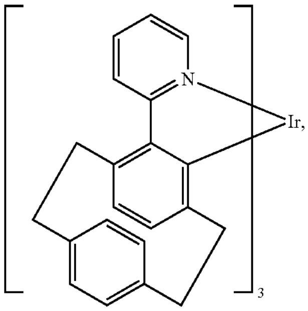
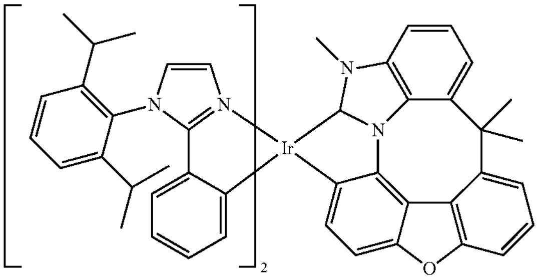
,
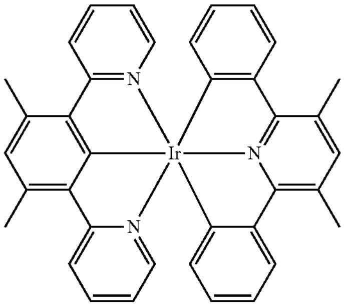
,
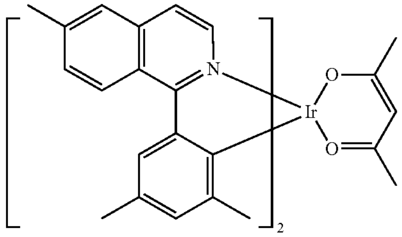
,
-continued
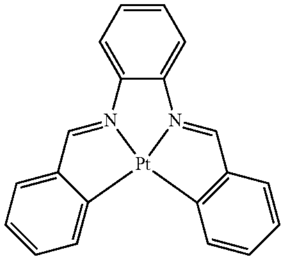
,
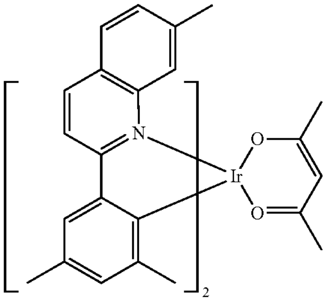
,
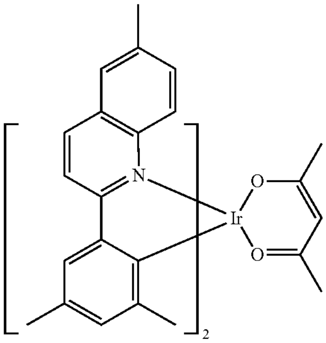
,
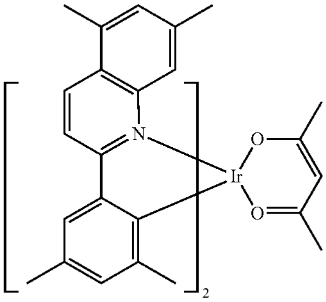
,
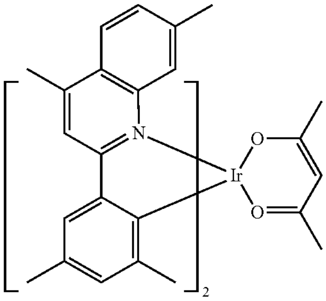
, -continued
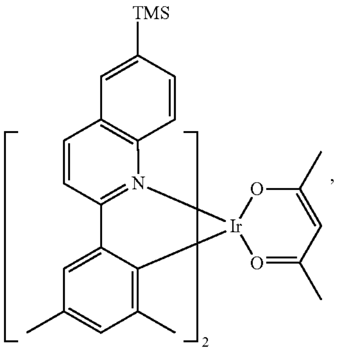
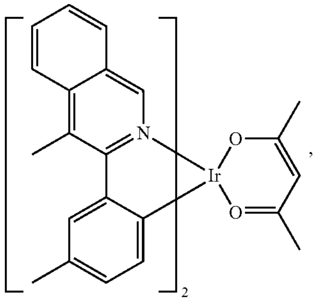
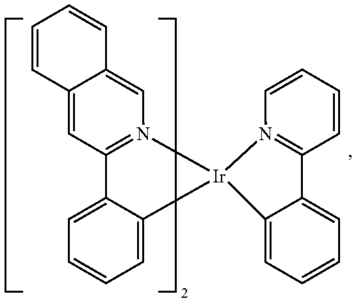
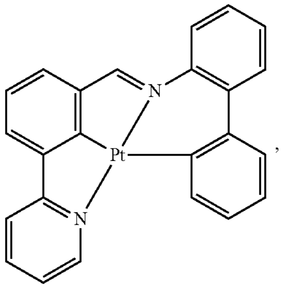
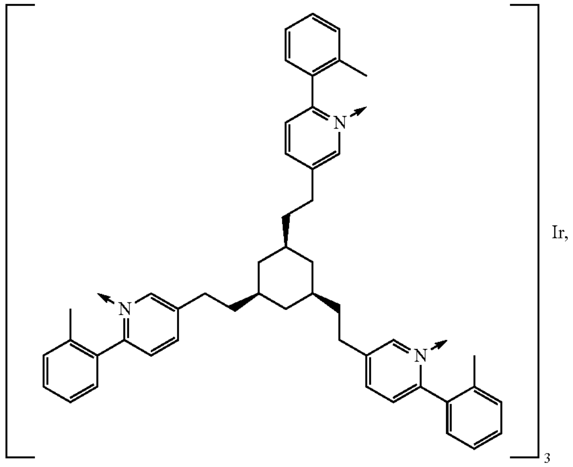
-continued
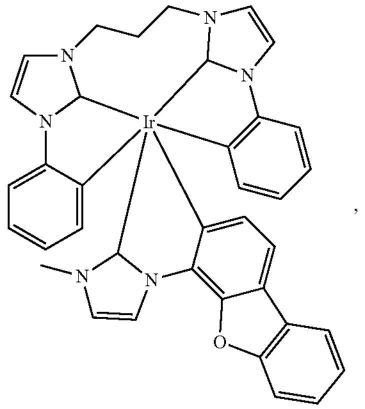
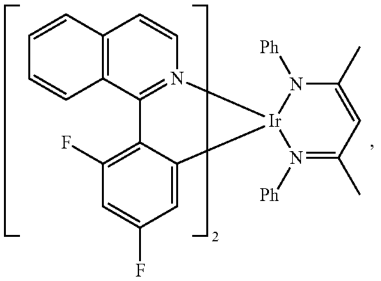
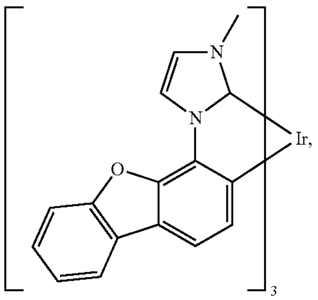
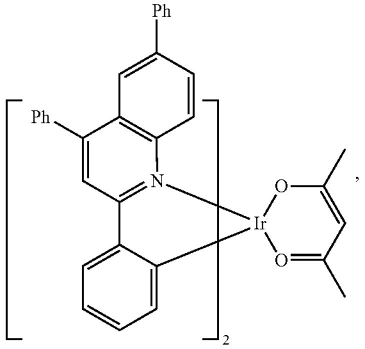
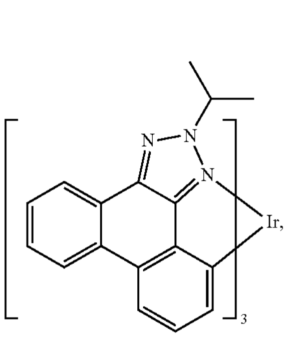

-continued

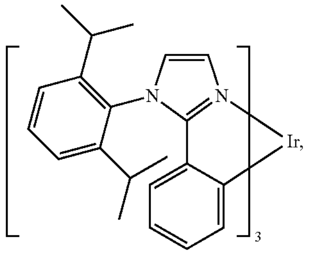

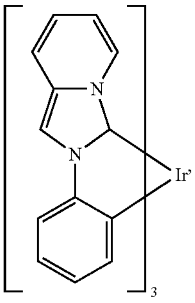

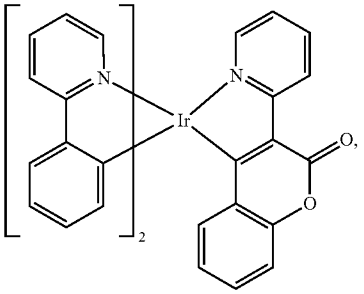

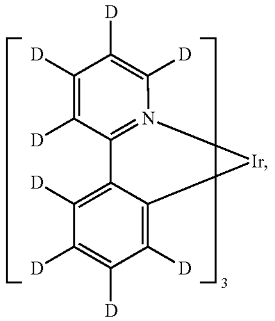

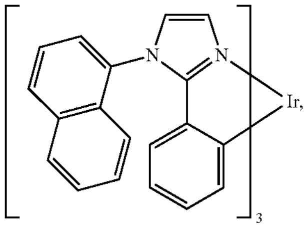

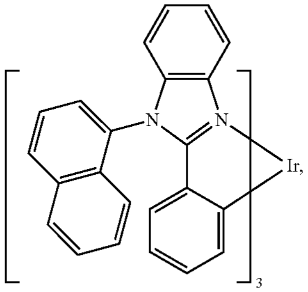

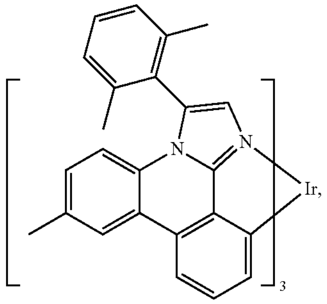

-continued

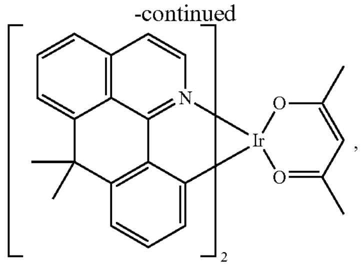

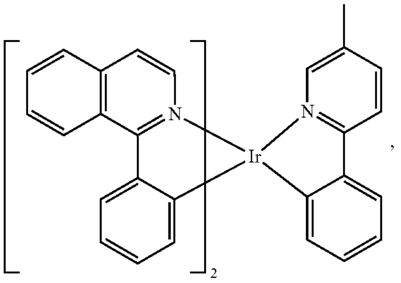

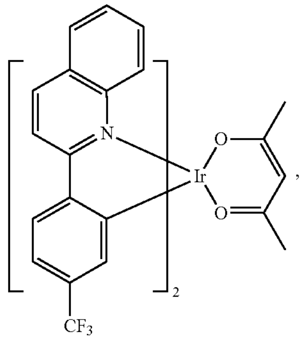

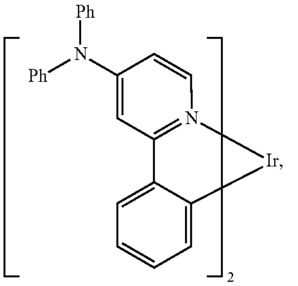

and

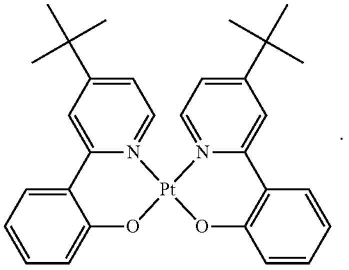

f) HBL:

A hole blocking layer (HBL) may be used to reduce the number of holes and/or excitons that leave the emissive layer. The presence of such a blocking layer in a device may result in substantially higher efficiencies and/or longer lifetime as compared to a similar device lacking a blocking layer. Also, a blocking layer may be used to confine emission to a desired region of an OLED. In some embodiments, the HBL material has a lower HOMO (further from the vacuum level) and/or higher triplet energy than the emitter closest to the HBL interface. In some embodiments, the HBL material has a lower HOMO (further from the vacuum level) and/or higher triplet energy than one or more of the hosts closest to the HBL interface.

In one aspect, compound used in HBL contains the same molecule or the same functional groups used as host described above.

In another aspect, compound used in HBL contains at least one of the following groups in the molecule:

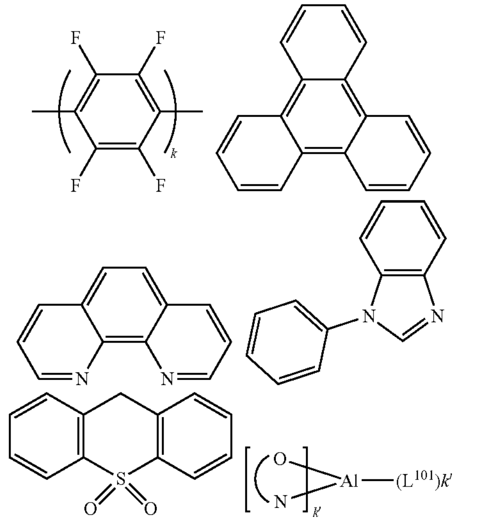

wherein k is an integer from 1 to 20; $L^{101}$ is another ligand, k' is an integer from 1 to 3.

g) ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

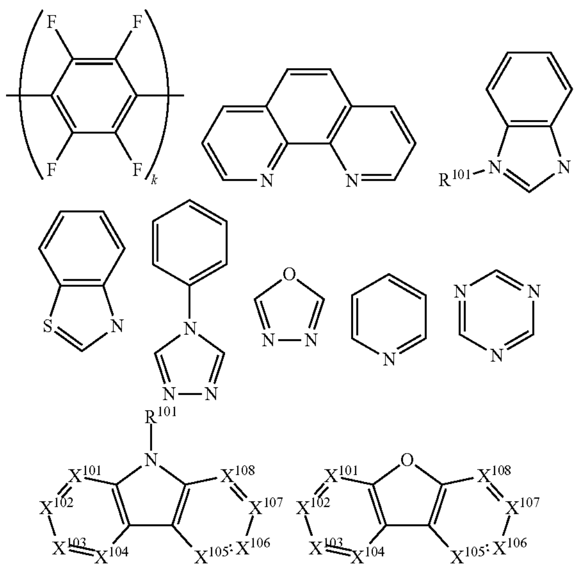

-continued

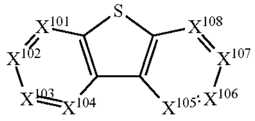

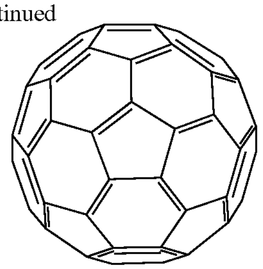

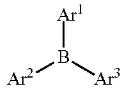

wherein $R^{101}$ is selected from the group consisting of hydrogen, deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL contains, but not limit to the following general formula:

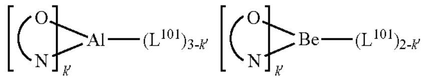

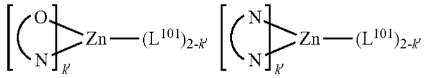

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

Non-limiting examples of the ETL materials that may be used in an OLED in combination with materials disclosed herein are exemplified below together with references that disclose those materials: CN103508940, EP01602648, EP01734038, EP01956007, JP2004-022334, JP2005149918, JP2005-268199, KR0117693, KR20130108183, US20040036077, US20070104977, US2007018155, US20090101870, US20090115316, US20090140637, US20090179554, US2009218940, US2010108990, US2011156017, US2011210320, US2012193612, US2012214993, US2014014925, US2014014927, US20140284580, U.S. Pat. Nos. 6,656,612, 8,415,031, WO2003060956, WO2007111263, WO2009148269, WO2010067894, WO2010072300, WO2011074770, WO2011105373, WO2013079217, WO2013145667, WO2013180376, WO2014104499, WO2014104535, -continued
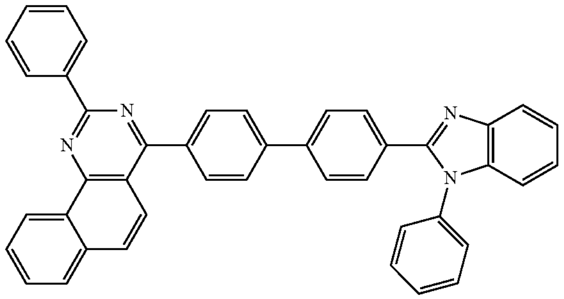
,
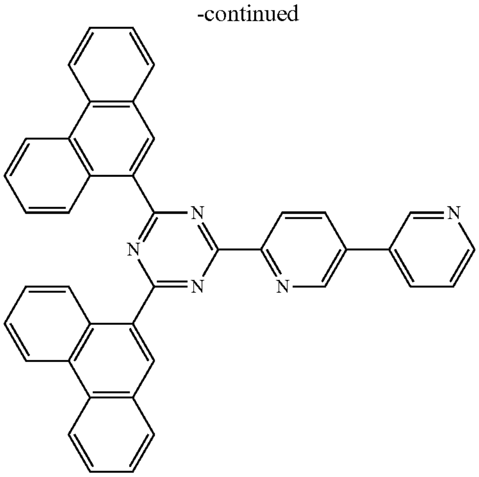
,
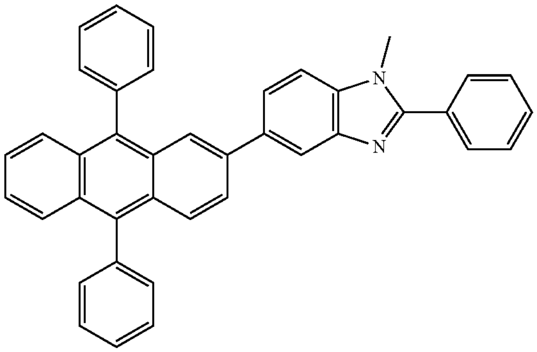
,
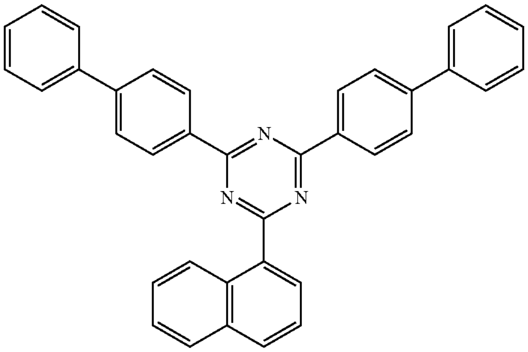
,
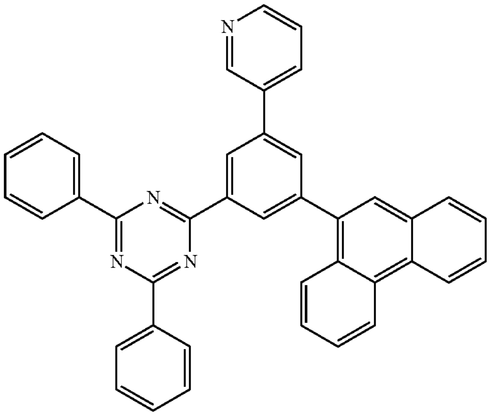
,
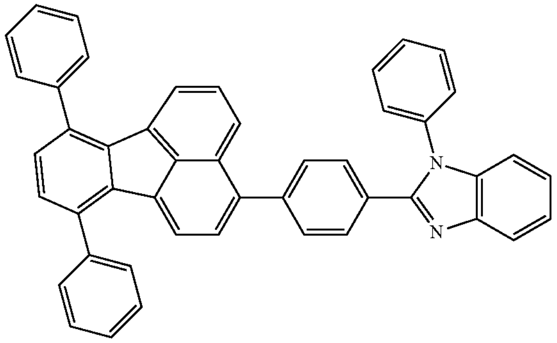
,
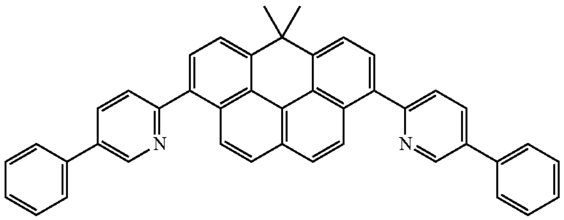
,
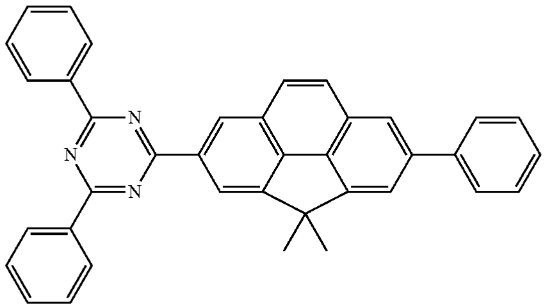
, -continued
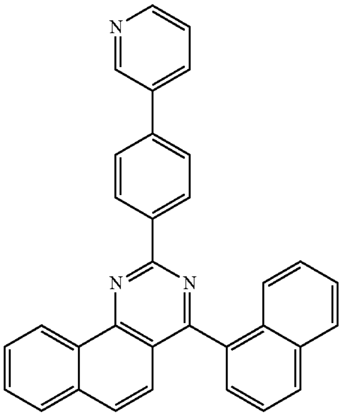
,
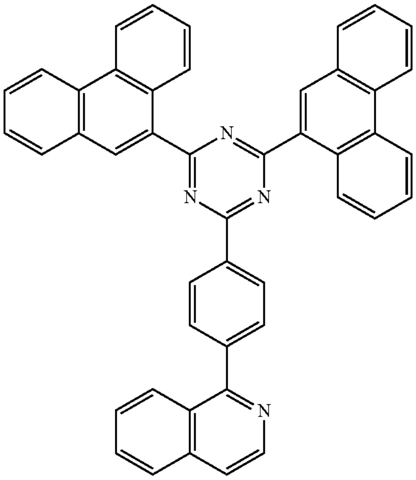
,
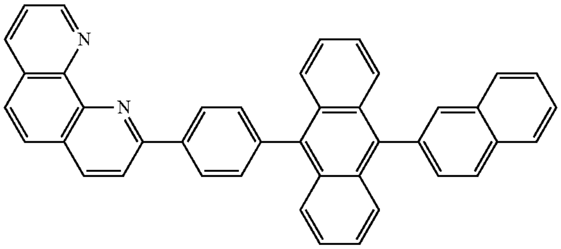
,
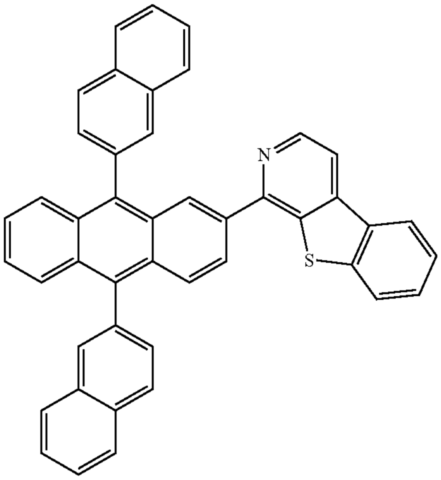
,
-continued
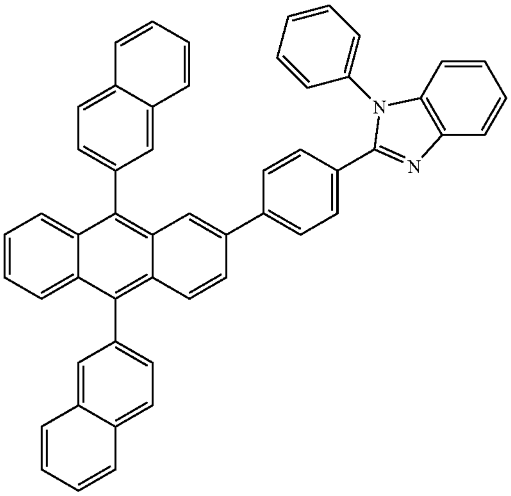
,
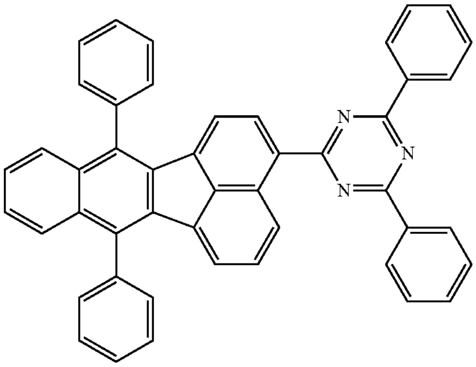
,
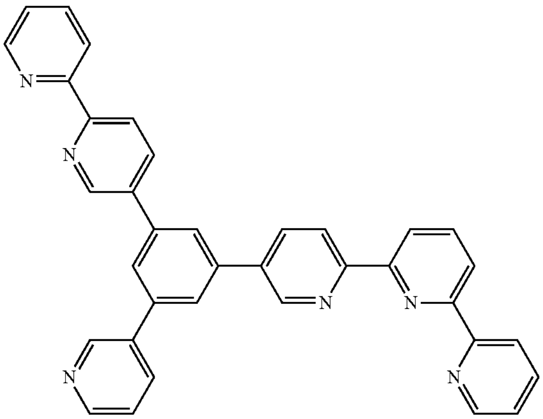
, -continued
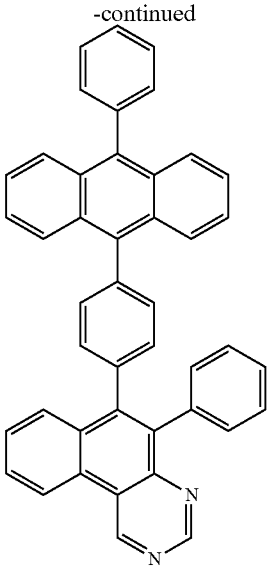
,
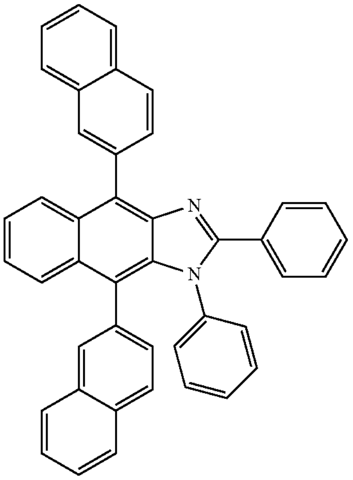
,
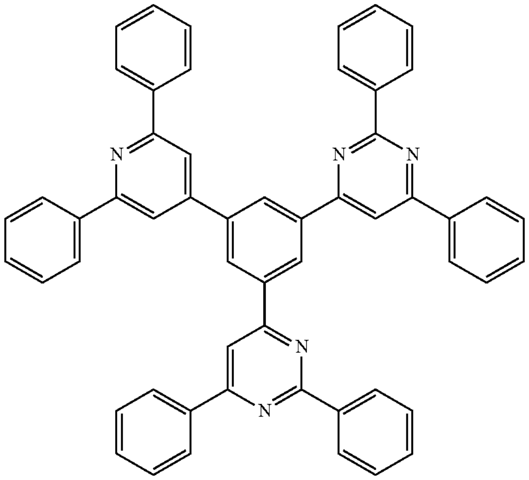
,
-continued
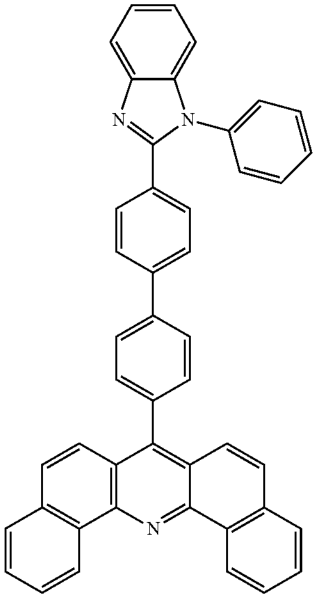
,
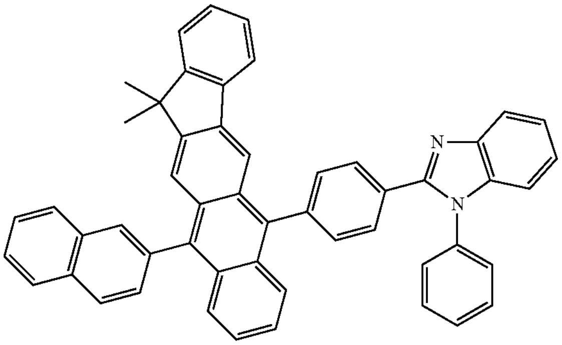
,
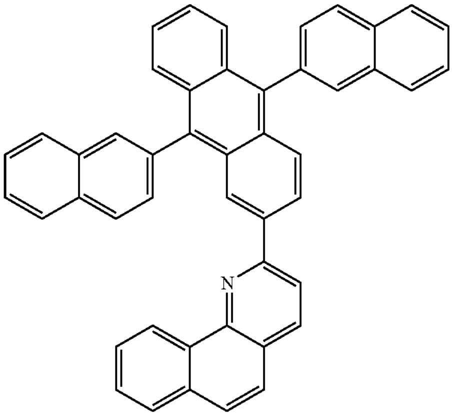
,
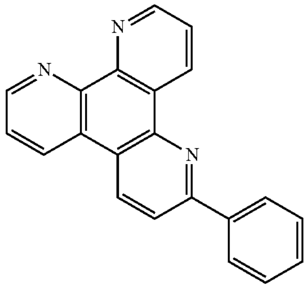
, -continued
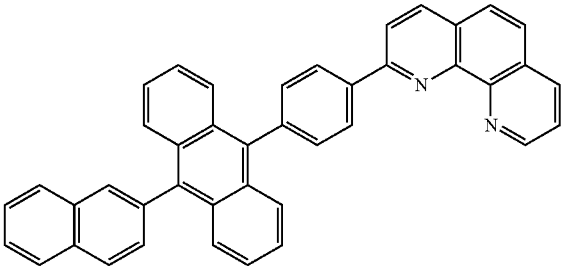
,
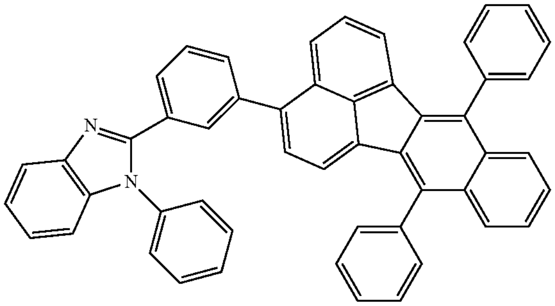
,
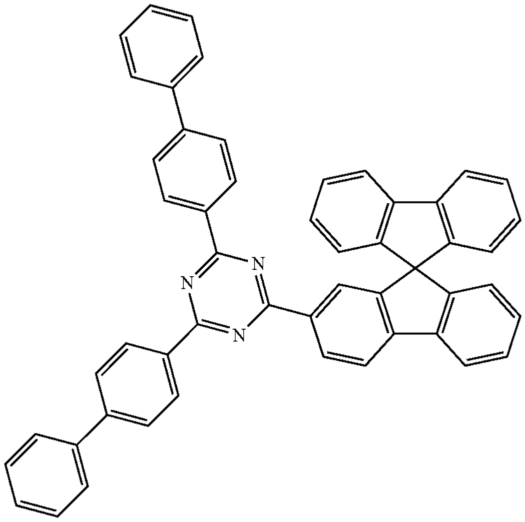
,
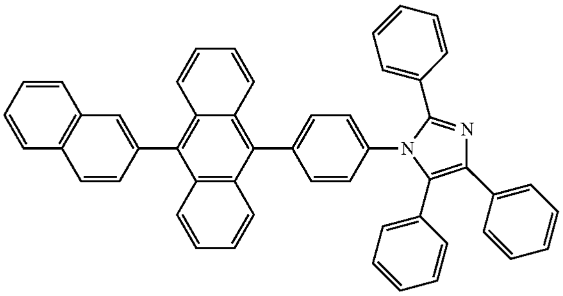
,
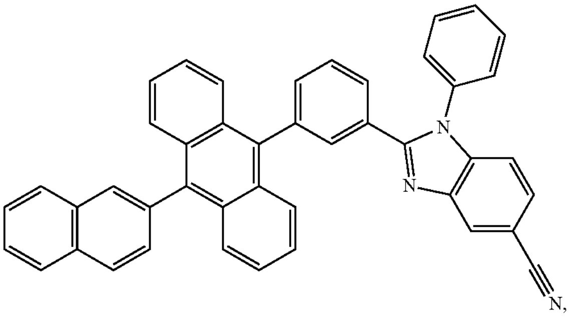
,
-continued
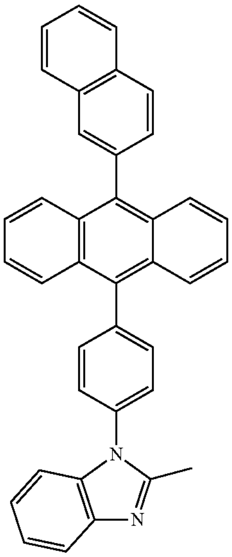
,
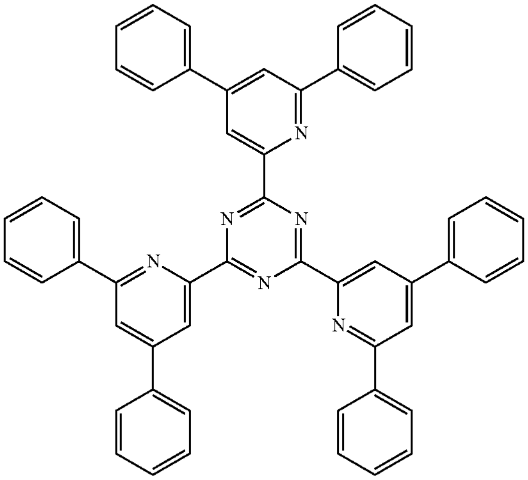
,
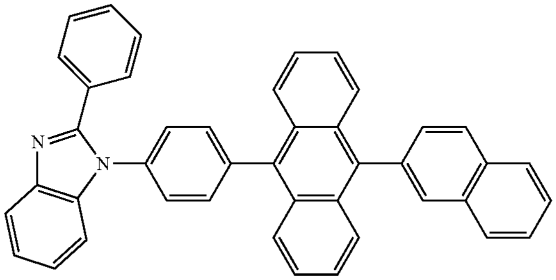
,
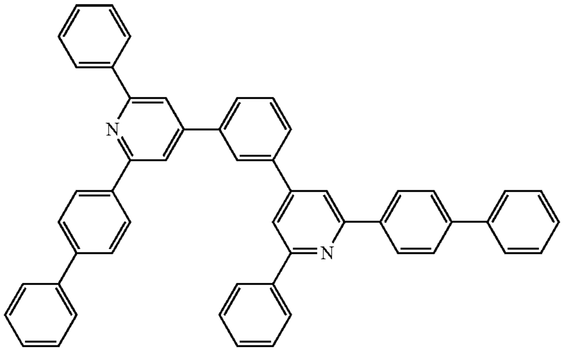
, -continued

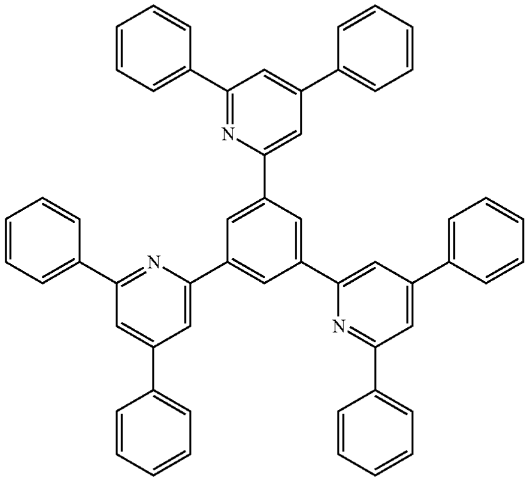

,

-continued

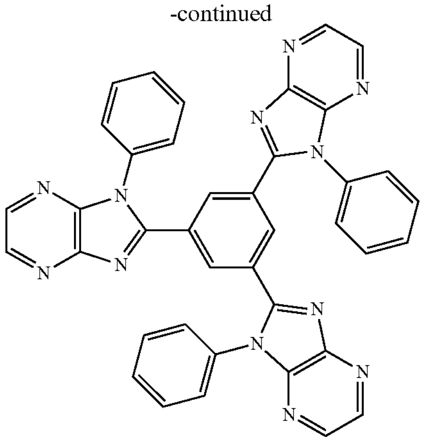

.

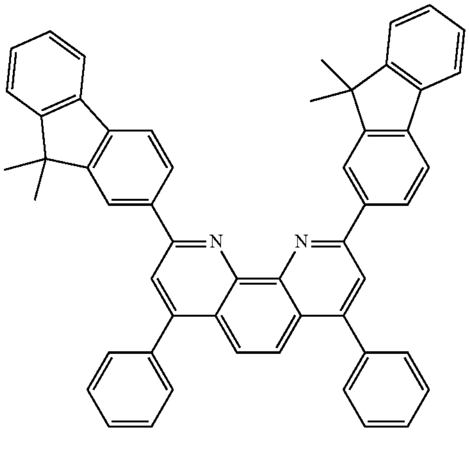

, and h) Charge Generation Layer (CGL)

In tandem or stacked OLEDs, the CGL plays an essential role in the performance, which is composed of an n-doped layer and a p-doped layer for injection of electrons and holes, respectively. Electrons and holes are supplied from the CGL and electrodes. The consumed electrons and holes in the CGL are refilled by the electrons and holes injected from the cathode and anode, respectively; then, the bipolar currents reach a steady state gradually. Typical CGL materials include n and p conductivity dopants used in the transport layers.

In any above-mentioned compounds used in each layer of the OLED device, the hydrogen atoms can be partially or fully deuterated. Thus, any specifically listed substituent, such as, without limitation, methyl, phenyl, pyridyl, etc. may be undeuterated, partially deuterated, and fully deuterated versions thereof. Similarly, classes of substituents such as, without limitation, alkyl, aryl, cycloalkyl, heteroaryl, etc. also may be undeuterated, partially deuterated, and fully deuterated versions thereof.

It is understood that the various embodiments described herein are by way of example only and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

EXPERIMENTAL DATA
Synthesis of 7-(4-(6-([1,1'-biphenyl]-4-yl)dibenzo[b, d]thiophen-4-yl)phenyl)-5,9-dioxa-13b-boranaphtho [3,2,1-de]anthracene (Compound 1)
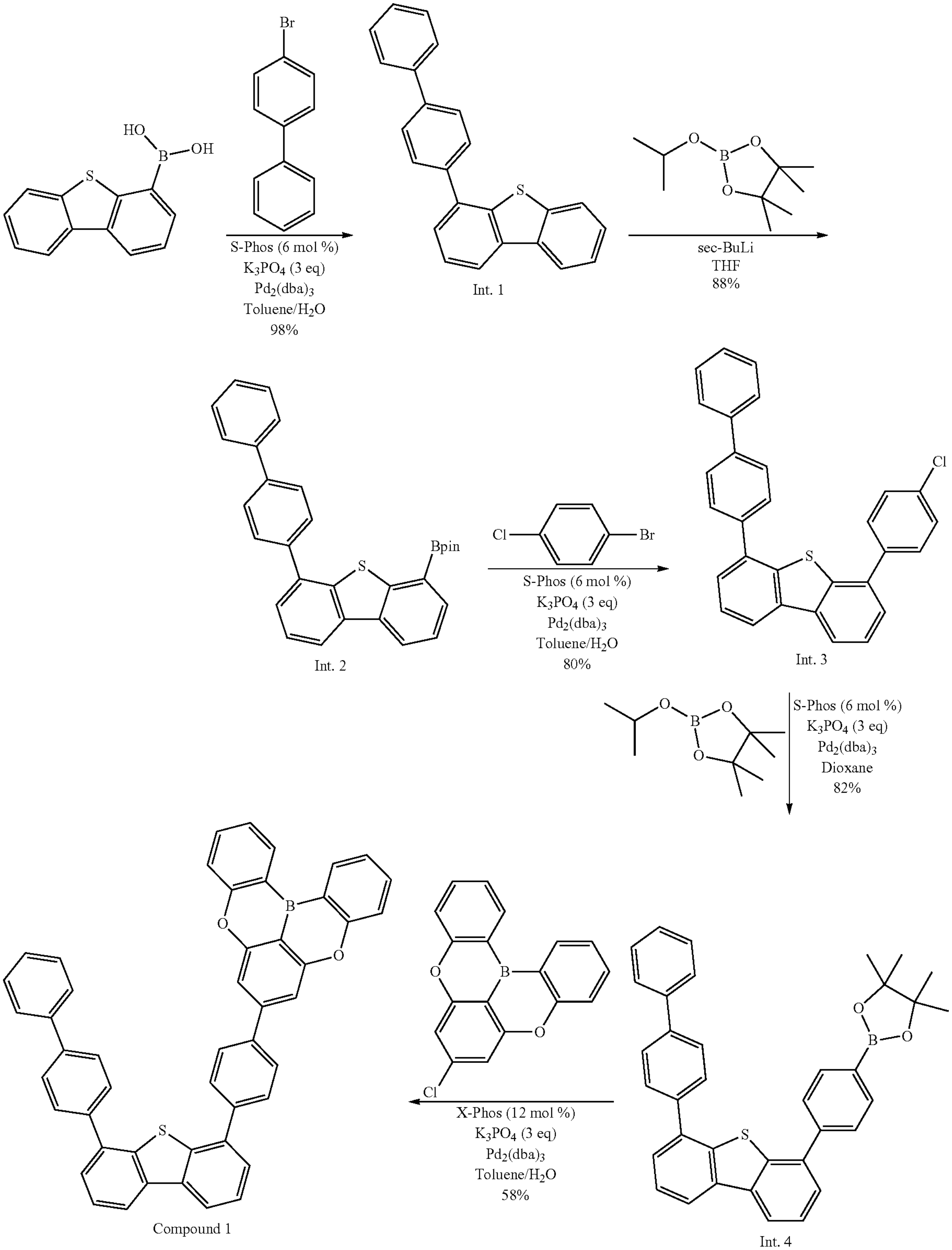

Step 1 To a 5 L 3 neck flask equipped with a water condenser, magnetic stirrer and thermowell, dibenzo[b,d] thiophen-4-ylboronic acid (60 g, 263 mmol) 4-bromo-1,1'-biphenyl (73.6 g, 316 mmol), potassium phosphate, tribasic (168 g, 789 mmol), toluene (1196 mL) and water (120 mL) were added and the mixture was degassed (nitrogen bubbling). $Pd_2(dba)_3$ (7.23 g, 7.89 mmol) and dicyclohexyl(2',4',6'-triisopropyl-[1,1'-biphenyl]-2-yl)phosphane 6.48 g, 15.78 mmol) were added and the mixture was degassed. The reaction mixture was heated to reflux and stirred for 6 hours. The reaction mixture was allowed to cool to room temperature and the precipitated solid was collected by filtration. This solid was triturated with methanol to give 4-([1,1'-biphenyl]-4-yl)dibenzo[b,d]thiophene (87 g, 98% yield).

Step 2 To a dry 2 L flask under nitrogen was added 4-([1,1'-biphenyl]-4-yl)dibenzo[b,d]thiophene (50 g, 149 mmol) and THF (743 ml). The resulting solution was stirred and cooled to −78° C. A solution of sec-butyllithium in cyclohexane (1.4 M, 186 ml, 260 mmol) was added slowly and the reaction mixture was stirred at this temperature for 1 hour. 2-isopropoxy-4,4,5,5-tetramethyl-1,3,2-dioxaborolane (48.4 g, 260 mmol) was then added dropwise and the reaction mixture was allowed to slowly warm to room temperature overnight (~16 hours). Saturated $NH_4Cl$ (250 mL) and water (250 mL) were added and the layers were separated. The aqueous layer was extracted with DCM (3×500 mL) and the combined organic layer was washed with brine, dried over $Na_2SO_4$ and concentrated. The resulting solid was triturated with heptane to give 2-(6-([1,1'-biphenyl]-4-yl)dibenzo[b,d]thiophen-4-yl)-4,4,5,5-tetramethyl-1,3,2-dioxaborolane (60.4 g, 88%) as a white solid.

Step 3 To a 1 L 3 neck flask equipped with a water condenser, magnetic stirrer and thermowell, 2-(6-([1,1'-biphenyl]-4-yl)dibenzo[b,d]thiophen-4-yl)-4,4,5,5-tetramethyl-1,3,2-dioxaborolane (40 g, 87 mmol), 1-bromo-4-chlorobenzene (19.87 g, 104 mmol), potassium phosphate tribasic (55.1 g, 260 mmol), toluene (393 mL) and water (39 mL) were added and the mixture was purged with nitrogen. $Pd_2(dba)_3$ (0.92 g, 1.00 mmol) and dicyclohexyl(2',4',6'-triisopropyl-[1,1'-biphenyl]-2-yl)phosphane (2.131 g, 5.19 mmol) were added and the mixture was degassed. The reaction was heated to reflux and stirred for 6 hours. The reaction mixture was allowed to cool to room temperature and the precipitated solid was collected by filtration. The white solid was further triturated with methanol to obtain 4-([1,1'-biphenyl]-4-yl)-6-(4-chlorophenyl)dibenzo[b,d] thiophene (30.9 g, 80% yield).

Step 4 To a 200 mL flask was added 4-([1,1'-biphenyl]-4-yl)-6-(4-chlorophenyl)dibenzo[b,d]thiophene (9.16 g, 20.49 mmol), 4,4,4',4',5,5,5',5'-octamethyl-2,2'-bi(1,3,2-dioxaborolane) (10.41 g, 41.0 mmol), potassium acetate (6.03 g, 61.5 mmol), and dioxane (72 mL). Resulting reaction mixture was stirred and degassed by vacuum-nitrogen backfill. $Pd_2(dba)_3$ (0.75 g, 0.82 mmol) and dicyclohexyl(2',6'-dimethoxy-[1,1'-biphenyl]-2-yl)phosphane (0.67 g, 1.64 mmol) were added and the mixture was degassed further. The reaction mixture was then heated to 100° C. and stirred for 16 hours. The reaction mixture was concentrated, and the residue was dissolved in toluene. The solution was passed through a pad of silica gel and plug was washed with toluene. The filtrate was concentrated and the resulting solid was triturated with heptane to give 2-(4-(6-([1,1'-biphenyl]-4-yl)dibenzo[b,d]thiophen-4-yl)phenyl)-4,4,5,5-tetramethyl-1,3,2-dioxaborolane (9 g, 82% yield).

Step 5 To a 500 mL 3 neck flask equipped with a water condenser, magnetic stirrer, and thermowell, 2-(4-(6-([1,1'-biphenyl]-4-yl)dibenzo[b,d]thiophen-4-yl)phenyl)-4,4,5,5-tetramethyl-1,3,2-dioxaborolane (9 g, 16.71 mmol), 7-chloro-5,9-dioxa-13b-boranaphtho[3,2,1-de]anthracene (5.60 g, 18.38 mmol), potassium phosphate, tribasic (10.64 g, 50.10 mmol), toluene (85 mL) and water (8.5 mL) were added and the mixture was degassed by nitrogen bubbling. $Pd_2(dba)_3$ (0.92 g, 1.00 mmol) and dicyclohexyl(2',4',6'-triisopropyl-[1,1'-biphenyl]-2-yl)phosphane (0.96 g, 2.01 mmol) were added and the mixture was degassed. The reaction mixture was then heated to 77° C. and stirred for 8 hours. The reaction mixture was allowed to cool to room temperature and precipitated solid was collected by filtration. The solid was dissolved in hot toluene (3 L) and filtered through a pad of silica and alumina. The filtrate was concentrated and the resulting solid was triturated with methanol, followed by ethyl acetate, DCM/methanol, DCM/acetone and acetone to give 7-(4-(6-([1,1'-biphenyl]-4-yl) dibenzo[b,d]thiophen-4-yl)phenyl)-5,9-dioxa-13b-boranaphtho[3,2,1-de]anthracene (Compound 1) (6.6 g, 58% yield).

Synthesis of 3-(6-(4-(5,9-dioxa-13b-boranaphtho[3,2,1-de]anthracen-7-yl)phenyl)dibenzo[b,d]thiophen-4-yl)-9-phenyl-9H-carbazole (Compound 2)

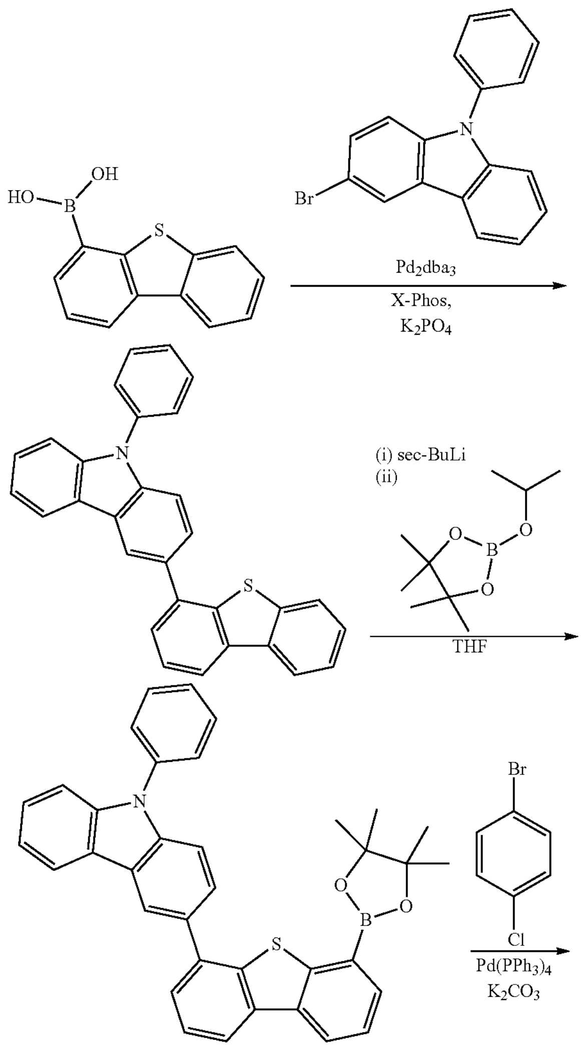

-continued

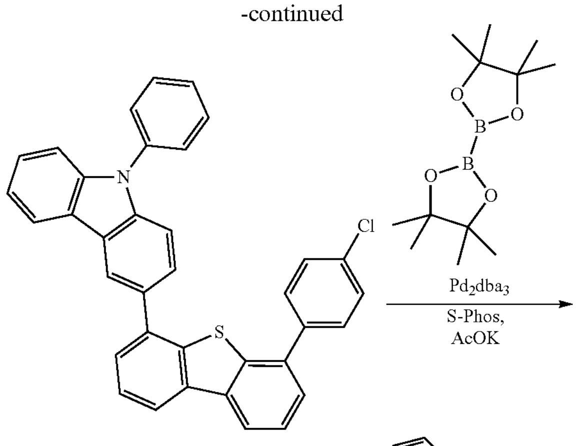

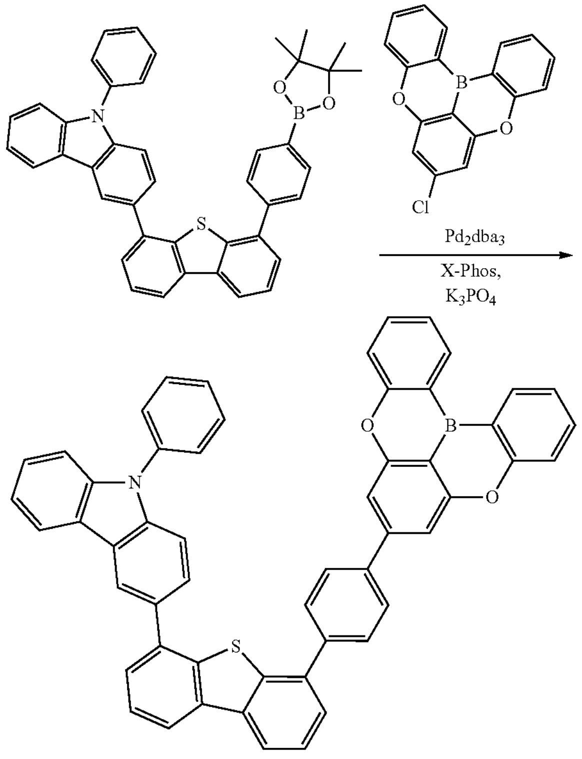

Compound 2

Step 1 To a dry 1-L 3-neck flask under nitrogen, equipped with a water condenser, magnetic stirrer and thermowell, dibenzo[b,d]thiophen-4-ylboronic acid (10 g, 43.8 mmol), 3-bromo-9-phenyl-9H-carbazole (14.13 g, 43.8 mmol), potassium phosphate, tribasic (27.9 g, 132 mmol), Toluene (199 ml) and Water (19.93 ml) were added and the mixture was degassed by purging with nitrogen for 5 minutes. Dicyclohexyl(2',6'-dimethoxy-[1,1'-biphenyl]-2-yl)phosphane (1.080 g, 2.63 mmol) and $Pd_2dba_3$ (1.205 g, 1.315 mmol) were added and the resulting mixture was further degassed. The reaction mixture was heated to reflux. After 16 hours, the reaction mixture was cooled, and the organic layer was separated. The organic layer was filtered through Celite and concentrated to dryness to provide 3-(dibenzo[b,d]thiophen-4-yl)-9-phenyl-9H-carbazole (17.5 g, 94%).

Step 2 To a dry 500 mL 3-neck flask equipped with a magnetic stirrer and thermowell, 3-(dibenzo[b,d]thiophen-4-yl)-9-phenyl-9H-carbazole (17 g, 39.9 mmol) was added followed by anhydrous THF (200 ml) via cannulation. The resulting solution was stirred, cooled to −75° C. and a solution of sec-butyllithium in cyclohexane (1.4 M, 49.9 ml, 69.9 mmol) was added dropwise. The mixture was allowed to warm to −40° C. over 90 minutes. The mixture was then cooled down to −68° C. and 2-isopropoxy-4,4,5,5-tetramethyl-1,3,2-dioxaborolane (14.26 ml, 69.9 mmol) was added dropwise. The reaction mixture was slowly warmed to room temperature overnight (~16 hours). After overnight stirring, the reaction mixture was cooled in an ice bath quenched with and aqueous saturated ammonium and stirred for 10 minutes. The organic layer was separated, and the aqueous layer was extracted with Dichloromethane. The combined organic layer was dried over sodium sulfate, filtered and concentrated to dryness to afford an off-white solid which was triturated in Heptane and filtered to obtain 9-phenyl-3-(6-(4,4,5,5-tetramethyl-1,3,2-dioxaborolan-2-yl)dibenzo[b,d]thiophen-4-yl)-9Hcarbazole (20 g, 91%).

Step 3 To a dry 500 mL, 3-neck flask equipped with a water condenser, magnetic stirrer and thermowell, 1-bromo-4-chlorobenzene (8.33 g, 43.5 mmol), 9-phenyl-3-(6-(4,4,5,5-tetramethyl-1,3,2-dioxaborolan-2-yl)dibenzo[b,d]thiophen-4-yl)-9H-carbazole (20 g, 36.3 mmol), Toluene (183 ml), and Water (18.32 ml) were added. Resulting mixture was stirred and degassed by purging with nitrogen for 5 minutes. To this mixture was added $Pd(PPh_3)_4$ (2.095 g, 1.813 mmol) and degassed further. The reaction mixture was then heated to reflux for 16 hours. The reaction mixture was cooled to room temperature, organic layer was separated and concentrated to dryness. The resulting residue was purified by silica gel column chromatography (DCM in Cyclohexane) to obtain 3-(6-(4-chlorophenyl)dibenzo[b,d]thiophen-4-yl)-9-phenyl-9H-carbazole (15 g, 77%).

Step 4 To a dry 250 mL, 3-neck flask equipped with a water condenser, magnetic stirrer and thermowell, 3-(6-(4-chlorophenyl)dibenzo[b,d]thiophen-4-yl)-9-phenyl-9H-carbazole (15 g, 28.0 mmol), 4,4,4',4',5,5,5',5'-octamethyl-2,2'-bi(1,3,2-dioxaborolane) (14.21 g, 56.0 mmol), potassium acetate (8.24 g, 84 mmol) and anhydrous dioxane (112 ml) were added and the mixture was degassed. $Pd_2dba_3$ (1.025 g, 1.119 mmol) and dicyclohexyl(2',6'-dimethoxy-[1,1'-biphenyl]-2-yl)phosphane (0.919 g, 2.238 mmol) were added and the resulting mixture was further degassed. The reaction mixture was then heated to 100° C. After 16 hours, TLC indicated complete consumption of the starting material. The reaction mixture was cooled to room temperature and filtered through a silica pad and the filtrate was concentrated. The resulting residue was dissolved in Toluene and filtered through a short pad of silica. The filtrate was concentrated and the resulting solid was triturated in Heptane to afford 9-phenyl-3-(6-(4-(4,4,5,5-tetramethyl-1,3,2-dioxaborolan-2-yl)phenyl)dibenzo[b,d]thiophen-4-yl)-9H-carbazole (13.4 g, 76%).

Step 5 To a dry 250 mL, 3-neck flask under nitrogen, equipped with a water condenser, magnetic stirrer and thermowell, 7-chloro-5,9-dioxa-13b-boranaphtho[3,2,1-de]anthracene (5 g, 16.42 mmol), 9-phenyl-3-(6-(4-(4,4,5,5-tetramethyl-1,3,2-dioxaborolan-2-yl)phenyl)dibenzo[b,d]thiophen-4-yl)-9H-carbazole (10.30 g, 16.42 mmol), potassium phosphate (10.46 g, 49.3 mmol), Toluene (83 ml), and Water (9 ml) were added and the mixture was degassed (vacuum-nitrogen backfill for 5 times). Dicyclohexyl(2',4',6'-triisopropyl-[1,1'-biphenyl]-2-yl)phosphane (0.939 g, 1.970 mmol) and $Pd_2dba_3$ (0.902 g, 0.985 mmol) were added and the resulting mixture was further degassed (vacuum-nitrogen backfill for 3 times). The reaction mixture was then heated to 75° C. for 16 hours. Reaction mixture was cooled to room temperature and the precipitated solid was collected by filtration. The solid was then dissolved in hot Toluene and filtered through a pad of silica and alumina. The filtrate was concentrated and the resulting solid was triturated in Methanol, Acetone, Ethyl acetate, DCM and Chloroform to obtain 3-(6-(4-(5,9-dioxa-13b-boranaphtho[3,2,1-de]anthracen-7-yl)phenyl)dibenzo[b,d]thiophen-4-yl)-9-phenyl-9H-carbazole as a white solid (Compound 2) (4.7 g, 37%).

Synthesis of 9-(6-(5,9-dioxa-13b-boranaphtho[3,2,1-de]anthracen-7-yl)dibenzo[b,d]furan-4-yl)-9H-3,9'-bicarbazole (Compound 3)

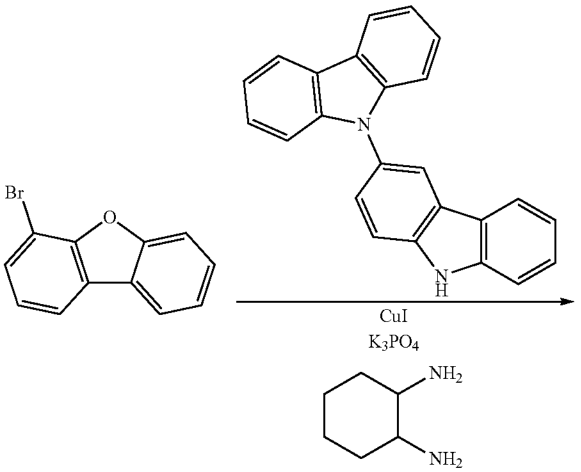

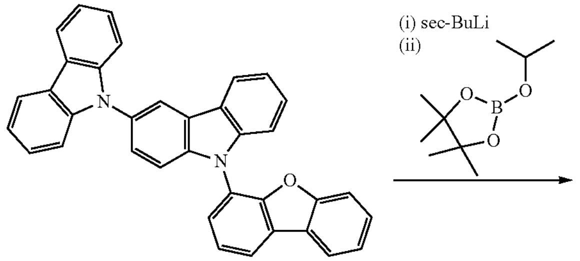

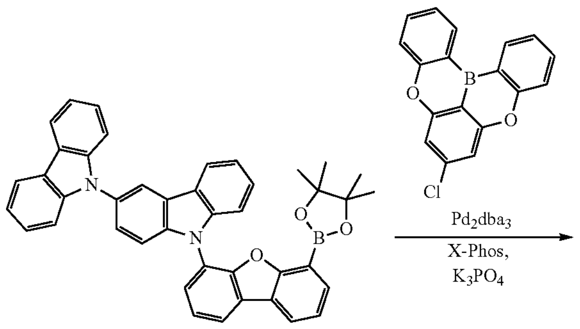

-continued

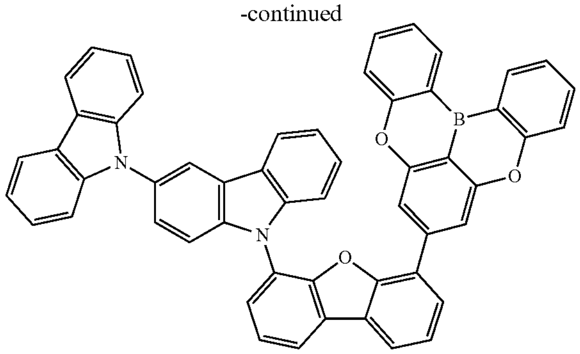

Compound 3

Step 1 To a dry 500 mL 3-neck flask under nitrogen, equipped with a water condenser, magnetic stirrer and thermowell, 4-bromodibenzo[b,d]furan (7.28 g, 29.5 mmol), 9H-3,9'-bicarbazole (10 g, 29.5 mmol), potassium phosphate (18.77 g, 88 mmol), copper(I) iodide (5.61 g, 29.5 mmol), cyclohexane-1,2-diamine (7.08 ml, 59.0 mmol) and Toluene (236 ml) were added and the mixture was degassed (vacuum-nitrogen backfill for 3 times). The reaction mixture was heated to reflux. After 18 hours, TLC showed complete consumption of starting material. The reaction mixture was filtered through a pad of Celite. The filtrate was concentrated and the solid obtained was triturated in Methanol for 20 minutes. The suspension was filtered to afford 9-(dibenzo[b,d]furan-4-yl)-9H-3,9'-bicarbazole (12 g, 82%).

Step 2 To a dry 500 mL 3-neck flask under nitrogen, equipped with a magnetic stirrer, addition funnel and thermowell, 9-(dibenzo[b,d]furan-4-yl)-9H-3,9'-bicarbazole (12 g, 24.07 mmol) was added. Anhydrous THF (540 ml) was added and the resulting solution was cooled to −75° C. To this mixture was added a solution of sec-Butyllithium in cyclohexane (1.4 M, 30.1 ml, 42.1 mmol) dropwise. The reaction mixture was then allowed to warm to −40° C. over 90 minutes. The mixture was cooled to −68° C. and 2-isopropoxy-4,4,5,5-tetramethyl-1,3,2-dioxaborolane (8.59 ml, 42.1 mmol) was added dropwise. The reaction mixture was slowly warmed to room temperature overnight (~16 hours). The reaction mixture was cooled in an ice bath, quenched with saturated ammonium chloride aqueous solution, and stirred for 10 minutes. The organic layer was separated, and the aqueous layer was extracted with Dichloromethane. The organic layers were combined and dried over sodium sulfate, filtered and the filtrate was evaporated to dryness to afford 9-(6-(4,4,5,5-tetramethyl-1,3,2-dioxaborolan-2-yl)dibenzo[b,d]furan-4-yl)-9H-3,9'-bicarbazole (13.1 g, 87%).

Step 3 To a dry 250 mL, 3-neck flask equipped with a water condenser, magnetic stirrer and thermowell, 7-chloro-5,9-dioxa-13b-boranaphtho[3,2,1-de]anthracene (5 g, 16.42 mmol), 9-(6-(4,4,5,5-tetramethyl-1,3,2-dioxaborolan-2-yl)dibenzo[b,d]furan-4-yl)-9H-3,9'-bicarbazole (12.30 g, 19.70 mmol), potassium phosphate (10.46 g, 49.3 mmol), Toluene (83 ml) and Water (9 ml) were added. Resulting mixture was stirred and degassed (vacuum-nitrogen backfill for 5 times). Dicyclohexyl(2',4',6'-triisopropyl-[1,1'-biphenyl]-2-yl)phosphane (0.939 g, 1.970 mmol) and $Pd_2dba_3$ (0.902 g, 0.985 mmol) were added and the reaction mixture was further degassed (vacuum-nitrogen backfill for 3 times). The reaction mixture was then heated to 75° C. for 16 hours. The reaction mixture was cooled to room temperature and the precipitated solid was collected by filtration. This solid was dissolved in hot toluene and filtered through a pad of silica and alumina. The filtrate was concentrated and the resulting solid was triturated sequentially with toluene, methanol, ethyl acetate and DCM/acetone to provide 9-(6-(5,9-dioxa-13b-boranaphtho[3,2,1-de]anthracen-7-yl)dibenzo[b,d]furan-4-yl)-9H-3,9'-bicarbazole (Compound 3) (5.9 g, 43.2%).

Synthesis of 9-(6-(5,9-dioxa-13b-boranaphtho[3,2,1-de]anthracen-7-yl)dibenzo[b,d]thiophen-4-yl)-9H-3,9'-bicarbazole (Compound 4)

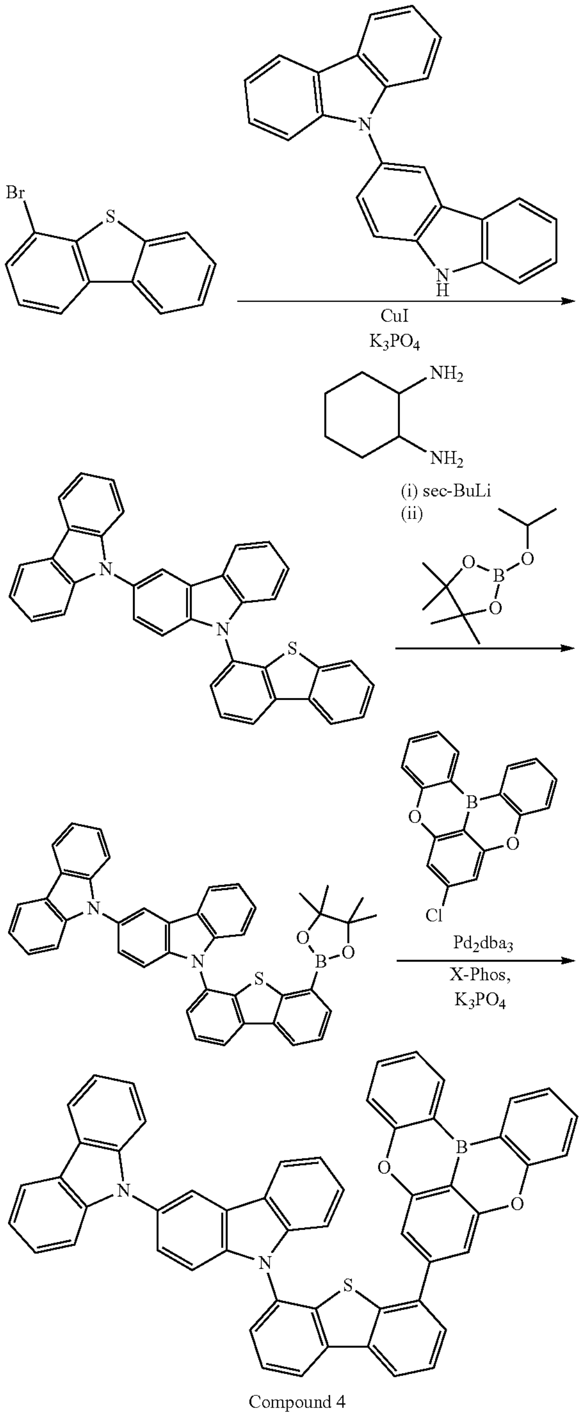

Compound 4

Step 1 To a dry 1 L 3-neck flask under nitrogen, equipped with a water condenser, magnetic stirrer and thermowell, 4-bromodibenzo[b,d]thiophene (23.75 g, 90 mmol), 9H-3,9'-bicarbazole (20 g, 60.2 mmol), potassium phosphate (38.3 g, 181 mmol), copper(I) iodide (11.46 g, 60.2 mmol), cyclohexane-1,2-diamine (14.45 ml, 120 mmol) and xylene (430 ml) were added and the mixture was degassed (vacuum-nitrogen backfill for 3 times). The reaction mixture was heated to reflux. After 3 days, additional 4-bromodibenzo[b,d]thiophene (23.75 g, 90 mmol), potassium phosphate (38.3 g, 181 mmol), copper(I) iodide (11.46 g, 60.2 mmol), cyclohexane-1,2-diamine (14.45 ml, 120 mmol) were added and reaction was continued. After 6 days, TLC showed unreacted starting Bicarbazole. Additional 4-bromodibenzo[b,d]thiophene (23.75 g, 90 mmol), potassium phosphate (38.3 g, 181 mmol), copper(I) iodide (11.46 g, 60.2 mmol), cyclohexane-1,2-diamine (14.45 ml, 120 mmol) were added and reaction was continued. After 15 days, the reaction mixture was filtered through a pad of silica. The filtrate was concentrated and the solid obtained was triturated in Toluene/Methanol to obtain 9-(dibenzo[b,d]thiophen-4-yl)-9H-3,9'-bicarbazole (25 g, 81%).

Step 2 To a dry 250 mL 3-neck flask under nitrogen, equipped with a magnetic stirrer, addition funnel and thermowell, 9-(dibenzo[b,d]thiophen-4-yl)-9H-3,9'-bicarbazole (7.34 g, 14.26 mmol) was added. Anhydrous THF (57 ml) was added and the resulting solution was cooled to −78° C. To this mixture was added a solution of sec-Butyllithium in cyclohexane (1.4 M, 15.28 ml, 21.39 mmol) dropwise. The reaction mixture was then allowed to warm to −40° C. over 90 minutes. The mixture was cooled to −68° C. and 2-isopropoxy-4,4,5,5-tetramethyl-1,3,2-dioxaborolane (5.09 ml, 24.96 mmol) was added dropwise. The reaction mixture was slowly warmed to room temperature overnight (~16 hours). The reaction mixture was cooled in an ice bath, quenched with saturated ammonium chloride aqueous solution, and stirred for 10 minutes. The organic layer was separated, and the aqueous layer was extracted with Dichloromethane. The organic layers were combined and dried over sodium sulfate, filtered and the filtrate was evaporated to dryness to afford 9-(6-(4,4,5,5-tetramethyl-1,3,2-dioxaborolan-2-yl)dibenzo[b,d]thiophen-4-yl)-9H-3,9'-bicarbazole (8.2 g, 90%).

Step 3 To a dry 250 mL, 3-neck flask equipped with a water condenser, magnetic stirrer and thermowell, 7-chloro-5,9-dioxa-13b-boranaphtho[3,2,1-de]anthracene (6.21 g, 20.40 mmol), 9-(6-(4,4,5,5-tetramethyl-1,3,2-dioxaborolan-2-yl)dibenzo[b,d]thiophen-4-yl)-9H-3,9'-bicarbazole (13.09 g, 20.40 mmol), potassium phosphate (12.99 g, 61.2 mmol), Toluene (103 ml) and Water (10.3 ml) were added. Resulting mixture was stirred and degassed (vacuum-nitrogen backfill for 5 times). Dicyclohexyl(2',4',6'-triisopropyl-[1,1'-biphenyl]-2-yl)phosphane (1.167 g, 2.448 mmol) and $Pd_2dba_3$ (1.121 g, 1.224 mmol) were added and the reaction mixture was further degassed (vacuum-nitrogen backfill for 3 times). The reaction mixture was then heated to 75° C. for 3 hours. The reaction mixture was cooled to room temperature and the precipitated solid was collected by filtration. This solid was dissolved in hot toluene and filtered through a pad of silica and alumina. Filtrate was concentrated and the resulting solid was triturated sequentially with toluene, methanol, ethyl acetate and DCM/acetone to provide 9-(6-(5,9-dioxa-13b-boranaphtho[3,2,1-de]anthracen-7-yl)dibenzo[b,d]thiophen-4-yl)-9H-3,9'-bicarbazole (Compound 4) (6 g, 37.6%).

Synthesis of 9-(6-(5,9-dioxa-13b-boranaphtho[3,2,1-de]anthracen-7-yl)dibenzo[b,d]thiophen-4-yl)-9'-phenyl-9H,9'H-3,3'-bicarbazole (Compound 5)
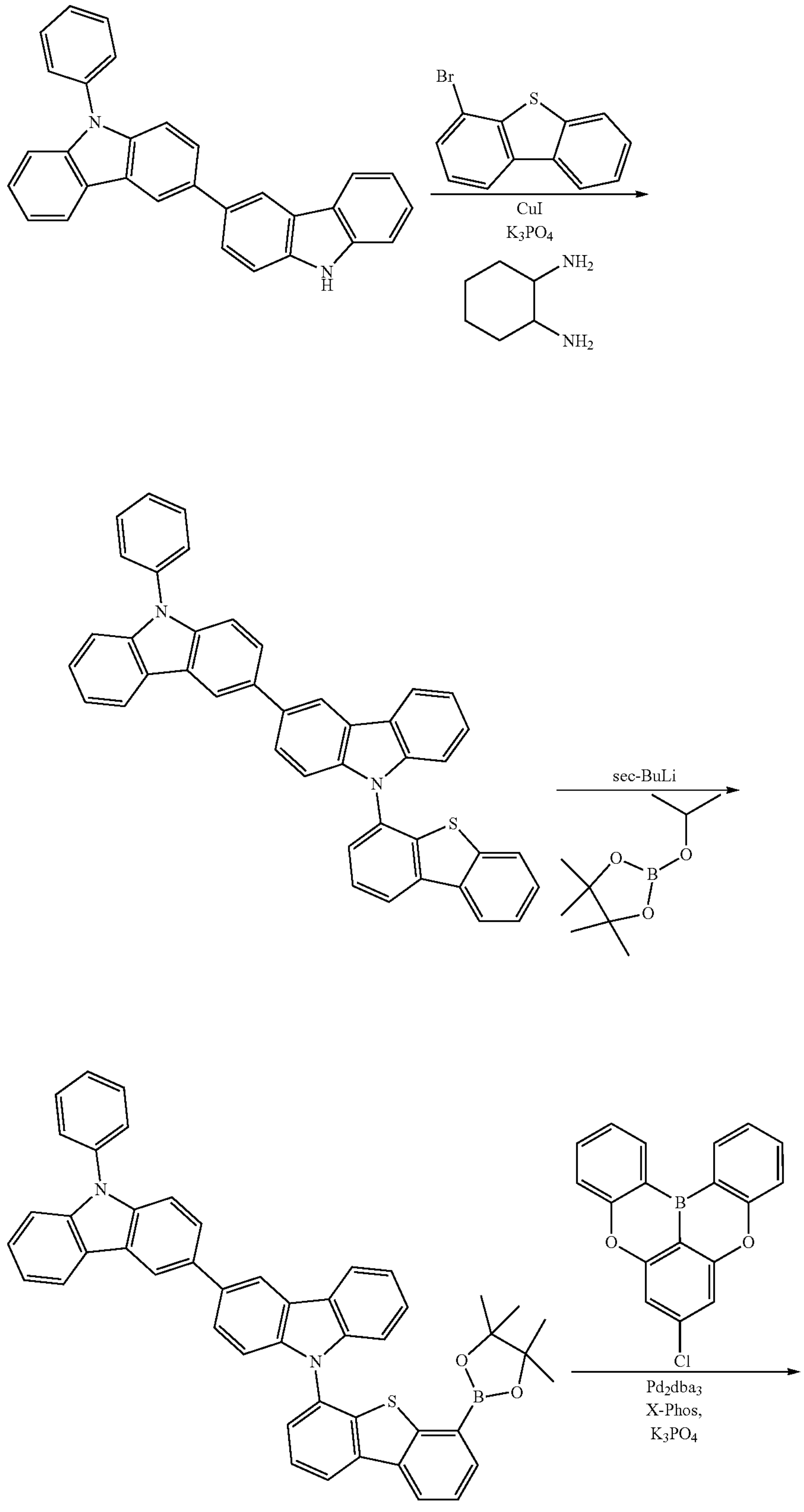

-continued

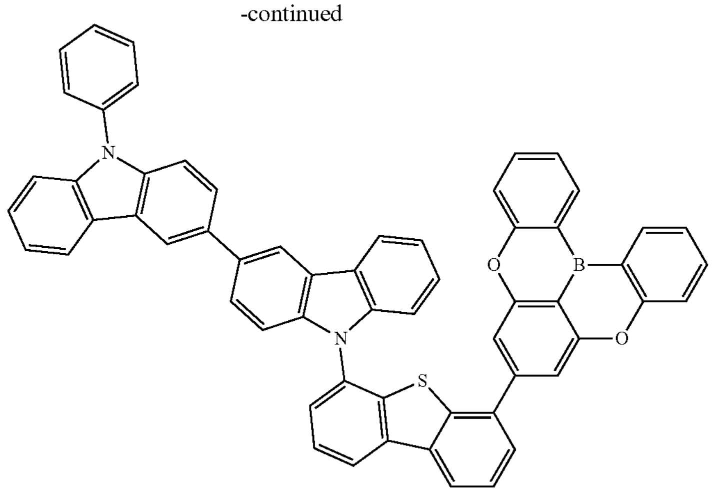

Compound 5

Step 1 To a dry 1 L 3-neck flask under nitrogen, equipped with a water condenser, magnetic stirrer and thermowell, 4-bromodibenzo[b,d]thiophene (19.33 g, 73.4 mmol), 9-phenyl-9H,9'H-3,3'-bicarbazole (15 g, 36.7 mmol), potassium phosphate (23.38 g, 110 mmol), copper(I) iodide (6.99 g, 36.7 mmol), cyclohexane-1,2-diamine (11.02 ml, 92 mmol) and Xylene (400 ml) were added and the mixture was degassed (vacuum-nitrogen backfill for 3 times). The reaction mixture was heated to reflux. After 3 days, additional 4-bromodibenzo[b,d]thiophene (19.33 g, 73.4 mmol), potassium phosphate (23.38 g, 110 mmol), copper(I) iodide (6.99 g, 36.7 mmol), cyclohexane-1,2-diamine (11.02 ml, 92 mmol) were added and reaction was continued. After 7 days, the reaction mixture was filtered through a pad of Celite. The filtrate was concentrated and the solid obtained was triturated in Methanol for 20 minutes. The suspension was filtered to afford 9-(dibenzo[b,d]thiophen-4-yl)-9'-phenyl-9H,9'H-3,3'-bicarbazole (17 g, 78%).

Step 2 To a dry 250 mL 3-neck flask under nitrogen, equipped with a magnetic stirrer, addition funnel and thermowell, 9-(dibenzo[b,d]thiophen-4-yl)-9'-phenyl-9H,9'H-3,3'-bicarbazole (5.2 g, 8.8 mmol) was added. Anhydrous THF (44 ml) was added and the resulting solution was cooled to −78° C. To this mixture was added a solution of sec-Butyllithium in cyclohexane (1.4 M, 9.43 ml, 13.20 mmol) dropwise. The reaction mixture was then allowed to warm to −40° C. over 90 minutes. The mixture was cooled to −68° C. and 2-isopropoxy-4,4,5,5-tetramethyl-1,3,2-dioxaborolane (3.14 ml, 15.40 mmol) was added dropwise. The reaction mixture was slowly warmed to room temperature overnight (~16 hours). The reaction mixture was cooled in an ice bath, quenched with saturated ammonium chloride aqueous solution, and stirred for 10 minutes. The organic layer was separated, and the aqueous layer was extracted with Dichloromethane. The organic layers were combined and dried over sodium sulfate, filtered and the filtrate was evaporated to dryness to afford 9-phenyl-9'-(6-(4,4,5,5-tetramethyl-1,3,2-dioxaborolan-2-yl)dibenzo[b,d]thiophen-4-yl)-9H,9'H-3,3'-bicarbazole (5.5 g, 87%).

Step 3 To a dry 250 mL, 3-neck flask equipped with a water condenser, magnetic stirrer and thermowell, 7-chloro-5,9-dioxa-13b-boranaphtho[3,2,1-de]anthracene (1.99 g, 6.52 mmol), 9-phenyl-9'-(6-(4,4,5,5-tetramethyl-1,3,2-dioxaborolan-2-yl)dibenzo[b,d]thiophen-4-yl)-9H,9'H-3,3'-bicarbazole (4.68 g, 6.52 mmol), potassium phosphate (4.15 g, 19.57 mmol), toluene (32.9 ml) and Water (3.29 ml) were added. Resulting mixture was stirred and degassed (vacuum-nitrogen backfill for 5 times). Dicyclohexyl(2',4',6'-triisopropyl-[1,1'-biphenyl]-2-yl)phosphane (0.373 g, 0.783 mmol) and $Pd_2dba_3$ (0.358 g, 0.391 mmol) were added and the reaction mixture was further degassed (vacuum-nitrogen backfill for 3 times). The reaction mixture was then heated to 75° C. for 3 hours. The reaction mixture was cooled to room temperature and the precipitated solid was collected by filtration. This solid was dissolved in hot toluene and filtered through a pad of silica and alumina. Filtrate was concentrated and the resulting solid was triturated sequentially with toluene, methanol, ethyl acetate and DCM/acetone to 9-(6-(5,9-dioxa-13b-boranaphtho[3,2,1-de]anthracen-7-yl)dibenzo[b,d]thiophen-4-yl)-9'-phenyl-9H,9'H-3,3'-bicarbazole (Compound 5) (3.5 g, 62.5%).

Synthesis of 5,9-Dioxa-13b-boranaphtho[3,2,1-de]anthracen-7-yltriphenylsilane (Compound 6)

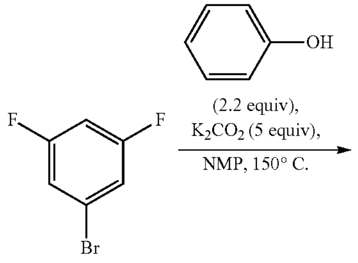

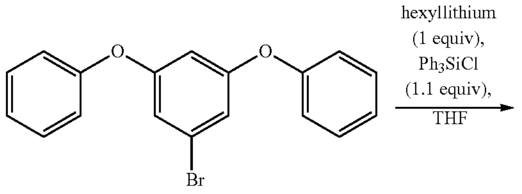

-continued

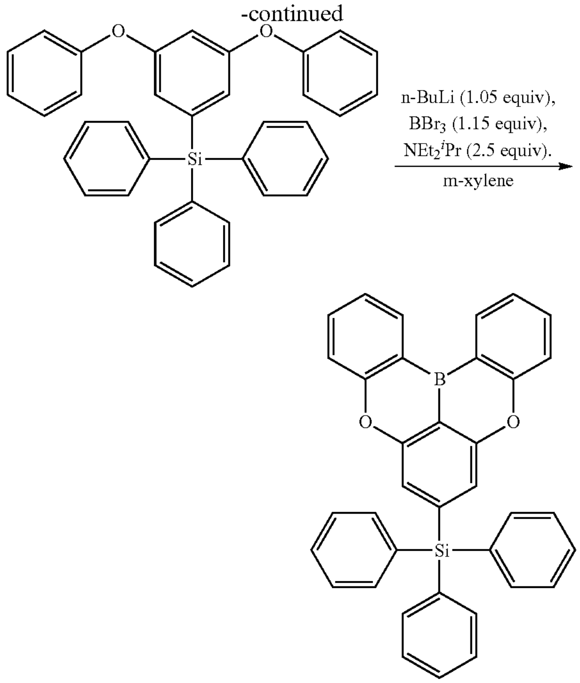

Compound 6

Step 1 To a 3 neck 2 L flask equipped with a mechanical stirrer, thermowell and water condenser was added potassium carbonate (358 g, 2591 mmol) and NMP (661 mL) under nitrogen. Resulting mixture was stirred and Phenol (107 g, 1140 mmol) was added slowly in portions. 1-bromo-3,5-difluorobenzene (100 g, 518 mmol) was then added and the mixture was heated to 150° C. for 2 days. After cooling to room temperature, the mixture was poured into ice cold water (2.5 L). The resulting solid was collected via suction filtration and triturated with MeOH (2×1 L). The white solid was further triturated in water (500 mL) and then in MeOH (500 mL) to obtain 119 g (349 mmol) of ((5-Bromo-1,3-phenylene)bis(oxy))dibenzene Step 2 To a 3 L flask was added ((5-bromo-1,3-phenylene)bis(oxy))dibenzene (45 g, 132 mmol) and THF (900 mL). The resulting solution was stirred and cooled to −78° C. To this mixture was added a solution hexyllithium in hexane (2.3 M, 60.2 mL, 138 mmol) and stirred for 45 min. A solution of chlorotriphenylsilane (42.8 g, 145 mmol) in THF (360 mL) was added slowly and the reaction mixture was allowed to warm to room temperature. After 16 hours stirring at room temperature, the reaction mixture was concentrated under reduced pressure and the resulting residue was partitioned in DCM and water. The organic layer was separated, and aqueous layer was extracted with DCM. Combined organic layer was dried over $Na_2SO_4$, filtered, and concentrated. The resultant brown oil was dissolved in heptane (100 mL) and filtered through a plug of silica gel (300 g) eluting with DCM/heptane. All fractions containing product were combined, concentrated and the resulting solid was triturated with heptane (150 mL) followed by MeOH (150 mL) to obtain (3,5-Diphenoxyphenyl)triphenylsilane (44.14 g, 80 mmol).

Step 3 To 1 L flask was added (3,5-diphenoxyphenyl)triphenylsilane (24.12 g, 46.3 mmol) and m-xylene (172 mL). Resulting mixture was stirred and cooled to 0° C. To this mixture was added a solution of n-butyllithium in hexane (2.5 M, 19.46 mL, 48.6 mmol) dropwise. The reaction mixture was allowed to warm to room temperature and then heated to 60° C. for 3 hours. The reaction mixture was then cooled to −30° C. and tribromoborane (5.04 mL, 53.3 mmol) was added slowly. After completion of the addition, the reaction mixture was allowed to warm to room temperature and stirred for 18 hours. The reaction mixture was then cooled to 0° C. and N-ethyl-N-isopropylpropan-2-amine (20.23 mL, 116 mmol) was added slowly. The reaction mixture was then heated to 127° C. for 2.5 h. The reaction mixture was cooled to room temperature and quenched with sat. $NaOAc_{(aq)}$ (400 mL) and brine (100 mL). The organic layer was separated, and the aqueous layer was extracted with DCM (2×100 mL). Combined organic layer was dried over $Na_2SO_4$, filtered, and concentrated. The resulting thick yellow oil was dissolved in acetone (100 mL) and dropped in MeOH (400 mL). The precipitated solid was collected via suction filtration and then triturated with DCM/MeOH (100 mL/400 mL). The solid was collected via suction filtration, dissolved in warm toluene (100 mL) and filtered through a plug of silica gel (200 g). Further trituration with Toluene and MeOH gave 5,9-Dioxa-13b-boranaphtho[3,2,1-de]anthracen-7-yltriphenylsilane (Compound 6) (3.73 g, 6.96 mmol) as an off-white solid.

Synthesis of Di(5,9-dioxa-13b-boranaphtho[3,2,1-de]anthracen-7-yl)diphenylsilane (Compound 7)

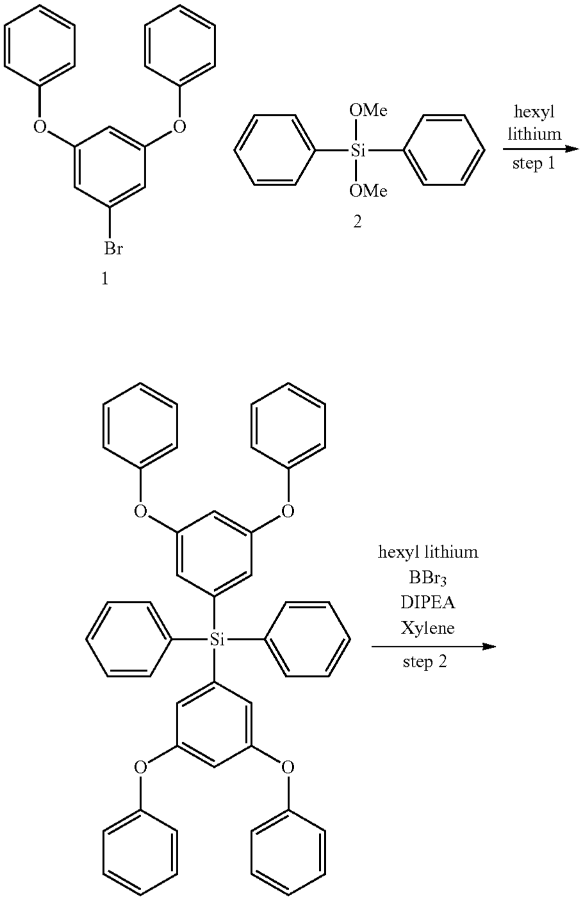

1

2

3

-continued

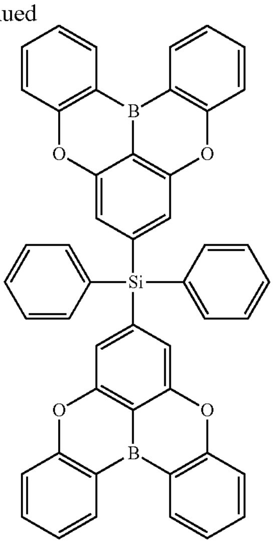

Compound 7

Synthesis of 9-(3-(5,9-dioxa-13b-boranaphtho[3,2,1-de]anthracen-7-yldiphenylsilyl)phenyl)-9H-carbazole (Compound 8)

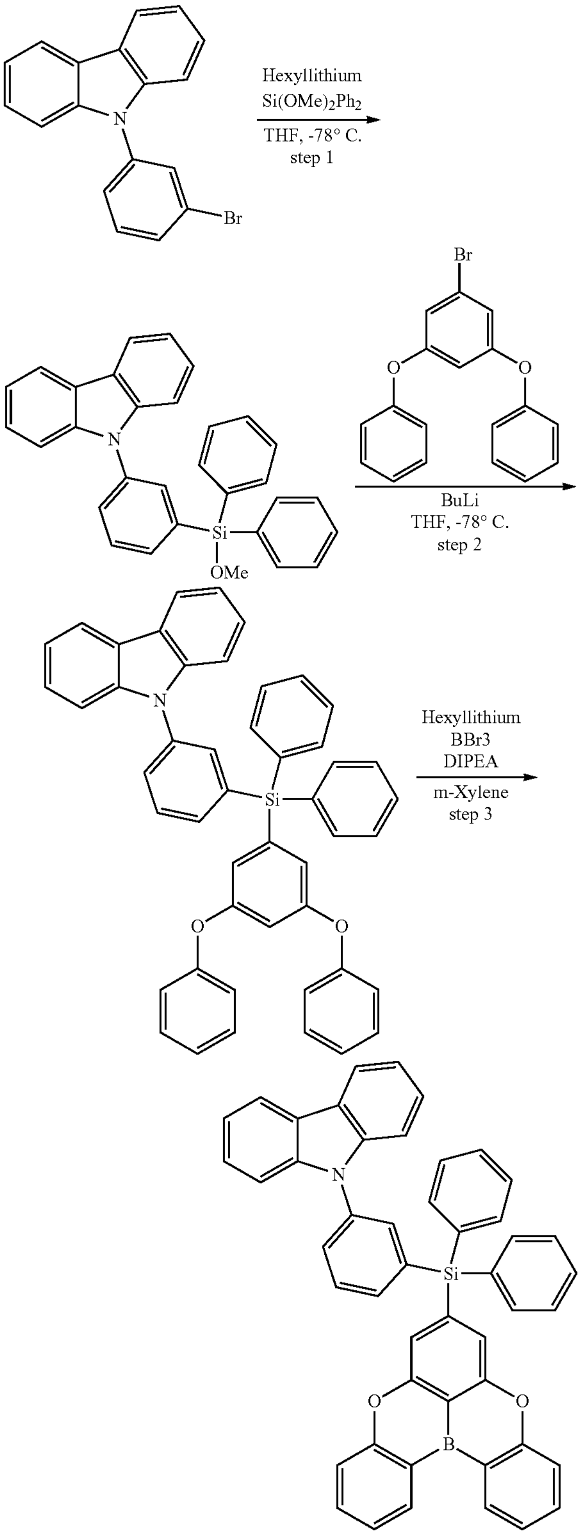

Compound 8

Step 1 To a 3 L 3-neck flask, equipped with a thermowell, nitrogen inlet was added ((5-bromo-1,3-phenylene)bis(oxy))dibenzene (84 g, 245 mmol) and THF (762 ml) under nitrogen. The resulting mixture was stirred and cooled to −78° C. To this mixture was added a solution of hexyllithium in hexane (2.3 M, 106 ml, 245 mmol) and stirred for 1 h. A solution of dimethoxydiphenylsilane (28.5 g, 117 mmol) in THF (400 mL) was then added slowly and the reaction mixture was allowed to warm to RT. After 16 hours, the reaction mixture was cooled in an ice bath, quenched with aqueous saturated ammonium chloride solution (20 mL), and extracted with ethyl acetate (3×300 mL). The combined organic layer was washed with water, dried over $Na_2SO_4$ and concentrated under reduced pressure. The resulting residue was purified by silica gel column chromatography (DCM/heptane) followed by trituration with heptane to obtain 55 g (78 mmol, 66.9% yield) of bis(3,5-diphenoxyphenyl)diphenylsilane.

Step 2 To a 2 L flask was added bis(3,5-diphenoxyphenyl)diphenylsilane (54 g, 77 mmol) and m-xylene (550 mL). Resulting mixture was stirred and cooled to −40° C. To this mixture was added a solution of n-hexyllithium in hexane (2.3 M, 69.9 ml, 161 mmol) dropwise. The reaction mixture was allowed to warm to RT and then heated to 60° C. for 3 hours. The reaction mixture was then cooled to −30° C. and tribromoborane (17.45 ml, 184 mmol) was added slowly. After completion of the addition, the reaction mixture was allowed to warm to RT and stirred for 16 hours. The reaction mixture was then cooled to −30° C. and N-ethyl-N-isopropylpropan-2-amine (49.5 g, 383 mmol) was added slowly. The reaction mixture was then heated to 127° C. for 5 h. The reaction mixture was cooled to RT and quenched with sat. $NaOAc_{(aq)}$ (200 mL) and brine (200 mL). The organic layer was separated, and the aqueous layer was extracted with DCM (3×200 mL). Combined organic layer was dried over $Na_2SO_4$, filtered, and concentrated. The resulting residue was purified by silica gel column chromatography (DCM/heptane) followed by trituration with toluene, EtOAc and $CHCl_3$ to obtain di(5,9-dioxa-13b-boranaphtho[3,2,1-de]anthracen-7-yl)diphenylsilane (Compound 7) (4.5 g, 6.23 mmol, 8.13% yield).

Step 1 To a 1 L 3-neck flask equipped with a thermowell, nitrogen inlet and magnetic stir bar was added 9-(3-bromophenyl)-9H-carbazole (60 g, 186 mmol) and THF (232 ml) under nitrogen. The resulting mixture was stirred and cooled to −78° C. To this mixture was added a solution of hexyllithium in hexane (2.3 M, 85 ml, 196 mmol) slowly and stirred for 1 h. Resulting solution was slowly dropped into a 2 L flask containing a solution of dimethoxydiphenylsilane (45.5 g, 186 mmol) in THF (232 ml) at −78° C. The resulting reaction mixture was allowed to warm to RT. After 16 hours stirring, the reaction mixture was quenched with water and extracted with EtOAc (3×150 mL). Combined organic layer was dried over $Na_2SO_4$, filtered and concentrated. Resulting residue was purified by silica gel column chromatography (DCM/heptane) followed by trituration with heptane to obtain 57 g (67.2% yield) of 9-(3-(methoxydiphenylsilyl)phenyl)-9H-carbazole.

Step 2 To a 2 L 3-neck flask, equipped with a thermowell, nitrogen inlet was added ((5-bromo-1,3-phenylene)bis(oxy))dibenzene (51.2 g, 150 mmol) and THF (407 ml) under nitrogen. The resulting mixture was stirred and cooled to −78° C. To this mixture was added a solution of a hexyllithium in hexane (2.3 M, 65.3 ml, 150 mmol) and stirred for 45 minutes. A solution of 9-(3-(methoxydiphenylsilyl)phenyl)-9H-carbazole (57 g, 125 mmol) in THF (100 mL) was then added slowly and the reaction mixture was allowed to warm to room temperature. After 16 hours, the reaction mixture was cooled in an ice bath, quenched with aqueous saturated ammonium chloride solution (5 mL), and extracted with ethyl acetate (3×50 mL). The combined organic layer was washed with water, dried over $Na_2SO_4$ and concentrated under reduced pressure. The resulting residue was purified by silica gel column chromatography (DCM/heptane) to obtain 9-(3-((3,5-diphenoxyphenyl)diphenylsilyl)phenyl)-9H-carbazole (7.2 g, 10.50 mmol, 68.3% yield).

Step 3 To a 2 L flask three neck flask equipped with a reflux condenser, thermowell, nitrogen inlet, and a mechanical stirrer was added 9-(3-((3,5-diphenoxyphenyl)diphenylsilyl)phenyl)-9H-carbazole (65.9 g, 96 mmol) and m-xylene (329 ml). Resulting mixture was stirred and cooled to −40° C. To this mixture was added a solution of hexyllithium in hexane (2.3 M, 46.0 ml, 106 mmol) dropwise. The reaction mixture was allowed to warm to room temperature and then heated to 60° C. for 3 hours. The reaction mixture was then cooled to −30° C. and tribromoborane (11.11 ml, 115 mmol) was added slowly. After completion of the addition, the reaction mixture was allowed to warm to room temperature and stirred for 16 hours. The reaction mixture was then cooled to −30° C. and N-ethyl-N-isopropylpropan-2-amine (42.0 ml, 240 mmol) was added slowly. The reaction mixture was then heated to 120° C. for 2 h. The reaction mixture was cooled to room temperature and quenched with sat. $NaOAc_{(aq)}$ (300 mL) and brine (300 mL). The organic layer was separated, and the aqueous layer was extracted with DCM (250 mL). Combined organic layer was dried over $Na_2SO_4$, filtered, and concentrated. The resulting residue was purified by silica gel column chromatography (DCM/heptane) followed by trituration's with methanol, acetone, DCM/MeOH, DCM/Acetone to provide 9-(3-(5,9-dioxa-13b-boranaphtho[3,2,1-de]anthracen-7-yldiphenylsilyl)phenyl)-9H-carbazole (Compound 8) (9.9 g, 15%) as a white solid.

Synthesis of 9-(5,9-Dioxa-13b-boranaphtho[3,2,1-de]anthracen-7-yl)-3-(triphenylsilyl)-9H-carbazole (Compound 9)

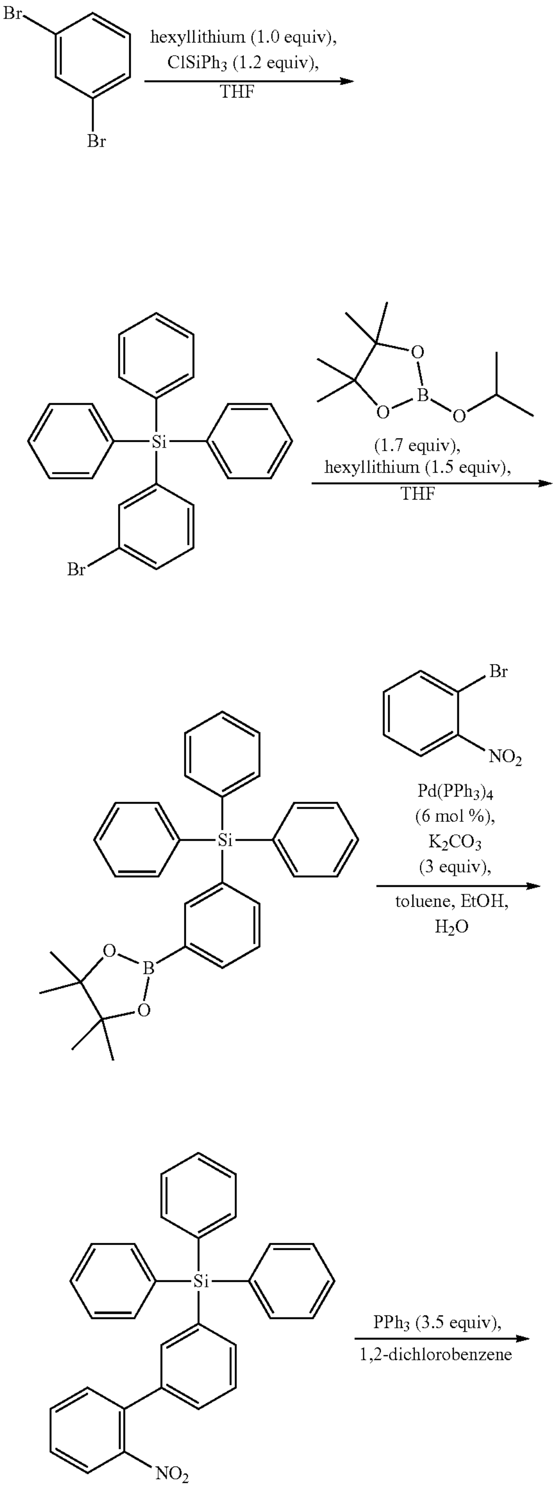

-continued

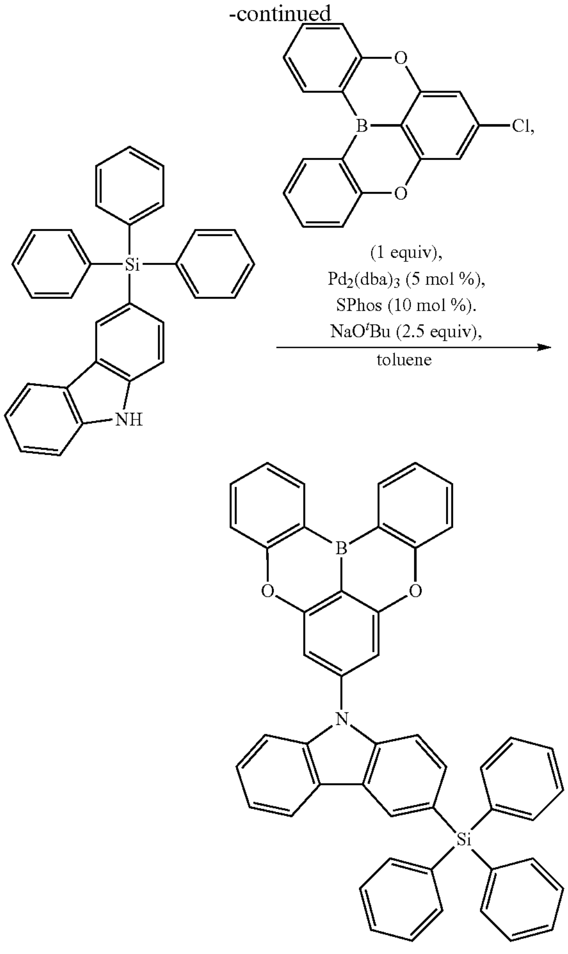

Compound 9

Step 1 To a 5 L flask was added 1,3-dibromobenzene (77 ml, 636 mmol) and THF (2000 ml) under nitrogen. The resulting reaction mixture was cooled to −78° C. and a solution of hexyllithium in hexane (2.3 M, 290 ml, 668 mmol) was added over 20 min and stirred for 45 minutes. A solution of chlorotriphenylsilane (225 g, 763 mmol) in THF (800 ml) was then added slowly and reaction mixture was allowed warm to room temperature and stirred overnight. The reaction mixture was then concentrated, and the resulting solid was triturated with warm EtOAc/MeOH (800 mL/800 mL) to obtain (3-bromophenyl)triphenylsilane (72 g) as a white solid.

Step 2 To a 5 L flask was added (3-bromophenyl)triphenylsilane (72.0 g, 173 mmol) and THF (1576 ml). The resulting reaction mixture was stirred and cooled to −78° C. A solution of hexyllithium in hexane (2.3 M, 113 ml, 260 mmol) was added over 20 min and stirred for 45 min. A solution of 2-isopropoxy-4,4,5,5-tetramethyl-1,3,2-dioxaborolane (60.1 ml, 295 mmol) in THF (158 ml) was then added slowly and the reaction mixture was allowed to warm to room temperature and stirred overnight (~16 hours). The reaction mixture was quenched with ice-cold water (1 L) and the organic layer was separated. The aqueous layer was extracted with EtOAc (2×700 mL), the combined organic layer was dried over $Na_2SO_4$, filtered, and concentrated. The off-white solid was triturated with heptane (500 mL) to give a triphenyl(3-(4,4,5,5-tetramethyl-1,3,2-dioxaborolan-2-yl)phenyl)silane (64.97 g) as a white solid.

Step 3 To a 2 L flask was added 1-bromo-2-nitrobenzene (25 g, 124 mmol, potassium carbonate (51.3 g, 371 mmol), $Pd(PPh_3)_4$ (8.58 g, 7.43 mmol), toluene (300 mL), water (100 mL) and ethanol (100 mL). The resulting reaction mixture was heated to reflux and allowed to stir for 20 hours. After cooling to room temperature, the reaction mixture was diluted with water (500 mL) and the organic layer was separated. The aqueous layer was then extracted with EtOAc (2×400 mL). The combined organic layer was dried over $Na_2SO_4$, filtered, and concentrated. The resulting residue was purified by of silica gel column chromatography (DCM/heptane) to obtain (2'-nitro-[1,1'-biphenyl]-3-yl)triphenylsilane (31.3 g) as a white solid.

Step 4 To a 2 L flask equipped with a mechanical stirrer was added (2'-nitro-[1,1'-biphenyl]-3-yl)triphenylsilane (31.26 g, 68.3 mmol), triphenylphosphine (62.7 g, 239 mmol) and 1,2-dichlorobenzene (683 mL). The reaction mixture was heated to reflux and stirred for 18 hours. 1,2-dichlorobenzene was then removed under reduced pressure and the crude residue was triturated with DCM/heptane. Resulting solid was further purified by silica gel column chromatography (DCM/heptane) to obtain 3-(Triphenylsilyl)-9H-carbazole (12.05 g).

Step 5 To a 250 mL flask under nitrogen was added 7-chloro-5,9-dioxa-13b-boranaphtho[3,2,1-de]anthracene (5.75 g, 18.88 mmol), 3-(triphenylsilyl)-9H-carbazole (8.0 g, 18.80 mmol), sodium 2-methylpropan-2-olate (4.54 g, 47.2 mmol), dicyclohexyl(2',6'-dimethoxy-[1,1'-biphenyl]-2-yl)phosphane (0.775 g, 1.888 mmol), $Pd_2(dba)_3$ (0.865 g, 0.944 mmol), and Toluene (95 mL). The resulting mixture was degassed and heated to reflux (107° C.). After 3 h, TLC and NMR showed complete consumption of the starting material. The reaction mixture was cooled to room temperature, filtered through a mixed silica/alumina plug and the plug was washed with toluene. Filtrate was concentrated and the resulting residue was purified by silica gel column chromatography with DCM/heptane as an eluent followed by the recrystallization with Toluene to obtain 9-(5,9-dioxa-13b-boranaphtho[3,2,1-de]anthracen-7-yl)-3-(triphenylsilyl)-9H-carbazole (Compound 9) (4.2 g) as a white solid.

Synthesis of 9-(5,9-Dioxa-13b-boranaphtho[3,2,1-de]anthracen-7-yl)-9H-1,9'-bicarbazole (Compound 10)

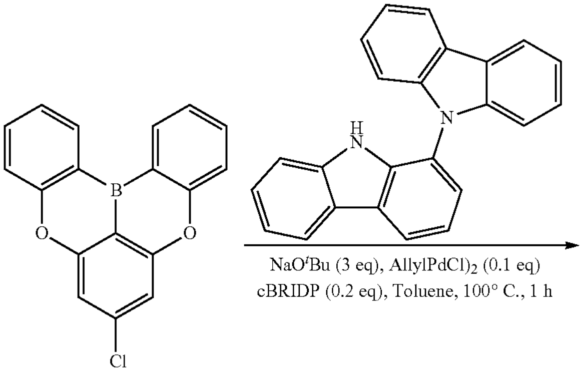

-continued

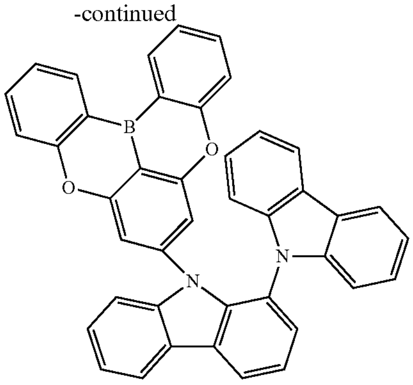

Compound 10

A suspension of 7-chloro-5,9-dioxa-13b-boranaphtho[3,2,1-de]anthracene (5.50 g, 18.1 mmol), 9H-1,9'-bicarbazole (5.0 g, 15 mmol), sodium tert-butoxide (4.34 g, 45.1 mmol), allylpalladium(II) chloride dimer (0.550 g, 1.50 mmol) and di-tert-butyl(2,2-diphenyl-1-methyl-1-cyclopropyl)phosphine [cBRIDP] (1.06 g, 3.01 mmol) in toluene (100 mL) was sparged with nitrogen for 10 min, then heated at 100° C. for 1 hour under nitrogen. The reaction mixture was cooled to RT, preabsorbed onto silica gel and purified by flash column chromatography (silica gel, 220 g cartridge, solid load, 0-20% DCM/isohexane) to give the product. This material was triturated in refluxing methanol followed by trituration in refluxing EtOAc. This material was then recrystallized from refluxing toluene (40 mL) twice to give 9-(5,9-dioxa-13b-boranaphtho[3,2,1-de]anthracen-7-yl)-9H-1,9'-bicarbazole (Compound 10) (4.25 g, 7.01 mmol, 47% yield) as a white solid.

Synthesis of 9-(5,9-Dioxa-13b-boranaphtho[3,2,1-de]anthracen-7-yl)-9H-3,9'-bicarbazole (Compound 11)

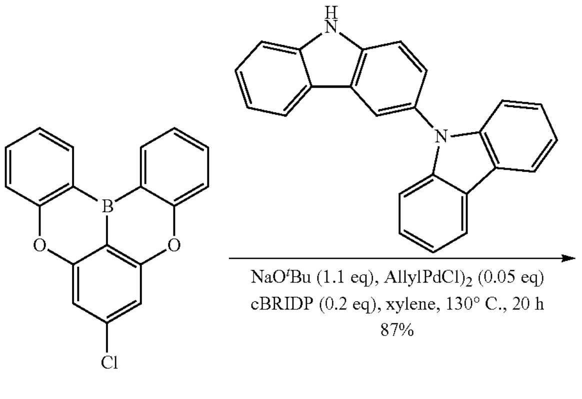

-continued

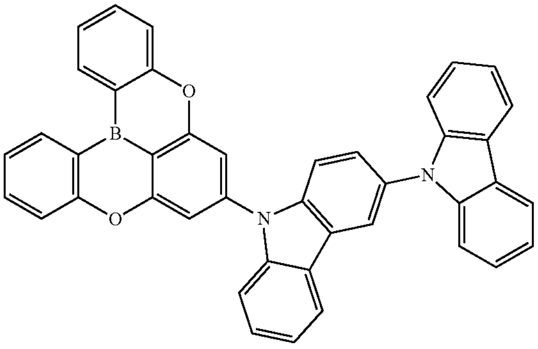

Compound 11

A degassed, preheated (~130° C.) solution of allylpalladium chloride dimer (0.183 g, 0.5 mmol) and cBRIDP (0.705 g, 2.001 mmol) in m-xylene (75 mL) was added to a degassed, preheated (130° C.) mixture of $NaO^tBu$ (1.923 g, 20.01 mmol), 9H-3,9'-bicarbazole (6.65 g, 20.01 mmol) and 7-Chloro-5,9-dioxa-13b-boranaphtho[3,2,1-de]anthracene (6.70 g, 22.01 mmol) in m-xylene (250 mL) and toluene (25 mL). The mixture was stirred at 130° C. under Ar for 20 hours. Tlc (15% DCM in hexanes) showed the reaction completed. After cooling to room temperature, water was added. The mixture was filtered. The liquor was extracted with EtOAc, dried over $Na_2SO_4$. The collected grey solid (10.5 g) was dissolved in THF (5 L), filtered through a pad of Celite, concentrated to give 9-(5,9-Dioxa-13b-boranaphtho[3,2,1-de]anthracen-7-yl)-9H-3,9'-bicarbazole (Compound 11) (10.18 g) as a white solid.

OLED devices were fabricated using Compound 6, Compound 10, Compound 11, and Compound 12 as either single hosts for a sky blue Ir emitter (Emitter 1) or as an electron transporting cohost for a deep blue Pt emitter (Emitter 2). The device results are shown in Table 1 where the EQE and Voltage are taken at 10 $mA/cm^2$ and the lifetime (LT90) is the time in hours to reduction of brightness to 90% of the initial luminance from 1000 $cd/m^2$.

HIL1

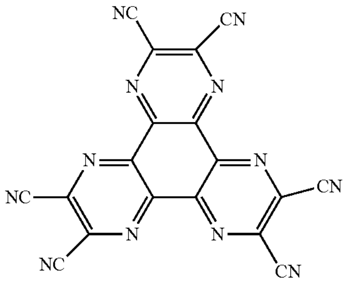

-continued
HTL1
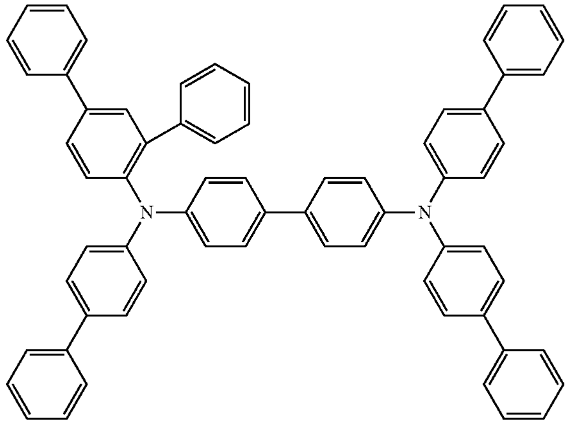
EBL1
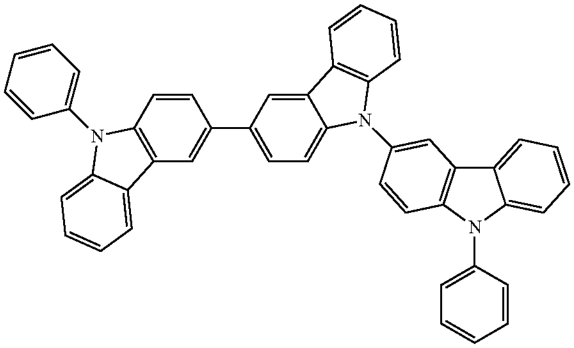
EBL2
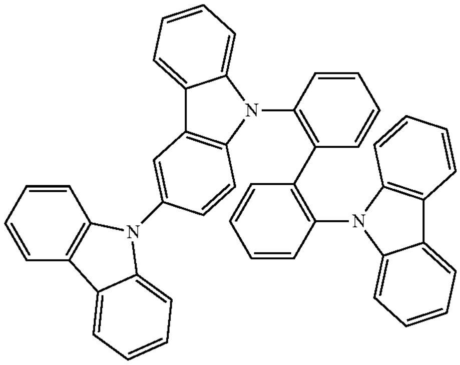
HBL1
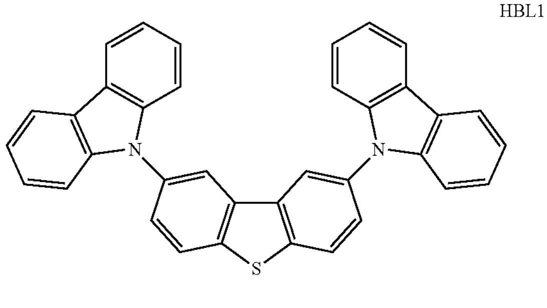
-continued
HBL2
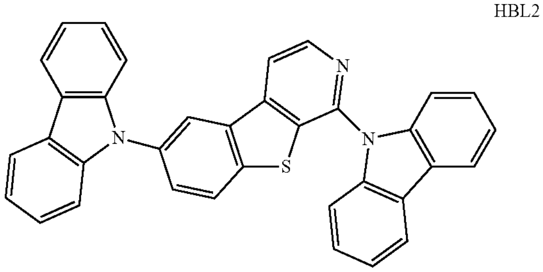
ETL1
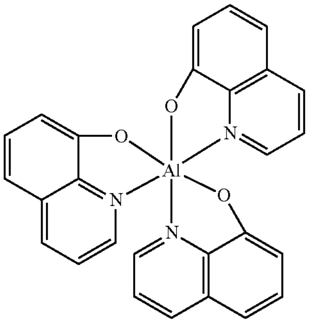
ETL2
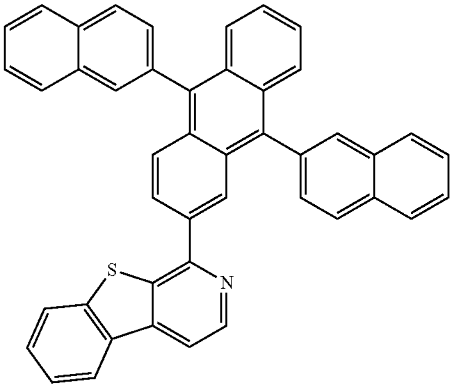
EIL 1
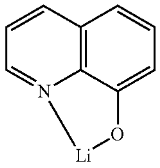
Emitter 1
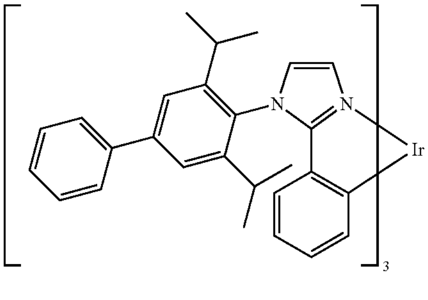

-continued

Emitter 2

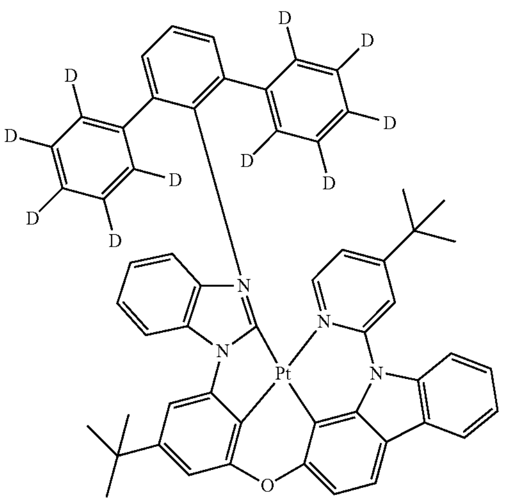

Compound 12

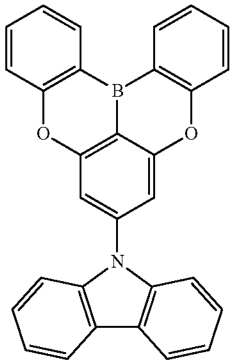

TABLE 1

| Device | Host | Emitter | λmax (nm) | CIE | Voltage (V) | EQE (relative to Comparison 1) | LT90 (relative to Comparison 1) |
|---|---|---|---|---|---|---|---|
| Example 1 | Compound 6 | Emitter 2 | 468 | (0.133, 0.216) | 4.2 | 106% | 68% |
| Example 2 | Compound 10 | Emitter 2 | 468 | (0.133, 0.227) | 3.8 | 109% | 186% |
| Example 3 | Compound 11 | Emitter 2 | 471 | (0.132, 0.248) | 4.2 | 109% | 272% |
| Example 4 | Compound 12 | Emitter 2 | 469 | (0.132, 0.231) | 3.9 | 107% | 203% |
| Comparison 1 | HBL2 | Emitter 2 | 468 | (0.133, 0.218) | 4.1 | 100% | 100% |
| Comparison 2 | Compound 12 | Emitter 1 | 552 | (0.390, 0.539) | 5.4 | 30% | 147% |
| Comparison 3 | HBL1 | Emitter 1 | 475 | (0.178, 0.408) | 6.6 | 141% | 287% |

OLEDs were grown on a glass substrate pre-coated with an indium-tin-oxide (ITO) layer having a sheet resistance of 15-2/sq. Prior to any organic layer deposition or coating, the substrate was degreased with solvents and then treated with an oxygen plasma for 1.5 minutes with 50 W at 100 mTorr and with UV ozone for 5 minutes. The devices in Table 1 were fabricated in high vacuum ($<10^{-6}$ Torr) by thermal evaporation. The anode electrode was 750 Å of indium tin oxide (ITO). All devices were encapsulated with a glass lid sealed with an epoxy resin in a nitrogen glove box (<1 ppm of $H_2O$ and $O_2$) immediately after fabrication with a moisture getter incorporated inside the package. Doping percentages are in volume percent. Two device structures were used.

Device Structure 1 had organic layers consisting of, sequentially, from the ITO surface, 100 Å thick HIL 1 (HIL), 250 Å layer of HTL1 (HTL), 50 Å of EBL2 (EBL), 300 Å of EBL2 with 40% of the co-host and 12% Emitter2 (EML), 50 of HBL2 (HBL), 300 Å of ETL2 doped with 35% of EIL1 (ETL), 10 Å of EIL1 (EIL) followed by 1,000 Å of Al (Cath).

Device Structure 2 had organic layers consisting of, sequentially, from the ITO surface, 100 Å thick HIL 1 (HIL), 250 Å layer of HTL1 (HTL), 50 Å of EBL1 (EBL), 300 Å of host doped with 20% Emitter 1 (EML), 50 of HBL1 (HBL), 300 Å of ETL1 (ETL), 10 Å of EIL1 (EIL) followed by 1,000 Å of Al (Cath).

Device Example 1 uses a cohost of Compound 6 in Device Structure 1.

Device Example 2 uses a cohost of Compound 10 in Device Structure 1.

Device Example 3 uses a cohost of Compound 11 in Device Structure 1.

Device Example 4 uses a cohost of Compound 12 in Device Structure 1.

Device Comparison 1 uses a cohost of HBL2 in Device Structure 1.

Device Comparison 2 uses a of Compound 12 in Device Structure 2.

Device Comparison 3 uses a cohost of HBL1 in Device Structure 2.

The above data shows that the device Example 1, with inventive Compound 6, exhibited a bluer color than the comparative compound, Compound 12, as the host. The blue shift by 1 nm and the reduction of CIEy by 0.015 is beyond any value that could be attributed to experimental error and the observed improvement is significant. Based on the fact that Compound 6 has a similar structure as Compound 12 with the only difference being that the triphenyl silane replacement for carbazole moiety, the significant performance improvement observed in the above data was unexpected. Without being bound by any theories, this improvement may be attributed to the increased steric bulk introduced by the tetrahedral silane moiety which inhibits the formation of any low energy exciplex between the inventive molecule and the platinum complex, Emitter 2.

The above data shows that the device Examples 2 and 3, with inventive Compound 10 and Compound 11 respectively, exhibited higher EQE than the comparative compound, Compound 12, as the host. The increase in EQE is beyond any value that could be attributed to experimental error and the observed improvement is significant. Based on the fact that Compound 10 and Compound 11 has a similar structure as Compound 12 with the only difference being the substitution of an extra carbazole moiety, the significant performance improvement observed in the above data was unexpected. Without being bound by any theories, this improvement may be attributed to the improved charge transport properties of the biscarbazole for the inventive compounds Compound 10 and Compound 11 compared to the single carbazole substitution for the comparative Compound 12.

As shown in Table 1, all of the devices using the boron containing hosts (Examples 1-4) have higher EQE than the comparison compound HBL2 in Comparison 1. The increase in EQE is beyond any value that could be attributed to experimental error and the observed improvement is significant. Furthermore, the enhancement from using the boron containing hosts was only achieved using the Pt complex (Emitter 2). In Comparison 2, when the Ir emitter was used, the device exhibited a redshifted emission and a reduced EQE compared to Comparison 3. The improved performance for the boron containing hosts with platinum emitters was unexpected considering the reduced performance of Compound 12 when used with an Iridium phosphor. Without being bound by any theories, this improvement may be attributed to the suppression of exciplex formation in the devices with the Platinum phosphor compared with the iridium phosphor.

The invention claimed is:

1. An organic light emitting device (OLED) comprising:

an anode;

a cathode; and an emissive layer disposed between the anode and the cathode, wherein the emissive layer comprises a first compound and a second compound;

wherein the first compound is a boron compound possessing a trigonal planar geometry;

wherein the second compound is a Pt(II) complex possessing a square planar geometry; and wherein the first compound is an acceptor, and the second compound is a sensitizer.

2. The OLED of claim 1 wherein the first compound comprises a structure of Formula I:

Formula I

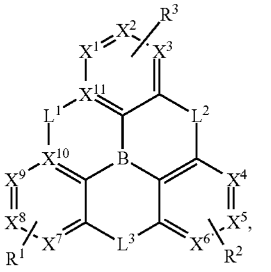

wherein:

$X^1$-$X^9$ are each independently C or N;

no more than two N atoms are bonded to one another;

$L^1$, $L^2$, and $L^3$ are each independently selected from the group consisting of O, S, Se, BR, NR, CRR', SiRR', and GeRR';

$L^1$ is optionally present, and $L^2$ and $L^3$ are always present;

$R^1$, $R^2$, and $R^3$ each independently represent zero, mono, or up to a maximum allowed substitution to its associated ring;

each of R, R', $R^1$, $R^2$, and $R^3$ is independently a hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof; and the second compound is a Pt complex capable of emitting light at room temperature upon photo or electrical excitation.

3. The OLED of claim 1, wherein the Pt complex comprises a tetradentate ligand.

4. The OLED of claim 1, wherein the Pt complex comprises at least one Pt—C bond, and at least one Pt—N bond.

5. The OLED of claim 1, wherein the Pt complex is a phosphorescent emitter.

6. The OLED of claim 1, wherein the Pt complex has at least one ligand or part of the ligand if the ligand is more than bidentate selected from the group consisting of:

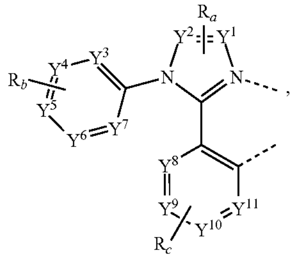

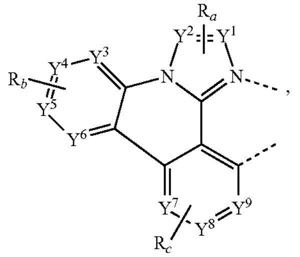

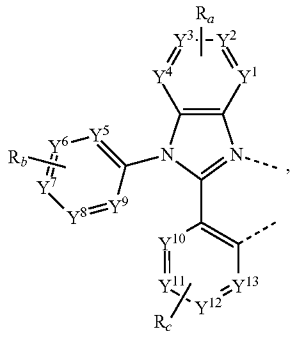

-continued

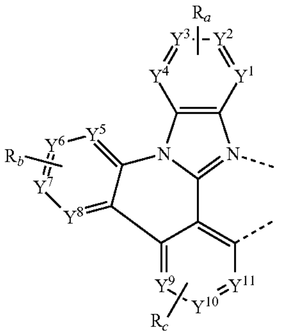

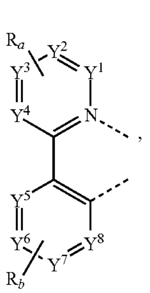

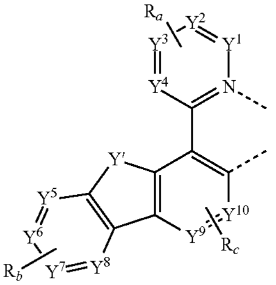

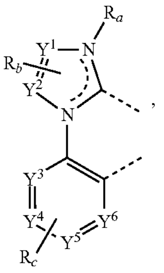

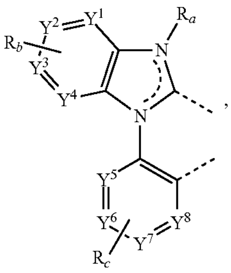

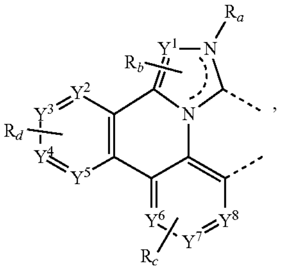

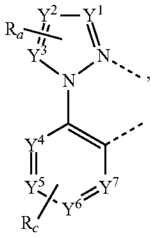

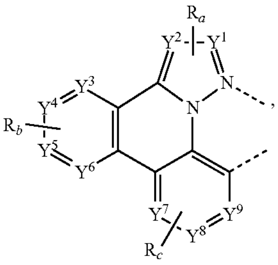

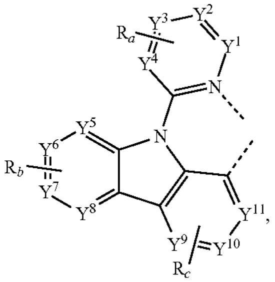

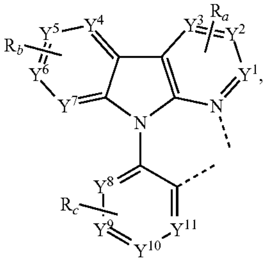

and

-continued

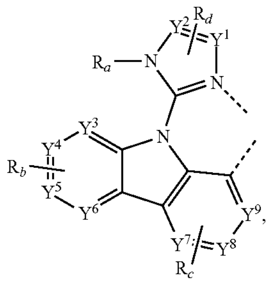

wherein each $Y^1$ to $Y^{13}$ are independently selected from the group consisting of carbon and nitrogen;

wherein Y' is selected from the group consisting of $BR_e$, $NR_e$, $PR_e$, O, S, Se, C=O, S=O, $SO_2$, $CR_eR_f$, $SiR_eR_f$, and $GeR_eR_f$;

wherein $R_e$ and $R_f$ are optionally fused or joined to form a ring;

wherein each $R_a$, $R_b$, $R_c$, and $R_d$ may independently represent from mono substitution to the maximum possible number of substitution, or no substitution;

wherein each of $R_a$, $R_b$, $R_c$, $R_d$, $R_e$ and $R_f$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; and wherein any two adjacent substituents of $R_a$, $R_b$, $R_c$, and $R_d$ are optionally fused or joined to form a ring or form a multidentate ligand.

7. The OLED of claim 1, wherein the Pt complex is selected from the group consisting of:

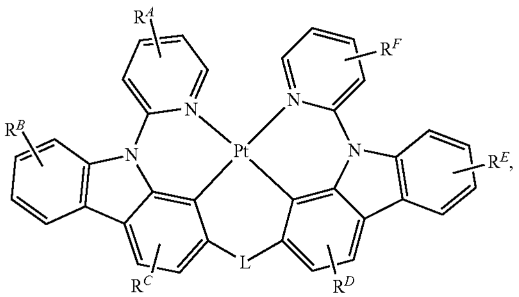

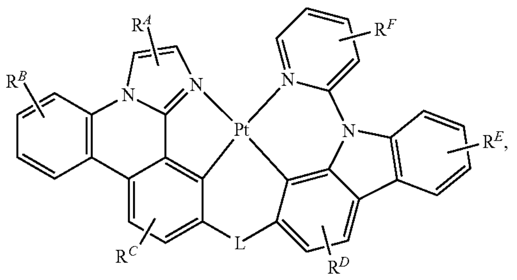

-continued
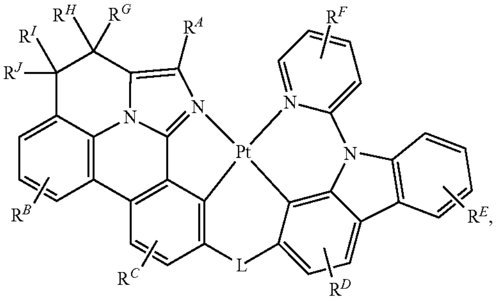
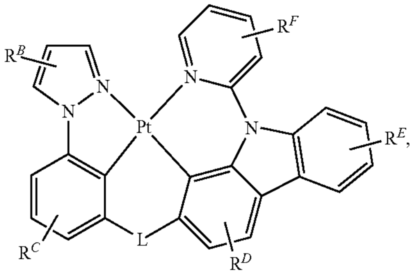
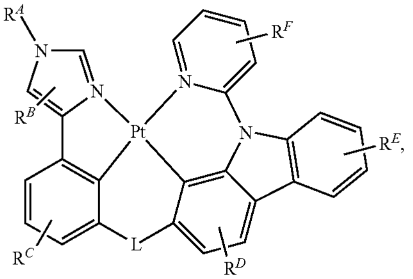
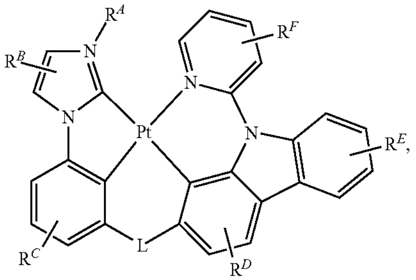
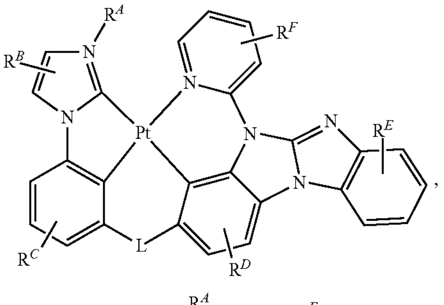
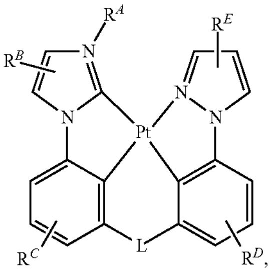
-continued
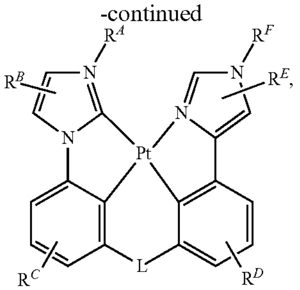
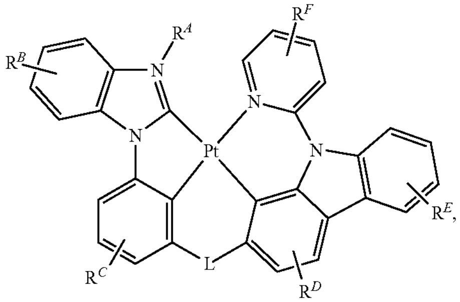
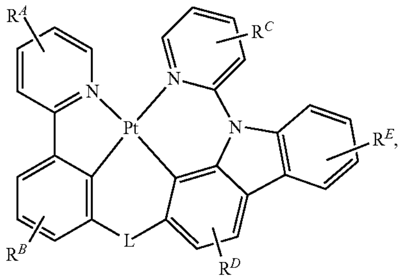
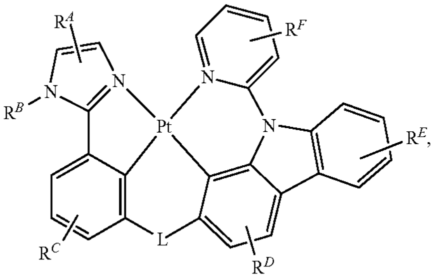
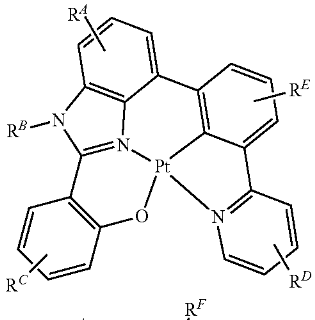
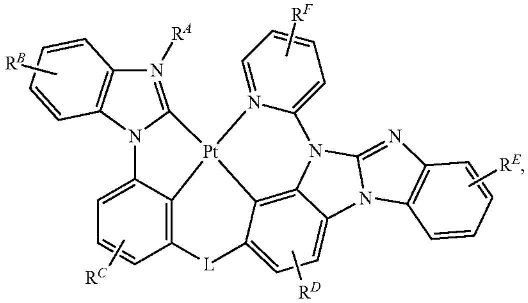

-continued
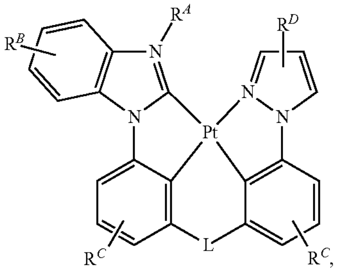
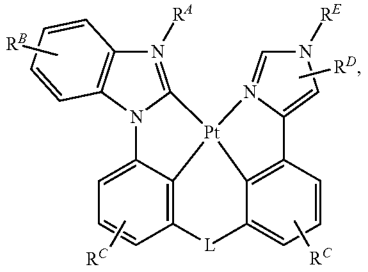
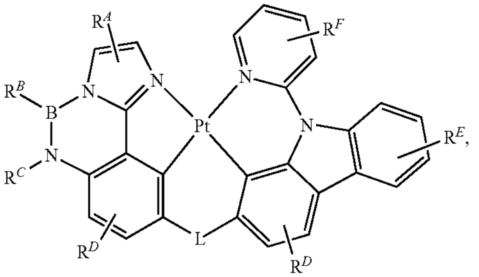
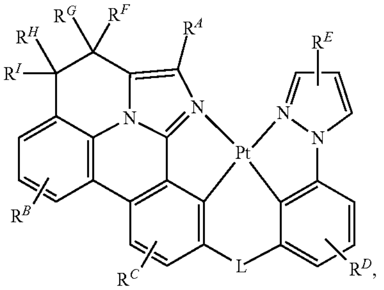
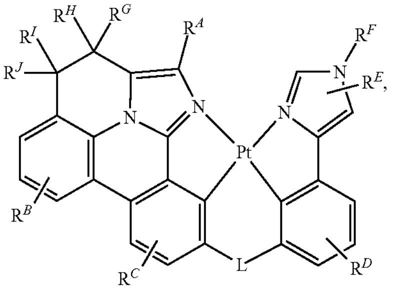
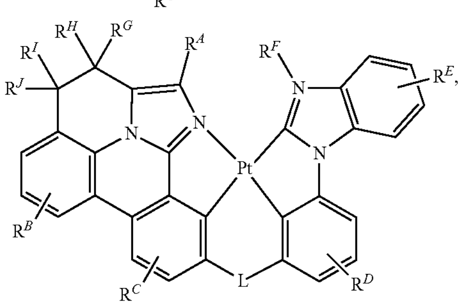
-continued
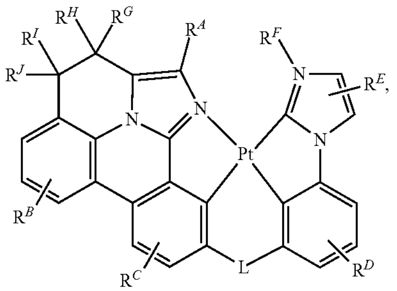
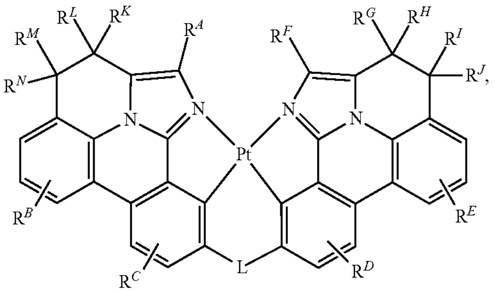
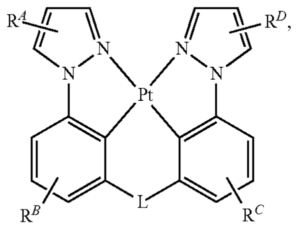
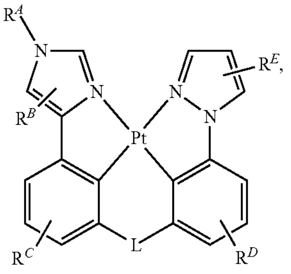
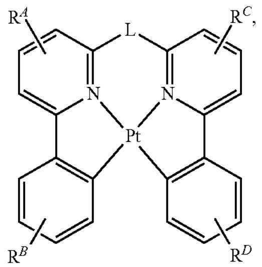
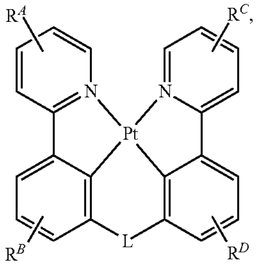
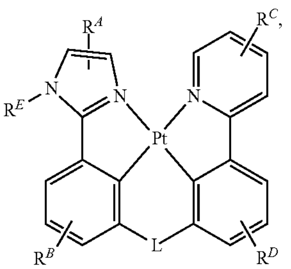
and -continued

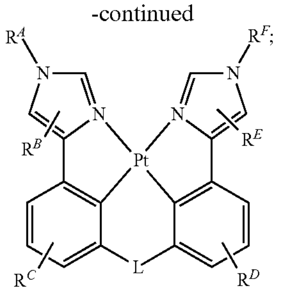

wherein L, for each occurrence, is independently O, S, Se, BR, NR, CRR', SiRR', and GeRR';

wherein each of R, R', $R^A$, $R^B$, $R^C$, $R^D$, $R^E$, $R^F$, $R^G$, $R^H$, $R^I$, $R^J$, $R^K$, $R^L$, $R^M$, and $R^N$ is independently a hydrogen or a substituent selected from the group consisting of deuterium, fluorine, alkyl, cycloalkyl, heteroalkyl, alkoxy, aryloxy, amino, silyl, boryl, alkenyl, cycloalkenyl, heteroalkenyl, aryl, heteroaryl, nitrile, isonitrile, sulfanyl, and combinations thereof.

8. The OLED of claim 1, wherein each R, R', $R^1$, $R^2$, and $R^3$ is independently a hydrogen or a substituent selected from the group consisting of deuterium, fluorine, alkyl, cycloalkyl, heteroalkyl, alkoxy, aryloxy, amino, silyl, alkenyl, cycloalkenyl, heteroalkenyl, aryl, heteroaryl, nitrile, isonitrile, sulfanyl, and combinations thereof.

9. The OLED of claim 1, wherein $L^1$ is not present.

10. The OLED of claim 1, wherein $L^2$ and $L^3$ are each O.

11. The OLED of claim 1, wherein $L^2$ and $L^3$ are each NR.

12. The OLED of claim 1, wherein one of $L^2$ and $L^3$ is O, and the other is NR.

13. The OLED of claim 1, wherein R is a 6-membered aromatic ring.

14. The OLED of claim 1, wherein at least one of $R^1$, $R^2$, and $R^3$ comprises a chemical group selected from the group consisting of carbazole, dibenzofuran, dibenzothiophene, tetraphenylene, triazine, pyrimidine, pyridine, tetraphenylene, 512-enzo[d]benzo[4,5]imidazo[3,2-a]imidazole, benzo[d]benzo[4,5]imidazo[2,1-b]oxazole, benzo[d]benzo[4,5]imidazo[2,1-b]thiazole, 5H-612-indolo[2,3-b]indole, 6H-benzofuro[2,3-b]indole, 6H-benzo[4,5]thieno[2,3-b]indole, and aza variants thereof.

15. The OLED of claim 1, wherein the first compound comprises a structure from the group consisting of:

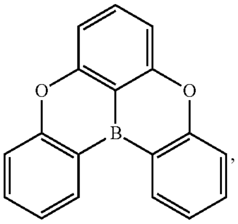
,
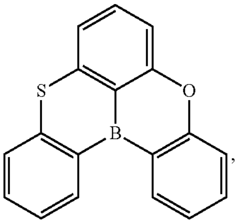
,
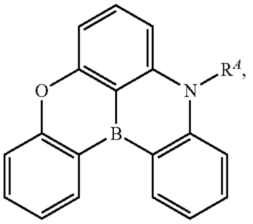

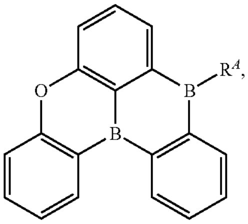

-continued

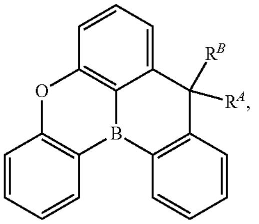

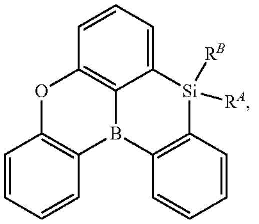

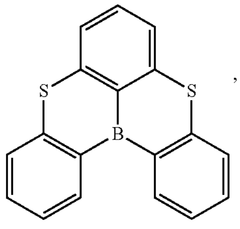
,
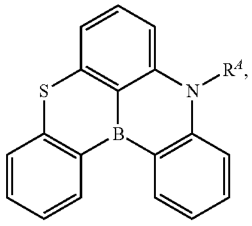

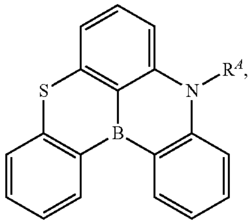

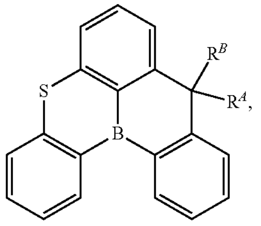

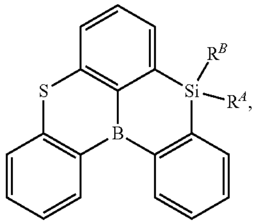

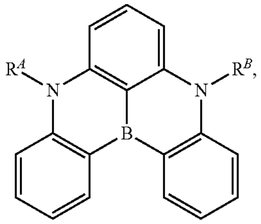

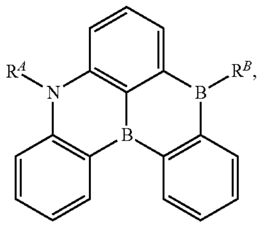

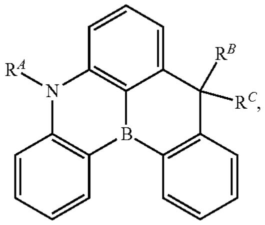

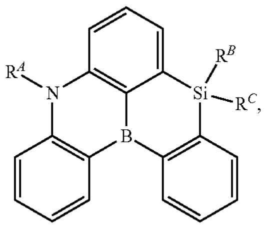

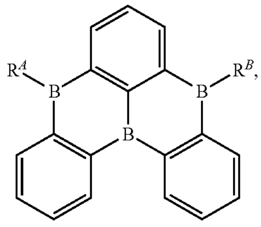

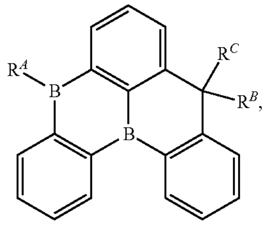

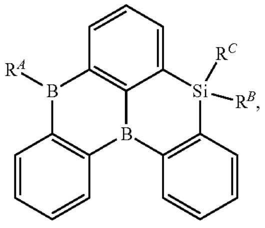

-continued
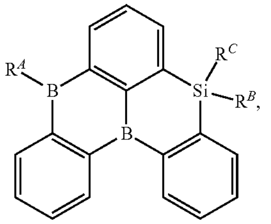
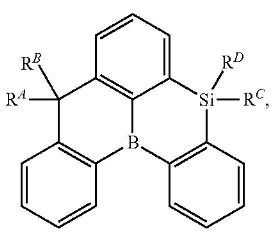
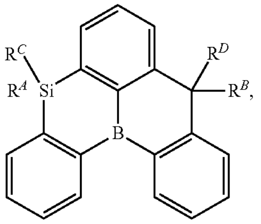
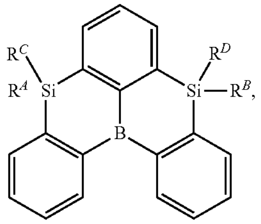
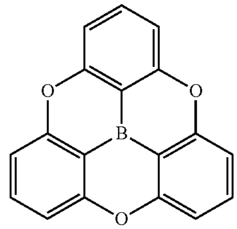
,
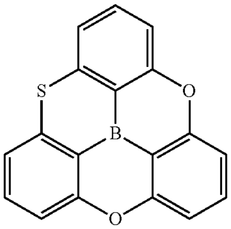
,
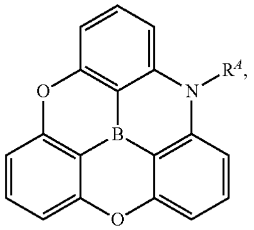
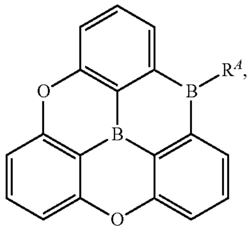
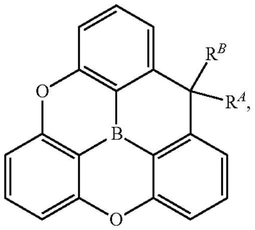
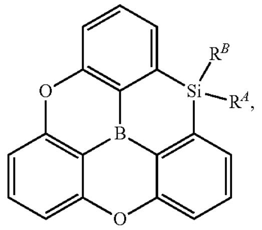
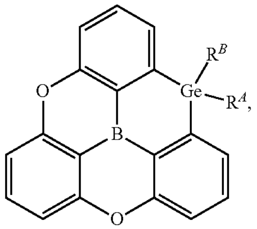
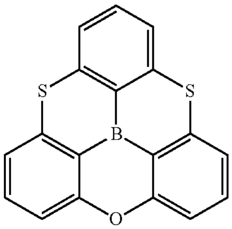
,
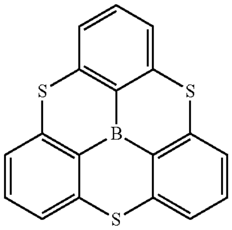
,
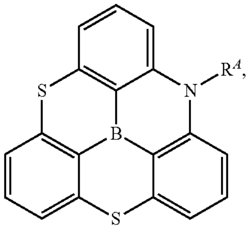
-continued
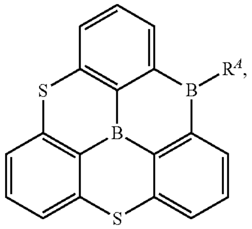
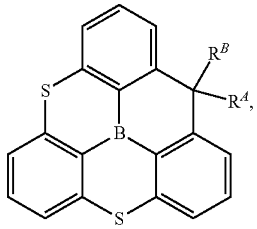
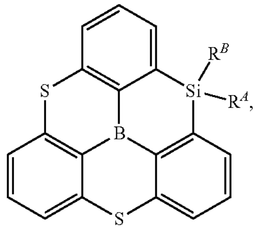
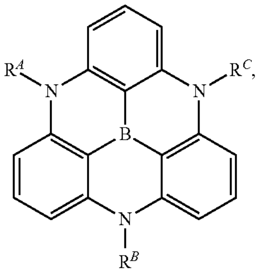
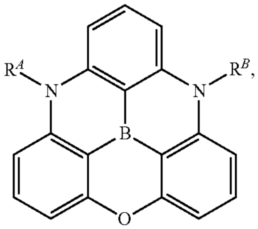
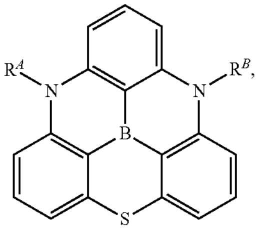
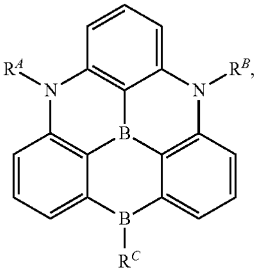
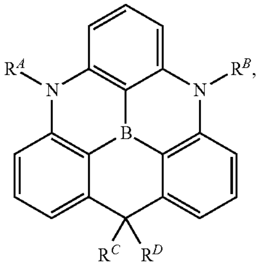
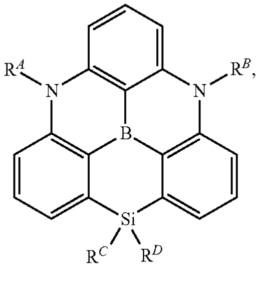
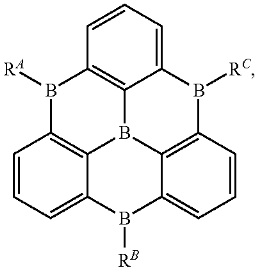
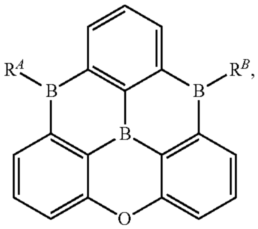
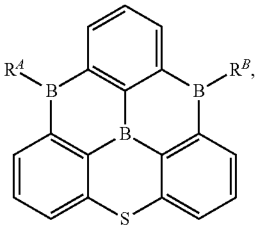

-continued
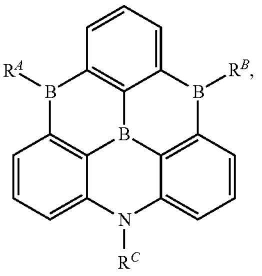
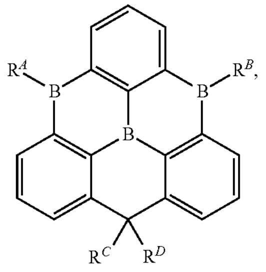
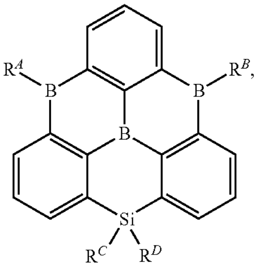
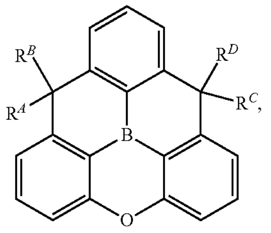
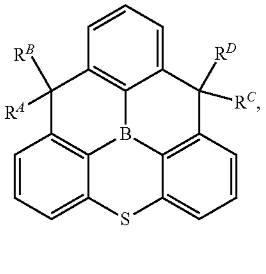
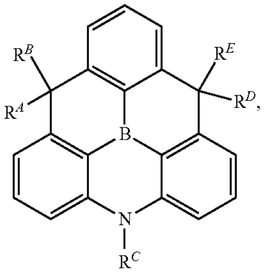
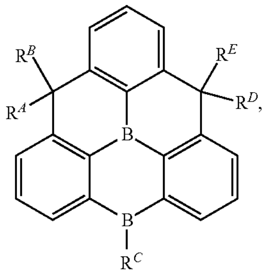
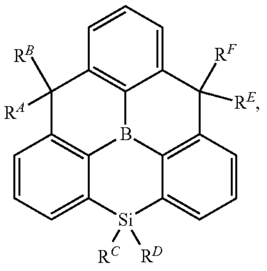
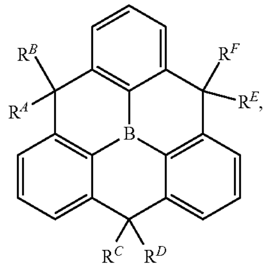
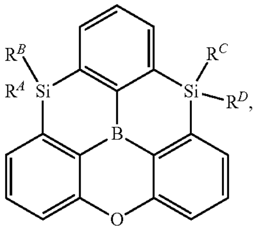
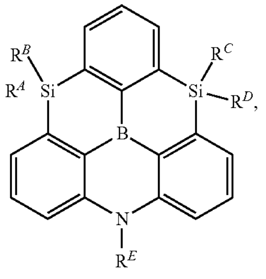
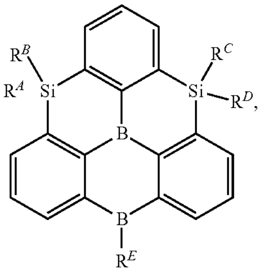
-continued
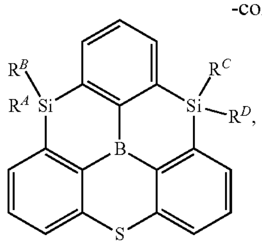
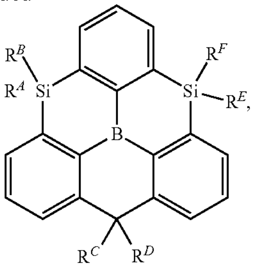
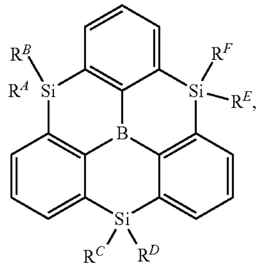
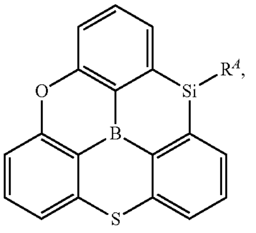
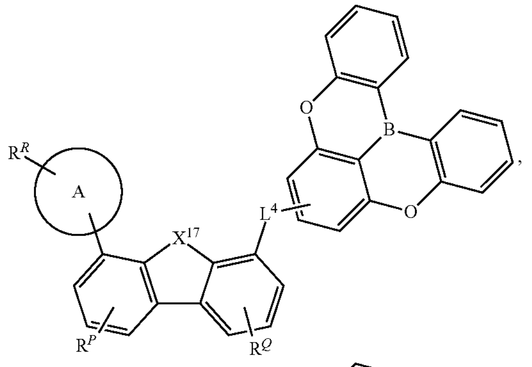
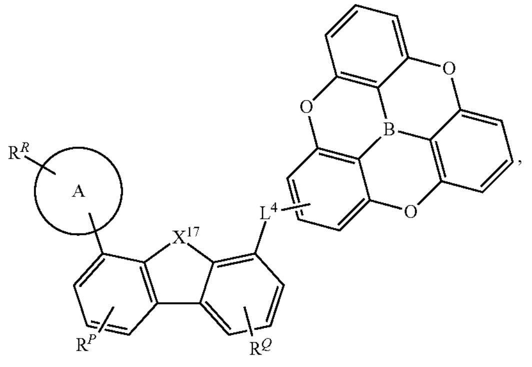
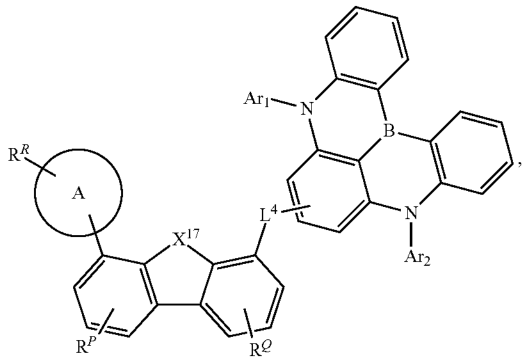

-continued
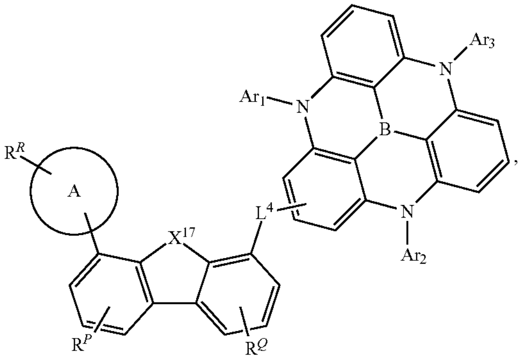
,
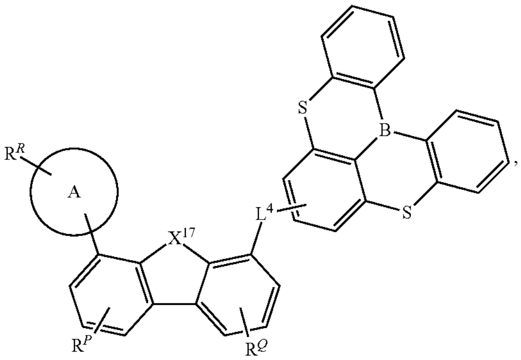
,
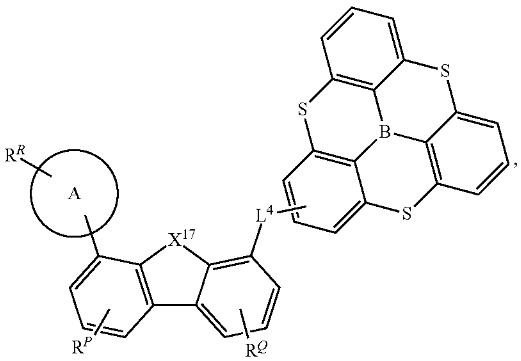
,
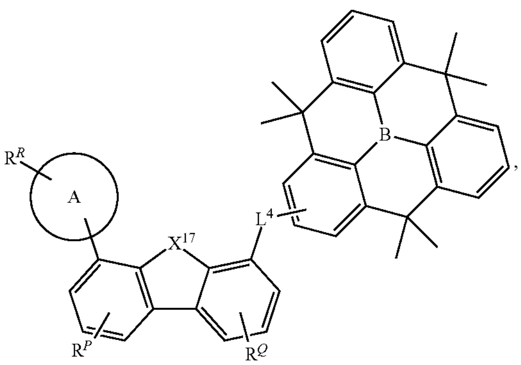
,
-continued
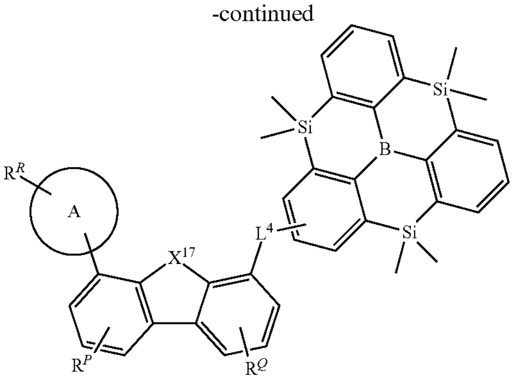
,
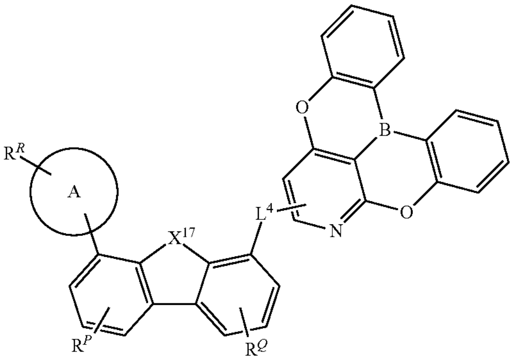
,
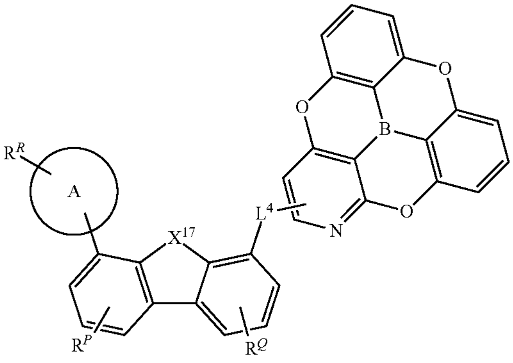
,
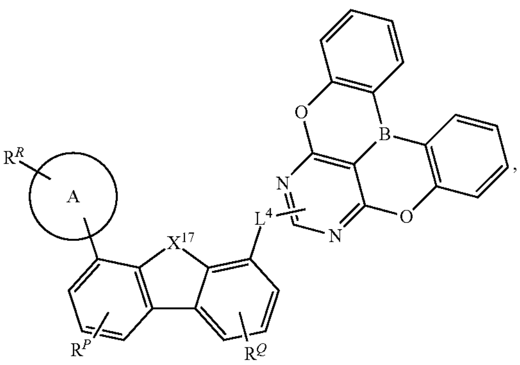
, and -continued

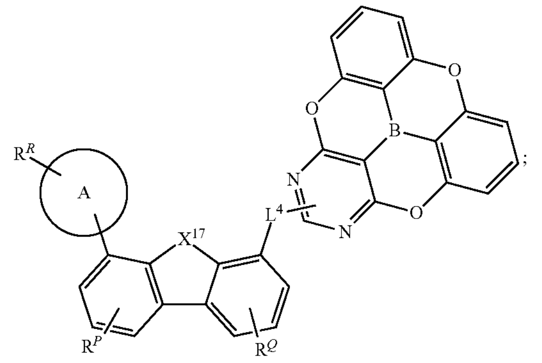

ring A and D are each independently a monocyclic or multicyclic ring system comprising one or more fused 5-membered or 6-membered carbocyclic or heterocyclic rings;

$L^4$ is a direct bond or an aromatic group comprising one or more fused or unfused aromatic rings which can be further substituted;

wherein $X^{17}$ is selected from the group consisting of O, S, Se, and $NR^4$;

wherein each of $R^F$, $R^P$, $R^Q$, and $R^R$ is independently represent zero, mono, or up to a maximum allowed substitution to its associated ring;

wherein each $R^4$, $R^A$, $R^B$, $R^C$, $R^D$, $R^E$, $R^F$, $R^P$, $R^Q$, and $R^R$ is independently a hydrogen or a substituent selected from the group consisting of deuterium, fluorine, alkyl, cycloalkyl, heteroalkyl, alkoxy, aryloxy, amino, silyl, boryl, alkenyl, cycloalkenyl, heteroalkenyl, aryl, heteroaryl, nitrile, isonitrile, sulfanyl, and combinations thereof.

16. The OLED of claim 1, wherein the first compound is selected from the group consisting of

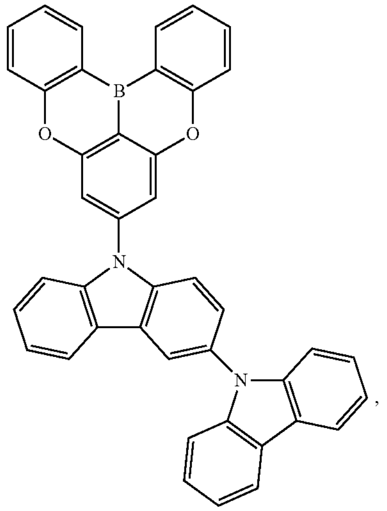

-continued

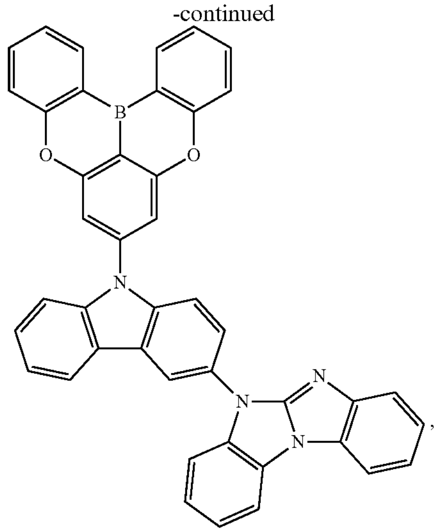

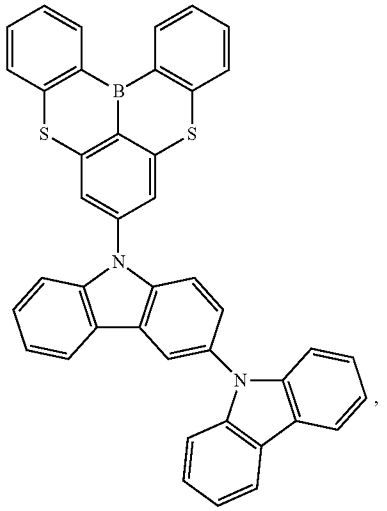

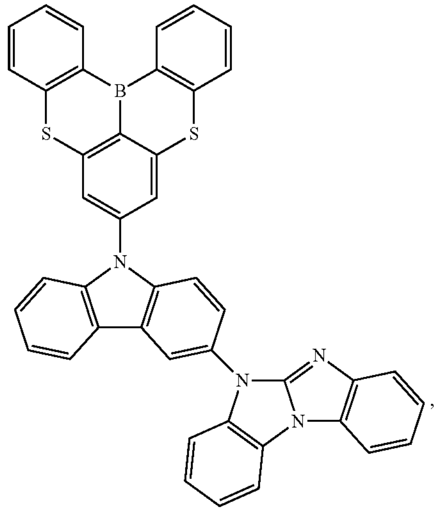

-continued
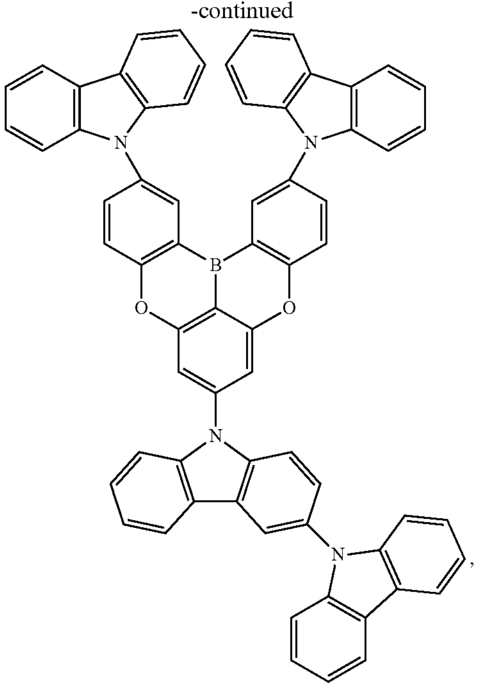
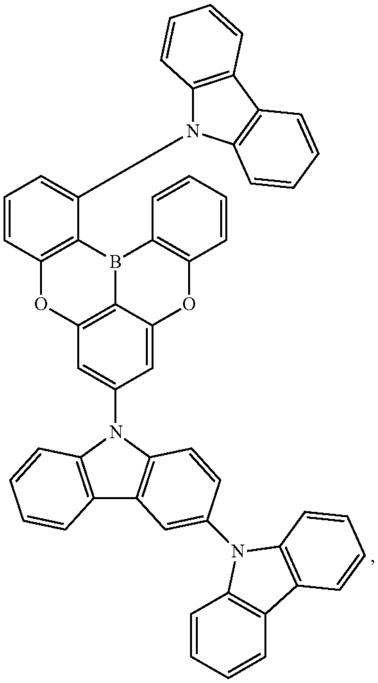
-continued
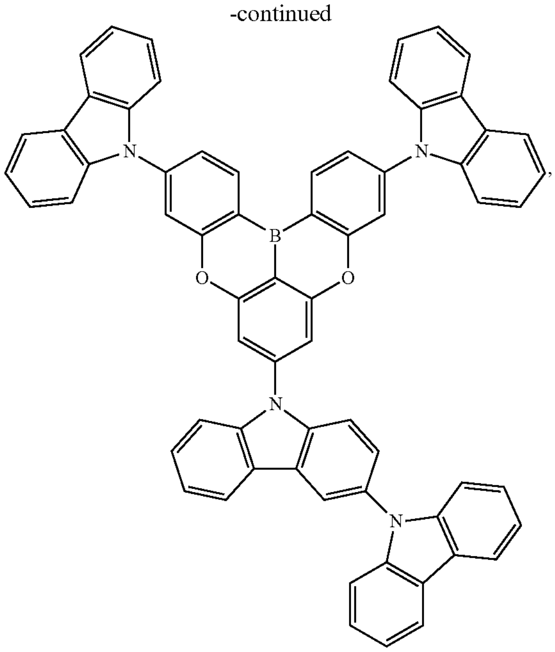
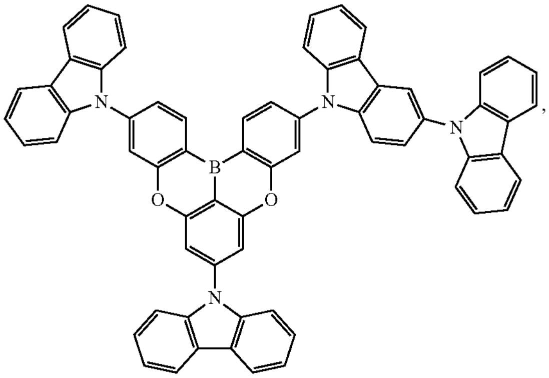
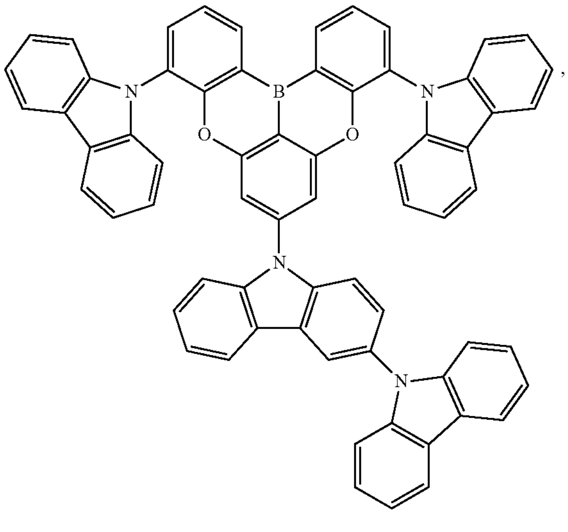

-continued
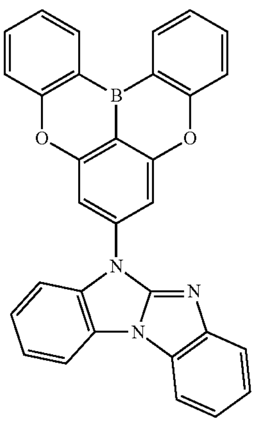
,
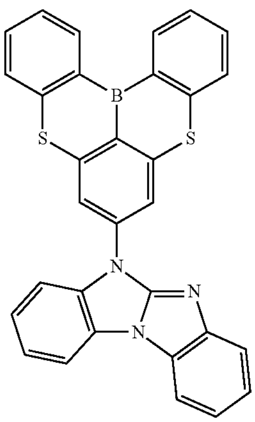
,
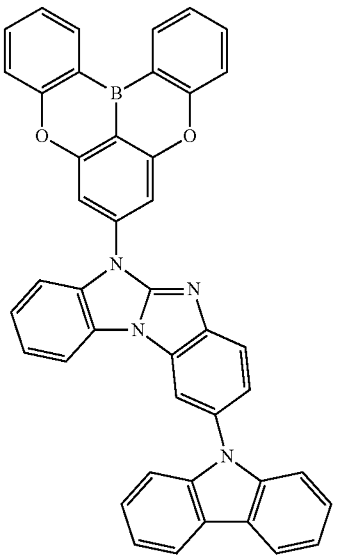
,
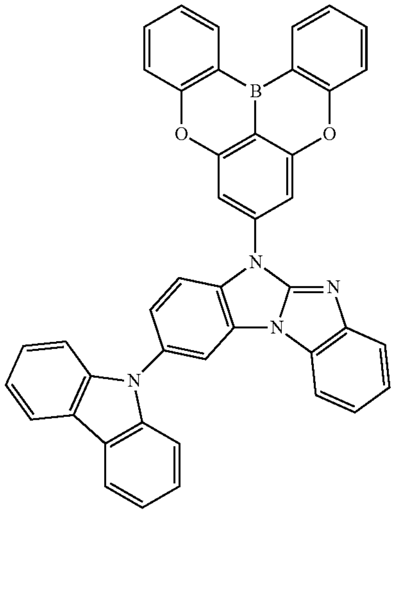
,
-continued
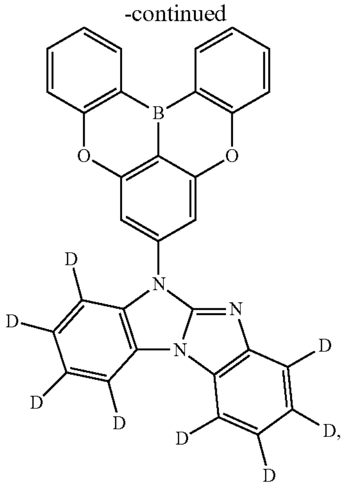
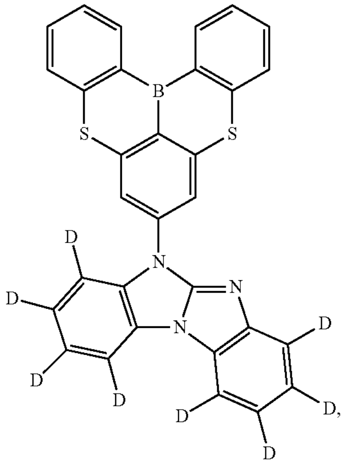
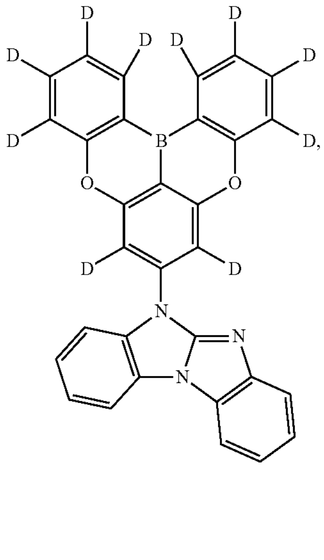

-continued
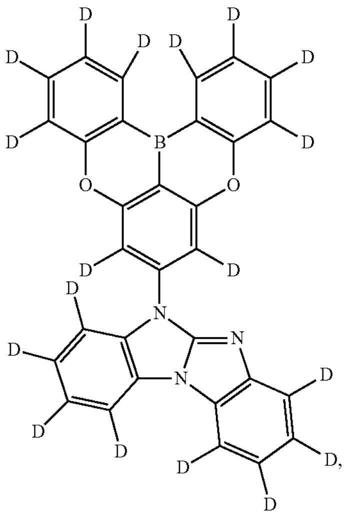
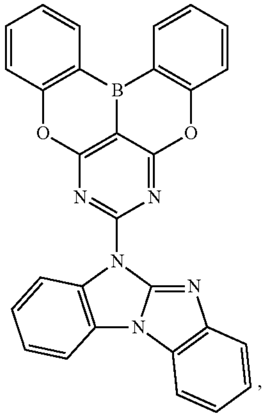
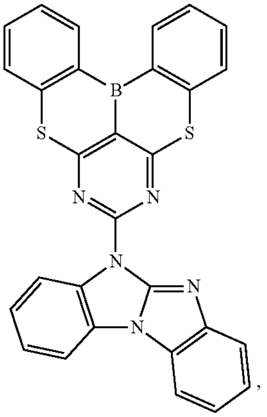
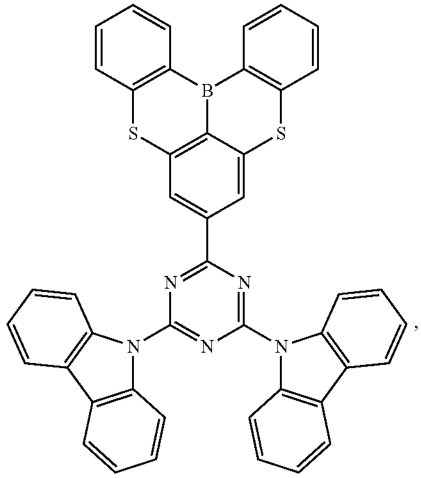
-continued
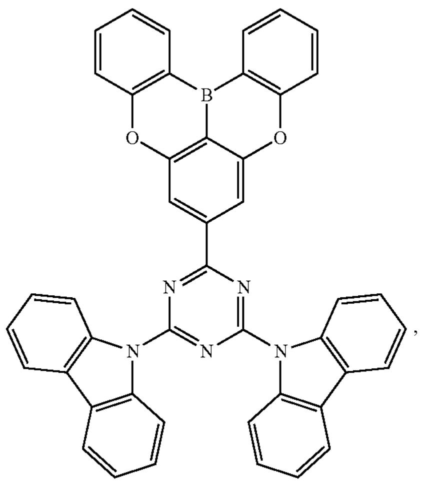
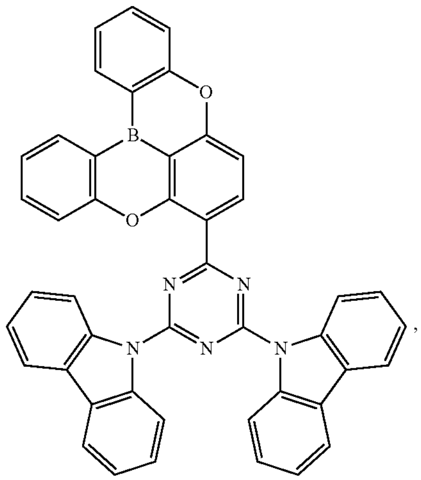
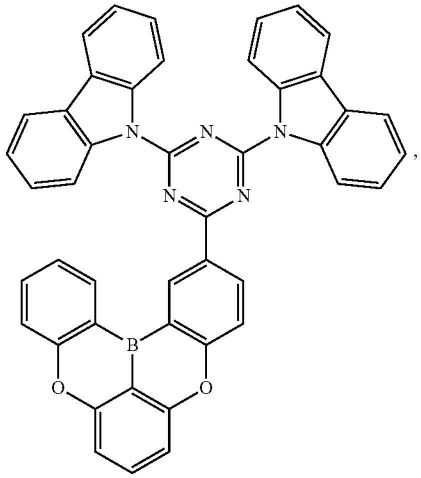

-continued
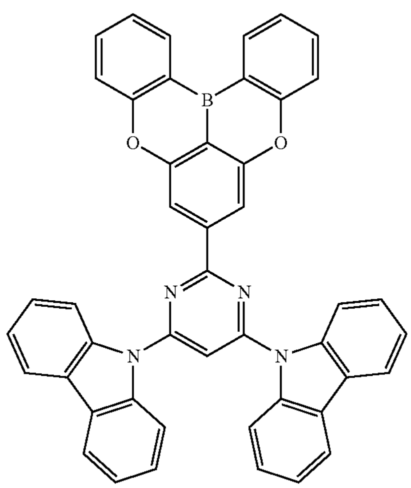,
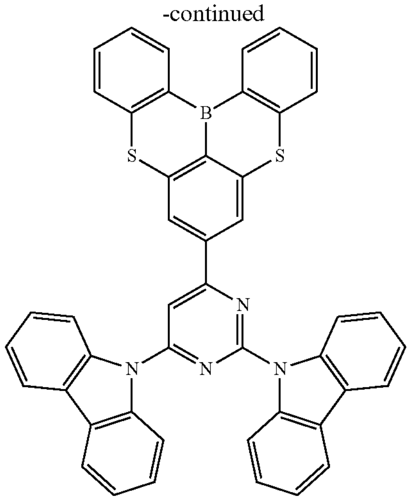,
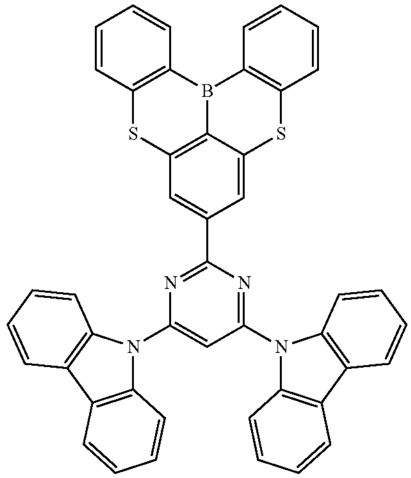,
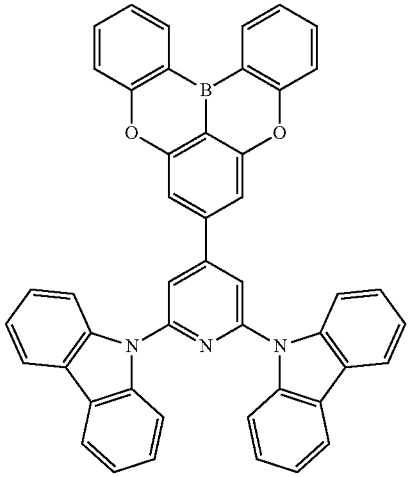,
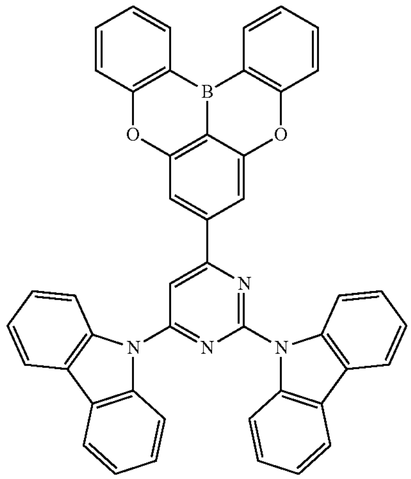,
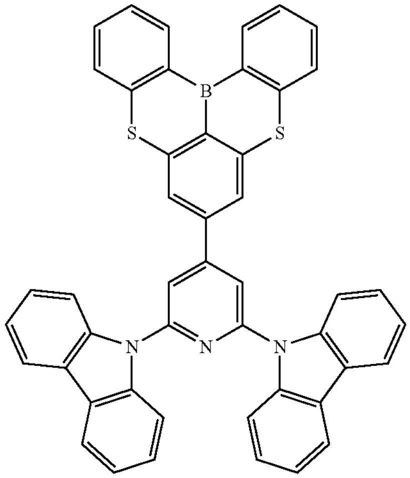, -continued
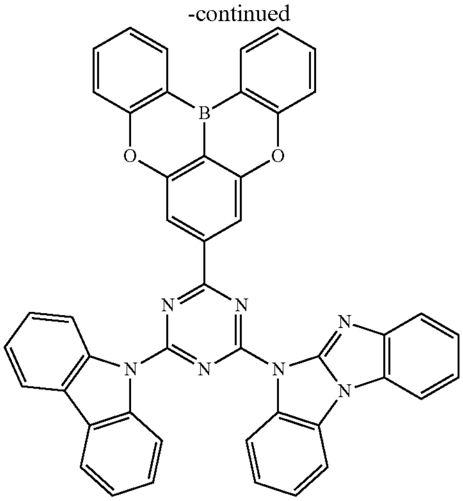
,
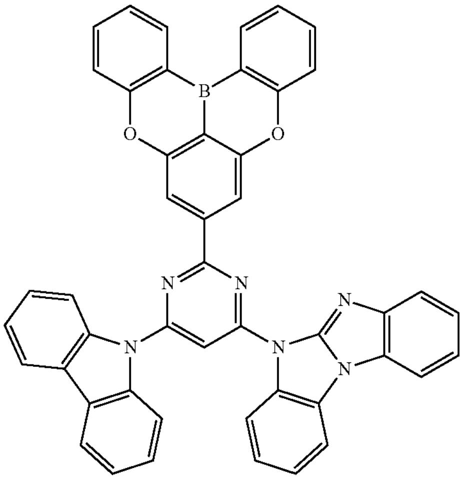
,
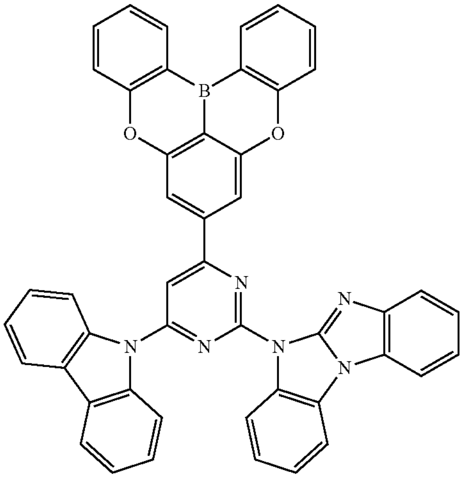
,
-continued
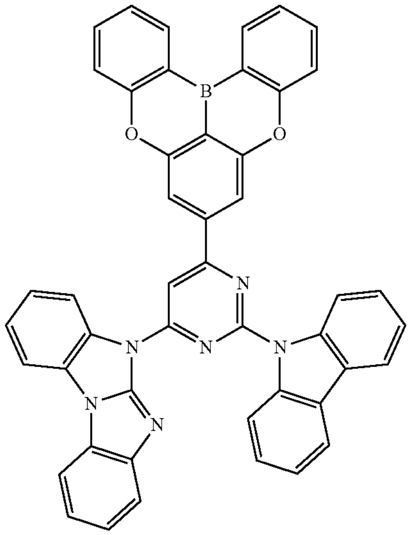
,
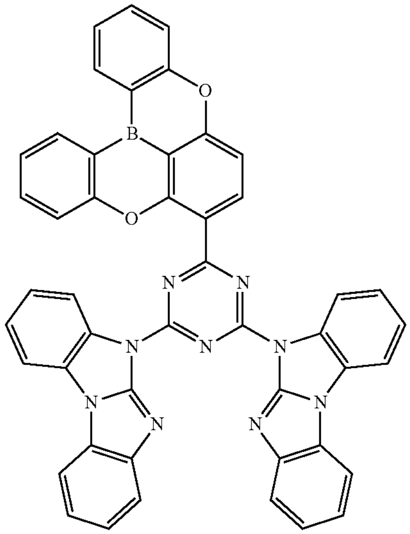
,
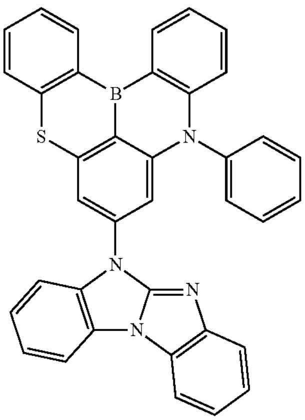
, -continued
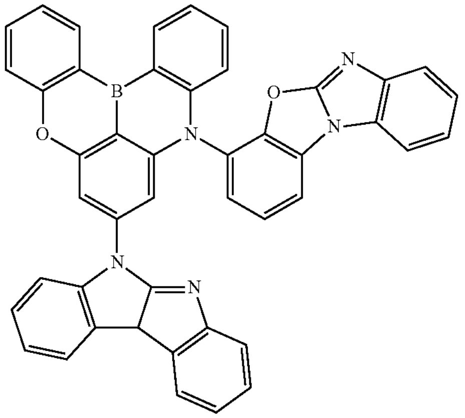
,
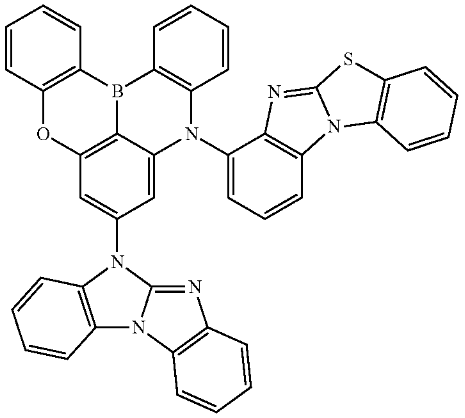
,
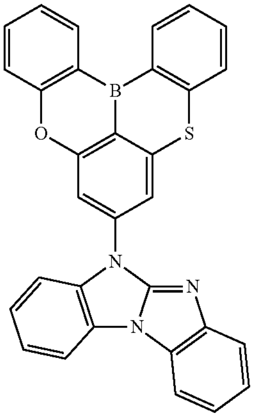
,
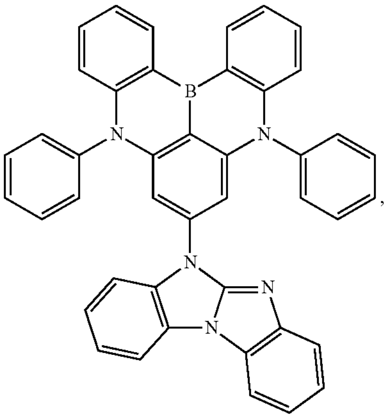
,
-continued
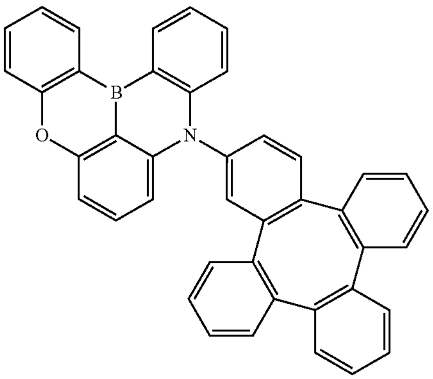
,
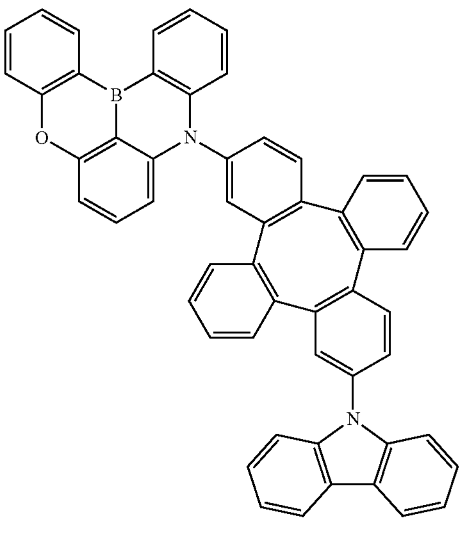
,
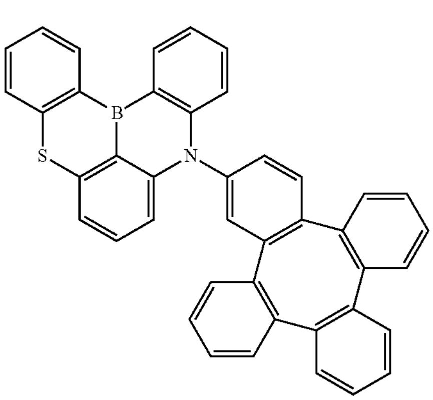
, -continued
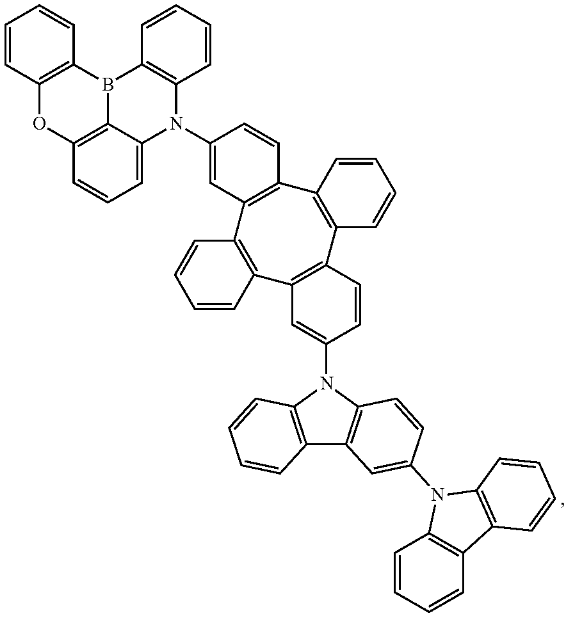
,
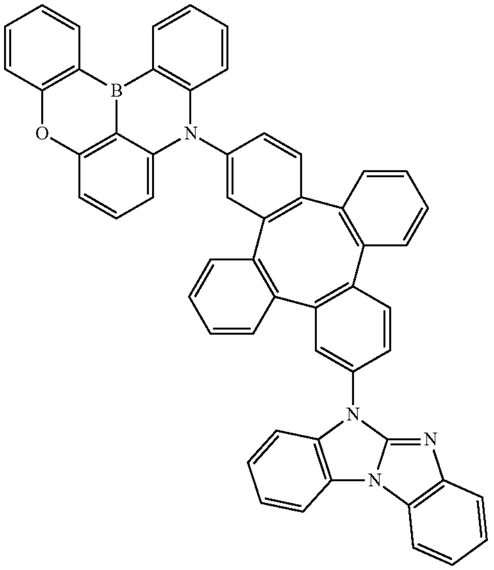
,
-continued
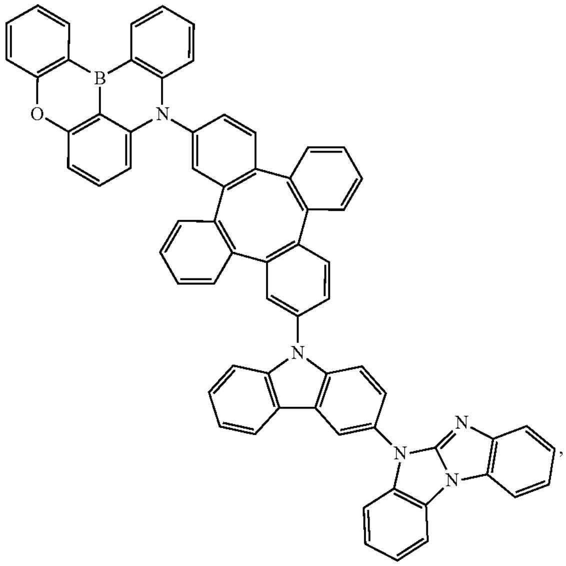
,
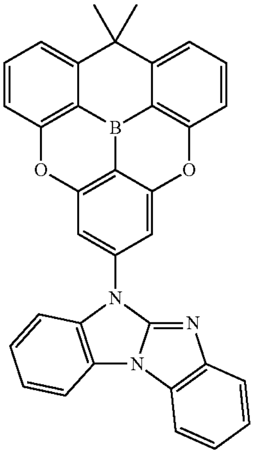
,
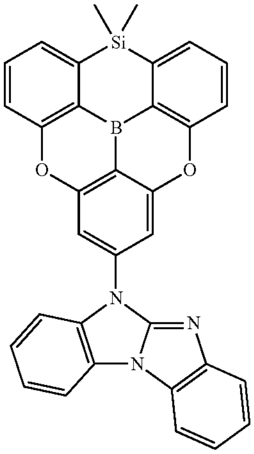
,
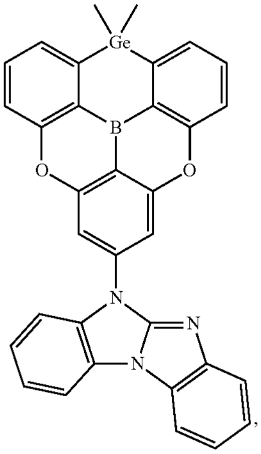
,
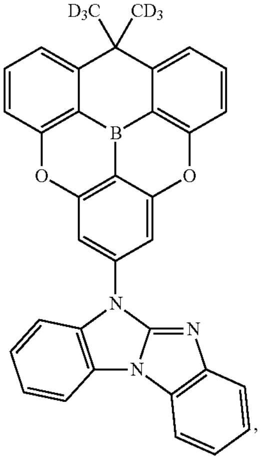
, -continued
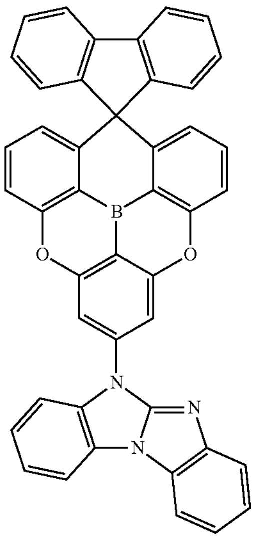
,
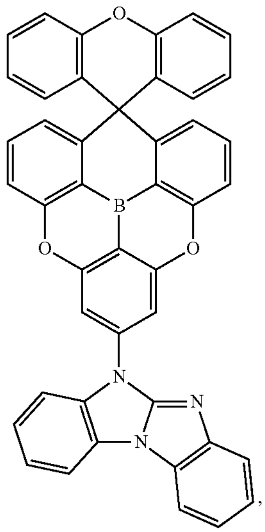
,
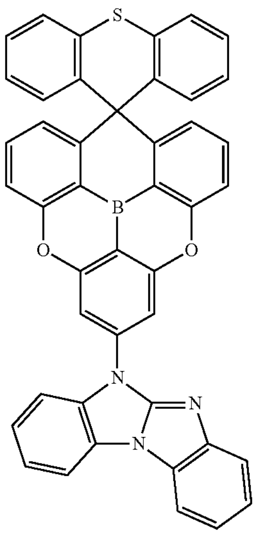
,
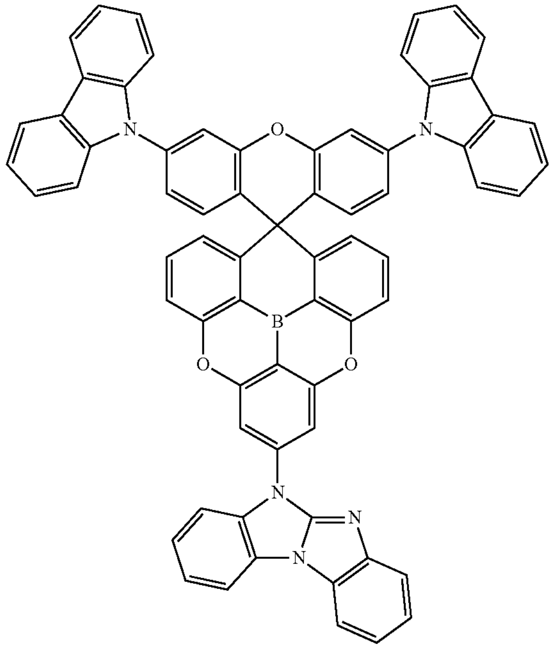
,
-continued
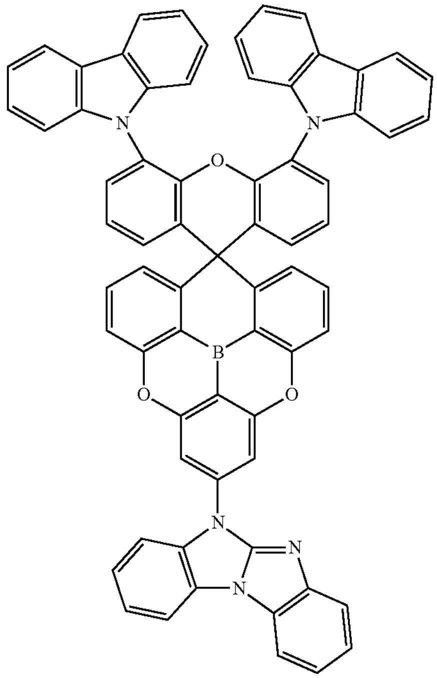
,
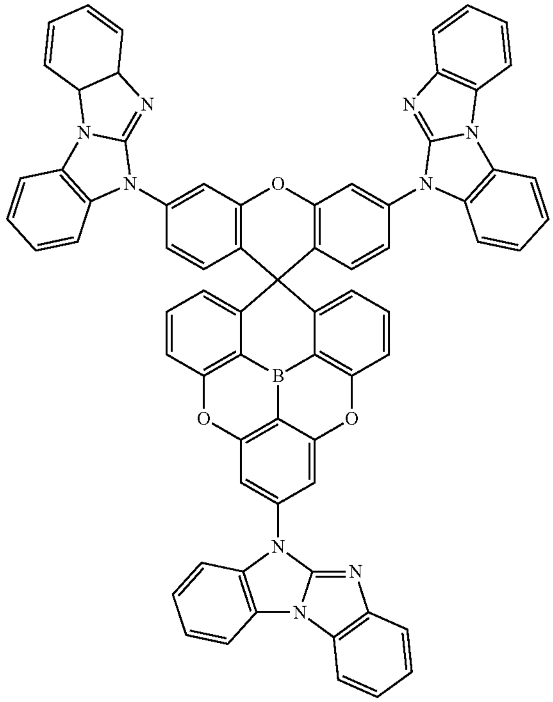
, -continued
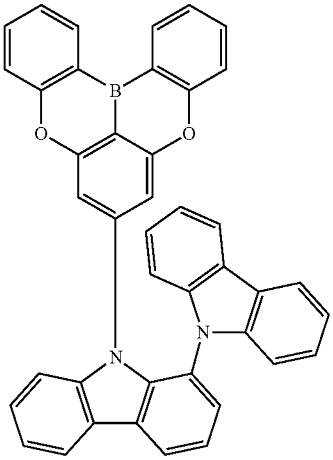
,
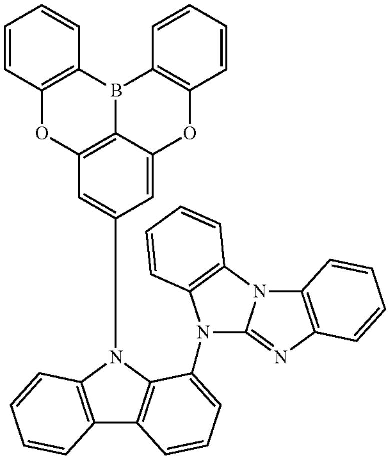
,
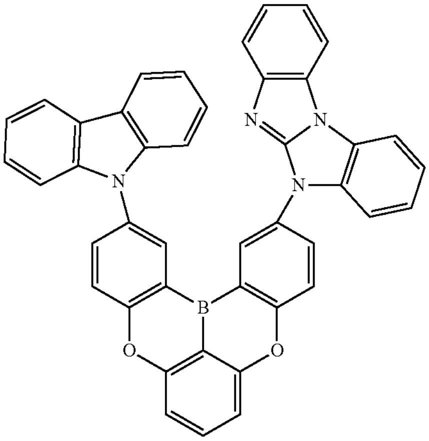
,
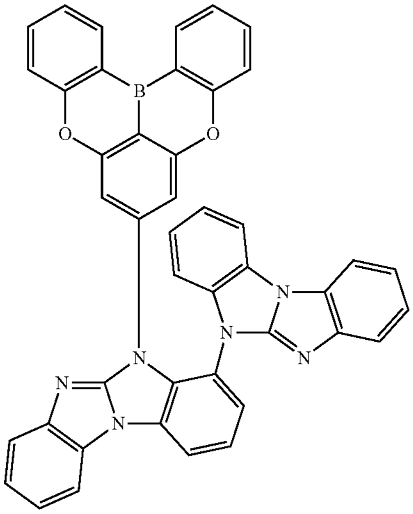
,
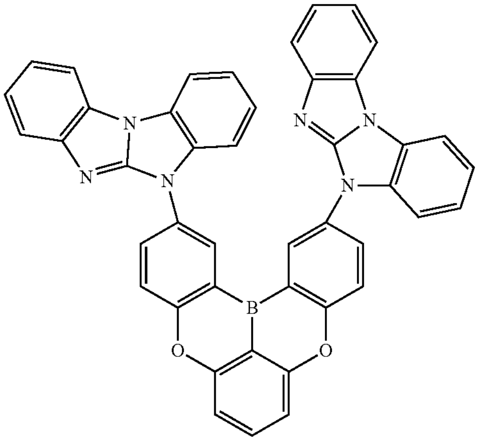
,
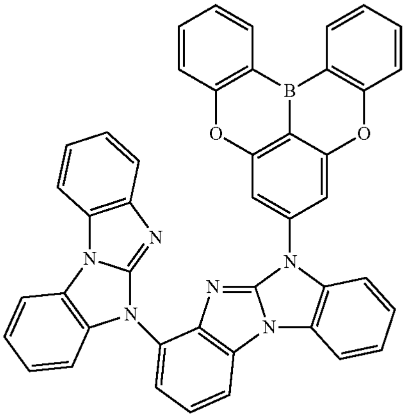
, -continued
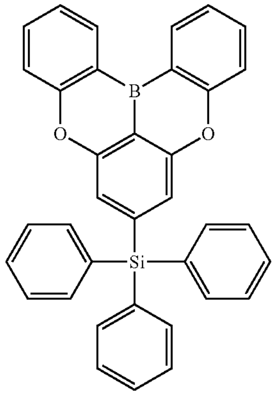
,
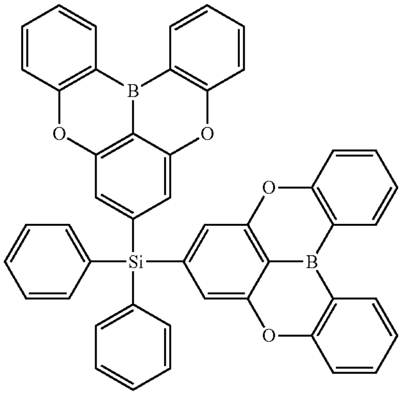
,
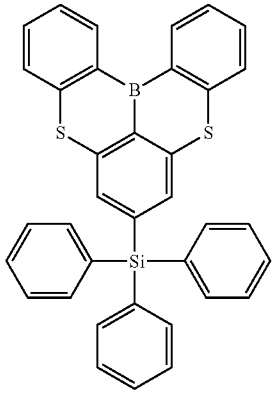
,
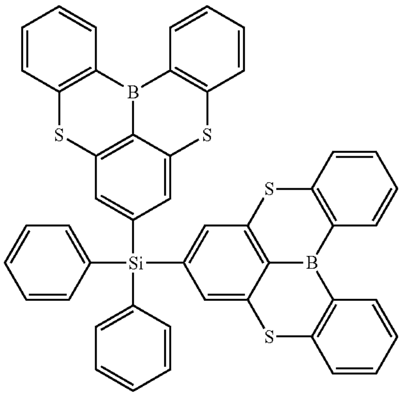
,
-continued
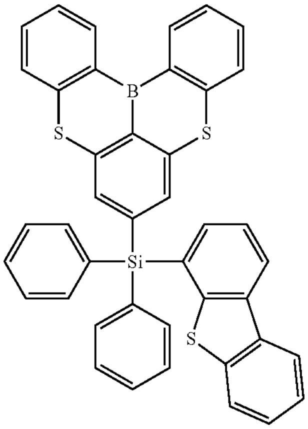
,
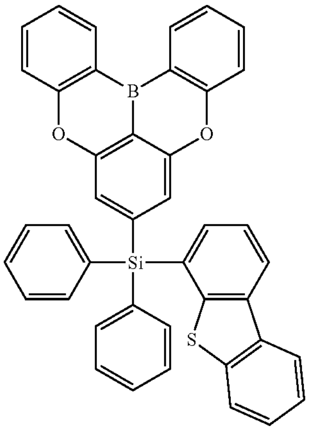
,
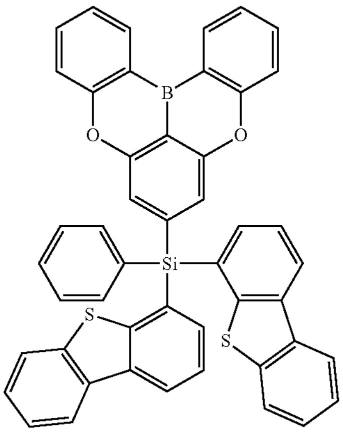
, -continued
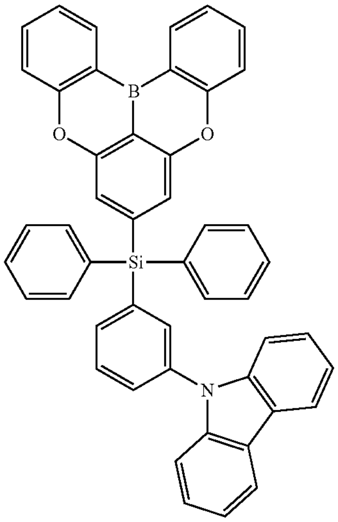
,
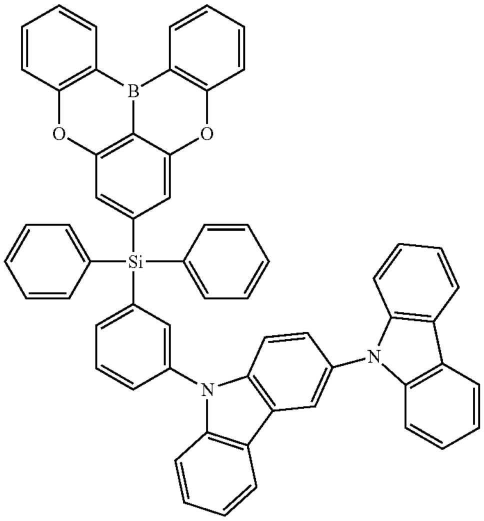
,
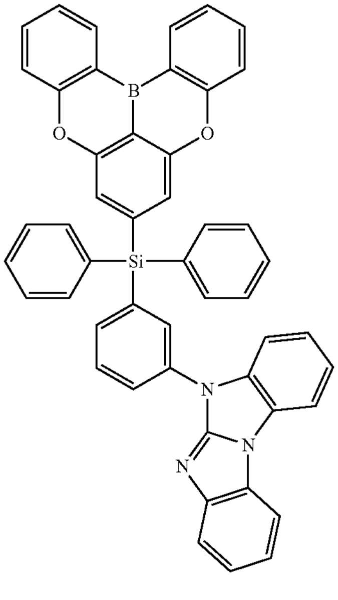
,
-continued
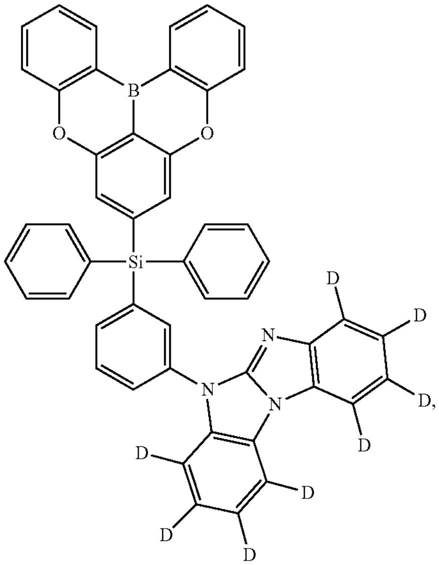
,
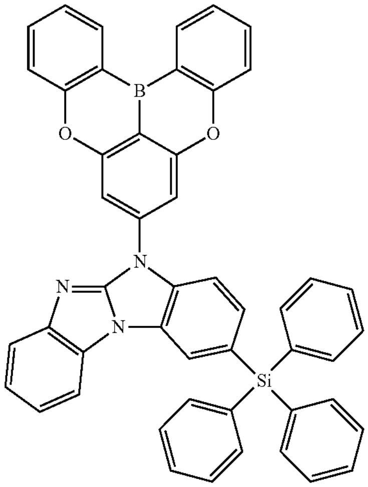
,
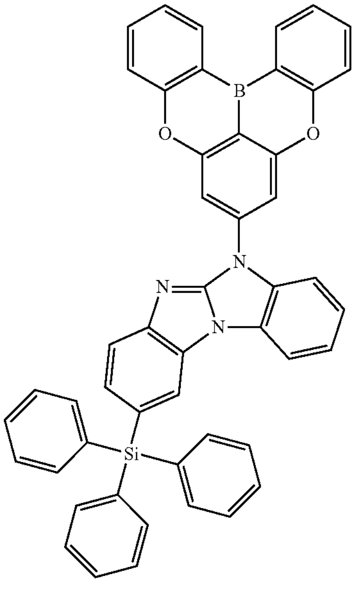
, -continued
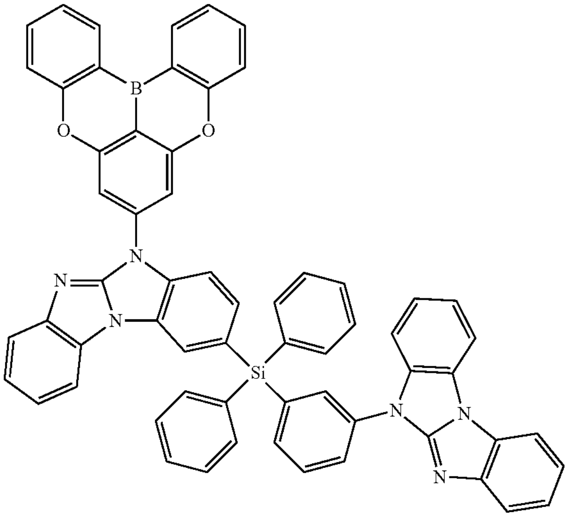
,
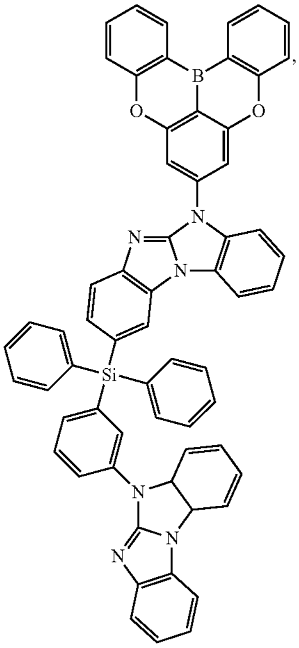
,
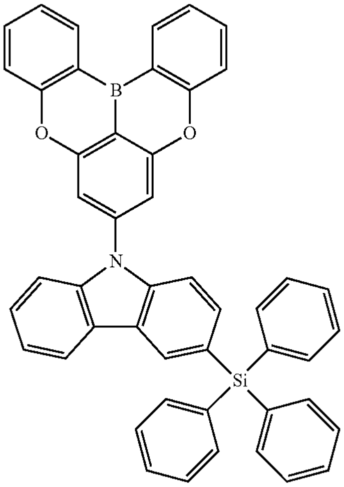
,
-continued
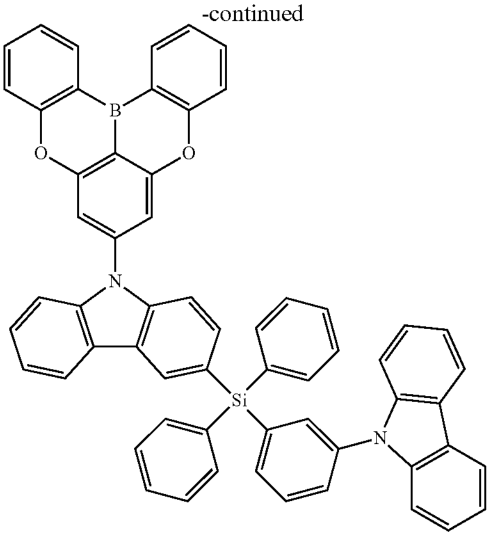
,
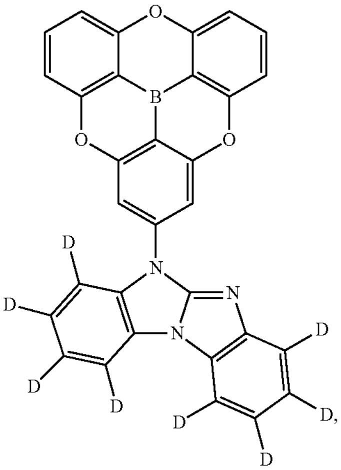
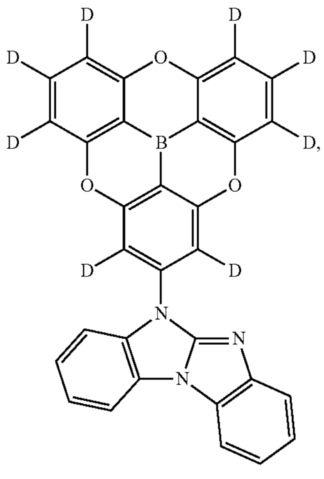

-continued
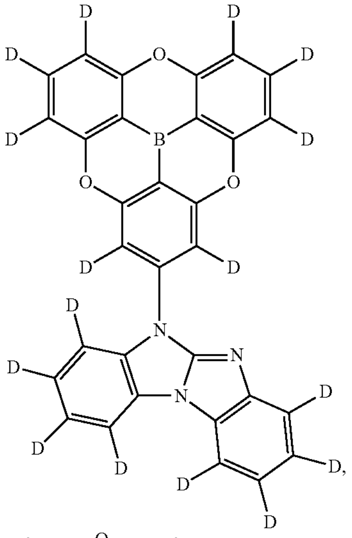
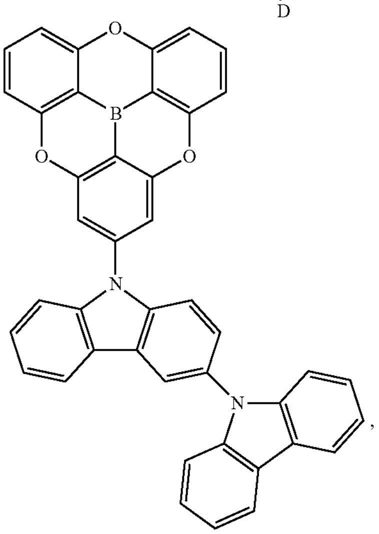
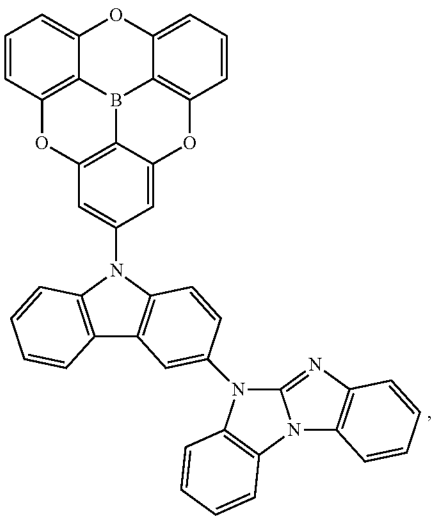
-continued
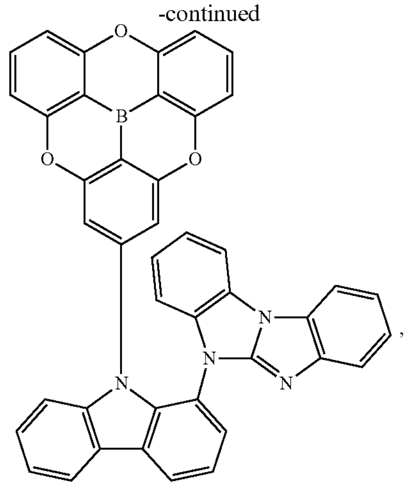
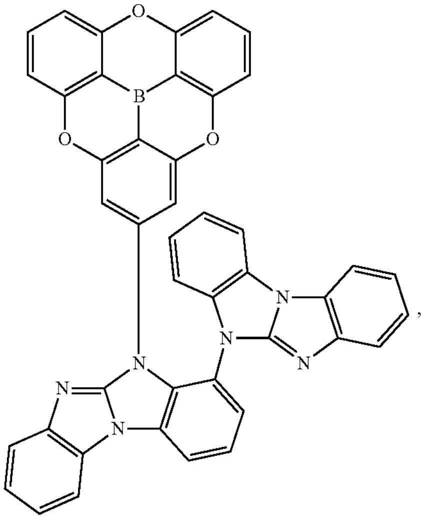
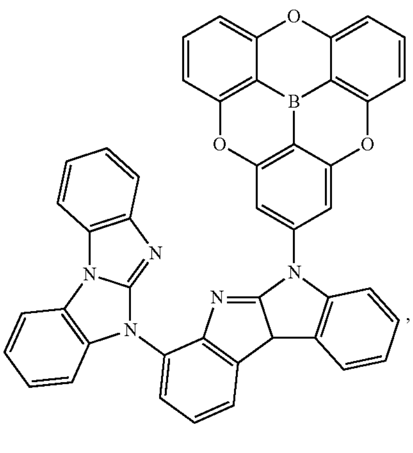

-continued
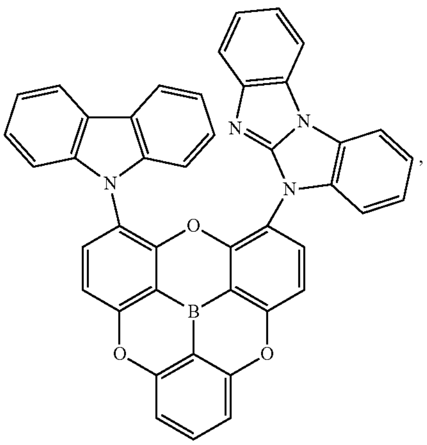
,
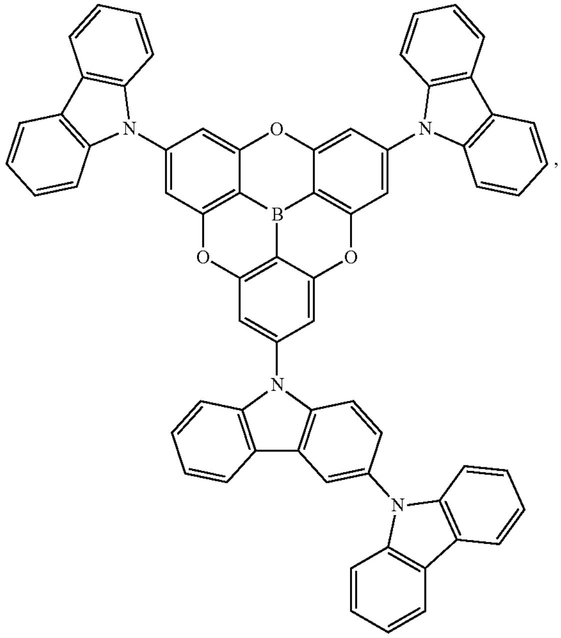
,
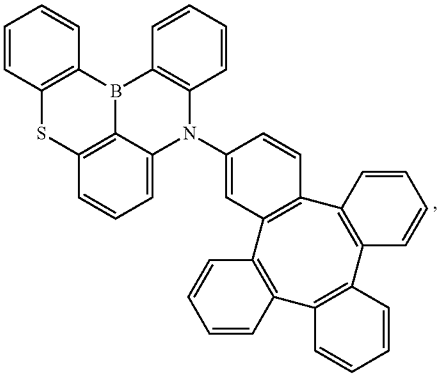
,
-continued
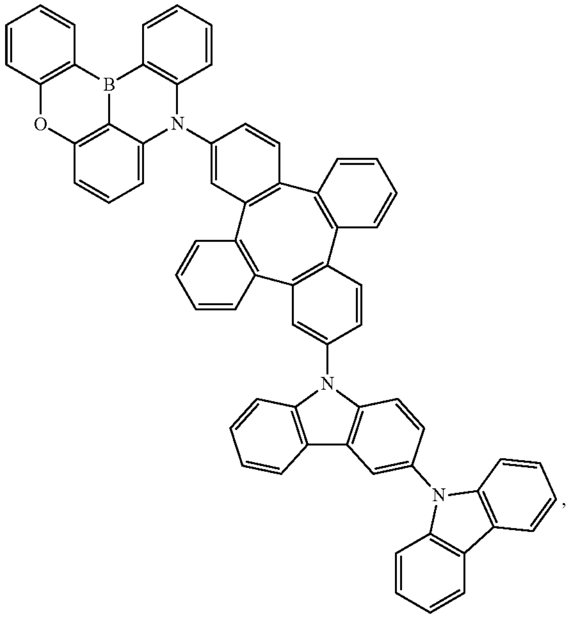
,
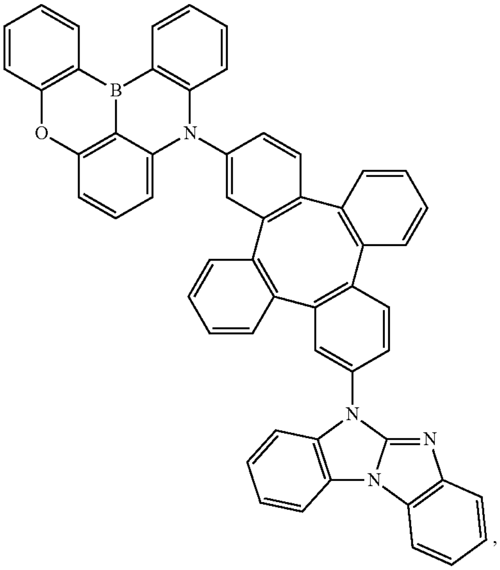
, -continued
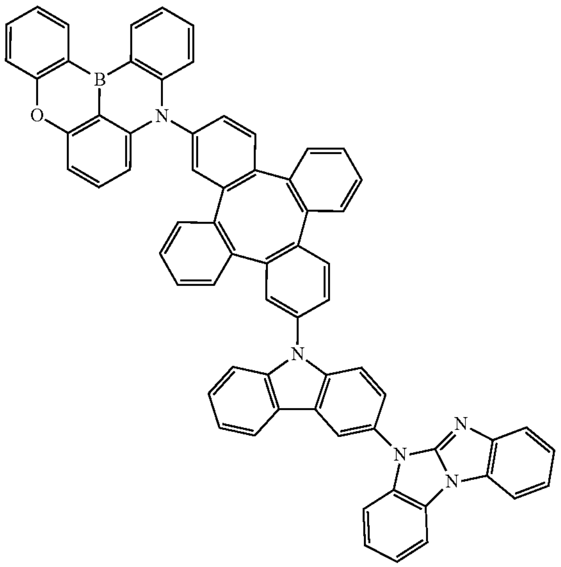
,
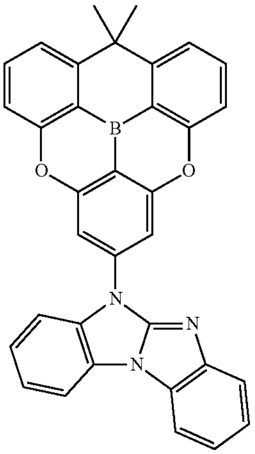
,
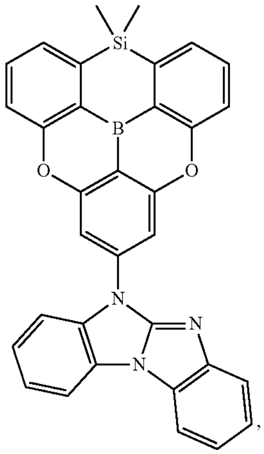
,
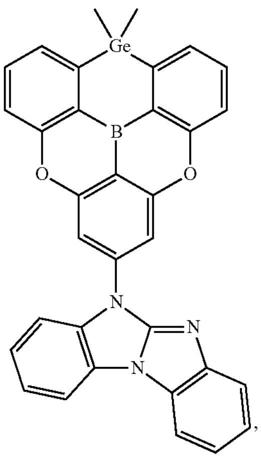
,
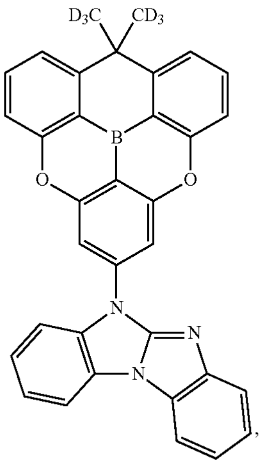
,
-continued
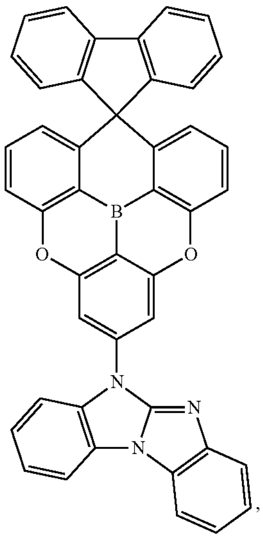
,
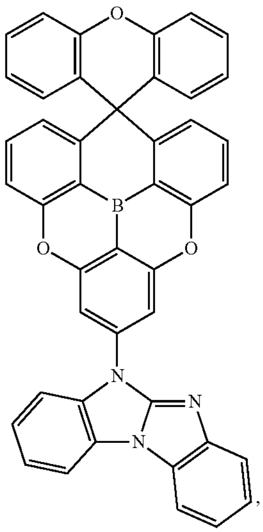
,
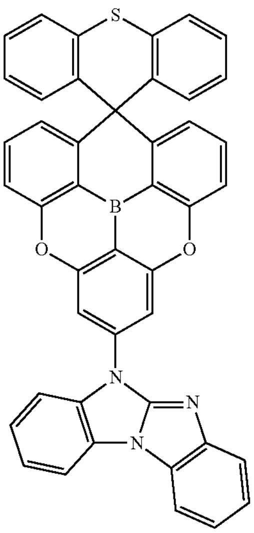
,
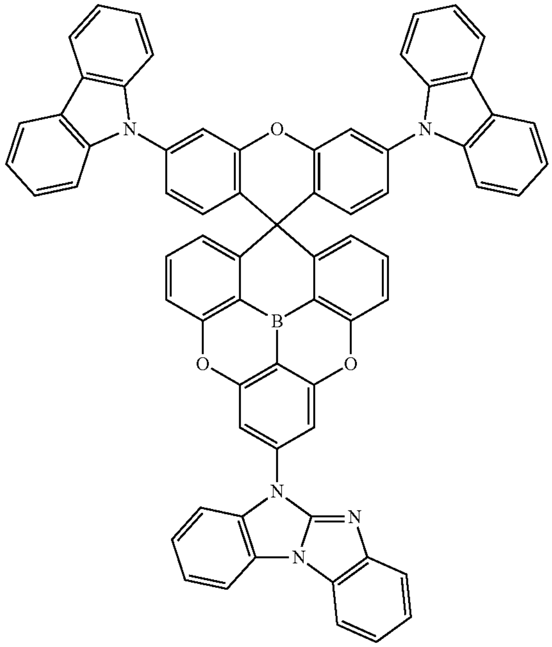
, -continued
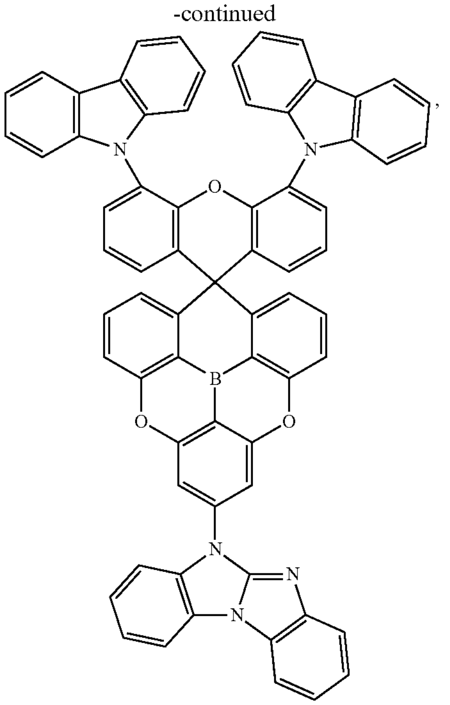
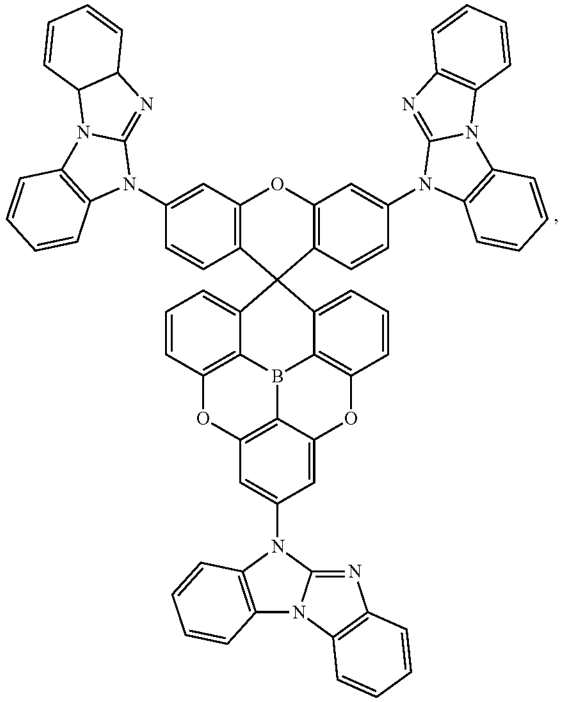
-continued
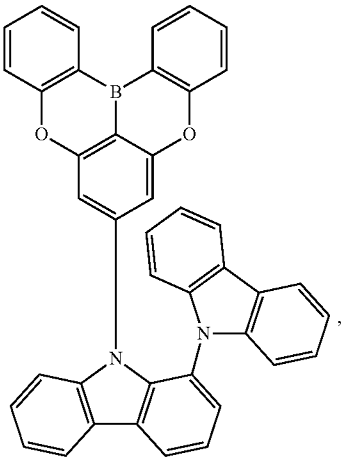
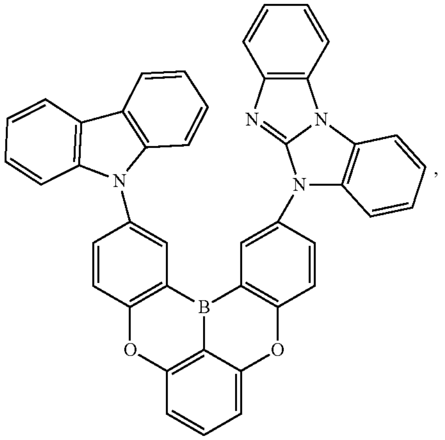
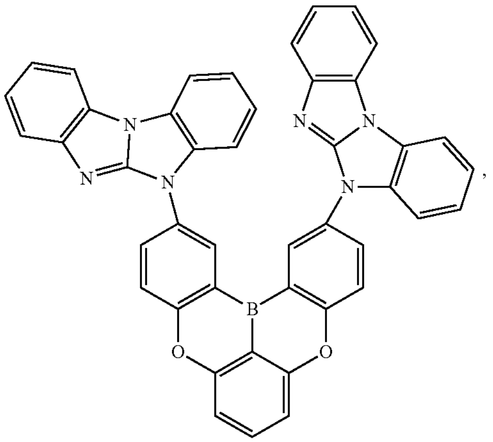

-continued
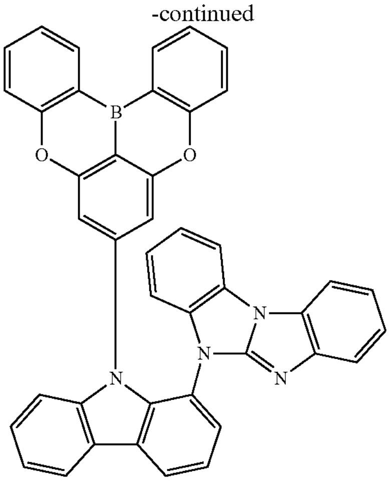
,
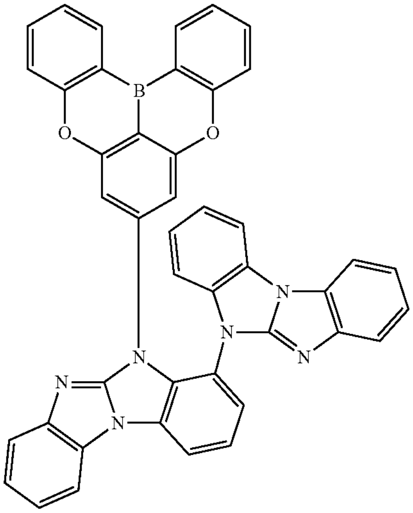
,
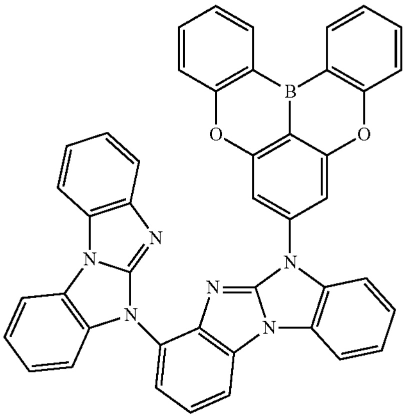
,
-continued
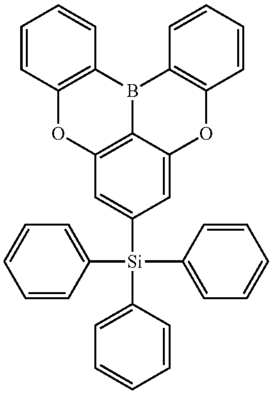
,
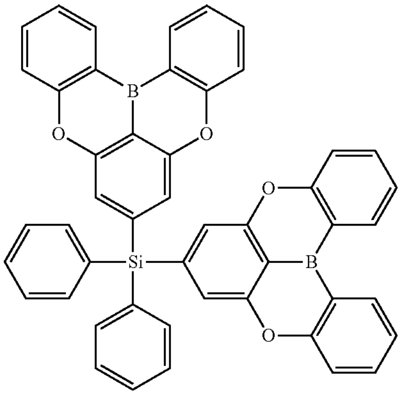
,
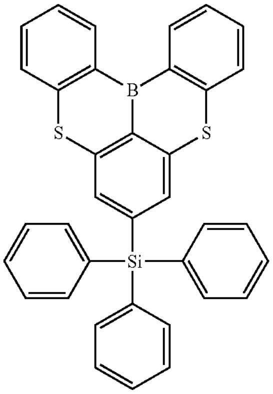
,
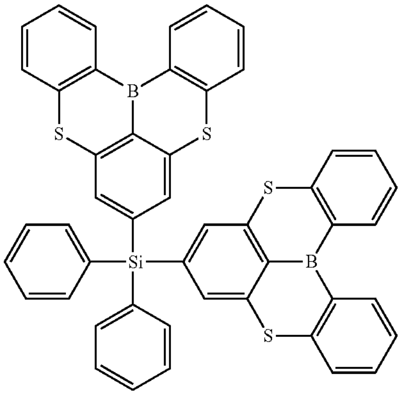
, -continued
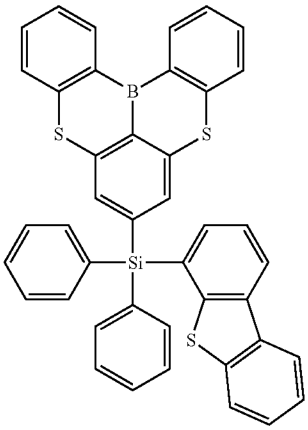
,
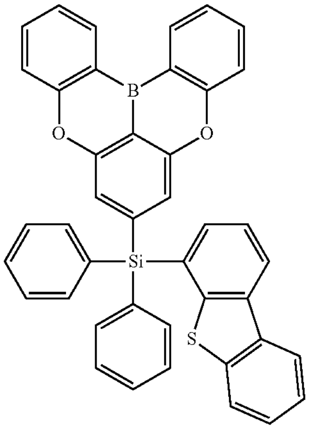
,
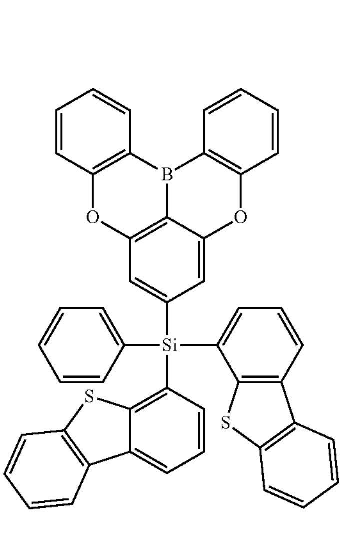
,
-continued
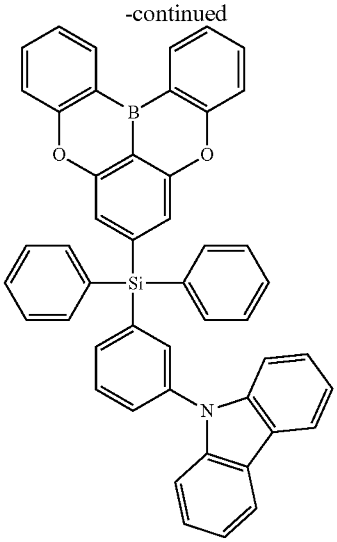
,
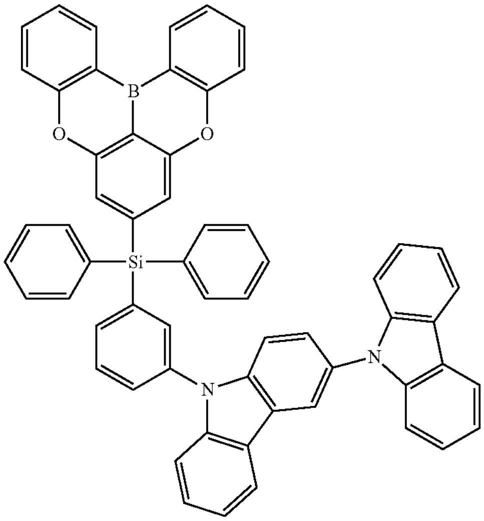
,
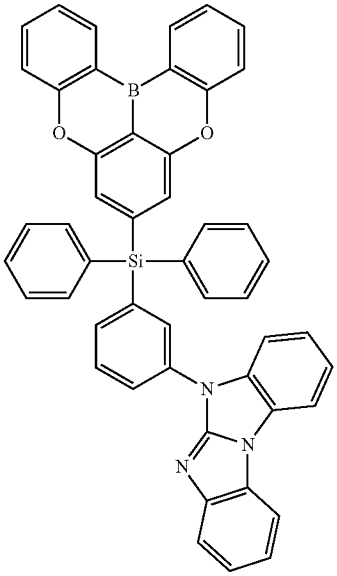
, -continued
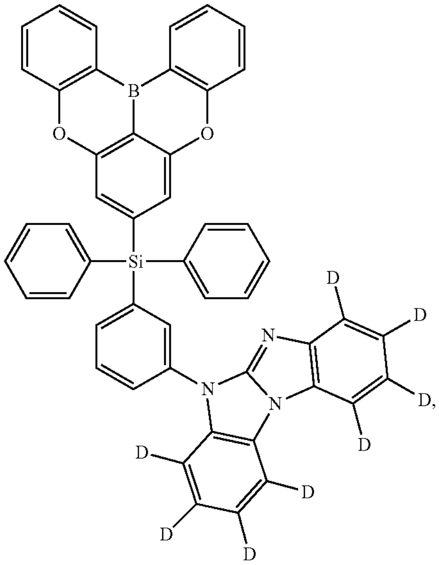
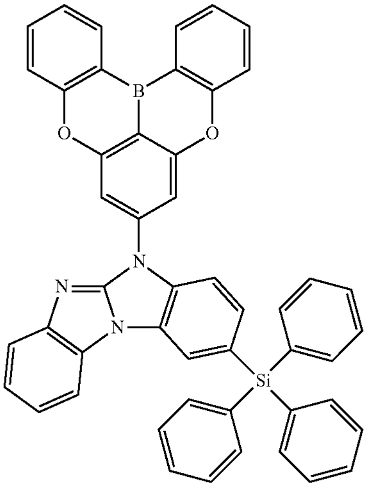
,
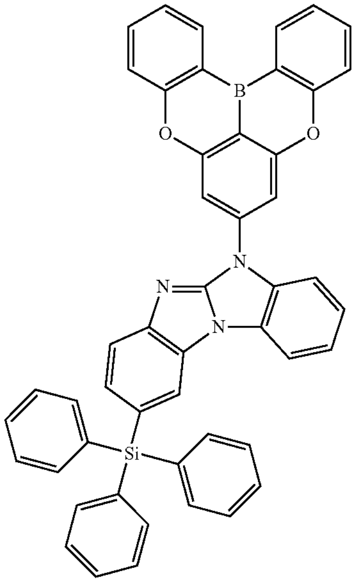
,
-continued
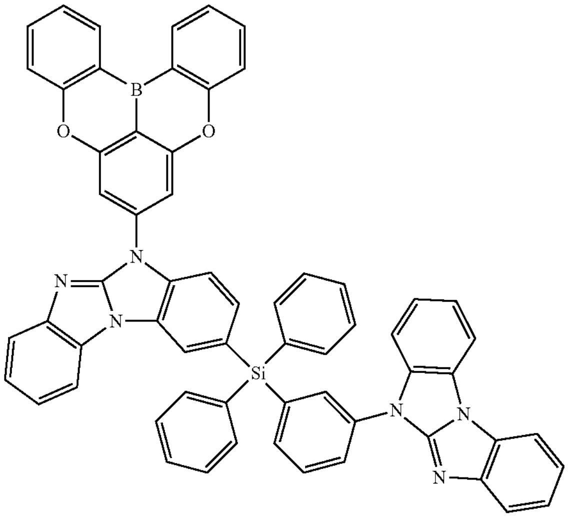
,
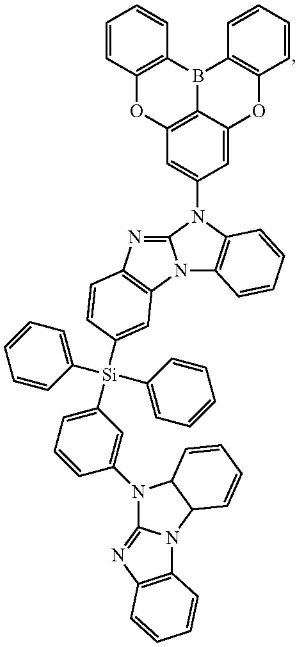
,
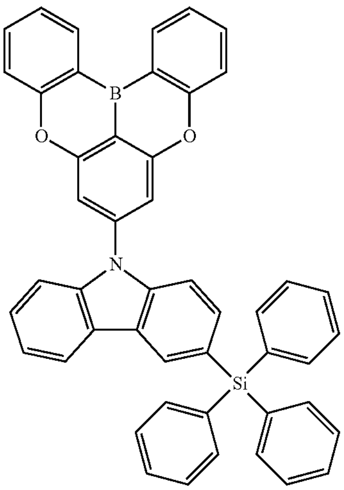
, -continued
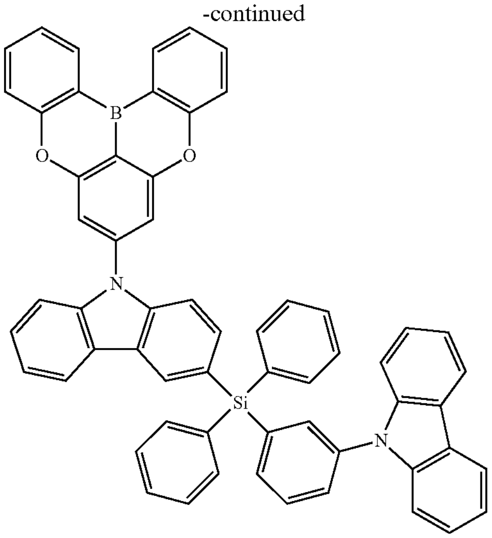
,
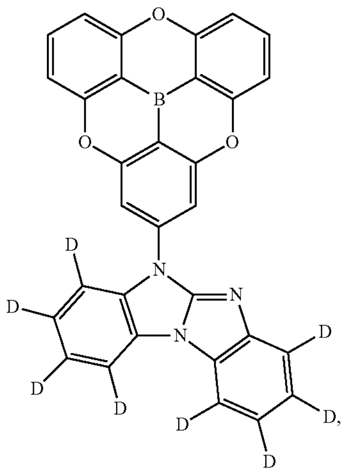
,
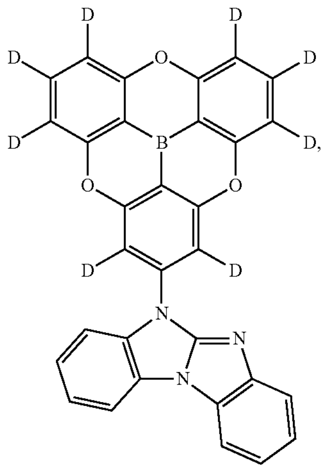
,
-continued
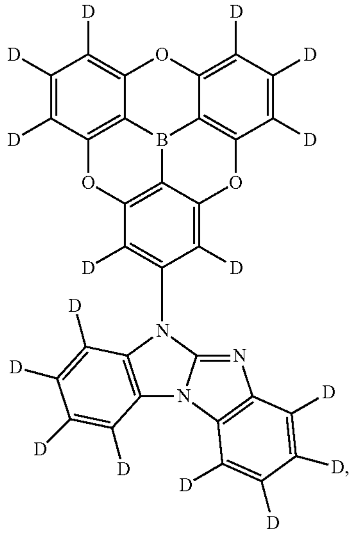
,
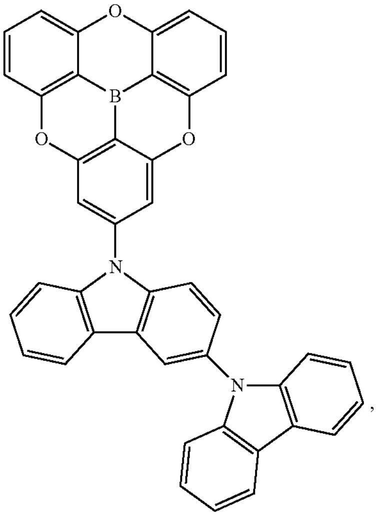
,
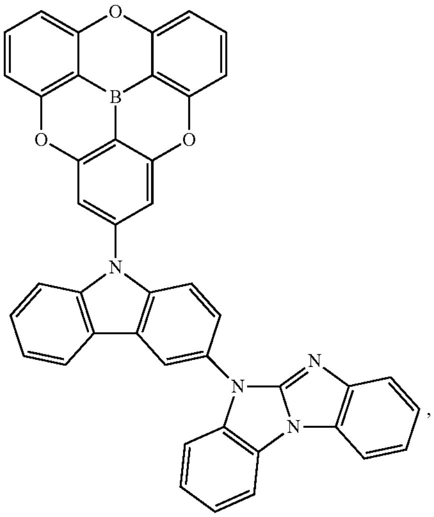
, -continued
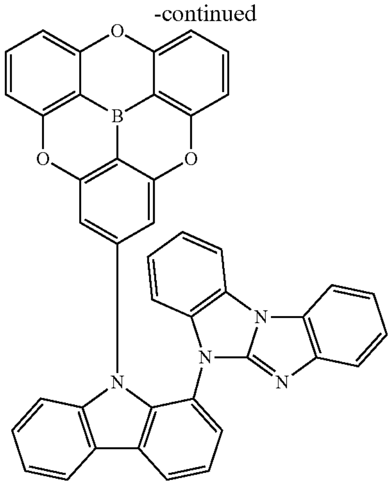
,
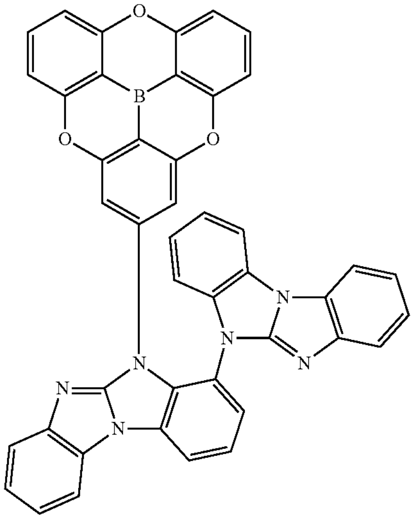
,
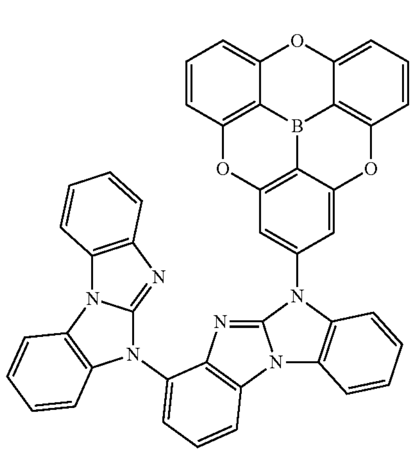
,
-continued
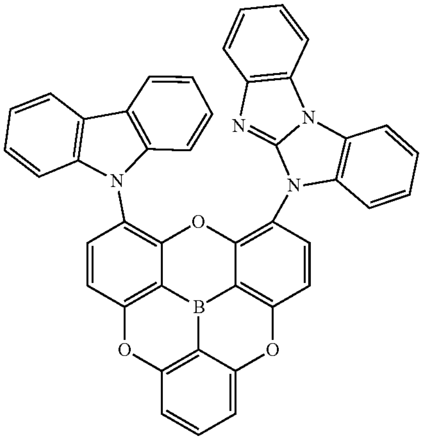
,
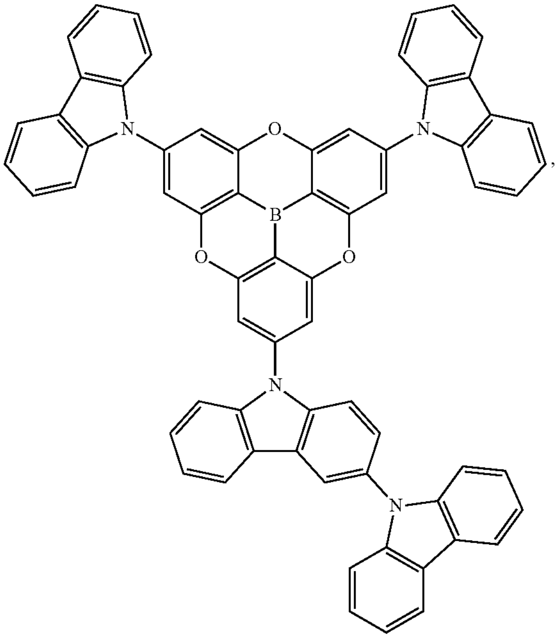
,
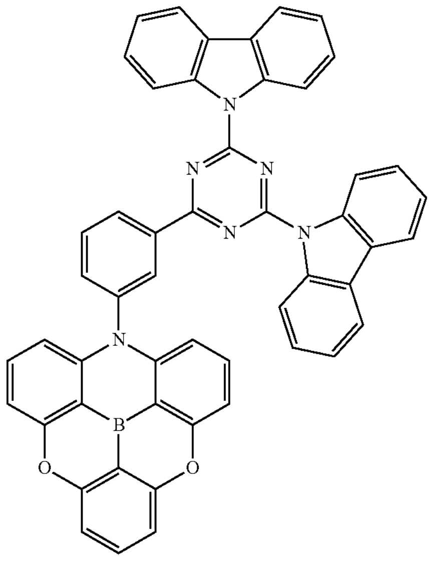
, -continued
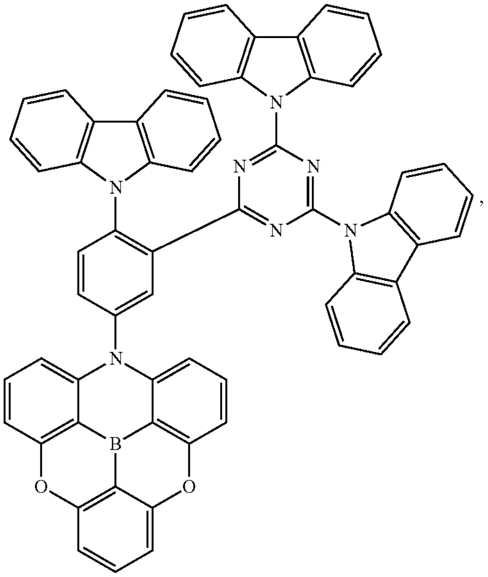
,
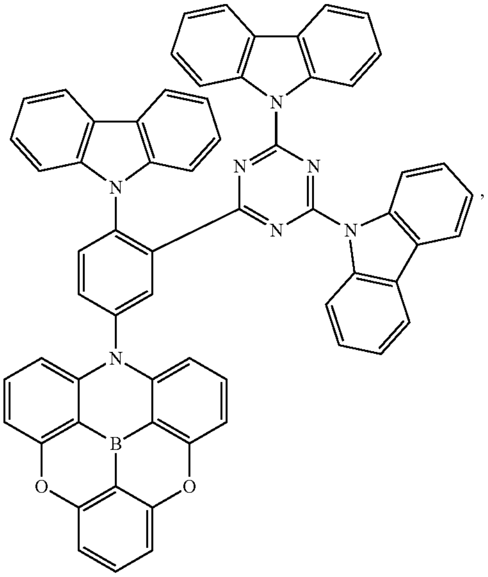
,
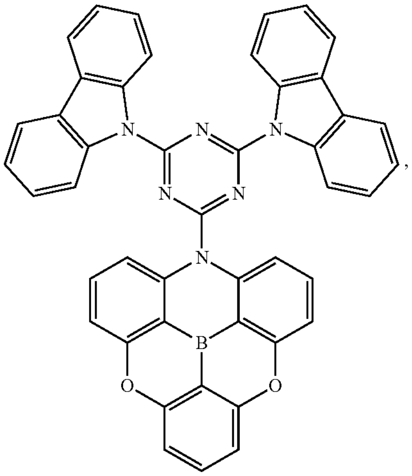
,
-continued
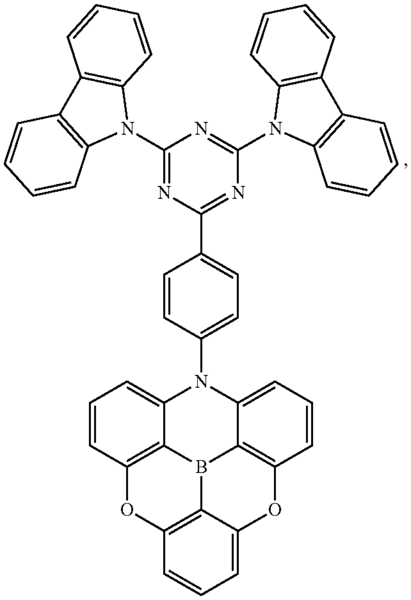
,
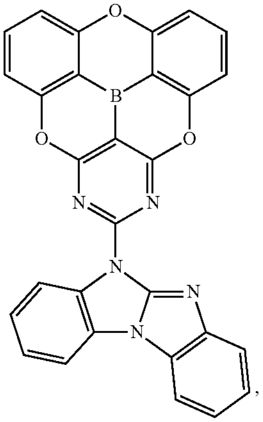
,
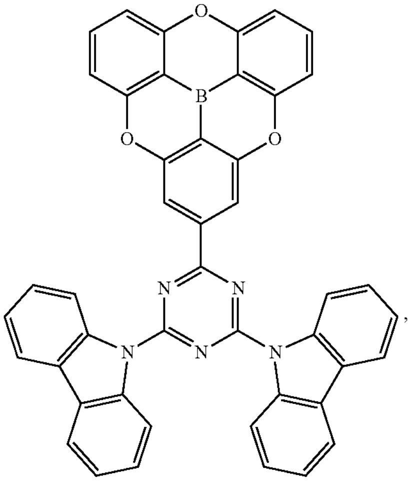
, -continued
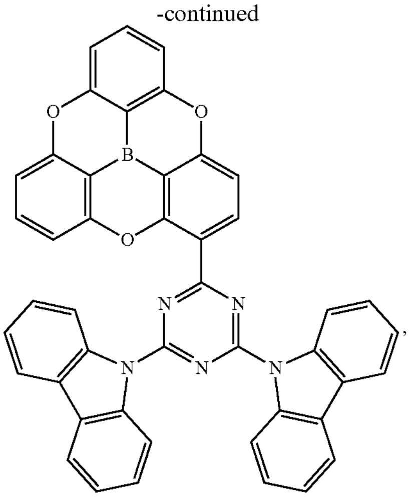
,
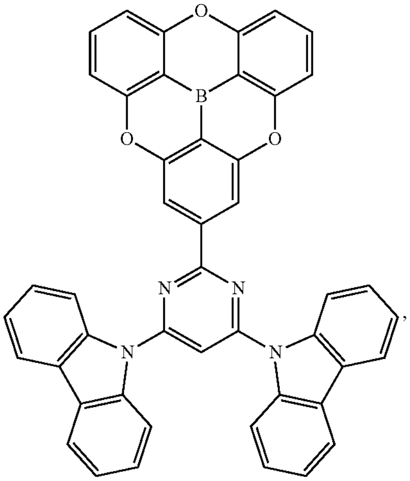
,
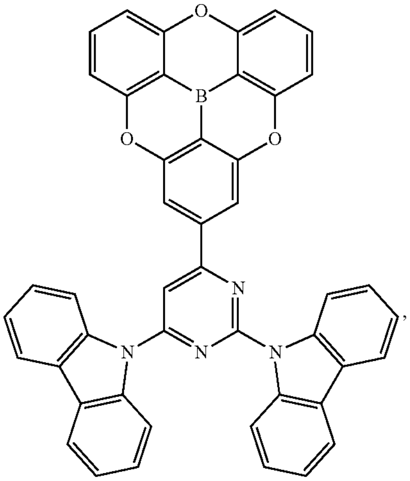
,
-continued
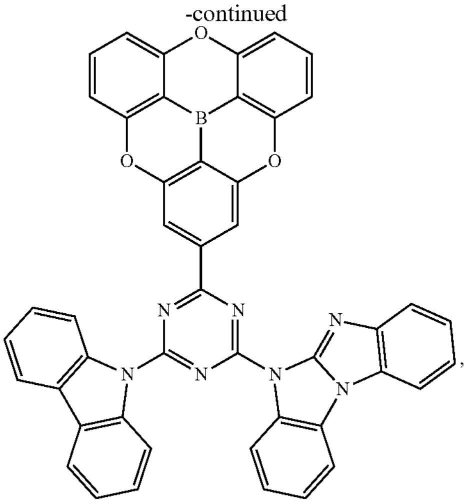
,
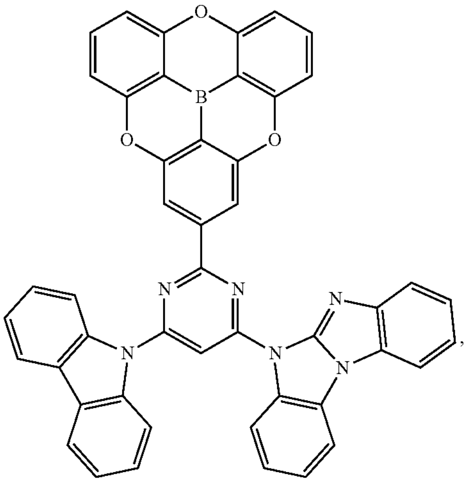
,
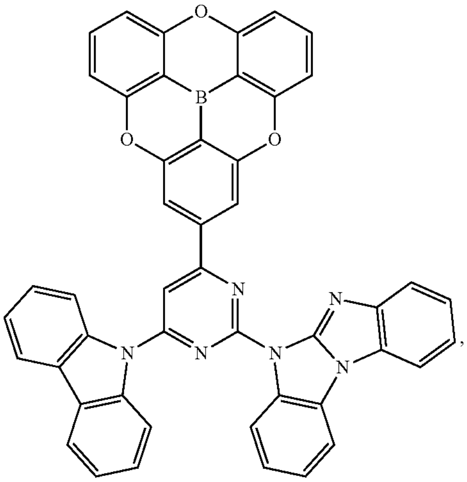
, -continued
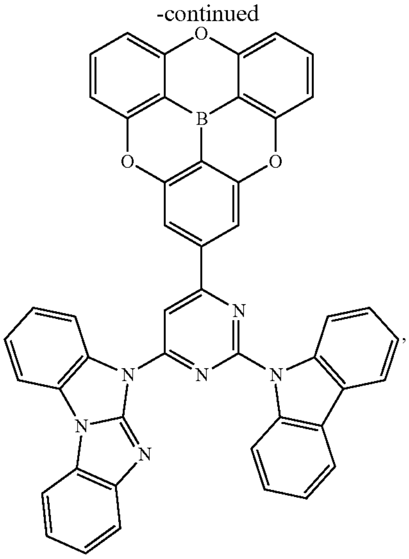
,
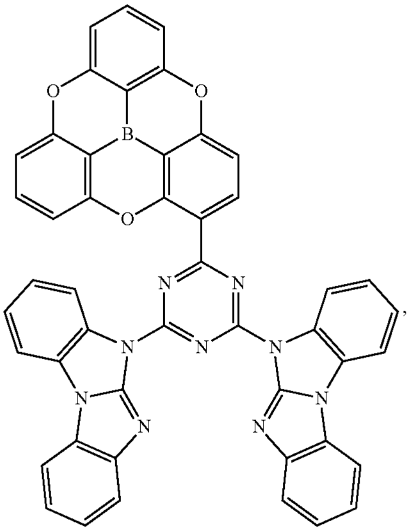
,
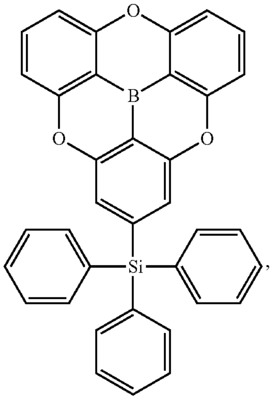
,
-continued
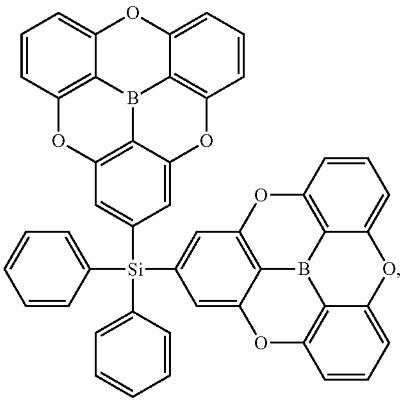
,
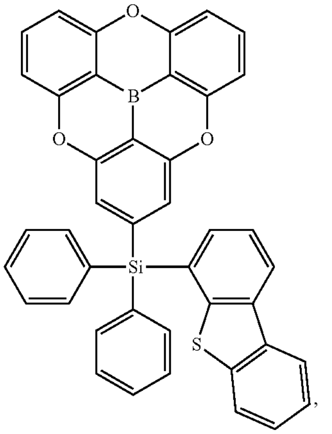
,
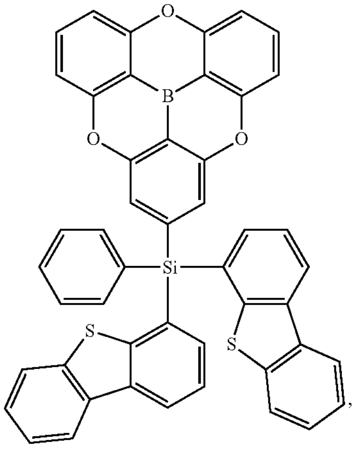
, -continued
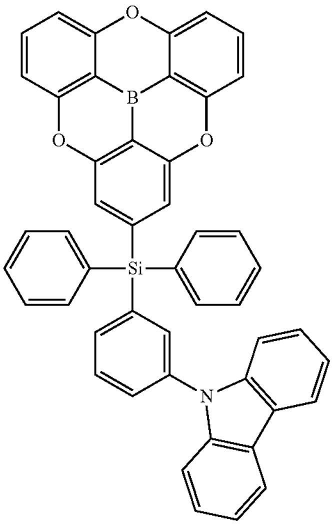
,
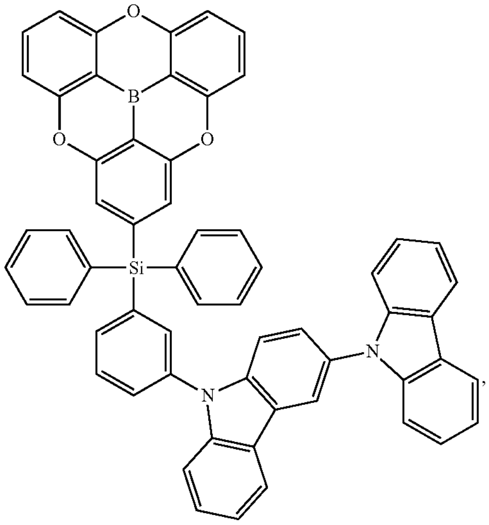
,
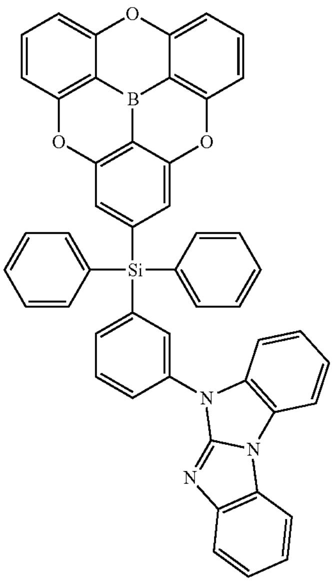
,
-continued
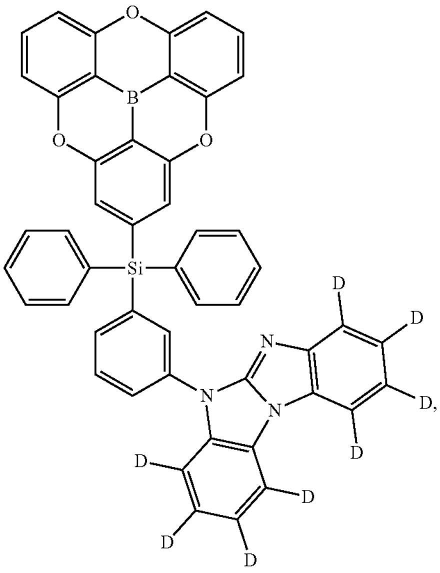
,
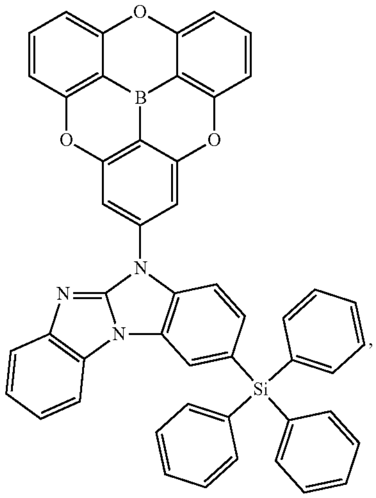
,
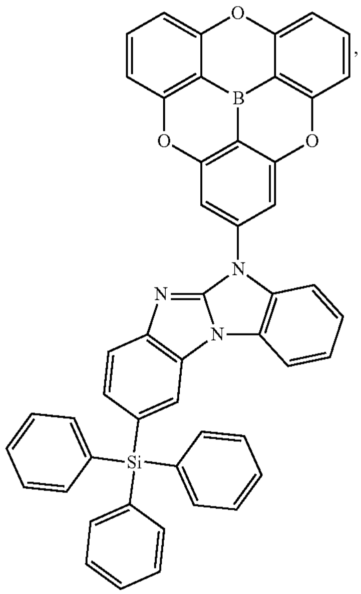
, -continued
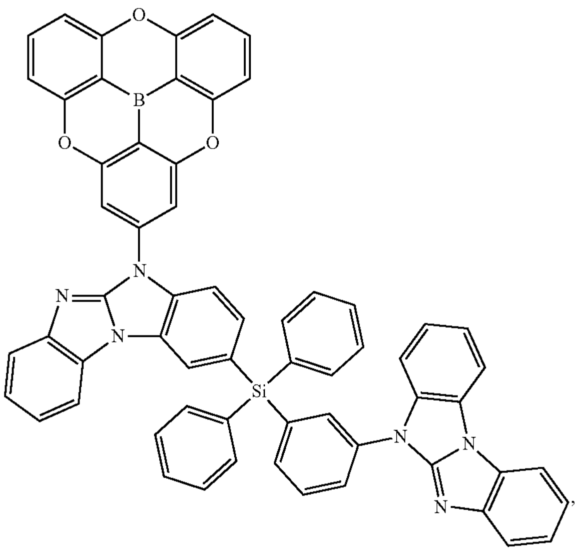
,
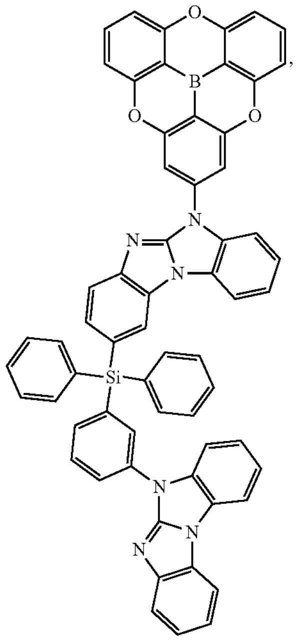
,
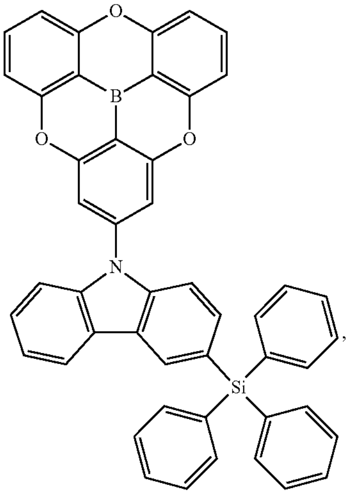
,
-continued
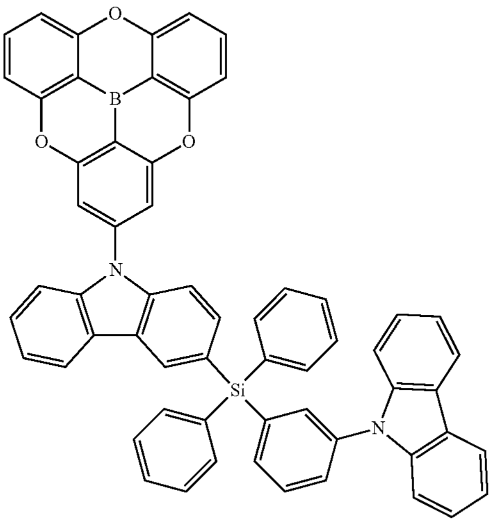
,
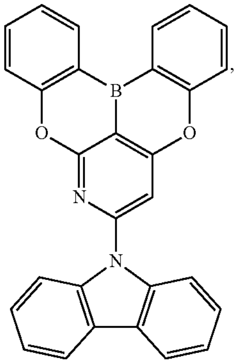
,
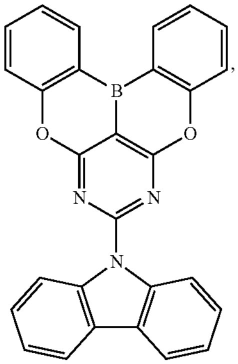
,
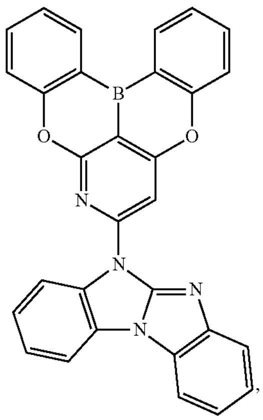
,
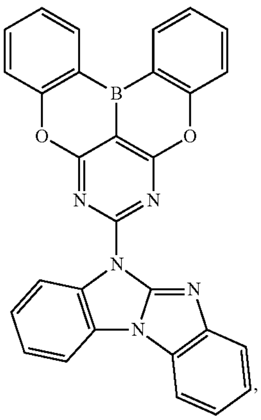
,
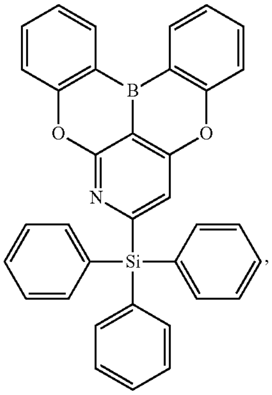
,
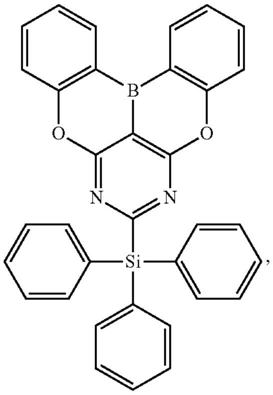
, -continued
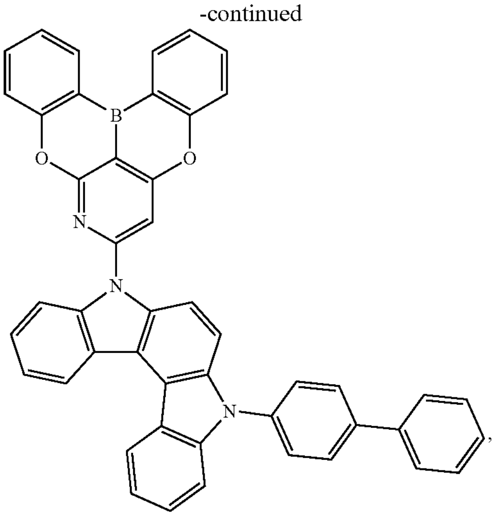
,
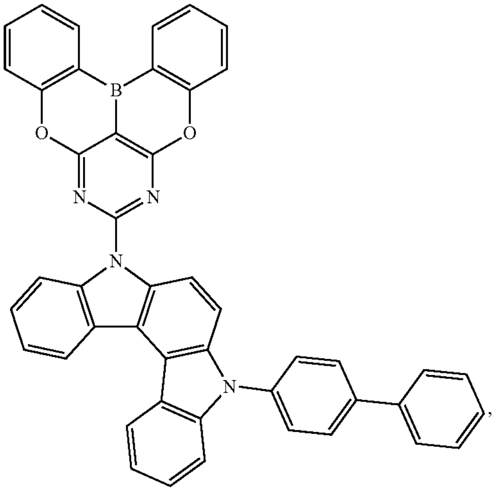
,
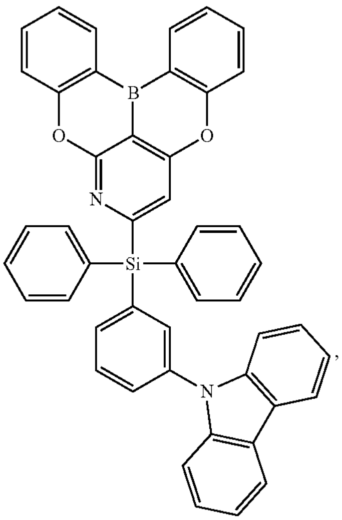
,
-continued
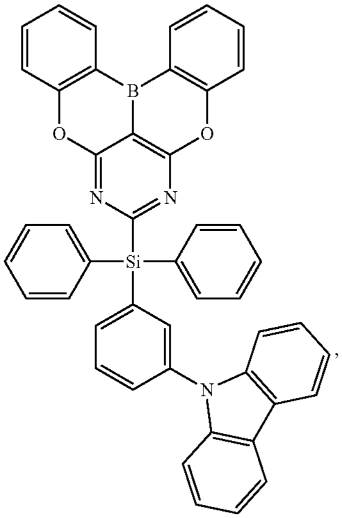
,
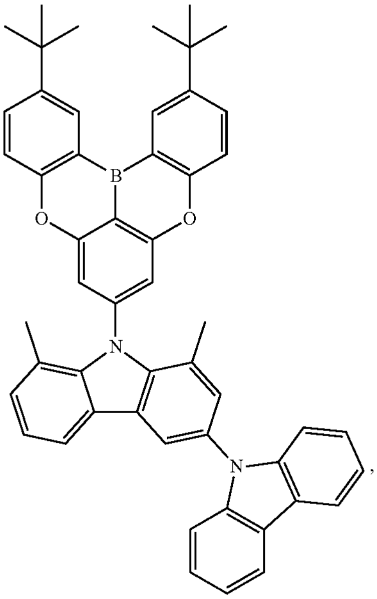
, -continued
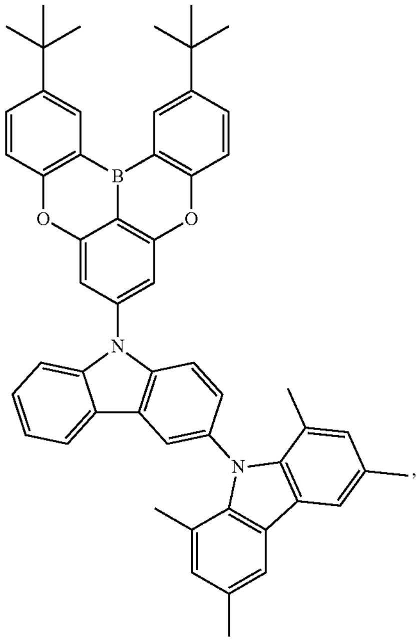
,
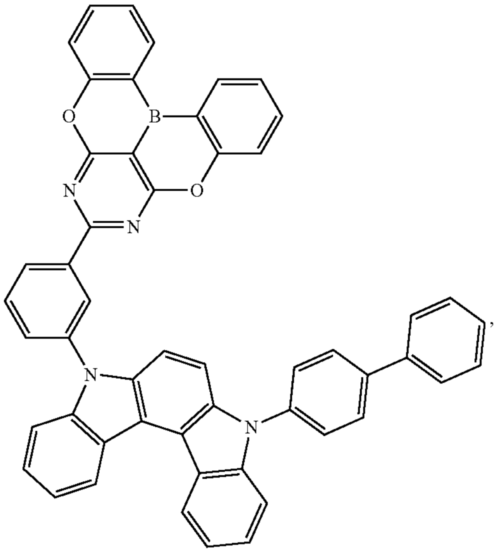
,
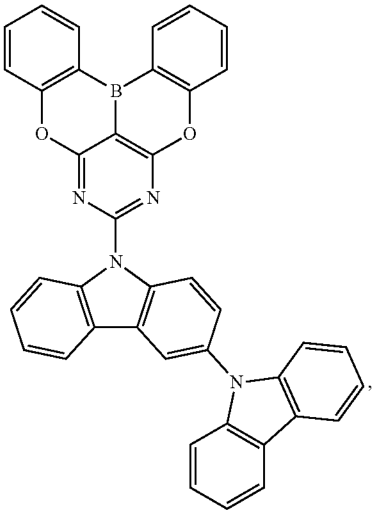
,
-continued
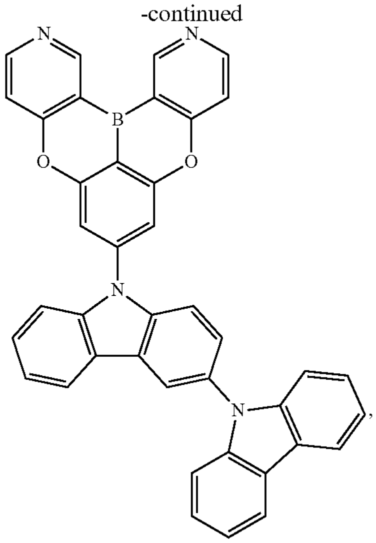
,
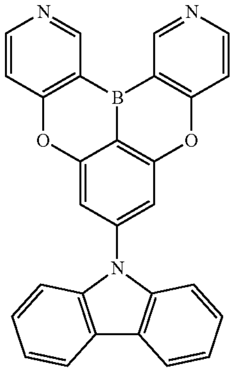
,
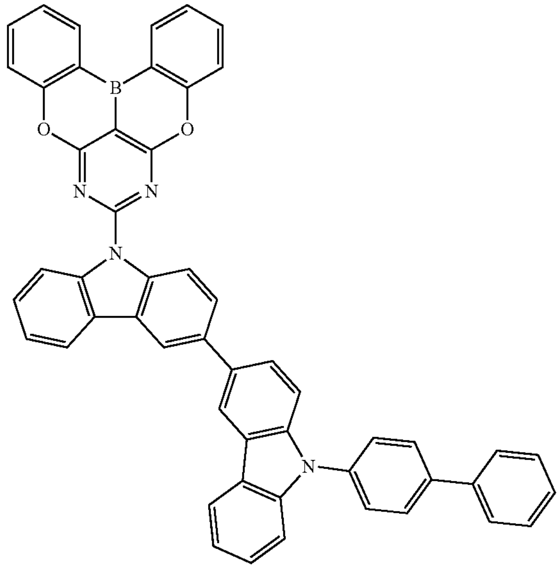
, -continued
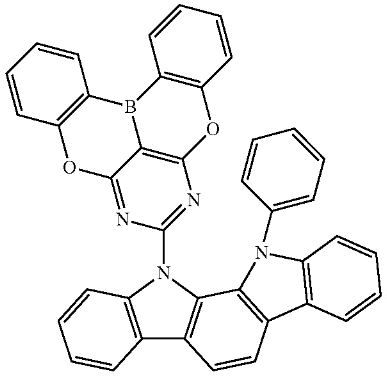
,
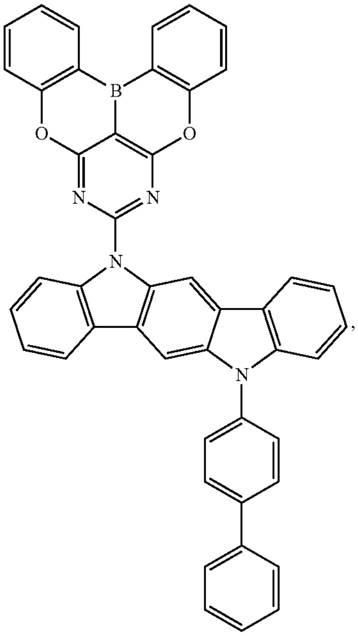
,
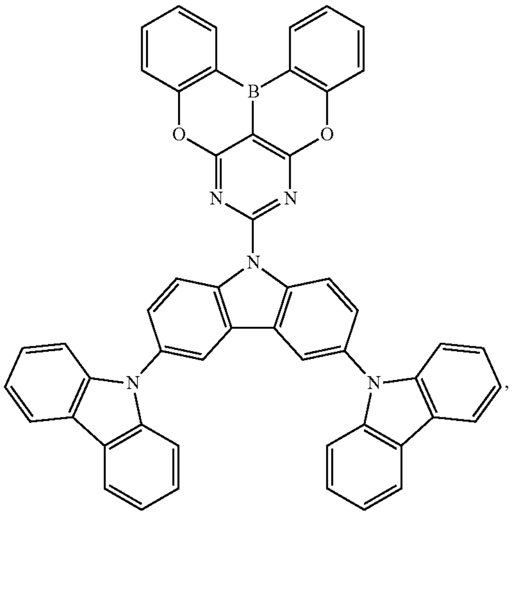
,
-continued
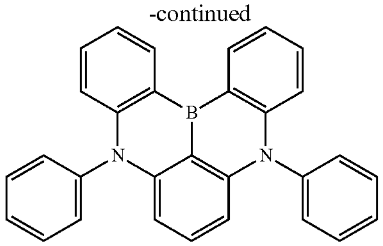
,
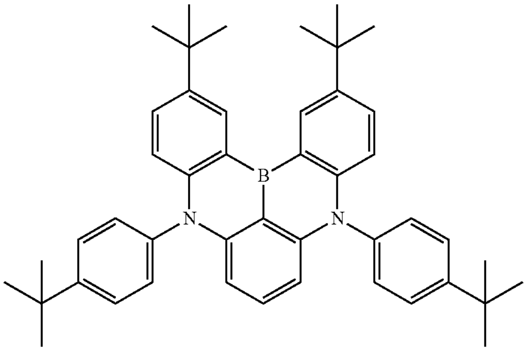
,
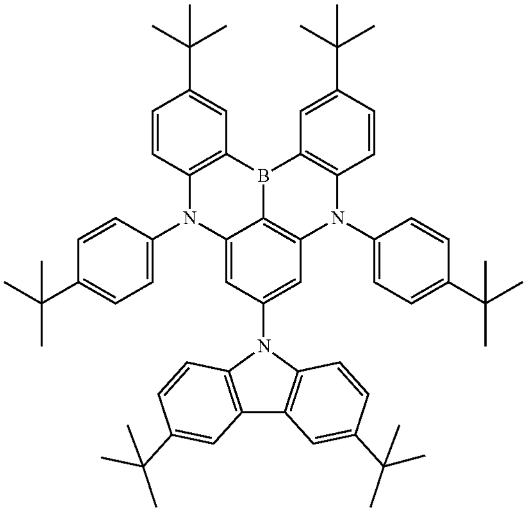
,
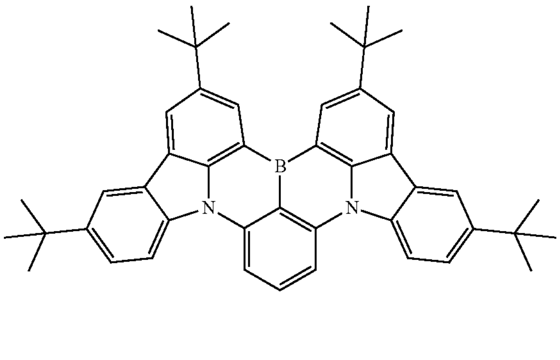
, -continued
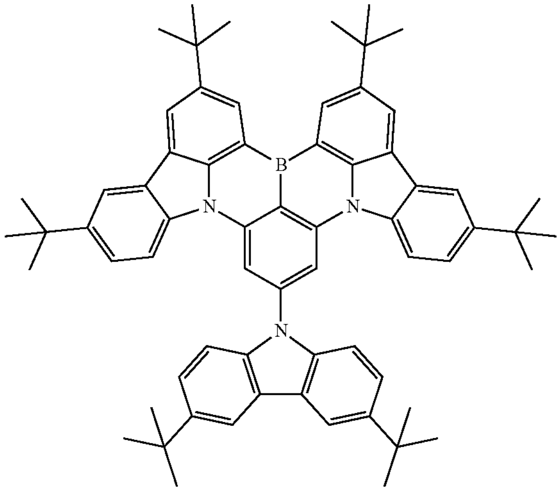
,
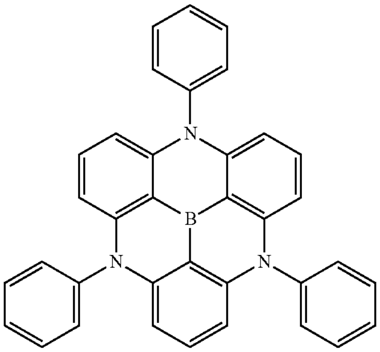
,
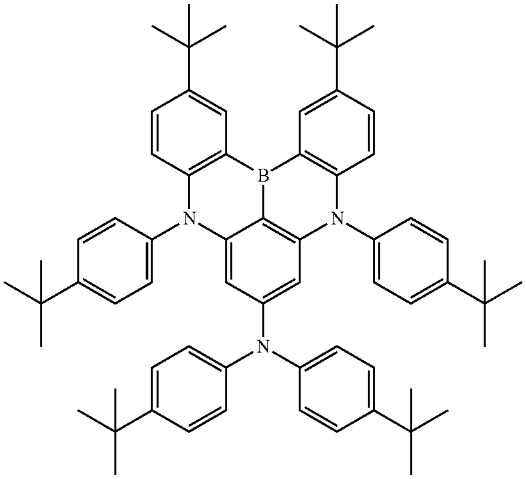
,
-continued
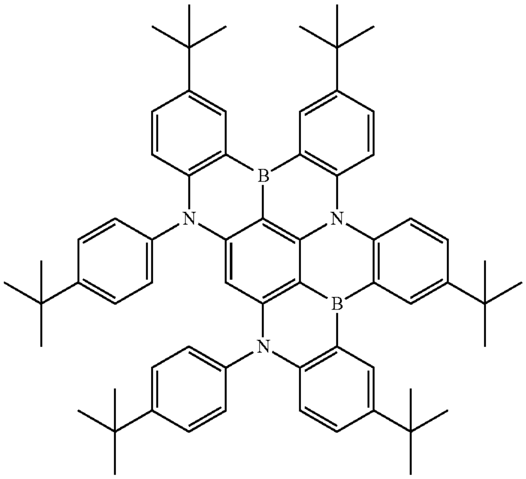
,
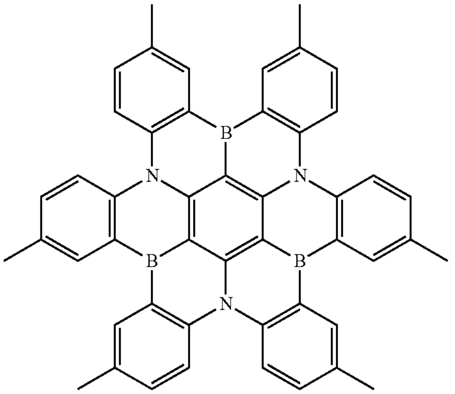
,
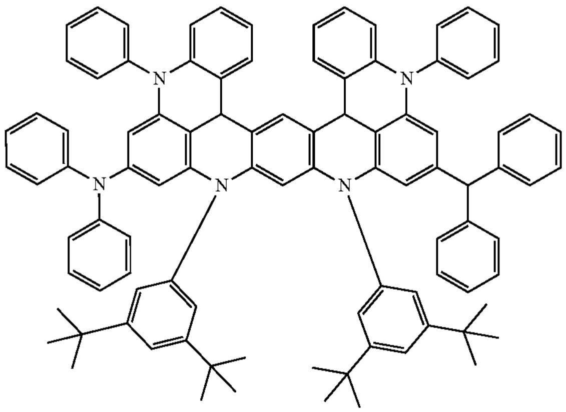
,
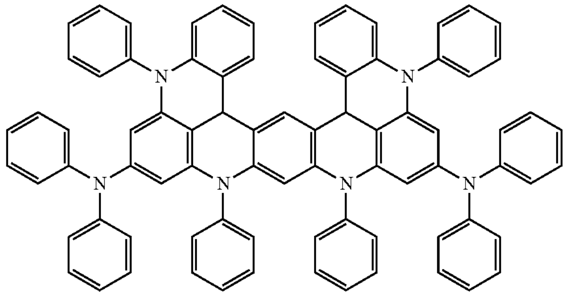
, -continued
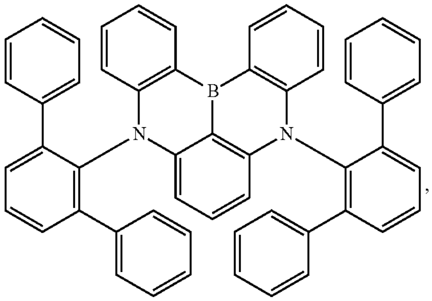
,
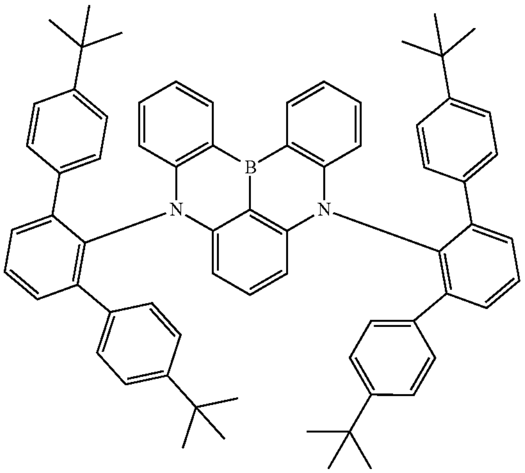
,
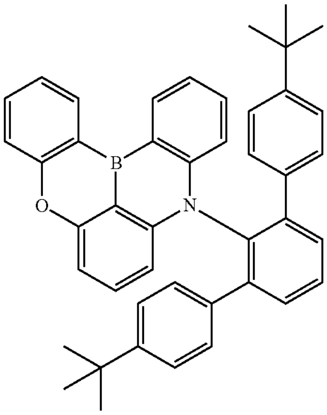
,
-continued
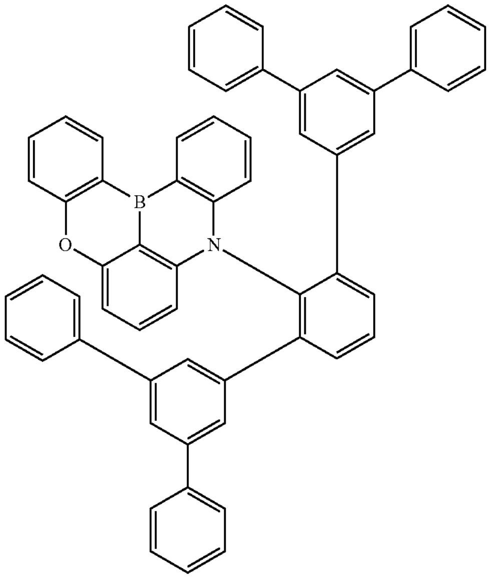
,
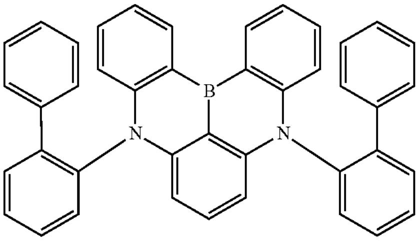
,
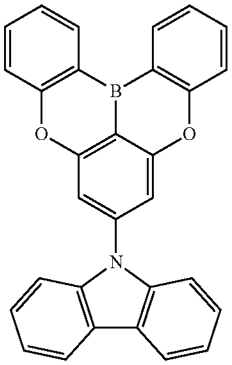
,
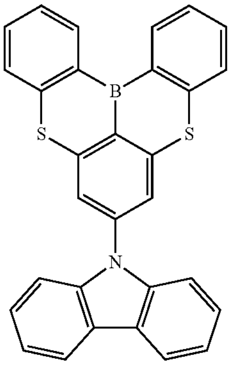
,
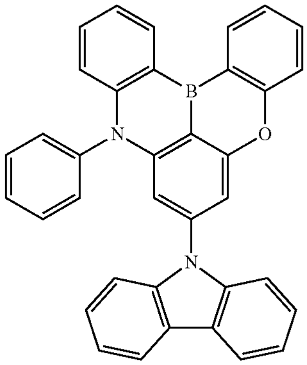
, -continued
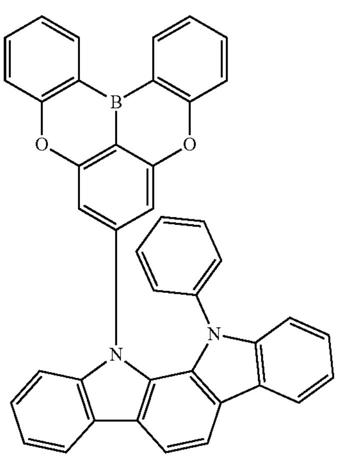
,
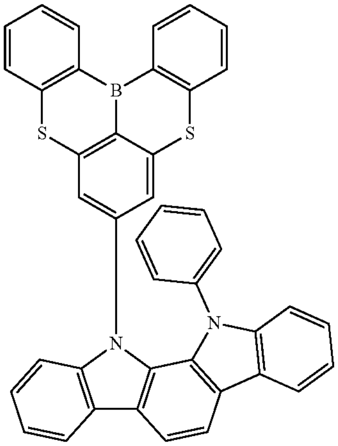
,
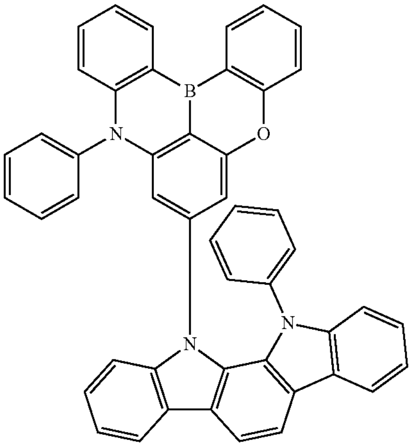
,
-continued
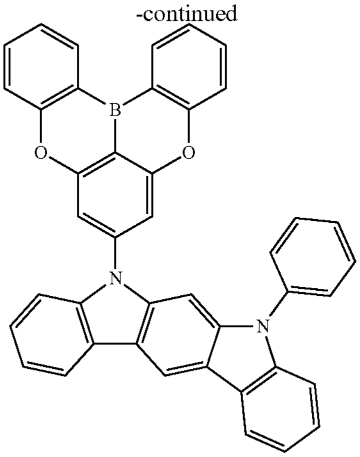
,
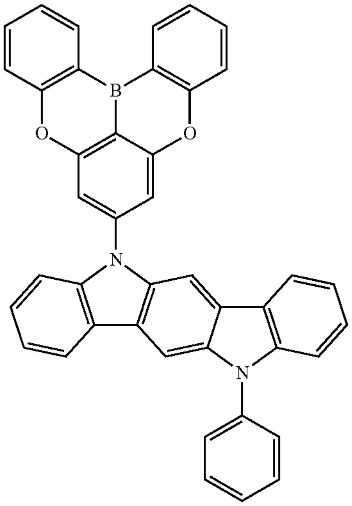
,
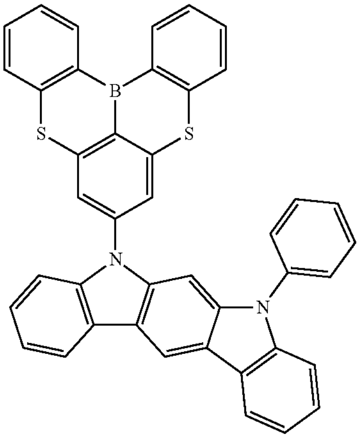
, -continued
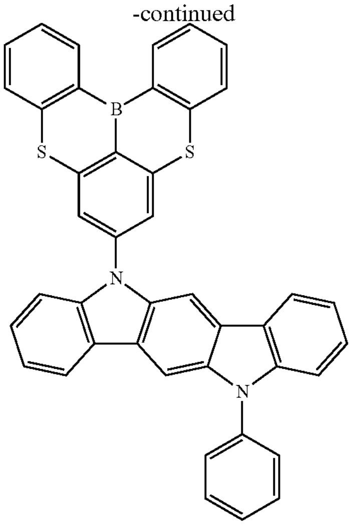
,
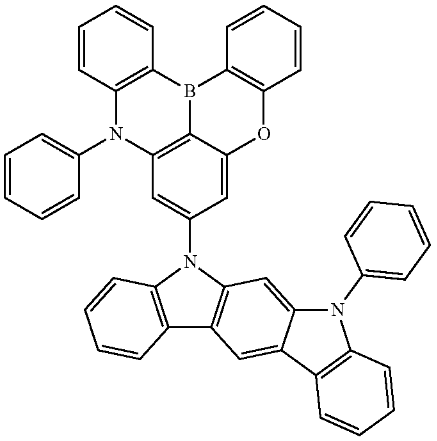
,
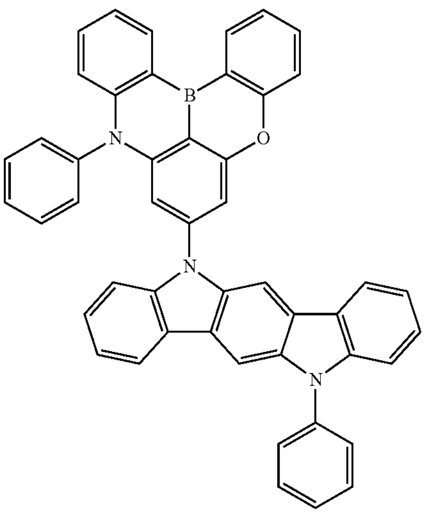
,
-continued
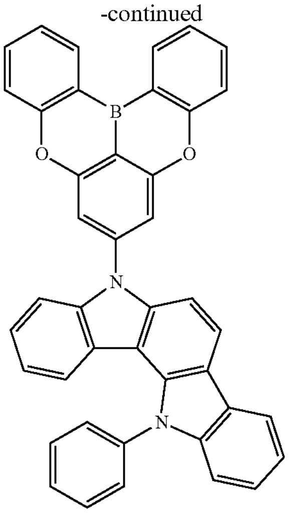
,
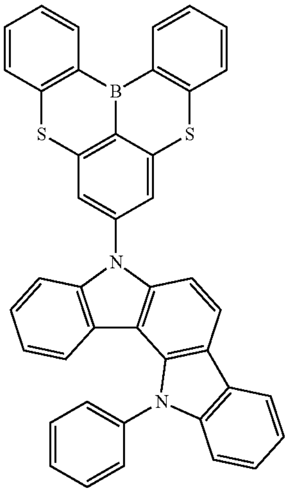
,
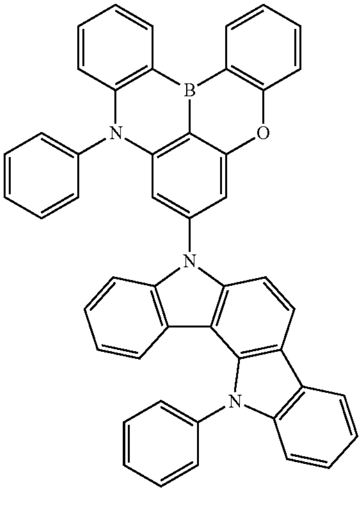
, -continued
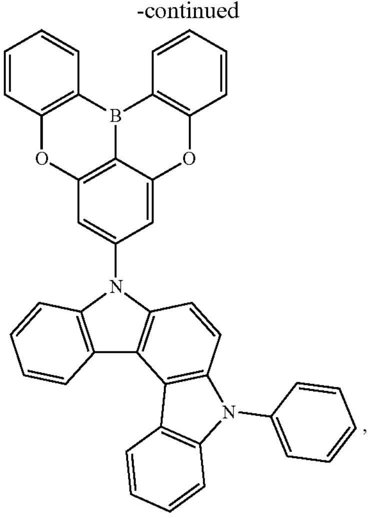
,
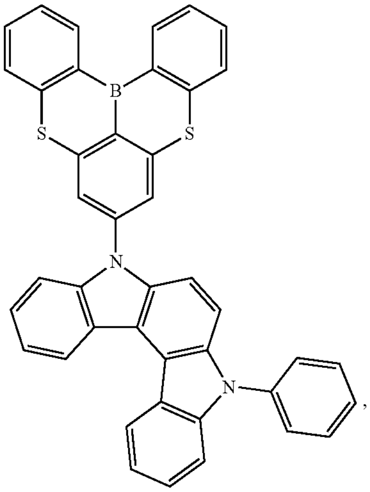
,
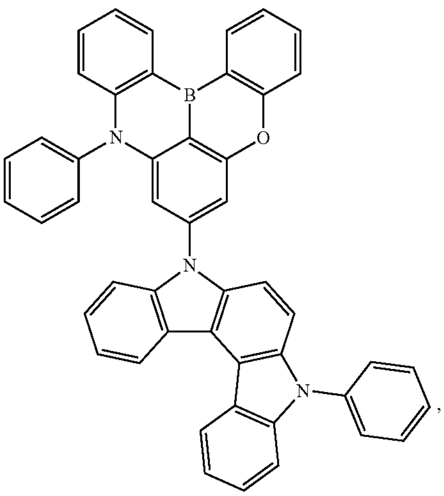
,
-continued
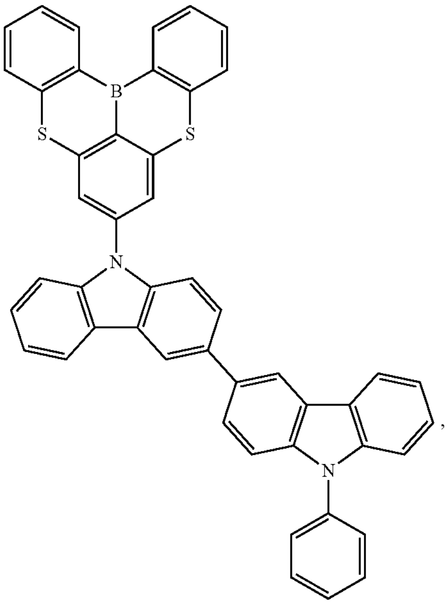
,
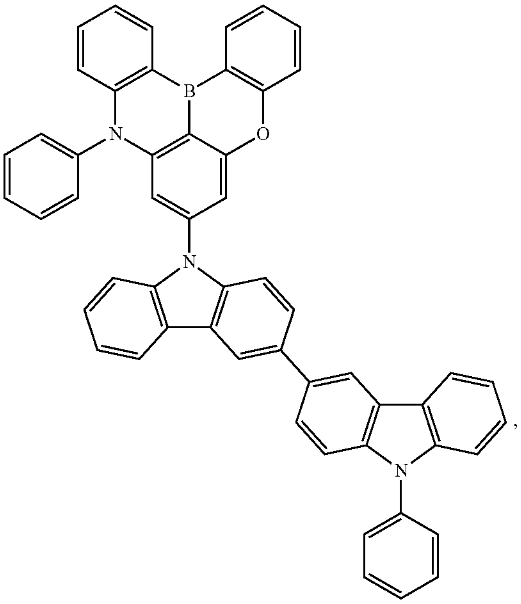
, -continued
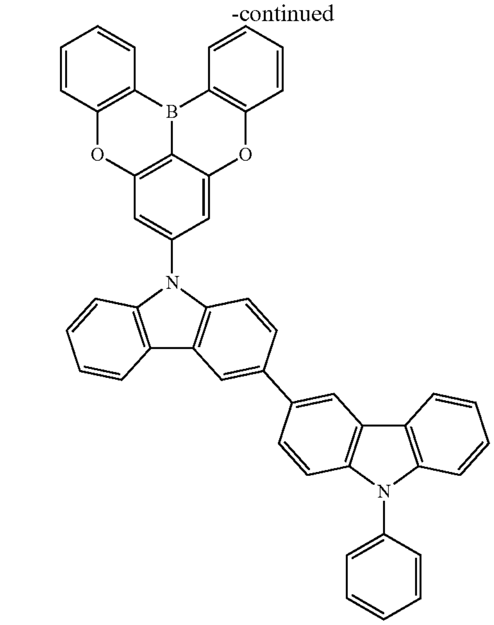
,
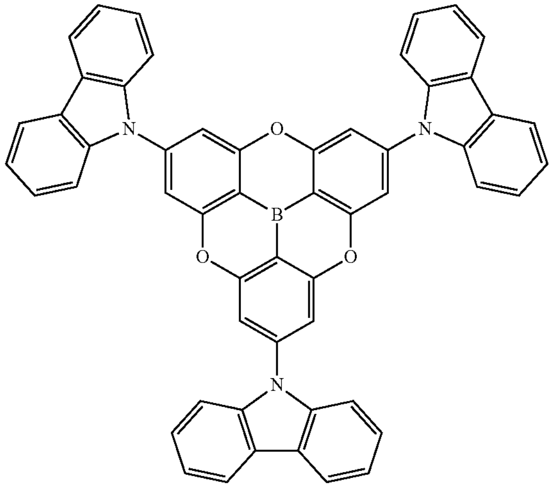
,
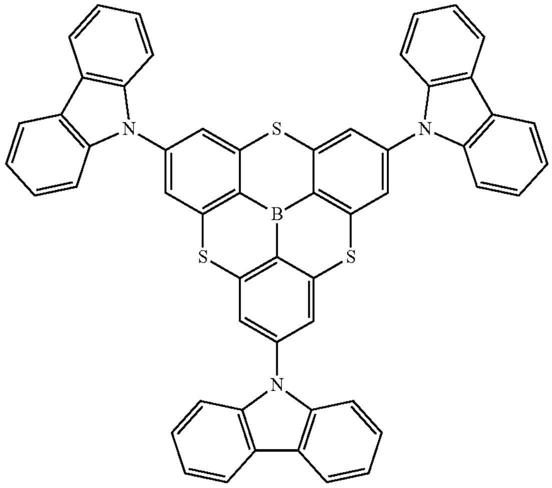
,
-continued
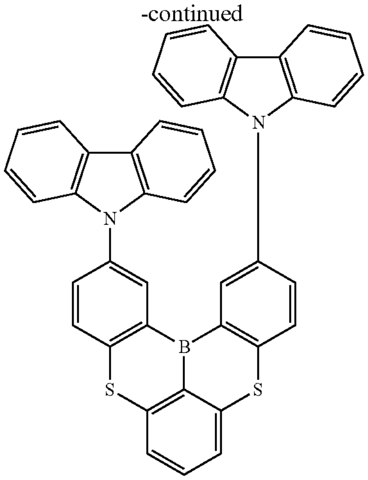
,
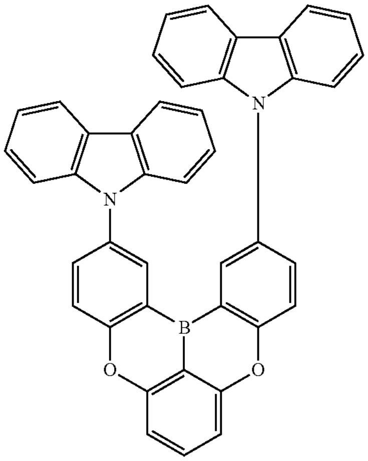
,
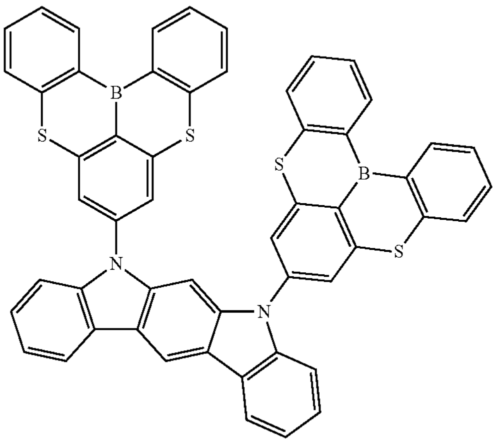
, -continued
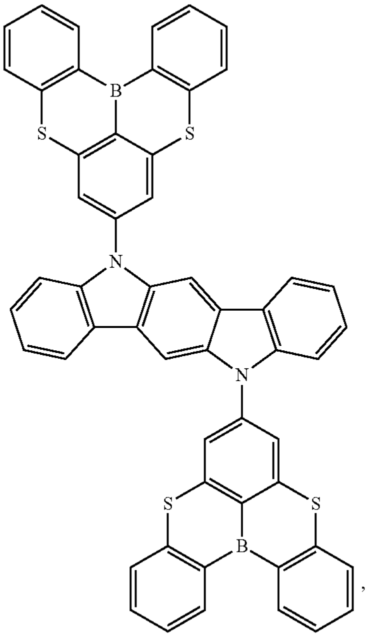
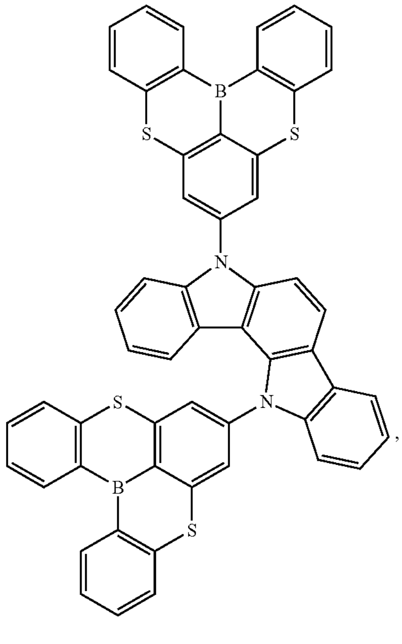
-continued
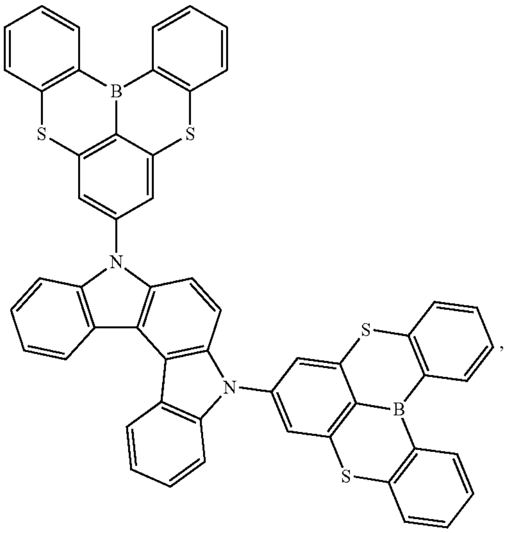
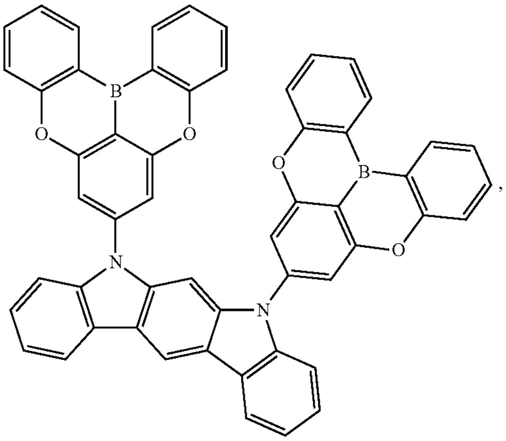
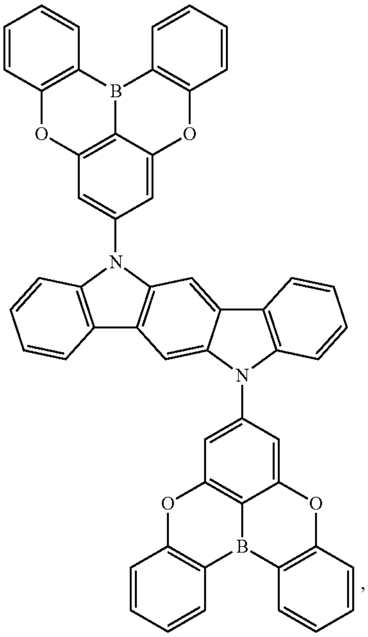 [SMILES: c1ccc2c(c1)Oc1cc(-n3c4ccccc4c4cc5c(cc43)c3ccccc3n5-c3cc4c5c(c3)Oc3ccccc3B5c3ccccc3O4)cc3c1B2c1ccccc1O3]

-continued
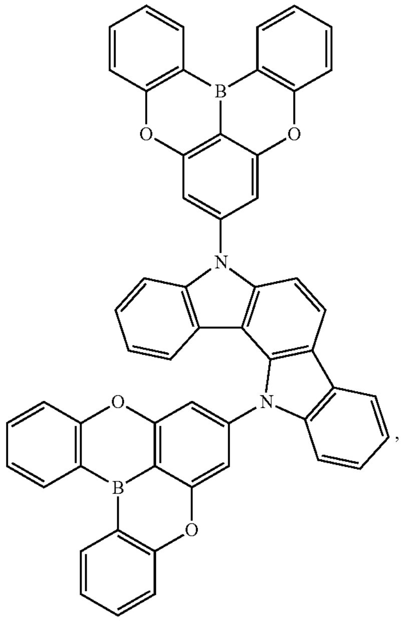
,
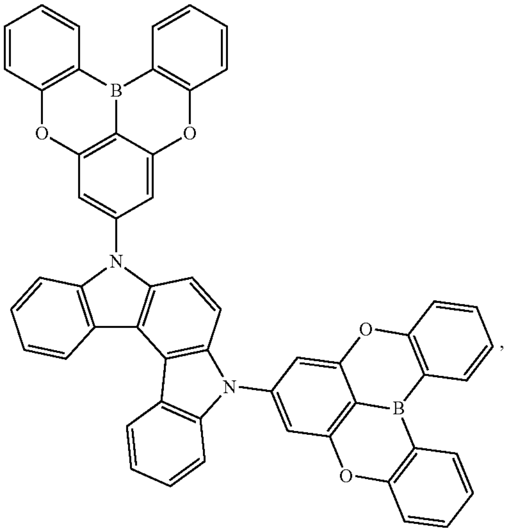
,
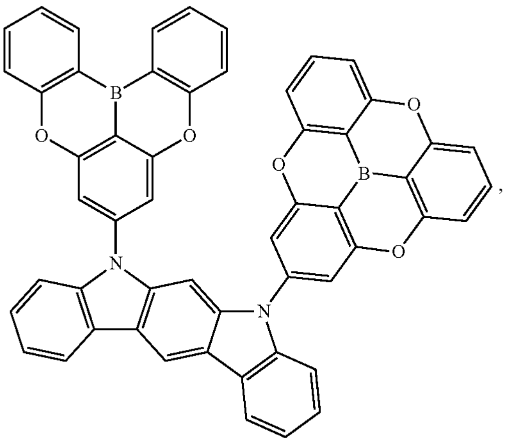
,
-continued
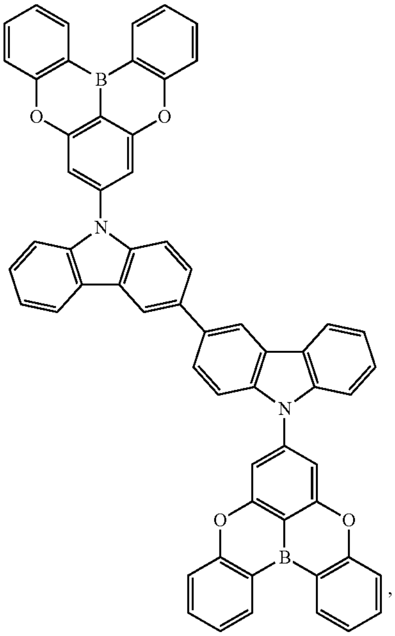
,
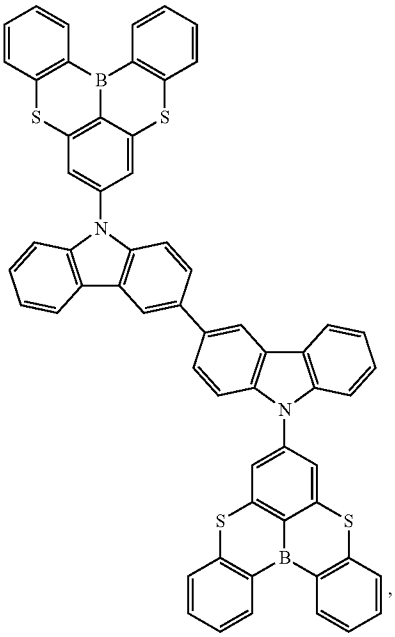
, -continued
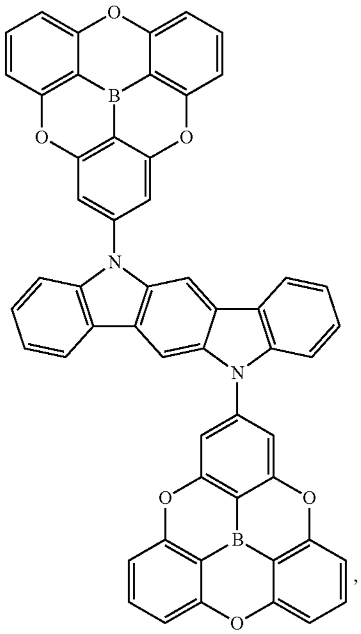
,
-continued
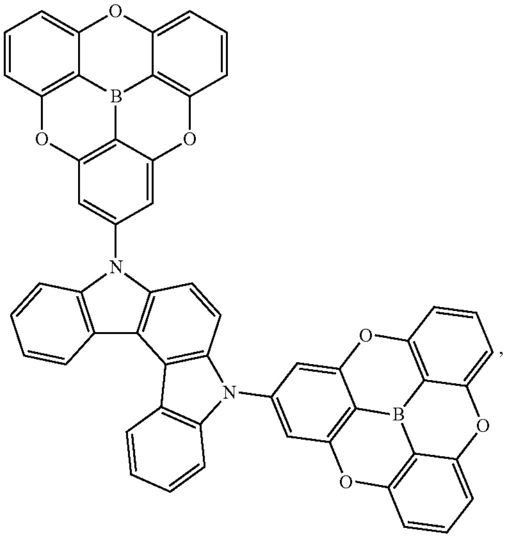
,
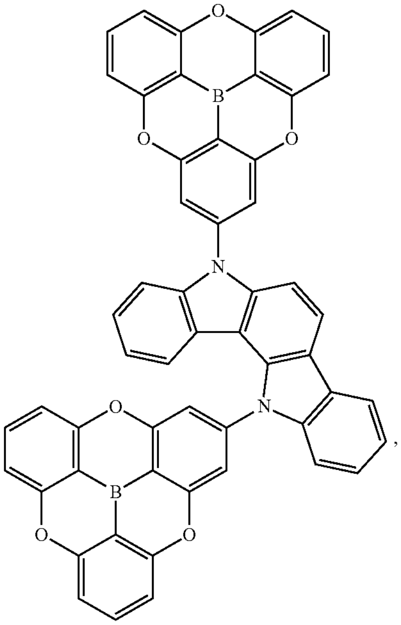
,
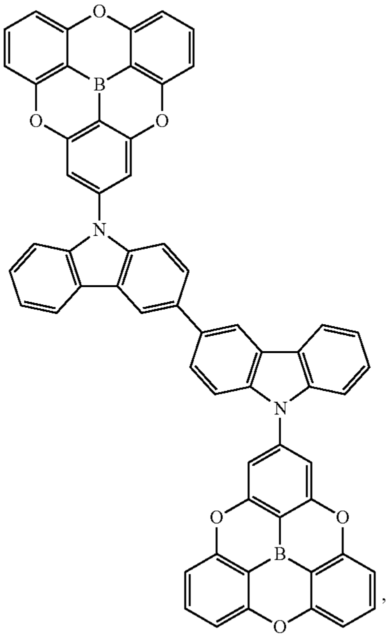
, -continued
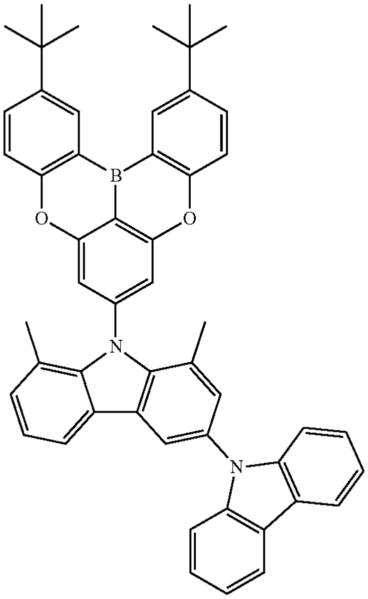
,
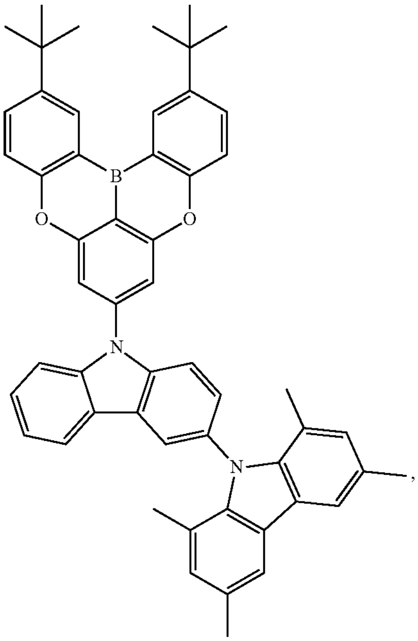
,
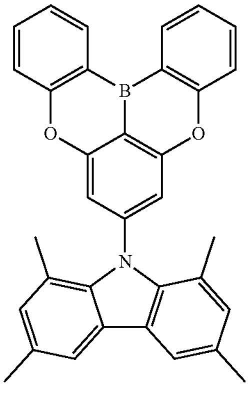
,
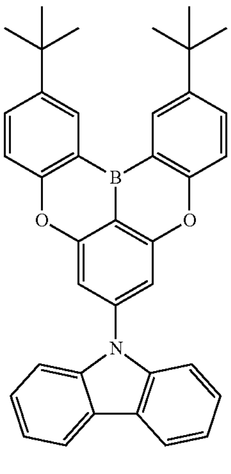
,
-continued
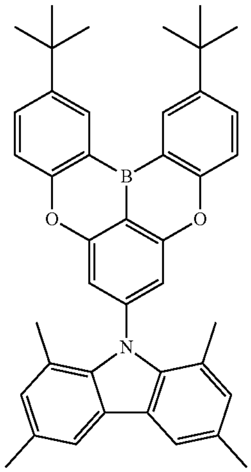
,
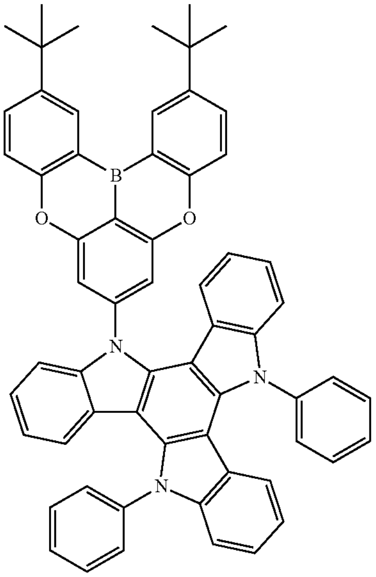
,
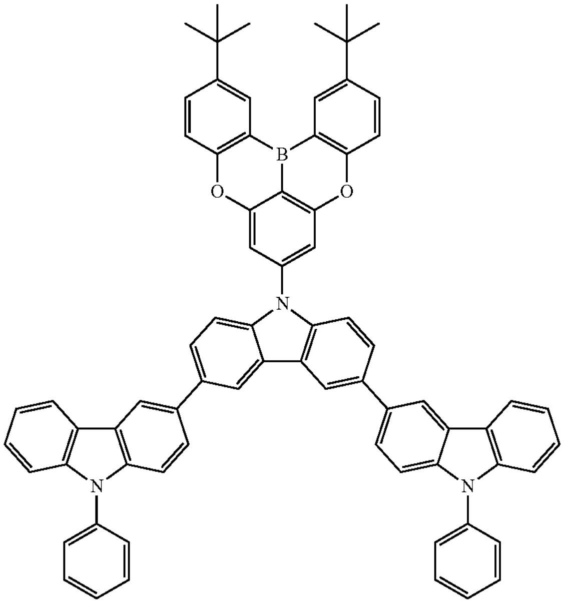
, -continued
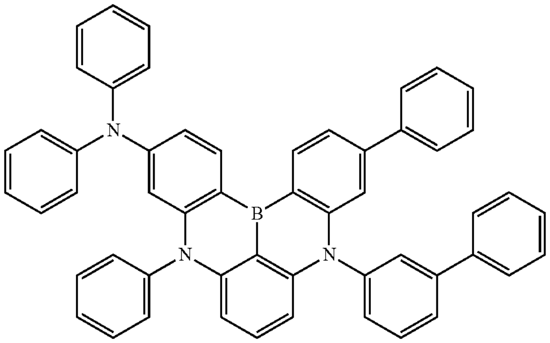
,
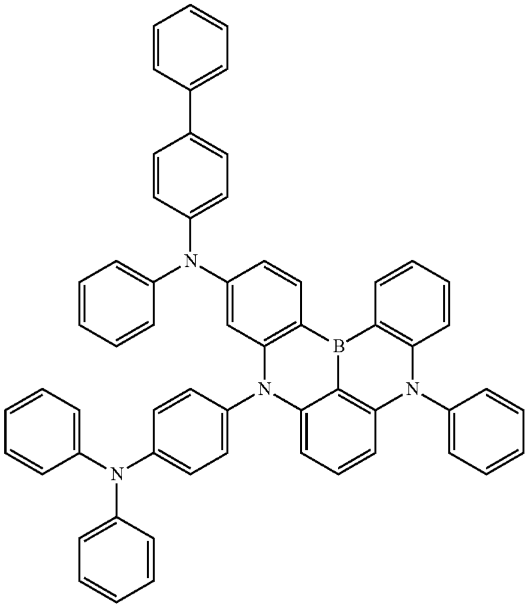
,
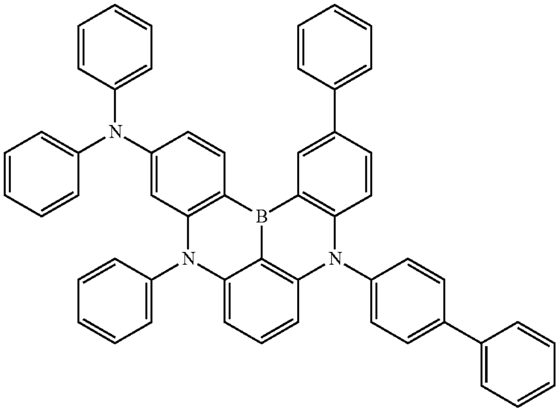
,
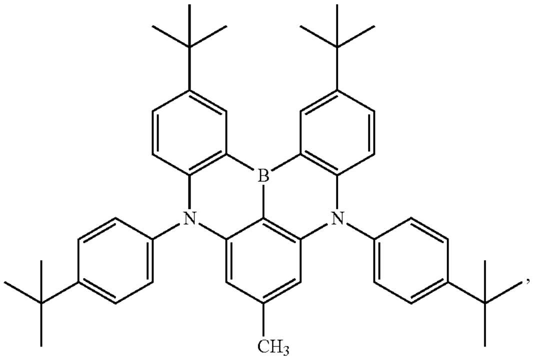
,
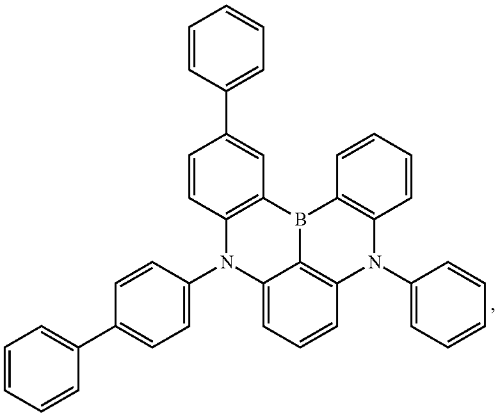
,
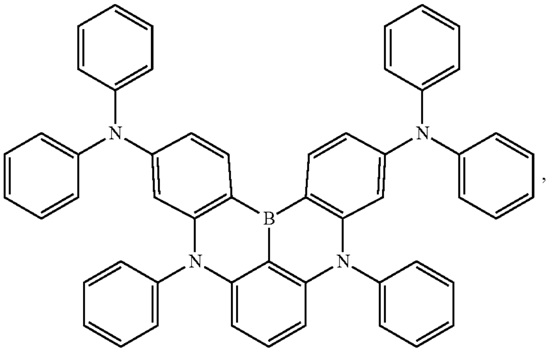
,
-continued -continued
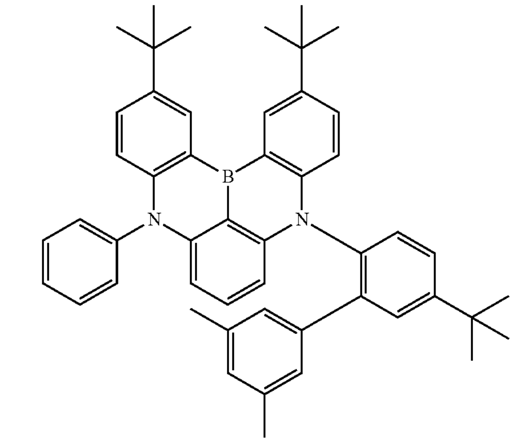
,
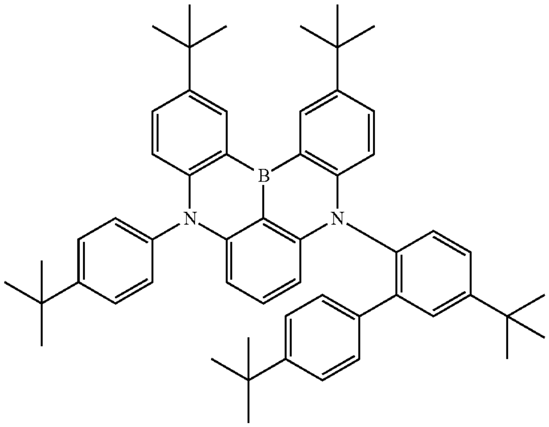
,
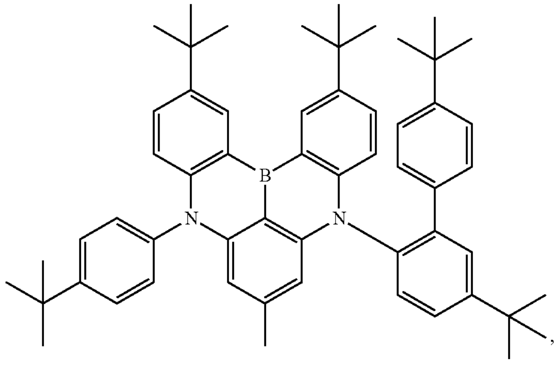
,
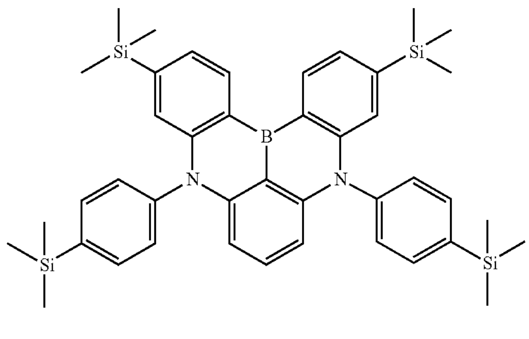
,
-continued
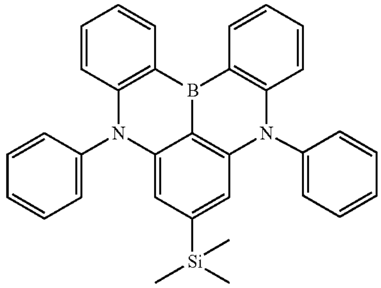
,
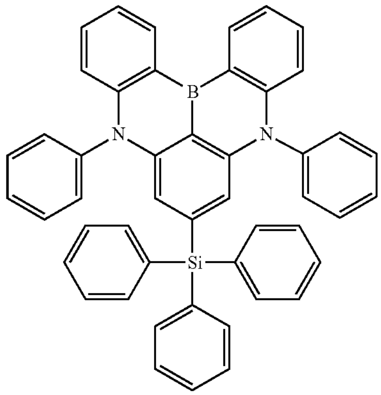
,
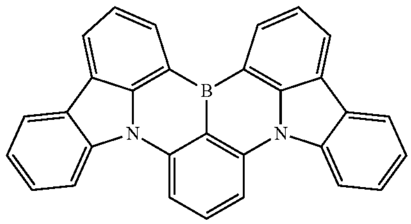
,
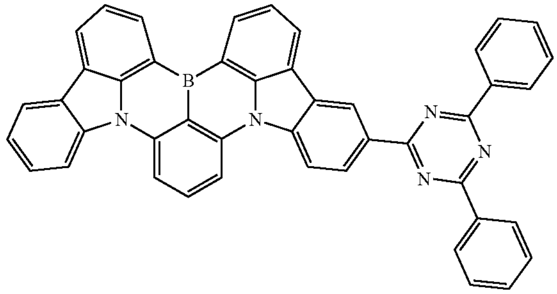
,
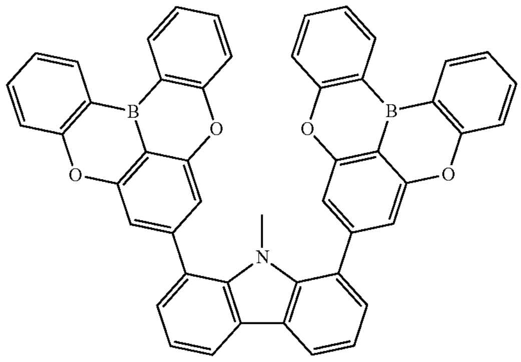
, -continued
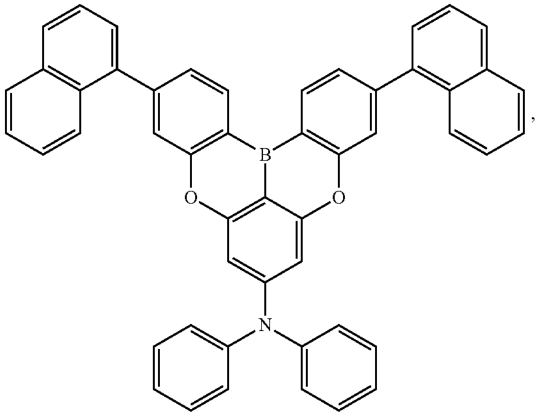
,
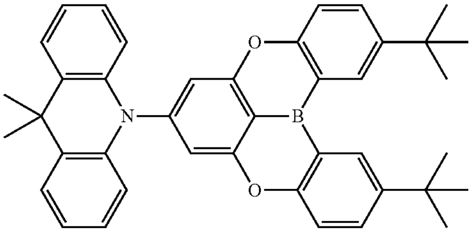
,
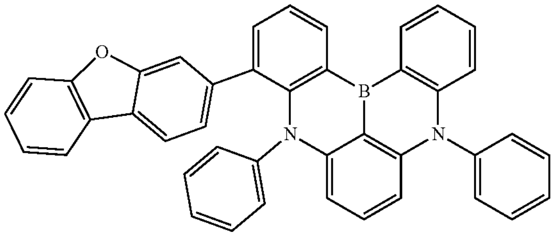
,
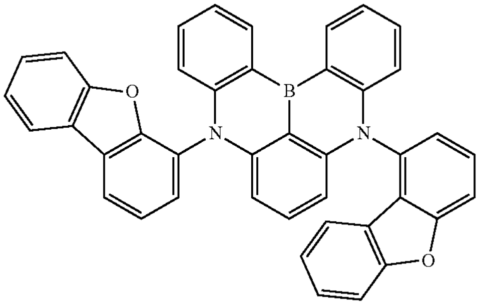
,
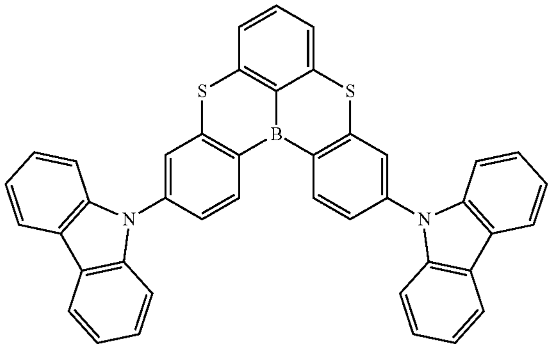
,
-continued
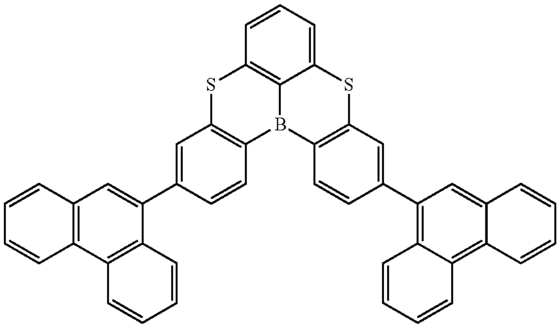
,
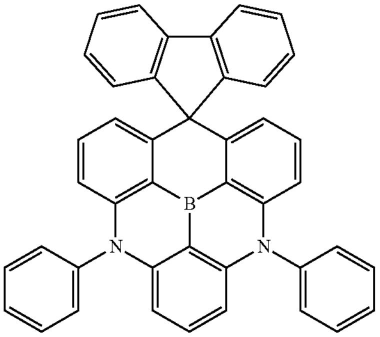
,
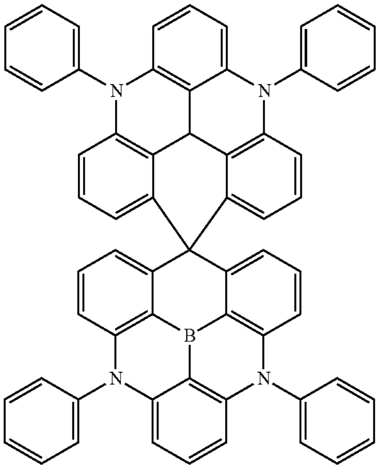
,
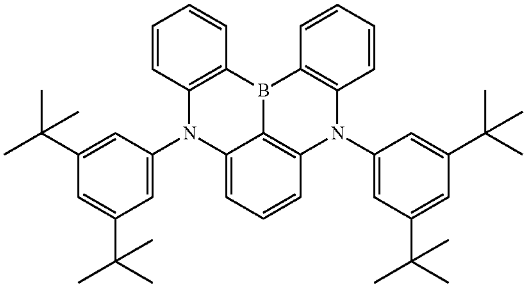
, -continued
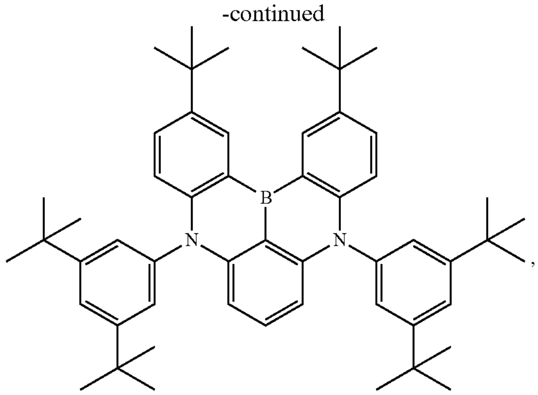,
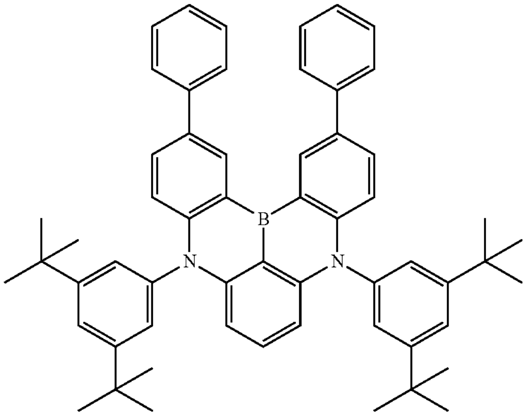,
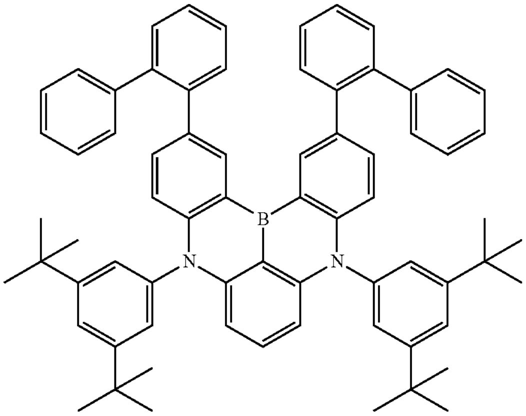,
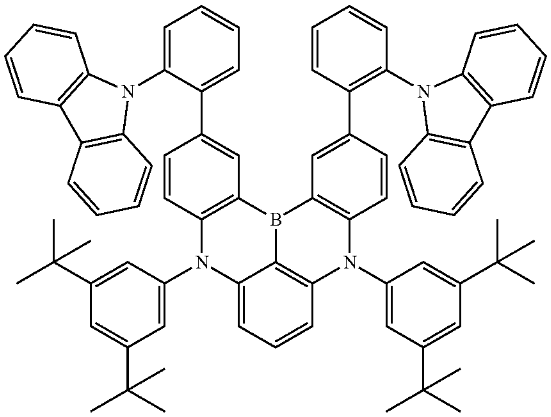,
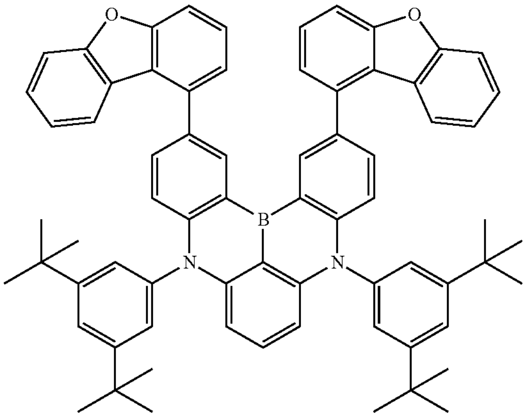,
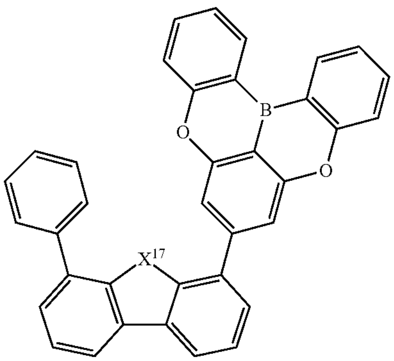,
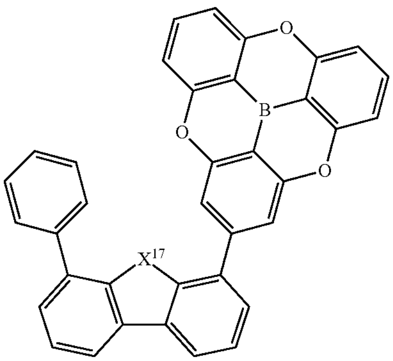, -continued
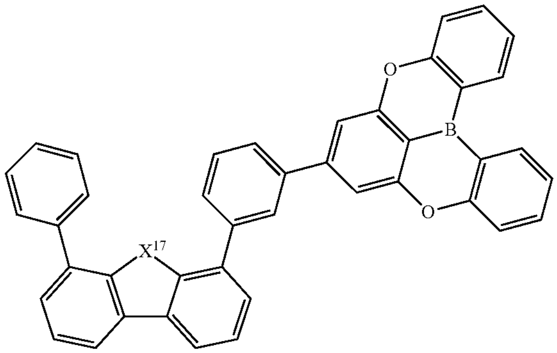
,
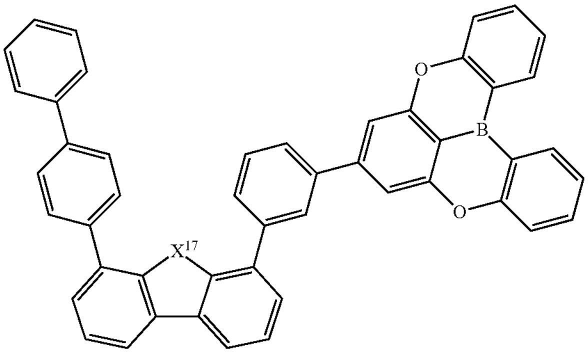
,
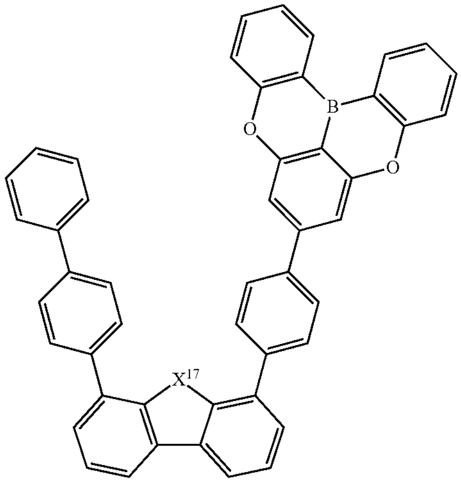
,
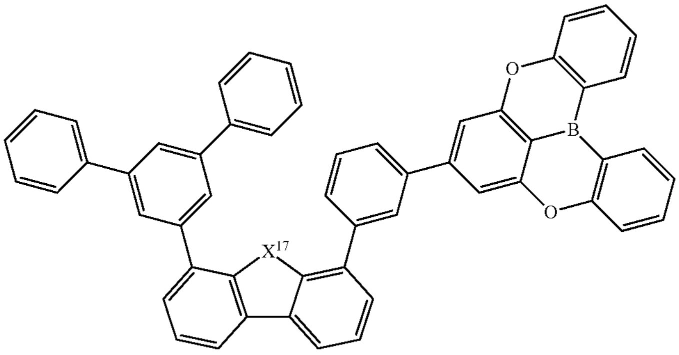
,
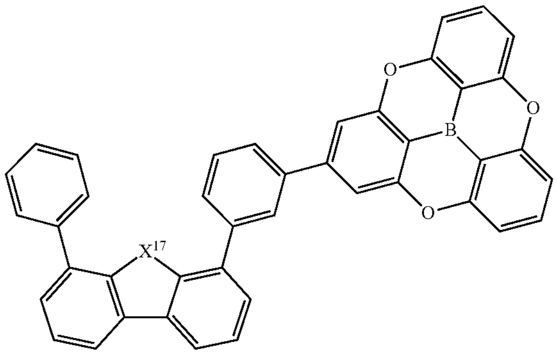
,
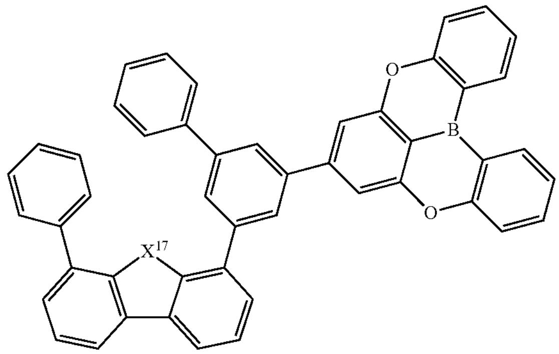
,
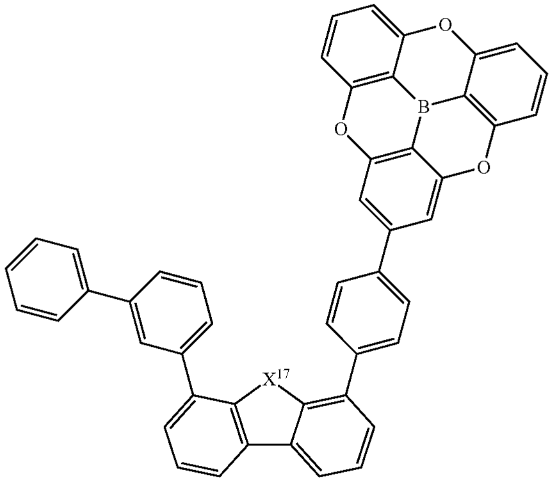
,
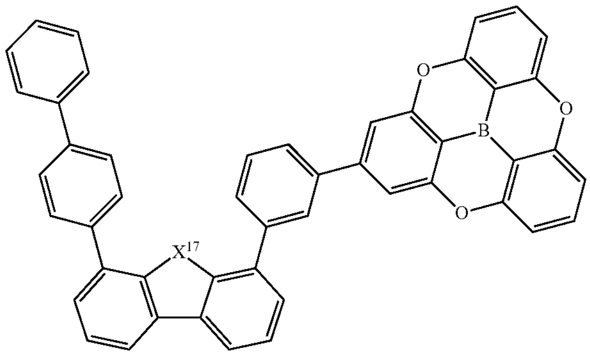
, -continued
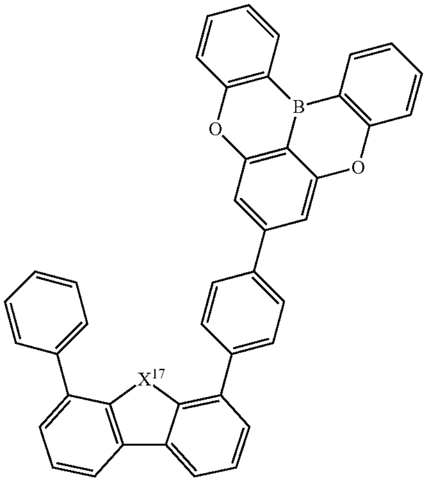
,
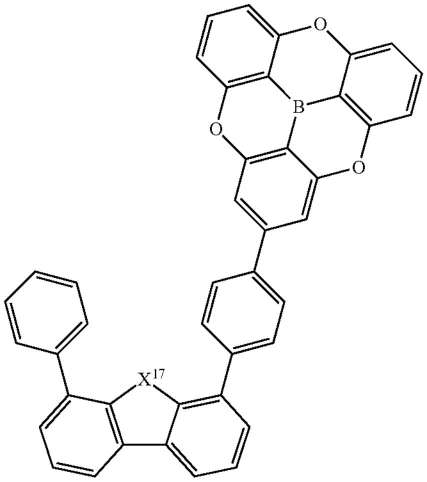
,
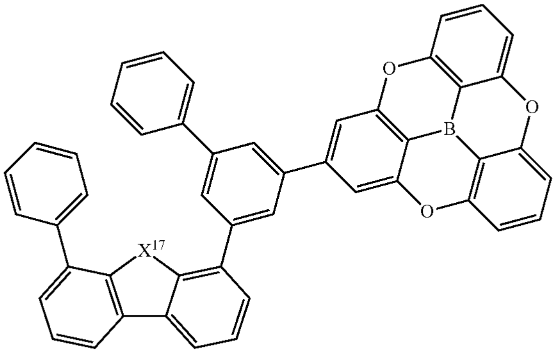
,
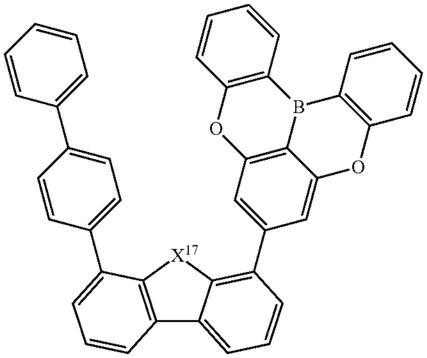
,
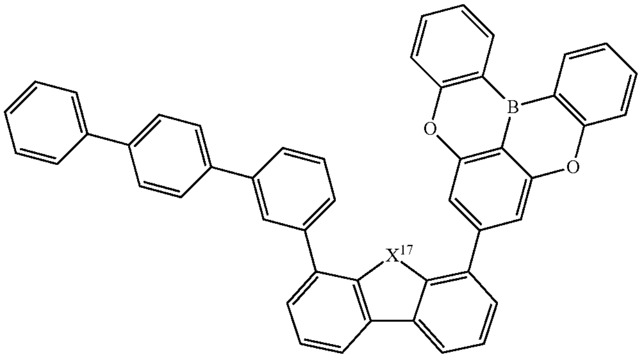
,
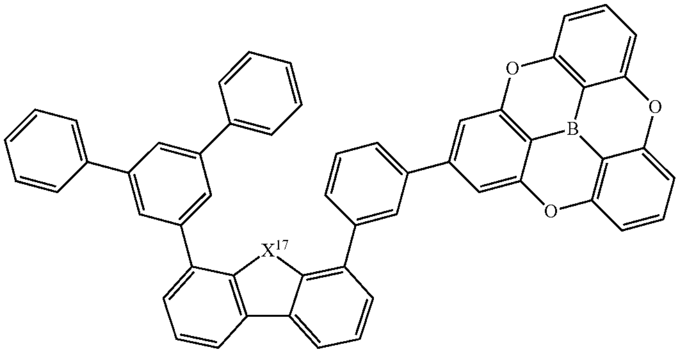
, -continued
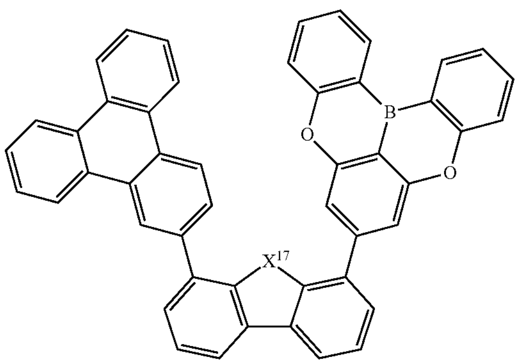
,
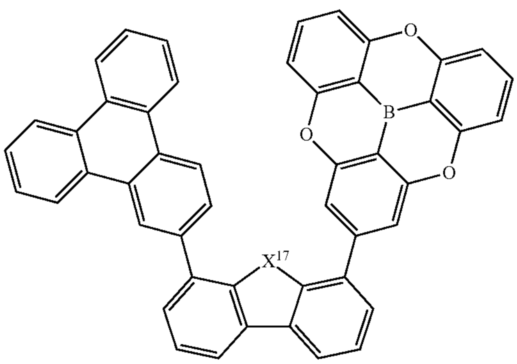
,
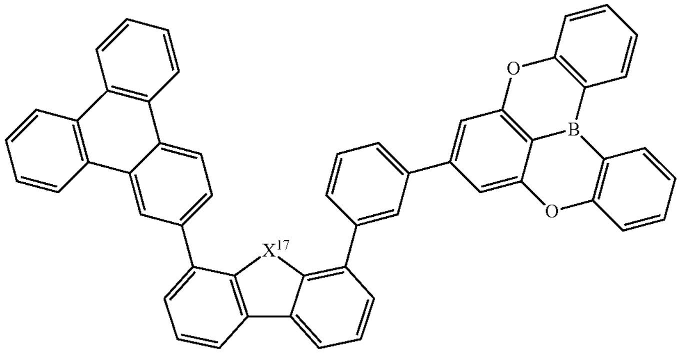
,
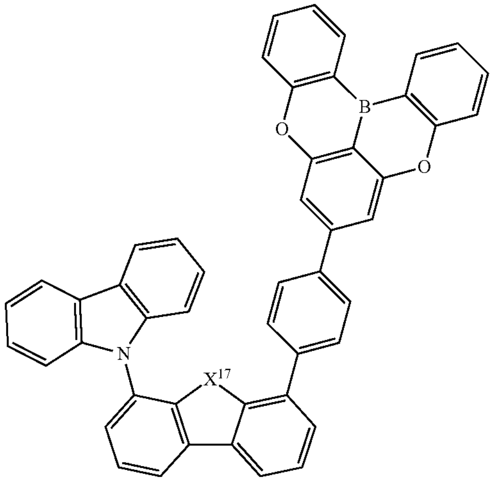
,
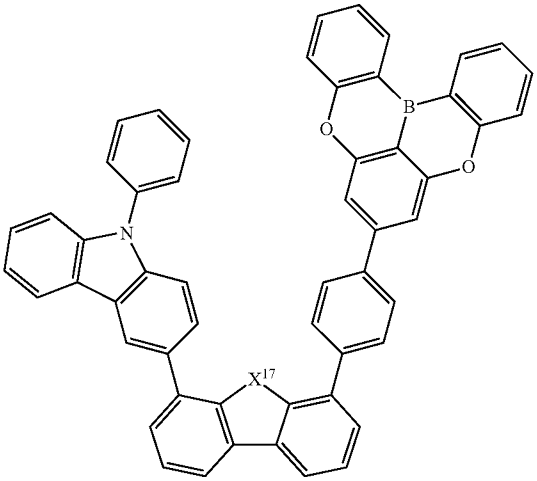
,
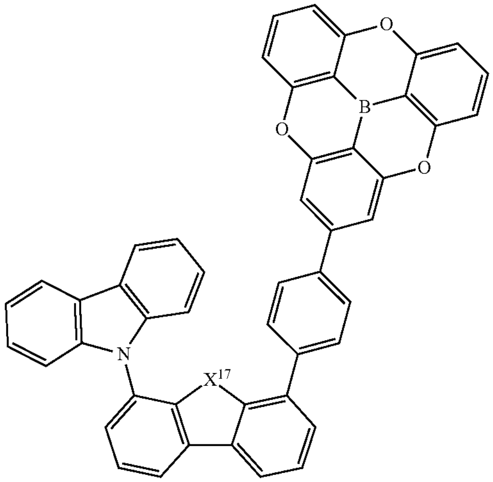
,
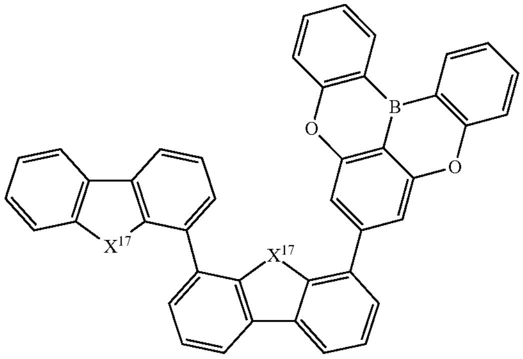
, -continued
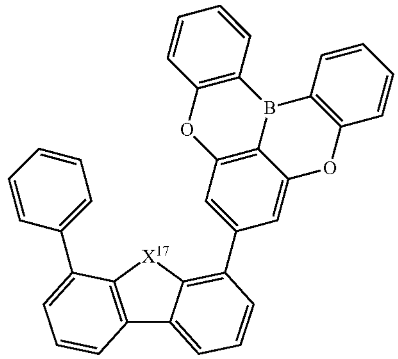
,
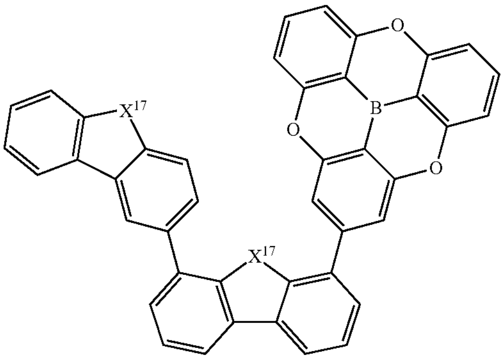
,
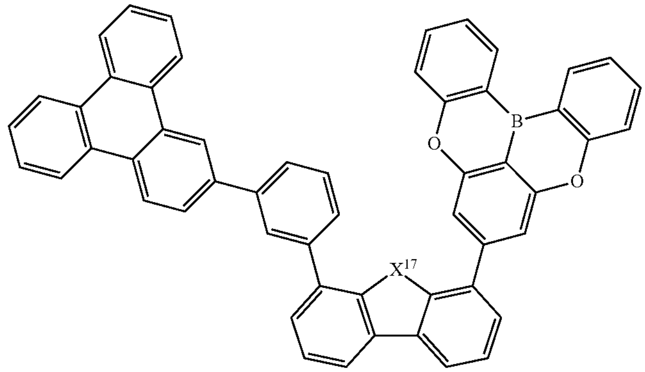
,
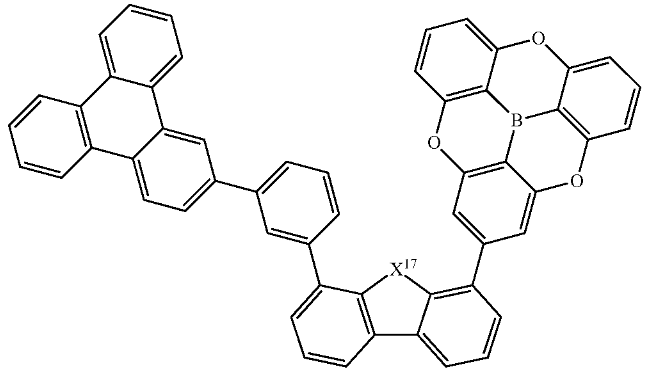
,
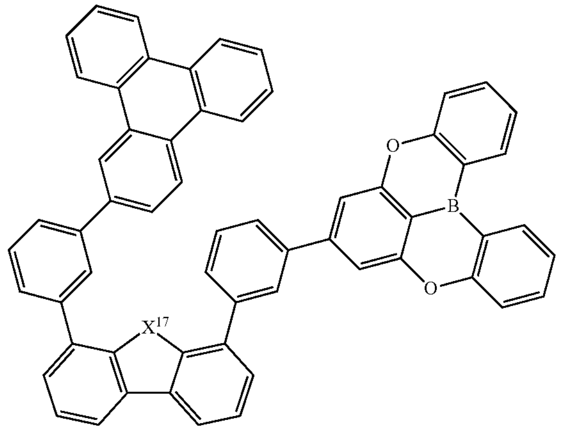
,
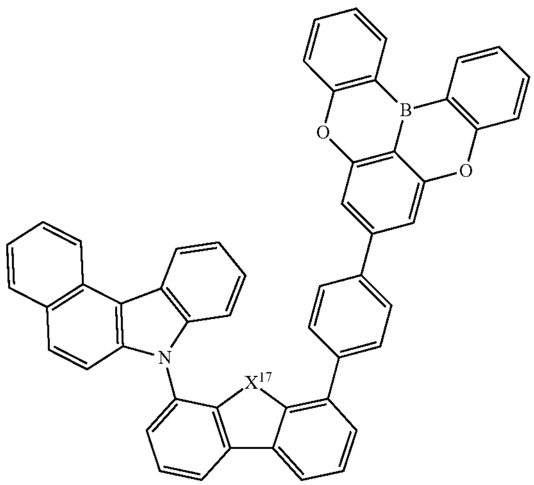
, -continued
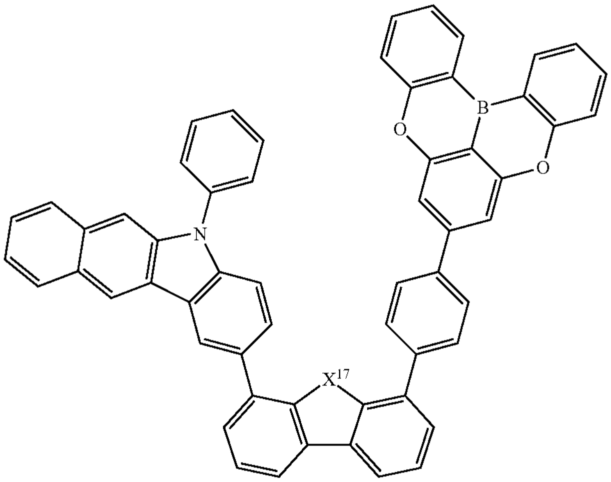
,
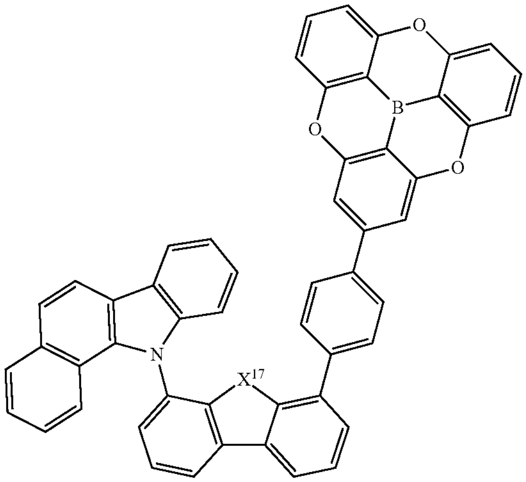
,
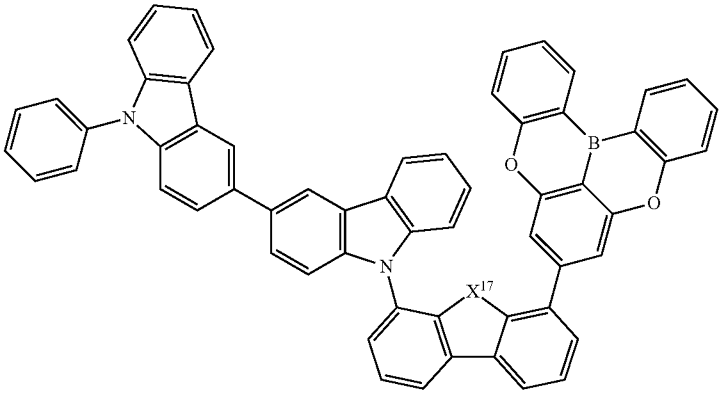
,
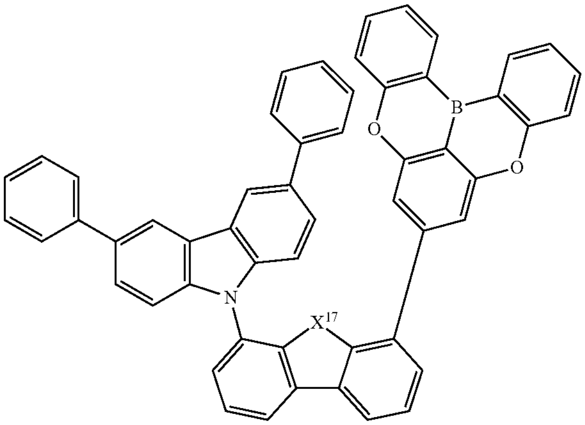
,
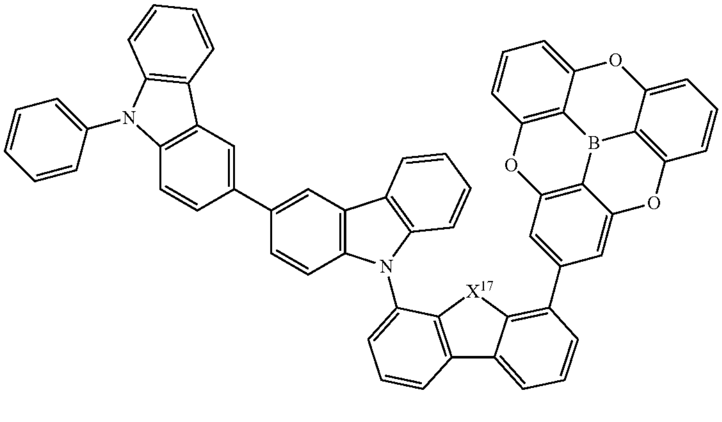
, -continued
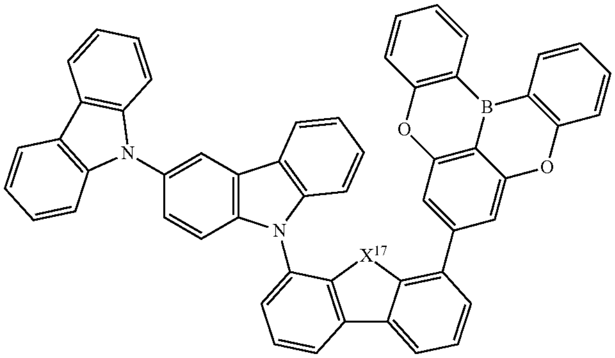
,
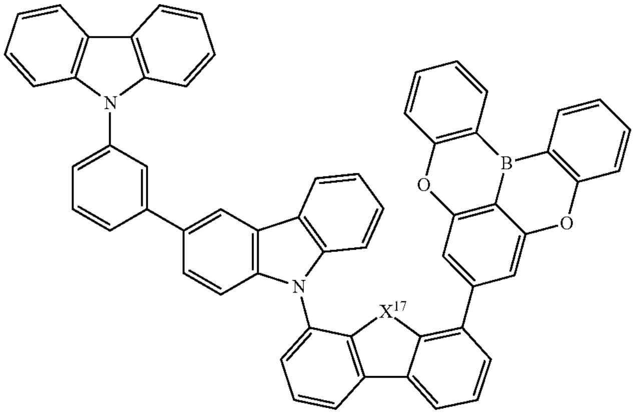
,
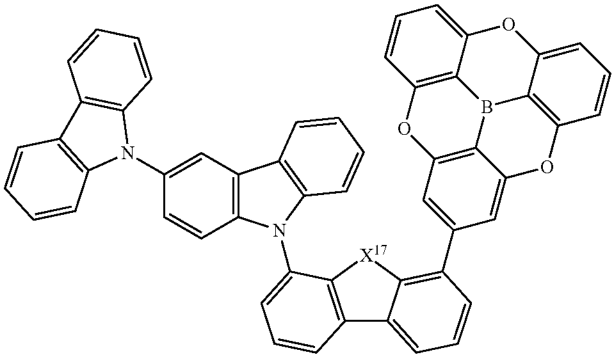
,
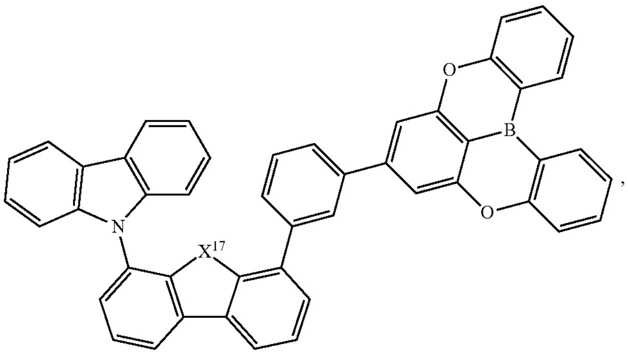
, -continued
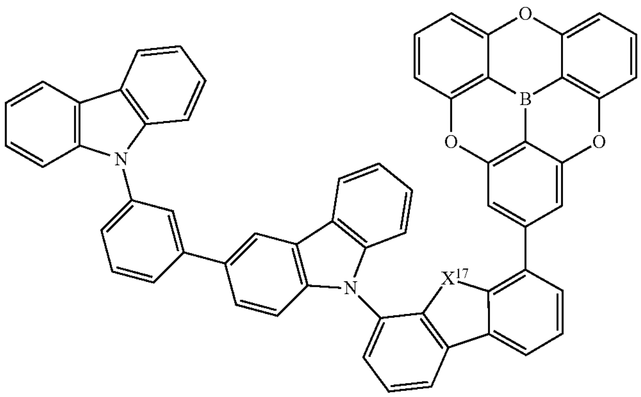
,
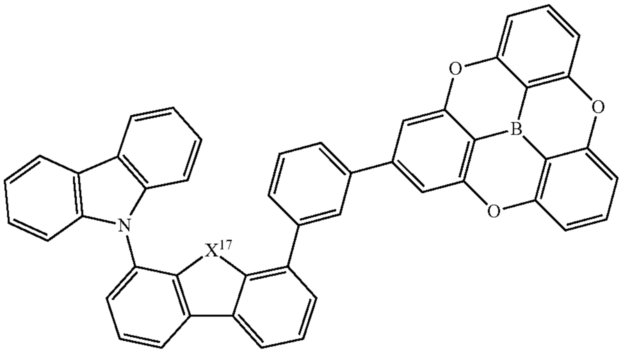
,
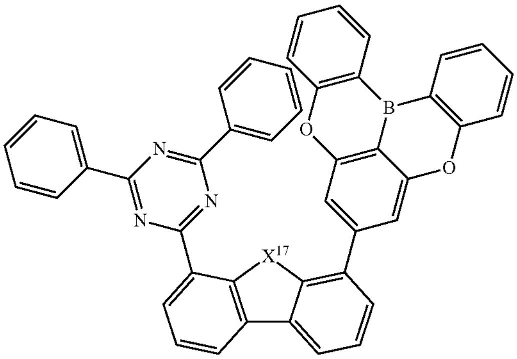
,
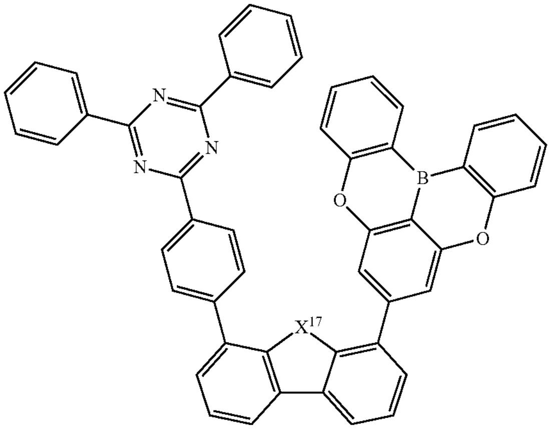
,
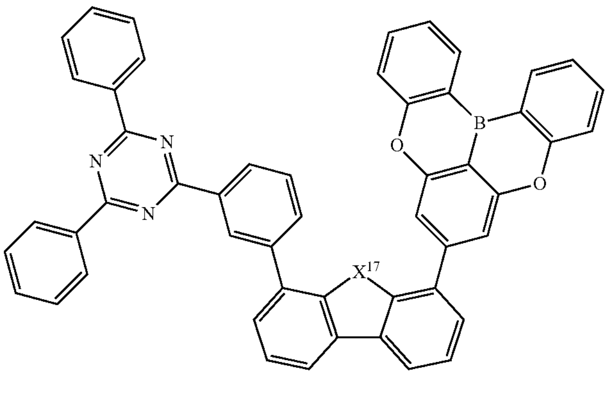
,
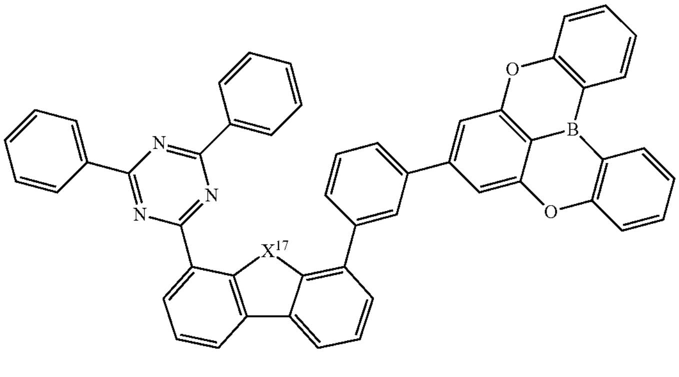
, -continued
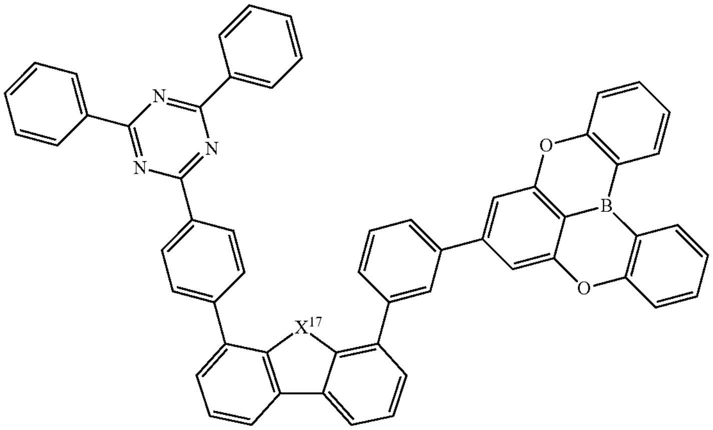
,
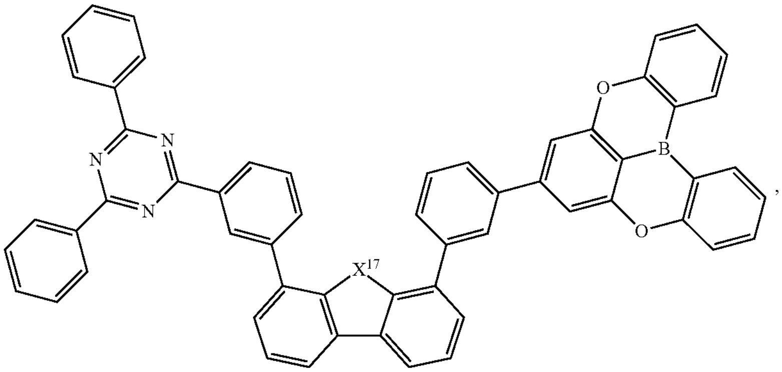
,
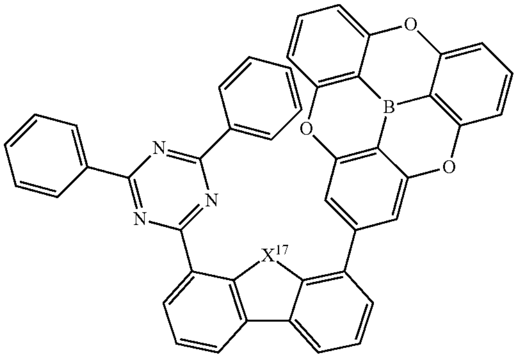
,
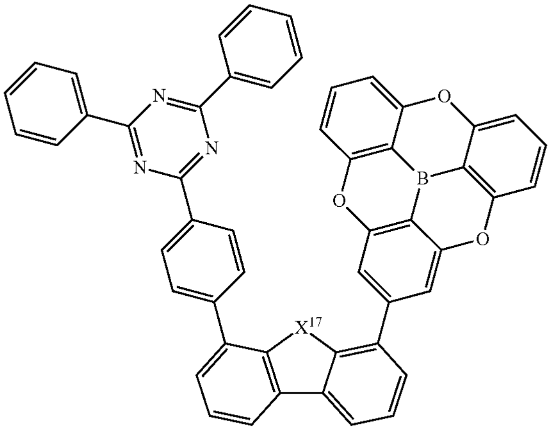
,
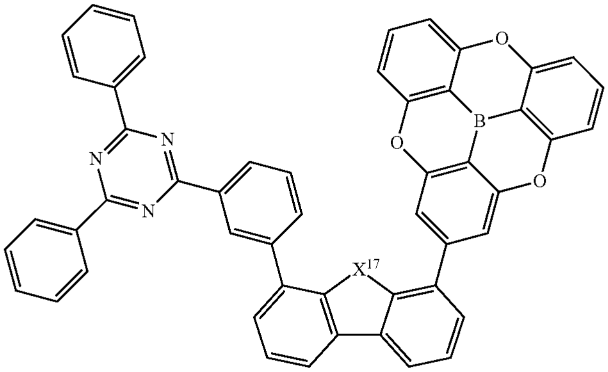
, -continued
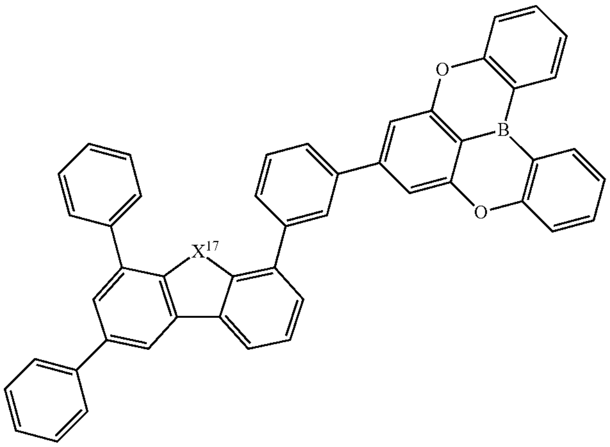
,
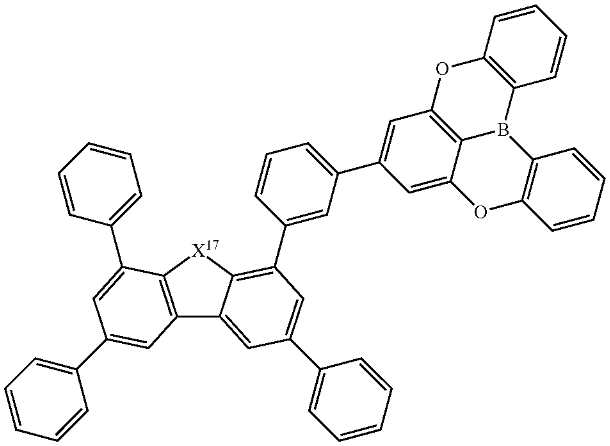
,
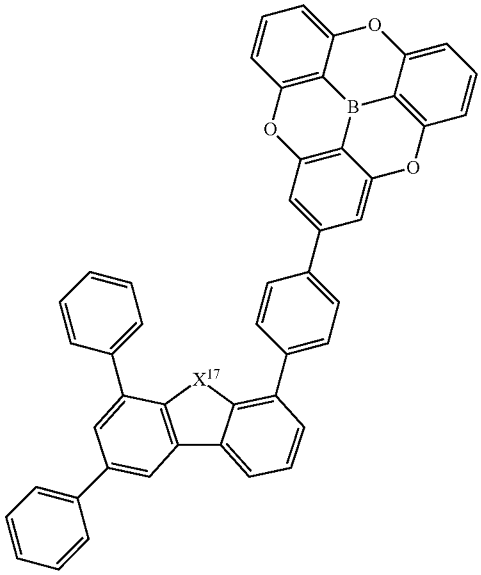
,
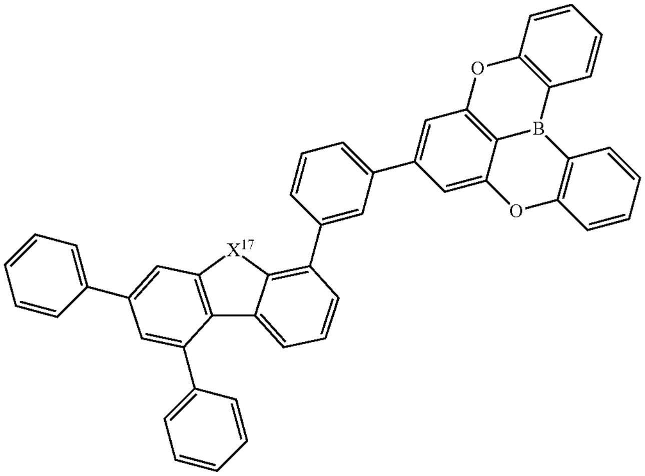
, -continued
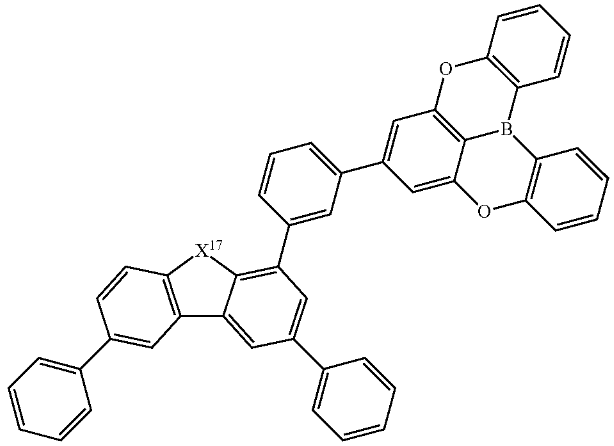
,
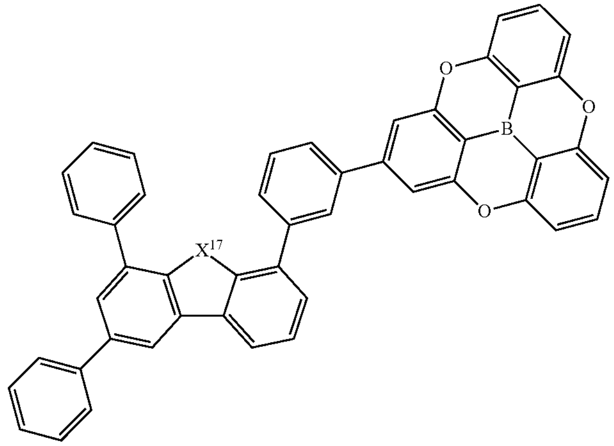
,
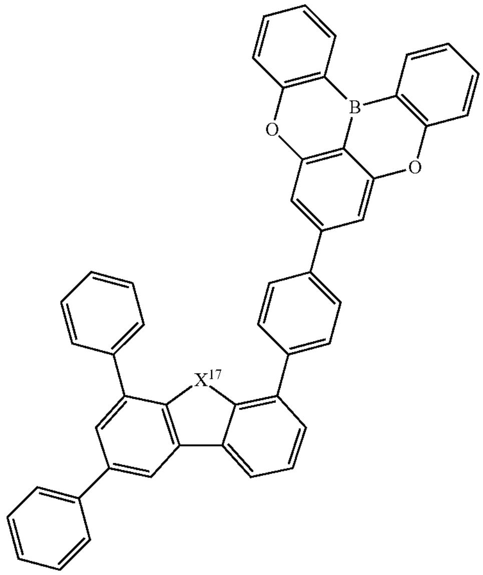
,
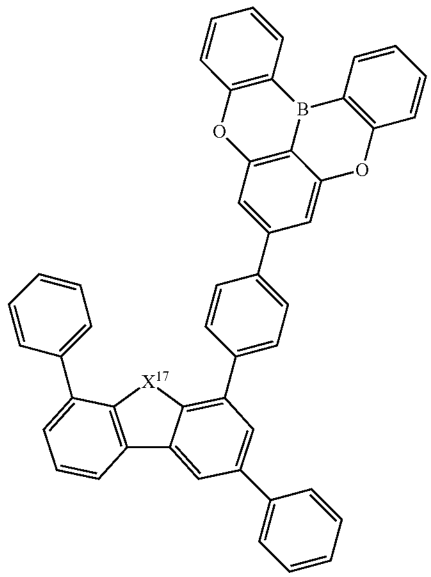
,
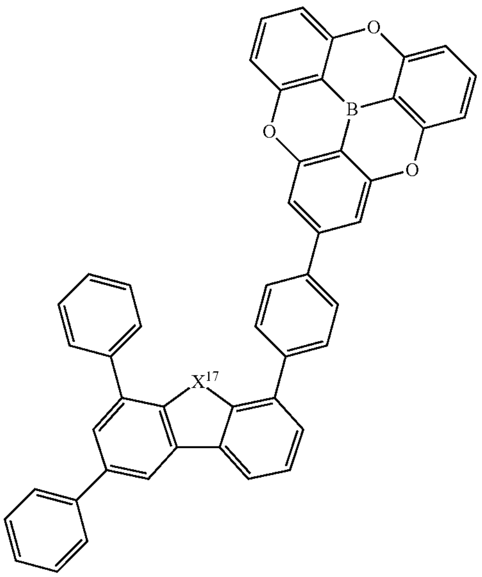
, -continued
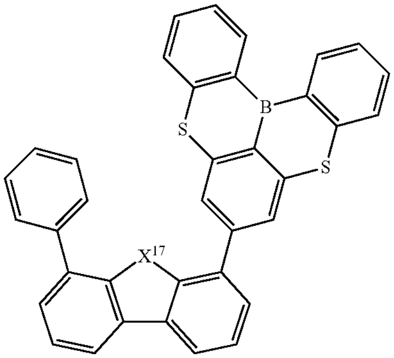
,
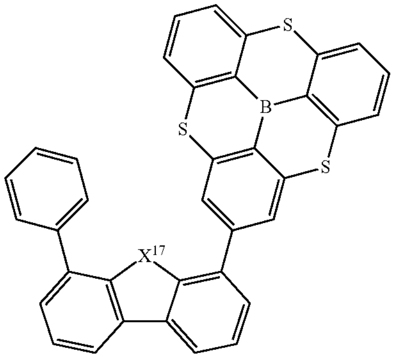
,
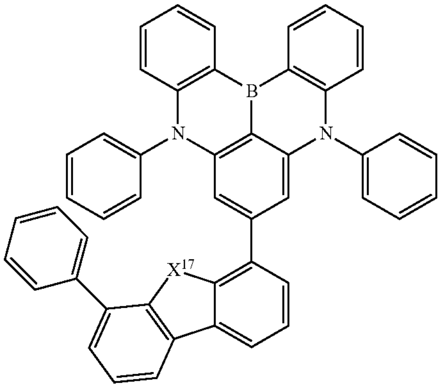
,
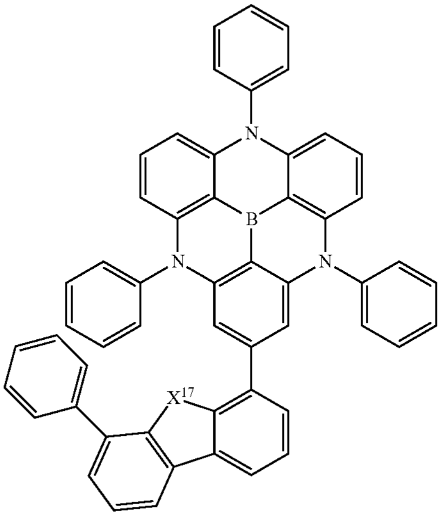
,
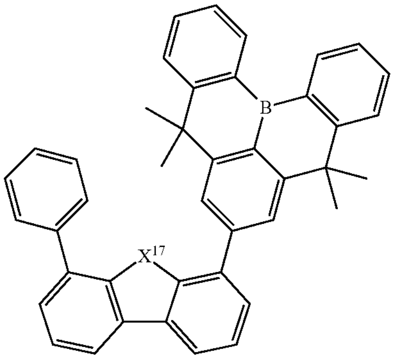
,
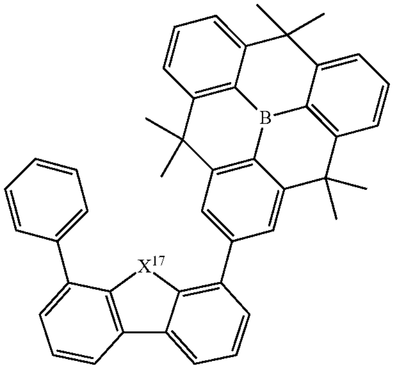
,
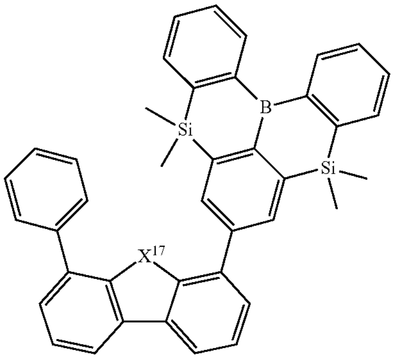
,
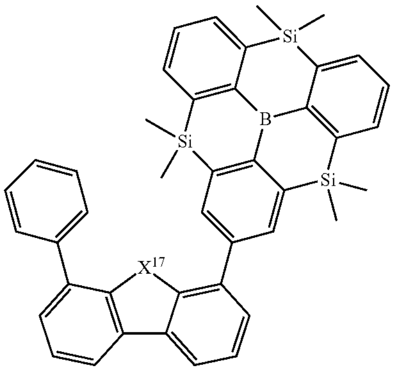
, -continued
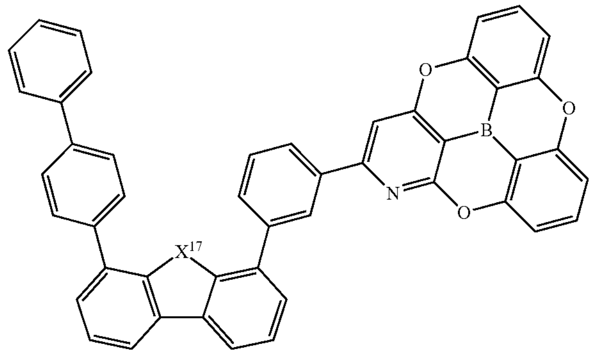
,
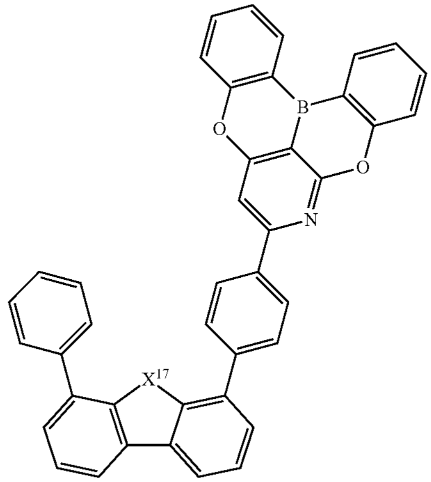
,
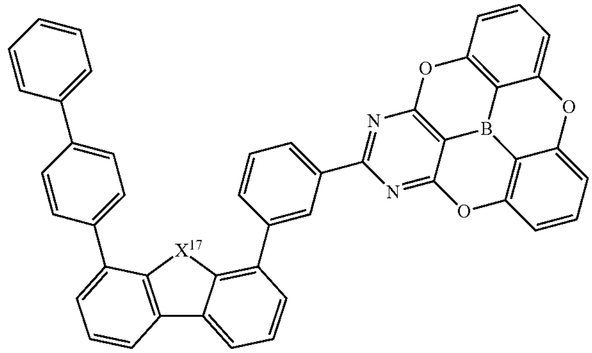
,
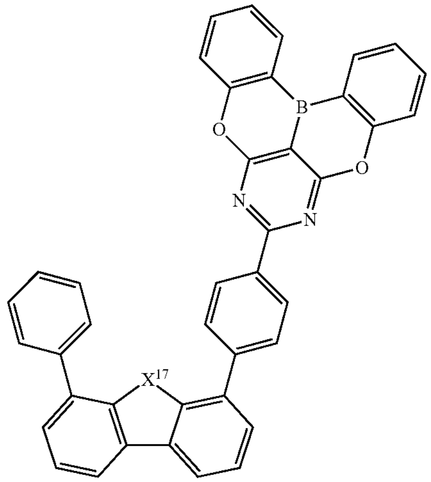
,
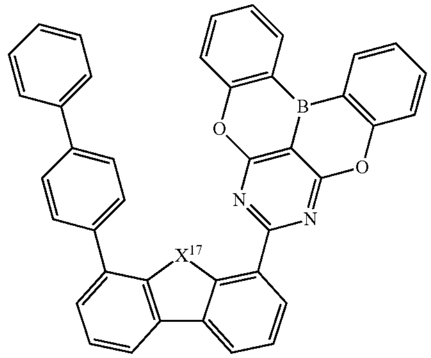
,
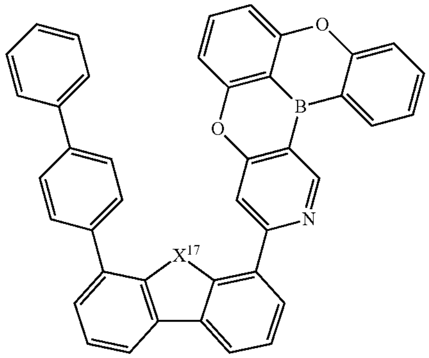
,
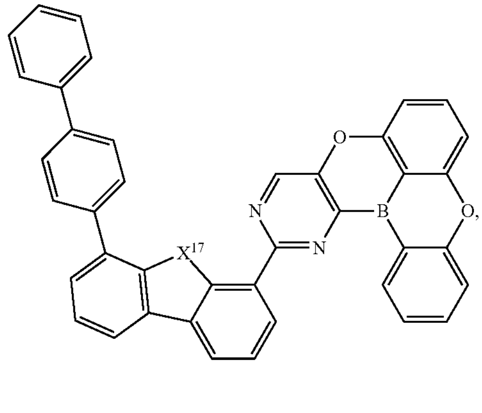
,
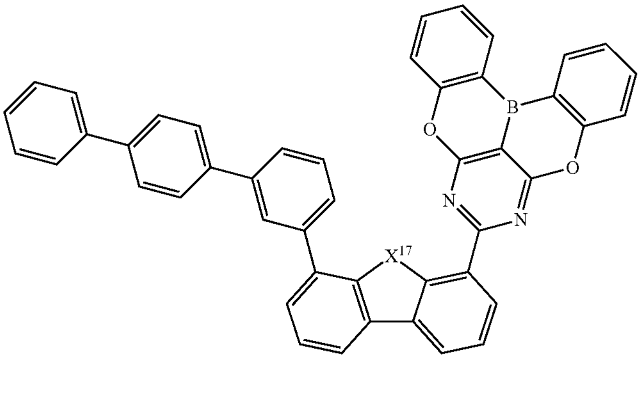
, -continued

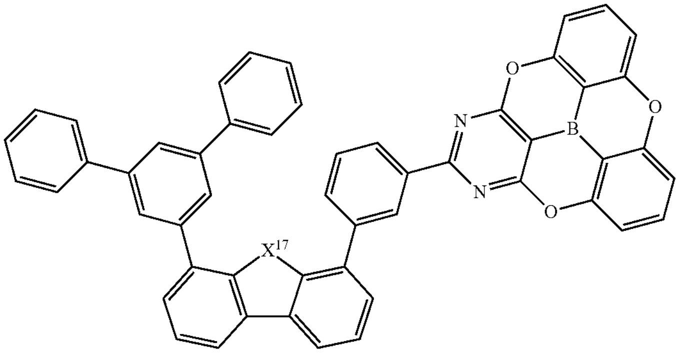

,

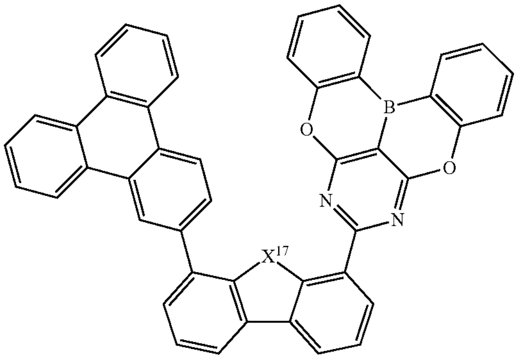

,

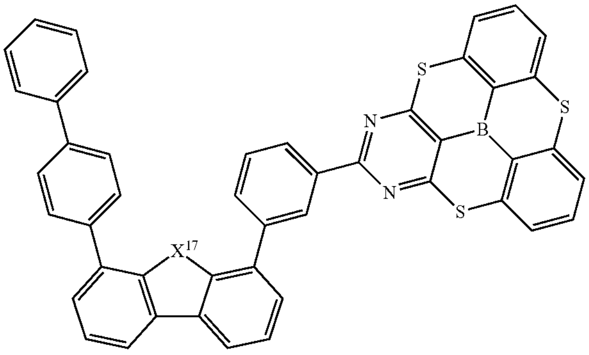

, and

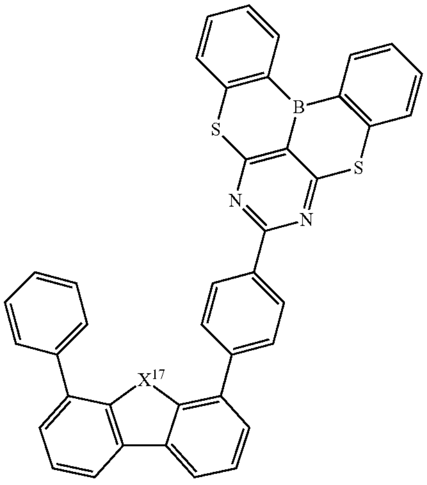

, wherein, for each occurrence, $X^{17}$ is independently selected from the group consisting of O, S, Se, and $NR^4$; and wherein $R^4$ is a hydrogen or a substituent selected from the group consisting of deuterium, halogen, alkyl, cycloalkyl, heteroalkyl, heterocycloalkyl, boryl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof.

17. The OLED of claim 1, wherein the first compound is a host, and the second compound is an emitter.

18. The OLED of claim 1, wherein the first compound is a fluorescent emitter or a delayed fluorescent emitter.

19. A consumer product comprising an organic light-emitting device (OLED) according to claim 1.

20. The OLED of claim 16, wherein the first compound is fully deuterated.

* * * * *